US012441735B2

(12) United States Patent
Kimbara et al.

(10) Patent No.: US 12,441,735 B2
(45) Date of Patent: *Oct. 14, 2025

(54) NITROGEN-CONTAINING HETEROCYCLIC COMPOUND HAVING NRF2 ACTIVATION EFFECT

(71) Applicant: CHUGAI SEIYAKU KABUSHIKI KAISHA, Tokyo (JP)

(72) Inventors: Atsushi Kimbara, Kamakura (JP); Takeo Harada, Gotemba (JP); Susumu Komiyama, Kamakura (JP); Mizuki Okuyama, Kamakura (JP); Yoshihito Ohtake, Gotemba (JP); Yoshihisa Murata, Gotemba (JP); Rie Saito, Kamakura (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/033,289

(22) Filed: Jan. 21, 2025

(65) Prior Publication Data

US 2025/0171457 A1 May 29, 2025

Related U.S. Application Data

(63) Continuation of application No. 18/726,155, filed as application No. PCT/JP2023/000211 on Jan. 6, 2023.

(30) Foreign Application Priority Data

Jan. 7, 2022 (JP) ................................ 2022-001804

(51) Int. Cl.

*C07D 491/08* (2006.01)
*A61K 31/472* (2006.01)
*A61K 31/4725* (2006.01)
*A61K 31/502* (2006.01)
*A61K 31/536* (2006.01)
(Continued)

(52) U.S. Cl.

CPC .......... *C07D 491/08* (2013.01); *A61K 31/472* (2013.01); *A61K 31/4725* (2013.01); *A61K 31/502* (2013.01); *A61K 31/536* (2013.01); *A61K 31/5365* (2013.01); *A61K 31/5377* (2013.01); *A61K 31/538* (2013.01); *A61K 31/5383* (2013.01); *A61K 31/5386* (2013.01); *A61K 31/541* (2013.01); *A61K 31/5415* (2013.01); *A61K 31/55* (2013.01); *A61K 31/551* (2013.01); *C07D 217/06* (2013.01); *C07D 237/32* (2013.01); *C07D 265/02* (2013.01); *C07D 265/16* (2013.01); *C07D 401/10* (2013.01); *C07D 401/14* (2013.01); *C07D 403/10* (2013.01); *C07D 413/10* (2013.01); *C07D 413/12* (2013.01); *C07D 413/14* (2013.01); *C07D 417/10* (2013.01); *C07D 471/04* (2013.01); *C07D 487/04* (2013.01); *C07D 487/10* (2013.01); *C07D 491/107* (2013.01); *C07D 519/00* (2013.01)

(58) Field of Classification Search

CPC .................................................... C07D 491/08
USPC .................................................... 514/210.02
See application file for complete search history.

(56) References Cited

FOREIGN PATENT DOCUMENTS

| | | | |
|---|---|---|---|
| CN | 110294744 | A | 10/2019 |
| CN | 114507181 | A | 5/2022 |

(Continued)

OTHER PUBLICATIONS

Boltromeûk, V. V., "General chemistry," Minsk, Vyšejšaâškola, 65 (2012).

Cuadrado, A., et al., "Therapeutic targeting of the NRF2 and KEAP1 partnership in chronic diseases," Nat Rev Drug Discov., 18(4):295-317 (2019).

Chin, M. P., et al., "Mechanisms Contributing to Adverse Cardiovascular Events in Patients with Type 2 Diabetes Mellitus and Stage 4 Chronic Kidney Disease Treated with Bardoxolone Methyl," Am J Nephrol., 39:499-508 (2014).

Dinkova-Kostova, A. T. and Kazantsev, A. G., "Activation of Nrf2 Signaling as a Common Treatment of Neurodegenerative Diseases," Neurodegener Dis Manag., 7(2):97-100 (2017).

(Continued)

*Primary Examiner* — Kahsay Habte
(74) *Attorney, Agent, or Firm* — Nixon & Vanderhye P.C.

(57) ABSTRACT

Provided is a low-molecular compound or a salt thereof, or a solvate thereof which has the ability to activate Nrf2. The present invention provides a compound represented by the formula (1) or a salt thereof, or a solvate thereof, wherein $X_{a1}$ is $CR_{a1}$ or N, $X_{a3}$ is $CR_{a3}$ or N, $R_{a1}$, $R_{a2}$ and $R_{a3}$ are each independently selected from the group consisting of hydrogen, halogen and $C_1$-$C_6$ alkoxy, $X_{b1}$, $X_{b2}$ and $X_{b3}$ are each independently selected from the group consisting of $CH_2$, O, NH, S and C═O, Y is $C_6$-$C_{10}$ aryl optionally having a substituent or 5- to 10-membered heteroaryl optionally having a substituent, and Z is $C_6$-$C_{10}$ aryl optionally having a substituent, 5- to 10-membered heteroaryl optionally having a substituent or $C_1$-$C_6$ alkyl optionally having a substituent.

(1)

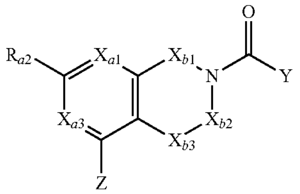

28 Claims, No Drawings

(51) Int. Cl.

| | |
|---|---|
| ***A61K 31/5365*** | (2006.01) |
| ***A61K 31/5377*** | (2006.01) |
| ***A61K 31/538*** | (2006.01) |
| ***A61K 31/5383*** | (2006.01) |
| ***A61K 31/5386*** | (2006.01) |
| ***A61K 31/541*** | (2006.01) |
| ***A61K 31/5415*** | (2006.01) |
| ***A61K 31/55*** | (2006.01) |
| ***A61K 31/551*** | (2006.01) |
| ***C07D 217/06*** | (2006.01) |
| ***C07D 237/32*** | (2006.01) |
| ***C07D 265/02*** | (2006.01) |
| ***C07D 265/16*** | (2006.01) |
| ***C07D 401/10*** | (2006.01) |
| ***C07D 401/14*** | (2006.01) |
| ***C07D 403/10*** | (2006.01) |
| ***C07D 413/10*** | (2006.01) |
| ***C07D 413/12*** | (2006.01) |
| ***C07D 413/14*** | (2006.01) |
| ***C07D 417/10*** | (2006.01) |
| ***C07D 471/04*** | (2006.01) |
| ***C07D 487/04*** | (2006.01) |
| ***C07D 487/10*** | (2006.01) |
| ***C07D 491/107*** | (2006.01) |
| ***C07D 519/00*** | (2006.01) |

(56) References Cited

FOREIGN PATENT DOCUMENTS

| | | | |
|---|---|---|---|
| WO | WO9965478 | A1 | 12/1999 |
| WO | WO2014059214 | A1 | 4/2014 |
| WO | WO2014176415 | A1 | 10/2014 |
| WO | WO2016036633 | A1 | 3/2016 |
| WO | WO2016090154 | A1 | 6/2016 |
| WO | WO2020084300 | A1 | 4/2020 |
| WO | WO2020165776 | A1 | 8/2020 |

OTHER PUBLICATIONS

Lee, S. and Hu, L., "Nrf2 activation through the inhibition of Keap1-Nrf2 protein-protein interaction," Med Chem Res., 29(5):846-867 (2020).

Liu, Q., et al., "Role of Nrf2 and Its Activators in Respiratory Diseases," Oxid Med Cell Longev., Article ID 7090534 (2019).

Robledinos-Antón, N., et al., "Activators and Inhibitors of NRF2: A Review of Their Potential for Clinical Development," Oxid Med Cell Longev., Article ID 9372182 (2019).

Shi, Z., et al., "Discovery of Propionic Acid Derivatives with a 5-THIQ Core as Potent and Orally Bioavailable Keap1-Nrf2 Protein-Protein Interaction Inhibitors for Acute Kidney Injury," J Med Chem., 67(21):19247-19266 (2024).

Wang, M., et al., "Potential Protective and Therapeutic Roles of the Nrf2 Pathway in Ocular Diseases: An Update," Oxid Med Cell Longev., Article ID 9410952 (2020).

Zhuang, C., et al., "Small molecules inhibiting Keap1-Nrf2 protein-protein interactions: a novel approach to activate Nrf2 function," Med Chem Commun., 8:286-294 (2017).

NITROGEN-CONTAINING HETEROCYCLIC COMPOUND HAVING NRF2 ACTIVATION EFFECT

CROSS-REFERENCE TO RELATED APPLICATIONS

This application is a continuation of U.S. application Ser. No. 18/726,155, filed Jul. 2, 2024, which is a U.S. National Phase of PCT Application No. PCT/JP2023/000211, filed Jan. 6, 2023, which claims the benefit of Japanese Patent Application No. 2022-001804, filed Jan. 7, 2022, each of which is incorporated herein by reference in its entirety.

TECHNICAL FIELD

The present invention relates to a nitrogen-containing heterocyclic compound or a salt thereof, or a solvate thereof which has a Nrf2-activating effect and use thereof. The present invention also relates to a medicament and a pharmaceutical composition containing the same as an active ingredient.

BACKGROUND ART

Nrf2 is a control factor for gene groups involved in various body's defenses and is a transcriptional factor that is activated in response to oxidative stress. In a normal state, Nrf2 binds to Keap1 and undergoes ubiquitination and degradation through the proteasome pathway. Under stress conditions, Nrf2 circumvents degradation by dissociation from Keap1 and translocates into the nucleus. Then, Nrf2 forms a heterodimer with a small Maf group factor, and this heterodimer binds to antioxidant response elements (ARE) to induce the transcription of downstream molecules.

The activation of Nrf2 exhibits an antioxidative effect as well as a wide range of pharmacological effects such as an anti-inflammatory effect, an antifibrotic effect, and an anti-apoptotic effect, and is considered to defensively act on various diseases. Specific examples of such a disease include neurodegenerative disease including Alzheimer's disease, Parkinson's disease, Huntington's disease, Friedreich's ataxia, and amyotrophic lateral sclerosis, lung disease including idiopathic pulmonary fibrosis, acute respiratory distress syndrome, chronic obstructive pulmonary disease, pulmonary arterial hypertension, and asthma, kidney disease including chronic kidney disease and acute kidney injury, ophthalmic disease including uveitis, glaucoma, and age-related macular degeneration, liver disease including non-alcoholic steatohepatitis, and immunological or inflammatory disease including multiple sclerosis, rheumatoid arthritis, and ulcerative colitis (Non Patent Literatures 3 to 7). In actuality, bardoxolone methyl (CDDO-Me; Patent Literature 1) which targets various chronic kidney diseases and RTA-408 (omaveloxolone; Patent Literature 2) which targets Friedreich's ataxia or the like are each under clinical trial as a compound having a Nrf2 activation-inducing effect. Dimethyl fumarate (Patent Literature 3) is used as a therapeutic drug for multiple sclerosis. However, these compounds are compounds that covalently bind to Keap1. A fear of the risk of heart failure ascribable to the interaction of the covalent binding site of bardoxolone methyl with a non-target protein has been reported (Non Patent Literature 8).

For example, compounds described in Patent Literature 4 have been reported so far as Nrf2 activators. However, these compounds have not yet been clinically developed. Thus, there is a demand for a non-covalently binding type of Nrf2 activator which can be expected to reduce interaction with a non-target protein (Non Patent Literatures 1 to 3).

CITATION LIST

Patent Literature

Patent Literature 1: International Publication No. WO 1999/065478

Patent Literature 2: International Publication No. WO 2014/176415

Patent Literature 3: International Publication No. WO 2016/090154

Patent Literature 4: International Publication No. WO 2020/165776

Non Patent Literature

Non Patent Literature 1: Med Chem Commun, 2017, 8, 286-294.

Non Patent Literature 2: Medicinal Chemistry Research, 2020, 29, 846-867.

Non Patent Literature 3: Nature Reviews Drug Discovery, 2019, 18, 295-317.

Non Patent Literature 4: Oxydative Medicine and Cellular Longevity, 2019, Article ID 9372182, 1-20.

Non Patent Literature 5: Neurodegenr Dis Manag, 2017, 7, 97-100.

Non Patent Literature 6: Oxydative Medicine and Cellular Longevity, 2019, Article ID 7090534, 1-17.

Non Patent Literature 7: Oxydative Medicine and Cellular Longevity, 2020, Article ID 9410952, 1-22.

Non Patent Literature 8: Am J Nephrol, 2014, 39, 499-508

SUMMARY OF INVENTION

Technical Problem

An object of the present invention is to provide a low-molecular compound or a salt thereof, or a solvate thereof which has the ability to activate Nrf2 and reduces interaction with a non-target protein attributed to covalent binding. Another object of the present invention is to provide a prophylactic agent or a therapeutic agent for various diseases, for example, neurodegenerative disease, lung disease, and kidney disease, containing the same as an active ingredient.

Solution to Problem

The present inventors have conducted diligent studies to attain the objects and consequently completed the present invention by finding that a compound having a backbone represented by the formula (I) which largely differs in chemical structure from Nrf2 activators known in the art, or a pharmacologically acceptable salt thereof or a solvate of the compound or the salt has an excellent Nrf2-activating effect.

Specifically, one aspect of the present invention provides the following invention.

[1]

A compound represented by the formula (1) or a salt thereof, or a solvate thereof:

[Formula 1]

(1)

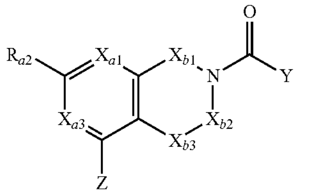

where $X_{a1}$ is $CR_{a1}$ or N, $X_{a3}$ is $CR_{a3}$ or N, $R_{a1}$, $R_{a2}$ and $R_{a3}$ are each independently selected from the group consisting of hydrogen, halogen and $C_1$-$C_6$ alkoxy, $X_{b1}$, $X_{b2}$ and $X_{b3}$ are each independently selected from the group consisting of $CH_2$, O, NH, S and C═O, Y is $C_6$-$C_{10}$ aryl or 5- to 10-membered heteroaryl, wherein the $C_6$-$C_{10}$ aryl and the 5- to 10-membered heteroaryl are each optionally substituted by one or more groups selected from the group consisting of $R_{y1}$, $R_{y2}$, $R_{y3}$, $R_{y4}$ and $R_{y5}$, $R_{y1}$, $R_{y2}$, $R_{y3}$, $R_{y4}$ and $R_{y5}$ are each independently selected from the group consisting of hydrogen, halogen, cyano, $C_1$-$C_6$ alkyl, $C_2$-$C_6$ alkenyl, $C_3$-$C_8$ cycloalkyl, $C_1$-$C_6$ alkoxy, 4- to 10-membered heterocyclyl $C_1$-$C_6$ alkoxy, hydroxy $C_2$-$C_6$ alkoxy, 4- to 10-membered heterocyclyloxy, $C_1$-$C_6$ alkylamino $C_1$-$C_6$ alkoxy, 5- to 10-membered heteroaryloxy, $C_1$-$C_6$ alkylthio, a 4- to 10-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent and $C_1$-$C_6$ alkyl($C_1$-$C_6$ alkoxy $C_1$-$C_6$ alkyl)amino, Z is $C_6$-$C_{10}$ aryl, 5- to 10-membered heteroaryl or $C_1$-$C_6$ alkyl, wherein the $C_6$-$C_{10}$ aryl, the 5- to 10-membered heteroaryl and the $C_1$-$C_6$ alkyl are each substituted by $R_{z3}$ and optionally substituted by one or more groups selected from the group consisting of $R_{z1}$, $R_{z2}$, $R_{z4}$ and $R_{z5}$, $R_{z3}$ is a group selected from the following substituent group A:

[Formula 2]

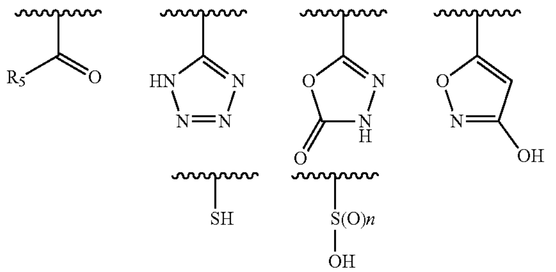

wherein the wavy line represents a binding point with the $C_6$-$C_{10}$ aryl, the 5- to 10-membered heteroaryl or the $C_1$-$C_6$ alkyl, $R_5$ is hydroxy, $C_1$-$C_6$ alkoxy, mono- or di-$C_1$-$C_6$ alkylamino or $C_1$-$C_6$ alkylsulfonylamino, and n is 1 or 2, and $R_{z1}$, $R_{z2}$, $R_{z4}$ and $R_{z5}$ are each independently selected from the group consisting of hydrogen, halogen, $C_1$-$C_6$ alkyl, $C_1$-$C_6$ alkyl(5- to 10-membered heteroaryl $C_1$-$C_6$ alkyl)amino optionally having a substituent, $C_1$-$C_6$ alkyl(4- to 10-membered heterocyclyl)amino optionally having a substituent and 4- to 8-membered cyclic amino optionally having a substituent.

[2]

The compound according to [1] or a salt thereof, or a solvate thereof, wherein $X_{b1}$ is $CH_2$, $X_{b2}$ is $CH_2$, O, NH or C═O, and $X_{b3}$ is $CH_2$, O, NH, S or C═O.

[3]

The compound according to [1] or [2] or a salt thereof, or a solvate thereof, wherein each of $X_{b1}$ and $X_{b2}$ is $CH_2$, and $X_{b3}$ is O;

each of $X_{b1}$ and $X_{b3}$ is $CH_2$, and $X_{b2}$ is O;

each of $X_{b1}$ and $X_{b2}$ is $CH_2$, and $X_{b3}$ is S;

$X_{b1}$ is $CH_2$, $X_{b2}$ is NH, and $X_{b3}$ is C═O;

each of $X_{b1}$ and $X_{b2}$ is $CH_2$, and $X_{b3}$ is NH;

$X_{b1}$ is $CH_2$, $X_{b2}$ is C═O, and $X_{b3}$ is NH;

each of $X_{b1}$ and $X_{b3}$ is $CH_2$, and $X_{b2}$ is NH; or each of $X_{b1}$, $X_{b2}$ and $X_{b3}$ is $CH_2$.

[4]

The compound according to any of [1] to [3] or a salt thereof, or a solvate thereof, wherein $X_{a1}$ is $CR_{a1}$, and $X_{a3}$ is $CR_{a3}$ or N.

[5]

The compound according to any of [1] to [4] or a salt thereof, or a solvate thereof, wherein Z is phenyl, pyridyl or $C_2$-$C_5$ alkyl, wherein the phenyl, the pyridyl and the $C_2$-$C_5$ alkyl are each substituted by $R_{z3}$ and optionally substituted by one or more groups selected from the group consisting of $R_{z1}$, $R_{z2}$, $R_{z4}$ and $R_{z5}$, and $R_{z3}$ is a group selected from the following substituent group B:

[Formula 3]

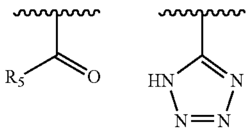

wherein the wavy line represents a binding point with the phenyl, the pyridyl or the $C_2$-$C_5$ alkyl, and $R_5$ is hydroxy, $C_1$-$C_6$ alkoxy, mono-$C_1$-$C_6$ alkylamino or $C_1$-$C_6$ alkylsulfonylamino, and $R_{z1}$, $R_{z2}$, $R_{z4}$ and $R_{z5}$ are each independently selected from the group consisting of hydrogen, halogen, $C_1$-$C_6$ alkyl, $C_1$-$C_6$ alkyl(5- to 10-membered heteroaryl $C_1$-$C_6$ alkyl)amino optionally having a substituent, $C_1$-$C_6$ alkyl(4- to 10-membered heterocyclyl)amino optionally having a substituent and 4- to 8-membered cyclic amino optionally having a substituent.

[6]

The compound according to any of [1] to [5] or a salt thereof, or a solvate thereof, wherein $R_{z1}$, $R_{z2}$ and $R_{z5}$ are each independently selected from the group consisting of hydrogen, halogen and $C_1$-$C_6$ alkyl, and $R_{z4}$ is $C_1$-$C_6$ alkyl(5- to 10-membered heteroaryl $C_1$-$C_2$ alkyl)amino optionally having a substituent, $C_1$-$C_6$ alkyl(4- to 10-membered heterocyclyl)amino optionally having a substituent or 4- to 8-membered cyclic amino optionally having a substituent.

[7]

The compound according to any of [1] to [6] or a salt thereof, or a solvate thereof, wherein Y is phenyl or 6- to 10-membered heteroaryl, wherein the phenyl and the 6- to 10-membered heteroaryl are each optionally substituted by one or more groups selected from the group consisting of $R_{y1}$, $R_{y2}$, $R_{y3}$, $R_{y4}$ and $R_{y5}$, and $R_{y1}$, $R_{y2}$, $R_{y3}$, $R_{y4}$ and $R_{y5}$ are each independently selected from the group consisting of hydrogen, halogen, cyano, $C_1$-$C_3$ alkyl, $C_2$-$C_4$ alkenyl, $C_3$-$C_6$ cycloalkyl, $C_1$-$C_3$ alkoxy, 5- or 6-membered heterocyclyl $C_1$-$C_4$ alkoxy, hydroxy $C_3$-$C_6$ alkoxy, 5- or 6-membered heterocyclyloxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent and $C_1$-$C_3$ alkyl($C_1$-$C_3$ alkoxy $C_1$-$C_2$ alkyl)amino.

[8]

The compound according to any of [1] to [7] or a salt thereof, or a solvate thereof, wherein Y is phenyl or 6- to 10-membered heteroaryl, wherein the phenyl and the 6- to 10-membered heteroaryl are each substituted by $R_{y3}$ and optionally substituted by one or more groups selected from the group consisting of $R_{y1}$, $R_{y2}$, $R_{y4}$ and $R_{y5}$, $R_{y1}$, $R_{y2}$, $R_{y4}$ and $R_{y5}$ are each independently selected from the group consisting of hydrogen, halogen, cyano, $C_1$-$C_3$ alkyl, $C_2$-$C_4$ alkenyl, $C_3$-$C_6$ cycloalkyl and $C_1$-$C_3$ alkoxy, and $R_{y3}$ is 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent or $C_1$-$C_3$ alkyl($C_1$-$C_3$ alkoxy $C_1$-$C_2$ alkyl)amino.

[9]

The compound according to any of [1] to [8] or a salt thereof, or a solvate thereof, wherein Z is a group represented by the following formula (2):

[Formula 4]

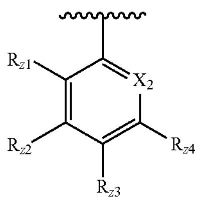

(2)

wherein the wavy line represents a binding point of Z, $R_{z3}$ is a group selected from the following substituent group B:

[Formula 5]

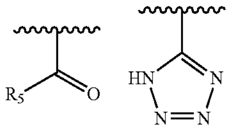

wherein the wavy line represents a binding point, and $R_5$ is hydroxy, $C_1$-$C_6$ alkoxy, mono-$C_1$-$C_6$ alkylamino or $C_1$-$C_6$ alkylsulfonylamino, $X_z$ is $CR_{z5}$ or N, $R_{z1}$, $R_{z2}$ and $R_{z5}$ are each independently selected from the group consisting of hydrogen, halogen and $C_1$-$C_6$ alkyl, and $R_{z4}$ is $C_1$-$C_6$ alkyl(5- to 10-membered heteroaryl $C_1$-$C_2$ alkyl)amino optionally having a substituent, $C_1$-$C_6$ alkyl(4- to 10-membered heterocyclyl)amino optionally having a substituent or 4- to 8-membered cyclic amino optionally having a substituent.

[10]

The compound according to any of [1] to [9] or a salt thereof, or a solvate thereof, wherein Y is a group represented by the following formula (3):

[Formula 6]

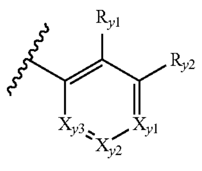

(3)

wherein the wavy line represents a binding point of Y, $X_{y1}$ is $CR_{y3}$ or N, $X_{y2}$ is $CR_{y4}$ or N, $X_{y3}$ is $CR_{y5}$ or N, $R_{y1}$ and $R_{y5}$ are each independently selected from the group consisting of hydrogen, halogen, cyano and $C_1$-$C_3$ alkyl, $R_{y2}$ and $R_{y4}$ are each independently selected from the group consisting of hydrogen, halogen, cyano, $C_1$-$C_3$ alkyl, $C_2$-$C_4$ alkenyl, $C_3$-$C_6$ cycloalkyl and $C_1$-$C_3$ alkoxy, $R_{y3}$ is 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent or $C_1$-$C_3$ alkyl($C_1$-$C_3$ alkoxy $C_1$-$C_2$ alkyl)amino, when $X_{y1}$ is $CR_{y3}$, a 5- or 6-membered heteroaryl ring is optionally formed together with the carbon atoms bonded to $R_{y2}$ and $R_{y3}$, when $X_{y1}$ is $CR_{y3}$ and $X_{y2}$ is $CR_{y4}$, a 5- or 6-membered heteroaryl ring is optionally formed together with the carbon atoms bonded to $R_{y3}$ and $R_{y4}$, and when $X_{y2}$ is $CR_{y4}$ and $X_{y3}$ is $CR_{y5}$, a 5- or 6-membered heteroaryl ring is optionally formed together with the carbon atoms bonded to $R_{y4}$ and $R_{y5}$.

[11]

The compound according to any of [1] to [10] or a salt thereof, or a solvate thereof, wherein the compound is a compound represented by the formula (4):

[Formula 7]

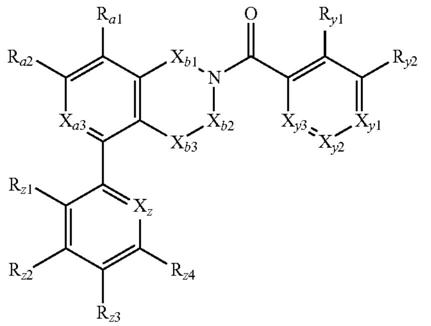

(4)

wherein $X_{a3}$ is $CR_{a3}$ or N, $R_{a1}$, $R_{a2}$, and Ra are each independently selected from the group consisting of hydrogen, halogen and $C_1$-$C_6$ alkoxy, each of $X_{b1}$ and $X_{b2}$ is $CH_2$, and $X_{b3}$ is O;

each of $X_{b1}$ and $X_{b3}$ is $CH_2$, and $X_{b2}$ is O;

each of $X_{b1}$ and $X_{b2}$ is $CH_2$, and $X_{b3}$ is S;

$X_{b1}$ is $CH_2$, $X_{b2}$ is NH, and $X_{b3}$ is C═O;

each of $X_{b1}$ and $X_{b2}$ is $CH_2$, and $X_{b3}$ is NH;

$X_{b1}$ is $CH_2$, $X_{b2}$ is C═O, and $X_{b3}$ is NH;

each of $X_{b1}$ and $X_{b3}$ is $CH_2$, and $X_{b2}$ is NH; or each of $X_{b1}$, $X_{b2}$ and $X_{b3}$ is $CH_2$, $X_{y1}$ is $CR_{y3}$ or N, $X_{y2}$ is $CR_{y4}$ or N, $X_{y3}$ is $CR_{y5}$ or N, $R_{y1}$ and $R_{y5}$ are each independently selected from the group consisting of hydrogen, halogen, cyano and $C_1$-$C_3$ alkyl, $R_{y2}$ and $R_{y4}$ are each independently selected from the group consisting of hydrogen, halogen, cyano, $C_1$-$C_3$ alkyl, $C_2$-$C_4$ alkenyl, $C_3$-$C_6$ cycloalkyl and $C_1$-$C_3$ alkoxy, $R_{y3}$ is selected from the group consisting of 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy, $C_1$-$C_4$ alkylamino $C_1$-$C_3$ alkoxy, 5- or 6-membered heteroaryloxy, $C_1$-$C_4$ alkylthio, 5- or 6-membered saturated heterocyclic ring having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent and $C_1$-$C_3$ alkyl($C_1$-$C_3$ alkoxy $C_1$-$C_2$ alkyl)amino, when $X_{y1}$ is $CR_{y3}$, a 5- or 6-membered heteroaryl ring is optionally formed together with the carbon atoms bonded to $R_{y2}$ and $R_{y3}$, when $X_{y1}$ is $CR_{y3}$ and $X_{y2}$ is $CR_{y4}$, a 5- or 6-membered heteroaryl ring is optionally formed together with the carbon atoms bonded to $R_{y3}$ and $R_{y4}$, when $X_{y2}$ is $CR_{y4}$ and $X_{y3}$ is $CR_{y5}$, a 5- or 6-membered heteroaryl ring is optionally formed together with the carbon atoms bonded to $R_{y4}$ and $R_{y5}$, $R_{z3}$ is a group selected from the following substituent group B:

[Formula 8]

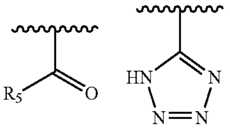

wherein the wavy line represents a binding point with the ring bonded to $R_{z3}$ and $R_{z3}$, and $R_5$ is hydroxy, $C_1$-$C_6$ alkoxy, mono-$C_1$-$C_6$ alkylamino or $C_1$-$C_6$ alkylsulfonylamino, $X_z$ is $CR_{z5}$ or N, $R_{z1}$, $R_{z2}$ and $R_{z5}$ are each independently selected from the group consisting of hydrogen, halogen and $C_1$-$C_6$ alkyl, and $R_{z4}$ is $C_1$-$C_6$ alkyl(5- to 10-membered heteroaryl $C_1$-$C_2$ alkyl)amino optionally having a substituent, $C_1$-$C_6$ alkyl(4- to 10-membered heterocyclyl)amino optionally having a substituent or 4- to 8-membered cyclic amino optionally having a substituent.

[12]

The compound according to any of [1] to [11] or a salt thereof, or a solvate thereof, wherein each of $X_{b1}$ and $X_{b2}$ is $CH_2$, and $X_{b3}$ is O.

[13]

The compound according to any of [1] to [12] or a salt thereof, or a solvate thereof, wherein $R_5$ is hydroxy or $C_1$-$C_6$ alkylsulfonylamino.

[14]

The compound according to any of [1] to [13] or a salt thereof, or a solvate thereof, wherein $X_z$ is $CR_{z5}$, and $R_{z1}$, $R_{z2}$ and $R_{z5}$ are each independently selected from the group consisting of hydrogen, fluorine, chlorine, methyl and ethyl.

[15]

The compound according to any of [1] to [14] or a salt thereof, or a solvate thereof, wherein $R_{z4}$ is 4- to 6-membered cyclic amino optionally having one or more substituents selected from the group consisting of hydrogen, halogen, $C_1$-$C_6$ alkyl and $C_1$-$C_6$ alkoxy, or is 4- to 6-membered cyclic amino having a cross-linking group selected from the group consisting of $C_1$-$C_2$ alkylene and $C_1$-$C_2$ alkylene containing one oxygen atom on a ring.

[16]

The compound according to any of [1] to [14] or a salt thereof, or a solvate thereof, wherein $R_{z4}$ is $C_1$-$C_3$ alkyl(5- or 6-membered heteroaryl $C_1$-$C_2$ alkyl)amino optionally having a substituent selected from the group consisting of hydrogen, halogen and $C_1$-$C_6$ alkyl, or is $C_1$-$C_3$ alkyl(4- to 6-membered heterocyclyl)amino optionally having a substituent selected from the group consisting of hydrogen, halogen and $C_1$-$C_6$ alkyl.

[17]

The compound according to any of [1] to [16] or a salt thereof, or a solvate thereof, wherein $R_{y1}$ is chlorine, $X_{y1}$ is $CR_{y3}$, $X_{y2}$ is $CR_{y4}$, $X_{y3}$ is $CR_{y5}$, $R_{y3}$ is a 4- to 10-membered saturated heterocyclic group having a bond in a nitrogen atom on a ring and optionally having a substituent or 5- to 10-membered heteroaryl optionally having a substituent, and each of $R_{y2}$, $R_{y4}$ and $R_{y5}$ is hydrogen.

[18]

The compound according to any of [1] to [17] or a salt thereof, or a solvate thereof, wherein $R_{a1}$ is hydrogen or fluorine, $R_{a2}$ is hydrogen or methoxy, and $R_{a3}$ is hydrogen or fluorine.

[19]

The compound according to any of [1] to [18] or a salt thereof, or a solvate thereof, wherein $R_{z4}$ is 3-oxa-8-azabicyclo[3.2.1]octan-8-yl, morpholin-4-yl, 8-oxa-3-azabicyclo[3.2.1]octan-3-yl, (2S,3S)-3-methoxy-2-methylazetidin-1-yl, 1,3,3a,4,6,6a-hexahydrofuro[3,4-c]pyrrol-5-yl, 4,4-difluoropiperidin-1-yl, pyrrolidin-1-yl, piperidin-1-yl, methyl(1,2-oxazol-3-ylmethyl)amino, methyl(oxetan-3-yl)amino, methyl-[(3R)-oxolan-3-yl]amino or methyl-(3-methyloxetan-3-yl)amino.

[20]

The compound according to any of [1] to [19] or a salt thereof, or a solvate thereof, wherein $R_{y3}$ is 1-methylpyrazol-4-yl, 7,7-dimethyl-5,9-dioxa-2-azaspiro[3.5]nonan-2-yl, 4-methylpiperazin-1-yl, (2R)-2,4-dimethylpiperazin-1-yl, 6-methoxy-2-azaspiro[3.3]heptan-2-yl, 4-(2-methoxyethyl)piperazin-1-yl, 3-methoxyazetidin-1-yl, 4-(oxetan-3-yl)piperazin-1-yl, 2-oxa-6-azaspiro[3.3]heptan-6-yl, (2R,5R)-2,4,5-trimethylpiperazin-1-yl, 4-(2-hydroxy-2-methylpropyl)piperazin-1-yl or morpholin-4-yl.

[21]

A compound selected from the following compounds or a salt thereof, or a solvate thereof: compound 17-1, compound 17-2, compound 17-3, compound 17-4, compound 17-5, compound 17-8, compound 17-9, compound 17-10, compound 17-15, compound 17-16, compound 17-23, compound 1-1, compound 1-2, compound 1-3, compound 1-4, compound 1-5, compound 1-6, compound 1-7, compound 1-8, compound 1-9, compound 1-10, compound 1-11, compound 1-12, compound 1-13, compound 1-14, compound 1-15, compound 1-16, compound 1-17, compound 1-18, compound 1-19, compound 1-20, compound 1-21, compound 1-22, compound 1-23, compound 1-24, compound 1-25, compound 1-26, compound 1-27, compound 1-30, compound 1-31, compound 1-32, compound 1-33, compound 1-34, compound 1-35, compound 1-36, compound 1-37, compound 1-38, compound 1-39, compound 1-40, compound 1-41, compound 1-42, compound 1-43, compound 1-44, compound 1-45, compound 1-46, compound 1-47, compound 1-48, compound 1-49, compound 1-50, compound 1-51, compound 1-52, compound 1-53, compound 1-54, compound 1-55, compound 1-56, compound 1-57, compound 1-58, compound 1-59, compound 1-60, compound 1-61, compound 1-62, compound 1-63, compound 1-64, compound 1-65, compound 1-66, compound 1-67, compound 1-68, compound 1-69, compound 1-70, compound 1-71, compound 1-72, compound 1-73, compound 1-74, compound 1-75, compound 1-76, compound 1-77, compound 1-78, compound 1-79, compound 1-80, compound 1-81, compound 1-82, compound 1-83, compound 1-84, compound 1-85, compound 1-86, compound 1-87, compound 1-88, compound 2-1, compound 2-2, compound 2-3, compound 2-4, compound 2-5, compound 2-6, compound 3-1, compound 3-2, compound 3-3, compound 3-4, compound 3-5, compound 3-6, compound 3-7, compound 3-8, compound 3-9, compound 3-10, compound 3-11, compound 3-12, compound 3-13, compound 3-14, compound 3-15, compound 3-16, compound 3-17, compound 3-18, compound 3-19, compound 3-20, compound 3-21, compound 3-22, compound 3-23, compound 3-24, compound 3-25, compound 3-26, compound 3-27, compound 3-28, compound 4-1, compound 4-2, compound 4-3, compound 4-4, compound 4-5, compound 4-6, compound 4-7, compound 4-8, compound 4-9, compound 4-10, compound 4-11, compound 4-12, compound 4-13, compound 4-14, compound 4-15, compound 4-16, compound 4-17, compound 4-18, compound 4-19, compound 4-20, compound 4-21, compound 4-22, compound 4-23, compound 4-24, compound 4-25, compound 4-26, compound 4-27, compound 4-28, compound 4-29, compound 4-30, compound 4-31, compound 4-32, compound 4-33, compound 4-34, compound 4-35, compound 4-36, compound 4-37, compound 4-38, compound 4-39, compound 4-40, compound 4-41, compound 4-42, compound 4-43, compound 4-44, compound 4-45, compound 4-46, compound 4-47, compound 4-48, compound 4-49, compound 4-50, compound 4-51, compound 4-52, compound 4-53, compound 4-54, compound 4-55, compound 4-56, compound 4-57, compound 4-58, compound 4-59, compound 4-60, compound 5-1, compound 5-2, compound 5-3, compound 5-4, compound 5-5, compound 5-6, compound 5-7, compound 5-8, compound 5-9, compound 5-10, compound 5-11, compound 5-12, compound 5-13, compound 5-14, compound 5-15, compound 5-16, compound 6-1, compound 6-2, compound 6-3, compound 6-4, compound 6-5, compound 6-6, compound 6-7, compound 6-8, compound 6-9, compound 6-10, compound 6-11, compound 6-12, compound 6-13, compound 7-1, compound 7-2, compound 7-3, compound 7-4, compound 7-5, compound 7-6, compound 7-7, compound 7-8, compound 7-9, compound 7-10, compound 7-11, compound 7-12, compound 7-13, compound 7-14, compound 7-15, compound 7-16, compound 7-17, compound 7-18, compound 8-1, compound 8-2, compound 8-3, compound 8-4, compound 8-5, compound 8-6, compound 8-7, compound 8-8, compound 8-9, compound 9-1, compound 9-2, compound 9-3, compound 9-4, compound 9-5, compound 9-6, compound 9-7, compound 9-8, compound 9-9, compound 9-10, compound 9-11, compound 9-12, compound 9-13, compound 9-14, compound 9-15, compound 9-16, compound 9-17, compound 9-18, compound 9-19, compound 9-20, compound 9-21, compound 9-22, compound 9-23, compound 9-24, compound 9-25, compound 10-1, compound 10-2, compound 10-3, compound 10-4, compound 10-5, compound 10-6, compound 10-7, compound 10-8, compound 10-9, compound 10-10, compound 10-11, compound 10-12, compound 10-13, compound 11-1, compound 11-2, compound 11-3, compound 11-4, compound 11-5, compound 11-6, compound 11-7, compound 11-8, compound 11-9, compound 11-10, compound 12-1, compound 12-2, compound 12-3, compound 12-4, compound 13-1, compound 13-2, compound 13-3, compound 13-4, compound 13-5, compound 13-6, compound 13-7, compound 13-8, compound 13-9, compound 13-10, compound 13-11, compound 13-12, compound 13-13, compound 13-14, compound 13-15, compound 13-16, compound 13-17, compound 13-18, compound 13-19, compound 13-20, compound 13-21, compound 14-1, compound 14-2, compound 14-3, compound 14-4, compound 14-5, compound 14-6, compound 14-7, compound 14-8, compound 14-9, compound 15-1, compound 15-2, compound 15-3, compound 15-4, compound 16-1, compound 16-2, compound 16-3, compound 16-4, compound 16-5, compound 16-6, compound 16-7, compound 16-8, compound 16-9, compound 16-10, compound 16-11, compound 16-12, compound 16-13, compound 16-14, compound 16-15, compound 16-16, compound 16-17, compound 17-18, compound 17-21, compound 18-1, compound 18-2, compound 18-3, compound 18-4, compound 18-5, compound 18-6, compound 18-7, compound 18-8, compound 18-9, compound 18-10, compound 18-11, compound 18-12, compound 19-2, compound 19-3, compound 19-4, compound 19-5, compound 19-6, compound 19-7, compound 19-8, compound 19-9, compound 19-10, compound 19-11, compound 19-12, compound 19-13, compound 19-14, compound 19-15, compound 19-16, compound 19-17, compound 19-18, and compound 19-19.

[22]

A compound selected from the following compounds or a salt thereof, or a solvate thereof:

compound 1-4, compound 1-18, compound 1-21, compound 1-33, compound 1-54, compound 1-83, compound 1-88, compound 2-2, compound 4-8, compound 4-37, compound 5-1, compound 5-2, compound 5-7, compound 5-9, compound 5-10, compound 5-16, compound 7-2, compound 13-16, compound 13-21, compound 14-1, compound 19-9, and compound 19-15.

[23]

A pharmaceutical composition comprising a compound according to any of [1] to [22] or a salt thereof, or a solvate thereof.

[24]

The pharmaceutical composition according to [23] for the prevention and/or treatment of neurodegenerative disease, lung disease, or kidney disease.

[25]

A method for preventing and/or treating neurodegenerative disease, lung disease, or kidney disease, comprising administering an effective amount of a compound according to any of [1] to [22] or a salt thereof, or a solvate thereof to a subject.

[26]

The compound according to any of [1] to [22] or a salt thereof, or a solvate thereof for use in the prevention and/or treatment of neurodegenerative disease, lung disease, or kidney disease.

[27]

Use of a compound according to any of [1] to [22] or a salt thereof, or a solvate thereof for producing a pharmaceutical composition for the prevention and/or treatment of neurodegenerative disease, lung disease, or kidney disease.

[28]

4-[3-[2,6-Dichloro-4-[(2R,3R)-3-methoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[29]

4-[3-[2,6-Dichloro-4-(7-oxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[30]

4-[3-[2,6-Dichloro-4-[6-(difluoromethoxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[31]

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[32]

4-[3-[2,6-Dichloro-4-[4-(2-methoxyethyl)piperazin-1-yl]benzoyl]-2,4-dihydro-1,3-benzoxazin-8-yl]-5-fluoro-2-morpholin-4-ylbenzoic acid or a salt thereof, or a solvate thereof.

[33]

4-[3-[2,6-Dichloro-4-(6-methoxy-2-azaspiro[3.3]heptan-2-yl)benzoyl]-2,4-dihydro-1,3-benzoxazin-8-yl]-2-(3-oxa-8-azabicyclo[3.2.1]octan-8-yl)benzoic acid or a salt thereof, or a solvate thereof.

[34]

4-[3-[2-Chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[35]

4-[3-[2,6-Dichloro-4-(6-methoxypyridin-3-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[36]

4-[3-[2,6-Dichloro-4-(4-ethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[37]

4-[3-[2,6-Dichloro-4-(2-methoxyethoxy)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[38]

4-[3-[2,6-Dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[39]

4-[3-[2,6-Dichloro-4-(5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[40]

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[41]

4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[42]

4-[3-[2,6-Dichloro-4-(7,11-dioxa-2-azadispiro[3.1.56.14]dodecan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[43]

4-[3-[2,6-Dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoic acid or a salt thereof, or a solvate thereof.

[44]

4-[3-[2,6-Dichloro-4-[6-(2,2-difluoroethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[44]

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[45]

4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[46]

4-[3-[2,6-Dichloro-4-(1-methylpyrazol-4-yl)benzoyl]-2,4-dihydro-1,3-benzoxazin-8-yl]-2-morpholin-4-ylbenzoic acid or a salt thereof, or a solvate thereof.

[47]

4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[48]

4-[3-[5-Chloro-7-(6-methoxy-2-azaspiro[3.3]heptan-2-yl)-2,3-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid or a salt thereof, or a solvate thereof.

[49]

4-[3-[2,6-Dichloro-4-[(2R,3R)-3-methoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid.

[50]

4-[3-[2,6-Dichloro-4-(7-oxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[51]

4-[3-[2,6-Dichloro-4-[6-(difluoromethoxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid.

[52]

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

[53]

4-[3-[2,6-Dichloro-4-[4-(2-methoxyethyl)piperazin-1-yl]benzoyl]-2,4-dihydro-1,3-benzoxazin-8-yl]-5-fluoro-2-morpholin-4-ylbenzoic acid.

[54]

4-[3-[2,6-Dichloro-4-(6-methoxy-2-azaspiro[3.3]heptan-2-yl)benzoyl]-2,4-dihydro-1,3-benzoxazin-8-yl]-2-(3-oxa-8-azabicyclo[3.2.1]octan-8-yl)benzoic acid.

[55]

4-[3-[2-Chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

[56]

4-[3-[2,6-Dichloro-4-(6-methoxypyridin-3-yl)benzoyl]-2,4-dihydro-1,3-benzoxazin-8-yl]-5-fluoro-2-(3-oxa-8-azabicyclo[3.2.1]octan-8-yl)benzoic acid.

[57]

4-[3-[2,6-Dichloro-4-(4-ethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid.

[58]

4-[3-[2,6-Dichloro-4-(2-methoxyethoxy)benzoyl]-2,4-dihydro-1,3-benzoxazin-8-yl]-5-fluoro-2-(3-oxa-8-azabicyclo[3.2.1]octan-8-yl)benzoic acid.

[59]

4-[3-[2,6-Dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid.

[60]

4-[3-[2,6-Dichloro-4-(5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[61]

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[62]

4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[63]

4-[3-[2,6-Dichloro-4-(7,11-dioxa-2-azadispiro[3.1.56.14]dodecan-2-yl)benzoyl]-2,4-dihydro-1,3-benzoxazin-8-yl]-5-fluoro-2-(3-oxa-8-azabicyclo[3.2.1]octan-8-yl)benzoic acid.

[64]

4-[3-[2,6-Dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoic acid.

[65]

4-[3-[2,6-Dichloro-4-[6-(2,2-difluoroethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid.

[66]

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

[67]

4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

[68]

4-[3-[2,6-Dichloro-4-(1-methylpyrazol-4-yl)benzoyl]-2,4-dihydro-1,3-benzoxazin-8-yl]-2-morpholin-4-ylbenzoic acid.

[69]

4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

[70]

4-[3-[5-Chloro-7-(6-methoxy-2-azaspiro[3.3]heptan-2-yl)-2,3-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid.

[71]

A hydrate of 4-[3-[2,6-dichloro-4-[(2R,3R)-3-methoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid.

[72]

A hydrate of 4-[3-[2,6-dichloro-4-(7-oxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[73]

A hydrate of 4-[3-[2,6-dichloro-4-[6-(difluoromethoxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid.

[74]

A hydrate of 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

[75]

A hydrate of 4-[3-[2,6-dichloro-4-[4-(2-methoxyethyl)piperazin-1-yl]benzoyl]-2,4-dihydro-1,3-benzoxazin-8-yl]-5-fluoro-2-morpholin-4-ylbenzoic acid.

[76]

A hydrate of 4-[3-[2,6-dichloro-4-(6-methoxy-2-azaspiro[3.3]heptan-2-yl)benzoyl]-2,4-dihydro-1,3-benzoxazin-8-yl]-2-(3-oxa-8-azabicyclo[3.2.1]octan-8-yl)benzoic acid.

[77]

A hydrate of 4-[3-[2-chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

[78]

A hydrate of 4-[3-[2,6-dichloro-4-(6-methoxypyridin-3-yl)benzoyl]-2,4-dihydro-1,3-benzoxazin-8-yl]-5-fluoro-2-(3-oxa-8-azabicyclo[3.2.1]octan-8-yl)benzoic acid.

[79]

A hydrate of 4-[3-[2,6-dichloro-4-(4-ethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid.

[80]

A hydrate of 4-[3-[2,6-dichloro-4-(2-methoxyethoxy)benzoyl]-2,4-dihydro-1,3-benzoxazin-8-yl]-5-fluoro-2-(3-oxa-8-azabicyclo[3.2.1]octan-8-yl)benzoic acid.

[81]

A hydrate of 4-[3-[2,6-dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid.

[82]

A hydrate of 4-[3-[2,6-dichloro-4-(5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[83]

A hydrate of 4-[3-[2,6-dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[84]

A hydrate of 4-[3-[2,6-dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

[85]

A hydrate of 4-[3-[2,6-dichloro-4-(7,11-dioxa-2-azadispiro[3.1.56.14]dodecan-2-yl)benzoyl]-2,4-dihydro-1,3-benzoxazin-8-yl]-5-fluoro-2-(3-oxa-8-azabicyclo[3.2.1]octan-8-yl)benzoic acid.

[86]

A hydrate of 4-[3-[2,6-dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoic acid.

[87]

A hydrate of 4-[3-[2,6-dichloro-4-[6-(2,2-difluoroethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid.

[88]

A hydrate of 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

[89]

A hydrate of 4-[3-[2-chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

[90]

A hydrate of 4-[3-[2,6-dichloro-4-(1-methylpyrazol-4-yl)benzoyl]-2,4-dihydro-1,3-benzoxazin-8-yl]-2-morpholin-4-ylbenzoic acid.

[91]

A hydrate of 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

[92]

A hydrate of 4-[3-[5-chloro-7-(6-methoxy-2-azaspiro[3.3]heptan-2-yl)-2,3-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid.

Advantageous Effects of Invention

The compound according to the present invention or a pharmacologically acceptable salt thereof or a solvate of the compound or the salt has a Nrf2-activating effect and provides a prophylactic agent or a therapeutic agent for various diseases, for example, neurodegenerative disease, lung disease, and kidney disease.

DESCRIPTION OF EMBODIMENTS

Hereinafter, the present invention will be described in detail with reference to the definition of symbols, terms, and the like described in the present specification, the mode for carrying out the present invention, etc.

In the present specification, examples of the "halogen" include F, Cl, Br and I.

In the present specification, the "alkyl" is a monovalent group derived from aliphatic hydrocarbon by the removal of one arbitrary hydrogen atom, and has a subset of a hydrocarbyl or hydrocarbon group structure that contains neither a heteroatom (which refers to an atom other than carbon and hydrogen atoms) nor an unsaturated carbon-carbon bond in the skeleton and contains hydrogen and carbon atoms. The alkyl includes not only a linear form but a branched form. The alkyl is preferably alkyl having 1 to 20 carbon atoms ($C_1$-$C_{20}$; hereinafter, the term "$C_p$-$C_q$" means that the number of carbon atoms is p to q), more preferably $C_1$-$C_{10}$ alkyl, further preferably $C_1$-$C_6$ alkyl. Specifically, examples thereof include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

In the present specification, the “alkenyl” is a monovalent group having at least one double bond (two adjacent $sp^2$ carbon atoms). Depending on the configuration of the double bond and a substituent (if present), the geometric form of the double bond can assume entgegen (E) or zusammen (Z), cis or trans configuration. The alkenyl includes not only a linear form but a branched form. The alkenyl is preferably $C_2$-$C_{10}$ alkenyl, more preferably $C_2$-$C_6$ alkenyl. Specifically, examples thereof include vinyl, allyl, 1-propenyl, 2-propenyl, 1-butenyl, 2-butenyl (including cis and trans), 3-butenyl, pentenyl, 3-methyl-2-butenyl, and hexenyl.

In the present specification, the “alkynyl” is a monovalent group having at least one triple bond (two adjacent SP carbon atoms). The alkynyl includes not only a linear form but a branched form. The alkynyl is preferably $C_2$-$C_{10}$ alkynyl, more preferably $C_2$-$C_6$ alkynyl. Specifically, examples thereof include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

In the present specification, the “cycloalkyl” means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl. Specifically, examples thereof include cyclopropyl, cyclobutyl, cyclopentyl, cyclohexyl, cycloheptyl, cyclooctyl, bicyclo[2.2.1]heptyl, and spiro[3.3]heptyl.

In the present specification, the “cycloalkylalkyl” means a group in which one or more hydrogen atoms of the “alkyl” defined above are replaced with the “cycloalkyl” defined above. The cycloalkylalkyl is preferably $C_3$-$C_5$ cycloalkyl $C_1$-$C_6$ alkyl, more preferably $C_3$-$C_6$ cycloalkyl $C_1$-$C_2$ alkyl. Specifically, examples of the cycloalkylalkyl include cyclopropylmethyl, cyclobutylmethyl, cyclopentylmethyl, and cyclohexylmethyl.

In the present specification, the “aminoalkyl” means a group in which one or more hydrogen atoms of the “alkyl” defined above are replaced with “amino” defined below. The aminoalkyl is preferably amino $C_1$-$C_6$ alkyl. Specifically, examples of the aminoalkyl include 1-pyridylmethyl, 2-(1-piperidyl)ethyl, 3-(1-piperidyl)propyl, and 4-aminobutyl.

In the present specification, the “protected aminoalkyl” means a group in which an amino group contained in the “aminoalkyl” defined above is protected with an arbitrary protective group. Specifically, examples of the protective group for the amino group include Fmoc, Boc, Cbz, Alloc, Teoc, trifluoroacetyl, pentafluoropropionyl, phthaloyl, tosyl, 2-nitrobenzenesulfonyl, 4-nitrobenzenesulfonyl, and 2,4-dinitrobenzenesulfonyl.

In the present specification, the “hydroxyalkyl” means a group in which one or more hydrogen atoms of the “alkyl” defined above are replaced with a hydroxy group. The hydroxyalkyl is preferably hydroxy $C_1$-$C_6$ alkyl. Specifically, examples of the hydroxyalkyl include hydroxymethyl, 1-hydroxyethyl, 2-hydroxyethyl, 2-hydroxy-2-methylpropyl, and 5-hydroxypentyl.

In the present specification, the “haloalkyl” means a group in which one or more hydrogen atoms of the “alkyl” defined above are replaced with halogen. The haloalkyl is preferably halo $C_1$-$C_6$ alkyl, more preferably $C_1$-$C_6$ fluoroalkyl. Specifically, examples of the haloalkyl include difluoromethyl, trifluoromethyl, 2,2-difluoroethyl, 2,2,2-trifluoroethyl, 3,3-difluoropropyl, 4,4-difluorobutyl, and 5,5-difluoropentyl.

In the present specification, the “carboxyalkyl” means a group in which one or more hydrogen atoms of the “alkyl” defined above are replaced with carboxy. The carboxyalkyl is preferably carboxy $C_1$-$C_6$ alkyl. Specifically, examples of the carboxyalkyl include carboxymethyl.

In the present specification, the “aryl” means a monovalent aromatic hydrocarbon ring and an aromatic hydrocarbon ring group. The aryl is preferably $C_6$-$C_{10}$ aryl. Specifically, examples thereof include phenyl and naphthyl (e.g., 1-naphthyl and 2-naphthyl).

In the present specification, the “heterocyclyl” means a non-aromatic cyclic monovalent group containing a carbon atom as well as 1 to 5 heteroatoms. The heterocyclyl may have a double and/or triple bond in a ring, and a carbon atom in a ring may be oxidized to form carbonyl. The heterocyclyl may be a monocyclic ring or may be a condensed ring. In the case of a condensed ring, the condensed ring may be formed with an aromatic ring such as a benzene ring, a pyridine ring, or a pyrimidine ring. The condensed ring may be formed with a saturated alicyclic ring such as a cyclopentane ring or a cyclohexane ring, or a saturated heterocyclic ring such as a tetrahydropyran ring, a dioxane ring, or a pyrrolidine ring. The number of atoms constituting the ring of the heterocyclyl is preferably 4 to 10 (4- to 10-membered heterocyclyl), more preferably 4 to 7 (4- to 7-membered heterocyclyl). Specifically, examples of the heterocyclyl include azetidinyl, oxoazetidinyl, oxiranyl, oxetanyl, azetidinyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, oxopyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, oxazolidonyl, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, 2,4,5-trimethylpiperazin-1-yl, sultam, 2-oxaspiro[3.3]heptyl, 6,7-dihydro-pyrrolo[1,2-a]imidazolyl, 4,5,6,7-tetrahydropyrazolo[1,5-a]pyrazinyl, azepanyl, dioxepanyl, and 5,9-dioxaspiro[3.5]nonanyl.

In the present specification, the “heteroaryl” means an aromatic cyclic monovalent group and an aromatic heterocyclic group containing a carbon atom as well as 1 to 5 heteroatoms. The ring may be a monocyclic ring or may be a condensed ring with another ring, and may be partially saturated. The number of atoms constituting the ring of the heteroaryl is preferably 5 to 10 (5- to 10-membered heteroaryl), more preferably 5 to 7 (5- to 7-membered heteroaryl). Specifically, examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, benzodioxolyl, indolizinyl, imidazopyridyl, pyrazolopyridyl, imidazopyridyl, triazolopyridyl, pyrrolopyrazinyl, and furopyridyl.

In the present specification, the "aralkyl (arylalkyl)" means a group in which at least one hydrogen atom of the "alkyl" defined above is replaced with the "aryl" defined above. The aralkyl is preferably $C_7$-$C_{14}$ aralkyl, more preferably $C_7$-$C_{10}$ aralkyl. Specifically, examples of the aralkyl include benzyl, phenethyl, and 3-phenylpropyl.

In the present specification, the "heteroarylalkyl" means a group in which at least one hydrogen atom of the "alkyl" defined above is replaced with the "heteroaryl" defined above. The heteroarylalkyl is preferably 5- to 10-membered heteroaryl $C_1$-$C_6$ alkyl, more preferably 5- to 10-membered heteroaryl $C_1$-$C_2$ alkyl. Specifically, examples of the heteroarylalkyl include 3-thienylmethyl, 4-thiazolylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

In the present specification, the "heterocyclylalkyl" means a group in which one or more hydrogen atoms of the "alkyl" defined above are replaced with the "heterocyclyl" defined above. The heterocyclylalkyl is preferably 4- to 7-membered heterocyclyl $C_1$-$C_6$ alkyl, more preferably 4- to 7-membered heterocyclyl $C_1$-$C_2$ alkyl. Specifically, examples of the heterocyclylalkyl include 2-(tetrahydro-2H-pyran-4-yl)ethyl, 2-(azetidin-3-yl)ethyl, and 4-(oxolan-2-yl-methyl)piperazin-1-yl.

In the present specification, the "saturated heterocyclic group" means a non-aromatic cyclic monovalent group containing a carbon atom as well as 1 to 5 heteroatoms. The saturated heterocyclic group may have a double and/or triple bond in a ring, and a carbon atom in a ring may be oxidized to form carbonyl. The saturated heterocyclic group may be a monocyclic ring or may form a condensed ring with another ring, for example, an aromatic ring such as a benzene ring, a pyridine ring, or a pyrimidine ring, a saturated alicyclic ring such as a cyclopentane ring or a cyclohexane ring, or a saturated heterocyclic ring such as a tetrahydropyran ring, a dioxane ring, or a pyrrolidine ring. The saturated heterocyclic group is preferably a 4- to 10-membered saturated heterocyclic group. Specifically, examples of the saturated heterocyclic group include azetidinyl, oxoazetidinyl, oxetanyl, tetrahydrofuranyl, tetrahydropyranyl, morpholinyl, thiomorpholinyl, pyrrolidinyl, 2-oxopyrrolidinyl, 4-oxopyrrolidinyl, piperidinyl, 4-oxopiperidinyl, piperazinyl, pyrazolidinyl, imidazolidinyl, oxazolidinyl, isoxazolidinyl, thiazolidinyl, isothiazolidinyl, thiadiazolidinyl, oxazolidonyl, dioxolanyl, dioxanyl, thietanyl, octahydroindolyl, indolinyl, 5,9-dioxaspiro[3.5]nonanyl, 3-oxa-8-azabicyclo[3.2.1]octan-8-yl, morpholin-4-yl, 8-oxa-3-azabicyclo[3.2.1]octan-3-yl, 3-methoxy-2-methyl-azetidin-1-yl, 1,3,3a,4,6,6a-hexahydrofuro[3,4-c]pyrrol-5-yl, 4,4-difluoropiperidin-1-yl, pyrrolidin-1-yl, piperidin-1-yl, 1-methylpyrazol-4-yl, 7,7-dimethyl-5,9-dioxa-2-azaspiro[3.5]nonan-2-yl, 4-methylpiperazin-1-yl, 2,4-dimethylpiperazin-1-yl, 6-methoxy-2-azaspiro[3.3]heptan-2-yl, 4-(2-methoxyethyl)piperazin-1-yl, 3-methoxyazetidin-1-yl, 4-(oxetan-3-yl)piperazin-1-yl, 2-oxa-6-azaspiro[3.3]heptan-6-yl, 2,4,5-trimethylpiperazin-1-yl, and 4-(2-hydroxy-2-methylpropyl)piperazin-1-yl.

In the present specification, the "alkoxy" means an oxy group bonded to the "alkyl" defined above. The alkoxy is preferably $C_1$-$C_6$ alkoxy. Specifically, examples of the alkoxy include methoxy, ethoxy, 1-propoxy, 2-propoxy, n-butoxy, i-butoxy, s-butoxy, t-butoxy, pentyloxy, and 3-methylbutoxy.

In the present specification, the "haloalkoxy" means a group in which one or more hydrogen atoms of the "alkoxy" defined above are replaced with halogen. The haloalkoxy is preferably $C_1$-$C_6$ haloalkoxy, more preferably $C_1$-$C_6$ fluoroalkoxy. Specifically, examples of the haloalkoxy include difluoromethoxy, trifluoromethoxy, 2,2-difluoroethoxy, and 2,2,2-trifluoroethoxy.

In the present specification, the "cycloalkoxy" means an oxy group bonded to the "cycloalkyl" defined above. The cycloalkoxy is preferably $C_3$-$C_8$ cycloalkoxy. Specifically, examples of the cycloalkoxy include cyclopropoxy, cyclobutoxy, and cyclopentyloxy.

In the present specification, the "alkoxyalkyl" means a group in which one or more hydrogen atoms of the "alkyl" defined above are replaced with the "alkoxy" defined above. The alkoxyalkyl is preferably $C_1$-$C_6$ alkoxy $C_1$-$C_6$ alkyl, more preferably $C_1$-$C_6$ alkoxy $C_1$-$C_2$ alkyl. Specifically, examples of the alkoxyalkyl include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, and 2-ethoxyethyl.

In the present specification, the "cycloalkoxyalkyl" means a group in which one or more hydrogen atoms of the "alkyl" defined above are replaced with the "cycloalkoxy" defined above. The cycloalkoxyalkyl is preferably $C_3$-$C_8$ cycloalkoxy $C_1$-$C_6$ alkyl, more preferably $C_3$-$C_6$ cycloalkoxy $C_1$-$C_2$ alkyl. Specifically, examples of the cycloalkoxyalkyl include cyclopropoxymethyl and cyclobutoxymethyl.

In the present specification, the "aryloxy" means an oxy group bonded to the "aryl" defined above. The aryloxy is preferably $C_6$-$C_{10}$ aryloxy. Specifically, examples of the aryloxy include phenoxy, 1-naphthyloxy, and 2-naphthyloxy.

In the present specification, the "heterocyclyloxy" means an oxy group bonded to the "heterocyclyl" defined above. The number of atoms constituting the ring of the heterocyclyloxy is preferably 4 to 10 (4- to 10-membered heterocyclyloxy), more preferably 4 to 7 (4- to 7-membered heterocyclyloxy). Specifically, examples of the heterocyclyloxy include azetidinyloxy, oxiranyloxy, oxetanyloxy, azetidinyloxy, dihydrofuryloxy, tetrahydrofuryloxy, dihydropyranyloxy, tetrahydropyranyloxy, tetrahydropyridyloxy, tetrahydropyrimidyloxy, morpholinyloxy, thiomorpholinyloxy, pyrrolidinyloxy, piperidinyloxy, piperazinyloxy, pyrazolidinyloxy, imidazolinyloxy, imidazolidinyloxy, oxazolidinyloxy, isoxazolidinyloxy, thiazolidinyloxy, isothiazolidinyloxy, 1,2-thiazinaneoxy, thiadiazolidinyloxy, oxazolidoneoxy, benzodioxanyloxy, benzoxazolyloxy, dioxolanyloxy, dioxanyloxy, tetrahydropyrrolo[1,2-c]imidazoleoxy, thietanyloxy, 3,6-diazabicyclo[3.1.1]heptanyloxy, 2,5-diazabicyclo[2.2.1]heptanyloxy, 3-oxa-8-azabicyclo[3.2.1]octanyloxy, sultamoxy, and 2-oxaspiro[3.3]heptyloxy.

In the present specification, the "heteroaryloxy" means an oxy group bonded to the "heteroaryl" defined above. The number of atoms constituting the ring of the heteroaryloxy is preferably 5 to 10 (5- to 10-membered heteroaryloxy), more preferably 5 to 7 (5- to 7-membered heteroaryloxy). Specifically, examples of the heteroaryloxy include furyloxy, thienyloxy, pyrrolyloxy, imidazolyloxy, pyrazolyloxy, thiazolyloxy, isothiazolyloxy, oxazolyloxy, isoxazolyloxy, oxadiazolyloxy, thiadiazolyloxy, triazolyloxy, tetrazolyloxy, pyridyloxy, pyrimidyloxy, pyridazinyloxy, pyrazinyloxy, triazinyloxy, benzofuranyloxy, benzothienyloxy, benzothiadiazolyloxy, benzothiazolyloxy, benzoxazolyloxy, benzoxadiazolyloxy, benzimidazolyloxy, indolyloxy, isoindolyloxy, indazolyloxy, quinolyloxy, isoquinolyloxy, cinnolinyloxy, quinazolinyloxy, quinoxalinyloxy, benzodioxolyloxy, indolizinyloxy, and imidazopyridyloxy.

In the present specification, the “aralkoxy” means an oxy group bonded to the “aralkyl” defined above. The aralkoxy is preferably $C_7$-$C_{14}$ aralkoxy, more preferably $C_7$-$C_{10}$ aralkoxy. Specifically, examples of the aralkoxy include benzyloxy, phenethyloxy, and 3-phenylpropoxy.

In the present specification, the “heteroarylalkoxy” means an oxy group bonded to the “heteroarylalkyl” defined above. The heteroarylalkoxy is preferably 5- to 10-membered heteroaryl $C_1$-$C_6$ alkoxy, more preferably 5- to 10-membered heteroaryl $C_1$-$C_2$ alkoxy. Specifically, examples of the heteroarylalkoxy include 3-thienylmethoxy and 3-pyridylmethoxy.

In the present specification, the “aralkoxyalkyl” means a group in which one or more hydrogen atoms of the “alkyl” defined above are replaced with the “aralkoxy” defined above. The aralkoxyalkyl is preferably $C_7$-$C_{14}$ aralkoxy $C_1$-$C_6$ alkyl, more preferably $C_7$-$C_{14}$ aralkoxy $C_1$-$C_2$ alkyl. Specifically, examples of the aralkoxyalkyl include benzyloxymethyl and 1-(benzyloxy)ethyl.

In the present specification, the “heteroarylalkoxyalkyl” means a group in which one or more hydrogen atoms of the “alkyl” defined above are replaced with the “heteroarylalkoxy” defined above. The heteroarylalkoxyalkyl is preferably 5- to 10-membered heteroaryl $C_1$-$C_6$ alkoxy $C_1$-$C_6$ alkyl, more preferably 5- to 10-membered heteroaryl $C_1$-$C_2$ alkoxy $C_1$-$C_2$ alkyl. Specifically, examples of the heteroarylalkoxyalkyl include 3-pyridylmethoxymethyl.

In the present specification, the “heterocyclylalkoxy” means an oxy group in which the “alkyl” is bonded to the “heterocyclyl” defined above. The number of atoms constituting the ring of the heterocyclyl is preferably 4 to 10 (4- to 10-membered heterocyclyl), more preferably 4 to 7 (4- to 7-membered heterocyclyl), and the alkyl is preferably $C_1$-$C_6$ alkyl, more preferably $C_1$-$C_4$ alkyl. The heterocyclylalkoxy is preferably 4- to 10-membered heterocyclyl $C_1$-$C_6$ alkoxy, more preferably 4- to 7-membered heterocyclyl $C_1$-$C_2$ alkoxy. Specifically, examples of the heterocyclylalkoxy include oxolan-2-ylmethoxy, oxolan-3-ylmethoxy, oxan-4-ylmethoxy, 1,4-dioxan-2-ylmethoxy, (1-methylpiperidin-4-yl)methoxy, and 3-morpholin-4-ylpropoxy.

In the present specification, the “hydroxyalkoxy” means a group in which the “hydroxy” is bonded to the “alkoxy” defined above. The hydroxyalkoxy is preferably hydroxy $C_2$-$C_6$ alkoxy, more preferably hydroxy $C_3$-$C_6$ alkoxy. Specifically, examples of the hydroxyalkoxy include 3-hydroxy-3-methylbutoxy and 4-hydroxybutoxy.

In the present specification, the “alkoxyalkoxy” means a group in which the “alkoxy” is bonded to the “alkoxy” defined above. The alkoxyalkoxy is preferably $C_1$-$C_6$ alkoxy $C_1$-$C_6$ alkoxy, more preferably $C_1$-$C_3$ alkoxy $C_1$-$C_2$ alkoxy. Specifically, examples of the alkoxyalkoxy include 2-methoxyethoxy.

In the present specification, the “alkylaminoalkoxy” means a group in which the “alkylamino” is bonded to the “alkoxy” defined above. The alkylaminoalkoxy is preferably bis($C_1$-$C_6$ alkyl)amino $C_1$-$C_6$ alkoxy, more preferably bis ($C_1$-$C_4$ alkyl)amino $C_1$-$C_3$ alkoxy. Specifically, examples of the alkylaminoalkoxy include 2-(dimethylamino)ethoxy.

In the present specification, the “aryloxyalkyl” means a group in which one or more hydrogen atoms of the “alkyl” defined above are replaced with the “aryloxy” defined above. The aryloxyalkyl is preferably $C_6$-$C_{10}$ aryloxy $C_1$-$C_6$ alkyl, more preferably $C_6$-$C_{10}$ aryloxy $C_1$-$C_2$ alkyl. Specifically, examples of the aryloxyalkyl include phenoxymethyl and 2-phenoxyethyl.

In the present specification, the “amino” means $—NH_2$ in the narrow sense and means —NRR' in the broad sense. In this context, R and R' are each independently selected from hydrogen, alkyl, alkenyl, alkynyl, cycloalkyl, heterocyclyl, aryl, and heteroaryl, or R and R' form a ring together with the nitrogen atom bonded thereto. Examples of the amino preferably include $—NH_2$, mono-$C_1$-$C_6$ alkylamino, di-$C_1$-$C_6$ alkylamino, and 4- to 8-membered cyclic amino.

In the present specification, the “monoalkylamino” means a group of the “amino” defined above in which R is hydrogen, and R' is the “alkyl” defined above. The monoalkylamino is preferably mono-$C_1$-$C_6$ alkylamino. Specifically, examples of the monoalkylamino include methylamino, ethylamino, n-propylamino, i-propylamino, n-butylamino, s-butylamino, and t-butylamino.

In the present specification, the “dialkylamino” means a group of the “amino” defined above in which R and R' are each independently the “alkyl” defined above. The dialkylamino is preferably di-$C_1$-$C_6$ alkylamino. Specifically, examples of the dialkylamino include dimethylamino and diethylamino.

In the present specification, the “cyclic amino” means a group of the “amino” defined above in which R and R' form a ring together with the nitrogen atom bonded thereto. The cyclic amino is preferably 4- to 8-membered cyclic amino. Specifically, examples of the cyclic amino include 1-azetidinyl, 1-pyrrolidinyl, 1-piperidinyl, 1-piperazinyl, 4-morpholinyl, 3-oxazolidinyl, 1,1-dioxidothiomorpholinyl-4-yl, and 3-oxa-8-azabicyclo[3.2.1]octan-8-yl.

In the present specification, the “aminocarbonyl” means a carbonyl group bonded to the “amino” defined above. The aminocarbonyl is preferably $—CONH_2$, mono-$C_1$-$C_6$ alkylaminocarbonyl, di-$C_1$-$C_6$ alkylaminocarbonyl, or 4- to 8-membered cyclic aminocarbonyl. Specifically, examples of the aminocarbonyl include $—CONH_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidothiomorpholinyl-4-ylcarbonyl, and 3-oxa-8-azabicyclo[3.2.1]octan-8-ylcarbonyl.

In the present specification, the “aminocarbonylalkyl” means a group in which one or more hydrogen atoms of the “alkyl” defined above are replaced with the “aminocarbonyl” defined above. The aminocarbonylalkyl is preferably aminocarbonyl $C_1$-$C_6$ alkyl, more preferably aminocarbonyl $C_1$-$C_4$ alkyl. Specifically, examples of the aminocarbonylalkyl include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl, 2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl)propyl, and 4-(dimethylaminocarbonyl)butyl.

In the present specification, the “alkylsulfonyl” means a sulfonyl group bonded to the “alkyl” defined above. The alkylsulfonyl is preferably $C_1$-$C_6$ alkylsulfonyl. Specifically, examples of the alkylsulfonyl include methylsulfonyl and ethylsulfonyl.

In the present specification, the “alkylsulfonylamino” means a group in which sulfonyl is bonded to the “amino” defined above. Examples thereof preferably include $C_1$-$C_6$ alkylsulfonyl-NH— and ($C_1$-$C_6$ alkylsulfonyl-$)_2N$—. Specifically, examples of the aminoalkylsulfonyl include methylsulfonylamino, ethylsulfonylamino, bis(methylsulfonyl)amino, and bis(ethylsulfonyl)amino.

In the present specification, the "alkylsulfonylalkyl" means a group in which one or more hydrogen atoms of the "alkyl" defined above are replaced with the "alkylsulfonyl" defined above. The alkylsulfonylalkyl is preferably $C_1$-$C_6$ alkylsulfonyl $C_1$-$C_6$ alkyl, more preferably $C_1$-$C_6$ alkylsulfonyl $C_1$-$C_2$ alkyl. Specifically, examples of the alkylsulfonylalkyl include methylsulfonylmethyl and 2-(methylsulfonyl)ethyl.

In the present specification, the "alkylthio" means a thio group bonded to the "alkyl" defined above and is preferably $C_1$-$C_6$ alkylthio. Specifically, examples of the alkylthio include methylthio, ethylthio, 1-propylthio, 2-propylthio, n-butylthio, i-butylthio, s-butylthio, and t-butylthio.

In the present specification, the "acyl (alkanoyl)" means a group in which a carbonyl group is bonded to hydrogen or the "alkyl" described above. The acyl is preferably $C_1$-$C_6$ acyl, more preferably $C_2$-$C_4$ acyl. Specifically, examples of the acyl include formyl, acetyl, propionyl, and butanoyl.

In the present specification, the "haloacyl (haloalkanoyl)" means a group in which a carbonyl group is bonded to the "haloalkyl" described above. The haloacyl is preferably $C_2$-$C_6$ haloacyl, more preferably $C_2$-$C_4$ haloacyl. Specifically, examples of the haloacyl include trifluoroacetyl, trichloroacetyl, pentafluoropropionyl, 2,3,3,3-tetrafluoro-2-(trifluoromethyl)propionyl, and 3,3,3-trifluoro-2-(trifluoromethyl)propionyl.

In the present specification, the "alkylene" means a divalent group derived from the "alkyl" described above by the further removal of one arbitrary hydrogen atom, and is preferably $C_1$-$C_8$ alkylene, more preferably $C_4$-$C_8$ alkylene. Specifically, examples of the alkylene include $-CH_2-$, $-(CH_2)_2-$, $-(CH_2)_3-$, $-CH(CH_3)CH_2-$, $-C(CH_3)_2-$, $-(CH_2)_4-$, $-CH(CH_3)CH_2CH_2-$, $-C(CH_3)_2CH_2-$, $-CH_2CH(CH_3)CH_2-$, $-CH_2C(CH_3)_2-$, $-CH_2CH_2CH(CH_3)-$, $-CH_2CH(CH_2CH_3)-$, $-(CH_2)_5-$, $-CH(CH_3)CH(CH_2CH_3)-$, $-(CH_2)_6-$, $-(CH_2)_7-$, $-(CH_2)_8-$.

In the present specification, the "arylene" means a divalent group derived from the "aryl" described above by the further removal of one arbitrary hydrogen atom. The arylene may be a monocyclic ring or may be a condensed ring. The number of atoms constituting the ring of the arylene is not particularly limited and is preferably 6 to 10 ($C_6$ to $C_{10}$ arylene). Specifically, examples of the arylene include 1,2-phenylene, 1,3-phenylene, 1,4-phenylene, 1,2-naphthylene, 1,3-naphthylene, and 1,4-naphthylene.

In the present specification, the "aromatic hydrocarbon ring" means a hydrocarbon ring composed of a monocyclic ring or a condensed ring that exhibits aromaticity. The aromatic hydrocarbon ring is preferably a 6- to 10-membered aromatic hydrocarbon ring. Specifically, examples of the aromatic hydrocarbon ring include a benzene ring and a naphthalene ring.

In the present specification, the "aromatic heterocyclic ring" means a cyclic compound composed of a monocyclic ring or a condensed ring that exhibits aromaticity and contains one or more heteroatoms. The aromatic heterocyclic ring is preferably a 5- to 10-membered aromatic heterocyclic ring. Specifically, examples of the aromatic heterocyclic ring include a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, a triazine ring, a benzofuran ring, a benzothiophene ring, a benzothiadiazoline ring, a benzothiazoline ring, a benzoxazoline ring, a benzoxadiazoline ring, a benzimidazole ring, a benzotriazole ring, an indole ring, an isoindole ring, an indazole ring, an azaindole ring, a quinoline ring, an isoquinoline ring, a cinnoline ring, a quinazoline ring, a quinoxaline ring, a benzodioxol ring, an indolizine ring, an imidazopyridine ring, a pyrazolopyridine ring, an imidazopyridine ring, a triazolopyridine ring, a pyrrolopyrazine ring, and a furopyridine ring.

In the present specification, the "alicyclic ring" means a non-aromatic hydrocarbon ring. The alicyclic ring may have an unsaturated bond in a ring and may be a polycyclic ring having two or more rings. A carbon atom constituting the ring may be oxidized to form carbonyl. The alicyclic ring is preferably a 3- to 8-membered alicyclic ring. Specifically, examples of the alicyclic ring include a cyclopropane ring, a cyclobutane ring, a cyclopentane ring, a cyclohexane ring, a cycloheptane ring, a cyclooctane ring, and a bicyclo[2.2.1]heptane ring.

In the present specification, the "saturated heterocyclic ring" means a non-aromatic heterocyclic ring that contains a carbon atom as well as 1 to 5 heteroatoms and contains neither a double bond nor a triple bond in a ring. The saturated heterocyclic ring may be a monocyclic ring or may form a condensed ring with another ring, for example, an aromatic ring such as a benzene ring. The saturated heterocyclic ring is preferably a 4- to 10-membered saturated heterocyclic ring. Specifically, examples of the saturated heterocyclic ring include an azetidine ring, an oxoazetidine ring, an oxetane ring, a tetrahydrofuran ring, a tetrahydropyran ring, a morpholine ring, a thiomorpholine ring, a pyrrolidine ring, a 2-oxopyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, an indoline ring, an azepane ring, a dioxepane ring, and a 5,9-dioxaspiro[3.5]nonane ring.

In the present specification, the "heterocyclic ring" means a non-aromatic heterocyclic ring containing preferably 1 to 5, more preferably 1 to 3 heteroatoms among atoms constituting the ring. The heterocyclic ring may have a double and/or triple bond in a ring, and a carbon atom in a ring may be oxidized to form carbonyl. The heterocyclic ring may be a monocyclic ring, a condensed ring, or a spiro ring. The number of atoms constituting the ring of the heterocyclic ring is preferably 3 to 12 (3- to 12-membered heterocyclic ring), more preferably 4 to 10 (4- to 10-membered heterocyclic ring). Specifically, examples of the heterocyclic ring include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, a 6,7-dihydro-pyrrolo[1,2-a]imidazole ring, an azocane ring, a 4,5,6,7-tetrahydropyrazolo[1,5-a]pyrazine ring, an azepane ring, a dioxepane ring, a 5,9-dioxaspiro[3.5]nonane ring, and rings in which one or more single bonds in any of these saturated heterocyclic rings are replaced with a double bond or a triple bond.

In the present specification, examples of the "protective group for a carboxyl group" include alkyl ester-type protective groups, benzyl ester-type protective groups, and substituted alkyl ester-type protective groups.

In the present specification, examples of the "protective group for an amino group" include carbamate-type protective groups, amide-type protective groups, arylsulfonamide-type protective groups, alkylamine-type protective groups, and imide-type protective groups.

In the present specification, examples of the "protective group for hydroxy" include alkyl ether-type protective groups, aralkyl ether-type protective groups, silyl ether-type protective groups, and carbonic acid ester-type protective groups.

In the present specification, examples of the "halogen-derived substituent" include fluoro (—F), chloro (—Cl), bromo (—Br), and iodo (—I).

In the present specification, examples of the "oxygen atom-derived substituent" include hydroxy (—OH), oxy (—OR), carbonyl (—C(═O)—R), carboxyl (—$CO_2$H), oxycarbonyl (—C(═O)—OR), carbonyloxy (—O—C(═O)—R), thiocarbonyl (—C(═O)—SR), a carbonylthio group (—S—C(═O)—R), aminocarbonyl (—C(═O)—NHR), carbonylamino (—NH—C(═O)—R), oxycarbonylamino (—NH—C(═O)—OR), sulfonylamino (—NH—$SO_2$—R), aminosulfonyl (—$SO_2$—NHR), sulfamoylamino (—NH—$SO_2$—NHR), thiocarboxyl (—C(═O)—SH), and carboxylcarbonyl (—C(═O)—$CO_2$H).

In the present specification, examples of the "nitrogen atom-derived substituent" include azide (—$N_3$; also referred to as an "azide group"), cyano (—CN), primary amino (—$NH_2$), secondary amino (—NH—R), tertiary amino (—NR(R')), amidino (—C(═NH)—$NH_2$), substituted amidino (—C(═NR)—NR'R"), guanidino (—NH—C(═NH)—$NH_2$), substituted guanidino (—NR—C(═NR'")—NR'R"), and aminocarbonylamino (—NR—CO—NR'R").

In the present specification, examples of the "sulfur atom-derived substituent" include thiol (—SH), thio (—S—R), sulfinyl (—S(═O)—R), sulfonyl (—S(═O)$_2$—R), sulfo (—$SO_3$H), and pentafluorosulfanyl (—SFs).

In the present specification, examples of the "boron atom-derived substituent" include boryl (—BR(R')), dioxyboryl (—B(OR)(OR')), and trifluoroborate (—$BF_3$—). Specifically, examples of the "boron atom-derived substituent" include substituents in which these two substituents R and R' are each independently selected from among alkyl, cycloalkyl, alkenyl, alkynyl, aryl, heteroaryl, aralkyl, and the like, and a "boron atom-derived substituent" in which these two substituents R and R' form a ring together with the atoms respectively bonded to R and R', i.e., a cyclic boryl group. The "boron atom-derived substituent" is preferably a cyclic boryl group. More specifically, examples of the cyclic boryl group include a pinacolatoboryl group, a neopentanediolatoboryl group, a cathecolatoboryl group, and a 9-borabicyclo[3.3.1]nonan-9-yl group.

In the present specification, examples of the "zinc-derived group" include alkylzinc groups (—Zn—($C_1$-$C_6$ alkyl)) and zinc halide groups (—Zn—X). The "zinc-derived group" is preferably —ZnMe, —ZnEt, —ZnPr, —ZnCl, —ZnBr, or —ZnI. A compound having such a "zinc-derived group" can be produced with reference to March's Advanced Organic Chemistry: Reactions, Mechanisms, and Structure (8th edition, John Wiley & Sons, Inc. 2019) or R. C. Laroch, Comprehensive Organic Transformations (3rd edition, John Wiley & Sons, Inc. 2018).

In the present specification, the term "optionally substituted" means that a group may be substituted by an arbitrary substituent. A substituent may be further added to each substituent, such a substituent is not limited, and, for example, one or two or more groups may each independently be arbitrarily selected from among arbitrary substituents containing a halogen atom, an oxygen atom, a sulfur atom, a nitrogen atom, a boron atom, a silicon atom, or a phosphorus atom.

In the present specification, the term "optionally protected" means that a group may be protected with an arbitrary protective group.

In the present specification, the term "one or more" means 1 or any number of 2 or larger. When the term "one or more" is used in a context related to a substituent for a group, this term means any number from one to the maximum number of substituents accepted for the group.

In the present specification, the term "to" which indicates a numeric range includes values described at both ends thereof. For example, the term "A to B" means a numeric range of A or more and B or less.

In the present specification, the term "approximately", when used in combination with a numeric value, means a range of values of +10% and −10% of the numeric value.

In the present specification, the term "and/or" is meant to include every combination of the terms "and" and "or" appropriately combined. Specifically, for example, the term "A, B, and/or C" includes the following seven variations: (i) A, (ii) B, (iii) C, (iv) A and B, (v) A and C, (vi) B and C, and (vii) A, B, and C.

One embodiment of the present invention provides a compound represented by the general formula (1) (hereinafter, also referred to as a "compound (1)") or a salt thereof, or a solvate thereof.

In the compound (1), $X_{a1}$ is $CR_{a1}$ or N. $X_{a1}$ is preferably $CR_{a1}$.

In the compound (1), $X_{a3}$ is $CR_{a3}$ or N. $X_{a3}$ is preferably $CR_{a3}$.

In the compound (1), $R_{a1}$ is hydrogen, halogen or $C_1$-$C_6$ alkoxy. $R_{a1}$ is preferably hydrogen or fluorine.

In the compound (1), $R_{a2}$ is hydrogen, halogen or $C_1$-$C_6$ alkoxy. $R_{a2}$ is preferably hydrogen or methoxy.

In the compound (1), $R_{a3}$ is hydrogen, halogen or $C_1$-$C_6$ alkoxy. $R_{a3}$ is preferably hydrogen or fluorine.

In the compound (1), $X_{b1}$ is $CH_2$, O, NH, S or C═O. $X_{b1}$ is preferably $CH_2$.

In the compound (1), $X_{b2}$ is $CH_2$, O, NH, S or C═O. $X_{b2}$ is preferably $CH_2$, O, NH or C═O, more preferably $CH_2$.

In the compound (1), $X_{b3}$ is $CH_2$, O, NH, S or C═O. $X_{b3}$ is preferably $CH_2$, O, NH, S or C═O, more preferably O.

For the combination of $X_{b1}$, $X_{b2}$ and $X_{b3}$, preferably, $X_{b1}$ is $CH_2$, $X_{b2}$ is $CH_2$, O, NH or C═O, and $X_{b3}$ is $CH_2$, O, NH, S or C═O. More preferably, each of $X_{b1}$ and $X_{b2}$ is $CH_2$, and $X_{b3}$ is O; each of $X_{b1}$ and $X_{b3}$ is $CH_2$, and $X_{b2}$ is O; each of $X_{b1}$ and $X_{b2}$ is $CH_2$, and $X_{b3}$ is S; $X_{b1}$ is $CH_2$, $X_{b2}$ is NH, and $X_{b3}$ is C═O; each of $X_{b1}$ and $X_{b2}$ is $CH_2$, and $X_{b3}$ is NH; $X_{b1}$ is $CH_2$, $X_{b2}$ is C═O, and $X_{b3}$ is NH; each of $X_{b1}$ and $X_{b3}$ is $CH_2$, and $X_{b2}$ is NH; or each of $X_{b1}$, $X_{b2}$ and $X_{b3}$ is $CH_2$. Most preferably, each of $X_{b1}$ and $X_{b2}$ is $CH_2$, and $X_{b3}$ is O.

In the compound (1), Z is $C_6$-$C_{10}$ aryl, 5- to 10-membered heteroaryl or $C_1$-$C_6$ alkyl, and the $C_6$-$C_{10}$ aryl, the 5- to 10-membered heteroaryl and the $C_1$-$C_6$ alkyl are each substituted by $R_{z3}$ and optionally substituted by one or more groups selected from the group consisting of $R_{z1}$, $R_{z2}$, $R_{z4}$ and $R_{z5}$. Z is preferably phenyl, pyridyl or $C_2$-$C_5$ alkyl substituted by $R_{z3}$ and optionally substituted by one or more groups selected from the group consisting of $R_{z1}$, $R_{z2}$, $R_{z4}$ and $R_{z5}$.

In the compound (1), Z is preferably a group represented by the formula (2):

[Formula 9]

(2)

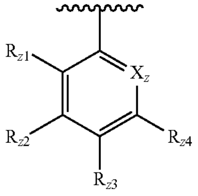

wherein the wavy line represents a binding point of Z, and $X_z$ is $CR_{z5}$ or N. In the formula (2), $X_z$ is preferably $CR_{z5}$.

In the compound (1), $R_{z1}$, $R_{z2}$ and $R_{z5}$ are each independently selected from the group consisting of hydrogen, halogen, $C_1$-$C_6$ alkyl, $C_1$-$C_6$ alkyl(5- to 10-membered heteroaryl $C_1$-$C_6$ alkyl)amino optionally having a substituent, $C_1$-$C_6$ alkyl(4- to 10-membered heterocyclyl)amino optionally having a substituent and 4- to 8-membered cyclic amino optionally having a substituent. $R_{z1}$, $R_{z2}$ and $R_{z5}$ are preferably each independently selected from the group consisting of hydrogen, halogen and $C_1$-$C_6$ alkyl, more preferably each independently selected from the group consisting of hydrogen, fluorine, chlorine, methyl and ethyl.

In the compound (1), $R_{z4}$ is hydrogen, halogen, $C_1$-$C_6$ alkyl, $C_1$-$C_6$ alkyl(5- to 10-membered heteroaryl $C_1$-$C_6$ alkyl)amino optionally having a substituent, $C_1$-$C_6$ alkyl(4- to 10-membered heterocyclyl)amino optionally having a substituent or 4- to 8-membered cyclic amino optionally having a substituent. $R_{z4}$ is preferably $C_1$-$C_6$ alkyl(5- to 10-membered heteroaryl $C_1$-$C_2$alkyl)amino optionally having a substituent, $C_1$-$C_6$ alkyl(4- to 10-membered heterocyclyl)amino optionally having a substituent or 4- to 8-membered cyclic amino optionally having a substituent, more preferably 4- to 6-membered cyclic amino optionally having one or more substituents selected from the group consisting of hydrogen, halogen, $C_1$-$C_6$ alkyl and $C_1$-$C_6$ alkoxy; 4- to 6-membered cyclic amino having a cross-linking group selected from the group consisting of $C_1$-$C_2$ alkylene and $C_1$-$C_2$ alkylene containing one oxygen atom on a ring; $C_1$-$C_3$ alkyl(5- or 6-membered heteroaryl $C_1$-$C_2$ alkyl)amino optionally having a substituent selected from the group consisting of hydrogen, halogen and $C_1$-$C_6$ alkyl; or $C_1$-$C_3$ alkyl(4- to 6-membered heterocyclyl)amino optionally having a substituent selected from the group consisting of hydrogen, halogen and $C_1$-$C_6$ alkyl, particularly preferably 3-oxa-8-azabicyclo[3.2.1]octan-8-yl, morpholin-4-yl, 8-oxa-3-azabicyclo[3.2.1]octan-3-yl, (2S,3S)-3-methoxy-2-methylazetidin-1-yl, 1,3,3a,4,6,6a-hexahydrofuro[3,4-c]pyrrol-5-yl, 4,4-difluoropiperidin-1-yl, pyrrolidin-1-yl, piperidin-1-yl, methyl(1,2-oxazol-3-ylmethyl)amino, methyl(oxetan-3-yl)amino, methyl-[(3R)-oxolan-3-yl]amino or methyl-(3-methyloxetan-3-yl)amino.

In the compound (1), $R_{z3}$ is a carboxyl group or a biological equivalent thereof. Examples of the biological equivalent include functional groups capable of biologically exhibiting a similar effect, though having a distinctive chemical structure, as described in Matsuoka et al. (Pharmacia, 2010, 46 (3), 215-222) and Thornber et al. (Chem. Soc. Rev., 1979, 8, 563-580). Examples of the equivalent of the carboxyl group include functional groups having an acidic proton. $R_{z3}$ may also include a compound capable of being converted to the carboxyl group or the biological equivalent thereof after administration to a subject, for example, their prodrugs.

In the compound (1), specifically, $R_{z3}$ is a group selected from the following substituent group A:

[Formula 10]

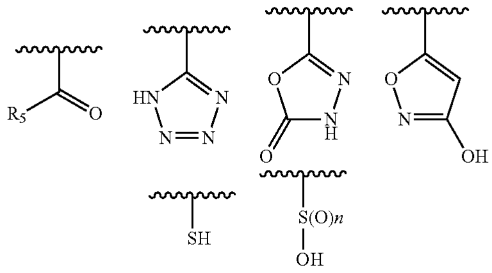

wherein the wavy line represents a binding point, $R_5$ is hydroxy, $C_1$-$C_6$ alkoxy, mono- or di-$C_1$-$C_6$alkylamino or $C_1$-$C_6$ alkylsulfonylamino, and n is 1 or 2. $R_{z3}$ is preferably a group selected from the following substituent group B:

[Formula 11]

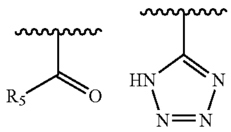

wherein the wavy line represents a binding point, and $R_5$ is hydroxy, $C_1$-$C_6$ alkoxy, mono-$C_1$-$C_6$ alkylamino or $C_1$-$C_6$ alkylsulfonylamino. $R_5$ is preferably hydroxy or $C_1$-$C_6$ alkylsulfonylamino.

In the compound (1), Y is $C_6$-$C_{10}$ aryl or 5- to 10-membered heteroaryl, and the $C_6$-$C_{10}$ aryl and the 5- to 10-membered heteroaryl are each optionally substituted by one or more groups selected from the group consisting of $R_{y1}$, $R_{y2}$, $R_{y3}$, $R_{y4}$ and $R_{y5}$. Y is preferably phenyl or 6- to 10-membered heteroaryl optionally substituted by one or more groups selected from the group consisting of $R_{y1}$, $R_{y2}$, $R_{y3}$, $R_{y4}$ and $R_{y5}$, more preferably phenyl or 6- to 10-membered heteroaryl substituted by $R_{y3}$ and optionally substituted by one or more groups selected from the group consisting of $R_{y1}$, $R_{y2}$, $R_{y4}$ and $R_{y5}$.

In the compound (1), Y is preferably a group represented by the formula (3):

[Formula 12]

(3)

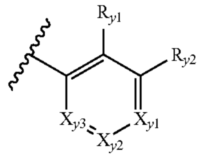

wherein the wavy line represents a binding point of Y, $X_{y1}$ is $CR_{y3}$ or N, $X_{y2}$ is $CR_{y4}$ or N, and $X_{y3}$ is $CR_{y5}$ or N. In the formula (3), preferably, $X_{y1}$ is $CR_{y3}$, $X_{y2}$ is $CR_{y4}$, and $X_{y3}$ is $CR_{y5}$.

In the compound (1), $R_{y1}$ is hydrogen, halogen, cyano, $C_1$-$C_6$ alkyl, $C_2$-$C_6$ alkenyl, $C_3$-$C_8$ cycloalkyl, $C_1$-$C_6$ alkoxy, 4- to 10-membered heterocyclyl $C_1$-$C_6$ alkoxy, hydroxy $C_2$-$C_6$ alkoxy, 4- to 10-membered heterocyclyloxy, $C_1$-$C_6$ alkoxy $C_1$-$C_6$ alkoxy, $C_1$-$C_6$ alkylamino $C_1$-$C_6$ alkoxy, 5- to 10-membered heteroaryloxy, $C_1$-$C_6$ alkylthio, a 4- to 10-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent or $C_1$-$C_6$ alkyl($C_1$-$C_6$ alkoxy $C_1$-$C_6$ alkyl)amino. $R_{y1}$ is preferably hydrogen, halogen, cyano, $C_1$-$C_3$ alkyl, $C_2$-$C_4$ alkenyl, $C_3$-$C_6$ cycloalkyl, $C_1$-$C_3$ alkoxy, 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy-$C_1$-$C_2$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent or $C_1$-$C_3$ alkyl($C_1$-$C_3$ alkoxy $C_1$-$C_2$ alkyl)amino, more preferably hydrogen, halogen, cyano, $C_1$-$C_3$ alkyl, $C_2$-$C_4$ alkenyl, $C_3$-$C_6$ cycloalkyl or $C_1$-$C_3$ alkoxy, further preferably hydrogen, halogen, cyano or $C_1$-$C_3$ alkyl, particularly preferably chlorine.

In the compound (1), $R_{y2}$ is hydrogen, halogen, cyano, $C_1$-$C_6$ alkyl, $C_2$-$C_6$ alkenyl, $C_3$-$C_8$ cycloalkyl, $C_1$-$C_6$ alkoxy, 4- to 10-membered heterocyclyl $C_1$-$C_6$ alkoxy, hydroxy $C_2$-$C_6$ alkoxy, 4- to 10-membered heterocyclyloxy, $C_1$-$C_6$ alkoxy $C_1$-$C_6$ alkoxy, $C_1$-$C_6$ alkylamino $C_1$-$C_6$ alkoxy, 5- to 10-membered heteroaryloxy, $C_1$-$C_6$ alkylthio, a 4- to 10-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent or $C_1$-$C_6$ alkyl($C_1$-$C_6$ alkoxy $C_1$-$C_6$ alkyl)amino. $R_{y2}$ is preferably hydrogen, halogen, cyano, $C_1$-$C_3$ alkyl, $C_2$-$C_4$ alkenyl, $C_3$-$C_6$ cycloalkyl, $C_1$-$C_3$ alkoxy, 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy-$C_1$-$C_2$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent or $C_1$-$C_3$ alkyl($C_1$-$C_3$ alkoxy $C_1$-$C_2$ alkyl)amino, more preferably hydrogen, halogen, cyano, $C_1$-$C_3$ alkyl, $C_2$-$C_4$ alkenyl, $C_3$-$C_6$ cycloalkyl or $C_1$-$C_3$ alkoxy, further preferably hydrogen.

In the compound (1), $R_{y3}$ is hydrogen, halogen, cyano, $C_1$-$C_6$ alkyl, $C_2$-$C_6$ alkenyl, $C_3$-$C_8$ cycloalkyl, $C_1$-$C_6$ alkoxy, 4- to 10-membered heterocyclyl $C_1$-$C_6$ alkoxy, hydroxy $C_2$-$C_6$ alkoxy, 4- to 10-membered heterocyclyloxy, $C_1$-$C_6$ alkoxy $C_1$-$C_6$ alkoxy, $C_1$-$C_6$ alkylamino $C_1$-$C_6$ alkoxy, 5- to 10-membered heteroaryloxy, $C_1$-$C_6$ alkylthio, a 4- to 10-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent or $C_1$-$C_6$ alkyl($C_1$-$C_6$ alkoxy $C_1$-$C_6$ alkyl) amino. $R_{y3}$ is preferably hydrogen, halogen, cyano, $C_1$-$C_3$ alkyl, $C_2$-$C_4$ alkenyl, $C_3$-$C_6$ cycloalkyl, $C_1$-$C_3$ alkoxy, 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy-$C_1$-$C_2$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent or $C_1$-$C_3$ alkyl($C_1$-$C_3$ alkoxy $C_1$-$C_2$ alkyl)amino, more preferably 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy $C_1$-$C_2$ alkoxy, $C_1$-$C_3$ alkoxy, $C_1$-$C_4$ alkylamino $C_1$-$C_3$ alkoxy, 5- or 6-membered heteroaryloxy, $C_1$-$C_4$ alkylthio, 5- or 6-membered saturated heterocyclic ring having a bond in a carbon atom on a ring and optionally having a substituent, a 4- to 10-membered saturated heterocyclic group having a bond in a nitrogen atom on a ring and optionally having a substituent, 5- to 10-membered heteroaryl optionally having a substituent or $C_1$-$C_3$ alkyl($C_1$-$C_3$ alkoxy $C_1$-$C_2$ alkyl)amino, further preferably a 4- to 10-membered saturated heterocyclic group having a bond in a nitrogen atom on a ring and optionally having a substituent or 5- to 10-membered heteroaryl optionally having a substituent, particularly preferably 1-methylpyrazol-4-yl, 7,7-dimethyl-5,9-dioxa-2-azaspiro[3.5]nonan-2-yl, 4-methylpiperazin-1-yl, (2R)-2,4-dimethylpiperazin-1-yl, 6-methoxy-2-azaspiro[3.3]heptan-2-yl, 4-(2-methoxyethyl) piperazin-1-yl, 3-methoxyazetidin-1-yl, 4-(oxetan-3-yl)piperazin-1-yl, 2-oxa-6-azaspiro[3.3]heptan-6-yl, (2R,5R)-2,4,5-trimethylpiperazin-1-yl, 4-(2-hydroxy-2-methylpropyl) piperazin-1-yl or morpholin-4-yl.

In the compound (1), $R_{y4}$ and $R_{y5}$ are each independently selected from the group consisting of hydrogen, halogen, cyano, $C_1$-$C_6$ alkyl, $C_2$-$C_6$ alkenyl, $C_3$-$C_8$ cycloalkyl, $C_1$-$C_6$ alkoxy, 4- to 10-membered heterocyclyl $C_1$-$C_6$ alkoxy, hydroxy $C_2$-$C_6$ alkoxy, 4- to 10-membered heterocyclyloxy, $C_1$-$C_6$ alkoxy $C_1$-$C_6$ alkoxy, $C_1$-$C_6$ alkylamino $C_1$-$C_6$ alkoxy, 5- to 10-membered heteroaryloxy, $C_1$-$C_6$ alkylthio, a 4- to 10-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent and $C_1$-$C_6$ alkyl($C_1$-$C_6$ alkoxy $C_1$-$C_6$ alkyl)amino. $R_{y4}$ and $R_{y5}$ are preferably each independently selected from the group consisting of hydrogen, halogen, cyano, $C_1$-$C_3$ alkyl, $C_2$-$C_4$ alkenyl, $C_3$-$C_6$ cycloalkyl, $C_1$-$C_3$ alkoxy, 5- or 6-membered heterocyclyl $C_1$-$C_4$ alkoxy, hydroxy $C_3$-$C_6$ alkoxy, 5- or 6-membered heterocyclyloxy, $C_1$-$C_3$ alkoxy-$C_1$-$C_2$ alkoxy, $C_1$-$C_4$ alkylamino $C_1$-$C_3$ alkoxy, 5- or 6-membered heteroaryloxy, $C_1$-$C_4$ alkylthio, a 5- or 6-membered saturated heterocyclic group having a bond in a carbon atom on a ring and optionally having a substituent, a 4- to 10-membered saturated heterocyclic group having a bond in a nitrogen atom on a ring and optionally having a substituent, a 5- to 10-membered aromatic heterocyclic group optionally having a substituent and $C_1$-$C_3$ alkyl($C_1$-$C_3$ alkoxy $C_1$-$C_2$ alkyl) amino, more preferably each independently selected from the group consisting of hydrogen, halogen, cyano, $C_1$-$C_3$ alkyl, $C_2$-$C_4$ alkenyl, $C_3$-$C_6$ cycloalkyl and $C_1$-$C_3$ alkoxy, further preferably each independently selected from the group consisting of hydrogen, halogen, cyano and $C_1$-$C_3$ alkyl, particularly preferably hydrogen.

In the compound (1), when $X_{y1}$ is $CR_{y3}$, a 5- or 6-membered heteroaryl ring is optionally formed together with the carbon atoms bonded to $R_{y2}$ and $R_{y3}$. When $X_{y1}$ is $CR_{y3}$ and $X_{y2}$ is $CR_{y4}$, a 5- or 6-membered heteroaryl ring is optionally formed together with the carbon atoms bonded to $R_{y3}$ and $R_{y4}$. When $X_{y2}$ is $CR_{y4}$ and $X_{y3}$ is $CR_{y5}$, a 5- or 6-membered heteroaryl ring is optionally formed together with the carbon atoms bonded to $R_{y4}$ and $R_{y5}$.

Another embodiment of the present invention provides a compound represented by the general formula (4) (hereinafter, also referred to as a "compound (4)") or a salt thereof, or a solvate thereof. In the compound (4), $X_{a3}$, $R_{a1}$, $R_{a2}$, $X_{b1}$, $X_{b2}$, $X_{b3}$, $R_{y1}$, $R_{y2}$, $X_{y1}$, $X_{y2}$, $X_{y3}$, $R_{z1}$, $R_{z2}$, $R_{z3}$, $R_{z4}$ and $X_z$ are as defined about $X_{a3}$, $R_{a1}$, $R_{a2}$, $X_{b1}$, $X_{b2}$, $X_{b3}$, $R_{y1}$, $R_{y2}$, $X_{y1}$, $X_{y2}$, $X_{y3}$, $R_{z1}$, $R_{z2}$, $R_{z3}$, $R_{z4}$ and $X_z$ in the compound (1) mentioned above.

The compound described in the present specification can be a salt thereof or a solvate of the compound or the salt. Examples of the salt of the compound include: hydrochloride; hydrobromide; hydroiodide; phosphate; phosphonate; sulfate; sulfonate such as methanesulfonate and p-toluenesulfonate; carboxylate such as acetate, citrate, malate, tartrate, succinate, and salicylate; alkali metal salts such as sodium salt and potassium salt; alkaline earth metal salts such as magnesium salt and calcium salt; and ammonium salts such as ammonium salt, alkylammonium salt, dialkylammonium salt, trialkylammonium salt, and tetraalkylammonium salt. These salts are produced, for example, by contacting the compound with an acid or a base. In the present specification, the solvate refers to one molecular population formed by the compound with a solvent and is not particularly limited as long as the solvate is formed from a solvent whose ingestion is accepted in association with the administration of a medicament. Examples thereof include not only hydrates, alcoholates (ethanolate, methanolate, 1-propanolate, 2-propanolate, etc.), and solvates with a single solvent such as dimethyl sulfoxide but a solvate formed from a plurality of solvents per molecule of the compound, and a solvate formed from plural types of solvents per molecule of the compound. The solvate is referred to as a hydrate when the solvent is water. The solvate of the compound of the present invention is preferably a hydrate. Specifically, such a hydrate is mono- to decahydrates, preferably mono- to pentahydrates, further preferably mono- to trihydrates.

In the case of obtaining the compound according to the present invention in a free form, the compound can be converted to the state of a salt that may be formed by the compound, or a hydrate or a solvate of the compound or the salt in accordance with a routine method. Examples thereof include hydrates and ethanolate of the compound represented by the formula (1) or a salt thereof. Specifically, examples thereof include, but are not limited to, hemihydrate, monohydrate, dihydrate, trihydrate, tetrahydrate, pentahydrate, hexahydrate, heptahydrate, octahydrate, nonahydrate, decahydrate and monoethanolate of the compound represented by the formula (1), hemihydrate, monohydrate, dihydrate, trihydrate, tetrahydrate, pentahydrate, hexahydrate, heptahydrate, octahydrate, nonahydrate, decahydrate and monoethanolate of sodium salt of the compound represented by the formula (1), and hydrates and ethanolate of hydrochloride of the compound represented by the formula (1). The hydrate or the solvate may be produced in a crystal form or a non-crystalline form. The crystal form may assume a crystal polymorph. A method for producing the hydrate or the solvate can involve, for example, adding a solvent such as ethanol and/or water to the compound represented by the formula (1), followed by a routine method such as stirring, cooling, concentration, and/or drying to obtain a hydrate or a solvate.

In the case of obtaining the compound according to the present invention as a salt of the compound, a hydrate, or a solvate, the compound can be converted to a free form thereof in accordance with a routine method.

The compound described in the present specification may contain a non-natural ratio of isotope atoms as one or more atoms constituting such a compound. A compound substituted by an isotope at an abundance ratio different from a natural abundance ratio of the isotope by replacing an arbitrary atom in the compound with another isotope atom having the same atomic number (proton number) and a different mass number (total number of protons and neutrons), i.e., a compound labeled with an isotope atom, is also included in the present invention. Examples of the isotope element contained in the compound of the present specification include a hydrogen atom, a carbon atom, a nitrogen atom, an oxygen atom, a phosphorus atom, a sulfur atom, a fluorine atom, and a chlorine atom, which are each contained as $^{2}H$, $^{3}H$, $^{13}C$, $^{14}C$, $^{15}N$, $^{17}O$, $^{18}O$, $^{32}P$, $^{3}S$, $^{18}F$, $^{36}Cl$, or the like. The compound labeled with an isotope atom is useful as a therapeutic or prophylactic agent, a research reagent (e.g., an assay reagent), and a diagnostic agent (e.g., an in vivo diagnostic imaging agent). The compound of the present specification containing every ratio of radioactive or non-radioactive isotope elements is encompassed in the scope of the present invention. The compound labeled with an isotope atom can be produced by using a regent or a solvent containing the corresponding isotope atom by the same approach as the method for producing the non-labeled compound.

The compound described in the present specification or a salt thereof, or a solvate thereof includes all stereoisomers (e.g., enantiomers and diastereomers (including cis and trans geometric isomers)) thereof, racemates of the isomers, and other mixtures. The compound of the present invention may have, for example, one or more asymmetric points. The present invention includes racemic mixtures, diastereomeric mixtures, and enantiomers of such compounds.

<General Process>

Exemplary methods for producing the compound represented by the formula (1) or a salt thereof, or a solvate thereof will be described with reference to a scheme group given below. The compound of the present invention may be synthesized by various methods, and the production methods described below are given for illustrative purposes. The present invention is not limited by chemical reaction and conditions disclosed herein. In the schemes of the production methods given below, some substituents are excluded for clear understanding, and these do not intend to limit the scheme disclosure. The typical compound of the present invention can be synthesized using a suitable intermediate, a compound known in the art, and a reagent. In formulas in the general synthesis methods described below, variable groups represented by $R_1$, $R_2$, and the like and variable numbers represented by n and the like have the same meanings as those of the variable groups represented by $R_1$, $R_2$, and the like and the variable numbers represented by n and the like in compounds represented by general formulas defined in the present specification. When a starting material or a target compound of a step is subject to undesired chemical conversion under reaction conditions of the step, the target compound of the step can be obtained, for example, by performing the protection and deprotection of a functional group. For the selection of a protective group and the selection of methods for protection and deprotection, see, for example T. W. Greene, P. G. M. Wuts, Protective Groups in Organic Synthesis (5th edition, John Wiley & Sons 2014). The protection and deprotection of some functional groups are also described in the schemes given below.

The compound of the present invention can be synthesized by, for example, the following production methods.

General Process A

[Formula 13]

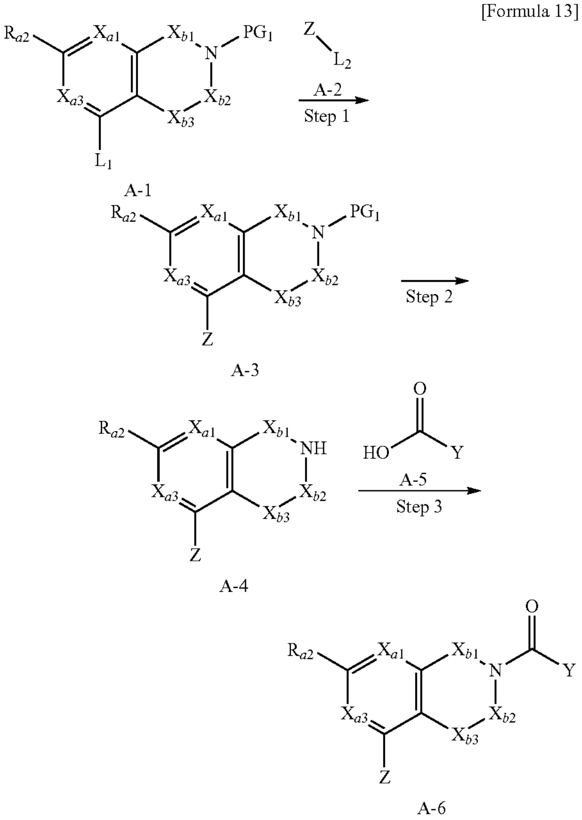

In the formulas, $PG_1$ represents a protective group for amino, $L_1$ and $L_2$ each independently represent a leaving group, and $X_{a1}$, $X_{a3}$, $R_{a2}$, $X_{b1}$, $X_{b2}$, $X_{b3}$, Y and Z are as defined in the item [1].

Examples of the protective group ($PG_1$) for amino include a formyl group, $C_1$-$C_6$ alkylcarbonyl groups (an acetyl group, a propionyl group, a butyryl group, an isobutyryl group, a valeryl group, an isovaleryl group, a pivaloyl group, etc.), a carbamoyl group, $C_1$-$C_6$ alkoxycarbonyl groups (a methoxycarbonyl group, an ethoxycarbonyl group, an isopropyloxycarbonyl group, a sec-butoxycarbonyl group, a t-butoxycarbonyl group, etc.), substituted silyl groups (a trimethylsilyl group, a triethylsilyl group, a triisopropylsilyl group, a t-butyldimethylsilyl group, a t-butyldiphenylsilyl group, etc.), aralkyloxycarbonyl groups (a benzyloxycarbonyl group, a 9-fluorenylmethyloxycarbonyl group, etc.), an allyl group, and aralkyl groups (a benzyl group, a cumyl group, etc.).

Examples of the leaving groups ($L_1$ and $L_2$) in the general process A include halogen atoms, a trifluoromethanesulfonyl group, a nonafluorobutanesulfonyl group, acetyloxy, a trifluoroacetyloxy group, a methanesulfonyloxy group, a p-toluenesulfonyloxy group, boron atom-derived groups (4,4,5,5-tetramethyl-1,3,2-dioxaborolane, 9-BBN, etc.), and zinc-derived groups.

Step 1

A compound (A-3) can be produced through the coupling reaction of a compound (A-1) having leaving group $L_1$ with a compound (A-2) having leaving group $L_2$ in the presence of a palladium catalyst, a ligand, and a base. Examples of the compound having leaving group $L_1$ and the compound having $L_2$ include compounds having a halogen atom as a leaving group, compounds having a sulfonic acid-derived leaving group, compounds having a boron atom-derived leaving group, and compounds having a zinc-derived group, which can be produced in accordance with well-known methods, for example, methods described in Comprehensive Organic Transformations, A Guide to Functional Group Preparations, 3rd Edition, (R. C. Larock) or March's Advanced Organic Chemistry: Reactions, Mechanisms, and Structure, 7th Edition (M. B. Smith, J. March), by those skilled in the art, and can be used in coupling reaction. The coupling reaction can be performed with reference to the method of Suzuki et al. (Chem. Rev. 1995, 95, 2457-2483) or the method of Negishi et al. (J. Org. Chem. 1977, 42, 1821-1823).

A catalyst available from a commercial supplier can be used as the palladium catalyst for use in coupling reaction. Examples thereof include complexes formed from palladium and a ligand, i.e., 1,1'-bis(diphenylphosphino)ferrocene-palladium(II) dichloride dichloromethane complexes, 1,1'-bis(diphenylphosphino)ferrocene-palladium(II) dichloride complexes, bis(triphenylphosphine)palladium(II) dichloride, dichlorobis(tricyclohexylphosphine)palladium (II), [1,3-bis(2,6-diisopropylphenyl)imidazol-2-ylidene](3-chloropyridyl)palladium(II) dichloride, (1,3-bis(2,6-diisopropylphenyl)imidazolidene)(3-chloropyridyl)palladium(II) dichloride, and [1,3-bis(2,6-di-3-pentylphenyl)imidazol-2-ylidene](3-chloropyridyl)palladium(II) dichloride, and catalysts of Buchwald et al., for example, SPhos Pd G3, XPhos Pd G3, CPhos Pd G3, and XantPhos Pd G3, described in Org. Lett. 2014, 16, 4638-4641 or J. Am. Chem. Soc., 2014, 136, 14027-14030. Alternatively, palladium and a ligand may be used in combination. Palladium available from a commercial supplier, for example, palladium acetate, allylpalladium(II) chloride (dimer), or $Pd_2(dba)_3$, and a ligand available from a commercial supplier, for example, dppf, SPhos, or Xantphos, can be appropriately used in combination.

Examples of the base for use in coupling reaction include tertiary amine (triethylamine, 4-methylmorpholine, N,N-diisopropylethylamine, DBU, DABCO, etc.), inorganic bases such as carbonate and phosphate (sodium carbonate, potassium carbonate, cesium carbonate, potassium phosphate, etc.), and metal alkoxide (sodium methoxide, sodium tert-butoxide, sodium tert-pentoxide, potassium tert-butoxide, potassium tert-pentoxide, etc.) and preferably include inorganic bases such as cesium carbonate.

Examples of the solvent for use in coupling reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), amide solvents (N,N-dimethylformamide, N,N-dimethylacetamide, 1-methylpyrrolidin-one, etc.), and acetonitrile and preferably include 2-methyltetrahydrofuran and 1-methylpyrrolidin-one.

The optimum reaction temperature in performing coupling reaction is, for example, usually in the range of 0° C. to a temperature around the boiling point of the solvent, preferably in the range of 10° C. to 120° C. The reaction time is, for example, usually in the range of 30 minutes to 24 hours, preferably in the range of 1 hour to 12 hours. The obtained target compound (A-3) may be isolated by a general technique and, if necessary, purified by crystallization or chromatography.

Step 2

A compound (A-4) can be produced by deprotecting the protective group of the compound (A-3). When the protective group $PG_1$ is a $C_1$-$C_6$ alkoxycarbonyl group such as t-butoxycarbonyl, deprotection reaction is preferably performed using an acid. Examples of the acid for use in deprotection reaction include inorganic acids (hydrogen chloride, hydrobromic acid, hydroiodic acid, sulfuric acid, phosphoric acid, etc.), sulfonic acid (methanesulfonic acid, benzenesulfonic acid, toluenesulfonic acid, etc.), and carboxylic acid (formic acid, acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid, tartaric acid, propionic acid, glutaric acid, etc.) and preferably include hydrogen chloride, methanesulfonic acid, and trifluoroacetic acid.

Examples of the solvent for use in deprotection reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), hydrocarbon solvents (hexane, heptane, benzene, toluene, etc.), amide solvents (N,N-dimethylformamide, N,N-dimethylacetamide, 1-methylpyrrolidin-2-one, etc.), and ester solvents (ethyl acetate, isopropyl acetate, etc.) and preferably include 1,4-dioxane and ethyl acetate.

The optimum reaction temperature in performing deprotection reaction is, for example, usually in the range of 0° C. to a temperature around the boiling point of the solvent, preferably in the range of 10° C. to 100° C. The optimum reaction time in performing deprotection reaction is, for example, usually in the range of 30 minutes to 12 hours, preferably in the range of 1 hour to 6 hours. The obtained compound (A-4) may be isolated by a general technique and, if necessary, purified by crystallization or chromatography. Although the compound (A-4) may be obtained as a salt with the acid used in the reaction, such a salt can also be subjected to the next step.

Step 3

A compound (A-6) can be produced by converting a compound (A-5) to an acid chloride, followed by amidation reaction in the presence of the compound (A-4) and a base. Examples of the reagent that converts the compound (A-5) to an acid chloride include thionyl chloride, oxalyl chloride, and Ghosez reagents. Examples of the base for use in amidation reaction include tertiary amine (triethylamine, 4-methylmorpholine, N,N-diisopropylethylamine, DBU, DABCO, etc.), diamine (N,N,N',N'-tetramethylethylenediamine, etc.), guanidine (guanidine, tetramethylguanidine, etc.), and pyridine (pyridine, 2,6-lutidine, 2,4,6-collidine, 4-dimethylaminopyridine, etc.) and preferably include tertiary amine such as N,N-diisopropylethylamine and 4-methylmorpholine.

Examples of the solvent for use in amidation reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), halogen solvents (dichloromethane, dichloroethane, chloroform, etc.), amide solvents (N,N-dimethylformamide, N,N-dimethylacetamide, 1-methylpyrrolidin-2-one, etc.), ester solvents (ethyl acetate, isopropyl acetate, etc.), acetonitrile, and water and preferably include dichloromethane and acetonitrile.

The optimum reaction temperature in performing amidation reaction is, for example, in the range of 0° C. to a temperature around the boiling point of the solvent, preferably in the range of 20° C. to 60° C. The optimum reaction time in performing deprotection reaction is, for example, in the range of 10 minutes to 24 hours, preferably in the range of 30 minutes to 12 hours.

The compound (A-6) can also be produced, in addition to the method via an acid chloride, for example, through the amidation reaction of the compound (A-4) with the compound (A-5) using a condensing agent in the presence of a base. Examples of the condensing agent for use in amidation reaction include BOP condensing agents such as benzotriazol-1-yloxy-tris(dimethylamino)phosphonium hexafluorophosphate (BOP), benzotriazol-1-yloxy-tris(pyrrolidino) phosphonium hexafluorophosphate (PyBOP(R)), PyAOP, BroP, PyCloP, PyBroP(R), and DEPBT, 4-(4,6-dimethoxy-1,3,5-triazin-2-yl)-4-methylmorpholium chloride n-hydrate (DMT-MM), 2-(1H-benzotriazol-1-yl)-1,1,3,3-tetramethyluronium tetrafluoroborate (TBTU), [dimethylamino(triazolo [4,5-b]pyridin-3-yloxy)methylidene]-dimethylazanium hexafluorophosphate (HATU), ethyl(hydroxyimino) cyanoacetate (Oxyma), and T3P and preferably include HATU.

Examples of the base for use in amidation reaction with the condensing agent include tertiary amine (triethylamine, 4-methylmorpholine, N,N-diisopropylethylamine, DBU, DABCO, etc.) and pyridine (pyridine, 2,6-lutidine, 2,4,6-collidine, 4-dimethylaminopyridine, etc.) and preferably include tertiary amine such as N,N-diisopropylethylamine and 4-methylmorpholine.

Examples of the solvent for use in amidation reaction with the condensing agent include ether solvents (tetrahydrofuran, methyltetrahydrofuran, diethyl ether, t-butyl methyl ether, diisopropyl ether, cyclopentyl methyl ether, 1,2-dimethoxyethane, 1,4-dioxane, etc.), halogen solvents (dichloromethane, dichloroethane, chloroform, etc.), amide solvents (N,N-dimethylformamide, N,N-dimethylacetamide, 1-methylpyrrolidin-2-one, etc.), ester solvents (ethyl acetate, isopropyl acetate, etc.), and acetonitrile and preferably include dichloromethane and N,N-dimethylformamide.

The optimum reaction temperature in performing amidation reaction with the condensing agent is, for example, in the range of 0° C. to a temperature around the boiling point of the solvent, preferably in the range of 20° C. to 60° C. The optimum reaction time in performing amidation reaction with the condensing agent is, for example, in the range of 1 minute to 24 hours, preferably in the range of 30 minutes to 12 hours. The obtained compound (A-6) may be isolated by a general technique and, if necessary, purified by crystallization or chromatography.

General Process B

[Formula 14]

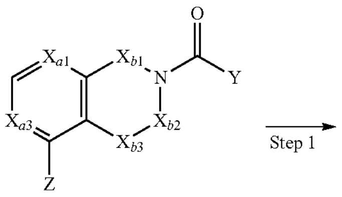

B-1

-continued

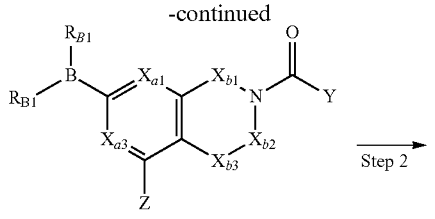

B-2

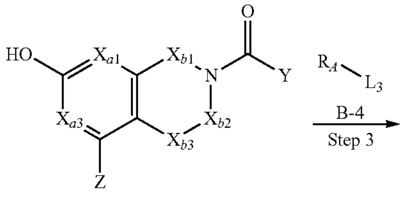

B-3

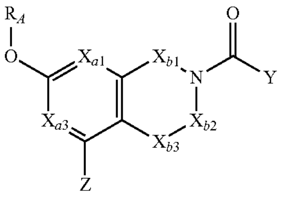

B-5

In the formulas, $L_3$ represents a leaving group, $R_A$ represents $C_1$-$C_6$ alkyl, $R_{B1}$ represents a pinacolato group, a neopentanediolato group, a catecholato group, or a bicyclo [3.3.1]nonan-9-yl group, and $X_{a1}$, $X_{a3}$, $X_{b1}$, $X_{b2}$, $X_{b3}$, Y and Z are as defined in the item [1]. Examples of the leaving group $L_3$ in the general process B include halogen atoms, an acetyloxy group, a trifluoroacetyloxy group, a methanesulfonyloxy group, a p-toluenesulfonyloxy group, a trifluoromethanesulfonyl group, and a nonafluorobutanesulfonyl group.

Step 1

A compound (B-2) can be produced through the boronation reaction of a compound (B-1) using various diborane reagents in the presence of an iridium catalyst and a ligand. The boronation reaction can be performed with reference to, for example, Angew. Chem. Int. Ed., 2021, 60, 2796-2821. Examples of the iridium catalyst and the ligand for use in boronation reaction include bis(1,5-cyclooctadiene)di-μ-methoxy diiridium(I) and 4,4'-di-tert-butyl-2,2'-bipyridine.

Examples of the solvent for use in boronation reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.) and hydrocarbon solvents (hexane, heptane, benzene, toluene, etc.) and preferably include tetrahydrofuran and hexane.

The optimum reaction temperature in performing boronation reaction is, for example, usually in the range of 0° C. to a temperature around the boiling point of the solvent, preferably in the range of 10° C. to 120° C. The reaction time is, for example, usually in the range of 30 minutes to 48 hours, preferably in the range of 1 hour to 24 hours. The obtained compound (B-2) may be isolated by a general technique and, if necessary, purified by crystallization or chromatography.

Step 2

A compound (B-3) can be produced by subjecting the compound (B-2) to oxidation reaction using an oxidizing agent, for example, hydrogen peroxide.

Examples of the solvent for use in oxidation reaction include ether solvents (tetrahydrofuran, methyltetrahydrofuran, diethyl ether, t-butyl methyl ether, diisopropyl ether, cyclopentyl methyl ether, 1,2-dimethoxyethane, 1,4-dioxane, etc.) and alcohol solvents (methanol, ethanol, isopropanol, butanol, etc.) and preferably include methanol.

The optimum reaction temperature in performing oxidation reaction is, for example, usually in the range of 0° C. to a temperature around the boiling point of the solvent, preferably in the range of 10° C. to 60° C. The reaction time is, for example, usually in the range of 30 minutes to 24 hours, preferably in the range of 1 hour to 12 hours. The obtained compound (B-3) may be isolated by a general technique and, if necessary, purified by crystallization or chromatography.

Step 3

A compound (B-5) can be produced through the etherification reaction of the compound (B-3) with a compound (B-4) having leaving group $L_3$ in the presence of a base. The etherification reaction can be performed with reference to the method of Williamson (Liebigs Ann. Chem. 1851, 77, 37-49).

Examples of the base for use in etherification reaction include tertiary amine (triethylamine, 4-methylmorpholine, N,N-diisopropylethylamine, DBU, DABCO, etc.) and inorganic bases (sodium carbonate, potassium carbonate, cesium carbonate, etc.) and preferably include inorganic bases such as potassium carbonate.

Examples of the solvent for use in etherification reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), amide solvents (N,N-dimethylformamide, N,N-dimethylacetamide, 1-methylpyrrolidin-2-one, etc.), ester solvents (ethyl acetate, isopropyl acetate, etc.), and acetonitrile and preferably include amide solvents such as 1-methylpyrrolidin-one.

The optimum reaction temperature in performing etherification reaction is, for example, usually in the range of 0° C. to a temperature around the boiling point of the solvent, preferably in the range of 10° C. to 60° C. The optimum reaction time in performing etherification reaction is, for example, usually in the range of 30 minutes to 24 hours, preferably in the range of 1 hour to 12 hours. The obtained compound (B-5) may be isolated by a general technique and, if necessary, purified by crystallization or chromatography.

General Process C

[Formula 15]

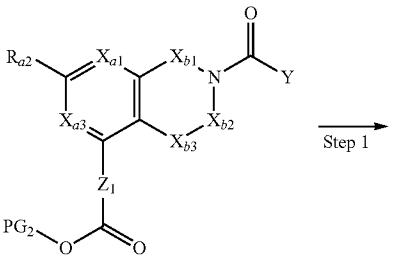

C-1

-continued

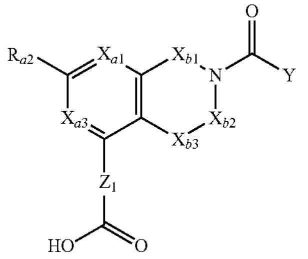

C-2

In the formulas, $PG_2$ represents a protective group for a carboxyl group, $Z_1$ represents a group selected from the group consisting of aryl, heteroaryl and alkylene optionally having an arbitrary substituent, and $X_{a1}$, $X_{a3}$, $R_{a2}$, $X_{b1}$, $X_{b2}$, $X_{b3}$ and Y are as defined in the item [1]. Examples of the protective group for a carboxyl group include $C_{1-6}$ alkyl ester (methyl ester, ethyl ester, propyl ester, butyl ester, etc.), benzyl ester, and aryl ester. A protective group other than such protective groups listed above and methods for protection and deprotection may be selected. See, for example, T. W. Greene, P. G. M. Wuts, Protective Groups in Organic Synthesis (5th edition, John Wiley & Sons 2014).

Step 1

A compound (C-2) can be produced by subjecting a compound (C-1) to deprotection reaction. When the protective group $PG_2$ is alkyl ester such as methyl ester, deprotection is preferably performed using a base. Examples of the base for use in deprotection reaction include inorganic bases (sodium hydroxide, potassium hydroxide, barium hydroxide, potassium trimethylsiloxide, etc.) and metal alkoxide (sodium methoxide, sodium tert-butoxide, sodium tert-pentoxide, potassium tert-butoxide, potassium tert-pentoxide, etc.) and preferably include inorganic bases such as potassium hydroxide. Examples of the solvent for use in deprotection reaction include ether solvents (tetrahydrofuran, methyltetrahydrofuran, diethyl ether, t-butyl methyl ether, diisopropyl ether, cyclopentyl methyl ether, 1,2-dimethoxyethane, 1,4-dioxane, etc.), alcohol solvents (methanol, ethanol, isopropanol, butanol, etc.), amide solvents (N,N-dimethylformamide, N,N-dimethylacetamide, 1-methylpyrrolidin-2-one, etc.), and water and preferably include tetrahydrofuran, methanol, and water, and mixed solvents of these solvents mixed at arbitrary ratios.

The optimum reaction temperature in performing deprotection reaction is, for example, usually in the range of 0° C. to a temperature around the boiling point of the solvent, preferably in the range of 20° C. to 120° C. The optimum reaction time in performing deprotection reaction is, for example, usually in the range of 30 minutes to 24 hours, preferably in the range of 1 hour to 6 hours. The obtained compound (C-2) may be isolated by a general technique and, if necessary, purified by crystallization or chromatography.

General Process D

[Formula 16]

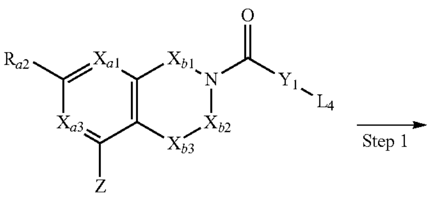

D-1

-continued

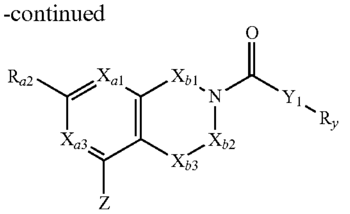

D-2

In the formulas, $L_4$ represents a leaving group, $Y_1$ represents a group selected from the group consisting of aryl, heteroaryl and alkylene optionally having a substituent, and $X_{a1}$, $X_{a3}$, $R_{a2}$, $X_{b1}$, $X_{b2}$, $X_{b3}$ and Z are as defined in the item [1]. Examples of the leaving group $L_4$ in the general process D include halogen atoms, a trifluoromethanesulfonyl group, and a nonafluorobutanesulfonyl group.

Step 1

A compound (D-2) can be produced through the coupling reaction of a compound (D-1) having leaving group $L_4$ with various nucleophilic agents in the presence of a palladium catalyst, a ligand and a base. Examples of the compound (D-1) having leaving group $L_4$ include compounds having a halogen atom as a leaving group, and compounds having a sulfonic acid-derived leaving group, which can be produced in accordance with well-known methods, for example, methods described in Comprehensive Organic Transformations, A Guide to Functional Group Preparations, 3rd Edition, (R. C. Larock) or March's Advanced Organic Chemistry: Reactions, Mechanisms, and Structure, 7th Edition (M. B. Smith, J. March), by those skilled in the art, and can be used in coupling reaction. Examples of the nucleophilic agent for use in coupling reaction include amine compounds, alcohol compounds, and compounds having a boron atom-derived group, with which the target compound can be produced by forming a C—N bond, a C—O bond, and a C—C bond, respectively. Such coupling reaction can be performed with reference to the method of Buchwald et al. (Org. Synth., 2002, 78, 23), the method of Suzuki et al. (Chem. Rev. 1995, 95, 2457-2483), and the method of Buchwald et al. (J. Am. Chem. Soc. 2001, 123, 12202-12206).

A palladium catalyst available from a commercial supplier, for example, allylpalladium(II) chloride (dimer), palladium acetate, or $Pd_2(dba)_3$, and a ligand available from a commercial supplier, for example, rac-BINAP, dppf, SPhos, or Xantphos are used in combination as the palladium catalyst and the ligand for use in coupling reaction. Alternatively, a complex of palladium and a ligand, such as SPhos Pd G3 or rac-BINAP Pd G4, is preferably used. Examples of the base for use in coupling reaction include tertiary amine (triethylamine, 4-methylmorpholine, N,N-diisopropylethylamine, DBU, DABCO, etc.), inorganic bases such as carbonate and phosphate (sodium carbonate, potassium carbonate, cesium carbonate, potassium phosphate, etc.), and metal alkoxide (sodium methoxide, sodium tert-butoxide, sodium tert-pentoxide, potassium tert-butoxide, potassium tert-pentoxide, etc.) and preferably include inorganic bases such as cesium carbonate.

Examples of the solvent for use in coupling reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), amide solvents (N,N-dimethylformamide, N,N-dimethylacetamide, 1-methylpyrrolidin-2-one, etc.), and acetonitrile and preferably include methyltetrahydrofuran and 1-methylpyrrolidin-2-one.

The optimum reaction temperature in performing coupling reaction is, for example, usually in the range of 0° C. to a temperature around the boiling point of the solvent, preferably in the range of 10° C. to 120° C. The optimum reaction time in performing coupling reaction is, for example, usually in the range of 30 minutes to 24 hours, preferably in the range of 1 hour to 12 hours. The obtained compound (D-2) may be isolated by a general technique and, if necessary, purified by crystallization or chromatography.

When the leaving group $L_4$ of the compound (D-1) is a fluorine atom, the compound (D-2) can be produced through the SNAr reaction of the compound (D-1) with various nucleophilic agents in the presence of a base. Examples of the base for use in SNAr reaction include tertiary amine (triethylamine, 4-methylmorpholine, N,N-diisopropylethylamine, DBU, DABCO, etc.), inorganic bases (sodium hydride, potassium hydride, sodium carbonate, potassium carbonate, cesium carbonate, etc.), and metal alkoxide (sodium methoxide, sodium tert-butoxide, sodium tert-pentoxide, potassium tert-butoxide, potassium tert-pentoxide, etc.) and preferably include DBU, sodium hydride, potassium carbonate, and potassium tert-butoxide.

Examples of the solvent for use in SNAr reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), hydrocarbon solvents (benzene, toluene, etc.), and amide solvents (N,N-dimethylformamide, N,N-dimethylacetamide, 1-methylpyrrolidin-2-one, etc.) and preferably include hydrocarbon solvents such as toluene, and amide solvents such as 1-methylpyrrolidin-2-one.

The optimum reaction temperature in performing SNAr reaction is, for example, usually in the range of 0° C. to a temperature around the boiling point of the solvent, preferably in the range of 20° C. to 120° C. The optimum reaction time in performing SNAr reaction is, for example, usually in the range of 30 minutes to 24 hours, preferably in the range of 1 hour to 12 hours. The obtained compound (D-2) may be isolated by a general technique and, if necessary, purified by crystallization or chromatography.

General Process E

[Formula 17]

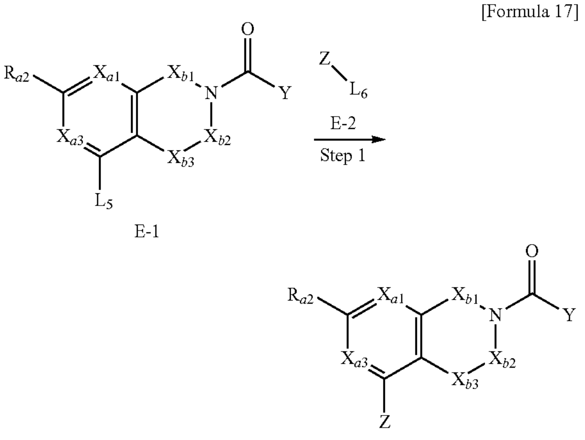

E-1

E-3

In the formulas, $L_5$ and $L_6$ each independently represent a leaving group, and $X_{a1}$, $X_{a3}$, $R_{a2}$, $X_{b1}$, $X_{b2}$, $X_{b3}$, Y and Z are as defined in the item [1]. Examples of the leaving groups $L_5$ and $L_6$ in the general process E include halogen atoms, a trifluoromethanesulfonyl group, a nonafluorobutanesulfonyl group, an acetyloxy group, a trifluoroacetyloxy group, a methanesulfonyloxy group, a p-toluenesulfonyloxy group, boron atom-derived groups (4,4,5,5-tetramethyl-1,3,2-dioxaborolane, 9-BBN, etc.), and zinc-derived groups.

Step 1

A compound (E-3) can be produced through the coupling reaction of a compound (E-1) having leaving group $L_5$ with a compound (E-2) having leaving group $L_6$ in the presence of a palladium catalyst, a ligand, and a base. When the leaving group $L_5$ of the compound (E-1) is a halogen atom, the coupling reaction may be performed after conversion of $L_5$ to another leaving group, for example, a boron atom-derived group or a zinc-derived group. Such compounds having these leaving groups can be produced in accordance with well-known methods, for example, methods described in Comprehensive Organic Transformations, A Guide to Functional Group Preparations, 3rd Edition, (R. C. Larock) or March's Advanced Organic Chemistry: Reactions, Mechanisms, and Structure, 7th Edition (M. B. Smith, J. March), by those skilled in the art, and can be used in coupling reaction. The coupling reaction can be performed with reference to the method of Suzuki et al. (Chem. Rev. 1995, 95, 2457-2483) or the method of Negishi et al. (J. Org. Chem. 1977, 42, 1821-1823).

A catalyst available from a commercial supplier can be used as the palladium catalyst for use in coupling reaction. Examples thereof include complexes formed from palladium and a ligand, i.e., 1,1'-bis(diphenylphosphino)ferrocene-palladium(II) dichloride dichloromethane complexes, 1,1'-bis(diphenylphosphino)ferrocene-palladium(II) dichloride complexes, bis(triphenylphosphine)palladium(II) dichloride, dichlorobis(tricyclohexylphosphine)palladium (II), [1,3-bis(2,6-diisopropylphenyl)imidazol-2-ylidene](3-chloropyridyl)palladium(II) dichloride, (1,3-bis(2,6-diisopropylphenyl)imidazolidene)(3-chloropyridyl)palladium(II) dichloride, and [1,3-bis(2,6-di-3-pentylphenyl)imidazol-2-ylidene](3-chloropyridyl)palladium(II) dichloride, and catalysts of Buchwald et al., for example, SPhos Pd G3, XPhos Pd G3, CPhos Pd G3, and XantPhos Pd G3, described in Org. Lett. 2014, 16, 4638-4641 or J. Am. Chem. Soc., 2014, 136, 14027-14030. Alternatively, palladium and a ligand may be used in combination. Palladium available from a commercial supplier, for example, palladium acetate, allylpalladium(II) chloride (dimer), or $Pd_2(dba)_3$, and a ligand available from a commercial supplier, for example, dppf, SPhos, or Xantphos, can be appropriately used in combination.

Examples of the base for use in coupling reaction include tertiary amine (triethylamine, 4-methylmorpholine, N,N-diisopropylethylamine, DBU, DABCO, etc.), inorganic bases such as carbonate and phosphate (sodium carbonate, potassium carbonate, cesium carbonate, potassium phosphate, etc.), and metal alkoxide (sodium methoxide, sodium tert-butoxide, sodium tert-pentoxide, potassium tert-butoxide, potassium tert-pentoxide, etc.) and preferably include inorganic bases such as cesium carbonate.

Examples of the solvent for use in coupling reaction include ether solvents (tetrahydrofuran, 2-methyltetrahydrofuran, diethyl ether, t-butyl methyl ether, diisopropyl ether, cyclopentyl methyl ether, 1,2-dimethoxyethane, 1,4-dioxane, etc.), amide solvents (N,N-dimethylformamide, N,N-dimethylacetamide, 1-methylpyrrolidine-2-one, etc.), and acetonitrile and preferably include 2-methyltetrahydrofuran and 1-methylpyrrolidine-2-one.

The optimum reaction temperature in performing coupling reaction is, for example, usually in the range of 0° C. to a temperature around the boiling point of the solvent, preferably in the range of 10° C. to 120° C. The reaction time is, for example, usually in the range of 30 minutes to 24 hours, preferably in the range of 1 hour to 12 hours. The obtained target compound (E-3) may be isolated by a general technique and, if necessary, purified by crystallization or chromatography.

<Pharmaceutical Composition>

The present invention provides a pharmaceutical composition containing the compound represented by the formula (1) of the present invention.

The pharmaceutical composition of the present invention may be formulated in accordance with a method known in the art by introducing a pharmaceutically acceptable carrier in addition to the compound represented by the formula (1) of the present invention, a salt of the compound represented by the formula (1), or a solvate of the compound or the salt. For the formulation, an excipient, a binder, a lubricant, a colorant, a corrigent, and optionally a stabilizer, an emulsifier, an absorption promoter, a surfactant, a pH adjuster, an antiseptic, an antioxidant, and the like which are usually used can be used. The formulation is performed in accordance with a routine method by blending components that are generally used as starting materials for pharmaceutical preparations.

For the formulation, the active ingredient for use in a medicament can be processed into the optimum shape or nature for a use method or a use purpose, i.e., a dosage form, by a method known in the art. Examples of the dosage form which is usually used include, but are not limited to, liquid pharmaceutical preparations (liquid agents) such as injections, suspensions, emulsions, and eye drops, and solid pharmaceutical preparations (solid preparations) such as tablets, powders, fine granules, granules, coated tablets, capsules, dry syrups, troches, and suppositories.

In order to produce, for example, a liquid agent, formulation is performed by appropriately adding pharmacologically acceptable carriers or media, specifically, pharmaceutically acceptable additives which are usually used in the pharmaceutical preparation field such as sterile water or physiological saline, a plant oil, an emulsifier, a suspending agent, a surfactant, a stabilizer, a flavor, an excipient, a vehicle, an antiseptic, and a binder, in combination to the compound represented by the formula (1) of the present invention or a salt thereof, or a solvate thereof, followed by mixing in a generally accepted unit dosage form required for pharmaceutical practice. Alternatively, a solid preparation prepared for liquid agents may be dissolved, when necessary, by the addition of an appropriate solvent, for example, sterile water or physiological saline, before administration and then subjected to administration.

Such a liquid agent may be parenterally used, for example, in the form of an injection of an antiseptic solution or suspension with water or any of other pharmaceutically acceptable liquids. Formulation can be performed, for example, by appropriately combining with pharmacologically acceptable carriers or media, specifically, sterile water or physiological saline, a plant oil, an emulsifier, a suspending agent, a surfactant, a stabilizer, a flavor, an excipient, a vehicle, an antiseptic, a binder, and the like, followed by mixing in a generally accepted unit dosage form required for pharmaceutical practice. Specifically, examples of the carrier can include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium-chain fatty acid triglyceride, polyoxyethylene hydrogenated castor oil 60, saccharose, carboxymethylcellulose, corn starch, and inorganic salts. The amount of the active ingredient in such a preparation is set so as to obtain an appropriate volume in a prescribed range.

An aseptic composition for injection can be formulated in accordance with usual pharmaceutical practice using a vehicle such as injectable distilled water.

Examples of the aqueous solution for injection include physiological saline and other isotonic liquids containing an adjuvant, for example, D-sorbitol, D-mannose, D-mannitol, and sodium chloride, which may be used in combination with an appropriate solubilizer (e.g., an alcohol, specifically ethanol, and a polyalcohol, for example, propylene glycol and polyethylene glycol) and/or a nonionic surfactant (e.g., polysorbate 80(R) and HCO-50).

Examples of the oily liquid include sesame oil and soybean oil, which may be used in combination with benzyl benzoate or benzyl alcohol as a solubilizer. Such a liquid may be blended with a buffer (e.g., phosphate buffer solutions and sodium acetate buffer solutions), a soothing agent (e.g., procaine hydrochloride), a stabilizer (e.g., benzyl alcohol and phenol), and an antioxidant. An appropriate ampule is usually packed with the prepared injection.

In order to produce, for example, a solid preparation, an excipient and optionally pharmaceutically acceptable additives which are usually used in the pharmaceutical preparation field such as a binder, a disintegrant, a lubricant, a colorant, and a corrigent are appropriately added in combination to the compound represented by the formula (1) of the present invention or a salt thereof, or a solvate thereof, and then prepared into tablets, powders, fine granules, granules, coated tablets, capsules, dry syrups, troches, suppositories, or the like by a routine method.

Examples of the pharmaceutically acceptable additive for use in such solid preparations include: animal or plant oils such as soybean oil, beef tallow, and synthetic glyceride; hydrocarbon such as liquid paraffin, squalane, and solid paraffin; ester oils such as octyl dodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylene sorbitan fatty acid ester, polyoxyethylene hydrogenated castor oil, and polyoxyethylene/polyoxypropylene block copolymers; water-soluble polymers such as hydroxyethylcellulose, polyacrylic acid, carboxyvinyl polymers, polyethylene glycol, polyvinylpyrrolidone, and methylcellulose; lower alcohols such as ethanol and isopropanol; polyhydric alcohols such as glycerin, propylene glycol, dipropylene glycol, and sorbitol; sugars such as lactose, lactose hydrate, fructose, and sucrose; inorganic powders such as silicic anhydride, aluminum magnesium silicate, and aluminum silicate; and purified water.

Examples of the excipient include sugars (e.g., lactose, lactose hydrate, fructose, and sucrose), sugar alcohols (e.g., mannitol), starch (corn starch, potato starch, wheat starch, rice starch, pregelatinized starch, gelatinized starch, etc.), cellulose (e.g., crystalline cellulose), and inorganic salts (e.g., calcium silicate, anhydrous calcium hydrogen phosphate, and precipitated calcium carbonate).

Examples of the binder include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, and polypropylene glycol/polyoxyethylene block copolymers.

Examples of the disintegrant include croscarmellose sodium, carmellose sodium, hydroxypropylcellulose, carmellose, carmellose calcium, methylcellulose, crystalline cellulose, sodium lauryl sulfate, povidone, and polysorbate.

Examples of the lubricant include magnesium stearate, calcium stearate, talc, sucrose fatty acid ester, sodium stearyl fumarate, and hydrogenated oils.

A colorant whose addition to medicaments is accepted is used. Cacao powder, menthol, aromatic powder, peppermint oil, camphol, powdered cinnamon bark, or the like is used as the corrigent.

These tablets or granules may be sugar-coated or appropriately coated in other manners, if necessary. In order to produce a liquid agent such as a syrup or a preparation for injection, formulation is performed in accordance with a routine method by adding a pH adjuster, a dissolving agent, a tonicity agent, and the like and optionally a solubilizer, a stabilizer, and the like to the compound according to the present invention or a pharmacologically acceptable salt thereof.

Administration is preferably parenteral administration, though the administration method is not limited to parenteral administration. Specifically, examples of the parenteral administration include injection dosage forms, transnasal administration dosage forms, transpulmonary administration dosage forms, and percutaneous administration forms. Examples of the injection dosage form include intravenous injection, intramuscular injection, intraperitoneal administration, and subcutaneous administration, which can attain systemic or local administration.

The administration method can be appropriately selected depending on the age and symptoms of a patient. The dose of the pharmaceutical composition containing the compound represented by the formula (1) of the present invention or a salt thereof, or a solvate thereof produced by the method of the present invention may be selected, for example, in the range of 0.0001 mg to 1000 mg per kg body weight per dose. Alternatively, the dose can be selected, for example, in the range of 0.001 to 100000 mg/body per patient, though the dose is not necessarily limited to these numeric values. The dose and the administration method vary depending on the body weight, age, symptoms, etc. of a patient and can be appropriately selected by those skilled in the art.

In an aspect, the compound of the present invention can be used for activating Nrf2 or for inhibiting Keap1 and activating Nrf2.

In an aspect, the pharmaceutical composition of the present invention can be used for treating or preventing, for example, a disease in a subject described in Nature Reviews Drug Discovery, 2019, 18, p. 295-317, more specifically, neurodegenerative disease such as Alzheimer's disease, Parkinson's disease, Huntington's disease, Friedreich's ataxia, or amyotrophic lateral sclerosis, lung disease such as idiopathic pulmonary fibrosis, acute respiratory distress syndrome, chronic obstructive pulmonary disease, pulmonary arterial hypertension, or asthma, kidney disease such as chronic kidney disease or acute kidney injury, ophthalmic disease such as uveitis, glaucoma, or age-related macular degeneration, liver disease such as nonalcoholic steatohepatitis, immunological or inflammatory disease such as multiple sclerosis, rheumatoid arthritis, or ulcerative colitis, and cell proliferative disease exemplified by solid cancer such as head and neck cancer (throat cancer, voice box cancer, tongue cancer, etc.), esophageal cancer, stomach cancer, large intestinal cancer (appendix cancer, colon cancer, rectal cancer, etc.), lung cancer (small-cell cancer, non-small cell cancer, etc.), thyroid gland cancer, breast cancer, gallbladder cancer, pancreatic cancer, liver cancer, prostate cancer, ovary cancer, uterine cancer (endometrial cancer, uterine cervical cancer, etc.), testicle cancer, renal cell cancer, urinary bladder cancer, renal pelvis/ureter cancer, malignant melanoma, and skin cancer, or cancer of blood or lymph such as leukemia (acute myeloid leukemia, acute lymphoid leukemia, chronic myeloid leukemia, chronic lymphoid leukemia, etc.), malignant lymphoma (Hodgkin's disease, non-Hodgkin lymphoma, etc.), multiple myeloma, and myelodysplastic syndrome in a subject.

In the present specification, the "subject" includes a mammal. The mammal is preferably a human.

EXAMPLES

The contents of the present invention will be further described with reference to Examples and Reference Examples given below. All starting materials and reagents were obtained from commercial suppliers or synthesized by use of methods known in the art. Room temperature (rt) refers to 5 to 35° C. The HPLC purification of compounds was performed using AutoPurification HPLC/MS System (manufactured by Waters Corp.) and Trilution (manufactured by Gilson Inc.). $^1$H-NMR spectra were measured with or without Me4Si as an internal standard using MR400 OneNMR probe (400 MHz, Agilent technology), AVANCE III HD 400 SMART-BBFO probe (400 MHz, Bruker), ECP400 (400 MHz, JEOL), AVANCE III HD 400 SMART-BBFO probe (400 MHz, Bruker), MR400 OneNMR probe (400 MHz, Agilent technology), or AVANCE NEO 400 iProbe (400 MHz, Bruker) (s=singlet, brs=broad singlet, d=doublet, t=triplet, q=quartet, dd=double doublet ddd=double double doublet, dt=double triplet, td=triple doublet, m=multiplet). NMR data was indicated by ppm (parts per million, δ). Mass spectral data was obtained using a single quadrupole mass spectrometer (LCMS-2020) with ultrahigh-performance liquid chromatography (Nexera UC or Nexera) manufactured by Shimadzu Corp. or a single quadrupole mass spectrometer (SQD or SQD2) with Acquity ultrahigh-performance liquid chromatography (UPLC or UPLC I-Class) manufactured by Waters Corp. Two retention times described respectively denote the retention times of rotational isomers. Microwave irradiation was performed using Initiator™ (manufactured by Biotage Japan Ltd.).

Analysis Condition A
- Apparatus: Nexera/2020
- Column used: Ascentis Express C18 2.1 mm I.D.×50 mm·L, 2.7 μm
- Column temperature: 35° C.
- Mobile phase and gradient: A) 0.05% TFA, $CH_3CN$, B) 0.05% TFA, $H_2O$, A/B=5/95→100/0 (1.5 min)→100/0 (0.5 min)
- Flow rate: 1 mL/min
- Detection wavelength (PDA total): 210-400 nm Analysis Condition B
- Apparatus: Nexera UC/2020
- Column used: XSelect CSH C18 2.1 mm I.D.×50 mm·L, 2.5 μm
- Column temperature: 35° C.
- Mobile phase and gradient: A) 0.1% FA, $CH_3CN$, B) 0.1% FA, $H_2O$, A/B=5/95→100/0 (1.75 min)→100/0 (1.25 min)
- Flow rate: 1 mL/min
- Detection wavelength (PDA total): 210-400 nm Analysis Condition C
- Apparatus: Nexera 2020
- Column used: Meteoric Core C18 2.1 mm I.D.×50 mm·L, 2.7 μm
- Column temperature: 35° C.

Mobile phase and gradient: A) 0.05% TFA, $CH_3CN$, B) 0.05% TFA, $H_2O$, A/B=5/95→100/0 (1.5 min)→100/0 (0.5 min)
Flow rate: 1 mL/min
Detection wavelength (PDA total): 210-400 nm Analysis Condition D
Apparatus: Acquity SQD/SQD2
Column used: Ascentis Express C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=5/95→100/0 (1.0 min)→100/0 (0.4 min)
Flow rate: 1 mL/min
Detection wavelength (PDA total): 210-400 nm Analysis Condition E
Apparatus: Acquity SQD/SQD2
Column used: Ascentis Express C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=40/60→100/0 (1.0 min)→100/0 (0.4 min)
Flow rate: 1 mL/min
Detection wavelength (PDA total): 210-400 nm Analysis Condition F
Apparatus: Acquity SQD/SQD2
Column used: Ascentis Express C18 2.1 mm I.D.×50 mm·L, 5 μm
Column temperature: 35° C.
Mobile phase and gradient: A) MeOH, $B)_{10}$ mM AA, $H_2O$, A/B=5/95→100/0 (1.0 min)→100/0 (0.4 min)
Flow rate: 0.9 mL/min
Detection wavelength (PDA total): 210-400 nm Analysis Condition G
Apparatus: Nexera/2020
Column used: Ascentis Express C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=5/95→100/0 (1.5 min)→100/0 (0.5 min)
Flow rate: 1 mL/min
Detection wavelength (PDA total): 210-400 nm Analysis Condition H
Apparatus: Nexera/2020
Column used: Meteoric Core C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=5/95→100/0 (1.5 min)→100/0 (0.5 min)
Flow rate: 1 mL/min
Detection wavelength (PDA total): 210-400 nm Analysis Condition I
Apparatus: Nexera/2020
Column used: Ascentis Express C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=50/50→100/0 (1.0 min)→100/0 (1.0 min)
Flow rate: 1 mL/min
Detection wavelength (PDA total): 210-400 nm Analysis Condition J
Apparatus: Nexera/2020
Column used: Meteoric Core C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=50/50→100/0 (1.0 min)→100/0 (1.0 min)
Flow rate: 1 mL/min
Detection wavelength (PDA total): 210-400 nm Analysis Condition K
Apparatus: Acquity SQD
Column used: Ascentis Express C18 2.1 mm I.D.×50 mm·L, 2.7 μm
Column temperature: 35° C.
Mobile phase and gradient: A) 0.05% TFA, $CH_3CN$, B) 0.05% TFA, $H_2O$, A/B=5/95→100/0 (1.0 min)→100/0 (0.4 min)
Flow rate: 1 mL/min
Detection wavelength (PDA total): 210-400 nm Analysis Condition L
Apparatus: Nexera/2020
Column used: Ascentis Express C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=5/95→100/0 (1.5 min)→100/0 (0.7 min)
Flow rate: 1 mL/min
Detection wavelength (PDA total): 210-400 nm Analysis Condition M
Apparatus: Nexera/2020
Column used: Ascentis Express C18 2.1 mm I.D.×50 mm·L, 5 μm
Column temperature: 35° C.
Mobile phase and gradient: A) 0.1% FA, $CH_3CN$, B) 0.1% FA, $H_2O$, A/B=5/95→100/0 (4.5 min)→100/0 (0.5 min)
Flow rate: 1 mL/min
Detection wavelength (PDA total): 210-400 nm Analysis Condition N
Apparatus: Nexera/2020
Column used: Speed Core C18 2.1 mm I.D.×50 mm·L, 2.7 μm
Column temperature: 35° C.
Mobile phase and gradient: A) 0.1% FA, $CH_3CN$, B) 0.1% FA, $H_2O$, A/B=5/95→100/0 (1.5 min)→100/0 (0.5 min)
Flow rate: 1 mL/min
Detection wavelength (PDA total): 210-400 nm Analysis Condition O
Apparatus: Acquity SQD
Column used: Ascentis Express C18 2.1 mm I.D.×50 mm·L, 2.7 μm
Column temperature: 35° C.
Mobile phase and gradient: A) 0.05% FA, $CH_3CN$, B) 0.05% FA, $H_2O$, A/B=5/95→100/0 (1.0 min)→100/0 (0.4 min)
Flow rate: 1 mL/min
Detection wavelength (PDA total): 210-400 nm Analysis Condition P
Apparatus: Nexera/2020
Column used: Ascentis Express C18 2.1 mm I.D.×50 mm·L, 2.7 μm
Column temperature: 35° C.
Mobile phase and gradient: A) 0.05% TFA, $CH_3CN$, B) 0.05% TFA, $H_2O$, A/B=50/50→100/0 (1.0 min) →100/0 (1.0 min)
Flow rate: 1 mL/min
Detection wavelength (PDA total): 210-400 nm Analysis Condition Q Apparatus: Nexera/2020

Column used: Kinetex 1.7u C18 2.1 mm I.D.×50 mm·L, 1.7 μm

Column temperature: 35° C.

Mobile phase and gradient: A) 0.05% TFA, $CH_3CN$, B) 0.05% TFA, $H_2O$, A/B=5/95→0/100 (1.5 min)→0/100 (0.5 min)

Flow rate: 1 mL/min

Detection wavelength (PDA total): 210-400 nm

Analysis Condition R

Apparatus: Shimadzu LCMS-2020

Column used: Shim-pack XR-ODS 3.0 mm·D×50 mm·L, 2.2 μm

Column temperature: 40° C.

Mobile phase and gradient: A) 0.05% TFA, $CH_3CN$, B) 0.05% TFA, $H_2O$, A/B=5/95→95/5 (2.0 min)→95/5 (0.7 min)

Flow rate: 1.2 mL/min

Detection wavelength (PDA total): 190-400 nm

Analysis Condition S

Apparatus: Shimadzu LCMS-2020

Column used: Shim-pack XR-ODS 2.1 mm·D×50 mm·L, 2.6 μm

Column temperature: 40° C.

Mobile phase and gradient: A) 0.05% TFA, $CH_3CN$, B) 0.05% TFA, $H_2O$, A/B=5/95→95/5 (2.0 min)→95/5 (0.7 min)

Flow rate: 1 mL/min

Detection wavelength (PDA total): 190-400 nm

Analysis Condition T

Apparatus: Shimadzu LCMS-2020

Column used: Halo C18 2.1 mm·D×30 mm·L, 2.0 μm

Column temperature: 40° C.

Mobile phase and gradient: A) 0.05% TFA, $CH_3CN$, B) 0.05% TFA, $H_2O$, A/B=5/95→100/0 (0.7 min)→100/0 (0.25 min)

Flow rate: 0.8 mL/min

Detection wavelength (PDA total): 190-400 nm

Analysis Condition U

Apparatus: Shimadzu LCMS-2020

Column used: InertCore C18 2.1 mm·D×50 mm·L, 2.6 μm

Column temperature: 40° C.

Mobile phase and gradient: A) 0.05% TFA, $CH_3CN$, B) 0.05% TFA, $H_2O$, A/B=5/95→100/0 (L min)→100/0 (0.5 min)

Flow rate: 1 mL/min

Detection wavelength (PDA total): 190-400 nm

Analysis Condition V

Apparatus: Shimadzu LCMS-2020

Column used: Shim-pack XR-ODS 3.0 mm·D×50 mm·L, 2.2 μm

Column temperature: 40° C.

Mobile phase and gradient: A) 0.05% TFA, $CH_3CN$, B) 0.05% TFA, $H_2O$, A/B=5/95→100/0 (1.1 min)→100/0 (0.6 min)

Flow rate: 1.2 mL/min

Detection wavelength (PDA total): 190-400 nm

Analysis Condition W

Apparatus: Shimadzu LCMS-2020

Column used: XSelect HSS T3 3.0 mm·D×50 mm·L, 2.5 μm

Column temperature: 40° C.

Mobile phase and gradient: A) 0.1% FA, $CH_3CN$, B) 0.1% TFA, $H_2O$, A/B=5/95→95/5 (1.1 min)→95/5 (0.6 min)

Flow rate: 1.2 mL/min

Detection wavelength (PDA total): 190-400 nm

Analysis Condition X

Apparatus: Shimadzu LCMS-2020

Column used: Shim-pack XR-ODS 3.0 mm·D×50 mm·L, 2.2 μm

Column temperature: 40° C.

Mobile phase and gradient: A) 0.1% FA, $CH_3CN$, B) 0.1% FA, $H_2O$, A/B=5/95→95/5 (1.1 min)→95/5 (0.6 min)

Flow rate: 1.2 mL/min

Detection wavelength (PDA total): 190-400 nm

Analysis Condition Y

Apparatus: Shimadzu LCMS-2020

Column used: CORTECS C18 2.1 mm·D×50 mm·L, 2.7 μm

Column temperature: 40° C.

Mobile phase and gradient: A) 0.1% FA, $CH_3CN$, B) 0.1% FA, $H_2O$, A/B=5/95→100/0 (1.2 min)→100/0 (0.5 min)

Flow rate: 1 mL/min

Detection wavelength (PDA total): 190-400 nm

Analysis Condition Z

Apparatus: Shimadzu LCMS-2020

Column used: Kinetex EVO C18 2.1 mm·D×50 mm·L, 2.6 μm

Column temperature: 40° C.

Mobile phase and gradient: A) $CH_3CN$, B) 6.5 mM $NH_4HCO_3$, $H_2O$, A/B=10/90-95/5 (1.1 min)→95/5 (0.5 min)

Flow rate: 1 mL/min

Detection wavelength (PDA total): 190-400 nm

Analysis Condition AA

Apparatus: Shimadzu LCMS-2020

Column used: Shim-pack XR-ODS 3.0 mm·D×50 mm·L, 2.2 μm

Column temperature: 40° C.

Mobile phase and gradient: A) 0.05% TFA, $CH_3CN$, B) 0.05% TFA, $H_2O$, A/B=30/70→80/20 (3.8 min)→80/20 to 100/0 (0.3 min)→100/0 (0.5 min)

Flow rate: 1.2 mL/min

Detection wavelength (PDA total): 190-400 nm

Analysis Condition AB

Apparatus: Shimadzu LCMS-2020

Column used: Waters T3 4.6 mm·D×100 mm·L, 3.0 μm

Column temperature: 40° C.

Mobile phase and gradient: A) 0.1% FA, $CH_3CN$, B) 0.1% FA, $H_2O$, A/B=5/95→100/0 (1.2 min)→100/0 (1.8 min)

Flow rate: 1.2 mL/min

Detection wavelength (PDA total): 190-400 nm

Analysis Condition AC

Apparatus: Shimadzu LCMS-2020

Column used: Kinetex XB—C18 3.0 mm·D×30 mm·L, 1.7 μm

Column temperature: 40° C.

Mobile phase and gradient: A) 0.1% FA, $CH_3CN$, B) 0.1% FA, $H_2O$, A/B=5/95→100/0 (1.2 min)→100/0 (1.8 min)

Flow rate: 1.2 mL/min

Detection wavelength (PDA total): 190-400 nm

Analysis Condition AD

Apparatus: Shimadzu LCMS-2020

Column used: halo-C18 3.0 mm·D×30 mm·L, 2.0 μm

Column temperature: 40° C.

Mobile phase and gradient: A) 0.1% FA, $CH_3CN$, B) 0.1% FA, $H_2O$, A/B=5/95→100/0 (1.5 min)→100/0 (1.5 min)

Flow rate: 1.5 mL/min

Detection wavelength (PDA total): 190-400 nm

Analysis Condition AE

Apparatus: Shimadzu LCMS-2020

Column used: Halo 90A C18 3.0 mm·D×30 mm·L, 2.0 μm

Column temperature: 40° C.

Mobile phase and gradient: A) 0.05% TFA, $CH_3CN$, B) 0.05% TFA, $H_2O$, A/B=5/95→100/0 (1.5 min)→100/0 (1.5 min)

Flow rate: 1.5 mL/min

Detection wavelength (PDA total): 190-400 nm

Analysis Condition AF

Apparatus: Nexera/2020

Column used: Ascentis Express C18 2.1 mm I.D.×50 mm·L, 5 μm

Column temperature: 35° C.

Mobile phase and gradient: A) 0.1% FA, $CH_3CN$, B) 0.1% FA, $H_2O$, A/B=5/95→100/0 (4.5 min)→100/0 (0.5 min)

Flow rate: 1 mL/min

Detection wavelength (PDA total): 210-400 nm

Analysis Condition AG

Apparatus: Acquity SQD/SQD2

Column used: Ascentis Express C18 2.1 mm I.D.×50 mm·L, 2.7 μm

Column temperature: 35° C.

Mobile phase and gradient: A) 0.1% FA, $CH_3CN$, B) 0.1% FA, $H_2O$, A/B=5/95→100/0 (4.5 min)→100/0 (0.5 min)

Flow rate: 1 mL/min

Detection wavelength (PDA total): 210-400 nm

Analysis Condition AH

Apparatus: Shimadzu LCMS-2020

Column used: Shim-pack XR-ODS 3 mm×5 cm, 2.2 μm

Column temperature: 40° C.

Mobile phase and gradient: A) 0.05% TFA, $CH_3CN$, B) 0.05% TFA, $H_2O$, A/B=5/95→100/0 (2.2 min)→100/0 (1.0 min)

Flow rate: 1 mL/min

Detection wavelength (PDA total): 220±4 nm

Analysis Condition AI

Apparatus: Shimadzu LCMS-2020

Column used: Shim-pack XR-ODS 2.2 μm 3 mm×5 cm

Column temperature: 40° C.

Mobile phase and gradient: A) 0.05% TFA, $CH_3CN$, B) 0.05% TFA, $H_2O$, A/B=5/95→100/0 (1.2 min)→100/0 (1.0 min)

Flow rate: 1 mL/min

Detection wavelength (PDA total): 254±4 nm

Compound 1-7

4-[3-[2,6-Dichloro-4-(2,2-difluoro-5-azaspiro[2.3]hexan-5-yl)benzoyl]-2,4-dihydro-1,3-benzoxazin-8-yl]-5-fluoro-2-(3-oxa-8-azabicyclo[3.2.1]octan-8-yl)benzoic acid First Step Compound A9 tert-Butyl N-[(3-bromo-2-hydroxyphenyl)methyl]carbamate

[Formula 18]

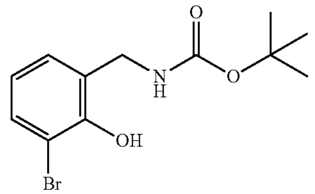

A solution of 3-bromo-2-hydroxybenzaldehyde (5.00 g, 24.9 mmol) and tert-butyl carbamate (8.74 g, 74.6 mmol) in acetonitrile (35.0 mL) was cooled to 0° C. Triethylsilane (11.9 mL, 74.6 mmol) and trifluoroacetic acid (3.81 mL, 49.7 mmol) were added to the reaction solution. The mixture was stirred at 35° C. for 5 hours and then cooled to room temperature. After stirring at room temperature for 15 hours, water was added to the reaction solution, and the mixture was stirred for 1 hour. Then, water was further added thereto, and the mixture was stirred for 30 minutes. The reaction solution was filtered, and the obtained solid was washed with acetonitrile/water (1/2). The solid was further washed with heptane and dried under reduced pressure to obtain the title compound (88%, 6.60 g).

LCMS: m/z 300[M−H]$^-$

HPLC retention time: 1.16 min (analysis condition G)

Second Step

Compound A10 tert-Butyl 8-bromo-2,4-dihydro-1,3-benzoxazine-3-carboxylate

[Formula 19]

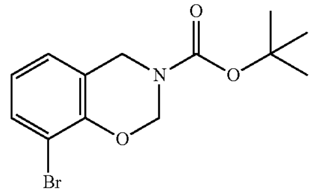

To a solution of tert-butyl N-[(3-bromo-2-hydroxyphenyl)methyl]carbamate (5.00 g, 16.6 mol) in acetonitrile (30.0 mL), a 36% aqueous formaldehyde solution (5.06 mL, 66.2 mmol) and formic acid (5.08 mL, 132 mmol) were added, and the mixture was stirred at 56° C. for 7 hours. The reaction solution was cooled to 25° C. Water was added thereto, and the mixture was stirred for 30 minutes. Water was further added thereto, and the mixture was stirred for 30 minutes. The reaction solution was filtered, and the obtained solid was washed with acetonitrile/water (1/2). The solid was dried under reduced pressure to obtain the title compound (81%, 4.20 g).

LCMS: m/z 214[M−Boc+H]$^+$

HPLC retention time: 1.31 min (analysis condition G)

Third Step

Compound A4

4-Bromo-5-fluoro-2-(3-oxa-8-azabicyclo[3.2.1]octan-8-yl)benzoic acid

[Formula 20]

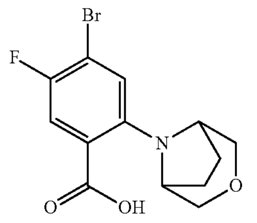

To a suspension of 4-bromo-2,5-difluorobenzoic acid (3.00 g, 12.7 mmol) and 3-oxa-8-azabicyclo[3.2.1]octane hydrochloride (2.46 g, 16.5 mmol) in tetrahydrofuran (6.00 mL), a solution of 1 M lithium(bistrimethylsilyl)amide in tetrahydrofuran (50.6 mL, 50.6 mmol) was added at room temperature over 12 minutes. The reaction solution was stirred at room temperature for 5.5 hours and then left standing at room temperature for 15 hours. 2 M hydrochloric acid was added to the reaction solution, followed by extraction with ethyl acetate. The aqueous layer was subjected to extraction with ethyl acetate again, and two organic layers were combined and washed with a 20% aqueous ammonium chloride solution and a 15% aqueous sodium chloride solution. The washed organic layer was concentrated to obtain the title compound as a crude product.

LCMS: m/z 330[M+H]$^+$

HPLC retention time: 0.61 min (analysis condition D)

Fourth Step

Compound A5

Methyl 4-bromo-5-fluoro-2-(3-oxa-8-azabicyclo[3.2.1]octan-8-yl)benzoate

[Formula 21]

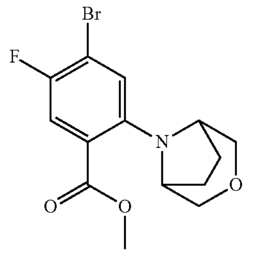

To a solution of 4-bromo-5-fluoro-2-(3-oxa-8-azabicyclo[3.2.1]octan-8-yl)benzoic acid (4.18 g, 12.7 mmol) in N,N-dimethylformamide (21.0 mL), potassium carbonate (2.10 g, 15.2 mmol) and iodomethane (1.58 mL, 25.3 mmol) were added, and the mixture was stirred at room temperature for 30 minutes. A 20% aqueous ammonium chloride solution and water were added to the reaction solution, followed by extraction with ethyl acetate. The organic layer was washed with a 20% aqueous ammonium chloride solution and concentrated. Methanol was added to the obtained crude product, and the mixture was heated to 60° C., then cooled to room temperature, and stirred for 30 minutes. Water was added to the reaction solution, and the mixture was stirred for 1 hour. Then, water was further added thereto, and the mixture was stirred for 30 minutes. The reaction solution was filtered, and the obtained solid was then washed with methanol/water (1/1) and dried under reduced pressure to obtain the title compound (55%, 2.38 g).

LCMS: m/z 344[M+H]$^+$

HPLC retention time: 1.18 min (analysis condition G)

Fifth Step

Compound A6 tert-Butyl 8-[2-fluoro-4-methoxycarbonyl-5-(3-oxa-8-azabicyclo[3.2.1]octan-8-yl)phenyl]-2,4-dihydro-1,3-benzoxazine-3-carboxylate

[Formula 22]

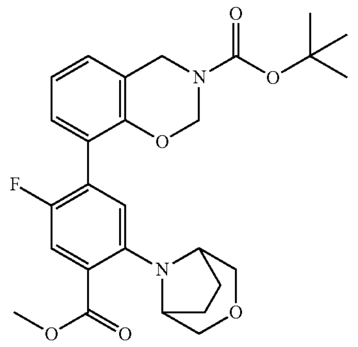

A solution of methyl 4-bromo-5-fluoro-2-(3-oxa-8-azabicyclo[3.2.1]octan-8-yl)benzoate (1.21 g, 3.50 mmol) in tetrahydrofuran (5.30 mL) was cooled to −10° C. A 2 M solution of isopropyl magnesium chloride in tetrahydrofuran (1.91 mL, 3.82 mmol) was added thereto, and the mixture was stirred for 1 hour. A 2 M solution of zinc(II) chloride in 2-methyltetrahydrofuran (0.955 mL, 1.91 mmol) was added to the reaction solution. tert-Butyl 8-bromo-2,4-dihydro-1,3-benzoxazine-3-carboxylate (1.00 g, 3.18 mmol) and SPhos Pd G3 (0.0250 g, 0.0320 mmol) were added to the reaction solution, and the mixture was warmed to 45° C. and stirred for 90 minutes. The reaction solution was cooled to room temperature, and ethyl acetate and an aqueous ammonium chloride solution were added thereto, followed by extraction with ethyl acetate. The organic layer was washed with an aqueous N-acetylcysteine solution and an aqueous sodium chloride solution and concentrated to obtain a crude product. Ethanol was added to the obtained crude product, which was dissolved by warming to 80° C., and the solution was then cooled to room temperature. Heptane was added to the obtained solution, and the mixture was cooled to 0° C. A solid obtained by filtration was washed with ethanol/heptane (1/2) and dried under reduced pressure to obtain the title compound (73%, 1.16 g).

LCMS: m/z 499[M+H]$^+$

HPLC retention time: 1.40 min (analysis condition G)

Sixth Step

Compound A7

Methyl 4-(3,4-dihydro-2H-1,3-benzoxazin-8-yl)-5-fluoro-2-(3-oxa-8-azabicyclo[3.2.1]octan-8-yl)benzoate dihydrochloride

[Formula 23]

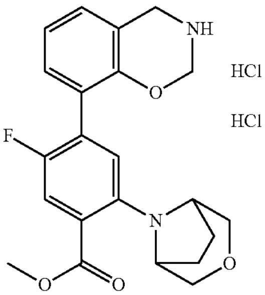

To tert-butyl 8-[2-fluoro-4-methoxycarbonyl-5-(3-oxa-8-azabicyclo[3.2.1]octan-8-yl)phenyl]-2,4-dihydro-1,3-benzoxazine-3-carboxylate (10.0 g, 20.1 mmol) in acetonitrile (100 mL), a 4 M solution of hydrochloric acid in ethyl acetate (25.1 mL, 100 mmol) was added, and the mixture was stirred at room temperature for 2 hours. The obtained solid was collected by filtration to obtain the title compound (76%, 7.16 g) as crystals.

LCMS: m/z 399[M+H]$^+$

HPLC retention time: 0.75 min (analysis condition G)

Seventh Step

Compound A2

4-Bromo-2,6-dichlorobenzoyl Chloride

[Formula 24]

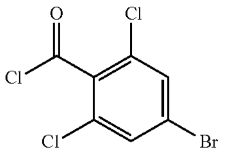

To a solution of 4-bromo-2,6-dichlorobenzoic acid (45.5 g, 169 mmol) in toluene (241 mL), thionyl chloride (24.5 mL, 337 mmol) and N,N-dimethylformamide (0.261 mL, 3.37 mmol) were added, and the mixture was stirred at 70° C. for 7 hours. The reaction solution was cooled to room temperature and concentrated, and the obtained residue was purified by silica gel column chromatography (hexane/ethyl acetate) to obtain the title compound (99%, 48.0 g).

HPLC retention time: 1.48 min (analysis condition G)

$^1$H-NMR (400 MHz, $CDCl_3$) δ 7.56 (s, 2H)

Eighth Step

Compound A

Methyl 4-[3-(4-bromo-2,6-dichlorobenzoyl)-2,4-dihydro-1,3-benzoxazin-8-yl]-5-fluoro-2-(3-oxa-8-azabicyclo[3.2.1]octan-8-yl)benzoate

[Formula 25]

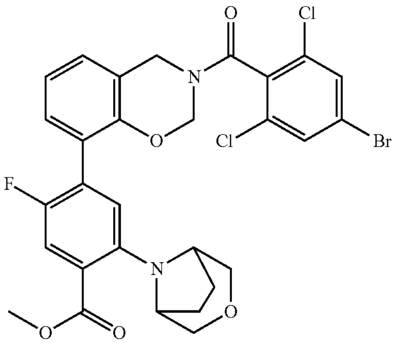

To a solution of methyl 4-(3,4-dihydro-2H-1,3-benzoxazin-8-yl)-5-fluoro-2-(3-oxa-8-azabicyclo[3.2.1]octan-8-yl)benzoate dihydrochloride (9.22 g, 19.6 mmol) in toluene (92.0 mL), 4-bromo-2,6-dichlorobenzoyl chloride (7.33 g, 25.4 mmol) and pyridine (11.1 mL, 137 mmol) were added, and the mixture was stirred at 70° C. for 12 hours. Ethyl acetate and 1 M hydrochloric acid were added to the reaction solution for extraction. The organic layer was washed with a 50% saturated aqueous solution of sodium bicarbonate and a 50% saturated aqueous solution of sodium chloride and dried over anhydrous magnesium sulfate. The desiccant was filtered off. Then, the filtrate was concentrated, and the obtained residue was triturated with hexane to obtain the title compound (48%, 6.06 g).

LCMS: m/z 649[M+H]$^+$

HPLC retention time: 1.42 min (analysis condition G)

Ninth Step

Compound 1-7

4-[3-[2,6-Dichloro-4-(2,2-difluoro-5-azaspiro[2.3]hexan-5-yl)benzoyl]-2,4-dihydro-1,3-benzoxazin-8-yl]-5-fluoro-2-(3-oxa-8-azabicyclo[3.2.1]octan-8-yl)benzoic acid

[Formula 26]

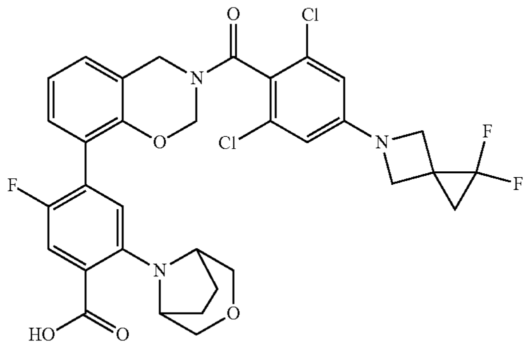

A suspension of compound A (30.0 mg, 0.0460 mmol), 2,2-difluoro-5-azaspiro[2.3]hexane hydrochloride (14.4 mg, 0.0920 mmol), rac-BINAP Pd G4 (2.32 mg, 0.00231 mmol) and cesium carbonate (45.1 mg, 0.138 mmol) in 1,4-dioxane (0.231 mL) was stirred at 110° C. for 1.5 hours. The reaction solution was cooled to room temperature. Methanol (0.230 mL) and an 8 M aqueous potassium hydroxide solution (0.0575 mL, 0.460 mmol) were added thereto, and the mixture was stirred at room temperature for 1 hour and then stirred at 50° C. for 1 hour. An aqueous formic acid solution was added to the reaction solution, and the mixture was then purified by HPLC (acetonitrile/water, 0.1% formic acid) to obtain the title compound (83%, 25.7 mg).

LCMS: m/z 674[M+H]$^+$

HPLC retention time: 1.61 min and 1.64 min (analysis condition B)

Compound 1-33

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound CP5

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl) benzoate

[Formula 27]

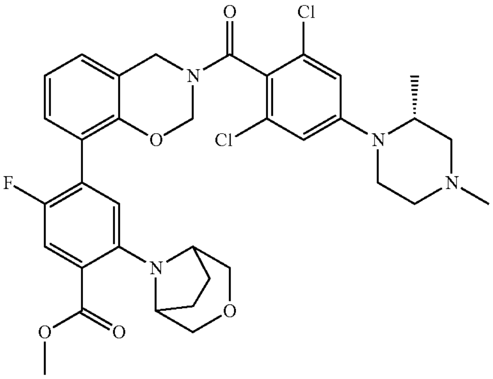

A solution of compound A (20.2 g, 31.1 mmol), (3R)-1,3-dimethylpiperazine (4.61 g, 40.4 mmol), rac-BINAP Pd G4 (938 mg, 0.932 mmol) and cesium carbonate (30.4 g, 93.0 mmol) in 1,4-dioxane (202 mL) was stirred at 80° C. for 7.5 hours. (3R)-1,3-Dimethylpiperazine (2.48 g, 21.7 mmol) was further added thereto, and the reaction solution was stirred at 100° C. for 49 hours. The reaction solution was filtered through celite and washed with ethyl acetate. The filtrate was washed with a 15% aqueous sodium chloride solution. The organic layer was concentrated, and the obtained residue was purified by silica gel column chromatography (hexane/ethyl acetate/methanol) to obtain the title compound (75%, 15.9 g).

LCMS: m/z 683[M+H]$^+$

HPLC retention time: 0.89 min (analysis condition G)

Second Step

Compound 1-33

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 28]

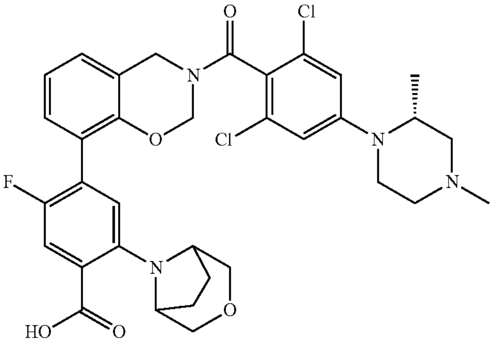

To a solution of methyl 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate (18.6 g, 27.2 mmol) in 1-methylpyrrolidin-one (186 mL), an 8 M aqueous palladium hydroxide solution (11.9 mL, 95.0 mmol) was added, and the mixture was stirred at 60° C. for 2 hours. An aqueous formic acid solution was added to the reaction solution, and the mixture was purified by reverse phase column chromatography (acetonitrile/water, 0.1% formic acid) to obtain the title compound (85%, 15.4 g).

LCMS: m/z 669[M+H]$^+$

HPLC retention time: 0.99 min and 1.04 min (analysis condition B)

Compounds shown in Table 1-1 were synthesized by the same operation as in the ninth step of compound 1-7 using documented or commercially available amine shown in Table 1-2 and compound A. However, a toluene solution was used instead of the 1,4-dioxane solution in the synthesis of compounds 1-1, 1-5, 1-34, 1-41, and 1-42; a 1-methylpyrrolidin-one solution was used in the synthesis of compounds 1-6, 1-16, 1-17, 1-43, and 1-45; and a solution of 1-methylpyrrolidin-2-one:water=10:1 was used in the synthesis of compounds 1-19, 1-20, and 1-44. Xantphos Pd G4 was used instead of rac-BINAP Pd G4 in the synthesis of compounds 1-32 and 1-46.

TABLE 1-1

| Compound No. | Structure | Compound Name | Analysis conditions | HPLC retention time (min) | m/z [M + H] |
|---|---|---|---|---|---|
| 1-2 | 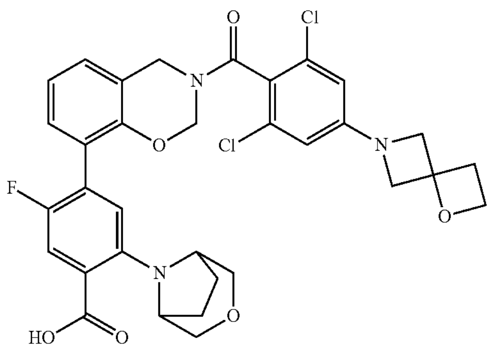 [SMILES: O=C(O)c1cc(F)c(-c2cccc3c2OCN(C(=O)c2c(Cl)cc(N4CC5(CCO5)C4)cc2Cl)C3)cc1N1C2CCC1COC2] | 4-[3-[2,6-Dichloro-4-(1-oxa-6-azaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.58, 1.59 | 654 |
| 1-3 | 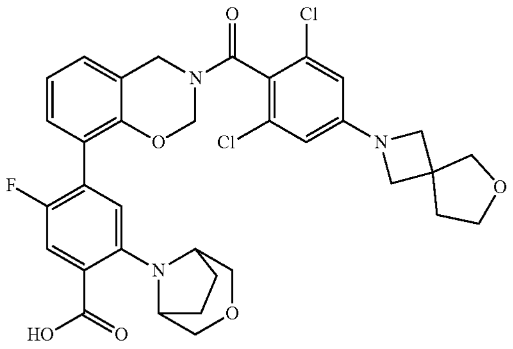 [SMILES: O=C(O)c1cc(F)c(-c2cccc3c2OCN(C(=O)c2c(Cl)cc(N4CC5(CCOC5)C4)cc2Cl)C3)cc1N1C2CCC1COC2] | 4-[3-[2,6-Dichloro-4-(6-oxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.60, 1.61 | 668 |
| 1-8 | 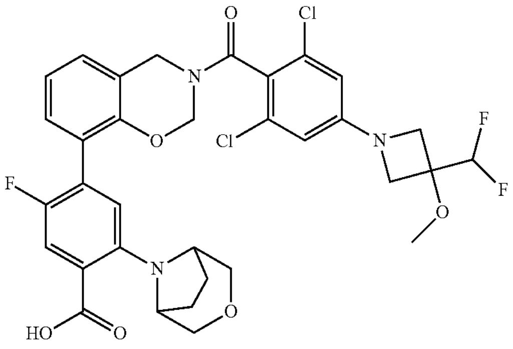 [SMILES: COC1(C(F)F)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-(difluoromethyl)-3-methoxyazetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.56, 1.57 | 692 |
| 1-10 | 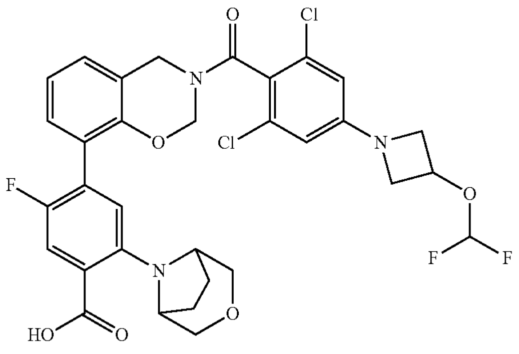 [SMILES: O=C(O)c1cc(F)c(-c2cccc3c2OCN(C(=O)c2c(Cl)cc(N4CC(OC(F)F)C4)cc2Cl)C3)cc1N1C2CCC1COC2] | 4-[3-[2,6-Dichloro-4-[3-(difluoromethoxy)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.57 | 678 |

TABLE 1-1-continued

| Compound No. | Structure | Compound Name | Analysis conditions | HPLC retention time (min) | m/z [M + H] |
|---|---|---|---|---|---|
| 1-11 | 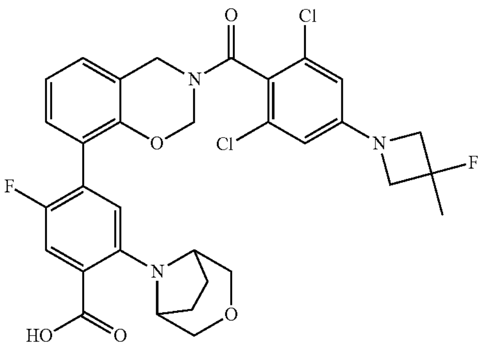 [SMILES: CC1(F)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-fluoro-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.57, 1.60 | 644 |
| 1-12 | 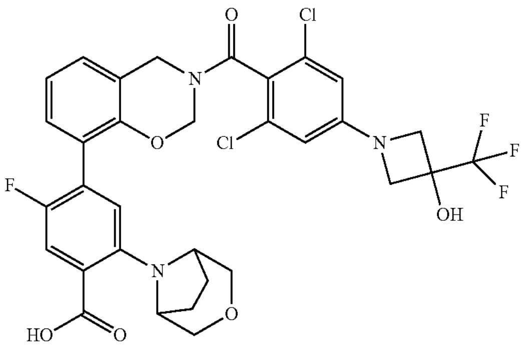 [SMILES: O=C(O)c1cc(F)c(-c2cccc3c2OCN(C(=O)c2c(Cl)cc(N4CC(O)(C(F)(F)F)C4)cc2Cl)C3)cc1N1C2CCC1COC2] | 4-[3-[2,6-Dichloro-4-[3-hydroxy-3-(trifluoromethyl) azetidin-1-yl]benzoyl]-2,4-dihydro-1,3-benzoxazin-8-yl]-5-fluoro-2-(3-oxa-8-azabicyclo [3.2.1]octan-8-yl)benzoic acid | B | 1.51 | 696 |
| 1-13 | 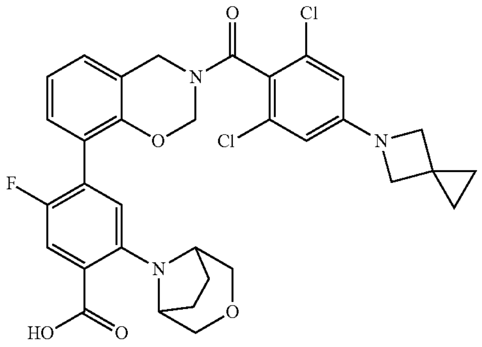 [SMILES: O=C(O)c1cc(F)c(-c2cccc3c2OCN(C(=O)c2c(Cl)cc(N4CC5(CC5)C4)cc2Cl)C3)cc1N1C2CCC1COC2] | 4-[3-[4-(5-Azaspiro[2.3]hexan-5-yl)-2,6-dichlorobenzoyl]-2,4-dihydro-1,3-benzoxazin-8-yl]-5-fluoro-2-(3-oxa-8-azabicyclo[3.2.1]octan-8-yl)benzoic acid | B | 1.66, 1.71 | 638 |
| 1-14 | 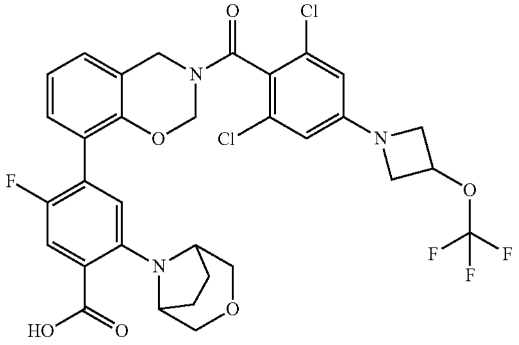 [SMILES: O=C(O)c1cc(F)c(-c2cccc3c2OCN(C(=O)c2c(Cl)cc(N4CC(OC(F)(F)F)C4)cc2Cl)C3)cc1N1C2CCC1COC2] | 4-[3-[2,6-Dichloro-4-[3-(trifluoromethoxy)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.65, 1.68 | 696 |

TABLE 1-1-continued

| Compound No. | Structure | Compound Name | Analysis conditions | HPLC retention time (min) | m/z [M + H] |
|---|---|---|---|---|---|
| 1-18 | 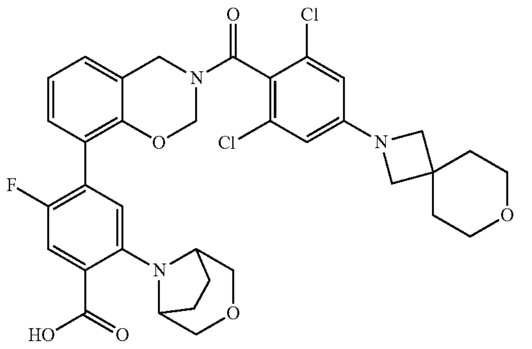 [SMILES: O=C(O)c1cc(F)c(-c2cccc3c2OCN(C(=O)c2c(Cl)cc(N4CC5(CCOCC5)C4)cc2Cl)C3)cc1N1C2CCC1COC2] | 4-[3-[2,6-Dichloro-4-(7-oxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.54, 1.56 | 682 |
| 1-21 | 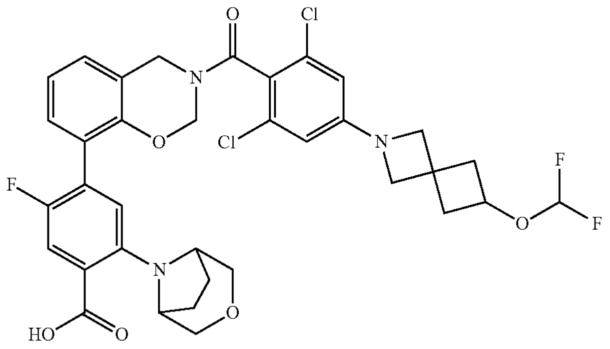 [SMILES: O=C(O)c1cc(F)c(-c2cccc3c2OCN(C(=O)c2c(Cl)cc(N4CC5(CC(OC(F)F)C5)C4)cc2Cl)C3)cc1N1C2CCC1COC2] | 4-[3-[2,6-Dichloro-4-[6-(difluoromethoxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.66, 1.68 | 718 |
| 1-32 | 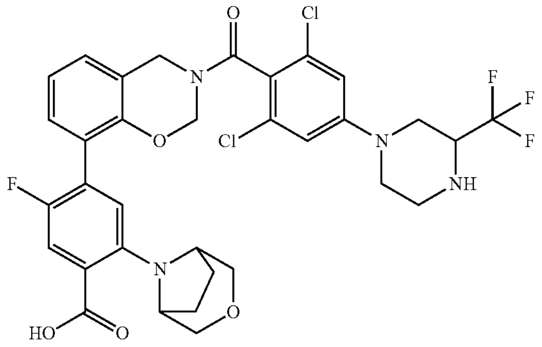 [SMILES: O=C(O)c1cc(F)c(-c2cccc3c2OCN(C(=O)c2c(Cl)cc(N4CCNC(C(F)(F)F)C4)cc2Cl)C3)cc1N1C2CCC1COC2] | 4-[3-[2,6-Dichloro-4-[3-(trifluoromethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.36 | 709 |
| 1-36 | 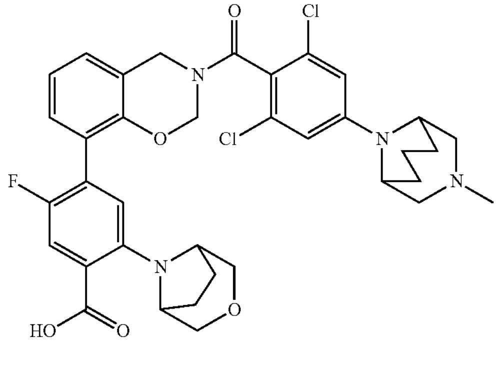 [SMILES: CN1CC2CCCC(C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-(3-methyl-3,9-diazabicyclo[3.3.1]nonan-9-yl)benzoyl]-2,4-dihydro-1,3-benzoxazin-8-yl]-5-fluoro-2-(3-oxa-8-azabicyclo[3.2.1]octan-8-yl)benzoic acid | B | 1.03, 1.07 | 695 |

TABLE 1-1-continued

| Compound No. | Structure | Compound Name | Analysis conditions | HPLC retention time (min) | m/z [M + H] |
| --- | --- | --- | --- | --- | --- |
| 1-37 | 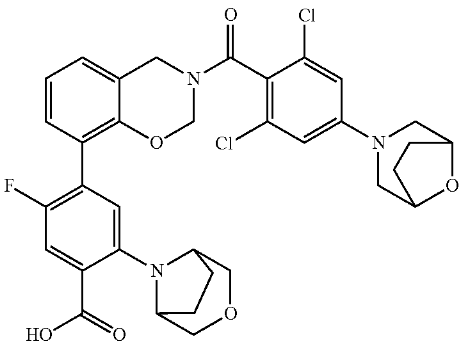 [SMILES: O=C(O)c1cc(F)c(-c2cccc3c2OCN(C(=O)c2c(Cl)cc(N4CC5CCC(C4)O5)cc2Cl)C3)cc1N1C2CCC1COC2] | 4-[3-[2,6-Dichloro-4-(8-oxa-3-azabicyclo[3.2.1]octan-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.51, 1.53 | 668 |
| 1-38 | 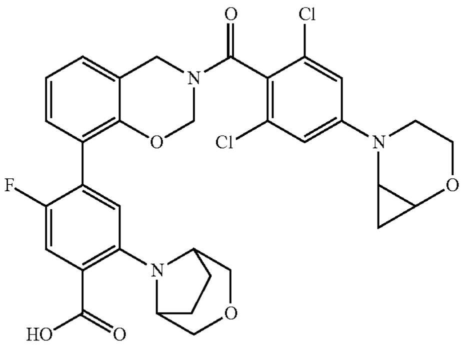 [SMILES: O=C(O)c1cc(F)c(-c2cccc3c2OCN(C(=O)c2c(Cl)cc(N4CCOC5CC54)cc2Cl)C3)cc1N1C2CCC1COC2] | 4-[3-[2,6-Dichloro-4-(2-oxa-5-azabicyclo[4.1.0]heptan-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.50, 1.51 | 654 |
| 1-39 | 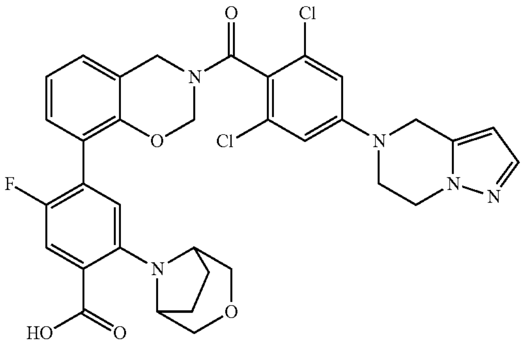 [SMILES: O=C(O)c1cc(F)c(-c2cccc3c2OCN(C(=O)c2c(Cl)cc(N4CCn5nccc5C4)cc2Cl)C3)cc1N1C2CCC1COC2] | 4-[3-[2,6-Dichloro-4-(6,7-dihydro-4H-pyrazolo[1,5-alpyrazin-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.42 | 678 |
| 1-40 | 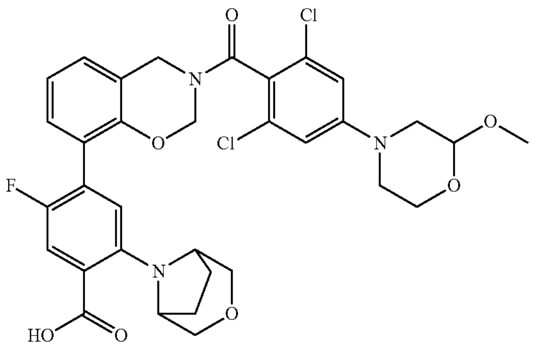 [SMILES: COC1CN(c2cc(Cl)c(C(=O)N3COc4c(cccc4-c4cc(N5C6CCC5COC6)c(C(=O)O)cc4F)C3)c(Cl)c2)CCO1] | 4-[3-[2,6-Dichloro-4-(2-methoxymorpholin-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.47, 1.48 | 672 |

TABLE 1-1-continued

| Compound No. | Structure | Compound Name | Analysis conditions | HPLC retention time (min) | m/z [M + H] |
|---|---|---|---|---|---|
| 1-1 | 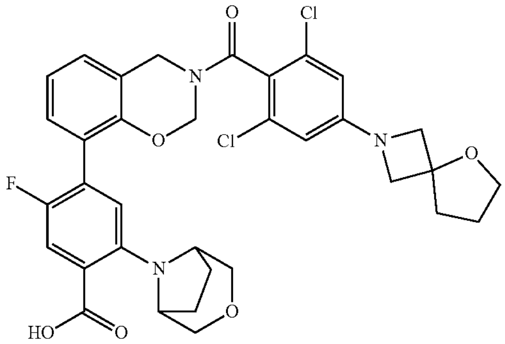 [SMILES: O=C(O)c1cc(F)c(-c2cccc3c2OCN(C(=O)c2c(Cl)cc(N4CC5(CCCO5)C4)cc2Cl)C3)cc1N1C2CCC1COC2] | 4-[3-[2,6-Dichloro-4-(5-oxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.66, 1.69 | 668 |
| 1-5 | 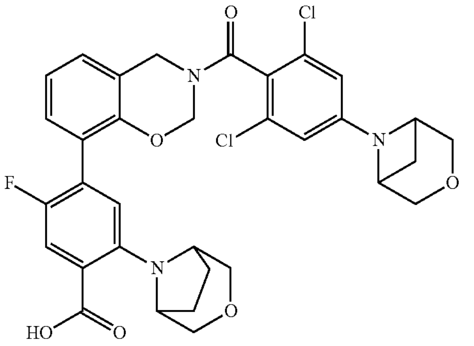 [SMILES: O=C(O)c1cc(F)c(-c2cccc3c2OCN(C(=O)c2c(Cl)cc(N4C5COCC4C5)cc2Cl)C3)cc1N1C2CCC1COC2] | 4-[3-[2,6-Dichloro-4-(3-oxa-6-azabicyclo[3.1.1]heptan-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.43, 1.44 | 654 |
| 1-34 | 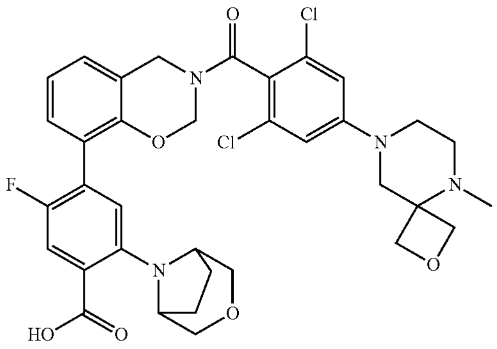 [SMILES: CN1CCN(c2cc(Cl)c(C(=O)N3COc4c(cccc4-c4cc(N5C6CCC5COC6)c(C(=O)O)cc4F)C3)c(Cl)c2)CC12COC2] | 4-[3-[2,6-Dichloro-4-(5-methyl-2-oxa-5,8-diazaspiro[3.5]nonan-8-yl)benzoyl]-2,4-dihydro-1,3-benzoxazin-8-yl]-5-fluoro-2-(3-oxa-8-azabicyclo[3.2.1]octan-8-yl)benzoic acid | B | 1.03, 1.06 | 697 |
| 1-41 | 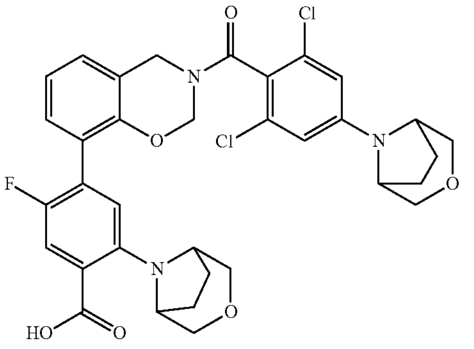 [SMILES: O=C(O)c1cc(F)c(-c2cccc3c2OCN(C(=O)c2c(Cl)cc(N4C5CCC4COC5)cc2Cl)C3)cc1N1C2CCC1COC2] | 4-[3-[2,6-Dichloro-4-(3-oxa-8-azabicyclo[3.2.1]octan-8-yl)benzoyl]-2,4-dihydro-1,3-benzoxazin-8-yl]-5-fluoro-2-(3-oxa-8-azabicyclo[3.2.1]octan-8-yl)benzoic acid | B | 1.50, 1.52 | 668 |

TABLE 1-1-continued

| Compound No. | Structure | Compound Name | Analysis conditions | HPLC retention time (min) | m/z [M + H] |
|---|---|---|---|---|---|
| 1-42 | 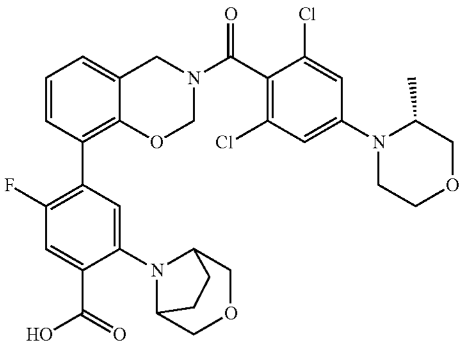 [SMILES: C[C@@H]1COCCN1c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(3R)-3-methylmorpholin-4-yl]benzoyl]-2,4-dihydro-1,3-benzoxazin-8-yl]-5-fluoro-2-(3-oxa-8-azabicyclo[3.2.1]octan-8-yl)benzoic acid | B | 1.50, 1.51 | 656 |
| 1-6 | 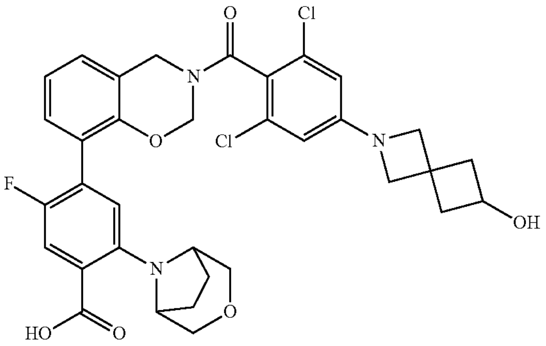 [SMILES: O=C(O)c1cc(F)c(-c2cccc3c2OCN(C(=O)c2c(Cl)cc(N4CC5(CC(O)C5)C4)cc2Cl)C3)cc1N1C2CCC1COC2] | 4-[3-[2,6-Dichloro-4-(6-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.40, 1.41 | 668 |
| 1-16 | 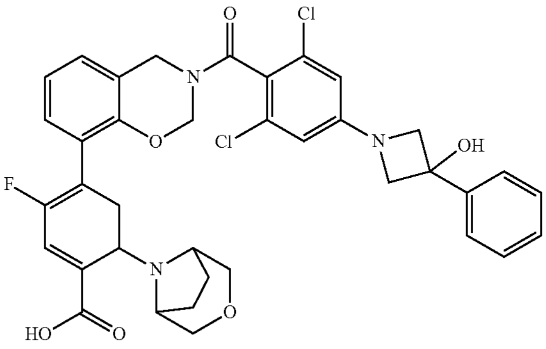 [SMILES: O=C(O)C1=CC(F)=C(c2cccc3c2OCN(C(=O)c2c(Cl)cc(N4CC(O)(c5ccccc5)C4)cc2Cl)C3)CC1N1C2CCC1COC2] | 4-[3-[2,6-Dichloro-4-(3-hydroxy-3-phenylazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.58, 1.59 | 704 |
| 1-17 | 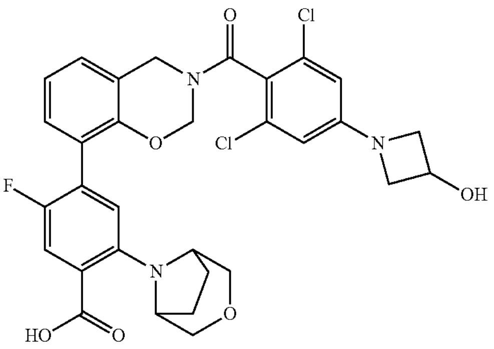 [SMILES: O=C(O)c1cc(F)c(-c2cccc3c2OCN(C(=O)c2c(Cl)cc(N4CC(O)C4)cc2Cl)C3)cc1N1C2CCC1COC2] | 4-[3-[2,6-Dichloro-4-(3-hydroxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.34, 1.35 | 628 |

TABLE 1-1-continued

| Compound No. | Structure | Compound Name | Analysis conditions | HPLC retention time (min) | m/z [M + H] |
|---|---|---|---|---|---|
| 1-19 | 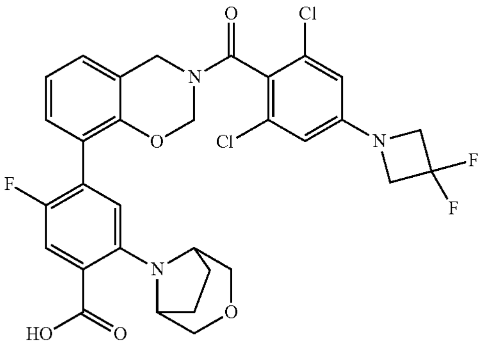 [SMILES: O=C(O)c1cc(F)c(-c2cccc3c2OCN(C(=O)c2c(Cl)cc(N4CC(F)(F)C4)cc2Cl)C3)cc1N1C2CCC1COC2] | 4-[3-[2,6-Dichloro-4-(3,3-difluoroazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.54, 1.56 | 648 |
| 1-20 | 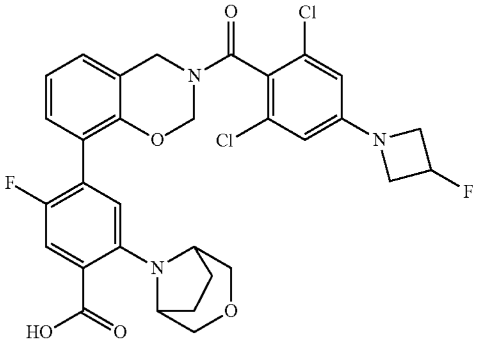 [SMILES: O=C(O)c1cc(F)c(-c2cccc3c2OCN(C(=O)c2c(Cl)cc(N4CC(F)C4)cc2Cl)C3)cc1N1C2CCC1COC2] | 4-[3-[2,6-Dichloro-4-(3-fluoroazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.51, 1. 52 | 630 |
| 1-43 | 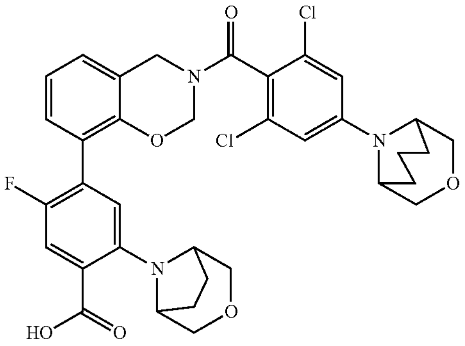 [SMILES: O=C(O)c1cc(F)c(-c2cccc3c2OCN(C(=O)c2c(Cl)cc(N4C5CCCC4COC5)cc2Cl)C3)cc1N1C2CCC1COC2] | 4-[3-[2,6-Dichloro-4-(3-oxa-9-azabicyclo[3.3.1]nonan-9-yl)benzoyl]-2,4-dihydro-1,3-benzoxazin-8-yl]-5-fluoro-2-(3-oxa-8-azabicyclo[3.2.1]octan-8-yl)benzoic acid | B | 1.58, 1.61 | 682 |
| 1-45 | 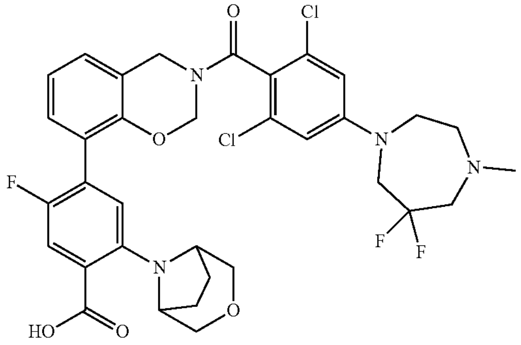 [SMILES: CN1CCN(c2cc(Cl)c(C(=O)N3COc4c(cccc4-c4cc(N5C6CCC5COC6)c(C(=O)O)cc4F)C3)c(Cl)c2)CC(F)(F)C1] | 4-[3-[2,6-Dichloro-4-(6,6-difluoro-4-methyl-1,4-diazepan-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.26 | 705 |

TABLE 1-1-continued

| Compound No. | Structure | Compound Name | Analysis conditions | HPLC retention time (min) | m/z [M + H] |
|---|---|---|---|---|---|
| 1-44 | 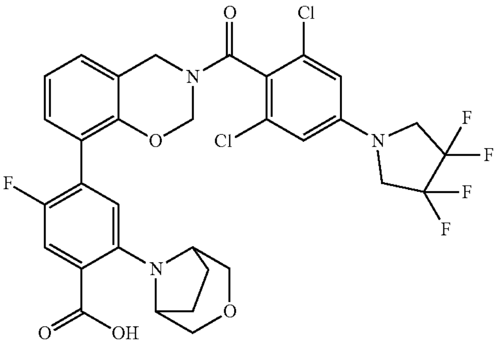 [SMILES: O=C(O)c1cc(F)c(-c2cccc3c2OCN(C(=O)c2c(Cl)cc(N4CC(F)(F)C(F)(F)C4)cc2Cl)C3)cc1N1C2CCC1COC2] | 4-[3-[2,6-Dichloro-4-(3,3,4,4-tetrafluoropyrrolidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.60, 1.62 | 698 |
| 1-46 | 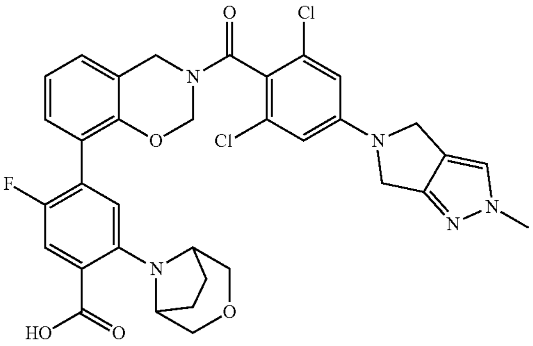 [SMILES: Cn1cc2c(n1)CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-(2-methyl-4,6-dihydropyrrolo[3,4-c]pyrazol-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.56 | 678 |

TABLE 1-2

| Final compound No. | Amine |
|---|---|
| 1-2 | 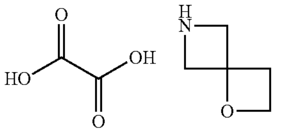 |
| 1-3 | 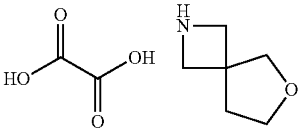 |
| 1-8 | 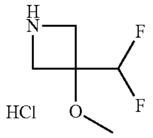 |
| 1-10 | 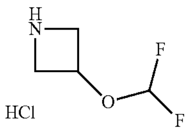 |
| 1-11 | 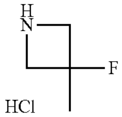 |

TABLE 1-2-continued

| Final compound No. | Amine |
|---|---|
| 1-12 | 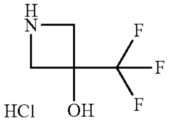 |
| 1-13 | 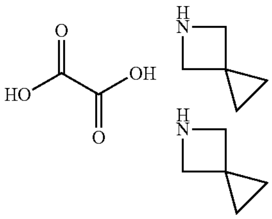 |
| 1-14 | 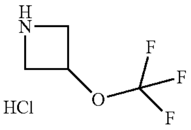 |
| 1-18 | 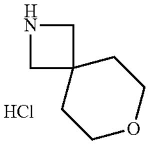 |

TABLE 1-2-continued
| Final compound No. | Amine |
|---|---|
| 1-21 | 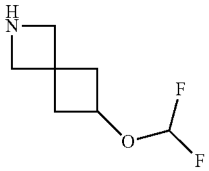 [SMILES: FC(F)OC1CC2(CNC2)C1] |
| 1-32 | 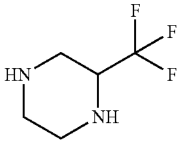 |
| 1-36 | 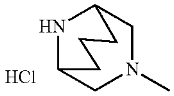 |
| 1-37 | 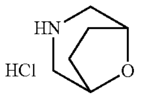 |
| 1-38 | 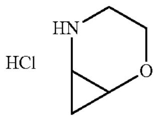 |
| 1-39 | 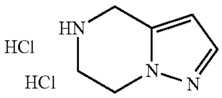 |
| 1-40 | 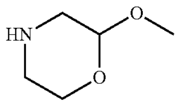 |
| 1-1 | 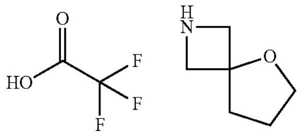 |
| 1-5 | 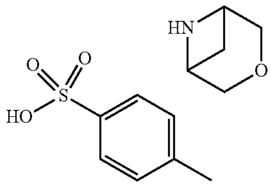 |
| 1-34 | 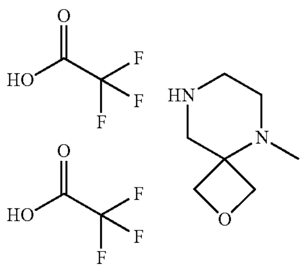 |
TABLE 1-2-continued
| Final compound No. | Amine |
|---|---|
| 1-41 | 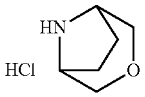 |
| 1-42 | 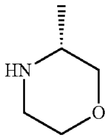 |
| 1-6 | 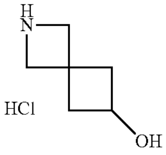 |
| 1-16 | 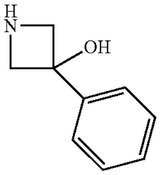 [SMILES: OC1(c2ccccc2)CNC1] |
| 1-17 | 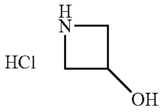 |
| 1-19 | 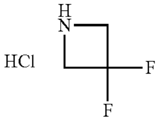 |
| 1-20 | 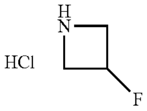 |
| 1-43 | 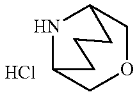 |
| 1-45 | 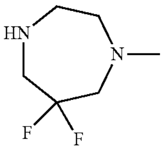 |
| 1-44 | 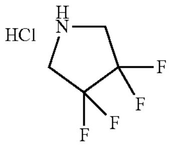 |
| 1-46 | 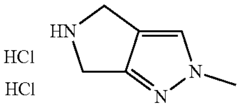 |

Compound 1-4

4-[3-[2,6-Dichloro-4-[(2R,3R)-3-methoxy-2-methyl-azetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound a1

Benzyl (2R,3R)-3-methoxy-2-methylazetidine-1-carboxylate

[Formula 29]

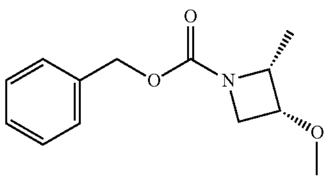

A solution of benzyl (2R,3R)-3-hydroxy-2-methylazetidine-1-carboxylate (267 mg, 1.21 mmol) and iodomethane (343 mg, 2.41 mmol) in tetrahydrofuran (3.02 mL) was cooled to 0° C. 60% sodium hydride (72.4 mg, 1.81 mmol) was added thereto, and the mixture was stirred at room temperature for 1.5 hours. An aqueous formic acid solution was added to the reaction solution, and the reaction mixture was purified by reverse phase column chromatography (acetonitrile/water, 0.1% formic acid) to obtain the title compound (92%, 261 mg).

LCMS: m/z 236[M+H]$^+$

HPLC retention time: 0.71 min (analysis condition D)

Second Step
Compound 1-4

4-[3-[2,6-Dichloro-4-[(2R,3R)-3-methoxy-2-methyl-azetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 30]

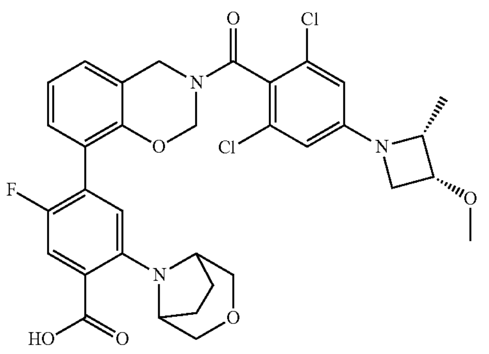

To a solution of benzyl (2R,3R)-3-methoxy-2-methylazetidine-1-carboxylate (260 mg, 1.11 mmol) in methanol (4.42 mL), 10% palladium/carbon (353 mg, 0.332 mmol) was added. The mixture was stirred at room temperature for 2 hours in a hydrogen atmosphere. The reaction solution was filtered through celite, and a hydrochloric acid-methanol solution was added to the filtrate. The reaction solution was concentrated to obtain (2R,3R)-3-methoxy-2-methylazetidine hydrochloride as a crude product. The title compound was obtained by the same operation as in the ninth step of compound 1-7 using the obtained crude product and compound A.

LCMS: m/z 656[M+H]$^+$

HPLC retention time: 1.57 min and 1.60 min (analysis condition B)

Compound 1-9

4-[3-[2,6-Dichloro-4-(3-methoxy-2,2-dimethylazetidin-1-yl)benzoyl]-2,4-dihydro-1,3-benzoxazin-8-yl]-5-fluoro-2-(3-oxa-8-azabicyclo[3.2.1]octan-8-yl) benzoic acid First Step
Compound b1

1-Benzhydryl-3-methoxy-2,2-dimethylazetidine

[Formula 31]

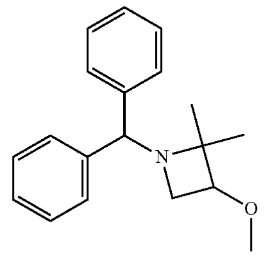

A solution of 1-benzhydryl-2,2-dimethylazetidin-3-ol (50.0 mg, 0.187 mmol) and iodomethane (53.1 mg, 0.374 mmol) in tetrahydrofuran (0.468 mL) was cooled to 0° C. 60% sodium hydride (11.2 mg, 0.281 mmol) was added thereto, and the mixture was stirred at room temperature for 2 hours. An aqueous formic acid solution was added to the reaction solution, and the mixture was purified by reverse phase column chromatography (acetonitrile/water, 0.1% formic acid) to obtain the title compound (94%, 49.7 mg).

LCMS: m/z 282[M+H]$^+$

HPLC retention time: 0.54 min (analysis condition D)

Second Step
Compound 1-9

4-[3-[2,6-Dichloro-4-(3-methoxy-2,2-dimethylazetidin-1-yl)benzoyl]-2,4-dihydro-1,3-benzoxazin-8-yl]-5-fluoro-2-(3-oxa-8-azabicyclo[3.2.1]octan-8-yl) benzoic acid

[Formula 32]

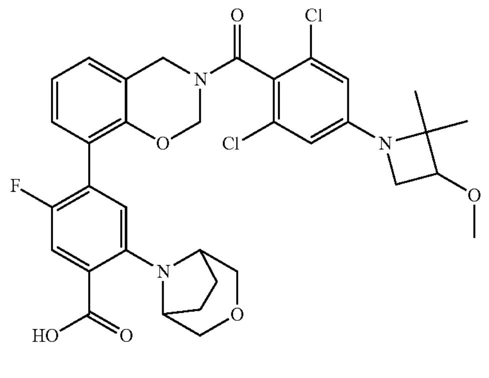

To 1-benzhydryl-3-methoxy-2,2-dimethylazetidine (49.0 mg, 0.174 mmol) in methanol (0.871 mL), 20% palladium hydroxide/carbon (122 mg, 0.174 mmol) was added. The mixture was stirred at room temperature for 2 hours in a hydrogen atmosphere. The reaction solution was filtered through celite, and a hydrochloric acid-methanol solution was added to the filtrate. The reaction solution was concentrated to obtain 3-methoxy-2,2-dimethylazetidine hydrochloride as a crude product. The title compound was obtained by the same operation as in the ninth step of compound 1-7 using the obtained crude product and compound A.

LCMS: m/z 670[M+H]$^+$

HPLC retention time: 1.61 min and 1.65 min (analysis condition B)

Compound 1-84

4-[3-[2,6-Dichloro-4-[(2R,3S)-2-methyl-3-morpholin-4-ylazetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound c1

Benzyl (2R,3S)-2-methyl-3-morpholin-4-ylazetidine-1-carboxylate

[Formula 33]

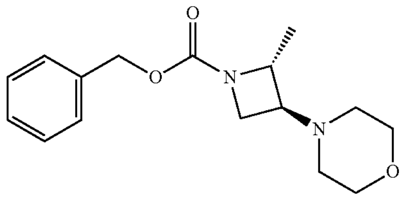

A solution of benzyl (2R,3R)-3-hydroxy-2-methylazetidine-1-carboxylate (36.0 mg, 0.163 mmol) and N,N-diisopropylethylamine (0.0425 mL, 0.244 mmol) in dichloromethane (1.63 mL) was cooled to −78° C. Trifluoromethanesulfonic anhydride (0.0401 mL, 0.244 mmol) was added thereto, and the mixture was stirred at −78° C. for 1 hour. Morpholine (0.142 mL, 1.63 mmol) was added thereto, and the mixture was stirred overnight at room temperature. Morpholine (0.142 mL, 1.63 mmol) was added thereto, and the mixture was stirred overnight at room temperature and then stirred at 40° C. for 4 hours. Methanol was added to the reaction solution, and the mixture was concentrated. The residue was purified by HPLC (acetonitrile/water, 0.1% formic acid) to obtain the title compound (57%, 27.0 mg).

LCMS: m/z 291[M+H]$^+$

HPLC retention time: 0.84 min (analysis condition F)

Second Step

Compound 1-84

4-[3-[2,6-Dichloro-4-[(2R,3S)-2-methyl-3-morpholin-4-ylazetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 34]

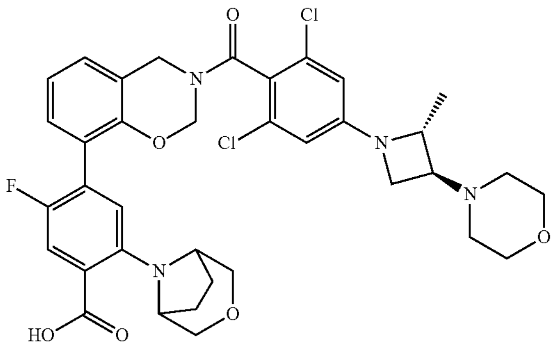

To a solution of benzyl (2R,3S)-2-methyl-3-morpholin-4-ylazetidine-1-carboxylate (25.0 mg, 0.0860 mmol) in methanol (0.344 mL), 10% palladium/carbon (27.5 mg, 0.0260 mmol) was added. The mixture was stirred at room temperature for 1 hour in a hydrogen atmosphere. The reaction solution was filtered through celite, and a hydrochloric acid-methanol solution was added to the filtrate. The reaction solution was concentrated to obtain 4-[(2R,3S)-2-methylazetidin-3-yl]morpholine hydrochloride as a crude product. The title compound was obtained by the same operation as in the ninth step of compound 1-7 using the obtained crude product and compound A.

LCMS: m/z 711 [M+H]$^+$

HPLC retention time: 1.14 min (analysis condition B)

Compound 1-85

4-[3-[2,6-Dichloro-4-[(2R,3R)-2-methyl-3-morpholin-4-ylazetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound c2

Benzyl (2R,3R)-2-methyl-3-morpholin-4-ylazetidine-1-carboxylate

[Formula 35]

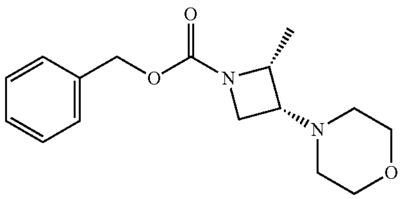

A solution of benzyl (2R)-2-methyl-3-oxoazetidine-1-carboxylate (60.0 mg, 0.274 mmol) and morpholine (0.0265 mL, 0.301 mmol) in dichloromethane (0.684 mL) was stirred at room temperature for 30 minutes. Sodium triacetoxyborohydride (69.6 mL, 0.328 mmol) was added thereto, and the mixture was stirred at room temperature for 1.5 hours. Dichloromethane was added to the reaction solution, and the mixture was washed with a saturated aqueous solution of sodium bicarbonate. The organic layer was concentrated, and the residue was purified by HPLC (acetonitrile/water, 0.1% formic acid) to obtain the title compound (45%, 36.0 mg).

LCMS: m/z 291[M+H]$^+$

HPLC retention time: 0.87 min (analysis condition F)

Second Step

Compound 1-85

4-[3-[2,6-Dichloro-4-[(2R,3R)-2-methyl-3-morpholin-4-ylazetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 36]

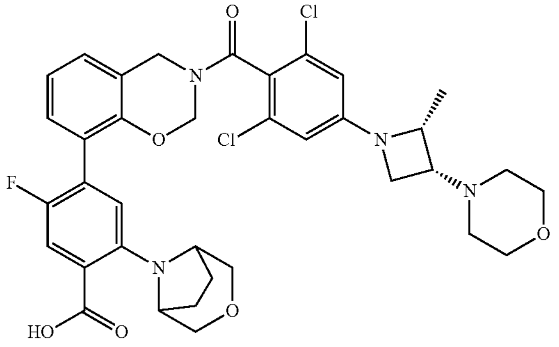

To a solution of benzyl (2R,3R)-2-methyl-3-morpholin-4-ylazetidine-1-carboxylate (32.0 mg, 0.110 mmol) in methanol (0.411 mL), 10% palladium/carbon (35.2 mg, 0.0330 mmol) was added. The mixture was stirred at room temperature for 1 hour in a hydrogen atmosphere. The reaction solution was filtered through celite, and a hydrochloric acid-methanol solution was added to the filtrate. The reaction solution was concentrated to obtain 4-[(2R,3R)-2-methylazetidin-3-yl]morpholine hydrochloride as a crude product. The title compound was obtained by the same operation as in the ninth step of compound 1-7 using the obtained crude product and compound A.

LCMS: m/z 711 [M+H]$^+$

HPLC retention time: 1.16 min (analysis condition B)

Compound 1-22

4-[3-[2,6-Dichloro-4-[(7S)-7-methoxy-5-oxa-2-azaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 37]

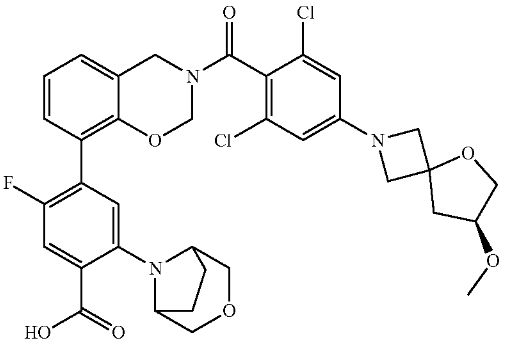

A solution of tert-butyl (7S)-7-hydroxy-5-oxa-2-azaspiro[3.4]octane-2-carboxylate (54.6 mg, 0.238 mmol) in tetrahydrofuran (2.38 mL) was cooled to 0° C. 60% sodium hydride (23.8 mg, 0.595 mmol) was added thereto, and the mixture was stirred at 0° C. for 5 minutes. Iodomethane (67.6 mg, 0.476 mmol) was added thereto, and the mixture was stirred at room temperature for 2.5 hours. 60% sodium hydride (23.8 mg, 0.595 mmol) and iodomethane (67.6 mg, 0.476 mmol) were added thereto, and the mixture was stirred at room temperature for 1.5 hours. 1-Methylpyrrolidin-one (0.238 mL) was added to the reaction solution, and the mixture was stirred at room temperature for 1 hour. Ethyl acetate was added thereto, and the mixture was washed with water and saturated saline. The organic layer was dried over anhydrous sodium sulfate and concentrated to obtain tert-butyl (7S)-7-methoxy-5-oxa-2-azaspiro[3.4]octane-2-carboxylate as a crude product. To a solution of the obtained crude product in dichloromethane (1.50 mL), trifluoroacetic acid (0.501 mL, 6.54 mmol) was added, and the mixture was stirred at room temperature for 1 hour. The reaction solution was concentrated to obtain (7S)-7-methoxy-5-oxa-2-azaspiro[3.4]octane trifluoroacetate as a crude product. The title compound was obtained by the same operation as in the ninth step of compound 1-7 using the obtained crude product and compound A. However, toluene was used instead of 1,4-dioxane as a solvent.

LCMS: m/z 698[M+H]$^+$

HPLC retention time: 1.63 min and 1.64 min (analysis condition B)

Compound 1-23

4-[3-[2,6-Dichloro-4-[(7R)-7-methoxy-5-oxa-2-azaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 38]

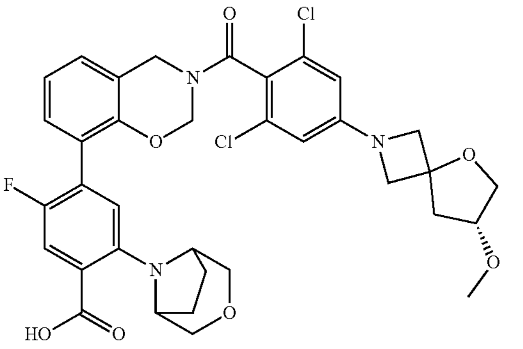

The title compound was obtained by the same operation as in the process of compound 1-22 using tert-butyl (7R)-7-hydroxy-5-oxa-2-azaspiro[3.4]octane-2-carboxylate.

LCMS: m/z 698[M+H]$^+$

HPLC retention time: 1.62 min and 1.63 min (analysis condition B)

Compound 1-31

4-[3-[2,6-Dichloro-4-[(8S)-8-methoxy-5-oxa-2-azaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound e1 tert-Butyl (8S)-8-methoxy-5-oxa-2-azaspiro[3.4]octane-2-carboxylate

[Formula 39]

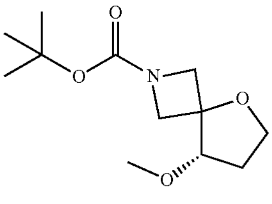

Compound e2 tert-Butyl (8R)-8-methoxy-5-oxa-2-azaspiro[3.4]octane-2-carboxylate

[Formula 40]

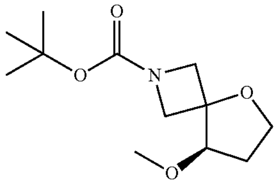

To a solution of tert-butyl 8-methoxy-5-oxa-2-azaspiro[3.4]oct-7-ene-2-carboxylate (33.8 mg, 0.140 mmol) in methanol (2.8 mL), 10% palladium/carbon (6.76 mg, 0.0640 mmol) was added. The mixture was stirred at room temperature for 15 hours in a hydrogen atmosphere. The reaction solution was filtered through celite, and the filtrate was concentrated. The residue was purified by silica gel column chromatography (hexane/ethyl acetate) to obtain tert-butyl 8-methoxy-5-oxa-2-azaspiro[3.4]octane-2-carboxylate as a racemic mixture. The obtained racemic mixture was purified by SFC (CHIRALPAK IG, supercritical carbon dioxide/ethanol/tert-butyl methyl ether) to obtain tert-butyl (8S)-8-methoxy-5-oxa-2-azaspiro[3.4]octane-2-carboxylate (31%, 10.7 mg) and tert-butyl (8R)-8-methoxy-5-oxa-2-azaspiro[3.4]octane-2-carboxylate (25%, 8.40 mg).

Compound e1 tert-Butyl (8S)-8-methoxy-5-oxa-2-azaspiro[3.4]octane-2-carboxylate

[Formula 41]

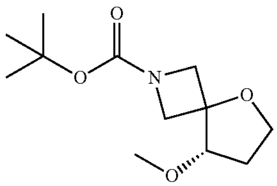

LCMS: m/z 244[M+H]$^+$

SFC retention time: 4.72 min (analysis condition: CHIRALPAK IG 4.6 mm I.D.×250 mm, 5 μm, supercritical carbon dioxide/[ethanol/tert-butyl methyl ether=1/1]=90/10 (10 min), 40° C., 210 nm)

Compound e2 tert-Butyl (8R)-8-methoxy-5-oxa-2-azaspiro[3.4]octane-2-carboxylate

[Formula 42]

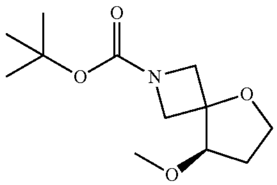

LCMS: m/z 244[M+H]$^+$

SFC retention time: 5.37 min (analysis condition: CHIRALPAK IG 4.6 mm I.D.×250 mm, 5 μm, supercritical carbon dioxide/[ethanol/tert-butyl methyl ether=1/1]=90/10 (10 min), 40° C., 210 nm)

Second Step

Compound 1-31

4-[3-[2,6-Dichloro-4-[(8S)-8-methoxy-5-oxa-2-azaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 43]

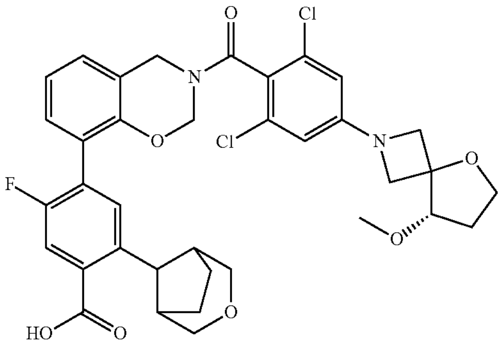

To a solution of tert-butyl (8S)-8-methoxy-5-oxa-2-azaspiro[3.4]octane-2-carboxylate (10.7 mg, 0.0440 mmol) in dichloromethane (0.750 mL), trifluoroacetic acid (0.250 mL, 3.26 mmol) was added, and the mixture was stirred at room temperature for 2 hours. The reaction solution was concentrated. The title compound was obtained by the same operation as in the ninth step of compound 1-7 using the obtained crude product and compound A. However, toluene was used instead of 1,4-dioxane as a solvent.

LCMS: m/z 698[M+H]$^+$

HPLC retention time: 1.67 min and 1.68 min (analysis condition B)

Compound 1-30

4-[3-[2,6-Dichloro-4-[(8R)-8-methoxy-5-oxa-2-azaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 44]

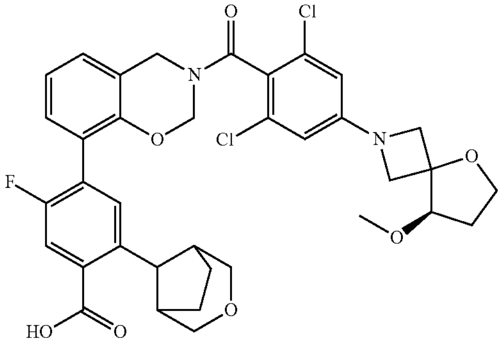

The title compound was obtained by the same operation as in the process of compound 1-31 using compound 1-31 and tert-butyl (8R)-8-methoxy-5-oxa-2-azaspiro[3.4]octane-2-carboxylate obtained in the first step.

LCMS: m/z 698[M+H]$^+$

HPLC retention time: 1.67 min and 1.68 min (analysis condition B)

Compound 1-24

4-[3-[2,6-Dichloro-4-[(1R,4r,6R)-6-methoxy-1-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound f1

O-tert-Butyl 6-methoxy-2-azaspiro[3.3]heptane-2-carbothioate

[Formula 45]

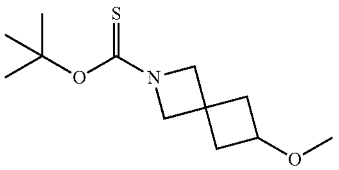

To a solution of carbon disulfide (0.0280 mL, 0.458 mmol) in tetrahydrofuran (1.00 mL), a 2 M solution of sodium tert-butoxide in tetrahydrofuran (0.489 mL, 0.978 mmol) was added, and the mixture was stirred at room temperature for 30 minutes. Iodomethane (0.0267 mL, 0.428 mL) was added thereto, and the mixture was stirred at room temperature for 15 minutes. The reaction solution was cooled to 0° C., 6-Methoxy-1-methyl-2-azaspiro[3.3]heptane hydrochloride (50.0 mg, 0.306 mmol) and triethylamine (0.0639 mL, 0.458 mmol) were added thereto, and the mixture was stirred at 0° C. for 1 hour. A 1 M aqueous palladium hydroxide solution was added to the reaction solution, followed by extraction with diethyl ether and subsequent passing through a phase separator. The organic layer was concentrated, and the residue was then purified by silica gel column chromatography (hexane/ethyl acetate) to obtain the title compound (85%, 63.3 mg).

LCMS: m/z 188[M−tBu+H]$^+$

HPLC retention time: 0.93 min (analysis condition D)

Second Step

Compound f2

O-tert-Butyl (4s,6s)-6-methoxy-1-methyl-2-azaspiro[3.3]heptane-2-carbothioate

[Formula 46]

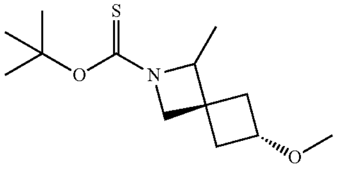

Compound f3

O-tert-Butyl (4r,6r)-6-methoxy-1-methyl-2-azaspiro [3.3]heptane-2-carbothioate

[Formula 47]

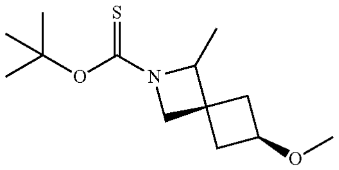

A solution of O-tert-butyl 6-methoxy-2-azaspiro[3.3]heptane-2-carbothioate (63.3 mg, 0.260 mmol) in tetrahydrofuran (1.30 mL) was cooled to −78° C. Tetramethylethylenediamine (0.118 mL, 0.780 mmol) and a 1.05 M solution of sec-butyllithium in cyclohexane and hexane (0.495 mL, 0.520 mmol) were added thereto, and the mixture was stirred at −78° C. for 35 minutes. Iodomethane (0.0650 mL, 1.04 mmol) was added thereto, and the mixture was stirred at −78° C. for 10 minutes and then stirred at room temperature for 40 minutes. Water was added to the reaction solution, followed by extraction with diethyl ether and subsequent passing through a phase separator. The organic layer was concentrated, and the residue was then purified by silica gel column chromatography (hexane/ethyl acetate) to obtain O-tert-butyl 6-methoxy-1-methyl-2-azaspiro[3.3]heptane-2-carbothioate (61%, 40.7 mg) as a diastereomeric mixture. The diastereomeric mixture (40.7 mg, 0.158 mmol) was purified by HPLC (CHIRALPAK IE, hexane/2-propanol) to obtain O-tert-butyl (4s,6s)-6-methoxy-1-methyl-2-azaspiro [3.3]heptane-2-carbothioate (47%, 19.0 mg) and O-tert-butyl (4r,6r)-6-methoxy-1-methyl-2-azaspiro[3.3]heptane-2-carbothioate (34%, 14.0 mg) as a racemic mixture.

Compound f2

O-tert-Butyl (4s,6s)-6-methoxy-1-methyl-2-azaspiro [3.3]heptane-2-carbothioate

[Formula 48]

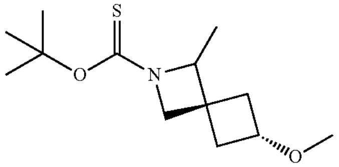

LCMS: m/z 202[M-tBu+H]$^+$

SFC retention time: 4.16 min and 5.18 min (analysis condition: CHIRALPAK IC 4.6 mm I.D.×250 mm, 5 μm, supercritical carbon dioxide/[ethanol/tert-butyl methyl ether=1/1]=90/10 (10 min), 40° C., 254 nm)

Compound f3

O-tert-Butyl (4r,6r)-6-methoxy-1-methyl-2-azaspiro [3.3]heptane-2-carbothioate

[Formula 49]

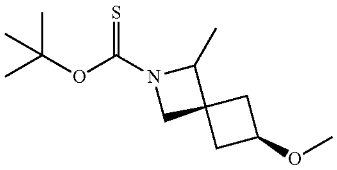

LCMS: m/z 202[M-tBu+H]$^+$

SFC retention time: 4.79 min and 5.88 min (analysis condition: CHIRALPAK IC 4.6 mm I.D.×250 mm, 5 μm, supercritical carbon dioxide/[ethanol/tert-butyl methyl ether=1/1]=90/10 (10 min). 40° C., 254 nm)

Third Step

Compound f4

O-tert-Butyl (1S,4s,6R)-6-methoxy-1-methyl-2-azaspiro[3.3]heptane-2-carbothioate

[Formula 50]

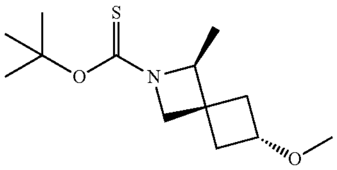

Compound f5

O-tert-Butyl (1R,4s,6S)-6-methoxy-1-methyl-2-azaspiro[3.3]heptane-2-carbothioate

[Formula 51]

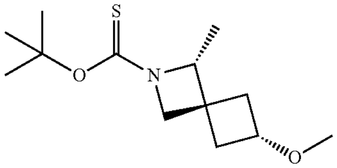

Compound f6

O-tert-Butyl (1S,4r,6S)-6-methoxy-1-methyl-2-azaspiro[3.3]heptane-2-carbothioate

[Formula 52]

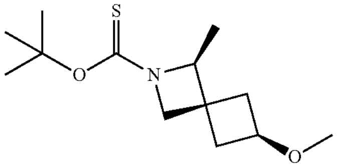

Compound 17

O-tert-Butyl (1R,4r,6R)-6-methoxy-1-methyl-2-azaspiro[3.3]heptane-2-carbothioate

[Formula 53]

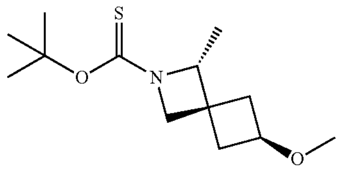

The racemic mixture of O-tert-butyl (4s,6s)-6-methoxy-1-methyl-2-azaspiro[3.3]heptane-2-carbothioate (19.0 mg, 0.0740 mmol) was purified by HPLC (CHIRALPAK IC, hexane/2-propanol) to obtain O-tert-butyl (1S,4s,6R)-6-methoxy-1-methyl-2-azaspiro[3.3]heptane-2-carbothioate (41%, 7.70 mg) and O-tert-butyl (1R,4s,6S)-6-methoxy-1-methyl-2-azaspiro[3.3]heptane-2-carbothioate (39%, 7.40 mg).

Compound f4

O-tert-Butyl (1S,4s,6R)-6-methoxy-1-methyl-2-azaspiro[3.3]heptane-2-carbothioate

[Formula 54]

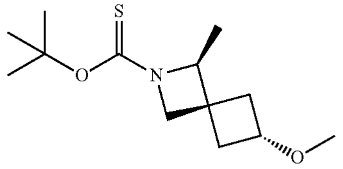

LCMS: m/z 202[M-tBu+H]+

SFC retention time: 4.09 min (analysis condition: CHIRALPAK IC 4.6 mm I.D.×250 mm, 5 μm, supercritical carbon dioxide/[ethanol/tert-butyl methyl ether=1/1]=90/10 (10 min), 40° C., 254 nm)

Compound f5

O-tert-Butyl (1R,4s,6S)-6-methoxy-1-methyl-2-azaspiro[3.3]heptane-2-carbothioate

[Formula 55]

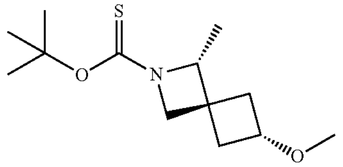

LCMS: m/z 202[M-tBu+H]$^+$

SFC retention time: 5.09 min (analysis condition: CHIRALPAK IC 4.6 mm I.D.×250 mm, 5 μm, supercritical carbon dioxide/[ethanol/tert-butyl methyl ether=1/1]=90/10 (10 min), 40° C., 254 nm)

The racemic mixture of O-tert-butyl (4r,6r)-6-methoxy-1-methyl-2-azaspiro[3.3]heptane-2-carbothioate (14.0 mg, 0.0540 mmol) was purified by HPLC (CHIRALPAK IC, hexane/2-propanol) to obtain O-tert-butyl (1S,4r,6S)-6-methoxy-1-methyl-2-azaspiro[3.3]heptane-2-carbothioate (36%, 5.10 mg) and O-tert-butyl (1R,4r,6R)-6-methoxy-1-methyl-2-azaspiro[3.3]heptane-2-carbothioate (40%, 5.60 mg).

Compound f6

O-tert-Butyl (1S,4r,6S)-6-methoxy-1-methyl-2-azaspiro[3.3]heptane-2-carbothioate

[Formula 56]

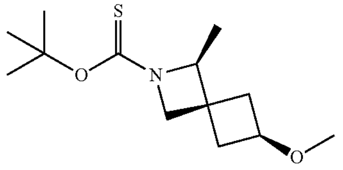

LCMS: m/z 202[M-tBu+H]$^+$

SFC retention time: 4.73 min (analysis condition: CHIRALPAK IC 4.6 mm I.D.×250 mm, 5 μm, supercritical carbon dioxide/[ethanol/tert-butyl methyl ether=1/1]=90/10 (10 min), 40° C., 254 nm)

Compound 17

O-tert-Butyl (1R,4r,6R)-6-methoxy-1-methyl-2-azaspiro[3.3]heptane-2-carbothioate

[Formula 57]

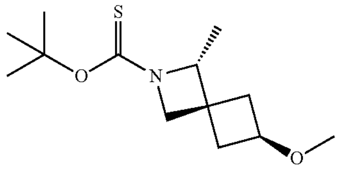

LCMS: m/z 202[M-tBu+H]$^+$

SFC retention time: 5.81 min (analysis condition: CHIRALPAK IC 4.6 mm I.D.×250 mm, 5 μm, supercritical carbon dioxide/[ethanol/tert-butyl methyl ether=1/1]=90/10 (10 min), 40° C., 254 nm)

Fourth Step

Compound 1-24

4-[3-[2,6-Dichloro-4-[(1R,4r,6R)-6-methoxy-1-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 58]

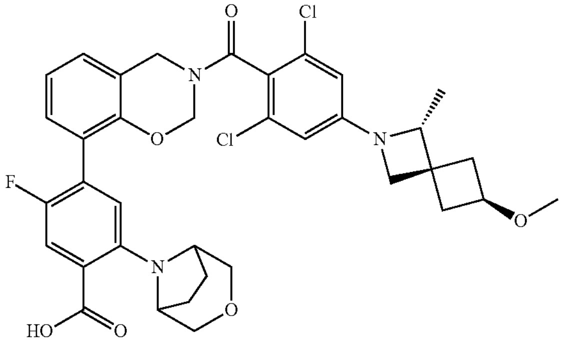

To a solution of O-tert-butyl (1R,4r,6R)-6-methoxy-1-methyl-2-azaspiro[3.3]heptane-2-carbothioate (5.60 mg, 0.0220 mmol) in dichloromethane (0.218 mL), trifluoroacetic acid (0.00335 mL, 0.0440 mmol) was added, and the mixture was stirred overnight at room temperature. Trifluoroacetic acid (0.0335 mL, 0.0440 mmol) was added thereto, and the mixture was further stirred at room temperature for 1 hour. The reaction solution was concentrated. The title compound was obtained by the same operation as in the ninth step of compound 1-7 using the obtained crude product and compound A.

LCMS: m/z 696[M+H]$^+$

HPLC retention time: 1.75 min and 1.78 min (analysis condition B)

Compound 1-25

4-[3-[2,6-Dichloro-4-[(1S,4r,6S)-6-methoxy-1-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 59]

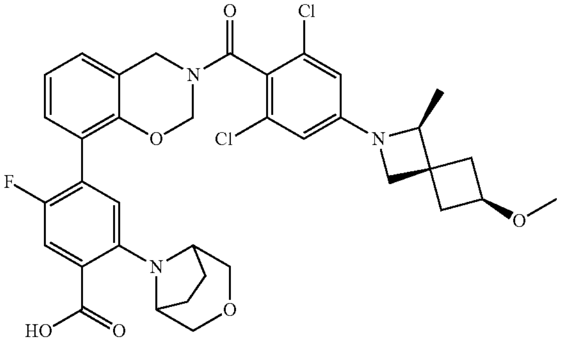

The title compound was obtained by the same operation as in the fourth step of compound 1-24 using O-tert-butyl (1S,4r,6S)-6-methoxy-1-methyl-2-azaspiro[3.3]heptane-2-carbothioate.

LCMS: m/z 696[M+H]$^+$

HPLC retention time: 1.75 min and 1.78 min (analysis condition B)

Compound 1-26

4-[3-[2,6-Dichloro-4-[(1R,4s,6S)-6-methoxy-1-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 60]

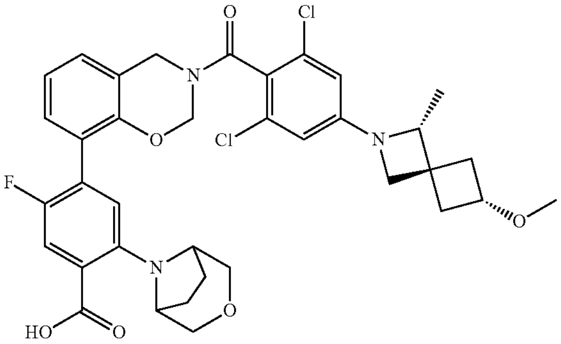

The title compound was obtained by the same operation as in the fourth step of compound 1-24 using O-tert-butyl (1R,4s,6S)-6-methoxy-1-methyl-2-azaspiro[3.3]heptane-2-carbothioate.

LCMS: m/z 696[M+H]$^+$

HPLC retention time: 1.75 min and 1.78 min (analysis condition B)

Compound 1-27

4-[3-[2,6-Dichloro-4-[(1S,4s,6R)-6-methoxy-1-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 61]

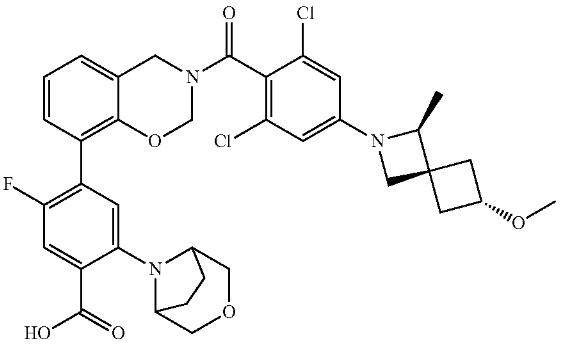

The title compound was obtained by the same operation as in the fourth step of compound 1-24 using O-tert-butyl (1S,4s,6R)-6-methoxy-1-methyl-2-azaspiro[3.3]heptane-2-carbothioate.

LCMS: m/z 696[M+H]$^+$

HPLC retention time: 1.74 min and 1.78 min (analysis condition B)

Compound 1-86

4-[3-[2,6-Dichloro-4-[rel-(6R,7R)-6-methoxy-7-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound g1 tert-Butyl 6-(dimethylhydrazinylidene)-2-azaspiro[3.3]heptane-2-carboxylate

[Formula 62]

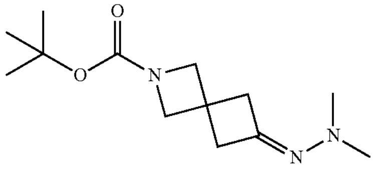

A solution of tert-butyl 6-oxo-2-azaspiro[3.3]heptane-2-carboxylate (100 mg, 0.473 mmol), 1,1-dimethylhydrazine (0.0470 mL, 0.615 mmol) and acetic acid (0.0310 mL, 0.544 mL) in tetrahydrofuran (2.00 mL) was stirred at 60° C. for 2 hours. Tetrahydrofuran was distilled off, and a 1 M aqueous sodium hydroxide solution was then added to the residue. The reaction solution was subjected to extraction with ethyl acetate, followed by passing through a phase separator. The organic layer was concentrated, and the residue was then purified by silica gel column chromatography (hexane/ethyl acetate and subsequently ethyl acetate/methanol) to obtain the title compound (93%, 111 mg).

LCMS: m/z 254$[M+H]^+$

HPLC retention time: 0.83 min (analysis condition F)

Second Step

Compound g2 rac-tert-Butyl (5R,6R)-6-hydroxy-5-methyl-2-azaspiro[3.3]heptane-2-carboxylate

[Formula 63]

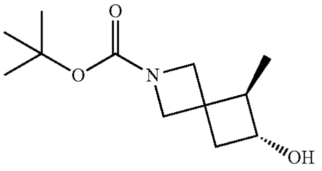

Compound g3 rac-tert-Butyl (5R,6S)-6-hydroxy-5-methyl-2-azaspiro[3.3]heptane-2-carboxylate

[Formula 64]

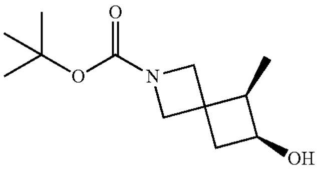

A solution of tert-butyl 6-(dimethylhydrazinylidene)-2-azaspiro[3.3]heptane-2-carboxylate (89.5 mg, 0.353 mmol) in tetrahydrofuran (3.60 mL) was cooled to −78° C., and a 1.5 M solution of lithium diisopropylamide in tetrahydrofuran, ethylbenzene, and heptane (0.283 mL, 0.424 mmol) was added thereto. The reaction solution was stirred at 0° C. for 30 minutes and then cooled to −78° C. Iodomethane (0.0660 mL, 1.06 mmol) was added thereto, and the mixture was stirred at room temperature for 40 minutes. After concentration of the reaction solution, a saturated aqueous solution of oxalic acid (1.80 mL) and ethyl acetate (1.80 mL) were added to the residue, and the mixture was stirred at room temperature for 1 hour. The reaction solution was subjected to extraction with ethyl acetate. The extract was washed with a saturated aqueous solution of sodium bicarbonate, followed by passing through a phase separator. The organic layer was concentrated to obtain tert-butyl 5-methyl-6-oxo-2-azaspiro[3.3]heptane-2-carboxylate as a crude product. A solution of the obtained crude product in dichloromethane (3.00 mL) and methanol (3.00 mL) was cooled to 0° C., and sodium borohydride (26.5 mg, 0.700 mmol) was added thereto. The reaction solution was stirred at 0° C. for 35 minutes. A saturated aqueous solution of sodium bicarbonate was added to the reaction solution, followed by extraction with dichloromethane and subsequent passing through a phase separator. The organic layer was concentrated to obtain tert-butyl 6-hydroxy-5-methyl-2-azaspiro[3.3]heptane-2-carboxylate (84%, 67.0 mg) as a diastereomeric mixture. The diastereomeric mixture (59.0 mg, 0.260 mmol) was purified by HPLC (CHIRALPAK IE, acetonitrile/water) to obtain rac-tert-butyl (5R,6R)-6-hydroxy-5-methyl-2-azaspiro[3.3]heptane-2-carboxylate (53%, 31.3 mg) and rac-tert-butyl (5R,6S)-6-hydroxy-5-methyl-2-azaspiro[3.3]heptane-2-carboxylate (28%, 16.5 mg).

Compound g2 rac-tert-Butyl (5R,6R)-6-hydroxy-5-methyl-2-azaspiro[3.3]heptane-2-carboxylate

[Formula 65]

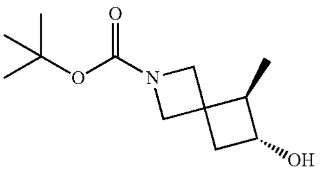

LCMS: m/z 228$[M+H]^+$ $^1$H-NMR (400 MHz, $CDCl_3$) δ: 4.03 (1H, d, J=8.7 Hz), 3.83 (2H, d, J=8.9 Hz), 3.79 (2H, d, J=8.9 Hz), 3.64-3.56 (1H, m), 3.63 (1H, d, J=8.7 Hz), 2.49 (1H, dd, J=11.5, 6.9 Hz), 2.13-2.06 (1H, m), 1.92 (1H, dd, J=11.5, 8.1 Hz), 1.43 (9H, s), 1.14 (3H, d, J=6.9 Hz).

Compound g3 rac-tert-Butyl (5R,6S)-6-hydroxy-5-methyl-2-azaspiro[3.3]heptane-2-carboxylate

[Formula 66]

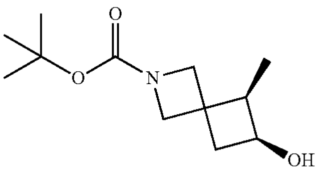

LCMS: m/z 228$[M+H]^+$ $^1$H-NMR (400 MHz, $CDCl_3$) δ: 4.32-4.25 (1H, m), 4.01 (1H, d, J=9.0 Hz), 3.88 (1H, d, J=8.6 Hz), 3.84 (1H, d, J=8.6 Hz), 3.66 (1H, d, J=9.0 Hz), 2.56-2.46 (2H, m), 2.11 (1H, dd, J=13.10, 6.92 Hz), 1.43 (9H, s), 1.07 (3H, d, J=7.25 Hz).

Third Step

Compound 1-86

4-[3-[2,6-Dichloro-4-[rac-(6R,7R)-6-methoxy-7-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 67]

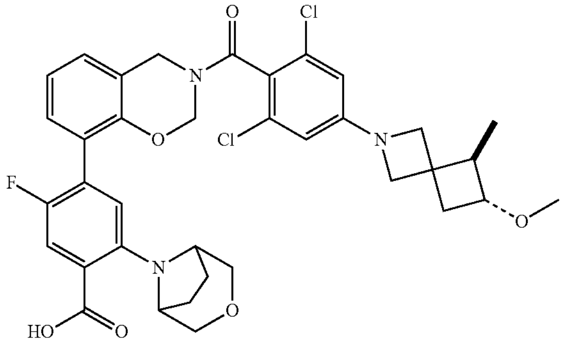

The title compound was obtained by the same operation as in the process of compound 1-22 using rac-tert-butyl (5R,6R)-6-hydroxy-5-methyl-2-azaspiro[3.3]heptane-2-carboxylate and compound A.

LCMS: m/z 696[M+H]$^+$

HPLC retention time: 1.74 min and 1.78 min (analysis condition B)

Compound 1-87

4-[3-[2,6-Dichloro-4-[rac-(6R,7S)-6-methoxy-7-methyl-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 68]

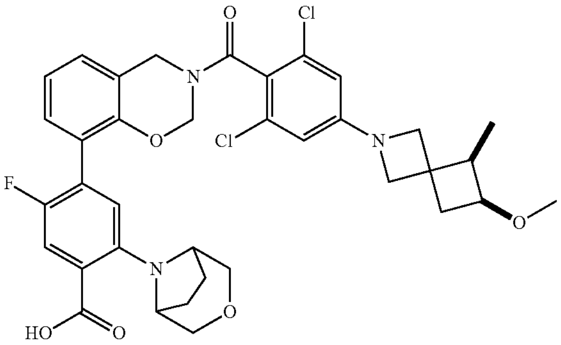

The title compound was obtained by the same operation as in the process of compound 1-22 using rac-tert-butyl (5R,6S)-6-hydroxy-5-methyl-2-azaspiro[3.3]heptane-2-carboxylate and compound A.

LCMS: m/z 696[M+H]$^+$

HPLC retention time: 1.78 min and 1.81 min (analysis condition B)

Compound 1-47

4-[3-[2,6-Dichloro-4-(6-cyano-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl) benzoic acid First Step Compound CP1

Methyl 4-[3-[2,6-dichloro-4-(6-cyano-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 69]

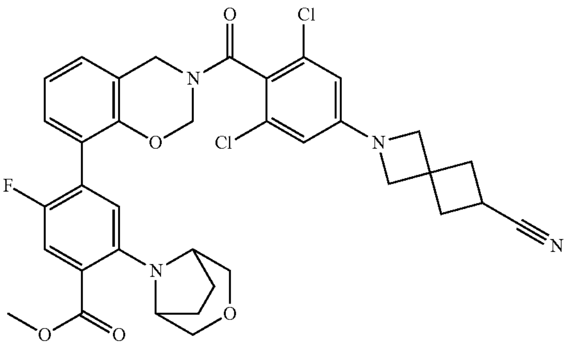

A suspension of compound A (35.5 mg, 0.0550 mmol), 2-azaspiro[3.3]heptane-6-carbonitrile (13.3 mg, 0.109 mmol), rac-BINAP Pd G4 (5.49 mg, 0.00546 mmol) and cesium carbonate (53.4 mg, 0.164 mmol) in 1,4-dioxane (0.550 mL) was stirred at 100° C. for 30 minutes. An aqueous formic acid solution was added to the reaction solution, and the mixture was purified by HPLC (acetonitrile/water, 0.1% formic acid) to obtain the title compound (78%, 29.6 mg).

LCMS: m/z 691[M+H]$^+$

HPLC retention time: 0.96 min (analysis condition D)

Second Step

Compound 1-47

4-[3-[2,6-Dichloro-4-(6-cyano-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl) benzoic acid

[Formula 70]

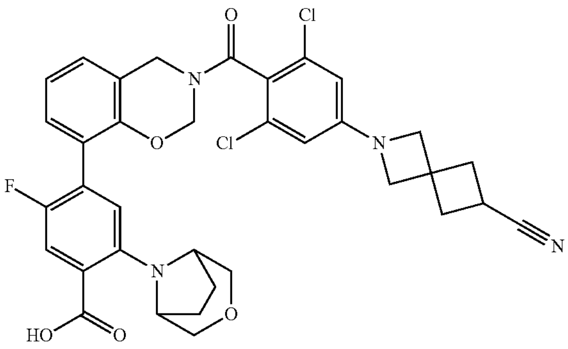

A solution of methyl 4-[3-[2,6-dichloro-4-(6-cyano-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (29.6 mg, 0.0430 mmol) and trimethylstanannol (77.0 mg, 0.428 mmol) in chlorobenzene (0.940 mL) was stirred at 135° C. for 14 hours. An aqueous formic acid solution was added to the reaction solution, and the reaction mixture was purified by HPLC (acetonitrile/water, 0.1% formic acid) to obtain the title compound (98%, 4.50 mg).

LCMS: m/z 677[M+H]$^+$

HPLC retention time: 1.62 min (analysis condition B)

Compound 1-15

4-[3-[2,6-Dichloro-4-(3-cyano-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoic acid First Step
Compound CP2

Methyl 4-[3-[2,6-dichloro-4-(3-cyano-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 71]

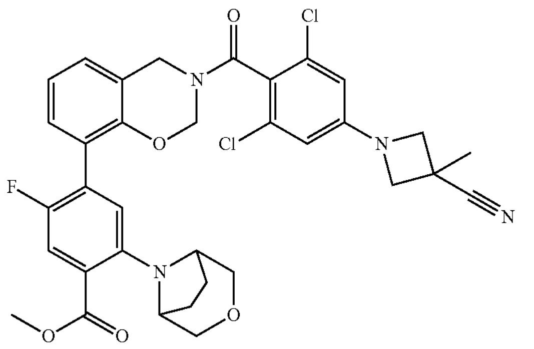

The title compound was synthesized by the same operation as in the first step of compound 1-47 using 3-methylazetidine-3-carbonitrile hydrochloride and compound A. However, 1-methylpyrrolidin-2-one was used instead of 1,4-dioxane as a solvent.

LCMS: m/z 665[M+H]$^+$

HPLC retention time: 0.95 min (analysis condition D)

Second Step
Compound 1-15

4-[3-[2,6-Dichloro-4-(3-cyano-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 72]

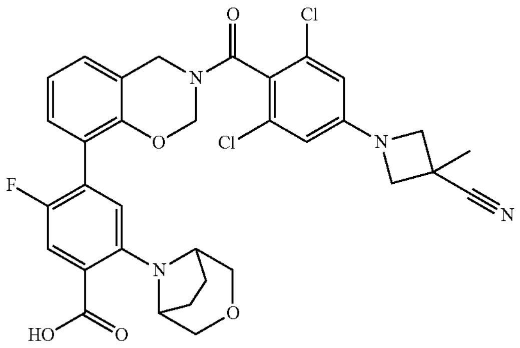

The title compound was synthesized by the same operation as in the second step of compound 1-47 using methyl 4-[3-[2,6-dichloro-4-(3-cyano-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 651 [M+H]$^+$

HPLC retention time: 1.50 min (analysis condition B)

Intermediates shown in Table 1-3 were used in the following synthesis.

TABLE 1-3

| Compound No. | Structure | Compound Name |
|---|---|---|
| B | 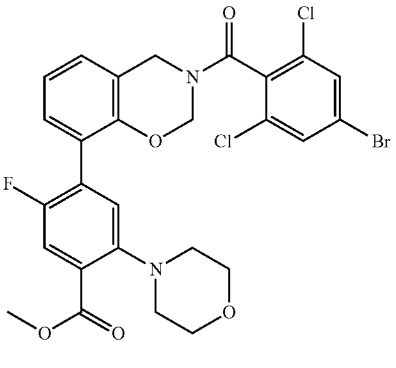 | Methyl 4-[3-(4-bromo-2,6-dichlorobenzoyl)-2,4-dihydro-1,3-benzoxazin-8-yl]-5-fluoro-2-morpholin-4-ylbenzoate |
| C | 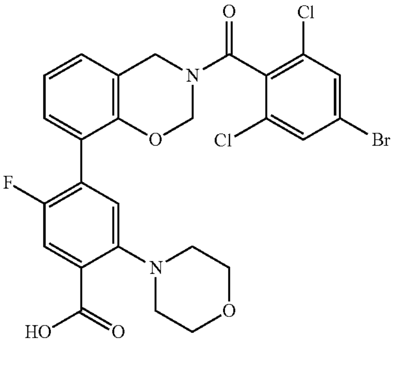 [SMILES: O=C(O)c1cc(F)c(-c2cccc3c2OCN(C(=O)c2c(Cl)cc(Br)cc2Cl)C3)cc1N1CCOCC1] | 4-[3-(4-Bromo-2,6-dichlorobenzoyl)-2,4-dihydro-1,3-benzoxazin-8-yl]-5-fluoro-2-morpholin-4-ylbenzoic acid |

TABLE 1-3-continued

| Compound No. | Structure | Compound Name |
|---|---|---|
| D | 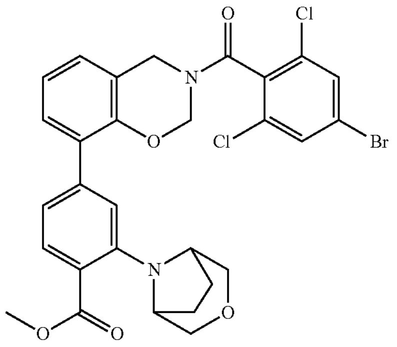 [SMILES: COC(=O)c1ccc(-c2cccc3c2OCN(C(=O)c2c(Cl)cc(Br)cc2Cl)C3)cc1N1C2CCC1COC2] | Methyl 4-[3-(4-bromo-2,6-dichlorobenzoyl)-2,4-dihydro-1,3-benzoxazin-8-yl]-2-(3-oxa-8-azabicyclo[3.2.1]octan-8-yl)benzoate |
| E | 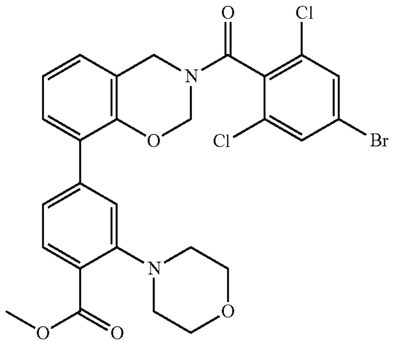 [SMILES: COC(=O)c1ccc(-c2cccc3c2OCN(C(=O)c2c(Cl)cc(Br)cc2Cl)C3)cc1N1CCOCC1] | Methyl 4-[3-(4-bromo-2,6-dichlorobenzoyl)-2,4-dihydro-1,3-benzoxazin-8-yl]-2-morpholin-4-ylbenzoate |
| F | 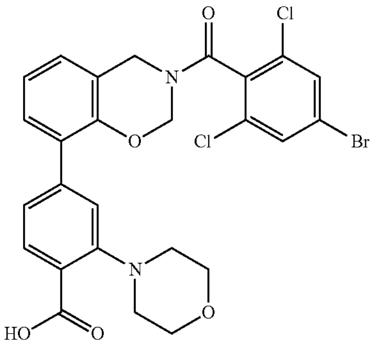 [SMILES: O=C(O)c1ccc(-c2cccc3c2OCN(C(=O)c2c(Cl)cc(Br)cc2Cl)C3)cc1N1CCOCC1] | 4-[3-(4-Bromo-2,6-dichlorobenzoyl)-2,4-dihydro-1,3-benzoxazin-8-yl]-2-morpholin-4-ylbenzoic acid |
| G | 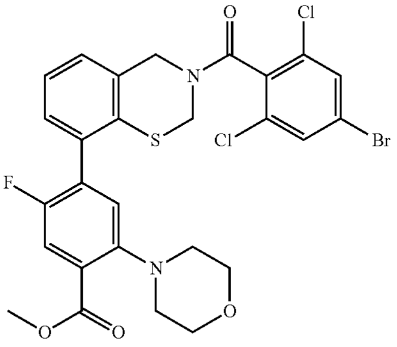 [SMILES: COC(=O)c1cc(F)c(-c2cccc3c2SCN(C(=O)c2c(Cl)cc(Br)cc2Cl)C3)cc1N1CCOCC1] | Methyl 4-[3-(4-bromo-2,6-dichlorobenzoyl)-2,4-dihydro-1,3-benzothiazin-8-yl]-5-fluoro-2-morpholin-4-ylbenzoate |

TABLE 1-3-continued

| Compound No. | Structure | Compound Name |
|---|---|---|
| H | 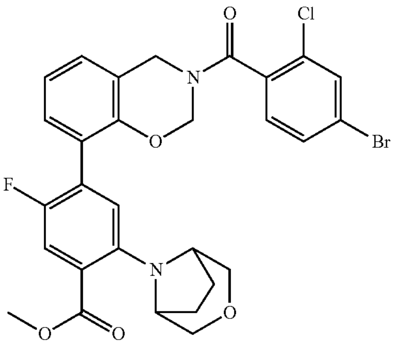 [SMILES: COC(=O)c1cc(F)c(-c2cccc3c2OCN(C(=O)c2ccc(Br)cc2Cl)C3)cc1N1C2CCC1COC2] | Methyl 4-[3-(4-bromo-2-chlorobenzoyl)-2,4-dihydro-1,3-benzoxazin-8-yl]-5-fluoro-2-(3-oxa-8-azabicyclo[3.2.1]octan-8-yl)benzoate |
| I | 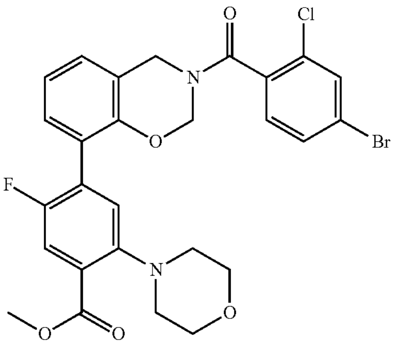 [SMILES: COC(=O)c1cc(F)c(-c2cccc3c2OCN(C(=O)c2ccc(Br)cc2Cl)C3)cc1N1CCOCC1] | Methyl 4-[3-(4-bromo-2-chlorobenzoyl)-2,4-dihydro-1,3-benzoxazin-8-yl]-5-fluoro-2-morpholin-4-ylbenzoate |
| J | 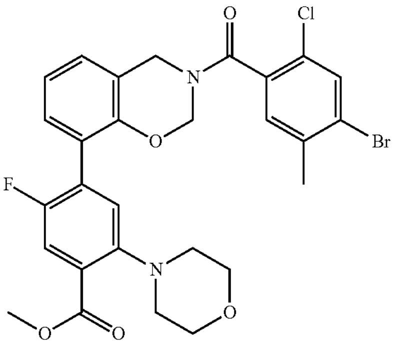 [SMILES: COC(=O)c1cc(F)c(-c2cccc3c2OCN(C(=O)c2cc(C)c(Br)cc2Cl)C3)cc1N1CCOCC1] | Methyl 4-[3-(4-bromo-2-chloro-5-methylbenzoyl)-2,4-dihydro-1,3-benzoxazin-8-yl]-5-fluoro-2-morpholin-4-ylbenzoate |
| K | 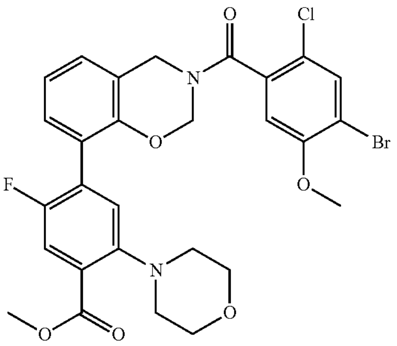 [SMILES: COC(=O)c1cc(F)c(-c2cccc3c2OCN(C(=O)c2cc(OC)c(Br)cc2Cl)C3)cc1N1CCOCC1] | Methyl 4-[3-(4-bromo-2-chloro-5-methoxybenzoyl)-2,4-dihydro-1,3-benzoxazin-8-yl]-5-fluoro-2-morpholin-4-ylbenzoate |

TABLE 1-3-continued

| Compound No. | Structure | Compound Name |
|---|---|---|
| L | 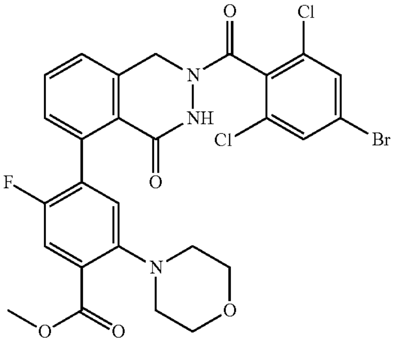 [SMILES: COC(=O)c1cc(F)c(-c2cccc3c2C(=O)NN(C(=O)c2c(Cl)cc(Br)cc2Cl)C3)cc1N1CCOCC1] | Methyl 4-[2-(4-bromo-2,6-dichlorobenzoyl)-4-oxo-1,3-dihydrophthalazin-5-yl]-2-morpholin-4-ylbenzoate |
| M | 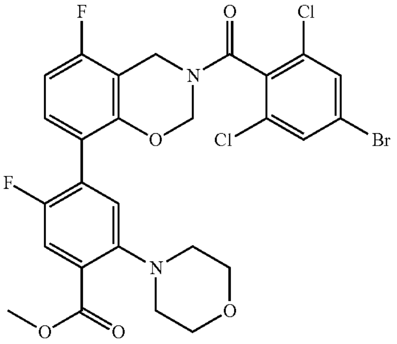 [SMILES: COC(=O)c1cc(F)c(-c2ccc(F)c3c2OCN(C(=O)c2c(Cl)cc(Br)cc2Cl)C3)cc1N1CCOCC1] | Methyl 4-[3-(4-bromo-2,6-dichlorobenzoyl)-5-fluoro-2,4-dihydro-1,3-benzoxazin-8-yl]-5-fluoro-2-morpholin-4-ylbenzoate |
| N | 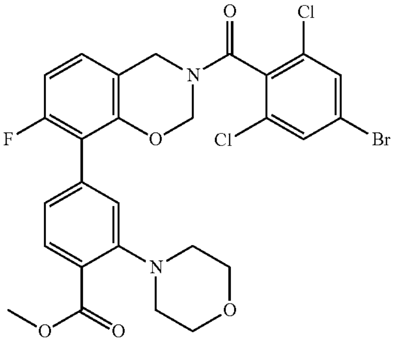 [SMILES: COC(=O)c1ccc(-c2c(F)ccc3c2OCN(C(=O)c2c(Cl)cc(Br)cc2Cl)C3)cc1N1CCOCC1] | Methyl 4-[3-(4-bromo-2,6-dichlorobenzoyl)-7-fluoro-2,4-dihydro-1,3-benzoxazin-8-yl]-2-morpholin-4-ylbenzoate |
| O | 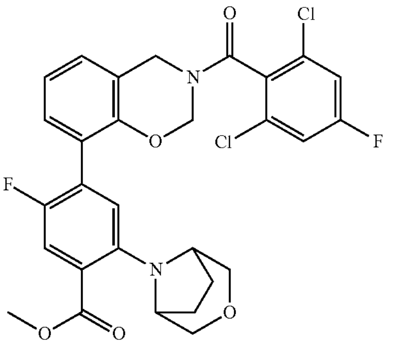 [SMILES: COC(=O)c1cc(F)c(-c2cccc3c2OCN(C(=O)c2c(Cl)cc(F)cc2Cl)C3)cc1N1C2CCC1COC2] | Methyl 4-[3-(2,6-dichloro-4-fluorobenzoyl)-2,4-dihydro-1,3-benzoxazin-8-yl]-5-fluoro-2-(3-oxa-8-azabicyclo[3.2.1]octan-8-yl)benzoate |

TABLE 1-3-continued

| Compound No. | Structure | Compound Name |
|---|---|---|
| P | 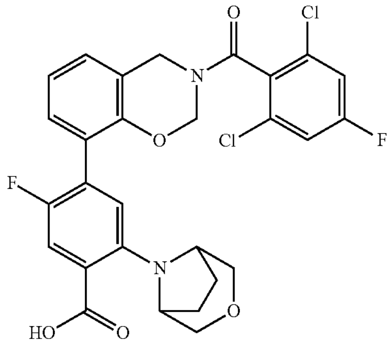 [SMILES: O=C(O)c1cc(F)c(-c2cccc3c2OCN(C(=O)c2c(Cl)cc(F)cc2Cl)C3)cc1N1C2CCC1COC2] | 4-[3-(2,6-Dichloro-4-fluorobenzoyl)-2,4-dihydro-1,3-benzoxazin-8-yl]-5-fluoro-2-(3-oxa-8-azabicyclo[3.2.1]octan-8-yl)benzoic acid |
| Q | 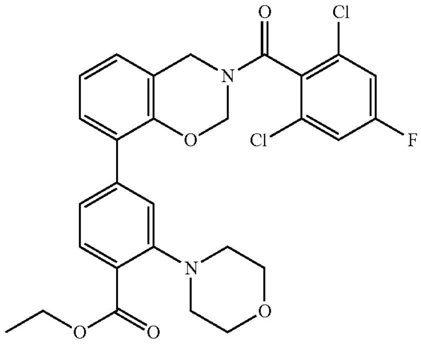 [SMILES: CCOC(=O)c1ccc(-c2cccc3c2OCN(C(=O)c2c(Cl)cc(F)cc2Cl)C3)cc1N1CCOCC1] | Ethyl 4-[3-(2,6-dichloro-4-fluorobenzoyl)-2,4-dihydro-1,3-benzoxazin-8-yl]-2-morpholin-4-ylbenzoate |
| R | 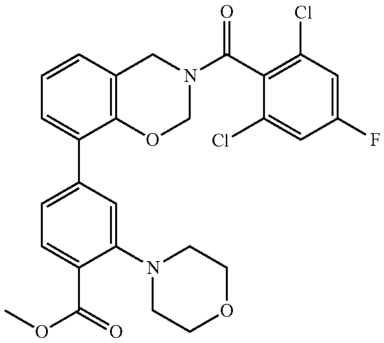 | Methyl 4-[3-(2,6-dichloro-4-fluorobenzoyl)-2,4-dihydro-1,3-benzoxazin-8-yl]-2-morpholin-4-ylbenzoate |
| S | 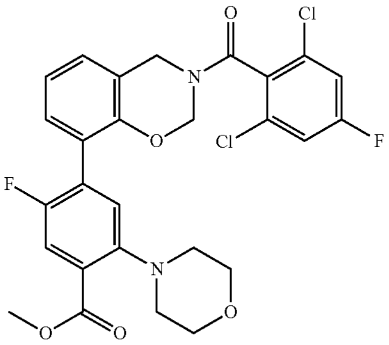 [SMILES: COC(=O)c1cc(F)c(-c2cccc3c2OCN(C(=O)c2c(Cl)cc(F)cc2Cl)C3)cc1N1CCOCC1] | Methyl 4-[3-(2,6-dichloro-4-fluorobenzoyl)-2,4-dihydro-1,3-benzoxazin-8-yl]-5-fluoro-2-morpholin-4-ylbenzoate |

TABLE 1-3-continued

| Compound No. | Structure | Compound Name |
|---|---|---|
| T | 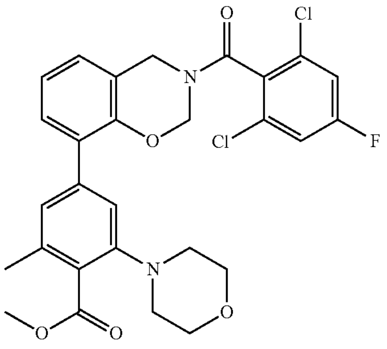 [SMILES: COC(=O)c1c(C)cc(-c2cccc3c2OCN(C(=O)c2c(Cl)cc(F)cc2Cl)C3)cc1N1CCOCC1] | Methyl 4-[3-(2,6-dichloro-4-fluorobenzoyl)-2,4-dihydro-1,3-benzoxazin-8-yl]-2-methyl-6-morpholin-4-ylbenzoate |
| U | 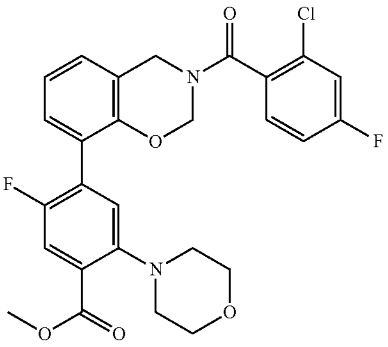 [SMILES: COC(=O)c1cc(F)c(-c2cccc3c2OCN(C(=O)c2ccc(F)cc2Cl)C3)cc1N1CCOCC1] | Methyl 4-[3-(2-chloro-4-fluorobenzoyl)-2,4-dihydro-1,3-benzoxazin-8-yl]-5-fluoro-2-morpholin-4-ylbenzoate |
| V | 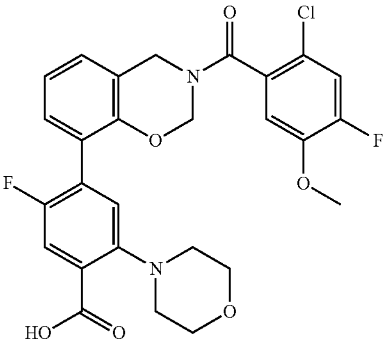 [SMILES: COc1cc(C(=O)N2COc3c(cccc3-c3cc(N4CCOCC4)c(C(=O)O)cc3F)C2)c(Cl)cc1F] | 4-[3-(2-Chloro-4-fluoro-5-methoxybenzoyl)-2,4-dihydro-1,3-benzoxazin-8-yl]-5-fluoro-2-morpholin-4-ylbenzoic acid |
| W | 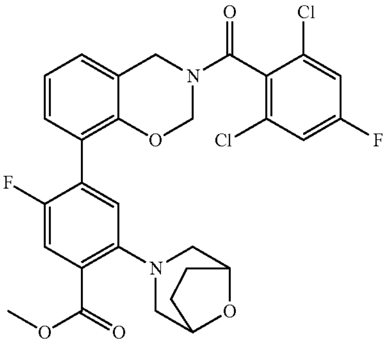 [SMILES: COC(=O)c1cc(F)c(-c2cccc3c2OCN(C(=O)c2c(Cl)cc(F)cc2Cl)C3)cc1N1CC2CCC(C1)O2] | Methyl 4-[3-(2,6-dichloro-4-fluorobenzoyl)-2,4-dihydro-1,3-benzoxazin-8-yl]-5-fluoro-2-(8-oxa-3-azabicyclo[3.2.1]octan-3-yl)benzoate |

TABLE 1-3-continued

| Compound No. | Structure | Compound Name |
|---|---|---|
| X | 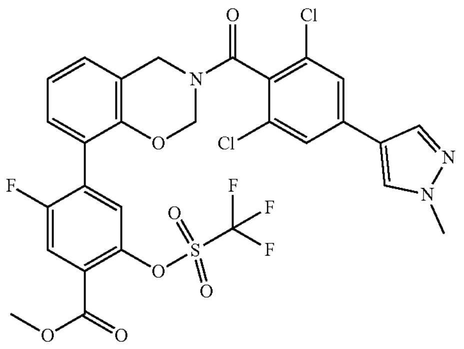 [SMILES: COC(=O)c1cc(F)c(-c2cccc3c2OCN(C(=O)c2c(Cl)cc(-c4cnn(C)c4)cc2Cl)C3)cc1OS(=O)(=O)C(F)(F)F] | Methyl 4-[3-[2,6-dichloro-4-(1-methylpyrazol-4-yl)benzoyl]-2,4-dihydro-1,3-benzoxazin-8-yl]-5-fluoro-2-(trifluoromethylsulfonyloxy) benzoate |
| Y | 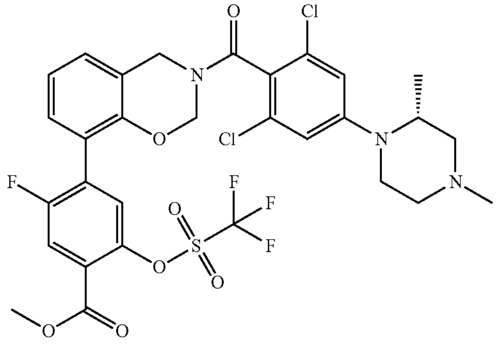 [SMILES: COC(=O)c1cc(F)c(-c2cccc3c2OCN(C(=O)c2c(Cl)cc(N4CCN(C)C[C@H]4C)cc2Cl)C3)cc1OS(=O)(=O)C(F)(F)F] | Methyl 4-[3-[2,6-dichloro-4-[(2R)-2,4-dimethylpiperazin-1-yl]benzoyl]-2,4-dihydro-1,3-benzoxazin-8-yl]-5-fluoro-2-(trifluoromethylsulfonyloxy) benzoate |
| Z | 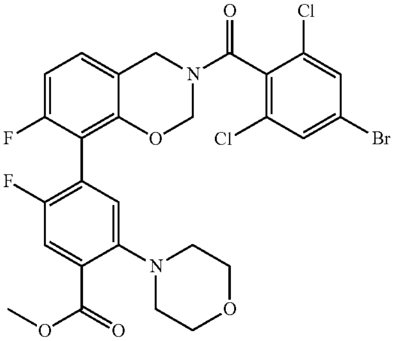 [SMILES: COC(=O)c1cc(F)c(-c2c(F)ccc3c2OCN(C(=O)c2c(Cl)cc(Br)cc2Cl)C3)cc1N1CCOCC1] | Methyl 4-[3-(4-bromo-2,6-dichlorobenzoyl)-7-fluoro-2,4-dihydro-1,3-benzoxazin-8-yl]-5-fluoro-2-morpholin-4-ylbenzoate |

Compound B

Methyl 4-[3-(4-bromo-2,6-dichlorobenzoyl)-2,4-dihydro-1,3-benzoxazin-8-yl]-5-fluoro-2-morpholin-4-ylbenzoate First Step Compound B1

4-Bromo-5-fluoro-2-morpholin-4-ylbenzoic acid

[Formula 73]

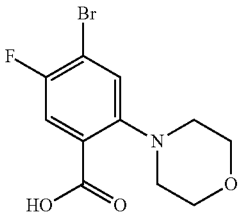

To 4-bromo-2,5-difluorobenzoic acid (950 mg, 4.01 mmol), morpholine (6.98 g, 80.0 mmol) was added, and the mixture was stirred at 100° C. for 24 hours. Ethyl acetate and hydrochloric acid were added to the reaction solution for extraction. Then, the extract was washed with saturated saline. The organic layer was concentrated to obtain the title compound (98%, 1.20 g).

LCMS: m/z 304[M+H]+

HPLC retention time: 0.77 min (analysis condition N)

Second Step

Compound B2

Methyl 4-bromo-5-fluoro-2-morpholin-4-ylbenzoate

[Formula 74]

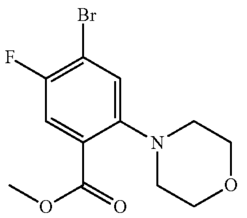

To a solution of 4-bromo-5-fluoro-2-morpholin-4-ylbenzoic acid (400 mg, 1.32 mmol) in dichloromethane (5.00 mL)-methanol (1.00 mL), a 2 M solution of trimethylsilyldiazomethane in hexane (1.32 mL, 2.63 mmol) was added, and the mixture was stirred at room temperature for 30 minutes. Acetic acid was added to the reaction solution, and the reaction solution was concentrated. Then, the reaction mixture was purified by silica gel chromatography (hexane/ethyl acetate) to obtain the title compound (81%, 341 mg).

LCMS: m/z 318[M+H]+

HPLC retention time: 1.10 min (analysis condition N)

Third Step

Compound B3 tert-Butyl 8-(2-fluoro-4-methoxycarbonyl-5-morpholin-4-ylphenyl)-2,4-dihydro-1,3-benzoxazine-3-carboxylate

[Formula 75]

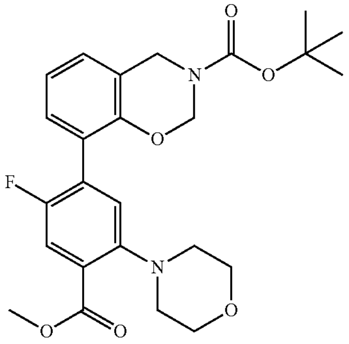

A solution of methyl 4-bromo-5-fluoro-2-morpholin-4-ylbenzoate (2.95 g, 9.28 mmol), bis(pinacolato)diboron (2.78 g, 11.0 mmol), potassium acetate (2.48 g, 25.3 mmol), and a 1,1'-bis(diphenylphosphino)ferrocene-palladium(II) dichloride dichloromethane complex (0.344 g, 0.422 mmol) in 1,4-dioxane (16.9 mL) was stirred at 90° C. for 5 hours. The reaction solution was cooled to room temperature. tert-Butyl 8-bromo-2,4-dihydro-1,3-benzoxazine-3-carboxylate (2.65 g, 8.43 mmol), a 1,1'-bis(diphenylphosphino) ferrocene-palladium(II) dichloride dichloromethane complex (0.344 g, 0.422 mmol), potassium carbonate (3.50 g, 25.3 mmol), and water (4.22 mL) were added thereto, and the mixture was stirred at 90° C. for 3 hours. The reaction solution was cooled to room temperature. Water and ethyl acetate were added thereto, and the mixture was filtered through celite. The organic layer was washed with saline, dried, and concentrated. The obtained residue was purified by silica gel chromatography (hexane/ethyl acetate) to obtain the title compound (91%, 3.63 g).

LCMS: m/z 473[M+H]+

HPLC retention time: 1.34 min (analysis condition G)

Fourth Step

Compound B4

Methyl 4-(3,4-dihydro-2H-1,3-benzoxazin-8-yl)-5-fluoro-2-morpholin-4-ylbenzoate dihydrochloride

[Formula 76]

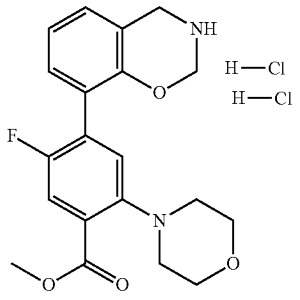

To a solution of tert-butyl 8-(2-fluoro-4-methoxycarbonyl-5-morpholin-4-ylphenyl)-2,4-dihydro-1,3-benzoxazine-3-carboxylate (100 mg, 0.212 mmol) in dichloromethane (1.058 mL), a 4 M solution of hydrochloric acid in 1,4-dioxane (0.794 mL, 3.17 mmol) was added, and the mixture was stirred at room temperature for 2 hours. The reaction solution was concentrated to obtain the title compound as a crude product.

LCMS: m/z 373[M+H]$^+$

HPLC retention time: 0.49 min (analysis condition D)

Fifth Step

Compound B

Methyl 4-[3-(4-bromo-2,6-dichlorobenzoyl)-2,4-dihydro-1,3-benzoxazin-8-yl]-5-fluoro-2-morpholin-4-ylbenzoate

[Formula 77]

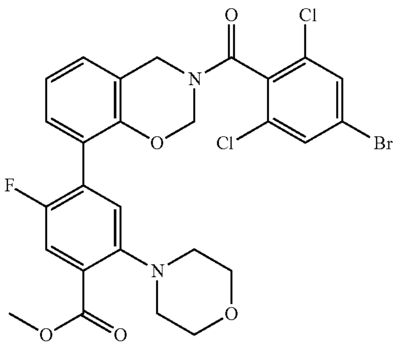

A solution of methyl 4-(3,4-dihydro-2H-1,3-benzoxazin-8-yl)-5-fluoro-2-(3-oxa-8-azabicyclo[3.2.1]octan-8-yl)benzoate dihydrochloride (141 mg, 0.317 mmol) and 4-bromo-2,6-dichlorobenzoyl chloride (137 mg, 0.476 mmol) in dichloromethane (1.585 mL) was cooled to 0° C. N,N-Diisopropylethylamine (0.166 mL, 0.951 mmol) was added thereto, and the mixture was stirred at room temperature for 3 hours. Ethanolamine was added to the reaction solution, and the mixture was purified by reverse phase column chromatography (acetonitrile/water, 0.1% formic acid) to obtain the title compound (56%, 110 mg).

LCMS: m/z 623[M+H]$^+$

HPLC retention time: 1.37 min (analysis condition G)

Compound C

4-[3-(4-Bromo-2,6-dichlorobenzoyl)-2,4-dihydro-1,3-benzoxazin-8-yl]-5-fluoro-2-morpholin-4-ylbenzoic acid

[Formula 78]

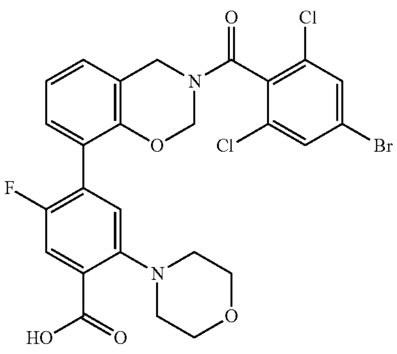

To methyl 4-[3-(4-bromo-2,6-dichlorobenzoyl)-2,4-dihydro-1,3-benzoxazin-8-yl]-5-fluoro-2-morpholin-4-ylbenzoate (16.0 mg, 0.0260 mmol), tetrahydrofuran (0.0641 mL) and methanol (0.0641 mL) were added, then a 5 M aqueous sodium hydroxide solution (0.0513 mL, 0.256 mmol) was added, and the mixture was stirred at 60° C. for 15 minutes. 1 M hydrochloric acid was added to the reaction solution, followed by extraction with ethyl acetate. The organic layer was concentrated to obtain the title compound (91%, 14.3 mg).

LCMS: m/z 609[M+H]$^+$

HPLC retention time: 1.15 min and 1.16 min (analysis condition G)

Compound D

Methyl 4-[3-(4-bromo-2,6-dichlorobenzoyl)-2,4-dihydro-1,3-benzoxazin-8-yl]-2-(3-oxa-8-azabicyclo[3.2.1]octan-8-yl)benzoate First Step Compound D2

4-Bromo-2-(3-oxa-8-azabicyclo[3.2.1]octan-8-yl)benzoic acid

[Formula 79]

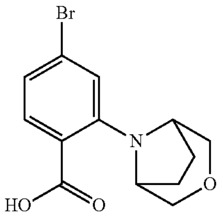

To a solution of 3-oxa-8-azabicyclo[3.2.1]octane hydrochloride (615 mg, 4.11 mmol) in 1-methylpyrrolidin-one (3.43 mL), potassium tert-butoxide (584 mg, 5.21 mmol) was added, and the mixture was stirred at room temperature for 5 hours. 4-Bromo-2-fluorobenzoic acid (300 mg, 1.37 mmol) was added thereto, and the mixture was stirred at 150° C. for 21 hours. Methanol was added to the reaction solution, and the reaction mixture was purified by reverse phase silica gel chromatography (acetonitrile/water, 0.1% formic acid) to obtain the title compound (94%, 400 mg).

LCMS: m/z 312[M+H]$^+$

HPLC retention time: 0.64 min (analysis condition F)

Second Step

Compound D3

Methyl 4-bromo-2-(3-oxa-8-azabicyclo[3.2.1]octan-8-yl)benzoate

[Formula 80]

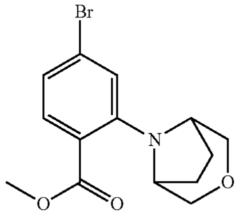

The title compound was obtained by the same operation as in the second step of compound B using 4-bromo-2-(3-oxa-8-azabicyclo[3.2.1]octan-8-yl)benzoic acid.

LCMS: m/z 326[M+H]$^+$

HPLC retention time: 0.82 min (analysis condition D)

Third Step

Compound D4 tert-Butyl 8-[4-methoxycarbonyl-3-(3-oxa-8-azabicyclo[3.2.1]octan-8-yl)phenyl]-2,4-dihydro-1,3-benzoxazine-3-carboxylate

[Formula 81]

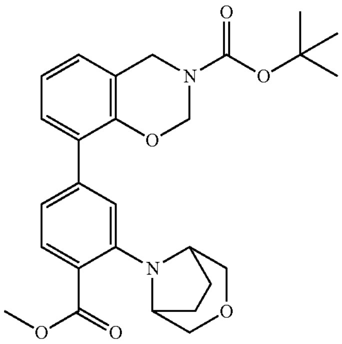

The title compound was obtained by the same operation as in the third step of compound B using methyl 4-bromo-2-(3-oxa-8-azabicyclo[3.2.1]octan-8-yl)benzoate.

LCMS: m/z 481[M+H]$^+$

HPLC retention time: 0.98 min (analysis condition D)

Fourth Step

Compound D5

Methyl 4-(3,4-dihydro-2H-1,3-benzoxazin-8-yl)-2-(3-oxa-8-azabicyclo[3.2.1]octan-8-yl)benzoate dihydrochloride

[Formula 82]

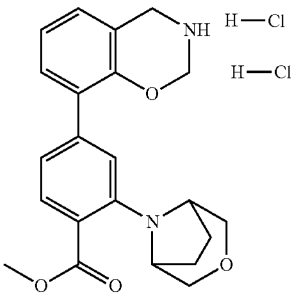

The title compound was obtained by the same operation as in the fourth step of compound B using tert-butyl 8-[4-methoxycarbonyl-3-(3-oxa-8-azabicyclo[3.2.1]octan-8-yl)phenyl]-2,4-dihydro-1,3-benzoxazine-3-carboxylate.

LCMS: m/z 381[M+H]$^+$

HPLC retention time: 0.52 min (analysis condition D)

Fifth Step

Compound D

Methyl 4-[3-(4-bromo-2,6-dichlorobenzoyl)-2,4-dihydro-1,3-benzoxazin-8-yl]-2-(3-oxa-8-azabicyclo[3.2.1]octan-8-yl)benzoate

[Formula 83]

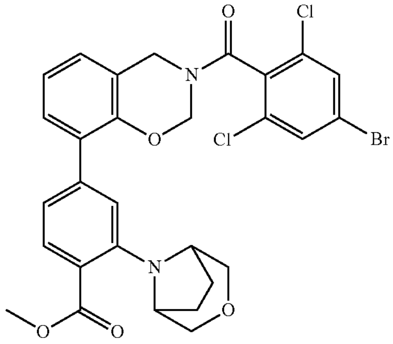

The title compound was obtained by the same operation as in the fifth step of compound B using methyl 4-(3,4-dihydro-2H-1,3-benzoxazin-8-yl)-2-(3-oxa-8-azabicyclo[3.2.1]octan-8-yl)benzoate dihydrochloride.

LCMS: m/z 631 [M+H]$^+$

HPLC retention time: 1.00 min (analysis condition D)

Compound E

Methyl 4-[3-(4-bromo-2,6-dichlorobenzoyl)-2,4-dihydro-1,3-benzoxazin-8-yl]-2-morpholin-4-ylbenzoate First Step Compound E1

4-Bromo-2-morpholin-4-ylbenzoic acid

[Formula 84]

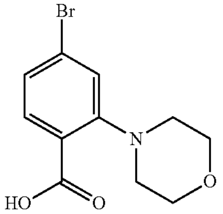

To a solution of 4-bromo-2-fluorobenzoic acid (672 mg, 3.07 mmol) in 1-methylpyrrolidin-2-one (3.07 mL), morpholine (5.76 mL, 66.1 mmol) was added, and the mixture was stirred at 150° C. for 1 hour. The reaction mixture was purified by reverse phase column chromatography (acetonitrile/water, 0.1% formic acid) to obtain the title compound (77%, 672 mg).

LCMS: m/z 286[M+H]$^+$

HPLC retention time: 0.75 min (analysis condition G)

Second Step

Compound E2

Methyl 4-bromo-2-morpholin-4-ylbenzoate

[Formula 85]

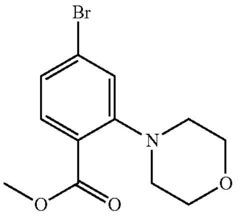

The title compound was obtained by the same operation as in the second step of compound B using 4-bromo-2-morpholin-4-ylbenzoic acid.

LCMS: m/z 300[M+H]$^+$

HPLC retention time: 1.10 min (analysis condition G)

Third Step

Compound E3 tert-Butyl 8-(4-methoxycarbonyl-3-morpholin-4-ylphenyl)-2,4-dihydro-1,3-benzoxazine-3-carboxylate

[Formula 86]

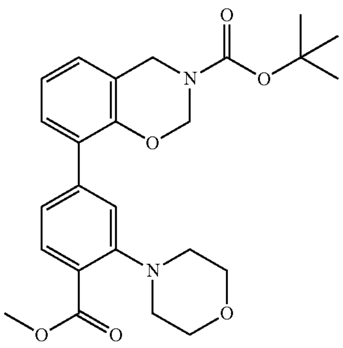

The title compound was obtained by the same operation as in the third step of compound B using methyl 4-bromo-2-morpholin-4-ylbenzoate.

LCMS: m/z 455[M+H]$^+$

HPLC retention time: 1.31 min (analysis condition G)

Fourth Step

Compound E4

Methyl 4-(3,4-dihydro-2H-1,3-benzoxazin-8-yl)-2-morpholin-4-ylbenzoate dihydrochloride

[Formula 87]

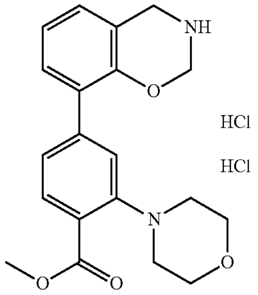

The title compound was obtained by the same operation as in the fourth step of compound B using tert-butyl 8-(4-methoxycarbonyl-3-morpholin-4-ylphenyl)-2,4-dihydro-1,3-benzoxazine-3-carboxylate.

LCMS: m/z 355[M+H]$^+$

HPLC retention time: 0.67 min (analysis condition G)

Fifth Step

Compound E

Methyl 4-[3-(4-bromo-2,6-dichlorobenzoyl)-2,4-dihydro-1,3-benzoxazin-8-yl]-2-morpholin-4-ylbenzoate

[Formula 88]

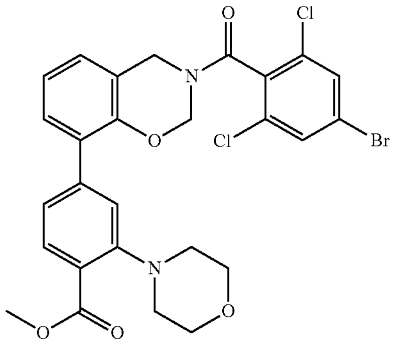

The title compound was obtained by the same operation as in the fifth step of compound B using methyl 4-(3,4-dihydro-2H-1,3-benzoxazin-8-yl)-2-morpholin-4-ylbenzoate dihydrochloride.

LCMS: m/z 605[M+H]$^+$

HPLC retention time: 1.35 min (analysis condition G)

Compound F

4-[3-(4-Bromo-2,6-dichlorobenzoyl)-2,4-dihydro-1,3-benzoxazin-8-yl]-2-morpholin-4-ylbenzoic acid

[Formula 89]

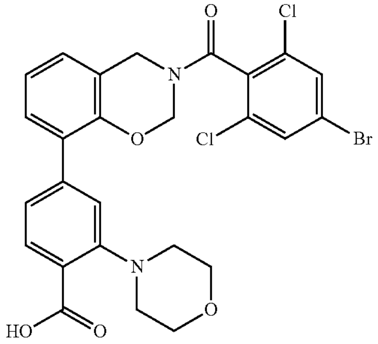

The title compound was obtained by the same operation as in the process of compound C using methyl 4-[3-(4-bromo-2,6-dichlorobenzoyl)-2,4-dihydro-1,3-benzoxazin-8-yl]-2-morpholin-4-ylbenzoate.

LCMS: m/z 591[M+H]$^+$

HPLC retention time: 1.13 min and 1.15 min (analysis condition G)

Compound G

Methyl 4-[3-(4-bromo-2,6-dichlorobenzoyl)-2,4-dihydro-1,3-benzothiazin-8-yl]-5-fluoro-2-morpholin-4-ylbenzoate First Step Compound G2

2-Ethylhexyl 3-(2-bromo-6-cyanophenyl)sulfanylpropanoate

[Formula 90]

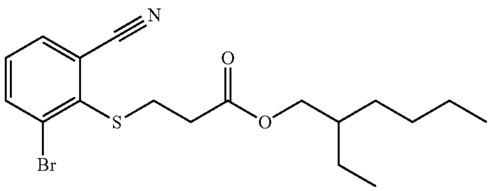

To a solution of 3-bromo-2-fluorobenzonitrile (2.00 g, 10.0 mmol) and 2-ethylhexyl 3-sulfanylpropanoate (2.49 mL, 11.0 mmol) in tetrahydrofuran (40.0 mL), potassium carbonate (4.15 g, 30.0 mmol) was added, and the mixture was stirred at 80° C. for 2 hours. The reaction mixture was purified by reverse phase column chromatography (acetonitrile/water, 0.1% formic acid) to obtain the title compound (97%, 3.87 g).

LCMS: m/z 398[M+H]$^+$

HPLC retention time: 1.60 min (analysis condition G)

Second Step

Compound G4

2-Ethylhexyl 3-[2-bromo-6-[[(2-methylpropan-2-yl)oxycarbonylamino]methyl]phenyl]sulfanylpropanoate

[Formula 91]

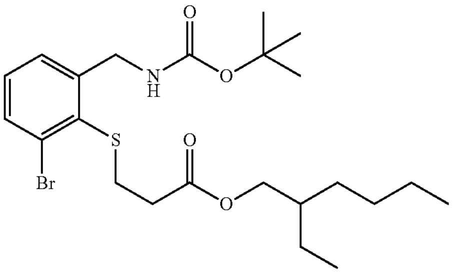

To a solution of 2-ethylhexyl 3-(2-bromo-6-cyanophenyl)sulfanylpropanoate (1.99 g, 5.00 mmol) and cobalt(II) chloride hexahydrate (2.38 g, 10.0 mmol) in methanol (25.0 mL), sodium borohydride (567 mg, 15.0 mmol) was added in small portions, and the mixture was stirred at room temperature for 2 hours. Di-tert-butyl dicarbonate (2.32 mL, 10.0 mmol) was added thereto, and the mixture was further stirred at room temperature for 1 hour. The reaction solution was cooled to 0° C., and 1 M hydrochloric acid was added thereto, followed by extraction with ethyl acetate. The organic layer was washed with a saturated aqueous solution of ammonium chloride, a saturated aqueous solution of sodium bicarbonate, and a saturated aqueous solution of sodium chloride, followed by passing through a phase separator. Then, the organic layer was concentrated. Methanol and formic acid were added to the obtained residue, and the mixture was purified by reverse phase column chromatography (acetonitrile/water, 0.1% formic acid) to obtain the title compound (95%, 965 mg).

LCMS: m/z 524[M+Na]$^+$

HPLC retention time: 1.73 min (analysis condition G)

Third Step

Compound G5 tert-Butyl N-[(3-bromo-2-sulfanylphenyl)methyl]carbamate

[Formula 92]

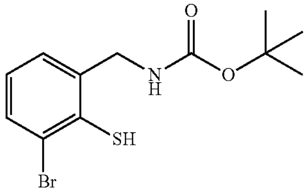

A solution of 2-ethylhexyl 3-[2-bromo-6-[[(2-methylpropan-2-yl)oxycarbonylamino]methyl]phenyl]sulfanylpropanoate (950 mg, 1.89 mmol) in tetrahydrofuran (12.6 mL) was cooled to −78° C. A 1.7 M solution of potassium tert-pentoxide in toluene (2.22 mL, 3.78 mmol) was added dropwise thereto, and the mixture was stirred at −78° C. for 30 minutes. 1 M hydrochloric acid was added thereto, followed by extraction with ethyl acetate. The organic layer was washed with a saturated aqueous solution of sodium chloride, followed by passing through a phase separator. The organic layer was concentrated to obtain the title compound as a crude product.

LCMS: m/z 262[M-tBu+H]$^+$

HPLC retention time: 1.27 min (analysis condition G)

Fourth Step

Compound G6 tert-Butyl 8-bromo-2,4-dihydro-1,3-benzothiazine-3-carboxylate

[Formula 93]

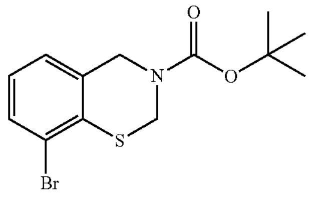

A solution of tert-butyl N-[(3-bromo-2-sulfanylphenyl)methyl]carbamate (602 mg, 1.89 mmol), paraformaldehyde (568 mg, 18.9 mmol) and p-toluenesulfonic acid (3.60 mg, 0.0190 mmol) in toluene (0.200 mL) was stirred at 90° C. for 1 hour. The reaction solution was poured to a saturated aqueous solution of sodium bicarbonate, followed by extraction with ethyl acetate. The organic layer was washed with a saturated aqueous solution of sodium chloride, followed by passing through a phase separator. The organic layer was concentrated. The residue was purified by silica gel chromatography (hexane/ethyl acetate) to obtain the title compound (99%, 620 mg).

LCMS: m/z 274[M-tBu+H]$^+$

HPLC retention time: 1.37 min (analysis condition G)

Fifth Step

Compound G7 tert-Butyl 8-(2-fluoro-4-methoxycarbonyl-5-morpholin-4-ylphenyl)-2,4-dihydro-1,3-benzothiazine-3-carboxylate

[Formula 94]

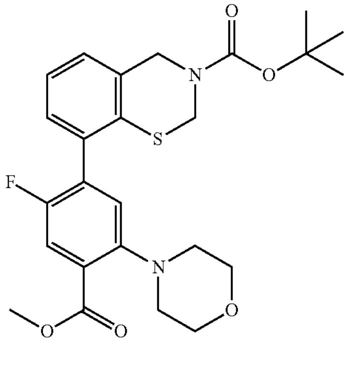

The title compound was obtained by the same operation as in the third step of compound B using tert-butyl 8-bromo-2,4-dihydro-1,3-benzothiazine-3-carboxylate and methyl 4-bromo-5-fluoro-2-morpholin-4-ylbenzoate.

LCMS: m/z 489[M+H]$^+$

HPLC retention time: 1.34 min (analysis condition G)

Sixth Step

Compound G8

Methyl 4-(3,4-dihydro-2H-1,3-benzothiazin-8-yl)-5-fluoro-2-morpholin-4-ylbenzoate dihydrochloride

[Formula 95]

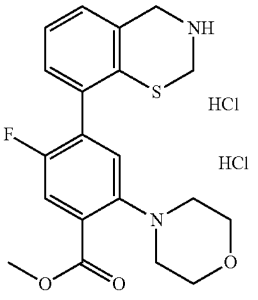

The title compound was synthesized by the same operation as in the fourth step of compound B using tert-butyl 8-(2-fluoro-4-methoxycarbonyl-5-morpholin-4-ylphenyl)-2,4-dihydro-1,3-benzothiazine-3-carboxylate.

LCMS: m/z 389[M+H]$^+$

HPLC retention time: 0.69 min (analysis condition G)

Seventh Step

Compound G

Methyl 4-[3-(4-bromo-2,6-dichlorobenzoyl)-2,4-dihydro-1,3-benzothiazin-8-yl]-5-fluoro-2-morpholin-4-ylbenzoate

[Formula 96]

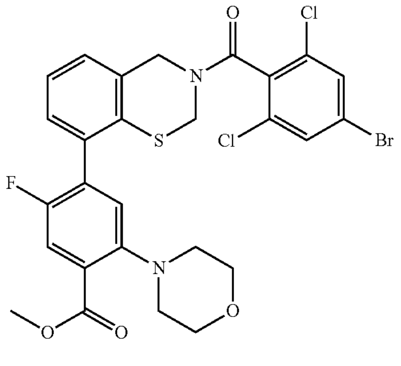

The title compound was obtained by the same operation as in the fifth step of compound B using methyl 4-(3,4-dihydro-2H-1,3-benzothiazin-8-yl)-5-fluoro-2-morpholin-4-ylbenzoate dihydrochloride. However, triethylamine was used instead of N,N-diisopropylethylamine.

LCMS: m/z 639[M+H]$^+$

HPLC retention time: 1.37 min and 1.39 min (analysis condition G)

Compound H

Methyl 4-[3-(4-bromo-2-chlorobenzoyl)-2,4-dihydro-1,3-benzoxazin-8-yl]-5-fluoro-2-(3-oxa-8-azabicyclo[3.2.1]octan-8-yl)benzoate

[Formula 97]

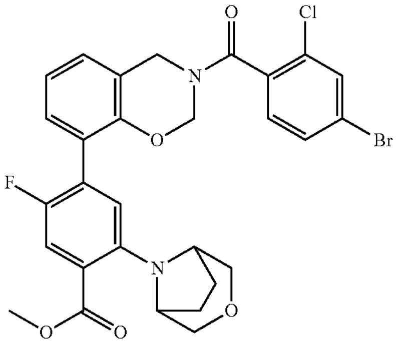

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2-chlorobenzoyl chloride.

LCMS: m/z 615[M+H]$^+$

HPLC retention time: 0.97 min (analysis condition N)

Compound I

Methyl 4-[3-(4-bromo-2-chlorobenzoyl)-2,4-dihydro-1,3-benzoxazin-8-yl]-5-fluoro-2-morpholin-4-ylbenzoate

[Formula 98]

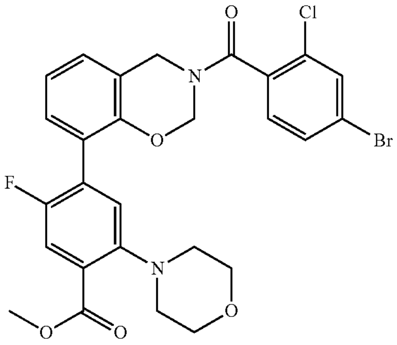

The title compound was obtained by the same operation as in the fifth step of compound B using methyl 4-(3,4-dihydro-2H-1,3-benzoxazin-8-yl)-5-fluoro-2-morpholin-4-ylbenzoate dihydrochloride and 4-bromo-2-chlorobenzoyl chloride.

LCMS: m/z 589[M+H]$^+$

HPLC retention time: 1.32 min (analysis condition N)

Compound J

Methyl 4-[3-(4-bromo-2-chloro-5-methylbenzoyl)-2,4-dihydro-1,3-benzoxazin-8-yl]-5-fluoro-2-morpholin-4-ylbenzoate First Step Compound J2

Methyl 4-bromo-2-chloro-5-methylbenzoate

[Formula 99]

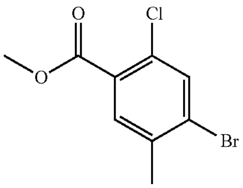

To a solution of methyl 4-bromo-3-methylbenzoate (500 mg, 2.18 mmol) in dichloromethane (5.46 mL), N-chlorosuccinimide (350 mg, 2.62 mmol), palladium(II) acetate (24.5 mg, 0.109 mmol), sodium peroxodisulfate (1.04 g, 4.37 mmol) and trifluoromethanesulfonic acid (0.579 mL, 6.55 mmol) were added, and the mixture was stirred at 60° C. for 7 hours. The reaction mixture was purified by reverse phase column chromatography (acetonitrile/water, 0.1% formic acid) to obtain the title compound (62%, 430 mg).

LCMS: m/z 263[M+H]$^+$

HPLC retention time: 0.94 min (analysis condition D)

Second Step

Compound J3

4-Bromo-2-chloro-5-methylbenzoic acid

[Formula 100]

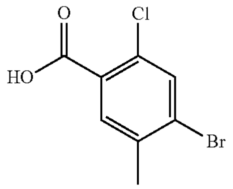

To a solution of methyl 4-bromo-2-chloro-5-methylbenzoate (429 mg, 1.63 mmol) in 1,4-dioxane (3.50 mL)/water (1.75 mL), lithium peroxide (117 mg, 4.88 mmol) was added, and the mixture was stirred at room temperature for 1 hour. 5 M hydrochloric acid (1.63 mL, 8.13 mmol) was added to the reaction solution, followed by extraction with ethyl acetate. The organic layer was washed with a saturated aqueous solution of sodium bicarbonate and a saturated aqueous solution of sodium chloride and dried over anhydrous sodium sulfate. The desiccant was filtered off, and the filtrate was concentrated to obtain the title compound as a crude product.

LCMS: m/z 247[M−H]$^-$

HPLC retention time: 0.72 min (analysis condition D)

Third Step
Compound J4

4-Bromo-2-chloro-5-methylbenzoyl Chloride

[Formula 101]

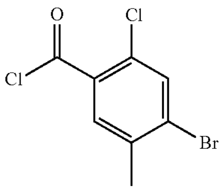

A solution of 4-bromo-2-chloro-5-methylbenzoic acid (250 mg, 1.00 mmol) and oxalyl chloride (0.175 mL, 2.00 mmol) in dichloromethane (5.01 mL) was cooled to 0° C. N,N-Dimethylformamide (0.000776 mL, 0.0100 mmol) was added thereto, and the mixture was stirred at room temperature for 2 hours. The reaction solution was concentrated to obtain the title compound as a crude product.

Fourth Step
Compound J

Methyl 4-[3-(4-bromo-2-chloro-5-methylbenzoyl)-2,4-dihydro-1,3-benzoxazin-8-yl]-5-fluoro-2-morpholin-4-ylbenzoate

[Formula 102]

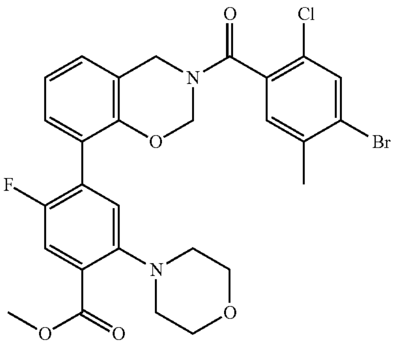

The title compound was obtained by the same operation as in the fifth step of compound B using methyl 4-(3,4-dihydro-2H-1,3-benzoxazin-8-yl)-5-fluoro-2-morpholin-4-ylbenzoate dihydrochloride and 4-bromo-2-chloro-5-methylbenzoyl chloride.

LCMS: m/z 629[M+H]$^+$

HPLC retention time: 1.02 min (analysis condition D)

Compound K

Methyl 4-[3-(4-bromo-2-chloro-5-methoxybenzoyl)-2,4-dihydro-1,3-benzoxazin-8-yl]-5-fluoro-2-morpholin-4-ylbenzoate First Step
Compound K2

Methyl 4-bromo-2-chloro-5-methoxybenzoate

[Formula 103]

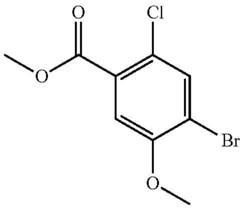

The title compound was obtained by the same operation as in the first step of compound J using methyl 4-bromo-3-methoxybenzoate.

LCMS: m/z 279[M+H]$^+$

HPLC retention time: 1.20 min (analysis condition G)

Second Step
Compound K3

4-Bromo-2-chloro-5-methoxybenzoic acid

[Formula 104]

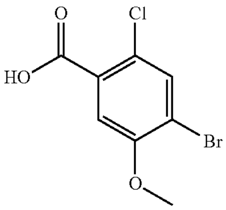

The title compound was obtained by the same method as in the second step of compound J using methyl 4-bromo-2-chloro-5-methoxybenzoate.

LCMS: m/z 263[M−H]$^-$

HPLC retention time: 0.69 min (analysis condition D)

Third Step
Compound K4

4-Bromo-2-chloro-5-methoxybenzoyl Chloride

[Formula 105]

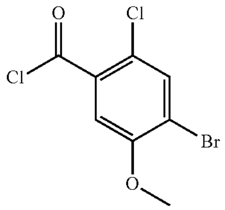

The title compound was obtained as a crude product by the same operation as in the third step of compound J using 4-bromo-2-chloro-5-methoxybenzoic acid.

Fourth Step
Compound K

Methyl 4-[3-(4-bromo-2-chloro-5-methoxybenzoyl)-2,4-dihydro-1,3-benzoxazin-8-yl]-5-fluoro-2-morpholin-4-ylbenzoate

[Formula 106]

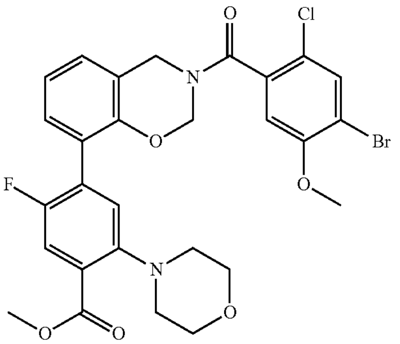

The title compound was synthesized by the same operation as in the fifth step of compound B using methyl 4-(3,4-dihydro-2H-1,3-benzoxazin-8-yl)-5-fluoro-2-morpholin-4-ylbenzoate dihydrochloride and 4-bromo-2-chloro-5-methoxybenzoyl chloride.

LCMS: m/z 619[M+H]$^+$

HPLC retention time: 0.95 min (analysis condition D)

Compound L

Methyl 4-[2-(4-bromo-2,6-dichlorobenzoyl)-4-oxo-1,3-dihydrophthalazin-5-yl]-2-morpholin-4-ylbenzoate First Step
Compound L4

Methyl 2-bromo-6-[[(2-methylpropan-2-yl)oxycarbonyl-[(2-methylpropan-2-yl)oxycarbonylamino]amino]methyl]benzoate

[Formula 107]

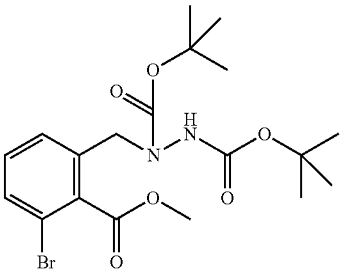

A solution of methyl 2-bromo-6-(bromomethyl)benzoate (6.80 g, 22.1 mmol) in N,N-dimethylformamide (100 mL) was cooled to 0° C. Di-tert-butyl hydrazodicarboxylate (20.5 g, 88.0 mmol) and cesium carbonate (14.4 g, 44.2 mmol) were added thereto, and the mixture was stirred at room temperature for 15 hours. A saturated aqueous solution of ammonium chloride was added to the reaction solution, followed by extraction with ethyl acetate. The organic layer was concentrated and purified by reverse phase column chromatography (acetonitrile/water, 0.1% formic acid) to obtain the title compound (55%, 5.62 g).

LCMS: m/z 481 [M+Na]$^+$

HPLC retention time: 1.34 min (analysis condition G)

Second Step
Compound L5 tert-Butyl 5-bromo-4-oxo-1,3-dihydrophthalazine-2-carboxylate

[Formula 108]

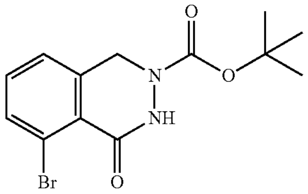

To a solution of methyl 2-bromo-6-[[(2-methylpropan-2-yl)oxycarbonyl-[(2-methylpropan-2-yl)oxycarbonylamino]amino]methyl]benzoate (5.61 g, 12.2 mmol) in tetrahydrofuran (150 mL), a 1 M lithium bis(trimethylsilyl)amide solution (15.9 mL, 15.9 mmol) was added, and the mixture was stirred at 60° C. for 12 hours. An aqueous formic acid solution was added to the reaction solution, followed by extraction with ethyl acetate. The obtained organic layer was concentrated and purified by reverse phase column chromatography (acetonitrile/water, 0.1% formic acid) to obtain the title compound (64%, 2.55 g).

LCMS: m/z 349[M+Na]$^+$

HPLC retention time: 0.97 min (analysis condition G)

Third Step
Compound L6 tert-Butyl 5-(4-methoxycarbonyl-3-morpholin-4-ylphenyl)-4-oxo-1,3-dihydrophthalazine-2-carboxylate

[Formula 109]

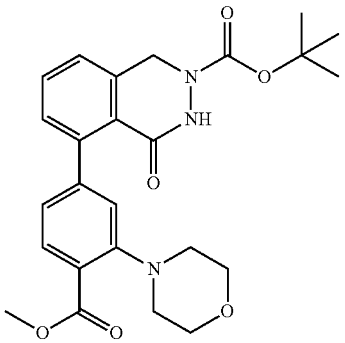

The title compound was synthesized by the same operation as in the third step of compound B using tert-butyl 5-bromo-4-oxo-1,3-dihydrophthalazine-2-carboxylate and methyl 4-bromo-2-morpholin-4-ylbenzoate.

LCMS: m/z 468[M+H]$^+$

HPLC retention time: 1.07 min (analysis condition G)

Fourth Step

Compound L

Methyl 4-[2-(4-bromo-2,6-dichlorobenzoyl)-4-oxo-1,3-dihydrophthalazin-5-yl]-2-morpholin-4-ylbenzoate

[Formula 110]

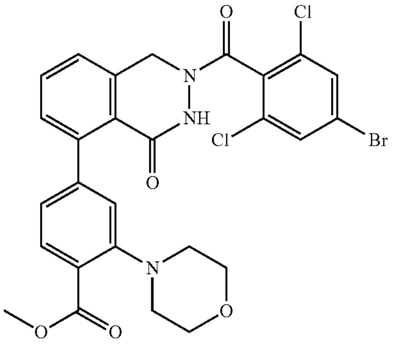

To tert-butyl 5-(4-methoxycarbonyl-3-morpholin-4-ylphenyl)-4-oxo-1,3-dihydrophthalazine-2-carboxylate (50 mg, 0.107 mmol), a 4 M solution of hydrochloric acid in 1,4-dioxane (0.535 mL, 2.14 mmol) was added, and the mixture was stirred at room temperature for 2 hours. The reaction solution was concentrated. Dichloromethane (1.00 mL) was added to the residue, and the mixture was cooled to 0° C. 4-Bromo-2,6-dichlorobenzoyl chloride (40.1 mg, 0.139 mmol) and N,N-diisopropylethylamine (0.0960 mL, 0.535 mmol) were added thereto, and the mixture was stirred at room temperature for 5 hours. The reaction solution was purified by silica gel column chromatography (hexane/ethyl acetate) to obtain the title compound (73%, 48.0 mg).

LCMS: m/z 618[M+H]$^+$

HPLC retention time: 1.19 min (analysis condition G)

Compound M

Methyl 4-[3-(4-bromo-2,6-dichlorobenzoyl)-5-fluoro-2,4-dihydro-1,3-benzoxazin-8-yl]-5-fluoro-2-morpholin-4-ylbenzoate First Step Compound M2 tert-Butyl N-[(2-fluoro-6-hydroxyphenyl)methyl] carbamate

[Formula 111]

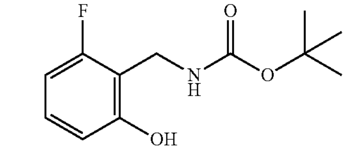

To a solution of 2-bromo-3-fluorophenol (500 mg, 2.62 mmol) in 1,4-dioxane (10.0 mL)-water (2.00 mL), cataCXium® A Pd G3 (28.6 mg, 0.0390 mmol), potassium carbonate (1.09 mg, 7.85 mmol) and potassium [[(tert-butoxycarbonyl)amino]methyl]trifluoroborate (1.24 g, 5.24 mmol) were added, and the mixture was stirred at 130° C. for 20 minutes under microwave. The reaction mixture was purified by reverse phase column chromatography (acetonitrile/water, 0.1% formic acid) to obtain the title compound (89%, 563 mg).

LCMS: m/z 186[M-tBu+H]$^+$

HPLC retention time: 1.05 min (analysis condition G)

Second Step

Compound M3 tert-Butyl N-[(3-bromo-6-fluoro-2-hydroxyphenyl) methyl]carbamate

[Formula 112]

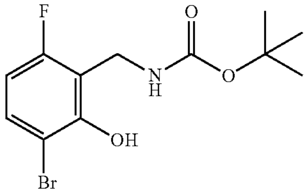

A solution of tert-butyl N-[(2-fluoro-6-hydroxyphenyl) methyl]carbamate (560 mg, 2.32 mmol) and N,N-diisopropylethylamine (0.992 mL, 6.96 mmol) in dichloromethane (40.0 mL) was cooled to 0° C., and a solution of N-bromosuccinimide (413 mg, 2.32 mmol) in dichloromethane (40.0 mL) was added dropwise thereto. The reaction solution was stirred at 0° C. for 30 minutes. The reaction mixture was purified by reverse phase column chromatography (acetonitrile/water, 0.1% formic acid) to obtain the title compound (96%, 715 mg).

LCMS: m/z 264[M-tBu+H]$^+$

HPLC retention time: 1.23 min (analysis condition G)

Third Step

Compound M4 tert-Butyl 8-bromo-5-fluoro-2,4-dihydro-1,3-benzoxazine-3-carboxylate

[Formula 113]

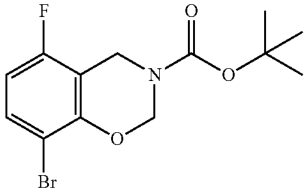

To a solution of tert-butyl N-[(3-bromo-6-fluoro-2-hydroxyphenyl)methyl]carbamate (600 mg, 1.87 mmol) in dichloroethane (30.0 mL), p-toluenesulfonic acid (35.6 mg, 0.187 mmol) and 90% paraformaldehyde (625 mg, 18.7 mmol) were added, and the mixture was stirred overnight at 90° C. The reaction solution was concentrated and purified by silica gel column chromatography (hexane/ethyl acetate) to obtain the title compound (64%, 399 mg).

LCMS: m/z 332[M+H]$^+$

HPLC retention time: 1.34 min (analysis condition G)

Fourth Step
Compound Z6

(2-Fluoro-4-methoxycarbonyl-5-morpholin-4-ylphenyl)boronic acid

[Formula 114]

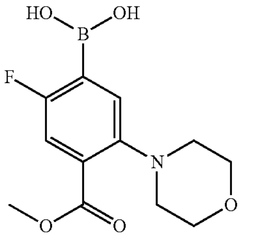

A solution of methyl 4-bromo-5-fluoro-2-morpholin-4-ylbenzoate (96.0 mg, 0.302 mmol), 1,1'-bis(diphenylphosphino)ferrocene-palladium(II) dichloride (11.0 mg, 0.0150 mmol), potassium acetate (44.4 mg, 0.453 mmol), and bis(pinacolato)diboron (77.0 mg, 0.302 mol) in 1,4-dioxane (1.51 mL) was stirred at 100° C. for 3 hours. The reaction solution was purified by reverse phase column chromatography (acetonitrile/water, 0.1% formic acid) to obtain the title compound (53%, 44.8 mg).

LCMS: m/z 284$[M+H]^+$

HPLC retention time: 0.63 min (analysis condition G)

Fifth Step
Compound M5 tert-Butyl 5-fluoro-8-(2-fluoro-4-methoxycarbonyl-5-morpholin-4-ylphenyl)-2,4-dihydro-1,3-benzoxazine-3-carboxylate

[Formula 115]

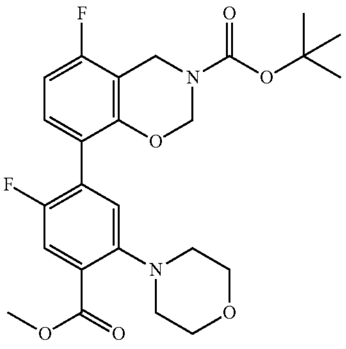

To a solution of tert-butyl 8-bromo-5-fluoro-2,4-dihydro-1,3-benzoxazine-3-carboxylate (200 mg, 0.602 mmol) in 1,4-dioxane (2.40 mL)-water (0.600 mL), (2-fluoro-4-methoxycarbonyl-5-morpholin-4-ylphenyl)boronic acid (205 mg, 0.723 mmol), 1,1'-bis(diphenylphosphino)ferrocene-palladium(II) dichloride (22.0 mg, 0.0300 mmol), and potassium carbonate (250 mg, 1.81 mmol) were added, and the mixture was stirred at 90° C. for 3 hours. 2-Fluoro-4-methoxycarbonyl-5-morpholin-4-ylphenyl)boronic acid (205 mg, 0.723 mmol) was added to the reaction solution, and the mixture was stirred overnight at 90° C. 2-Fluoro-4-methoxycarbonyl-5-morpholin-4-ylphenyl)boronic acid (205 mg, 0.723 mmol) and 1,1'-bis(diphenylphosphino)ferrocene-palladium(II) dichloride (22.0 mg, 0.0300 mmol) were added to the reaction solution, and the mixture was stirred at 90° C. for 3 hours. An aqueous formic acid solution was added to the reaction solution, and the mixture was purified by reverse phase column chromatography (acetonitrile/water, 0.1% formic acid) to obtain the title compound (69%, 205 mg).

LCMS: m/z 491$[M+H]^+$

HPLC retention time: 1.36 min (analysis condition G)

Sixth Step
Compound M6

Methyl 5-fluoro-4-(5-fluoro-3,4-dihydro-2H-1,3-benzoxazin-8-yl)-2-morpholin-4-ylbenzoate dihydrochloride

[Formula 116]

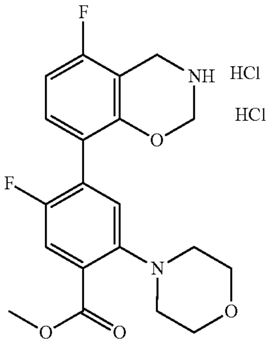

The title compound was obtained by the same operation as in the fourth step of compound B using tert-butyl 5-fluoro-8-(2-fluoro-4-methoxycarbonyl-5-morpholin-4-ylphenyl)-2,4-dihydro-1,3-benzoxazine-3-carboxylate.

LCMS: m/z 362[M−CH2+H]+

HPLC retention time: 0.69 min (analysis condition N)

$^1$H-NMR (400 MHz, DMSO-$D_6$) δ: 7.52 (1H, d, J=9.7 Hz), 7.41-7.39 (1H, m), 7.07 (2H, d, J=7.0 Hz), 5.16 (2H, s), 4.38 (2H, s), 3.85 (3H, s), 3.71 (4H, s), 2.96 (4H, s).

Seventh Step
Compound M

Methyl 4-[3-(4-bromo-2,6-dichlorobenzoyl)-5-fluoro-2,4-dihydro-1,3-benzoxazin-8-yl]-5-fluoro-2-morpholin-4-ylbenzoate

[Formula 117]

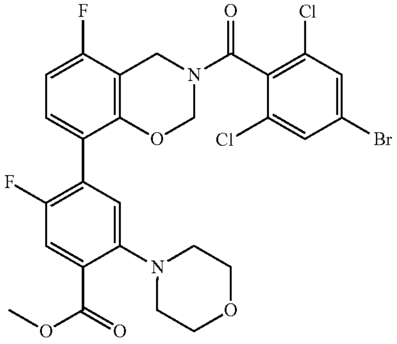

The title compound was obtained by the same operation as in the fifth step of compound B using methyl 5-fluoro-4-(5-fluoro-3,4-dihydro-2H-1,3-benzoxazin-8-yl)-2-morpholin-4-ylbenzoate dihydrochloride and 4-bromo-2,6-dichlorobenzoyl chloride.

LCMS: m/z 641[M+H]$^+$

HPLC retention time: 1.40 min (analysis condition N)

Compound N

Methyl 4-[3-(4-bromo-2,6-dichlorobenzoyl)-7-fluoro-2,4-dihydro-1,3-benzoxazin-8-yl]-2-morpholin-4-ylbenzoate First Step Compound N3 tert-Butyl N-[(3-bromo-4-fluoro-2-hydroxyphenyl) methyl]carbamate

[Formula 118]

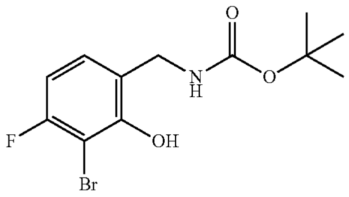

To a solution of 3-bromo-4-fluoro-2-hydroxybenzonitrile (970 mg, 4.49 mmol) in tetrahydrofuran (20.0 mL), a 1.2 M borane/tetrahydrofuran complex (9.36 mL, 11.2 mmol) was added. The reaction solution was stirred at 60° C. for 15 hours. Methanol was added to the reaction solution, and the mixture was concentrated. Tetrahydrofuran (10.0 mL) and 2 M hydrochloric acid (5.61 mL, 11.2 mmol) were added to the residue, and the mixture was heated at 60° C. for 3 hours. The reaction solution was cooled to 0° C. A saturated aqueous solution of sodium bicarbonate was added thereto, then di-tert-butyl dicarbonate (1.96 g, 8.98 mmol) was added, and the mixture was stirred at room temperature for 2 hours. The reaction solution was subjected to extraction with ethyl acetate. The extract was washed with a saturated aqueous solution of ammonium chloride and concentrated. The residue was purified by silica gel column chromatography (hexane/ethyl acetate) to obtain the title compound (79%, 1.13 g).

LCMS: m/z 318[M−H]$^-$

HPLC retention time: 1.18 min (analysis condition N)

Second Step

Compound N4 tert-Butyl 8-bromo-7-fluoro-2,4-dihydro-1,3-benzoxazine-3-carboxylate

[Formula 119]

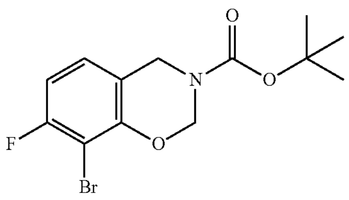

To a solution of tert-butyl N-[(3-bromo-4-fluoro-2-hydroxyphenyl)methyl]carbamate (600 mg, 1.87 mmol) in toluene (5.00 mL), p-toluenesulfonic acid monohydrate (1.78 mg, 0.00937 mmol) and paraformaldehyde (281 mg, 9.37 mmol) were added, and the mixture was stirred at 100° C. for 3 hours. The reaction solution was further stirred at 90° C. for 20 hours. The reaction mixture was purified by reverse phase column chromatography (acetonitrile/water, 0.1% formic acid) to obtain the title compound (24%, 152 mg).

LCMS: m/z 332[M+H]$^+$

HPLC retention time: 1.30 min (analysis condition G)

Third Step

Compound N7

Methyl 2-morpholin-4-yl-4-(4,4,5,5-tetramethyl-1,3,2-dioxaboloran-2-yl)benzoate

[Formula 120]

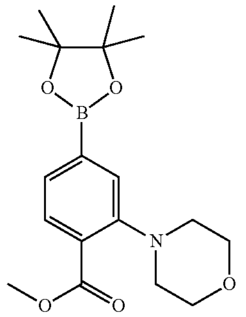

A solution of methyl 4-bromo-2-morpholin-4-ylbenzoate (1.60 g, 5.33 mmol), bis(pinacolato)diboron (2.71 g, 10.7 mmol), palladium(II) acetate (0.0600 g, 0.267 mmol), 2-dicyclohexylphosphino-2',4',6'-triisopropylbiphenyl (0.254 g, 0.533 mmol) and potassium acetate (1.31 g, 13.3 mmol) in 1,4-dioxane (10.0 mL) was stirred at 85° C. for 2 hours. A solution of ethyl acetate/hexane=1/1 was added to the reaction solution, and the mixture was filtered and then concentrated. The obtained residue was purified by silica gel column chromatography (hexane/ethyl acetate) to obtain the title compound (89%, 2.05 g).

LCMS: m/z 348[M+H]$^+$

HPLC retention time: 1.21 min (analysis condition G)

Fourth Step

Compound N5 tert-Butyl 7-fluoro-8-(4-methoxycarbonyl-3-morpholin-4-ylphenyl)-2,4-dihydro-1,3-benzoxazine-3-carboxylate

[Formula 121]

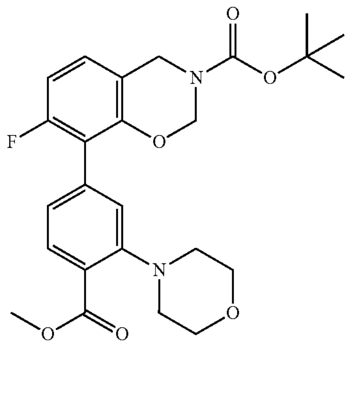

A solution of methyl 2-morpholin-4-yl-4-(4,4,5,5-tetramethyl-1,3,2-dioxaboloran-2-yl)benzoate (85.0 mg, 0.246 mmol), tert-butyl 8-bromo-7-fluoro-2,4-dihydro-1,3-benzoxazine-3-carboxylate (68.0 mg, 0.205 mmol), 1,1'-bis(diphenylphosphino)ferrocene-palladium(II) dichloride (15.0 mg, 0.0200 mmol) and a 2 M aqueous sodium carbonate solution (0.307 mL, 0.614 mmol) in 1,4-dioxane (1.00 mL) was stirred at 90° C. for 1.5 hours. The reaction solution was mixed with another compound obtained by the same method as described above. An aqueous formic acid solution was added thereto, and the mixture was purified by reverse phase column chromatography (acetonitrile/water, 0.1% formic acid) to obtain the title compound (71.0 mg).

LCMS: m/z 473[M+H]$^+$

HPLC retention time: 1.30 min (analysis condition G)

Fifth Step

Compound N

Methyl 4-[3-(4-bromo-2,6-dichlorobenzoyl)-7-fluoro-2,4-dihydro-1,3-benzoxazin-8-yl]-2-morpholin-4-ylbenzoate

[Formula 122]

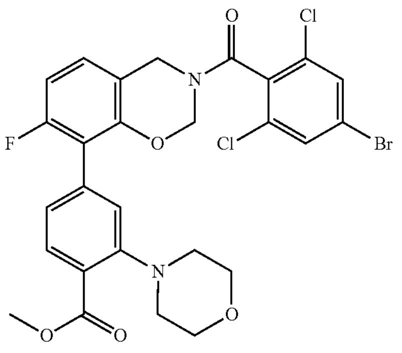

To tert-butyl 7-fluoro-8-(4-methoxycarbonyl-3-morpholin-4-ylphenyl)-2,4-dihydro-1,3-benzoxazine-3-carboxylate (344 mg, 0.728 mmol), a 4 M solution of hydrochloric acid in 1,4-dioxane (3.64 mL, 14.6 mmol) was added, and the mixture was stirred at room temperature for 1 hour. The reaction solution was concentrated. Dichloromethane (5.00 mL), 4-bromo-2,6-dichlorobenzoyl chloride (273 mg, 0.946 mmol) and N,N-diisopropylethylamine (0.634 mL, 3.64 mmol) were added to the obtained residue, and the mixture was stirred at room temperature for 1 hour. The reaction mixture was purified by reverse phase column chromatography (acetonitrile/water, 0.1% formic acid) to obtain the title compound (51%, 231 mg).

LCMS: m/z 623[M+H]$^+$

HPLC retention time: 0.98 min (analysis condition O)

Compound O

Methyl 4-[3-(2,6-dichloro-4-fluorobenzoyl)-2,4-dihydro-1,3-benzoxazin-8-yl]-5-fluoro-2-(3-oxa-8-azabicyclo[3.2.1]octan-8-yl)benzoate First Step Compound 01

2,6-Dichloro-4-fluorobenzoyl Chloride

[Formula 123]

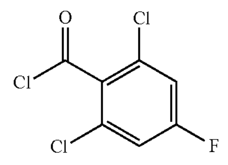

The title compound was obtained as a crude product by the same operation as in the third step of compound J using 2,6-dichloro-4-fluorobenzoic acid.

Second Step

Compound O

Methyl 4-[3-(2,6-dichloro-4-fluorobenzoyl)-2,4-dihydro-1,3-benzoxazin-8-yl]-5-fluoro-2-(3-oxa-8-azabicyclo[3.2.1]octan-8-yl)benzoate

[Formula 124]

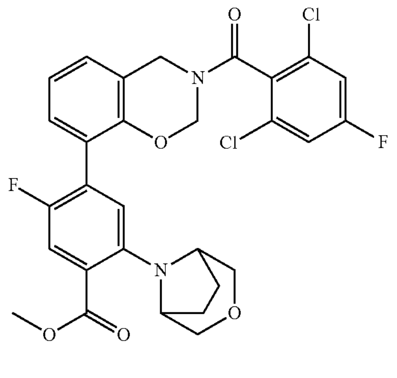

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 2,6-dichloro-4-fluorobenzoyl chloride.

LCMS: m/z 589[M+H]$^+$

HPLC retention time: 0.96 min (analysis condition D)

Compound P

4-[3-(2,6-Dichloro-4-fluorobenzoyl)-2,4-dihydro-1,3-benzoxazin-8-yl]-5-fluoro-2-(3-oxa-8-azabicyclo[3.2.1]octan-8-yl)benzoic acid

[Formula 125]

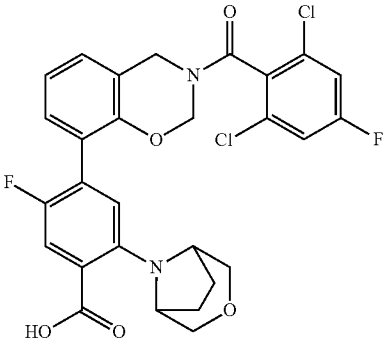

To a solution of methyl 4-[3-(2,6-dichloro-4-fluorobenzoyl)-2,4-dihydro-1,3-benzoxazin-8-yl]-5-fluoro-2-(3-oxa-8-azabicyclo[3.2.1]octan-8-yl)benzoate (100 mg, 0.170 mmol) in 1-methylpyrrolidin-one (1.70 mL), a 2 M aqueous lithium peroxide solution (0.424 mL, 0.848 mmol) was added, and the mixture was stirred at room temperature for 14 hours. 1-Methylpyrrolidin-one (1.70 mL) and a 2 M aqueous lithium peroxide solution (0.424 mL, 0.848 mmol) were added to the reaction solution, and the mixture was stirred at room temperature for 1.5 hours. An aqueous formic acid solution was added to the reaction mixture, and the mixture was purified by reverse phase column chromatography (acetonitrile/water, 0.1% formic acid) to obtain the title compound (63%, 61.9 mg).

LCMS: m/z 575[M+H]$^+$

HPLC retention time: 0.77 min (analysis condition D)

Compound Q

Ethyl 4-[3-(2,6-dichloro-4-fluorobenzoyl)-2,4-dihydro-1,3-benzoxazin-8-yl]-2-morpholin-4-ylbenzoate First Step Compound Q1

Ethyl 4-bromo-2-morpholin-4-ylbenzoate

[Formula 126]

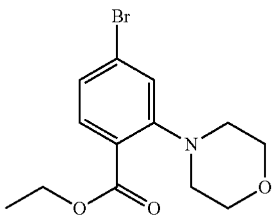

To a solution of 4-bromo-2-morpholin-4-ylbenzoic acid (1.50 g, 5.24 mmol) in N,N-dimethylformamide (26.2 mL), potassium carbonate (2.17 g, 15.7 mmol) and iodoethane (0.632 mL, 7.86 mmol) were added, and the mixture was stirred at 25° C. for 2.5 hours. The reaction solution was subjected to extraction with ethyl acetate. The extract was washed with a saturated aqueous solution of sodium chloride and dried over anhydrous sodium sulfate. The residue was purified by reverse phase column chromatography (acetonitrile/water, 0.1% formic acid) to obtain the title compound (99%, 1.63 g).

LCMS: m/z 314[M+H]$^+$

HPLC retention time: 0.86 min (analysis condition O)

Second Step

Compound Q4 tert-Butyl 8-(4,4,5,5-tetramethyl-1,3,2-dioxaboloran-2-yl)-2,4-dihydro-1,3-benzoxazine-3-carboxylate

[Formula 127]

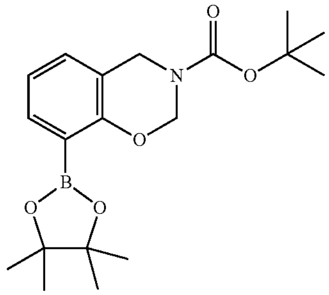

A solution of tert-butyl 8-bromo-2,4-dihydro-1,3-benzoxazine-3-carboxylate (3.40 g, 10.8 mmol), bis(pinacolato)diboron (5.50 g, 21.6 mmol), potassium acetate (4.25 g, 43.3 mmol) and a 1,1'-bis(diphenylphosphino)ferrocene-palladium(II) dichloride dichloromethane complex (0.792 g, 1.08 mmol) in 1,4-dioxane (108 mL) was stirred at 110° C. for 18 hours. The reaction mixture was purified by reverse phase column chromatography (acetonitrile/water, 0.1% formic acid) to obtain the title compound (32%, 1.26 g).

LCMS: m/z 362[M+H]$^+$

HPLC retention time: 1.36 min (analysis condition G)

Third Step

Compound Q2 tert-Butyl 8-(4-ethoxycarbonyl-3-morpholin-4-ylphenyl)-2,4-dihydro-1,3-benzoxazine-3-carboxylate

[Formula 128]

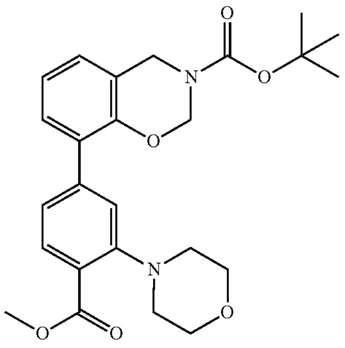

To a solution of ethyl 4-bromo-2-morpholin-4-ylbenzoate (1.30 g, 3.76 mmol) and tert-butyl 8-(4,4,5,5-tetramethyl-1,3,2-dioxaboloran-2-yl)-2,4-dihydro-1,3-benzoxazine-3-carboxylate (1.36 g, 4.14 mmol) in 1,4-dioxane (11.4 mL)/water (1.14 mL), a 1,1'-bis(diphenylphosphino)ferrocene-palladium(II) dichloride dichloromethane complex (0.275 g, 0.376 mmol) and potassium carbonate (1.56 g, 11.3 mmol) were added, and the mixture was stirred at 90° C. for 2 hours. The reaction solution was concentrated, followed by extraction with ethyl acetate. Then, the organic layer was washed with water. After concentration, the obtained residue was purified by reverse phase column chromatography (acetonitrile/water, 0.1% formic acid) to obtain the title compound (81%, 1.43 g).

LCMS: m/z 469[M+H]$^+$

HPLC retention time: 1.38 min (analysis condition G)

Fourth Step

Compound Q3

Ethyl 4-(3,4-dihydro-2H-1,3-benzoxazin-8-yl)-2-morpholin-4-ylbenzoate hydrochloride

[Formula 129]

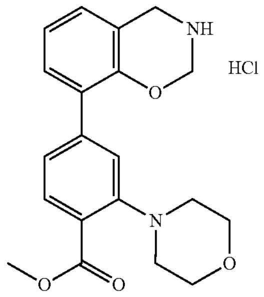

The title compound was obtained by the same operation as in the fourth step of compound B using tert-butyl 8-(4-ethoxycarbonyl-3-morpholin-4-ylphenyl)-2,4-dihydro-1,3-benzoxazine-3-carboxylate.

LCMS: m/z 369[M+H]$^+$

HPLC retention time: 0.74 min (analysis condition G)

Fifth Step

Compound Q

Ethyl 4-[3-(2,6-dichloro-4-fluorobenzoyl)-2,4-dihydro-1,3-benzoxazin-8-yl]-2-morpholin-4-ylbenzoate

[Formula 130]

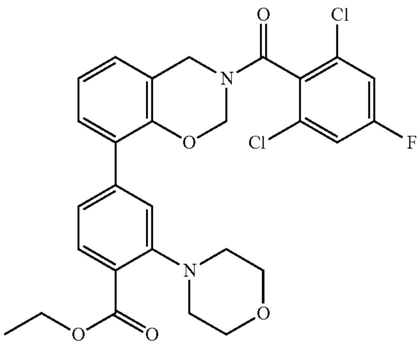

The title compound was obtained by the same operation as in the fifth step of compound B using ethyl 4-(3,4-dihydro-2H-1,3-benzoxazin-8-yl)-2-morpholin-4-ylbenzoate hydrochloride and 2,6-dichloro-4-fluorobenzoyl chloride.

LCMS: m/z 559[M+H]$^+$

HPLC retention time: 1.33 min (analysis condition G)

Compound R

Methyl 4-[3-(2,6-dichloro-4-fluorobenzoyl)-2,4-dihydro-1,3-benzoxazin-8-yl]-2-morpholin-4-ylbenzoate

[Formula 131]

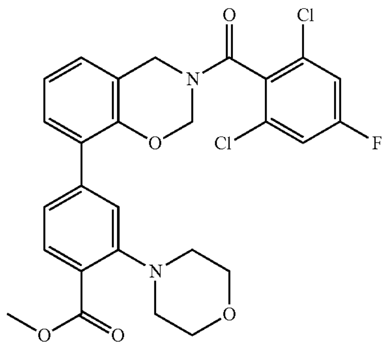

The title compound was obtained by the same operation as in the fifth step of compound B using methyl 4-(3,4-dihydro-2H-1,3-benzoxazin-8-yl)-2-morpholin-4-ylbenzoate dihydrochloride and 2,6-dichloro-4-fluorobenzoyl chloride.

LCMS: m/z 545[M+H]$^+$

HPLC retention time: 1.26 min (analysis condition G)

Compound S

Methyl 4-[3-(2,6-dichloro-4-fluorobenzoyl)-2,4-dihydro-1,3-benzoxazin-8-yl]-5-fluoro-2-morpholin-4-ylbenzoate

[Formula 132]

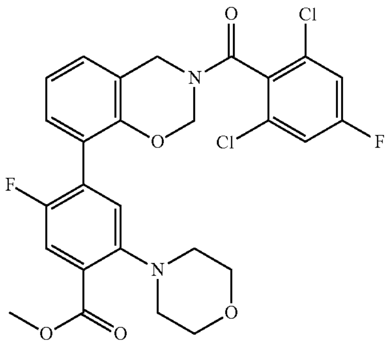

The title compound was obtained by the same operation as in the fifth step of compound B using methyl 4-(3,4-dihydro-2H-1,3-benzoxazin-8-yl)-5-fluoro-2-morpholin-4-ylbenzoate dihydrochloride and 2,6-dichloro-4-fluorobenzoyl chloride.

LCMS: m/z 563[M+H]$^+$

HPLC retention time: 0.91 min (analysis condition D)

Compound T

Methyl 4-[3-(2,6-dichloro-4-fluorobenzoyl)-2,4-dihydro-1,3-benzoxazin-8-yl]-2-methyl-6-morpholin-4-ylbenzoate First Step Compound T1

4-Bromo-2-methyl-6-morpholin-4-ylbenzoic acid

[Formula 133]

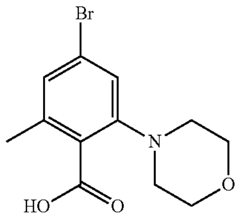

The title compound was obtained by the same operation as in the first step of compound B using 4-bromo-2-fluoro-6-methylbenzoic acid.

LCMS: m/z 300[M+H]$^+$

HPLC retention time: 0.89 min (analysis condition N)

Second Step

Compound T2

Methyl 4-bromo-2-methyl-6-morpholin-4-ylbenzoate

[Formula 134]

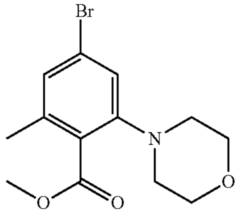

The title compound was obtained by the same operation as in the second step of compound B using 4-bromo-2-methyl-6-morpholin-4-ylbenzoic acid.

LCMS: m/z 314[M+H]$^+$

HPLC retention time: 0.91 min (analysis condition D)

Third Step

Compound T3 tert-Butyl 8-(4-methoxycarbonyl-3-methyl-5-morpholin-4-ylphenyl)-2,4-dihydro-1,3-benzoxazine-3-carboxylate

[Formula 135]

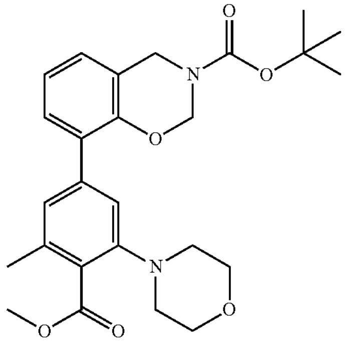

The title compound was obtained by the same operation as in the third step of compound Q using methyl 4-bromo-2-methyl-6-morpholin-4-ylbenzoate and tert-butyl 8-(4,4,5,5-tetramethyl-1,3,2-dioxaboloran-2-yl)-2,4-dihydro-1,3-benzoxazine-3-carboxylate.

LCMS: m/z 469[M+H]$^+$

HPLC retention time: 1.06 min (analysis condition D)

Fourth Step

Compound T4

Methyl 4-(3,4-dihydro-2H-1,3-benzoxazin-8-yl)-2-methyl-6-morpholin-4-ylbenzoate dihydrochloride

[Formula 136]

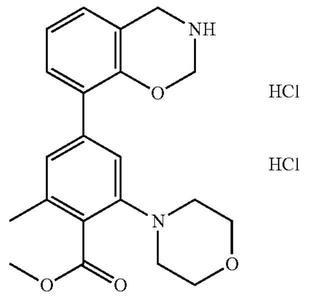

The title compound was obtained by the same operation as in the fourth step of compound B using tert-butyl 8-(4-methoxycarbonyl-3-methyl-5-morpholin-4-ylphenyl)-2,4-dihydro-1,3-benzoxazine-3-carboxylate.

LCMS: m/z 369[M+H]$^+$

HPLC retention time: 0.79 min (analysis condition N)

Fifth Step

Compound T

Methyl 4-[3-(2,6-dichloro-4-fluorobenzoyl)-2,4-dihydro-1,3-benzoxazin-8-yl]-2-methyl-6-morpholin-4-ylbenzoate

[Formula 137]

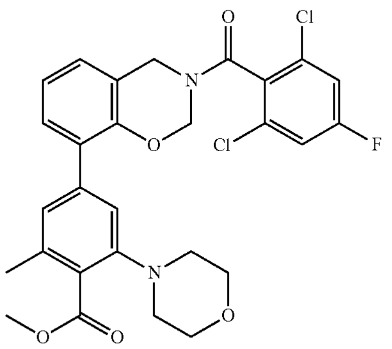

To a solution of 2,6-dichloro-4-fluorobenzoic acid (24.9 mg, 0.119 mmol) and oxalyl chloride (0.0109 mL, 0.125 mmol) in dichloromethane (0.566 mL), a catalytic amount of N,N-dimethylformamide was added, and the mixture was stirred at room temperature for 45 minutes. Methyl 4-(3,4-dihydro-2H-1,3-benzoxazin-8-yl)-2-methyl-6-morpholin-4-ylbenzoate dihydrochloride (50.0 mg, 0.113 mmol) was added to the reaction solution. The mixture was cooled to 0° C. N,N-Diisopropylethylamine (0.0990 mL, 0.566 mmol) was added thereto, and the mixture was stirred at room temperature for 1 hour. The reaction mixture was purified by reverse phase column chromatography (acetonitrile/water, 0.1% formic acid) to obtain the title compound (71%, 44.7 mg).

LCMS: m/z 559$[M+H]^+$

HPLC retention time: 1.02 min (analysis condition D)

Compound U

Methyl 4-[3-(2-chloro-4-fluorobenzoyl)-2,4-dihydro-1,3-benzoxazin-8-yl]-5-fluoro-2-morpholin-4-ylbenzoate First Step Compound U2

2-Chloro-4-fluorobenzoyl Chloride

[Formula 138]

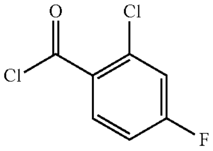

The title compound was obtained as a crude product by the same operation as in the third step of compound J using 2-chloro-4-fluorobenzoic acid.

Second Step

Compound U

Methyl 4-[3-(2-chloro-4-fluorobenzoyl)-2,4-dihydro-1,3-benzoxazin-8-yl]-5-fluoro-2-morpholin-4-ylbenzoate

[Formula 139]

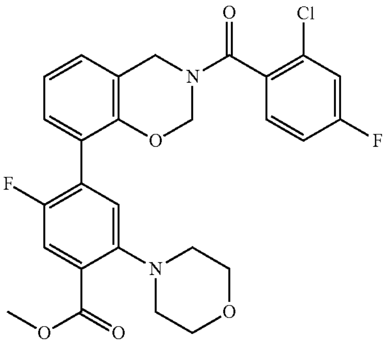

The title compound was obtained by the same operation as in the fifth step of compound B using 2-chloro-4-fluorobenzoyl chloride and methyl 4-(3,4-dihydro-2H-1,3-benzoxazin-8-yl)-5-fluoro-2-morpholin-4-ylbenzoate dihydrochloride.

LCMS: m/z 529$[M+H]^+$

HPLC retention time: 1.23 min (analysis condition G)

Compound V

4-[3-(2-Chloro-4-fluoro-5-methoxybenzoyl)-2,4-dihydro-1,3-benzoxazin-8-yl]-5-fluoro-2-morpholin-4-ylbenzoic acid First Step Compound V2

Methyl 2-chloro-4-fluoro-5-methoxybenzoate

[Formula 140]

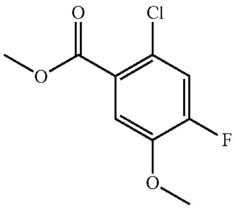

The title compound was obtained by the same operation as in the first step of compound J using methyl 4-fluoro-3-methoxybenzoate.

LCMS: m/z 219$[M+H]^+$

HPLC retention time: 1.08 min (analysis condition G)

Second Step

Compound V3

2-Chloro-4-fluoro-5-methoxybenzoic acid

[Formula 141]

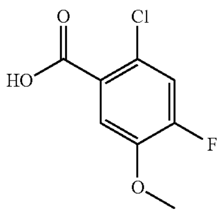

A solution of methyl 2-chloro-4-fluoro-5-methoxybenzoate (240 mg, 1.10 mmol) and lithium peroxide (79.0 mg, 3.29 mmol) in 1,4-dioxane (2.61 mL)-water (1.31 mL) was stirred at room temperature for 2 hours. Hydrochloric acid was added thereto, followed by extraction with ethyl acetate. The obtained organic layer was washed with water and a saturated aqueous solution of sodium chloride and dried over anhydrous sodium sulfate. After passing through a phase separator, the organic layer was concentrated to obtain the title compound as a crude product.

LCMS: m/z 205[M+H]$^+$

HPLC retention time: 0.59 min (analysis condition D)

Third Step

Compound V4

2-Chloro-4-fluoro-5-methoxybenzoyl Chloride

[Formula 142]

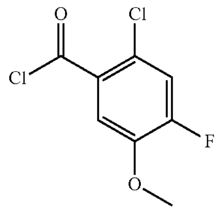

A crude product of the title compound was obtained by the same operation as in the third step of compound J using 2-chloro-4-fluoro-5-methoxybenzoic acid.

Fourth Step

Compound V5

Methyl 4-[3-(2-chloro-4-fluoro-5-methoxybenzoyl)-2,4-dihydro-1,3-benzoxazin-8-yl]-5-fluoro-2-morpholin-4-ylbenzoate

[Formula 143]

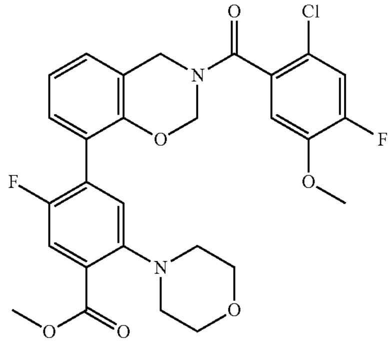

The title compound was obtained by the same operation as in the fifth step of compound B using methyl 4-(3,4-dihydro-2H-1,3-benzoxazin-8-yl)-5-fluoro-2-morpholin-4-ylbenzoate dihydrochloride and 2-chloro-4-fluoro-5-methoxybenzoyl chloride.

LCMS: m/z 558[M+H]$^+$

HPLC retention time: 0.88 min (analysis condition D)

Fifth Step

Compound V

4-[3-(2-Chloro-4-fluoro-5-methoxybenzoyl)-2,4-dihydro-1,3-benzoxazin-8-yl]-5-fluoro-2-morpholin-4-ylbenzoic acid

[Formula 144]

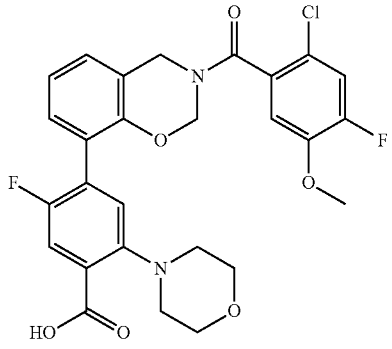

The title compound was obtained by the same operation as in the process of compound P using methyl 4-[3-(2-chloro-4-fluoro-5-methoxybenzoyl)-2,4-dihydro-1,3-benzoxazin-8-yl]-5-fluoro-2-morpholin-4-ylbenzoate.

LCMS: m/z 545[M+H]$^+$

HPLC retention time: 0.72 min (analysis condition D)

Compound W

Methyl 4-[3-(2,6-dichloro-4-fluorobenzoyl)-2,4-dihydro-1,3-benzoxazin-8-yl]-5-fluoro-2-(8-oxa-3-azabicyclo[3.2.1]octan-3-yl)benzoate First Step Compound X7

2-(Aminomethyl)-6-bromophenol hydrochloride

[Formula 145]

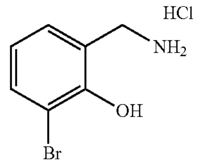

To a solution of tert-butyl N-[(3-bromo-2-hydroxyphenyl)methyl]carbamate (500 mg, 1.66 mmol) in 1,4-dioxane (4.14 mL), a 4 M 1,4-dioxane solution (4.14 mL, 16.6 mmol) was added, and the mixture was stirred at room temperature for 16 hours. The reaction solution was concentrated to obtain the title compound as a crude product.

LCMS: m/z 202[M+H]$^+$

HPLC retention time: 0.28 min (analysis condition D)

Second Step

Compound W1

N-[(3-Bromo-2-hydroxyphenyl)methyl]-2,6-dichloro-4-fluorobenzamide

[Formula 146]

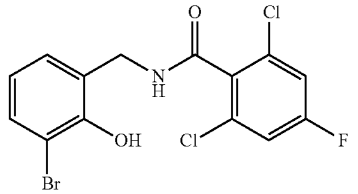

To a solution of 2,6-dichloro-4-fluorobenzoic acid (5.17 g, 24.7 mmol) in N,N-dimethylformamide (60.0 mL), N,N-diisopropylethylamine (9.59 g, 74.2 mmol) and HATU (9.41 g, 24.7 mmol) were added, and the mixture was stirred at room temperature for 1 hour. A solution of 2-(aminomethyl)-6-bromophenol hydrochloride (5.90 g, 24.7 mmol) and N,N-diisopropylethylamine (6.39 g, 49.5 mmol) in N,N-dimethylformamide (70.0 mL) was added dropwise to the reaction solution, and the mixture was stirred at room temperature for 1 hour. The reaction solution was subjected to extraction with ethyl acetate. The organic layer was washed with a saturated aqueous solution of sodium chloride, dried over anhydrous sodium sulfate, and then concentrated to obtain the title compound as a crude product.

LCMS: m/z 392[M+H]$^+$

HPLC retention time: 0.80 min (analysis condition Z)

Third Step

Compound W2

(8-Bromo-2,4-dihydro-1,3-benzoxazin-3-yl)-(2,6-dichloro-4-fluorophenyl)methanone

[Formula 147]

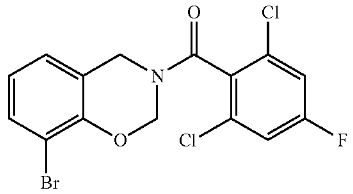

To a solution of N-[(3-bromo-2-hydroxyphenyl)methyl]-2,6-dichloro-4-fluorobenzamide (13.3 g, 33.8 mmol) in toluene (33.0 mL)/1,4-dioxane (33.0 mL), p-toluenesulfonic acid (6.43 g, 33.8 mmol) and paraformaldehyde (19.6 g, 677 mmol) were added, and the mixture was stirred at 90° C. for 5 hours. Ethyl acetate and a saturated aqueous solution of sodium carbonate were added to the reaction solution, followed by extraction with ethyl acetate. The organic layer was washed with a saturated aqueous solution of sodium chloride and dried over anhydrous sodium sulfate. The residue was mixed with another compound obtained by the same method as described above. Ethanol was added thereto, and the mixture was triturated to obtain the title compound (8.52 g).

LCMS: m/z 404[M+H]$^+$

HPLC retention time: 1.46 min (analysis condition S)

Fourth Step

Compound W9

Methyl 5-fluoro-2-hydroxy-4-(4,4,5,5-tetramethyl-1,3,2-dioxaborolan-2-yl)benzoate

[Formula 148]

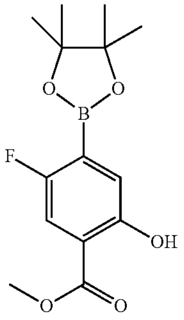

To a solution of methyl 4-bromo-5-fluoro-2-hydroxybenzoate (16.1 g, 64.7 mmol) in 1,4-dioxane (220 mL), bis(pinacolato)diboron (32.8 g, 129 mmol), potassium acetate (19.0 g, 194 mmol) and a 1,1'-bis(diphenylphosphino)ferrocene-palladium(II) dichloride dichloromethane complex (2.64 g, 3.23 mmol) were added, and the mixture was stirred at 100° C. for 16 hours. The obtained crude product was used in the subsequent reaction.

LCMS: m/z 297[M+H]$^+$

HPLC retention time: 0.96 min (analysis condition D)

Fifth Step

Compound W3

Methyl 4-[3-(2,6-dichloro-4-fluorobenzoyl)-2,4-dihydro-1,3-benzoxazin-8-yl]-5-fluoro-2-hydroxybenzoate

[Formula 149]

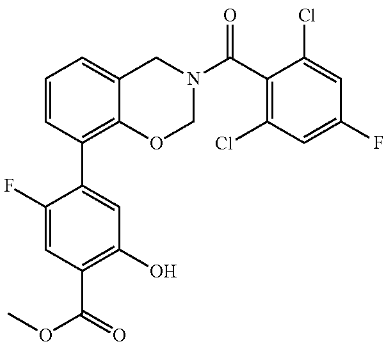

To a solution of methyl 5-fluoro-2-hydroxy-4-(4,4,5,5-tetramethyl-1,3,2-dioxaborolan-2-yl)benzoate (15.4 g, 51.8 mmol) and (8-bromo-2,4-dihydro-1,3-benzoxazin-3-yl)-(2,6-dichloro-4-fluorophenyl)methanone (21.0 g, 51.8 mmol) in 1,4-dioxane (210 mL)/water (21.0 mL), a 1,1'-bis(diphenylphosphino)ferrocene-palladium(II) dichloride dichloromethane complex (1.90 g, 2.59 mmol) and potassium carbonate (14.3 g, 104 mmol) were added, and the mixture was stirred at 100° C. for 16 hours. The reaction mixture was purified by silica gel column chromatography (hexane/ethyl acetate) to obtain the title compound (99%, 25.4 g).

LCMS: m/z 494[M+H]$^+$

HPLC retention time: 0.99 min (analysis condition D)

Sixth Step

Compound W4

Methyl 4-[3-(2,6-dichloro-4-fluorobenzoyl)-2,4-dihydro-1,3-benzoxazin-8-yl]-5-fluoro-2-(trifluoromethylsulfonyloxy)benzoate

[Formula 150]

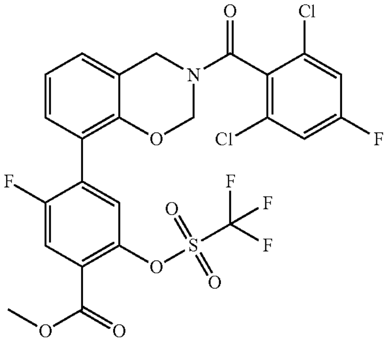

To a solution of methyl 4-[3-(2,6-dichloro-4-fluorobenzoyl)-2,4-dihydro-1,3-benzoxazin-8-yl]-5-fluoro-2-hydroxybenzoate (45.4 mg, 0.0920 mmol) in N,N-dimethylformamide (0.919 mL), N,N-diisopropylethylamine (0.0320 mL, 0.184 mmol) and N-phenylbis(trifluoromethanesulfonimide) (49.2 mg, 0.138 mmol) were added, and the mixture was stirred at room temperature for 2 hours. The reaction mixture was purified by reverse phase column chromatography (acetonitrile/water, 0.1% formic acid) to obtain the title compound (92%, 53.2 mg).

LCMS: m/z 626[M+H]$^+$

HPLC retention time: 1.04 min (analysis condition D)

Seventh Step

Compound W5

Methyl 4-[3-(2,6-dichloro-4-fluorobenzoyl)-2,4-dihydro-1,3-benzoxazin-8-yl]-5-fluoro-2-(4,4,5,5-tetramethyl-1,3,2-dioxaborolan-2-yl)benzoate

[Formula 151]

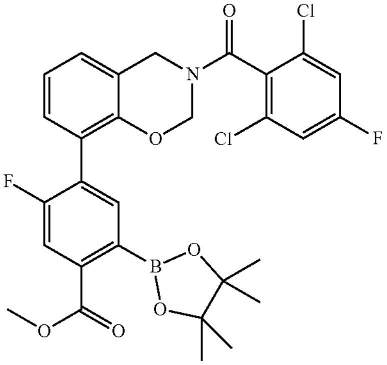

To a solution of methyl 4-[3-(2,6-dichloro-4-fluorobenzoyl)-2,4-dihydro-1,3-benzoxazin-8-yl]-5-fluoro-2-(trifluoromethylsulfonyloxy)benzoate (17.9 g, 28.6 mmol) in 1,4-dioxane (178 mL), bis(pinacolato)diboron (14.5 g, 57.1 mmol), a 1,1'-bis(diphenylphosphino)ferrocene-palladium (II) dichloride dichloromethane complex (1.05 g, 1.43 mmol) and potassium acetate (8.41 g, 85.7 mmol) were added, and the mixture was stirred at 100° C. for 16 hours.

LCMS: m/z 604[M+H]$^+$

HPLC retention time: 0.89 min (analysis condition T)

Eighth Step

Compound W6

Methyl 2-bromo-4-[3-(2,6-dichloro-4-fluorobenzoyl)-2,4-dihydro-1,3-benzoxazin-8-yl]-5-fluorobenzoate

[Formula 152]

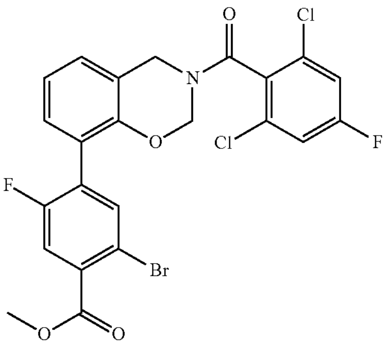

A solution of methyl 4-[3-(2,6-dichloro-4-fluorobenzoyl)-2,4-dihydro-1,3-benzoxazin-8-yl]-5-fluoro-2-(4,4,5,5-tetramethyl-1,3,2-dioxaborolan-2-yl)benzoate (200 mg, 0.331 mmol) and copper(II) bromide (222 mg, 0.993 mmol) in N,N-dimethylformamide (3.00 mL)-water (1.00 mL) was stirred at 80° C. for 1 hour. The reaction solution was subjected to extraction with ethyl acetate. The organic layer was washed with a saturated aqueous solution of sodium chloride, dried over anhydrous sodium sulfate, and then concentrated. The obtained residue was purified by reverse phase column chromatography (acetonitrile/water, 0.5% trifluoroacetic acid) to obtain the title compound (63%, 4.39 g).

LCMS: m/z 556[M+H]$^+$

HPLC retention time: 3.58 min (analysis condition AA)

Ninth Step

Compound W

Methyl 4-[3-(2,6-dichloro-4-fluorobenzoyl)-2,4-dihydro-1,3-benzoxazin-8-yl]-5-fluoro-2-(8-oxa-3-azabicyclo[3.2.1]octan-3-yl)benzoate

[Formula 153]

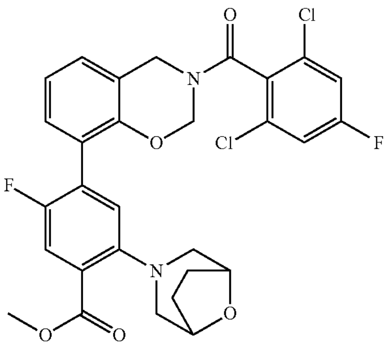

A solution of methyl 2-bromo-4-[3-(2,6-dichloro-4-fluorobenzoyl)-2,4-dihydro-1,3-benzoxazin-8-yl]-5-fluorobenzoate (400 mg, 0.718 mmol), 3-oxa-8-azabicyclo[3.2.1]octane (122 mg, 1.08 mmol), Xantphos Pd G4 (69.1 mg, 0.0720 mmol) and cesium carbonate (702 mg, 2.15 mmol) in toluene (4.79 mL) was stirred overnight at 100° C. 1-Methylpyrrolidin-2-one and an aqueous formic acid solution were added to the reaction solution, and the mixture was purified by HPLC (acetonitrile/water, 0.5% trifluoroacetic acid) to obtain the title compound (26%, 110 mg).

LCMS: m/z 589[M+H]$^+$

HPLC retention time: 0.96 min (analysis condition D)

Compound X

Methyl 4-[3-[2,6-dichloro-4-(1-methylpyrazol-4-yl)benzoyl]-2,4-dihydro-1,3-benzoxazin-8-yl]-5-fluoro-2-(trifluoromethylsulfonyloxy)benzoate First Step Compound X2

Methyl 2,6-dichloro-4-(1-methylpyrazol-4-yl)benzoate

[Formula 154]

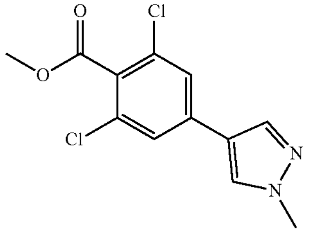

To a solution of methyl 4-bromo-2,6-dichlorobenzoate (523 mg, 1.842 mmol) and (1-methyl-4-(4,4,5,5-tetramethyl-1,3,2-dioxaborolan-2-yl)pyrazole (460 mg, 2.21 mmol) in 1,4-dioxane (8.37 mL)-water (0.837 mL), a 1,1'-bis(diphenylphosphino)ferrocene-palladium(II) dichloride dichloromethane complex (135 mg, 0.184 mmol) and potassium carbonate (764 mg, 5.53 mmol) were added, and the mixture was stirred at 100° C. for 1 hour. The mixed reaction solution was purified by reverse phase column chromatography (acetonitrile/water, 0.5% formic acid) to quantitatively (581 mg) obtain the title compound.

LCMS: m/z 285[M+H]$^+$

HPLC retention time: 0.74 min (analysis condition D)

Second Step

Compound X3

2,6-Dichloro-4-(1-methylpyrazol-4-yl)benzoic acid

[Formula 155]

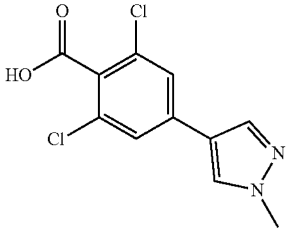

To a solution of methyl 2,6-dichloro-4-(1-methylpyrazol-4-yl)benzoate (582 mg, 2.04 mmol) in dimethyl sulfoxide (3.06 mL)-water (1.02 mL), a 5 M aqueous sodium hydroxide solution (2.04 mL, 10.2 mmol) was added, and the mixture was stirred at 60° C. for 3 hours. An aqueous formic acid solution was added to the reaction solution, and the mixture was purified by reverse phase column chromatography (acetonitrile/water, 0.5% formic acid) to obtain the title compound (86%, 477 mg).

LCMS: m/z 271 [M+H]$^+$

HPLC retention time: 0.56 min (analysis condition K)

Third Step

Compound X4

N-[(3-Bromo-2-hydroxyphenyl)methyl]-2,6-dichloro-4-(1-methylpyrazol-4-yl)benzamide

[Formula 156]

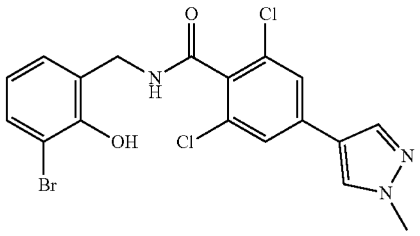

To a solution of 2,6-dichloro-4-(1-methylpyrazol-4-yl) benzoic acid (477 mg, 1.76 mmol) in N,N-dimethylformamide (8.20 mL), HATU (656 mg, 1.73 mmol), 2-(aminomethyl)-6-bromophenol hydrochloride (392 mg, 1.64 mmol) and N,N-diisopropylethylamine (1.15 mL, 6.57 mmol) were added, and the mixture was stirred at room temperature for 5 hours. The reaction solution was filtered and then purified by reverse phase column chromatography (acetonitrile/water, 0.5% formic acid) to obtain the title compound (90%, 198 mg).

LCMS: m/z 454[M+H]$^+$

HPLC retention time: 0.74 min (analysis condition D)

Fourth Step

Compound X5

(8-Bromo-2,4-dihydro-1,3-benzoxazin-3-yl)-[2,6-dichloro-4-(1-methylpyrazol-4-yl)phenyl]methanone

[Formula 157]

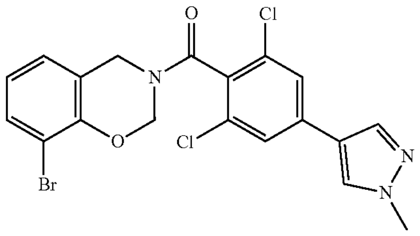

The title compound was obtained by the same operation as in the third step of compound W using N-[(3-bromo-2-hydroxyphenyl)methyl]-2,6-dichloro-4-(1-methylpyrazol-4-yl)benzamide.

LCMS: m/z 466[M+H]$^+$

HPLC retention time: 0.85 min (analysis condition D)

Fifth Step

Compound X6

Methyl 4-[3-[2,6-dichloro-4-(1-methylpyrazol-4-yl) benzoyl]-2,4-dihydro-1,3-benzoxazin-8-yl]-5-fluoro-2-hydroxybenzoate

[Formula 158]

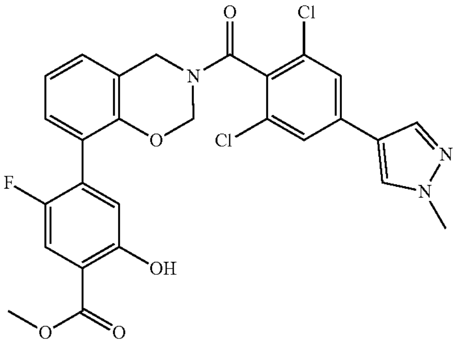

The title compound was obtained by the same operation as in the third step of compound B using (8-bromo-2,4-dihydro-1,3-benzoxazin-3-yl)-[2,6-dichloro-4-(1-methylpyrazol-4-yl)phenyl]methanone and methyl 4-bromo-5-fluoro-2-hydroxybenzoate.

LCMS: m/z 556[M+H]$^+$

HPLC retention time: 0.93 min (analysis condition D)

Sixth Step

Compound X

Methyl 4-[3-[2,6-dichloro-4-(1-methylpyrazol-4-yl) benzoyl]-2,4-dihydro-1,3-benzoxazin-8-yl]-5-fluoro-2-(trifluoromethylsulfonyloxy)benzoate

[Formula 159]

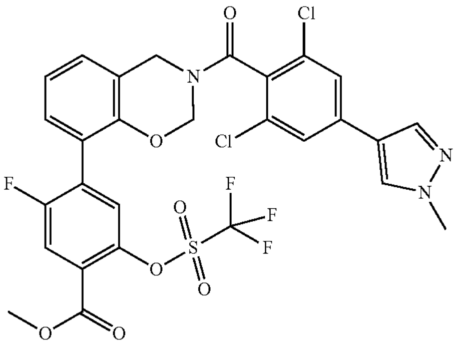

To a solution of methyl 4-[3-[2,6-dichloro-4-(1-methylpyrazol-4-yl)benzoyl]-2,4-dihydro-1,3-benzoxazin-8-yl]-5-fluoro-2-hydroxybenzoate (66.6 mg, 0.120 mmol) in N,N-dimethylformamide (1.20 mL), N,N-diisopropylethylamine (0.0417 mL, 0.239 mmol) and N-phenylbis(trifluoromethanesulfonimide) (64.1 mg, 0.180 mmol) were added, and the mixture was stirred overnight at room temperature. The mixed reaction solution was poured to 1 M hydrochloric acid, followed by extraction with ethyl acetate. The obtained residue was purified by silica gel column chromatography (hexane/ethyl acetate) to obtain the title compound (97%, 79.7 mg).

LCMS: m/z 688[M+H]$^+$

HPLC retention time: 0.99 min (analysis condition D)

Compound Y

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-(trifluoromethylsulfonyloxy)benzoate First Step Compound Y1

(8-Bromo-2,4-dihydro-1,3-benzoxazin-3-yl)-[2,6-dichloro-4-[(2R)-2,4-dimethylpiperazin-1-yl]phenyl]methanone

[Formula 160]

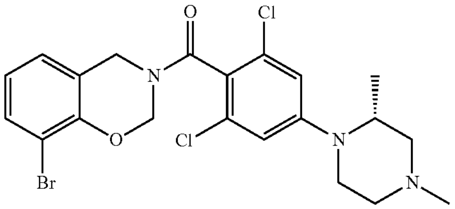

To a solution of (8-bromo-2,4-dihydro-1,3-benzoxazin-3-yl)-(2,6-dichloro-4-fluorophenyl)methanone (500 mg, 1.23 mmol) in 1-methylpyrrolidin-2-one (2.15 mL), (3R)-1,3-dimethylpiperazine (705 mg, 6.17 mmol) and N,N-diisopropylethylamine (0.00215 mL, 12.3 mmol) were added, and the mixture was stirred at 200° C. for 1.5 hours under microwave and then stirred at 220° C. for 1.5 hours. An aqueous formic acid solution was added to the reaction solution, and the mixture was purified by reverse phase column chromatography (acetonitrile/water, 0.5% formic acid) to obtain the title compound (66%, 406 mg).

LCMS: m/z 498[M+H]$^+$

HPLC retention time: 0.56 min (analysis condition D)

Second Step

Compound Y2

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-hydroxybenzoate

[Formula 161]

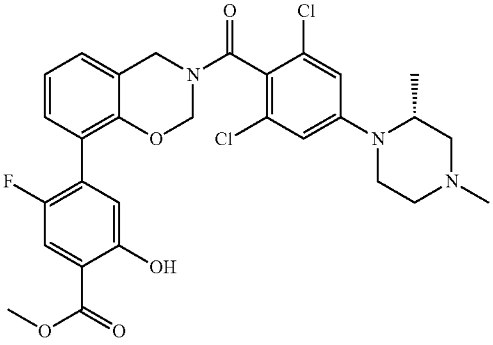

The title compound was obtained by the same operation as in the third step of compound B using (8-bromo-2,4-dihydro-1,3-benzoxazin-3-yl)-[2,6-dichloro-4-[(2R)-2,4-dimethylpiperazin-1-yl]phenyl]methanone and methyl 4-bromo-5-fluoro-2-hydroxybenzoate.

LCMS: m/z 588[M+H]$^+$

HPLC retention time: 0.71 min (analysis condition T)

Third Step

Compound Y

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-(trifluoromethylsulfonyloxy)benzoate

[Formula 162]

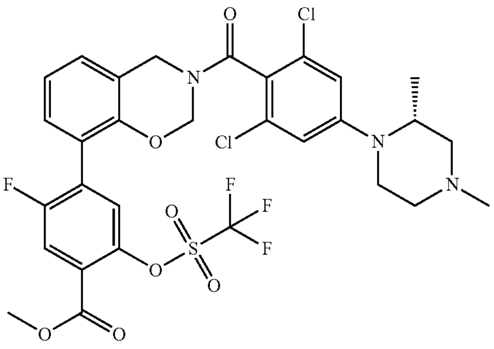

The title compound was obtained by the same operation as in the sixth step of compound W using methyl 4-[3-[2,6-dichloro-4-[(2R)-2,4-dimethylpiperazin-1-yl]benzoyl]-2,4-dihydro-1,3-benzoxazin-8-yl]-5-fluoro-2-hydroxybenzoate. However, triethylamine was used instead of N,N-diisopropylethylamine.

LCMS: m/z 720[M+H]$^+$

HPLC retention time: 0.68 min (analysis condition D)

Compound Z

Methyl 4-[3-(4-bromo-2,6-dichlorobenzoyl)-7-fluoro-2,4-dihydro-1,3-benzoxazin-8-yl]-5-fluoro-2-morpholin-4-ylbenzoate First Step Compound Z2 tert-Butyl N-[(3-bromo-4-fluoro-2-hydroxyphenyl)methyl]carbamate

[Formula 163]

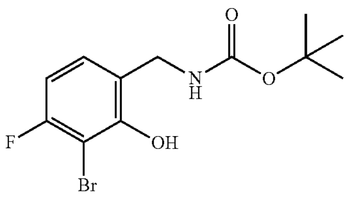

A solution of 3-bromo-4-fluoro-2-hydroxybenzonitrile (176 mg, 0.813 mmol) in tetrahydrofuran (1.63 mL) was cooled to 0° C. A 1 M borane-tetrahydrofuran complex (1.63 mL, 1.63 mmol) was added thereto, and the mixture was stirred at 60° C. for 2.5 hours. The reaction solution was cooled to 0° C. 5 M hydrochloric acid (0.358 mL, 1.79 mmol) was added thereto, and the mixture was stirred at 60°

C. for 2 hours. The reaction solution was cooled to 0° C. A 6 M aqueous sodium hydroxide solution (0.298 mL, 1.79 mmol) and di-tert-butyl dicarbonate (0.266 mL, 0.976 mmol) were added thereto, and the mixture was stirred at room temperature for 30 minutes. After extraction with ethyl acetate, the organic layer was washed with water and a saturated aqueous solution of sodium chloride, dried over anhydrous sodium sulfate, and concentrated. The residue was purified by reverse phase column chromatography (acetonitrile/water, 0.1% formic acid) to obtain the title compound (60%, 156 mg).

LCMS: m/z 264[M-tBu+H]$^+$

HPLC retention time: 0.86 min (analysis condition O)

Second Step

Compound Z3 tert-Butyl 8-bromo-7-fluoro-2,4-dihydro-1,3-benzoxazine-3-carboxylate

[Formula 164]

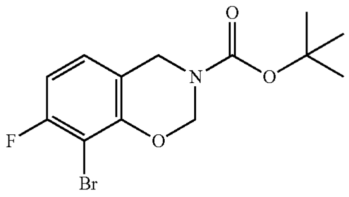

The title compound was obtained by the same method as in the third step of compound W using tert-butyl N-[(3-bromo-4-fluoro-2-hydroxyphenyl)methyl]carbamate.

LCMS: m/z 332[M+H]$^+$

HPLC retention time: 0.95 min (analysis condition O)

Third Step

Compound Z4 tert-Butyl 7-fluoro-8-(2-fluoro-4-methoxycarbonyl-5-morpholin-4-ylphenyl)-2,4-dihydro-1,3-benzoxazine-3-carboxylate

[Formula 165]

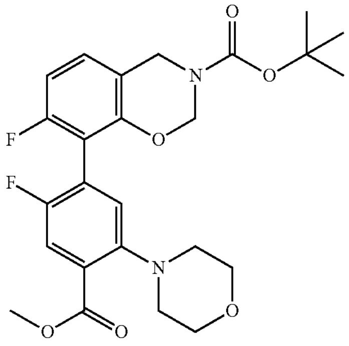

To a solution of tert-butyl 8-bromo-7-fluoro-2,4-dihydro-1,3-benzoxazine-3-carboxylate (400 mg, 1.20 mmol) and (2-fluoro-4-methoxycarbonyl-5-morpholin-4-ylphenyl)boronic acid (639 mg, 1.81 mmol) in 1,4-dioxane (5.02 mL)-water (1.00 mL), potassium phosphate (1.28 g, 6.02 mmol) and XPhos Pd G3 (51.0 mg, 0.0600 mmol) were added, and the mixture was stirred at 50° C. for 4.5 hours. After extraction with ethyl acetate, the organic layer was washed with water and a saturated aqueous solution of sodium chloride, dried over anhydrous sodium sulfate, and concentrated. The residue was purified by reverse phase column chromatography (acetonitrile/water, 0.1% formic acid) to obtain the title compound (92%, 544 mg).

LCMS: m/z 491[M+H]$^+$

HPLC retention time: 0.96 min (analysis condition O)

Fourth Step

Compound Z5

Methyl 5-fluoro-4-(7-fluoro-3,4-dihydro-2H-1,3-benzoxazin-8-yl)-2-morpholin-4-ylbenzoate hydrochloride

[Formula 166]

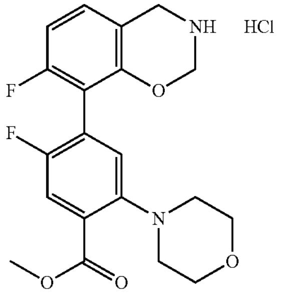

The title compound was obtained by the same operation as in the fourth step of compound B using tert-butyl 7-fluoro-8-(2-fluoro-4-methoxycarbonyl-5-morpholin-4-ylphenyl)-2,4-dihydro-1,3-benzoxazine-3-carboxylate.

LCMS: m/z 391[M+H]$^+$

HPLC retention time: 0.49 min (analysis condition O)

Fifth Step

Compound Z

Methyl 4-[3-(4-bromo-2,6-dichlorobenzoyl)-7-fluoro-2,4-dihydro-1,3-benzoxazin-8-yl]-5-fluoro-2-morpholin-4-ylbenzoate

[Formula 167]

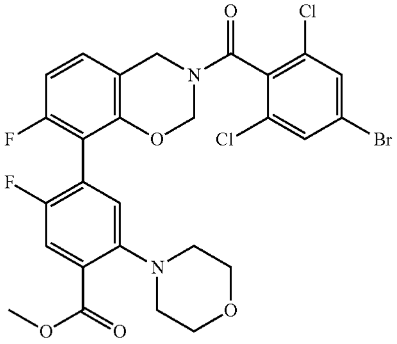

The title compound was obtained by the same operation as in the fifth step of compound B using methyl 5-fluoro-4-(7-fluoro-3,4-dihydro-2H-1,3-benzoxazin-8-yl)-2-morpholin-4-ylbenzoate hydrochloride and 4-bromo-2,6-dichlorobenzoyl chloride. However, diisopropylamine was used instead of N,N-diisopropylethylamine.

LCMS: m/z 641[M+H]$^+$

HPLC retention time: 0.99 min (analysis condition O)

Compound 1-61

4-[3-[2,6-Dichloro-4-(5-oxa-2-azaspiro[3.4]octan-2-yl)benzoyl]-2,4-dihydro-1,3-benzoxazin-8-yl]-2-(3-oxa-8-azabicyclo[3.2.1]octan-8-yl)benzoic acid

[Formula 168]

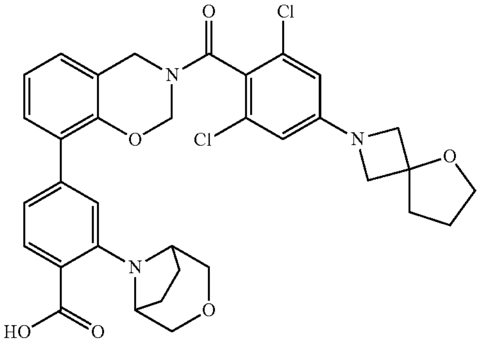

The title compound was obtained by the same operation as in the ninth step of compound 1-7 using compound D and 5-oxa-2-azaspiro[3.4]octane 2,2,2-trifluoroacetate.

LCMS: m/z 650[M+H]$^+$

HPLC retention time: 1.65 min and 1.68 min (analysis condition B)

Compound 1-71

4-[3-[2-Chloro-4-(3-methoxyazetidin-1-yl)-5-methylbenzoyl]-2,4-dihydro-1,3-benzoxazin-8-yl]-5-fluoro-2-(3-oxa-8-azabicyclo[3.2.1]octan-8-yl)benzoic acid First Step Compound CP8

Methyl 4-[3-(4-bromo-2-chloro-5-methylbenzoyl)-2,4-dihydro-1,3-benzoxazin-8-yl]-5-fluoro-2-(3-oxa-8-azabicyclo[3.2.1]octan-8-yl)benzoate

[Formula 169]

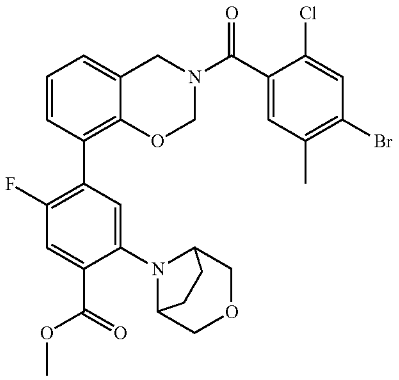

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2-chloro-5-methylbenzoyl chloride.

LCMS: m/z 629[M+H]$^+$

HPLC retention time: 1.02 min (analysis condition D)

Second Step

Compound 1-71

4-[3-[2-Chloro-4-(3-methoxyazetidin-1-yl)-5-methylbenzoyl]-2,4-dihydro-1,3-benzoxazin-8-yl]-5-fluoro-2-(3-oxa-8-azabicyclo[3.2.1]octan-8-yl)benzoic acid

[Formula 170]

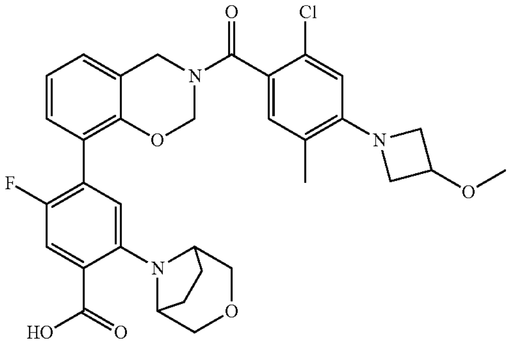

The title compound was obtained by the same operation as in the ninth step of compound 1-7 using methyl 4-[3-(4-bromo-2-chloro-5-methylbenzoyl)-2,4-dihydro-1,3-benzoxazin-8-yl]-5-fluoro-2-(3-oxa-8-azabicyclo[3.2.1]octan-8-yl)benzoate and 3-methoxyazetidine hydrochloride.

LCMS: m/z 622[M+H]$^+$

HPLC retention time: 1.48 min (analysis condition B)

Compound 1-74

4-[3-[2-Chloro-5-methoxy-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid First Step Compound CP9

Methyl 4-[3-(4-bromo-2-chloro-5-methoxybenzoyl)-2,4-dihydro-1,3-benzoxazin-8-yl]-5-fluoro-2-(3-oxa-8-azabicyclo[3.2.1]octan-8-yl)benzoate

[Formula 171]

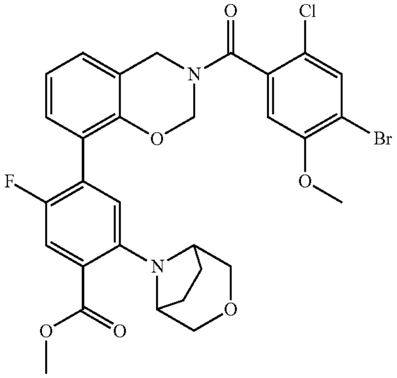

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2-chloro-5-methoxybenzoyl chloride.

LCMS: m/z 645[M+H]$^+$

HPLC retention time: 0.97 min (analysis condition D)

Second Step

Compound 1-74

4-[3-[2-Chloro-5-methoxy-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 172]

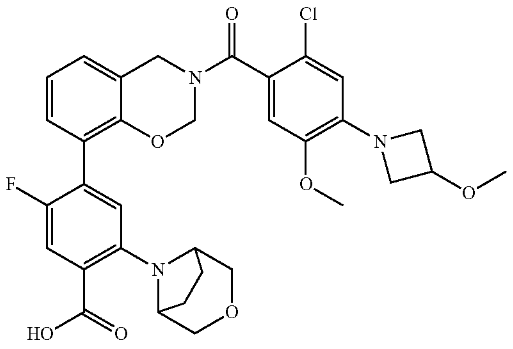

The title compound was obtained by the same operation as in the ninth step of compound 1-7 using methyl 4-[3-(4-bromo-2-chloro-5-methoxybenzoyl)-2,4-dihydro-1,3-benzoxazin-8-yl]-5-fluoro-2-(3-oxa-8-azabicyclo[3.2.1]octan-8-yl)benzoate and 3-methoxyazetidine hydrochloride.

LCMS: m/z 638[M+H]$^+$

HPLC retention time: 1.47 min (analysis condition B)

Compound 1-55

4-[3-[2,6-Dichloro-4-[4-(oxetan-3-yl)piperazin-1-yl]benzoyl]-2,4-dihydro-1,3-benzoxazin-8-yl]-5-fluoro-2-morpholin-4-ylbenzoic acid

[Formula 173]

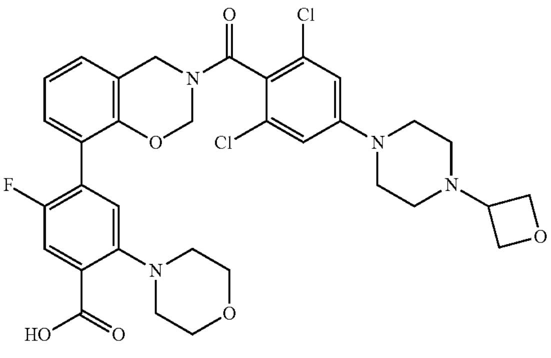

A solution of compound B (12.0 mg, 0.0190 mmol), 1-(oxetan-3-yl)piperazine (5.47 mg, 0.0380 mmol), [2,2'-bis(diphenylphosphino)-1,1'-binaphthyl]dichloropalladium(II) (1.54 mg, 0.00192 mmol), and cesium carbonate (18.8 mg, 0.0580 mmol) in toluene (0.192 mL) was heated at 100° C. for 1 hour. The reaction solution was cooled to room temperature, and the solvent was concentrated. Methanol (0.0950 mL), tetrahydrofuran (0.095 mL) and a 5 M aqueous sodium hydroxide solution (0.0380 mL, 0.190 mmol) were added to the residue, and the mixture was stirred at 60° C. for 30 minutes. The reaction mixture was purified by HPLC (acetonitrile/water, 0.1% formic acid) to obtain the title compound (64%, 8.20 mg).

LCMS: m/z 671[M+H]$^+$

HPLC retention time: 0.75 min and 0.80 min (analysis condition A)

Compound 1-54

4-[3-[2,6-Dichloro-4-[4-(2-methoxyethyl)piperazin-1-yl]benzoyl]-2,4-dihydro-1,3-benzoxazin-8-yl]-5-fluoro-2-morpholin-4-ylbenzoic acid

[Formula 174]

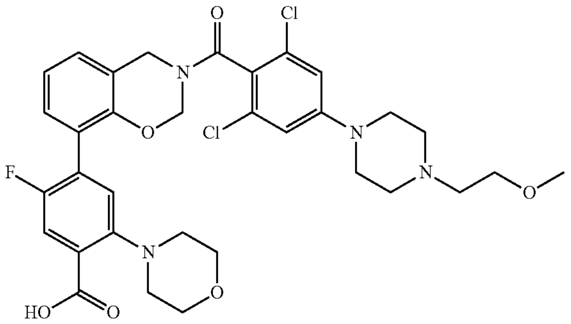

A solution of compound B (1.72 g, 2.76 mmol), 1-(2-methoxyethyl)piperazine (0.818 ml, 5.51 mmol), [2,2'-bis(diphenylphosphino)-1,1'-binaphthyl]dichloropalladium(II) (65.0 mg, 0.0810 mmol), and cesium carbonate (2.69 g, 8.27 mmol) in toluene (15.0 mL) was heated at 95° C. for 2 hours. The reaction solution was cooled to room temperature, and the solvent was concentrated. Dimethyl sulfoxide (5.00 mL), 1,4-dioxane (5.00 mL) and a 5 M aqueous sodium hydroxide solution (2.76 mL, 13.8 mmol) were added to the residue, and the mixture was stirred at 90° C. for 1 hour. The reaction solution was concentrated to remove 1,4-dioxane. Formic acid was added to the residue, and the reaction mixture was purified by reverse phase column chromatography (acetonitrile/water, 0.1% formic acid) to obtain the title compound (67%, 1.24 g).

LCMS: m/z 673[M+H]$^+$

HPLC retention time: 0.77 min and 0.82 min (analysis condition A)

Compound 1-88

4-[3-[2-Chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound CP6

Methyl 4-[3-[2-chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 175]

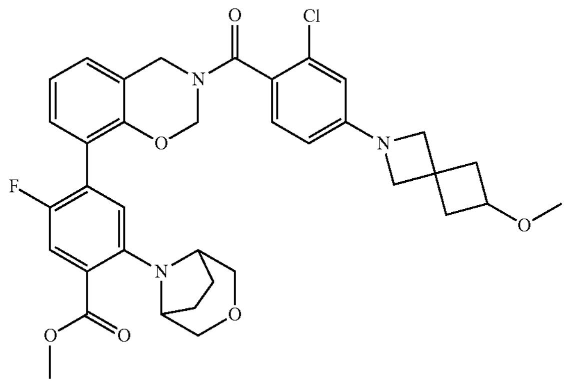

A solution of compound H (3.46 g, 5.62 mmol), 6-methoxy-2-azaspiro[3.3]heptane hydrochloride (1.84 g, 11.2 mmol), rac-BINAP Pd G4 (170 mg, 0.169 mmol), and cesium carbonate (9.15 g, 28.1 mmol) in 1,4-dioxane (34.6 mL) was heated at 100° C. for 2 hours. The reaction solution was filtered through celite and washed with ethyl acetate. The filtrate was washed with a 15% aqueous sodium chloride solution, dried over magnesium sulfate, and filtered. The filtrate was concentrated, and the obtained residue was purified by silica gel column chromatography (hexane/ethyl acetate) to obtain the title compound (86%, 3.20 g).

LCMS: m/z 662[M+H]$^+$

HPLC retention time: 3.1 min (analysis condition AF)

Second Step

Compound 1-88

4-[3-[2-Chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 176]

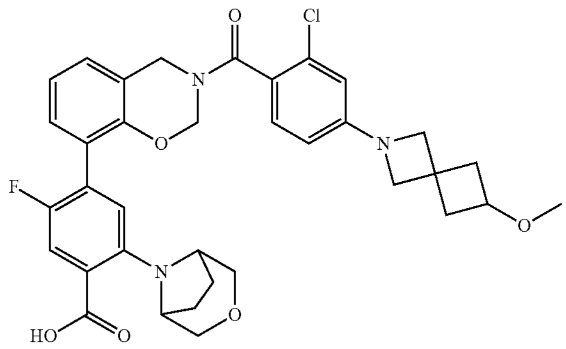

To a solution of methyl 4-[3-[2-chloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (3.17 g, 4.79 mmol) in tetrahydrofuran (7.61 mL), ethanol (7.61 mL) and an 8 M aqueous potassium hydroxide solution (2.99 mL, 23.9 mmol) were added, and the mixture was heated at 60° C. for 35 minutes. The reaction solution was cooled to 0° C., and 0.5 M hydrochloric acid was added thereto. The resulting solid was collected by filtration and washed with ethanol/water to obtain the title compound (97%, 3.01 g).

LCMS: m/z 648[M+H]$^+$

HPLC retention time: 1.64 min (analysis condition B)

Compound 1-83

4-[3-[2,6-Dichloro-4-(6-methoxy-2-azaspiro[3.3]heptan-2-yl)benzoyl]-2,4-dihydro-1,3-benzoxazin-8-yl]-2-(3-oxa-8-azabicyclo[3.2.1]octan-8-yl)benzoic acid First Step Compound CP7

4-[3-(4-Bromo-2,6-dichlorobenzoyl)-2,4-dihydro-1,3-benzoxazin-8-yl]-2-(3-oxa-8-azabicyclo[3.2.1]octan-8-yl)benzoic acid

[Formula 177]

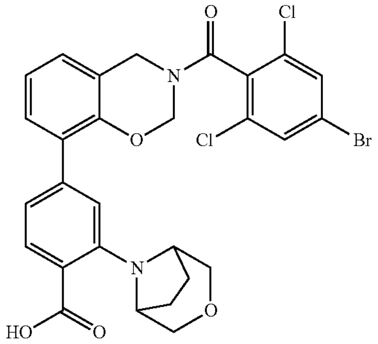

To a solution of compound D (24.0 g, 38.0 mmol) in 1,3-dimethyl-2-imidazolidinone (120 mL), an 8 M aqueous potassium hydroxide solution (23.7 mL, 190 mmol) was added, and the mixture was stirred at 60° C. for 3 hours. The reaction solution was cooled to room temperature. 2 M hydrochloric acid and water were added thereto, and the mixture was stirred at room temperature for 30 minutes. The resulting solid was collected by filtration and washed with water to obtain the title compound (90%, 21.0 g).

LCMS: m/z 617[M+H]$^+$

HPLC retention time: 1.17 min and 1.21 min (analysis condition G)

Second Step
Compound 1-83

4-[3-[2,6-Dichloro-4-(6-methoxy-2-azaspiro[3.3]heptan-2-yl)benzoyl]-2,4-dihydro-1,3-benzoxazin-8-yl]-2-(3-oxa-8-azabicyclo[3.2.1]octan-8-yl)benzoic acid

[Formula 178]

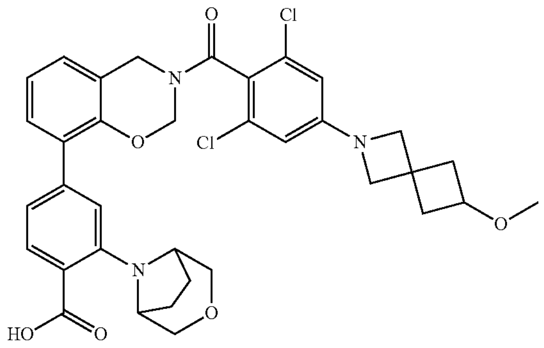

To a solution of 4-[3-(4-bromo-2,6-dichlorobenzoyl)-2,4-dihydro-1,3-benzoxazin-8-yl]-2-(3-oxa-8-azabicyclo[3.2.1]octan-8-yl)benzoic acid (21.0 g, 34.0 mmol), 6-methoxy-2-azaspiro[3.3]heptane hydrochloride (8.34 g, 50.9 mmol), allylpalladium(II) chloride (dimer) (621 mg, 1.70 mmol), 4,5-bis(diphenylphosphino)-9,9-dimethylxanthene (983 mg, 1.70 mmol) and dibenzylideneacetone (398 mg, 1.70 mmol) in tetrahydrofuran (679 mL), sodium tert-butoxide (13.1 g, 136 mmol) was added, and the mixture was stirred at 30° C. for 3 hours. A 0.5 M aqueous potassium bisulfate solution, ethyl acetate, N-acetylcysteine and water were added to the reaction solution, followed by extraction with ethyl acetate. The organic layer was washed with a saturated aqueous solution of sodium chloride. The organic layer was dried over magnesium sulfate, filtered, and concentrated. Acetonitrile was added to the residue, and the mixture was stirred at 50° C. for 15 minutes. After cooling to room temperature, water was added thereto, and the mixture was stirred at 25° C. for 30 minutes. The obtained solid was collected by filtration and washed with acetonitrile/water (1/2) to obtain the title compound (70%, 15.8 g).

LCMS: m/z 664[M+H]$^+$

HPLC retention time: 1.67, 1.70 min (analysis condition B)

Compounds shown in Table 1-4 were obtained by the same operation as in the process of compound 1-55 using the corresponding intermediates and commercially available amine reagents shown in Table 1-5. However, a 1,4-dioxane solution was used instead of the toluene solution in the synthesis of compound 1-59.

TABLE 1-4

| Compound No. | Intermediate No. | Structure | Compound Name | Analysis conditions | HPLC retention time (min) | m/z [M + H] |
|---|---|---|---|---|---|---|
| 1-56 | Compound B | 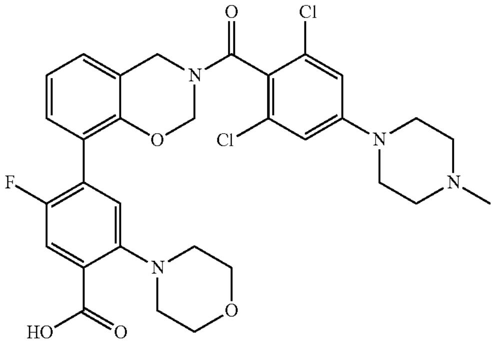 | 4-[3-[2,6-Dichloro-4-(4-methylpiperazin-1-yl)benzyl]-2,4-dihydro-1,3-benzoxazin-8-yl]-5-fluoro-2-morpholin-4-ylbenzoic acid | A | 0.76, 0.81 | 629 |
| 1-58 | Compound B | 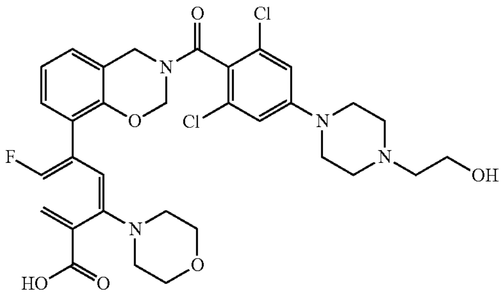 [SMILES: C=C(C(=O)O)/C(=C\C(=C\F)c1cccc2c1OCN(C(=O)c1c(Cl)cc(N3CCN(CCO)CC3)cc1Cl)C2)N1CCOCC1] | 4-[3-[2,6-Dichloro-4-[4-(2-hydroxyethyl)piperazin-1-yl]benzoyl]-2,4-dihydro-1,3-benzoxazin-8-yl]-5-fluoro-2-morpholin-4-ylbenzoic acid | A | 0.74, 0.80 | 659 |

TABLE 1-4-continued

| Compound No. | Intermediate No. | Structure | Compound Name | Analysis conditions | HPLC retention time (min) | m/z [M + H] |
|---|---|---|---|---|---|---|
| 1-59 | Compound B | 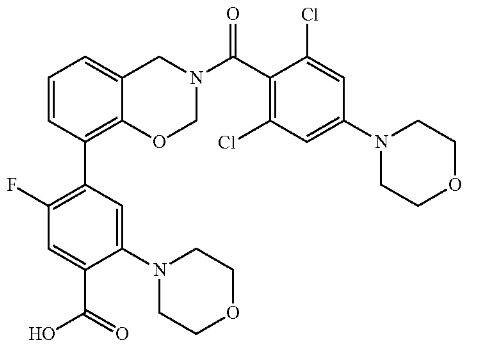 [SMILES: O=C(O)c1cc(F)c(-c2cccc3c2OCN(C(=O)c2c(Cl)cc(N4CCOCC4)cc2Cl)C3)cc1N1CCOCC1] | 4-[3-(2,6-Dichloro-4-morpholin-4-ylbenzoyl)-2,4-dihydro-1,3-benzoxazin-8-yl]-5-fluoro-2-morpholin-4-ylbenzoic acid | B | 1.42 | 616 |
| 1-62 | Compound E | 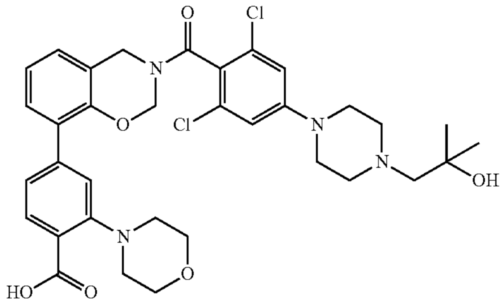 [SMILES: CC(C)(O)CN1CCN(c2cc(Cl)c(C(=O)N3COc4c(cccc4-c4ccc(C(=O)O)c(N5CCOCC5)c4)C3)c(Cl)c2)CC1] | 4-[3-[2,6-Dichloro-4-[4-(2-hydroxy-2-methylpropyl)piperazin-1-yl)benzoyl]-2,4-dihydro-1,3-benzoxazin-8-yl]-2-morpholin-4-ylbenzoic acid | A | 0.75, 0.80 | 669 |
| 1-63 | Compound E | 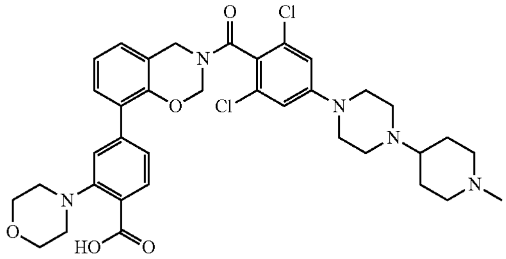 [SMILES: CN1CCC(N2CCN(c3cc(Cl)c(C(=O)N4COc5c(cccc5-c5ccc(C(=O)O)c(N6CCOCC6)c5)C4)c(Cl)c3)CC2)CC1] | 4-[3-[2,6-Dichloro-4-[4-(1-methylpiperidin-4-yl)piperazin-1-yl]benzoyl]-2,4-dihydro-1,3-benzoxazin-8-yl]-2-morpholin-4-ylbenzoic acid | B | 0.81, 0.86 | 694 |
| 1-68 | Compound G | 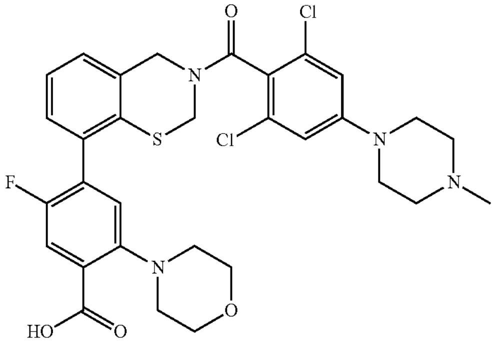 [SMILES: CN1CCN(c2cc(Cl)c(C(=O)N3CSc4c(cccc4-c4cc(N5CCOCC5)c(C(=O)O)cc4F)C3)c(Cl)c2)CC1] | 4-[3-[2,6-Dichloro-4-(4-methylpiperazin-1-yl)benzoyl]-2,4-dihydro-1,3-benzothiazin-8-yl]-5-fluoro-2-morpholin-4-ylbenzoic acid | A | 0.75, 0.79 | 645 |
| 1-69 | Compound G | 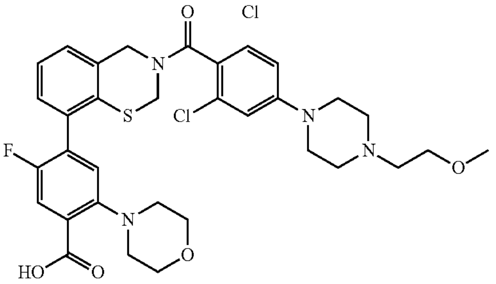 [SMILES: COCCN1CCN(c2ccc(C(=O)N3CSc4c(cccc4-c4cc(N5CCOCC5)c(C(=O)O)cc4F)C3)c(Cl)c2)CC1 ; Cl] | 4-[3-[2,6-Dichloro-4-[4-(2-methoxyethyl)piperazin-1-yl]benzoyl]-2,4-dihydro-1,3-benzothiazin-8-yl]-5-fluoro-2-morpholin-4-ylbenzoic acid | A | 0.78, 0.82 | 689 |

TABLE 1-4-continued

| Compound No. | Intermediate No. | Structure | Compound Name | Analysis conditions | HPLC retention time (min) | m/z [M + H] |
|---|---|---|---|---|---|---|
| 1-70 | Compound I | 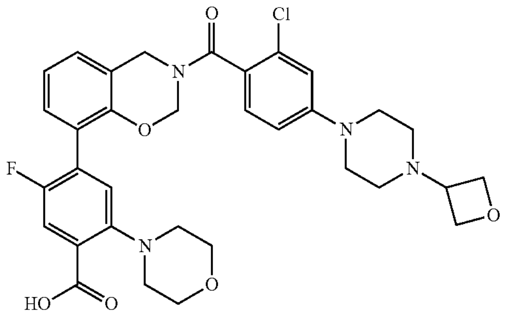 [SMILES: O=C(O)c1cc(F)c(-c2cccc3c2OCN(C(=O)c2ccc(N4CCN(C5COC5)CC4)cc2Cl)C3)cc1N1CCOCC1] | 4-[3-[2-Chloro-4-[4-(oxetan-3-yl)piperazin-1-yl]benzoyl]-2,4-dihydro-1,3-benzoxazin-8-yl]-5-fluoro-2-morpholin-4-ylbenzoic acid | A | 0.75 | 637 |
| 1-75 | Compound L | 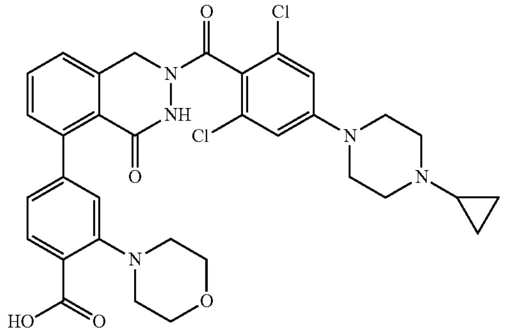 [SMILES: O=C(O)c1ccc(-c2cccc3c2C(=O)NN(C(=O)c2c(Cl)cc(N4CCN(C5CC5)CC4)cc2Cl)C3)cc1N1CCOCC1] | 4-[2-[2,6-Dichloro-4-(4-cyclopropylpiperazin-1-yl)benzoyl]-4-oxo-1,3-dihydrophthalazin-5-yl]-2-morpholin-4-ylbenzoic acid | A | 0.73 | 650 |
| 1-77 | Compound L | 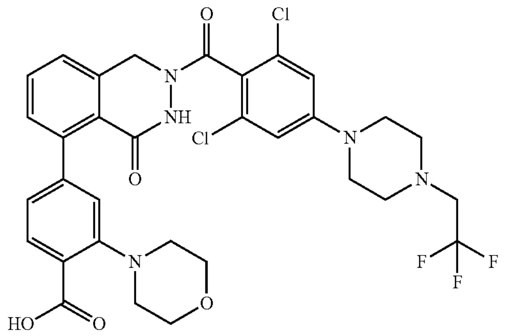 [SMILES: O=C(O)c1ccc(-c2cccc3c2C(=O)NN(C(=O)c2c(Cl)cc(N4CCN(CC(F)(F)F)CC4)cc2Cl)C3)cc1N1CCOCC1] | 4-[2-[2,6-Dichloro-4-[4-(2,2,2-trifluoroethyl)piperazin-1-yl]benzoyl]-4-oxo-1,3-dihydrophthalazin-5-yl]-2-morpholin-4-ylbenzoic acid | A | 1.01, 1.03 | 692 |
| 1-78 | Compound M | 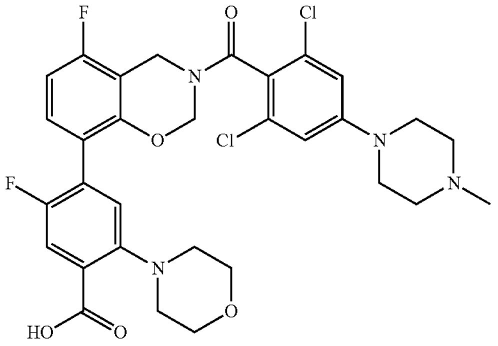 [SMILES: CN1CCN(c2cc(Cl)c(C(=O)N3COc4c(-c5cc(N6CCOCC6)c(C(=O)O)cc5F)ccc(F)c4C3)c(Cl)c2)CC1] | 4-[3-[2,6-Dichloro-4-(4-methylpiperazin-1-yl)benzoyl]-5-fluoro-2,4-dihydro-1,3-benzoxazin-8-yl]-5-fluoro-2-morpholin-4-ylbenzoic acid | A | 0.77, 0.84 | 647 |

TABLE 1-5

| Final compound No. | Amine |
|---|---|
| 1-56 | 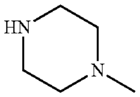 |
| 1-58 | 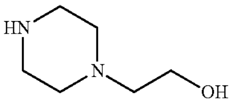 |
| 1-59 | 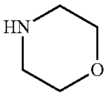 |
| 1-62 | 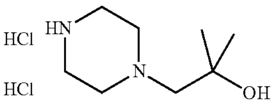 |
| 1-63 | 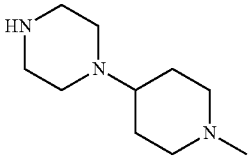 |
| 1-68 | 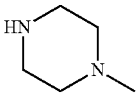 |
| 1-69 | 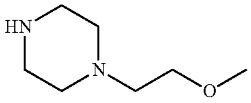 |
| 1-70 | 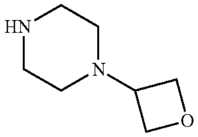 |
| 1-75 | 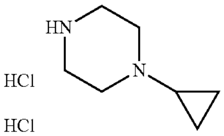 |
| 1-77 | 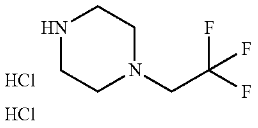 [SMILES: Cl ; FC(F)(F)CN1CCNCC1 ; Cl] |
| 1-78 | 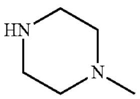 |

Compound 1-73

4-[3-[2-Chloro-5-methoxy-4-(2-oxa-6-azaspiro[3.3]heptan-6-yl)benzoyl]-2,4-dihydro-1,3-benzoxazin-8-yl]-5-fluoro-2-morpholin-4-ylbenzoic acid

[Formula 179]

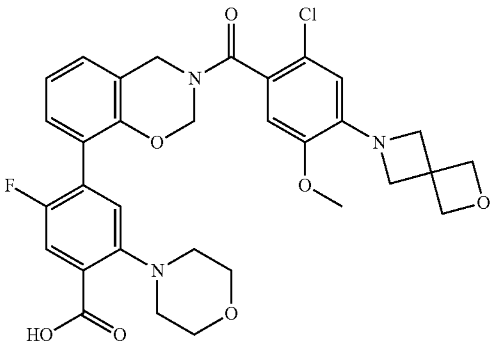

A solution of compound K (60.0 mg, 0.0970 mmol), 2-oxa-6-azaspiro[3.3]heptane oxalate (27.5 mg, 0.145 mmol), cesium carbonate (158 mg, 0.484 mmol), 2,2'-bis(diphenylphosphino)-1,1'-binaphthyl (12.1 mg, 0.0190 mmol), and tris(dibenzylideneacetone)dipalladium(0)-chloroform adduct (10.0 mg, 0.00968 mmol) in 1-methylpyrrolidin-2-one (0.960 mL) was stirred at 100° C. for 2 hours. The reaction solution was cooled to room temperature. Then, an 8 M aqueous potassium hydroxide solution (0.121 mL, 0.970 mmol) was added thereto, and the mixture was stirred at 60° C. for 30 minutes. An aqueous formic acid solution was added to the reaction solution, and the reaction mixture was purified by HPLC (acetonitrile/water, 0.1% formic acid) to obtain the title compound (55%, 33.2 mg).

LCMS: m/z 624[M+H]$^+$

HPLC retention time: 1.34 min (analysis condition B)

Compounds shown in Table 1-6 were obtained by the same operation as in the process of compound 1-73 using the corresponding intermediates and amine reagents shown in Table 1-7. However, palladium(II) acetate was used instead of the tris(dibenzylideneacetone)dipalladium(0)-chloroform adduct for compounds 1-57, 1-67, and 1-76. A toluene solvent was used instead of the 1-methylpyrrolidin-2-one solvent for compounds 1-57, 1-60, 1-65, 1-66, 1-67, 1-76, 1-79, 1-80, 1-81, 1-82, and 1-35.

TABLE 1-6

| Compound No. | Intermediate No. | Structure | Compound Name | Analysis conditions | HPLC retention time (min) | m/z [M + H] |
|---|---|---|---|---|---|---|
| 1-48 | Compound B | 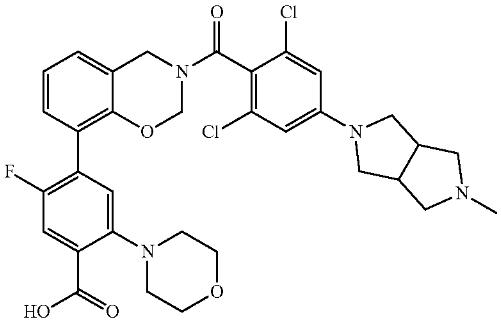 [SMILES: CN1CC2CN(c3cc(Cl)c(C(=O)N4COc5c(cccc5-c5cc(N6CCOCC6)c(C(=O)O)cc5F)C4)c(Cl)c3)CC2C1] | 4-[3-[2,6-Dichloro-4-(2-methyl-1,3,3a,4,6,6a-hexahydropyrrolo[3,4-c]pyrrol-5-yl)benzoyl]-2,4-dihydro-1,3-benzoxazin-8-yl]-5-fluoro-2-morpholin-4-ylbenzoic acid | B | 0.00, 1.03 | 655 |
| 1-49 | Compound B | 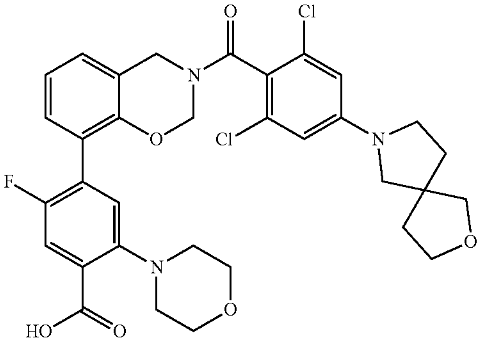 [SMILES: O=C(O)c1cc(F)c(-c2cccc3c2OCN(C(=O)c2c(Cl)cc(N4CCC5(CCOC5)C4)cc2Cl)C3)cc1N1CCOCC1] | 4-[3-[2,6-Dichloro-4-(2-oxa-7-azaspiro[4.4]nonan-7-yl)benzoyl]-2,4-dihydro-1,3-benzoxazin-8-yl]-5-fluoro-2-morpholin-4-ylbenzoic acid | B | 1.5 | 656 |
| 1-53 | Compound B | 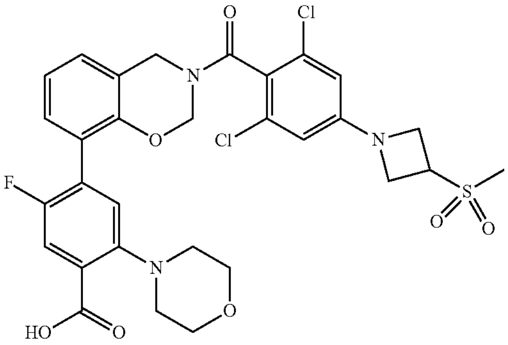 [SMILES: CS(=O)(=O)C1CN(c2cc(Cl)c(C(=O)N3COc4c(cccc4-c4cc(N5CCOCC5)c(C(=O)O)cc4F)C3)c(Cl)c2)C1] | 4-[3-[2,6-Dichloro-4-(3-methylsulfonylazetidin-1-yl)benzoyl]-2,4-dihydro-1,3-benzoxazin-8-yl]-5-fluoro-2-morpholin-4-ylbenzoic acid | B | 1.30, 1.34 | 664 |
| 1-57 | Compound B | 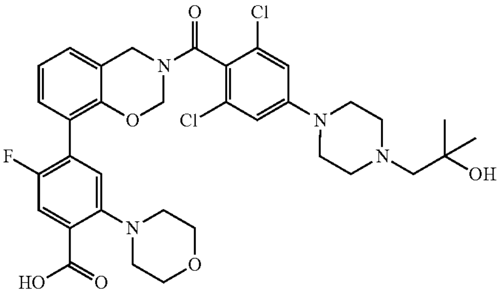 [SMILES: CC(C)(O)CN1CCN(c2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-[4-(2-hydroxy-2-methylpropyl)piperazin-1-yl]benzoyl]-2,4-dihydro-1,3-benzoxazin-8-yl]-5-fluoro-2-morpholin-4-ylbenzoic acid | A | 0.77, 0.82 | 687 |

TABLE 1-6-continued

| Compound No. | Intermediate No. | Structure | Compound Name | Analysis conditions | HPLC retention time (min) | m/z [M + H] |
|---|---|---|---|---|---|---|
| 1-60 | Compound B | 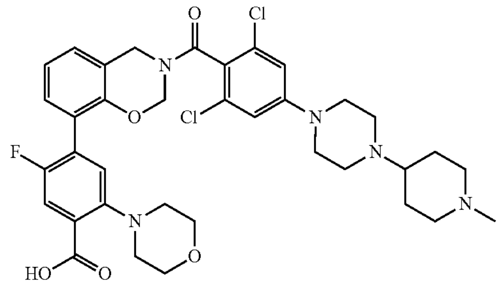 [SMILES: CN1CCC(N2CCN(c3cc(Cl)c(C(=O)N4COc5c(cccc5-c5cc(N6CCOCC6)c(C(=O)O)cc5F)C4)c(Cl)c3)CC2)CC1] | 4-[3-[2,6-Dichloro-4-[4-(1-methylpiperidin-4-yl)piperazin-1-yl]benzoyl]-2,4-dihydro-1,3-benzoxazin-8-yl]-5-fluoro-2-morpholin-4-ylbenzoic acid | A | 0.68, 0.75 | 712 |
| 1-65 | Compound E | 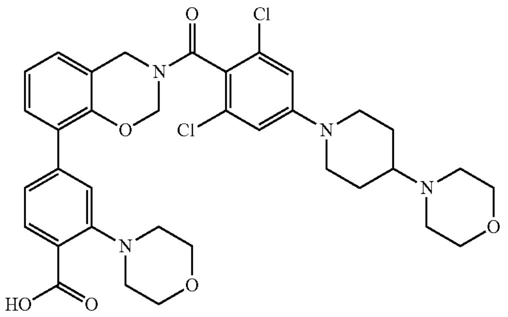 [SMILES: O=C(O)c1ccc(-c2cccc3c2OCN(C(=O)c2c(Cl)cc(N4CCC(N5CCOCC5)CC4)cc2Cl)C3)cc1N1CCOCC1] | 4-[3-[2,6-Dichloro-4-(4-morpholin-4-ylpiperidin-1-yl)benzoyl]-2,4-dihydro-1,3-benzoxazin-8-yl]-2-morpholin-4-ylbenzoic acid | A | 0.79, 0.83 | 681 |
| 1-66 | Compound E | 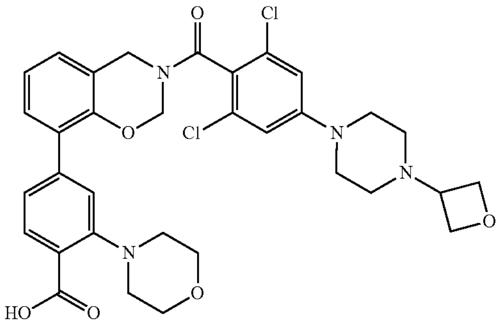 [SMILES: O=C(O)c1ccc(-c2cccc3c2OCN(C(=O)c2c(Cl)cc(N4CCN(C5COC5)CC4)cc2Cl)C3)cc1N1CCOCC1] | 4-[3-[2,6-Dichloro-4-[4-(oxetan-3-yl)piperazin-1-yl]benzoyl]-2,4-dihydro-1,3-benzoxazin-8-yl]-2-morpholin-4-ylbenzoic acid | A | 0.74, 0.80 | 653 |
| 1-67 | Compound E | 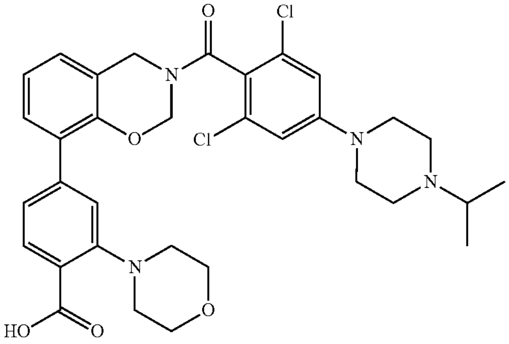 [SMILES: CC(C)N1CCN(c2cc(Cl)c(C(=O)N3COc4c(cccc4-c4ccc(C(=O)O)c(N5CCOCC5)c4)C3)c(Cl)c2)CC1] | 4-[3-[2,6-Dichloro-4-(4-propan-2-ylpiperazin-1-yl)benzoyl]-2,4-dihydro-1,3-benzoxazin-8-yl]-2-morpholin-4-ylbenzoic acid | A | 0.78, 0.83 | 639 |

TABLE 1-6-continued

| Compound No. | Intermediate No. | Structure | Compound Name | Analysis conditions | HPLC retention time (min) | m/z [M + H] |
|---|---|---|---|---|---|---|
| 1-76 | Compound L | 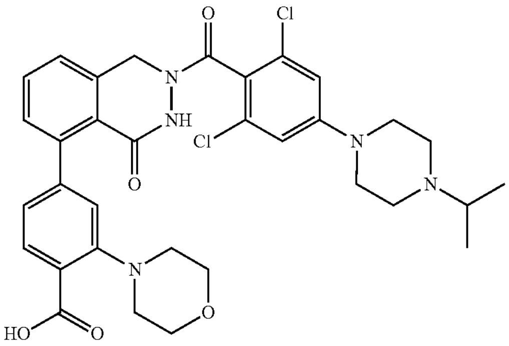 [SMILES: CC(C)N1CCN(c2cc(Cl)c(C(=O)N3Cc4cccc(-c5ccc(C(=O)O)c(N6CCOCC6)c5)c4C(=O)N3)c(Cl)c2)CC1] | 4-[2-[2,6-Dichloro-4-(4-propan-2-ylpiperazin-1-yl)benzoyl]-4-oxo-1,3-dihydrophthalazin-5-yl]-2-morpholin-4-ylbenzoic acid | A | 0.716 | 652 |
| 1-79 | Compound N | 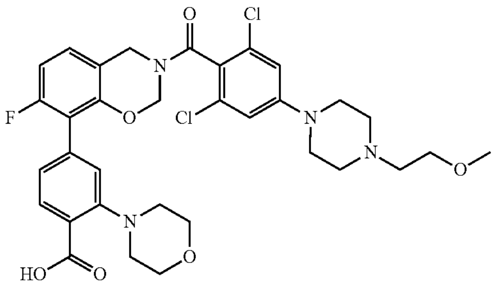 [SMILES: COCCN1CCN(c2cc(Cl)c(C(=O)N3COc4c(ccc(F)c4-c4ccc(C(=O)O)c(N5CCOCC5)c4)C3)c(Cl)c2)CC1] | 4-[3-[2,6-Dichloro-4-[4-(2-methoxyethyl)piperazin-1-yl]benzoyl]-7-fluoro-2,4-dihydro-1,3-benzoxazin-8-yl]-2-morpholin-4-ylbenzoic acid | A | 0.77, 0.82 | 673 |
| 1-80 | Compound Z | 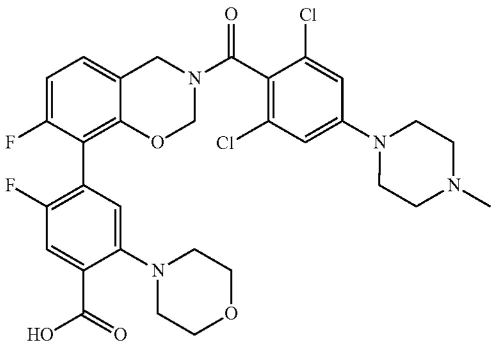 [SMILES: CN1CCN(c2cc(Cl)c(C(=O)N3COc4c(ccc(F)c4-c4cc(N5CCOCC5)c(C(=O)O)cc4F)C3)c(Cl)c2)CC1] | 4-[3-[2,6-Dichloro-4-(4-methylpiperazin-1-yl)benzoyl]-7-fluoro-2,4-dihydro-1,3-benzoxazin-8-yl]-5-fluoro-2-morpholin-4-ylbenzoic acid | A | 0.76, 0.82 | 647 |
| 1-81 | Compound Z | 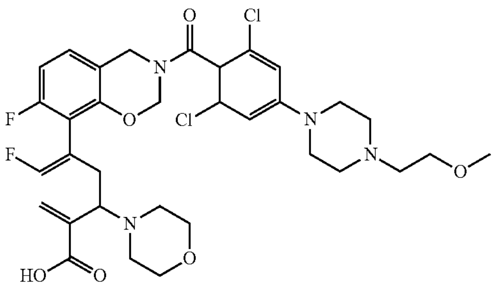 [SMILES: C=C(C(=O)O)C(C/C(=C/F)c1c(F)ccc2c1OCN(C(=O)C1C(Cl)=CC(N3CCN(CCOC)CC3)=CC1Cl)C2)N1CCOCC1] | 4-[3-[2,6-Dichloro-4-[4-(2-methoxyethyl)piperazin-1-yl]benzoyl]-7-fluoro-2,4-dihydro-1,3-benzoxazin-8-yl]-5-fluoro-2-morpholin-4-ylbenzoic acid | A | 0.79, 0.84 | 691 |

TABLE 1-6-continued

| Compound No. | Intermediate No. | Structure | Compound Name | Analysis conditions | HPLC retention time (min) | m/z [M + H] |
|---|---|---|---|---|---|---|
| 1-82 | Compound Z | 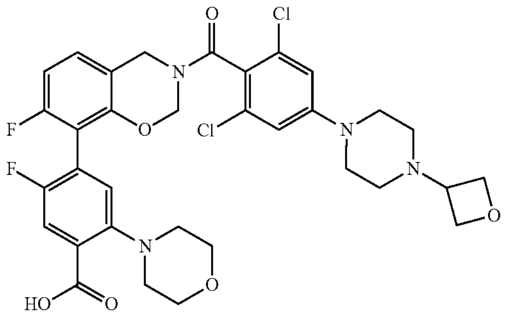 [SMILES: O=C(O)c1cc(F)c(-c2c(F)ccc3c2OCN(C(=O)c2c(Cl)cc(N4CCN(C5COC5)CC4)cc2Cl)C3)cc1N1CCOCC1] | 4-[3-[2,6-Dichloro-4-[4-(oxetan-3-yl)piperazin-1-yl]benzoyl]-7-fluoro-2,4-dihydro-1,3-benzoxazin-8-yl]-5-fluoro-2-morpholin-4-ylbenzoic acid | A | 0.76, 0.82 | 689 |
| 1-35 | Compound A | 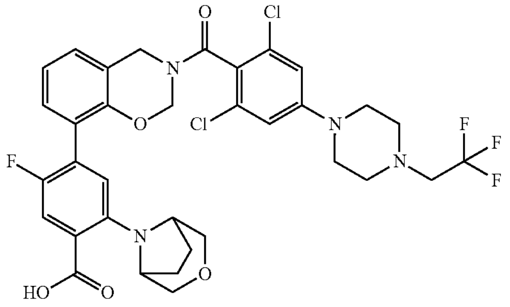 [SMILES: O=C(O)c1cc(F)c(-c2cccc3c2OCN(C(=O)c2c(Cl)cc(N4CCN(CC(F)(F)F)CC4)cc2Cl)C3)cc1N1C2CCC1COC2] | 4-[3-[2,6-Dichloro-4-[4-(2,2,2-trifluoroethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.63 | 723 |
| 1-72 | Compound K | 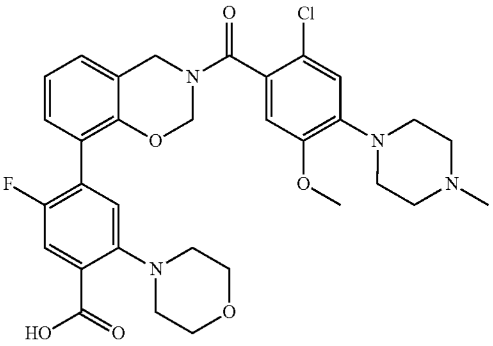 [SMILES: COc1cc(C(=O)N2COc3c(cccc3-c3cc(N4CCOCC4)c(C(=O)O)cc3F)C2)c(Cl)cc1N1CCN(C)CC1] | 4-[3-[2-Chloro-5-methoxy-4-(4-methylpiperazin-1-yl)benzoyl]-2,4-dihydro-1,3-benzoxazin-8-yl]-5-fluoro-2-morpholin-4-ylbenzoic acid | B | 0.96 | 625 |

TABLE 1-7

| Final compound No. | Amine |
|---|---|
| 1-48 | 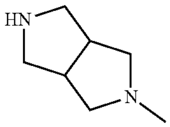 |
| 1-49 | 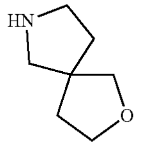 |

TABLE 1-7-continued

| Final compound No. | Amine |
|---|---|
| 1-53 | 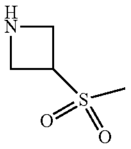 |
| 1-57 | HCl<br>HCl 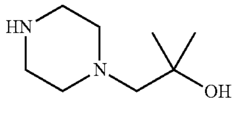 |

TABLE 1-7-continued

| Final compound No. | Amine |
|---|---|
| 1-60 | 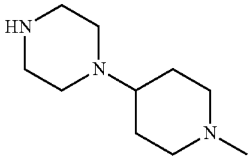 |
| 1-65 | 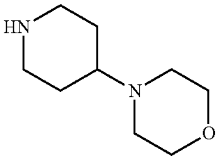 |
| 1-66 | 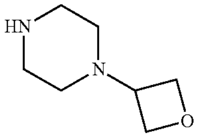 |
| 1-67 | 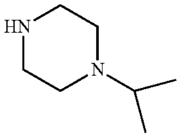 |
| 1-76 | 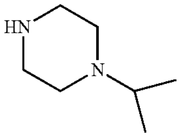 |
| 1-79 | 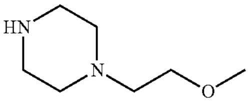 |
| 1-80 | 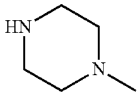 |
| 1-81 | 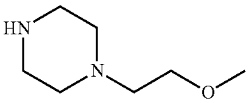 |
| 1-82 | 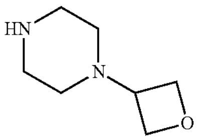 |
| 1-35 | 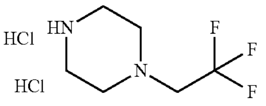 [SMILES: Cl ; Cl ; FC(F)(F)CN1CCNCC1] |
| 1-72 | 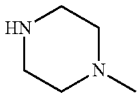 |

Compound 1-64

4-[3-[2,6-Dichloro-4-(4-methylpiperazin-1-yl)benzoyl]-2,4-dihydro-1,3-benzoxazin-8-yl]-2-morpholin-4-ylbenzoic acid

[Formula 180]

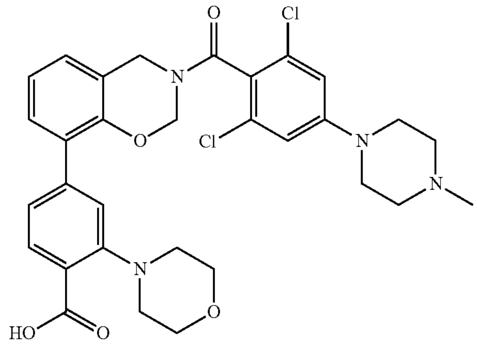

A solution of compound F (10.0 mg, 0.0170 mmol), 1-methylpiperazine (0.00376 mL, 0.0340 mmol), [2,2'-bis(diphenylphosphino)-1,1'-binaphthyl]dichloropalladium(II) (1.35 mg, 0.00169 mmol), and cesium carbonate (16.5 mg, 0.0510 mmol) in toluene (0.150 mL) was heated at 100° C. for 45 minutes. The reaction solution was cooled to room temperature. 1-Methylpiperazine (0.00376 mL, 0.0340 mmol), [2,2'-bis(diphenylphosphino)-1,1'-binaphthyl]dichloropalladium(II) (1.35 mg, 0.00169 mmol), and 1-methylpyrrolidin-2-one (0.100 mL) were further added thereto, and the mixture was heated at 100° C. for 45 minutes. The reaction mixture was purified by HPLC (acetonitrile/water, 0.1% formic acid) to obtain the title compound (35%, 3.60 mg).

LCMS: m/z 611[M+H]$^+$

HPLC retention time: 0.74 min and 0.80 min (analysis condition A)

Compound 1-51

4-[3-[2,6-Dichloro-4-(2-oxo-1,3-oxazolidin-3-yl)benzoyl]-2,4-dihydro-1,3-benzoxazin-8-yl]-5-fluoro-2-morpholin-4-ylbenzoic acid

[Formula 181]

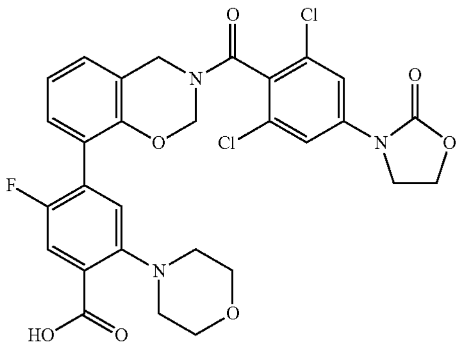

A solution of compound B (50.0 mg, 0.080 mmol), 1,3-oxazolidin-2-one (14.0 mg, 0.160 mmol), sodium tert-butoxide (15.4 mg, 0.160 mmol), and XantPhos Pd G4 (7.71 mg, 0.00801 mmol) in 1-methylpyrrolidin-2-one (1.00 mL)

was stirred at 100° C. for 15 hours. An aqueous formic acid solution was added to the reaction solution, and the reaction mixture was purified by HPLC (acetonitrile/water, 0.1% formic acid) to obtain the title compound (96%, 4.80 mg).

LCMS: m/z 616[M+H]$^+$

HPLC retention time: 1.32 min and 1.35 min (analysis condition B)

Compound 1-52

4-[3-[2,6-Dichloro-4-(2-oxopyrrolidin-1-yl)benzoyl]-2,4-dihydro-1,3-benzoxazin-8-yl]-5-fluoro-2-morpholin-4-ylbenzoic acid First Step Compound CP3

Methyl 4-[3-[2,6-dichloro-4-(2-oxopyrrolidin-1-yl)benzoyl]-2,4-dihydro-1,3-benzoxazin-8-yl]-5-fluoro-2-morpholin-4-ylbenzoate

[Formula 182]

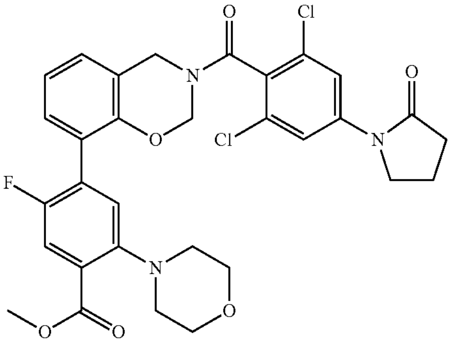

A solution of compound B (60.0 mg, 0.0960 mmol), pyrrolidin-2-one (16.4 mg, 0.192 mmol), potassium carbonate (39.8 mg, 0.288 mmol), copper(I) iodide (9.15 mg, 0.0480 mmol), and (1R,2R)-1-N,2-N-dimethylcyclohexane-1,2-diamine (13.7 mg, 0.0960 mmol) in 1-methylpyrrolidin-2-one (0.960 mL) was stirred at 100° C. for 4.5 hours. The reaction solution was cooled to room temperature. Pyrrolidin-2-one (8.18 mg, 0.0960 mmol), potassium carbonate (39.8 mg, 0.288 mmol), copper(I) iodide (3.66 mg, 0.0190 mmol), and (1R,2R)-1-N,2-N-dimethylcyclohexane-1,2-diamine (4.10 mg, 0.0290 mmol) were further added thereto, and the mixture was stirred at 100° C. for 4.5 hours. An aqueous formic acid solution was added to the reaction solution, and the reaction mixture was purified by HPLC (acetonitrile/water, 0.1% formic acid) to obtain the title compound (44%, 26.5 mg).

LCMS: m/z 628[M+H]$^+$

HPLC retention time: 0.99 min (analysis condition D)

Second Step

Compound 1-52

4-[3-[2,6-Dichloro-4-(2-oxopyrrolidin-1-yl)benzoyl]-2,4-dihydro-1,3-benzoxazin-8-yl]-5-fluoro-2-morpholin-4-ylbenzoic acid

[Formula 183]

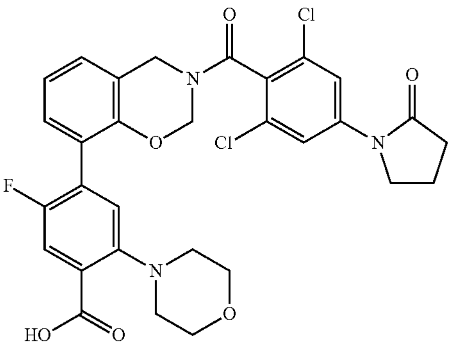

A solution of methyl 4-[3-[2,6-dichloro-4-(2-oxopyrrolidin-1-yl)benzoyl]-2,4-dihydro-1,3-benzoxazin-8-yl]-5-fluoro-2-morpholin-4-ylbenzoate (26.3 mg, 0.0420 mmol) and trimethylstannanol (30.3 mg, 0.167 mmol) in chlorobenzene (0.140 mL) was stirred at 200° C. for 0.75 hours under microwave. An aqueous formic acid solution was added to the reaction solution, and the reaction mixture was purified by HPLC (acetonitrile/water, 0.1% formic acid) to obtain the title compound (97%, 24.9 mg).

LCMS: m/z 614[M+H]$^+$

HPLC retention time: 1.35 min and 1.36 min (analysis condition B)

Compound 1-50

4-[3-[2,6-Dichloro-4-(2-oxoazetidin-1-yl)benzoyl]-2,4-dihydro-1,3-benzoxazin-8-yl]-5-fluoro-2-morpholin-4-ylbenzoic acid

[Formula 184]

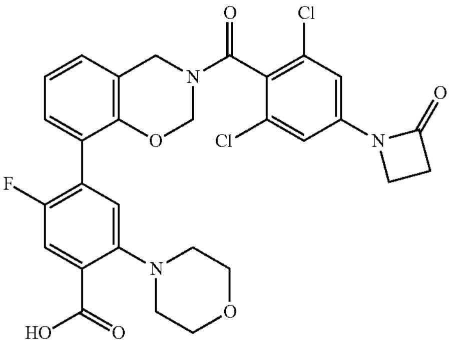

A solution of compound C (40.0 mg, 0.0660 mmol), azetidin-2-one (14.0 mg, 0.197 mmol), cesium carbonate (64.1 mg, 0.197 mmol), and XantPhos Pd G4 (6.31 mg, 0.00655 mmol) in 1,4-dioxane (0.800 mL) was stirred at 100° C. for 2 hours. An aqueous formic acid solution was added to the reaction solution, and the reaction mixture was purified by HPLC (acetonitrile/water, 0.1% formic acid) to obtain the title compound (52%, 20.3 mg).

LCMS: m/z 600[M+H]$^+$

HPLC retention time: 1.34 min and 1.36 min (analysis condition D)

Compound 2-6

4-[3-[2-Chloro-5-methoxy-4-(1-methylpyrazol-4-yl)benzoyl]-2,4-dihydro-1,3-benzoxazin-8-yl]-5-fluoro-2-morpholin-4-ylbenzoic acid

[Formula 185]

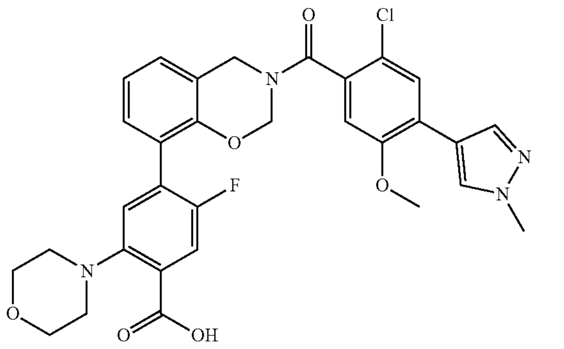

A solution of compound K (52.0 mg, 0.0840 mmol), 1-methyl-4-(4,4,5,5-tetramethyl-1,3,2-dioxaborolan-2-yl)-1H-pyrazole (22.7 mg, 0.109 mmol), potassium carbonate (34.8 mg, 0.252 mmol), and [1,1'-bis(diphenylphosphino)ferrocene]palladium(II) dichloride (6.14 mg, 0.00839 mmol) in 1,4-dioxane (0.400 mL) and water (0.0400 mL) was stirred at 100° C. for 2 hours. The reaction mixture was filtered and concentrated. Then, a 5 M aqueous sodium hydroxide solution (0.0503 mL, 0.252 mmol) and 1,4-dioxane (0.500 mL) were added to the obtained residue, and the mixture was stirred at 60° C. for 1 hour. An aqueous formic acid solution and dimethyl sulfoxide were added to the reaction mixture. Then, the mixture was purified by HPLC (acetonitrile/water, 0.1% formic acid) to obtain the title compound (69%, 35.0 mg).

LCMS: m/z 607[M+H]$^+$

HPLC retention time: 0.98 min (analysis condition A)

Compounds shown in Table 2-1 were synthesized by the same operation as in the process of compound 2-6 using each documented or commercially available boronic acid or boronic acid ester, or boronic acid or boronic acid ester shown in Table 2-2. However, tetrakis(triphenylphosphine)palladium was used instead of [1,1'-bis(diphenylphosphino)ferrocene]palladium(II) dichloride in the synthesis of compound 2-4, and toluene was used instead of 1,4-dioxane/water in the synthesis of compound 2-5.

TABLE 2-1

| Starting material | Compound No. | Structure | Compound Name | Analysis conditions | HPLC retention time (min) | m/z [M + H] |
|---|---|---|---|---|---|---|
| A | 2-1 | 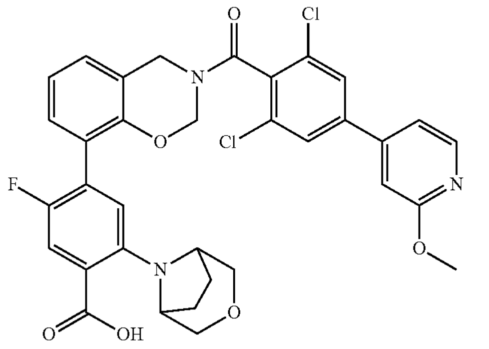 [SMILES: COc1cc(-c2cc(Cl)c(C(=O)N3COc4c(cccc4-c4cc(N5C6CCC5COC6)c(C(=O)O)cc4F)C3)c(Cl)c2)ccn1] | 4-[3-[2,6-Dichloro-4-(2-methoxypyridin-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.57 | 664 |
| A | 2-2 | 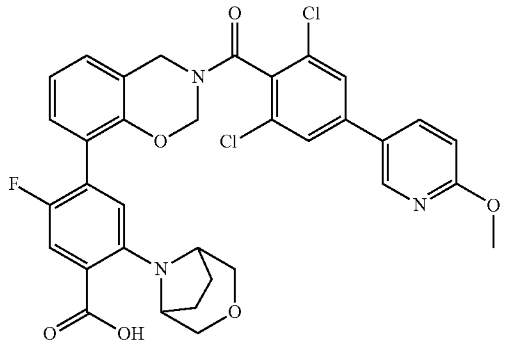 [SMILES: COc1ccc(-c2cc(Cl)c(C(=O)N3COc4c(cccc4-c4cc(N5C6CCC5COC6)c(C(=O)O)cc4F)C3)c(Cl)c2)cn1] | 4-[3-[2,6-Dichloro-4-(6-methoxypyridin-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.59, 1.60 | 664 |

TABLE 2-1-continued

| Starting material | Compound No. | Structure | Compound Name | Analysis conditions | HPLC retention time (min) | m/z [M + H] |
|---|---|---|---|---|---|---|
| B | 2-3 | 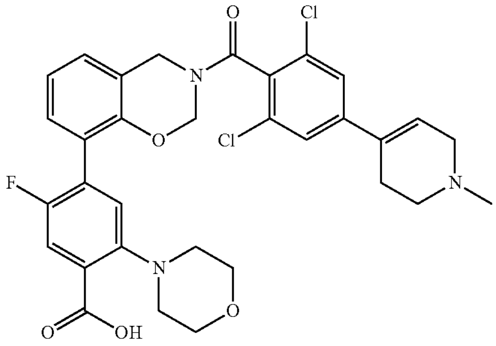 [SMILES: CN1CC=C(c2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-(1-methyl-3,6-dihydro-2H-pyridin-4-yl)benzoyl]-2,4-dihydro-1,3-benzoxazin-8-yl]-5-fluoro-2-morpholin-4-ylbenzoic acid | B | 0.95, 1.02 | 626 |
| E | 2-4 | 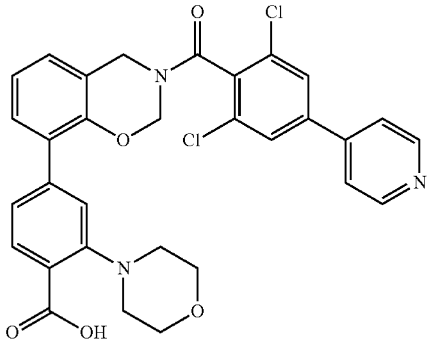 [SMILES: O=C(O)c1ccc(-c2cccc3c2OCN(C(=O)c2c(Cl)cc(-c4ccncc4)cc2Cl)C3)cc1N1CCOCC1] | 4-[3-(2,6-Dichloro-4-pyridin-4-ylbenzoyl)-2,4-dihydro-1,3-benzoxazin-8-yl]-2-morpholin-4-ylbenzoic acid | A | 0.76, 0.82 | 590 |
| K | 2-5 | 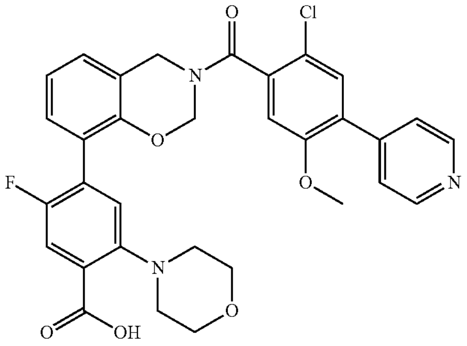 [SMILES: COc1cc(C(=O)N2COc3c(cccc3-c3cc(N4CCOCC4)c(C(=O)O)cc3F)C2)c(Cl)cc1-c1ccncc1] | 4-[3-(2-Chloro-5-methoxy-4-pyridin-4-ylbenzoyl)-2,4-dihydro-1,3-benzoxazin-8-yl]-5-fluoro-2-morpholin-4-ylbenzoic acid | B | 1.07 | 604 |

TABLE 2-2

| Final compound No. | |
|---|---|
| | Boronic acid |
| 2-1 | 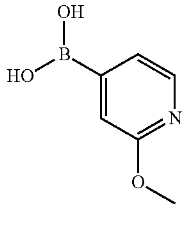 |
| 2-2 | 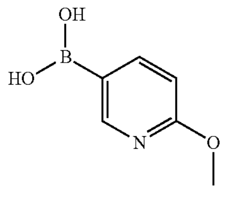 |
| 2-4 | 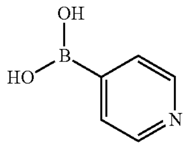 |
| | Boronic acid ester |
| 2-3 | 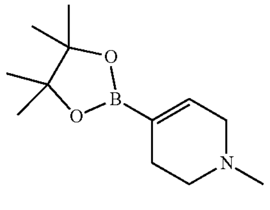 |
| 2-5 | 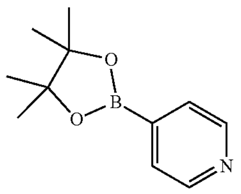 |

Compound 3-2

4-[3-[2,6-Dichloro-4-(5-methyl-6,7-dihydro-4H-pyrazolo[1,5-a]pyrazin-3-yl)benzoyl]-2,4-dihydro-1,3-benzoxazin-8-yl]-5-fluoro-2-(3-oxa-8-azabicyclo[3.2.1]octan-8-yl)benzoic acid First Step Compound BRO4

[3,5-Dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid

[Formula 186]

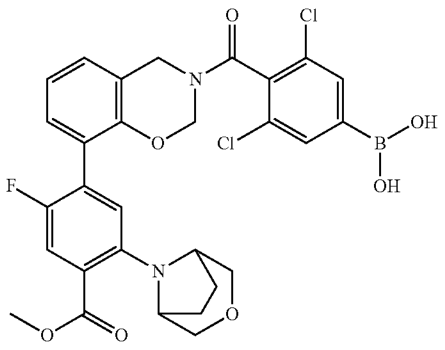

A solution of compound A (1.00 g, 1.54 mmol), bis(pinacolato)diboron (0.781 g, 3.08 mmol), a 1,1'-bis(diphenylphosphino)ferrocene-palladium(II) dichloride dichloromethane complex (0.126 g, 0.154 mmol), and potassium acetate (0.453 g, 4.61 mmol) in 1,4-dioxane (5.13 mL) was stirred at 100° C. for 2 hours. Ethyl acetate was added to the reaction solution, and the mixture was filtered through celite. Water was added to the filtrate, followed by extraction with ethyl acetate. The extract was washed with saturated saline. The organic layer was dried over anhydrous sodium sulfate, then filtered, and concentrated. To a solution of the residue in ethanol (14.0 mL), a solution of periodic acid (0.526 g, 2.06 mmol) in water (1.40 mL) was added. The reaction solution was stirred at room temperature for 1.5 hours. Water was added to the reaction solution, followed by extraction with ethyl acetate. The extract was washed with saturated saline. The organic layer was dried over anhydrous sodium sulfate, then filtered, and concentrated. The residue was purified by reverse phase column chromatography (acetonitrile/water, 0.1% formic acid) to obtain the title compound (89%, 0.845 g).

LCMS: m/z 615[M+H]$^+$

HPLC retention time: 0.82 min and 0.85 min (analysis condition D)

Second Step
Compound 3-2a

Methyl 4-[3-[2,6-dichloro-4-(5-methyl-6,7-dihydro-4H-pyrazolo[1,5-a]pyrazin-3-yl)benzoyl]-2,4-dihydro-1,3-benzoxazin-8-yl]-5-fluoro-2-(3-oxa-8-azabicyclo[3.2.1]octan-8-yl)benzoate

[Formula 186]

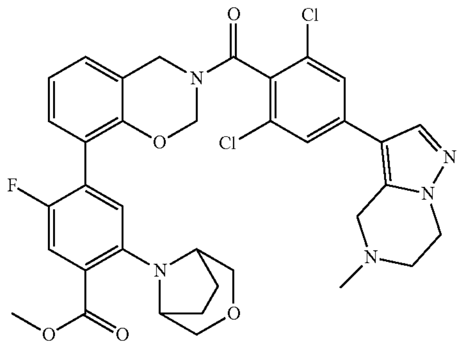

A solution of [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid (48.1 mg, 0.0780 mmol), 3-bromo-5-methyl-6,7-dihydro-4H-pyrazolo[1,5-a]pyrazine (13.0 mg, 0.0600 mmol), APhos Pd G3 (3.82 mg, 0.00602 mmol) and potassium carbonate (33.3 mg, 0.241 mmol) in 1,4-dioxane (0.540 mL) and water (0.00540 mL) was stirred at 60° C. for 1 hour. An aqueous formic acid solution was added to the reaction solution, and the mixture was purified by HPLC (acetonitrile/water, 0.1% formic acid) to obtain the title compound (92%, 38.9 mg).

LCMS: m/z 706[M+H]$^+$

HPLC retention time: 0.70 min (analysis condition D)

Third Step
Compound 3-2

4-[3-[2,6-Dichloro-4-(5-methyl-6,7-dihydro-4H-pyrazolo[1,5-a]pyrazin-3-yl)benzoyl]-2,4-dihydro-1,3-benzoxazin-8-yl]-5-fluoro-2-(3-oxa-8-azabicyclo[3.2.1]octan-8-yl)benzoic acid

[Formula 188]

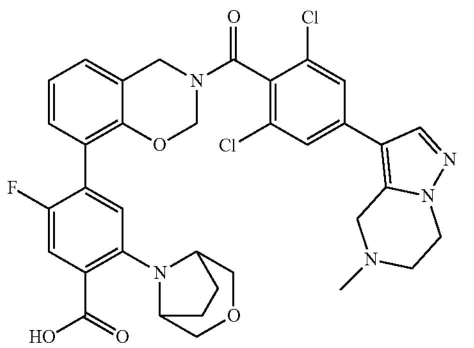

To a solution of methyl 4-[3-[2,6-dichloro-4-(5-methyl-6,7-dihydro-4H-pyrazolo[1,5-a]pyrazin-3-yl)benzoyl]-2,4-dihydro-1,3-benzoxazin-8-yl]-5-fluoro-2-(3-oxa-8-azabicyclo[3.2.1]octan-8-yl)benzoate (38.9 mg, 0.0550 mmol) in 1-methylpyrrolidin-2-one (0.550 mL), an 8 M aqueous potassium hydroxide solution (0.0688 mL, 0.551 mmol) was added. The reaction solution was stirred at 60° C. for 1 hour. An aqueous formic acid solution was added to the reaction solution, and the mixture was purified by HPLC (acetonitrile/water, 0.1% formic acid) to obtain the title compound (64%, 24.3 mg).

LCMS: m/z 692[M+H]$^+$

HPLC retention time: 1.14 min and 1.18 min (analysis condition B)

Compound 3-6

4-[3-[2,6-Dichloro-4-(2-methylpyrazolo[4,3-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid First Step
Compound h6

7-Bromo-2-methylpyrazolo[4,3-c]pyridine

[Formula 189]

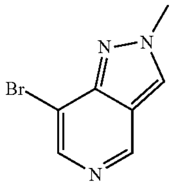

To a solution of 7-bromo-1H-pyrazolo[4,3-c]pyridine (80.0 mg, 0.404 mmol) in N,N-dimethylformamide (2.02 mL), 1 M solution of sodium bis(trimethylsilyl)amide in tetrahydrofuran (0.606 mL, 0.606 mmol) and iodomethane (0.0760 mL, 1.21 mmol) were added, and the mixture was stirred at room temperature for 15 minutes. An aqueous formic acid solution was added to the reaction solution, and the mixture was purified by reverse phase column chromatography (methanol/water, 0.01 M ammonium acetate) to obtain the title compound (12%, 10.4 mg).

$^1$H-NMR (400 MHz, $CDCl_3$) δ: 9.05 (1H, s), 8.44 (1H, s), 8.19 (1H, d, J=0.34 Hz), 4.32 (3H, d, J=0.34 Hz).

Second Step
Compound 3-6a

Methyl 4-[3-[2,6-dichloro-4-(2-methylpyrazolo[4,3-c]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 190]

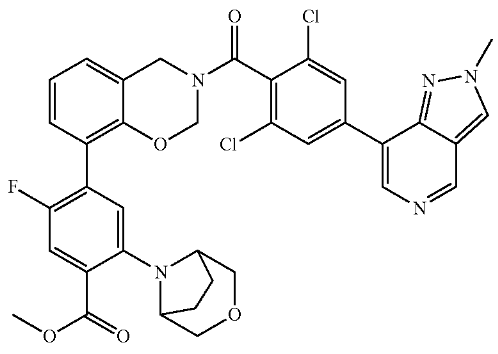

The title compound was obtained by the same operation as in the second step of compound 3-2 using [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid and 7-bromo-2-methylpyrazolo[4,3-c]pyridine.

LCMS: m/z 702[M+H]$^+$

HPLC retention time: 0.69 min and 0.72 min (analysis condition D)

Third Step

Compound 3-6

4-[3-[2,6-Dichloro-4-(2-methylpyrazolo[4,3-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 191]

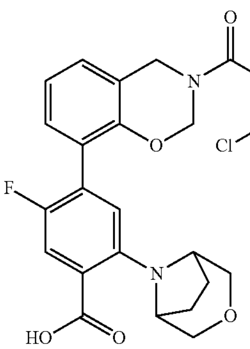

The title compound was obtained by the same operation as in the third step of compound 3-2 using methyl 4-[3-[2,6-dichloro-4-(2-methylpyrazolo[4,3-c]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 688[M+H]$^+$

HPLC retention time: 1.15 min and 1.19 min (analysis condition B)

Compound 3-10

4-[3-[2,6-Dichloro-4-(2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid First Step Compound h10

7-Bromo-2-methyltriazolo[4,5-c]pyridine

[Formula 192]

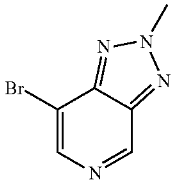

To a solution of 7-bromo-3H-triazolo[4,5-c]pyridine (199 mg, 1.00 mmol) in N,N-dimethylformamide (5.00 mL), a 1 M solution of sodium bis(trimethylsilyl)amide in tetrahydrofuran (1.50 mL, 1.50 mmol) and iodomethane (0.188 mL, 3.00 mmol) were added, and the mixture was stirred at room temperature for 30 minutes. An aqueous formic acid solution was added to the reaction solution, and the mixture was purified by reverse phase column chromatography (acetonitrile/water, 0.1% formic acid) to obtain the title compound (33%, 69.2 mg).

LCMS: m/z 213[M+H]$^+$

HPLC retention time: 0.50 min (analysis condition D)

Second Step

Compound 3-10a

Methyl 4-[3-[2,6-dichloro-4-(2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 193]

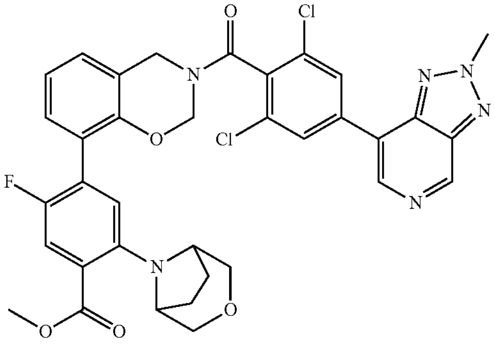

The title compound was obtained by the same operation as in the second step of compound 3-2 using [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid and 7-bromo-2-methyltriazolo[4,5-c]pyridine.

LCMS: m/z 703[M+H]$^+$

HPLC retention time: 0.91 min and 0.94 min (analysis condition D)

Third Step

Compound 3-10

4-[3-[2,6-Dichloro-4-(2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 194]

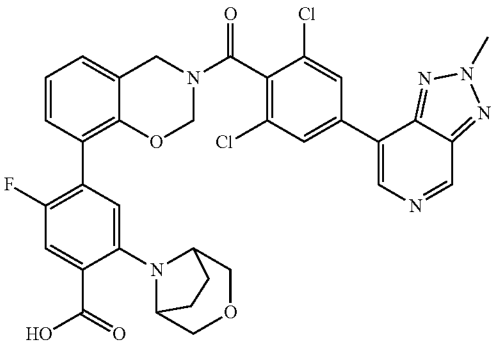

The title compound was obtained by the same operation as in the third step of compound 3-2 using methyl 4-[3-[2,6-dichloro-4-(2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 689[M+H]$^+$

HPLC retention time: 1.43 min and 1.45 min (analysis condition B)

Compound 3-17

4-[3-[2,6-Dichloro-4-(2-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl) benzoic acid First Step Compound 3-17a Methyl 4-[3-[2,6-dichloro-4-(2-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 195]

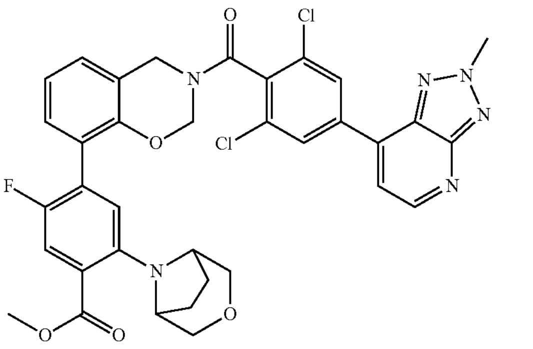

Compound 3-19a

Methyl 4-[3-[2,6-dichloro-4-(3-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 196]

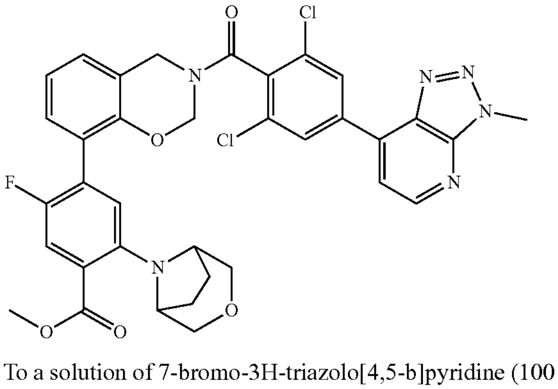

To a solution of 7-bromo-3H-triazolo[4,5-b]pyridine (100 mg, 0.502 mmol) in tetrahydrofuran (2.51 mL), a 1 M solution of sodium bis(trimethylsilyl)amide in tetrahydrofuran (0.754 mL, 0.754 mmol) and iodomethane (0.0940 mL, 1.51 mmol) were added, and the mixture was stirred at room temperature for 18 hours. A 1 M solution of sodium bis(trimethylsilyl)amide in tetrahydrofuran (0.754 mL, 0.754 mmol) was added thereto, and the mixture was stirred at room temperature for 1 hour. A 1 M solution of sodium bis(trimethylsilyl)amide in tetrahydrofuran (0.754 mL, 0.754 mmol) and iodomethane (0.094 mL, 1.51 mmol) were added thereto, and the mixture was stirred at room temperature for 1 hour. An aqueous formic acid solution was added to the reaction solution, and the mixture was purified by reverse phase column chromatography (methanol/water, 0.01 M ammonium acetate) to obtain a mixture (25%, 27.0 mg) of 7-bromo-2-methyltriazolo[4,5-b]pyridine and 7-bromo-3-methyltriazolo[4,5-b]pyridine. The title compound 3-17a and the title compound 3-19a were obtained by the same operation as in the second step of compound 3-2 using the obtained mixture and [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid. However, reverse phase column chromatography (acetonitrile/water, 0.1% formic acid) and subsequently SFC (ACQUITY UPC2 Torus 1-AA, supercritical carbon dioxide/methanol) were used in purification.

Compound 3-17a

LCMS: m/z 703[M+H]$^+$

SFC retention time: 3.18 min (analysis condition: ACQUITY UPC2 Torus 1-AA 4.6 mm I.D.×50 mm, 5 μm, supercritical carbon dioxide/methanol=70/30 (10 mini), 40° C., 270 nm)

Compound 3-19a

LCMS: m/z 703[M+H]$^+$

SFC retention time: 2.44 min (analysis condition: ACQUITY UPC2 Torus 1-AA 4.6 mm I.D.×50 mm, 5 μm, supercritical carbon dioxide/methanol=70/30 (10 min), 40° C., 270 nm)

Second Step

Compound 3-17

4-[3-[2,6-Dichloro-4-(2-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl) benzoic acid

[Formula 197]

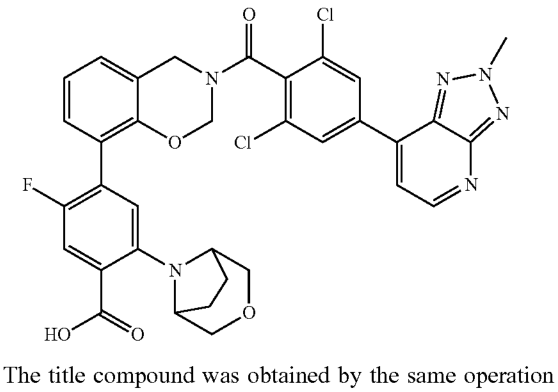

The title compound was obtained by the same operation as in the third step of compound 3-2 using methyl 4-[3-[2,6-dichloro-4-(2-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 689[M+H]$^+$

HPLC retention time: 1.52 min and 1.56 min (analysis condition B)

Compound 3-19

4-[3-[2,6-Dichloro-4-(3-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl) benzoic acid

[Formula 198]

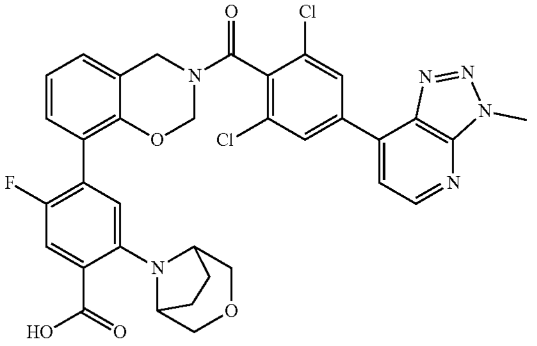

The title compound was obtained by the same operation as in the third step of compound 3-2 using methyl 4-[3-[2,6-dichloro-4-(3-methyltriazolo[4,5-b]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 689[M+H]$^+$

HPLC retention time: 1.57 min and 1.58 min (analysis condition B)

Compound 3-26

4-[3-[2,6-Dichloro-4-(4-methoxy-2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid First Step Compound h26

7-Bromo-4-methoxy-2-methyltriazolo[4,5-c]pyridine

[Formula 199]

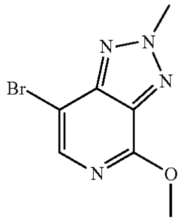

Compound h27

7-Bromo-4-methoxy-3-methyltriazolo[4,5-c]pyridine

[Formula 200]

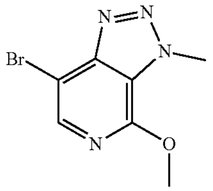

To a solution of 7-bromo-4-methoxy-3H-triazolo[4,5-c]pyridine (40.0 mg, 0.175 mmol) in tetrahydrofuran (0.900 mL), a 2.4 M solution of lithium bis(trimethylsilyl)amide in tetrahydrofuran (0.109 mL, 0.262 mmol) and iodomethane (0.0660 mL, 1.05 mmol) were added, and the mixture was stirred at room temperature for 68 hours. An aqueous formic acid solution was added to the reaction solution, followed by extraction with ethyl acetate. The extract was dried over anhydrous sodium sulfate. The desiccant was filtered off. After concentration of the filtrate, the obtained residue was purified by silica gel column chromatography (hexane/ethyl acetate) to obtain the title compound h26 (5.0%, 2.10 mg) and the title compound h27 (42%, 17.8 mg).

Compound h26

LCMS: m/z 243[M+H]$^+$

HPLC retention time: 0.66 min (analysis condition D)

Compound h27

LCMS: m/z 243[M+H]$^+$

HPLC retention time: 0.61 min (analysis condition D)

Second Step

Compound 3-26a

Methyl 4-[3-[2,6-dichloro-4-(4-methoxy-2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 201]

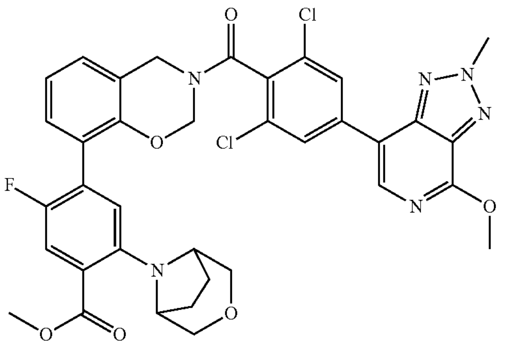

The title compound was obtained by the same operation as in the second step of compound 3-2 using [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid and 7-bromo-4-methoxy-2-methyltriazolo[4,5-c]pyridine.

LCMS: m/z 733[M+H]$^+$

HPLC retention time: 1.07 min and 1.10 min (analysis condition K)

Third Step

Compound 3-26

4-[3-[2,6-Dichloro-4-(4-methoxy-2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 202]

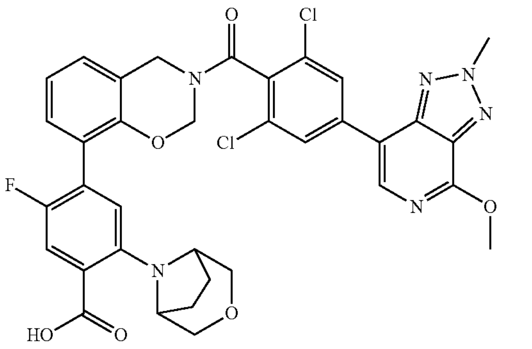

The title compound was obtained by the same operation as in the third step of compound 3-2 using methyl 4-[3-[2,6-dichloro-4-(4-methoxy-2-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 719[M+H]$^+$

HPLC retention time: 1.70 min and 1.71 min (analysis condition B)

Compound 3-27

4-[3-[2,6-Dichloro-4-(4-methoxy-3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid First Step Compound 3-27a Methyl 4-[3-[2,6-dichloro-4-(4-methoxy-3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate

[Formula 203]

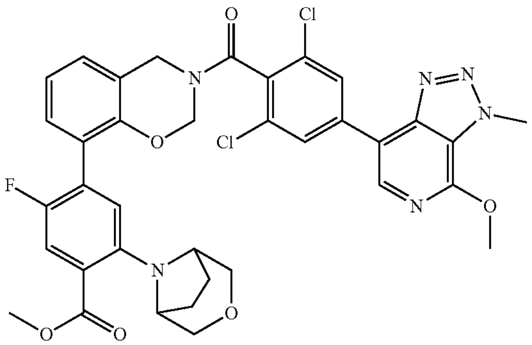

The title compound was obtained by the same operation as in the second step of compound 3-2 using [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid and 7-bromo-4-methoxy-3-methyltriazolo[4,5-c]pyridine obtained in the first step of compound 3-26.

LCMS: m/z 733[M+H]$^+$

HPLC retention time: 1.08 min (analysis condition K)

Second Step

Compound 3-27

4-[3-[2,6-Dichloro-4-(4-methoxy-3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 204]

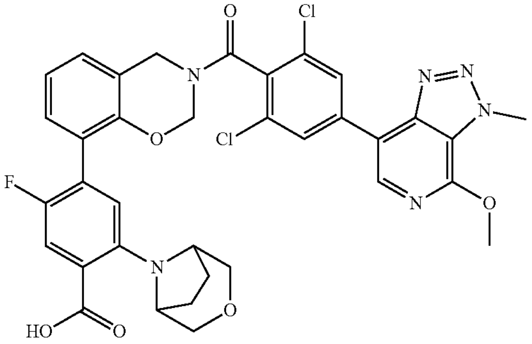

The title compound was obtained by the same operation as in the third step of compound 3-2 using methyl 4-[3-[2,6-dichloro-4-(4-methoxy-3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 719[M+H]$^+$

HPLC retention time: 1.69 min (analysis condition B)

First Step

Compounds shown in Table 3-1 were synthesized by the same operation as in the second step of compound 3-2 using [3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]boronic acid and aryl bromide shown in Table 3-1. However, tetrakis(triphenylphosphine)palladium(0) was used instead of XPhos Pd G3, and sodium carbonate was used instead of potassium carbonate, in the synthesis of compound Nos. 3-14a, 3-15a, and 3-18a.

TABLE 3-1

| Compound No. | Structure | Aryl bromide | Compound Name | Analysis conditions | HPLC retention time (min) | m/z [M + H]+ |
|---|---|---|---|---|---|---|
| 3-3a | 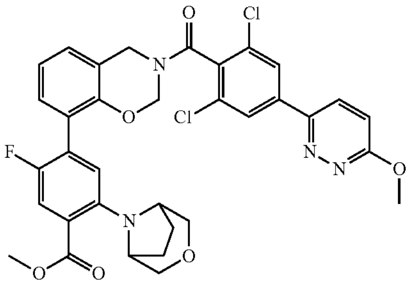 [SMILES: COC(=O)c1cc(F)c(-c2cccc3c2OCN(C(=O)c2c(Cl)cc(-c4ccc(OC)nn4)cc2Cl)C3)cc1N1C2CCC1COC2] | 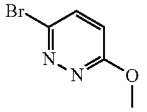 | Methyl 4-[3-[2,6-dichloro-4-(6-methoxypyridazin-3-yl)benzoyl]-2,4-dihydro-1,3-benzoxazin-8-yl]-5-fluoro-2-(3-oxa-8-azabicyclo[3.2.1]octan-8-yl)benzoate | D | 0.96 | 679 |
| 3-4a | 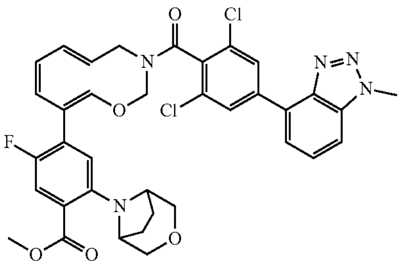 [SMILES: COC(=O)c1cc(F)c(C2=C\OCN(C(=O)c3c(Cl)cc(-c4cccc5c4nnn5C)cc3Cl)C/C=C/C=C\2)cc1N1C2CCC1COC2] | 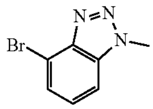 | Methyl 4-[3-[2,6-dichloro-4-(1-methylbenzotriazol-4-yl)benzoyl]-2,4-dihydro-1,3-benzoxazin-8-yl]-5-fluoro-2-(3-oxa-8-azabicyclo[3.2.1]octan-8-yl)benzoate | D | 0.99 | 702 |
| 3-5a | 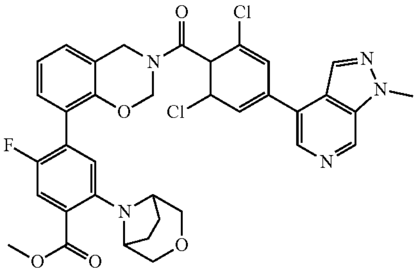 | 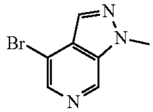 | Methyl 4-[3-[2,6-dichloro-4-(1-methylpyrazolo[3,4-c]pyridin-4-yl)benzoyl]-2,4-dihydro-1,3-benzoxazin-8-yl]-5-fluoro-2-(3-oxa-8-azabicyclo[3.2.1]octan-8-yl)benzoate | D | 0.88 | 702 |
| 3-7a | 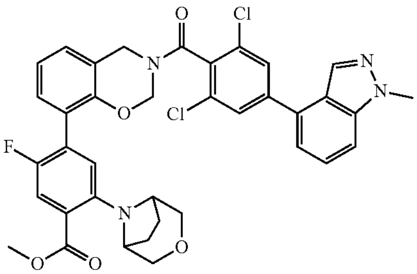 | 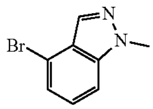 | Methyl 4-[3-[2,6-dichloro-4-(1-methylindazol-4-yl)benzoyl]-2,4-dihydro-1,3-benzoxazin-8-yl]-5-fluoro-2-(3-oxa-8-azabicyclo[3.2.1]octan-8-yl)benzoate | D | 1.02 | 701 |
| 3-8a | 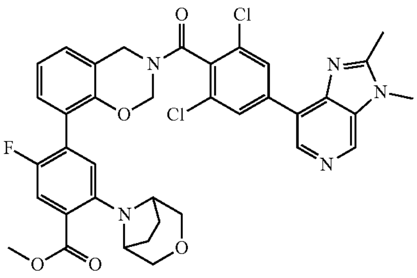 | 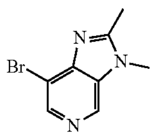 | Methyl 4-[3-[2,6-dichloro-4-(2,3-dimethylimidazo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate | D | 0.72, 0.74 | 716 |

TABLE 3-1-continued

| Compound No. | Structure | Aryl bromide | Compound Name | Analysis conditions | HPLC retention time (min) | m/z [M + H]+ |
|---|---|---|---|---|---|---|
| 3-9a | 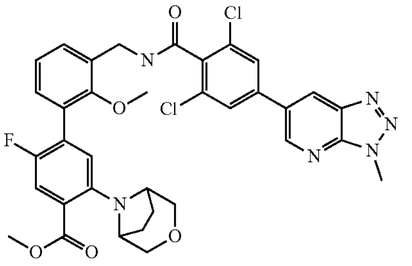 [SMILES: COC(=O)c1cc(F)c(-c2cccc(CNC(=O)c3c(Cl)cc(-c4cnc5c(c4)nnn5C)cc3Cl)c2OC)cc1N1C2CCC1COC2] | 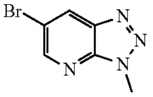 | Methyl 4-[3-[2,6-dichloro-4-(3-methyltriazolo[4,5-b]pyridin-6-yl)benzoyl]-2,4-dihydro-1,3-benzoxazin-8-yl]-5-fluoro-2-(3-oxa-8-azabicyclo[3.2.1]octan-8-yl)benzoate | D | 0.97, 0.98 | 703 |
| 3-11a | 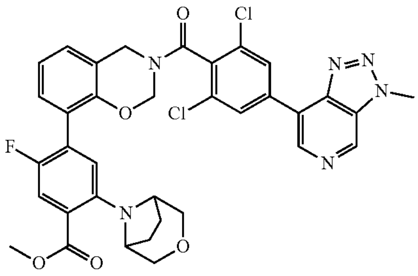 | 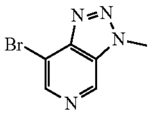 | Methyl 4-[3-[2,6-dichloro-4-(3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoate | D | 0.89, 0.91 | 703 |
| 3-12a | 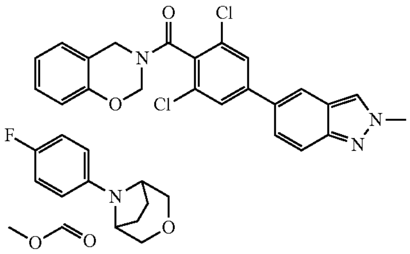 | 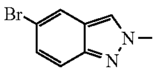 | Methyl 4-[3-[2,6-dichloro-4-(2-methylindazol-5-yl)benzoyl]-2,4-dihydro-1,3-benzoxazin-8-yl]-5-fluoro-2-(3-oxa-8-azabicyclo[3.2.1]octan-8-yl)benzoate | D | 0.95 | 701 |
| 3-13a | 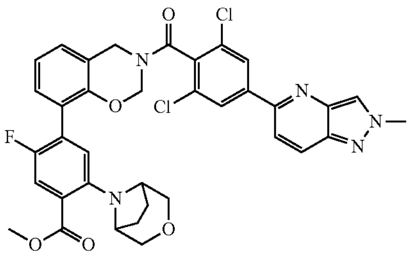 | 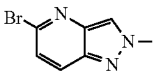 | Methyl 4-[3-[2,6-dichloro-4-(2-methylpyrazolo[4,3-b]pyridin-5-yl)benzoyl]-2,4-dihydro-1,3-benzoxazin-8-yl]-5-fluoro-2-(3-oxa-8-azabicyclo[3.2.1]octan-8-yl)benzoate | D | 0.92, 0.93 | 702 |
| 3-14a | 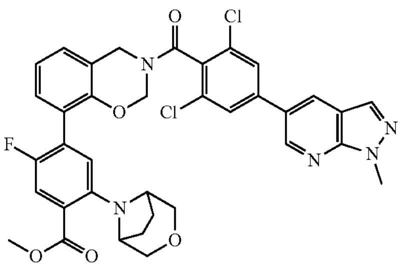 | 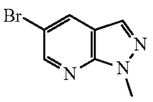 | Methyl 4-[3-[2,6-dichloro-4-(1-methylpyrazolo[3,4-b]pyridin-5-yl)benzoyl]-2,4-dihydro-1,3-benzoxazin-8-yl]-5-fluoro-2-(3-oxa-8-azabicyclo[3.2.1]octan-8-yl)benzoate | D | 0.96 | 702 |

TABLE 3-1-continued

| Compound No. | Structure | Aryl bromide | Compound Name | Analysis conditions | HPLC retention time (min) | m/z [M + H]+ |
|---|---|---|---|---|---|---|
| 3-15a | 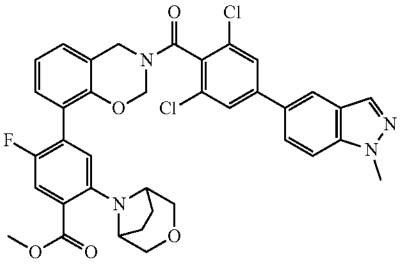 [SMILES: COC(=O)c1cc(F)c(-c2cccc3c2OCN(C(=O)c2c(Cl)cc(-c4ccc5c(cnn5C)c4)cc2Cl)C3)cc1N1C2CCC1COC2] | 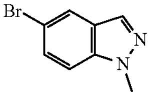 | Methyl 4-[3-[2,6-dichloro-4-(1-methylindazol-5-yl)benzoyl]-2,4-dihydro-1,3-benzoxazin-8-yl]-5-fluoro-2-(3-oxa-8-azabicyclo[3.2.1]octan-8-yl)benzoate | D | 1.00 | 701 |
| 3-16a | 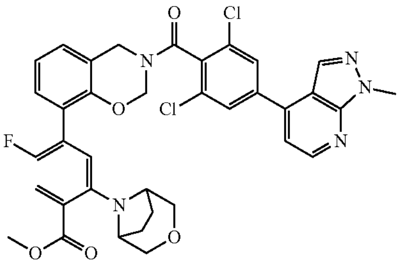 | 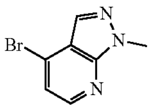 | Methyl 4-[3-[2,6-dichloro-4-(1-methylpyrazolo[3,4-b]pyridin-4-yl)benzoyl]-2,4-dihydro-1,3-benzoxazin-8-yl]-5-fluoro-2-(3-oxa-8-azabicyclo[3.2.1]octan-8-yl)benzoate | D | 0.97 | 702 |
| 3-18a | 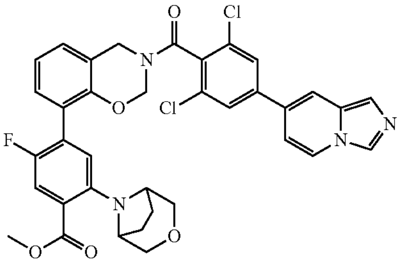 [SMILES: COC(=O)c1cc(F)c(-c2cccc3c2OCN(C(=O)c2c(Cl)cc(-c4ccn5cncc5c4)cc2Cl)C3)cc1N1C2CCC1COC2] | 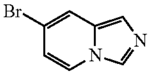 | Methyl 4-[3-(2,6-dichloro-4-imidazo[1,5-a]pyridin-7-ylbenzoyl)-2,4-dihydro-1,3-benzoxazin-8-yl]-5-fluoro-2-(3-oxa-8-azabicyclo[3.2.1]octan-8-yl)benzoate | D | 0.74, 0.76 | 687 |
| 3-20a | 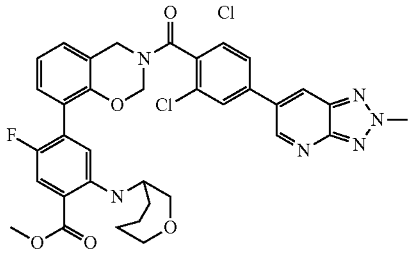 | 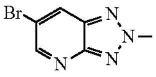 | Methyl 4-[3-[2,6-dichloro-4-(2-methyltriazolo[4,5-b]pyridin-6-yl)benzoyl]-2,4-dihydro-1,3-benzoxazin-8-yl]-5-fluoro-2-(3-oxa-8-azabicyclo[3.2.1]octan-8-yl)benzoate | D | 0.95, 0.97 | 703 |
| 3-21a | 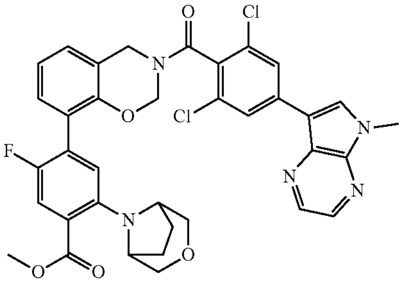 | 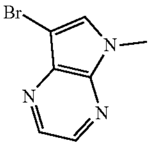 | Methyl 4-[3-[2,6-dichloro-4-(5-methylpyrrolo[2,3-b]pyrazin-7-yl)benzoyl]-2,4-dihydro-1,3-benzoxazin-8-yl]-5-fluoro-2-(3-oxa-8-azabicyclo[3.2.1]octan-8-yl)benzoate | D | 0.99 | 702 |

TABLE 3-1-continued

| Compound No. | Structure | Aryl bromide | Compound Name | Analysis conditions | HPLC retention time (min) | m/z [M + H]+ |
|---|---|---|---|---|---|---|
| 3-22a | 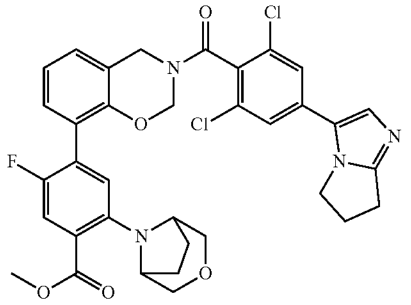 [SMILES: COC(=O)c1cc(F)c(-c2cccc3c2OCN(C(=O)c2c(Cl)cc(-c4cnc5n4CCC5)cc2Cl)C3)cc1N1C2CCC1COC2] | 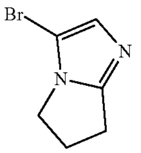 | Methyl 4-[3-[2,6-dichloro-4-(6,7-dihydro-5H-pyrrolo[1,2-a]imidazol-3-yl)benzoyl]-2,4-dihydro-1,3-benzoxazin-8-yl]-5-fluoro-2-(3-oxa-8-azabicyclo[3.2.1]octan-8-yl)benzoate | D | 0.61, 0.64 | 677 |
| 3-23a | 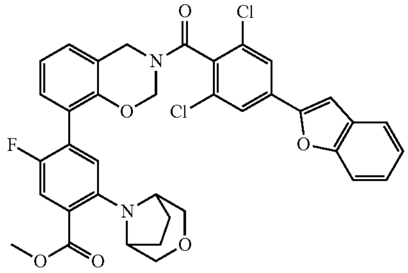 [SMILES: COC(=O)c1cc(F)c(-c2cccc3c2OCN(C(=O)c2c(Cl)cc(-c4cc5ccccc5o4)cc2Cl)C3)cc1N1C2CCC1COC2] | 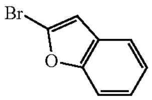 | Methyl 4-[3-[4-(1-benzofuran-2-yl)-2,6-dichlorobenzoyl]-2,4-dihydro-1,3-benzoxazin-8-yl]-5-fluoro-2-(3-oxa-8-azabicyclo[3.2.1]octan-8-yl)benzoate | D | 1.1 | 687 |
| 3-24a | 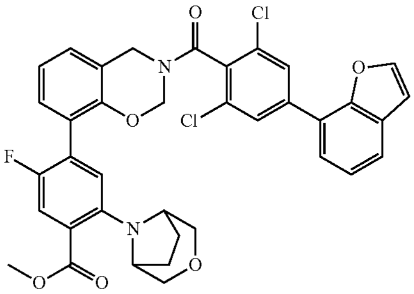 [SMILES: COC(=O)c1cc(F)c(-c2cccc3c2OCN(C(=O)c2c(Cl)cc(-c4cccc5ccoc45)cc2Cl)C3)cc1N1C2CCC1COC2] | 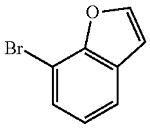 | Methyl 4-[3-[4-(1-benzofuran-7-yl)-2,6-dichlorobenzoyl]-2,4-dihydro-1,3-benzoxazin-8-yl]-5-fluoro-2-(3-oxa-8-azabicyclo[3.2.1]octan-8-yl)benzoate | D | 1.07 | 687 |
| 3-25a | 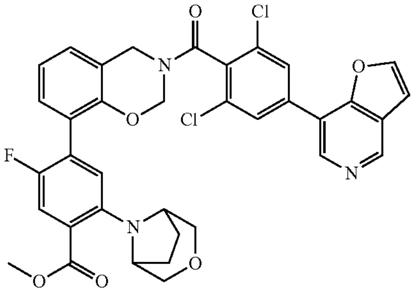 [SMILES: COC(=O)c1cc(F)c(-c2cccc3c2OCN(C(=O)c2c(Cl)cc(-c4cncc5ccoc45)cc2Cl)C3)cc1N1C2CCC1COC2] | 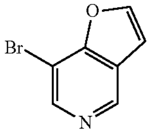 | Methyl 4-[3-(2,6-dichloro-4-furo[3,2-c]pyridin-7-ylbenzoyl)-2,4-dihydro-1,3-benzoxazin-8-yl]-5-fluoro-2-(3-oxa-8-azabicyclo[3.2.1]octan-8-yl)benzoate | D | 0.80, 0.82 | 688 |

Second Step

Compounds shown in Table 3-2 were synthesized by the same operation as in the second step of compound 3-2 using ester obtained in the first step and shown in Table 3-1.

TABLE 3-2

| Compound No. | Structure | Ester | Compound Name | Analysis conditions | HPLC retention time (min) | m/z [M + H]$^+$ |
|---|---|---|---|---|---|---|
| 3-3 | 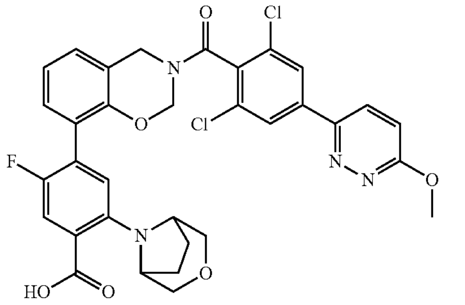 [SMILES: COc1ccc(-c2cc(Cl)c(C(=O)N3COc4c(cccc4-c4cc(N5C6CCC5COC6)c(C(=O)O)cc4F)C3)c(Cl)c2)nn1] | 3-3a | 4-[3-[2,6-Dichloro-4-(6-methoxypyridazin-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.50 | 665 |
| 3-4 | 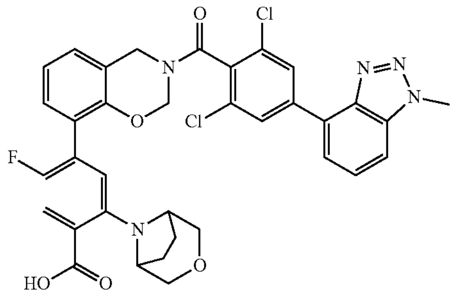 [SMILES: C=C(C(=O)O)/C(=C\C(=C\F)c1cccc2c1OCN(C(=O)c1c(Cl)cc(-c3cccc4c3nnn4C)cc1Cl)C2)N1C2CCC1COC2] | 3-4a | 4-[3-[2,6-Dichloro-4-(1-methylbenzotriazol-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.64 | 688 |
| 3-5 | 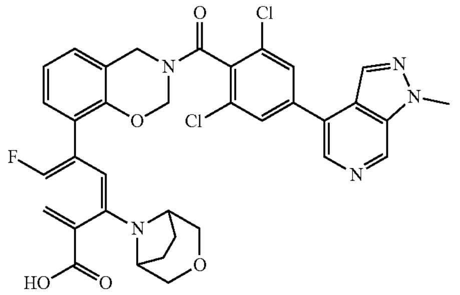 [SMILES: C=C(C(=O)O)/C(=C\C(=C\F)c1cccc2c1OCN(C(=O)c1c(Cl)cc(-c3cncc4c3cnn4C)cc1Cl)C2)N1C2CCC1COC2] | 3-5a | 4-[3-[2,6-Dichloro-4-(1-methylpyrazolo[3,4-c]pyridin-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.44, 1.46 | 688 |
| 3-7 | 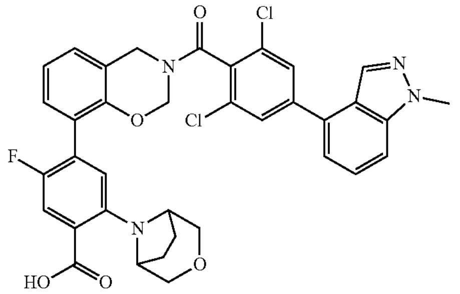 [SMILES: Cn1ncc2c(-c3cc(Cl)c(C(=O)N4COc5c(cccc5-c5cc(N6C7CCC6COC7)c(C(=O)O)cc5F)C4)c(Cl)c3)cccc21] | 3-7a | 4-[3-[2,6-Dichloro-4-(1-methylindazol-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.69 | 687 |

TABLE 3-2-continued

| Compound No. | Structure | Ester | Compound Name | Analysis conditions | HPLC retention time (min) | m/z [M + H]+ |
|---|---|---|---|---|---|---|
| 3-8 | 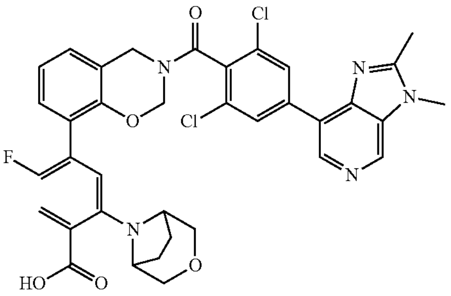 [SMILES: C=C(C(=O)O)/C(=C\C(=C\F)c1cccc2c1OCN(C(=O)c1c(Cl)cc(-c3cncc4c3nc(C)n4C)cc1Cl)C2)N1C2CCC1COC2] | 3-8a | 4-[3-[2,6-Dichloro-4-(2,3-dimethylimidazo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid | B | 1.15 | 702 |
| 3-9 | 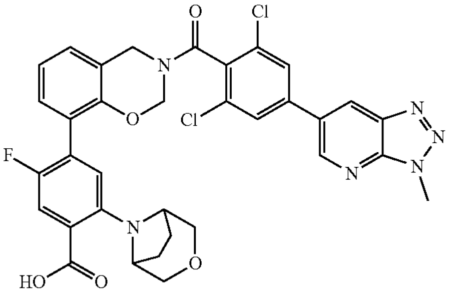 [SMILES: Cn1nnc2cc(-c3cc(Cl)c(C(=O)N4COc5c(cccc5-c5cc(N6C7CCC6COC7)c(C(=O)O)cc5F)C4)c(Cl)c3)cnc21] | 3-9a | 4-[3-[2,6-Dichloro-4-(3-methyltriazolo[4,5-b]pyridin-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.54, 1.56 | 689 |
| 3-11 | 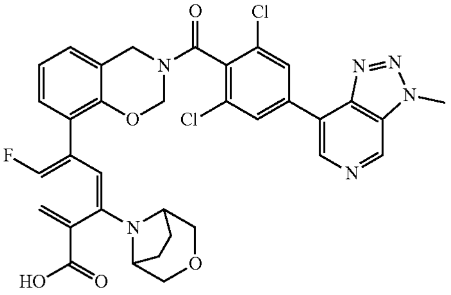 [SMILES: C=C(C(=O)O)/C(=C\C(=C\F)c1cccc2c1OCN(C(=O)c1c(Cl)cc(-c3cncc4c3nnn4C)cc1Cl)C2)N1C2CCC1COC2] | 3-11a | 4-[3-[2,6-Dichloro-4-(3-methyltriazolo[4,5-c]pyridin-7-yl)benzoyl]-2,4-dihydro-1,3-benzoxazin-8-yl]-5-fluoro-2-(3-oxa-8-azabicyclo[3.2.1]octan-8-yl)benzoic acid | B | 1.39, 1.42 | 689 |
| 3-12 | 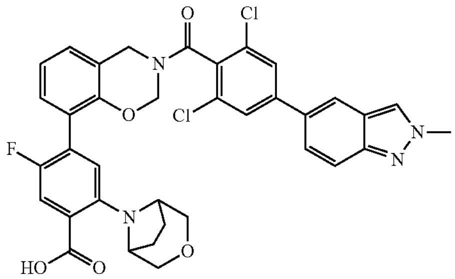 [SMILES: Cn1cc2cc(-c3cc(Cl)c(C(=O)N4COc5c(cccc5-c5cc(N6C7CCC6COC7)c(C(=O)O)cc5F)C4)c(Cl)c3)ccc2n1] | 3-12a | 4-[3-[2,6-Dichloro-4-(2-methylindazol-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.50 | 687 |
| 3-13 | 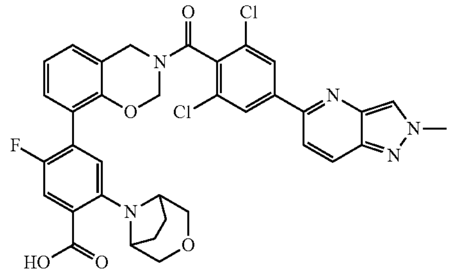 | 3-13a | 4-[3-[2,6-Dichloro-4-(2-methylpyrazolo[4,3-b]pyridin-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.44, 1.45 | 688 |

TABLE 3-2-continued

| Compound No. | Structure | Ester | Compound Name | Analysis conditions | HPLC retention time (min) | m/z [M + H]+ |
|---|---|---|---|---|---|---|
| 3-14 | 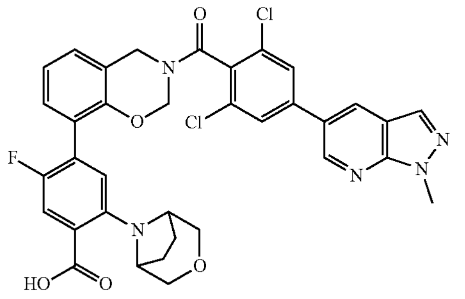 [SMILES: Cn1ncc2cc(-c3cc(Cl)c(C(=O)N4COc5c(cccc5-c5cc(N6C7CCC6COC7)c(C(=O)O)cc5F)C4)c(Cl)c3)cnc21] | 3-14a | 4-[3-[2,6-Dichloro-4-(1-methylpyrazolo[3,4-b]pyridin-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.50 | 688 |
| 3-15 | 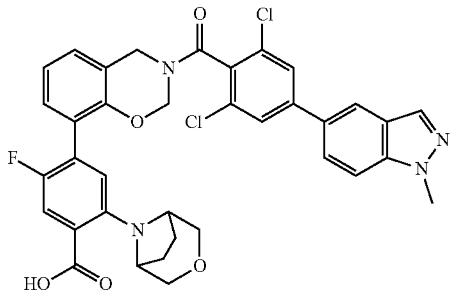 [SMILES: Cn1ncc2cc(-c3cc(Cl)c(C(=O)N4COc5c(cccc5-c5cc(N6C7CCC6COC7)c(C(=O)O)cc5F)C4)c(Cl)c3)ccc21] | 3-15a | 4-[3-[2,6-Dichloro-4-(1-methylindazol-5-yl)benzoyl]-2,4-dihydro-1,3-benzoxazin-8-yl]-5-fluoro-2-(3-oxa-8-azabicyclo[3.2.1]octan-8-yl)benzoic acid | B | 1.58 | 687 |
| 3-16 | 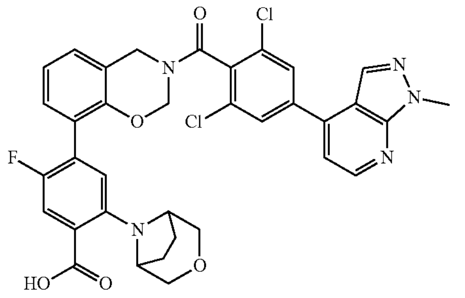 [SMILES: Cn1ncc2c(-c3cc(Cl)c(C(=O)N4COc5c(cccc5-c5cc(N6C7CCC6COC7)c(C(=O)O)cc5F)C4)c(Cl)c3)ccnc21] | 3-16a | 4-[3-[2,6-Dichloro-4-(1-methylpyrazolo[3,4-b]pyridin-4-yl)benzoyl]-2,4-dihydro-1,3-benzoxazin-8-yl]-5-fluoro-2-(3-oxa-8-azabicyclo[3.2.1]octan-8-yl)benzoic acid | B | 1.59 | 688 |
| 3-18 | 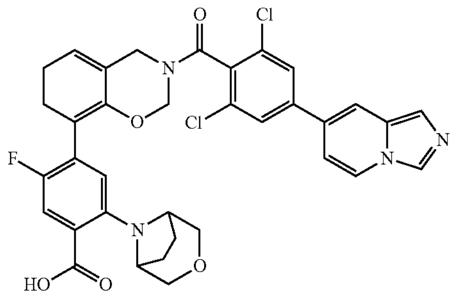 [SMILES: O=C(O)c1cc(F)c(C2=C3OCN(C(=O)c4c(Cl)cc(-c5ccn6cncc6c5)cc4Cl)CC3=CCC2)cc1N1C2CCC1COC2] | 3-18a | 4-[3-(2,6-Dichloro-4-imidazo[1,5-a]pyridin-7-ylbenzoyl)-2,4-dihydro-1,3-benzoxazin-8-yl]-5-fluoro-2-(3-oxa-8-azabicyclo[3.2.1]octan-8-yl)benzoic acid | B | 1.17, 1.19 | 673 |
| 3-20 | 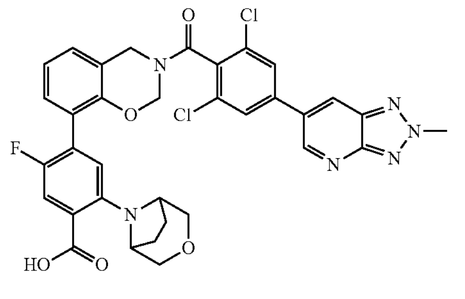 | 3-20a | 4-[3-[2,6-Dichloro-4-(2-methyltriazolo[4,5-b]pyridin-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.53, 1.55 | 689 |

TABLE 3-2-continued

| Compound No. | Structure | Ester | Compound Name | Analysis conditions | HPLC retention time (min) | m/z [M + H]+ |
|---|---|---|---|---|---|---|
| 3-21 | 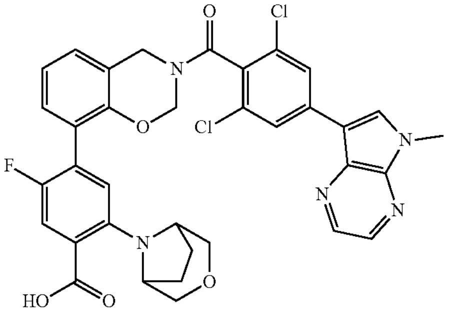 [SMILES: Cn1cc(-c2cc(Cl)c(C(=O)N3COc4c(cccc4-c4cc(N5C6CCC5COC6)c(C(=O)O)cc4F)C3)c(Cl)c2)c2nccnc21] | 3-21a | 4-[3-[2,6-Dichloro-4-(5-methylpyrrolo[2,3-b]pyrazin-7-yl)benzoyl]-2,4-dihydro-1,3-benzoxazin-8-yl]-5-fluoro-2-(3-oxa-8-azabicyclo[3.2.1]octan-8-yl)benzoic acid | B | 1.69 | 688 |
| 3-22 | 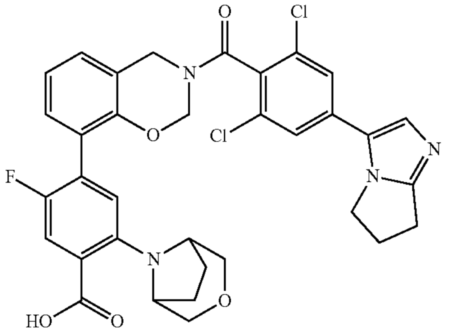 [SMILES: O=C(O)c1cc(F)c(-c2cccc3c2OCN(C(=O)c2c(Cl)cc(-c4cnc5n4CCC5)cc2Cl)C3)cc1N1C2CCC1COC2] | 3-22a | 4-[3-[2,6-Dichloro-4-(6,7-dihydro-5H-pyrrolo[1,2-a]imidazol-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.12 | 663 |
| 3-23 | 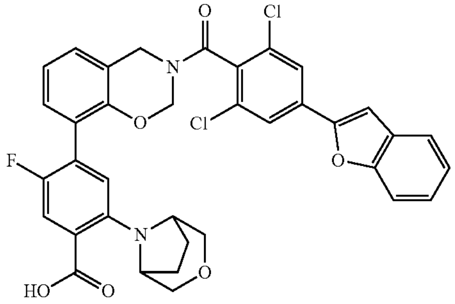 [SMILES: O=C(O)c1cc(F)c(-c2cccc3c2OCN(C(=O)c2c(Cl)cc(-c4cc5ccccc5o4)cc2Cl)C3)cc1N1C2CCC1COC2] | 3-23a | 4-[3-[4-(1-Benzofuran-2-yl)-2,6-dichlorobenzoyl]-2,4-dihydro-1,3-benzoxazin-8-yl]-5-fluoro-2-(3-oxa-8-azabicyclo[3.2.1]octan-8-yl)benzoic acid | B | 1.89, 1.93 | 673 |
| 3-24 | 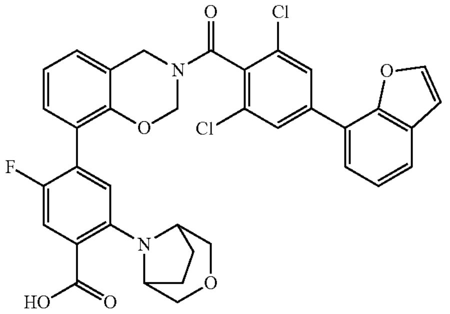 [SMILES: O=C(O)c1cc(F)c(-c2cccc3c2OCN(C(=O)c2c(Cl)cc(-c4cccc5ccoc45)cc2Cl)C3)cc1N1C2CCC1COC2] | 3-24a | 4-[3-[4-(1-Benzofuran-7-yl)-2,6-dichlorobenzoyl]-2,4-dihydro-1,3-benzoxazin-8-yl]-5-fluoro-2-(3-oxa-8-azabicyclo[3.2.1]octan-8-yl)benzoic acid | B | 1.84 | 673 |

TABLE 3-2-continued

| Compound No. | Structure | Ester | Compound Name | Analysis conditions | HPLC retention time (min) | m/z [M + H]+ |
|---|---|---|---|---|---|---|
| 3-25 | 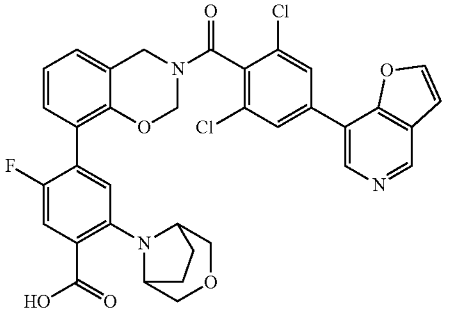 | 3-25a | 4-[3-(2,6-Dichloro-4-furo[3,2-c]pyridin-7-ylbenzoyl)-2,4-dihydro-1,3-benzoxazin-8-yl]-5-fluoro-2-(3-oxa-8-azabicyclo[3.2.1]octan-8-yl)benzoic acid | B | 1.40, 1.41 | 674 |

Compound 3-1

4-[3-[2,6-Dichloro-4-[1-(1-hydroxy-2-methylpropan-2-yl)pyrazol-4-yl]benzoyl]-2,4-dihydro-1,3-benzoxazin-8-yl]-5-fluoro-2-morpholin-4-ylbenzoic acid First Step Compound BRO1

[3,5-Dichloro-4-[8-(2-fluoro-4-methoxycarbonyl-5-morpholin-4-ylphenyl)-2,4-dihydro-1,3-benzoxazine-3-carbonyl]phenyl]boronic acid

[Formula 205]

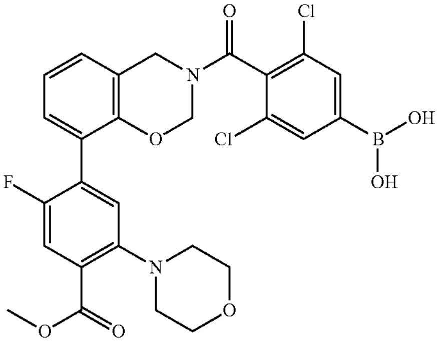

To a solution of compound B (300 mg, 0.481 mmol), bis(pinacolato)diboron (244 mg, 0.961 mmol) and potassium acetate (141 mg, 1.44 mmol) in 1,4-dioxane (2.40 mL), 1,1'-bis(diphenylphosphino)ferrocene-palladium(II) dichloride (35.2 mg, 0.0480 mmol) was added. The reaction solution was stirred at 100° C. for 1 hour. The reaction solution was concentrated, and the residue was then purified by reverse phase column chromatography (acetonitrile/water, 0.1% formic acid) to obtain the title compound (100%, 284 mg).

LCMS: m/z 589[M+H]+

HPLC retention time: 0.76 min and 0.79 min (analysis condition D)

Second Step

Compound 3-1a

Methyl 4-[3-[2,6-dichloro-4-[1-(1-hydroxy-2-methylpropan-2-yl)pyrazol-4-yl]benzoyl]-2,4-dihydro-1,3-benzoxazin-8-yl]-5-fluoro-2-morpholin-4-ylbenzoate

[Formula 206]

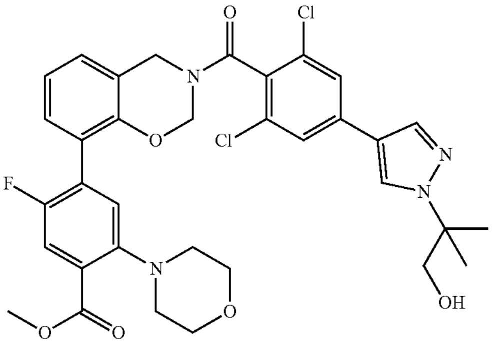

A solution of [3,5-dichloro-4-[8-(2-fluoro-4-methoxycarbonyl-5-morpholin-4-ylphenyl)-2,4-dihydro-1,3-benzoxazine-3-carbonyl]phenyl]boronic acid (30.0 mg, 0.0510 mmol), 2-(4-bromopyrazol-1-yl)-2-methylpropan-1-ol (16.7 mg, 0.0760 mmol), 1,1'-bis(diphenylphosphino)ferrocene-palladium(II) dichloride (3.73 mg, 0.00509 mmol) and potassium carbonate (21.1 mg, 0.153 mmol) in 1,4-dioxane (0.191 mL) and water (0.0636 mL) was stirred at 100° C. for 1 hour. The reaction solution was purified by reverse phase column chromatography (acetonitrile/water, 0.1% formic acid) to obtain the title compound (66%, 22.9 mg).

LCMS: m/z 683[M+H]+

HPLC retention time: 0.85 min and 0.86 min (analysis condition D)

Third Step

Compound 3-1

4-[3-[2,6-Dichloro-4-[1-(1-hydroxy-2-methylpropan-2-yl)pyrazol-4-yl]benzoyl]-2,4-dihydro-1,3-benzoxazin-8-yl]-5-fluoro-2-morpholin-4-ylbenzoic acid

[Formula 207]

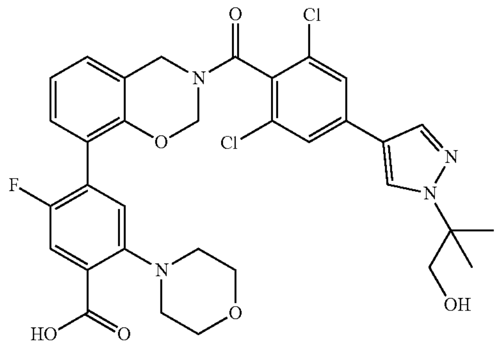

The title compound was obtained by the same operation as in the third step of compound 3-2 using methyl 4-[3-[2,6-dichloro-4-[1-(1-hydroxy-2-methylpropan-2-yl)pyrazol-4-yl]benzoyl]-2,4-dihydro-1,3-benzoxazin-8-yl]-5-fluoro-2-morpholin-4-ylbenzoate.

LCMS: m/z 669[M+H]$^+$

HPLC retention time: 1.01 min and 1.04 min (analysis condition A)

Compound 3-28

4-[3-[2,6-Dichloro-4-[1-(2-methoxyethyl)pyrazol-4-yl]benzoyl]-2,4-dihydro-1,3-benzoxazin-8-yl]-2-morpholin-4-ylbenzoic acid First Step Compound BRO2

[3,5-Dichloro-4-[8-(4-methoxycarbonyl-3-morpholin-4-ylphenyl)-2,4-dihydro-1,3-benzoxazine-3-carbonyl]phenyl]boronic acid

[Formula 208]

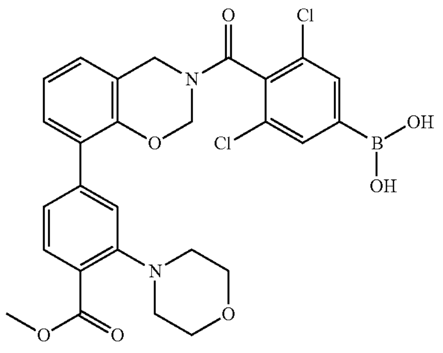

To a solution of compound E (175 mg, 0.289 mmol), bis(pinacolato)diboron (147 mg, 0.579 mmol) and potassium acetate (85.0 mg, 0.868 mmol) in 1,4-dioxane (3.00 mL), 1,1'-bis(diphenylphosphino)ferrocene-palladium(II) dichloride (21.2 mg, 0.0290 mmol) was added. The reaction solution was stirred at 90° C. for 1 hour. An aqueous formic acid solution was added to the reaction solution, and the reaction mixture was purified by reverse phase column chromatography (acetonitrile/water, 0.1% formic acid) to obtain the title compound (77%, 127 mg).

LCMS: m/z 571 [M+H]$^+$

HPLC retention time: 1.11 min (analysis condition G)

Second Step

Compound 3-28a

Methyl 4-[3-[2,6-dichloro-4-[1-(2-methoxyethyl)pyrazol-4-yl]benzoyl]-2,4-dihydro-1,3-benzoxazin-8-yl]-2-morpholin-4-ylbenzoate

[Formula 209]

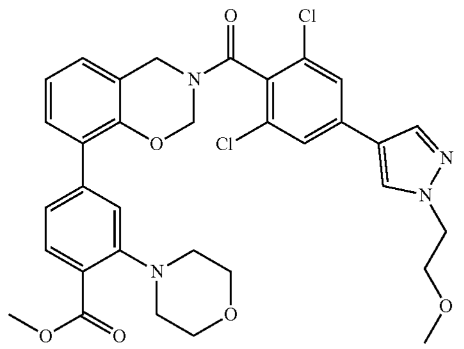

The title compound was obtained by the same approach as in the second step of compound 3-1 using [3,5-dichloro-4-[8-(4-methoxycarbonyl-3-morpholin-4-ylphenyl)-2,4-dihydro-1,3-benzoxazine-3-carbonyl]phenyl]boronic acid and 4-bromo-1-(2-methoxyethyl)pyrazole.

LCMS: m/z 651 [M+H]$^+$

HPLC retention time: 1.22 min and 1.24 min (analysis condition G)

Third Step

Compound 3-28

4-[3-[2,6-Dichloro-4-[1-(2-methoxyethyl)pyrazol-4-yl]benzoyl]-2,4-dihydro-1,3-benzoxazin-8-yl]-2-morpholin-4-ylbenzoic acid

[Formula 210]

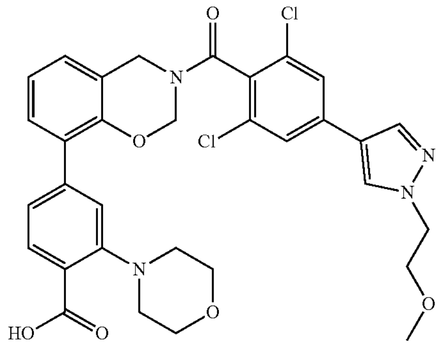

The title compound was obtained by the same operation as in the third step of compound 3-2 using methyl 4-[3-[2, 6-dichloro-4-[1-(2-methoxyethyl)pyrazol-4-yl]benzoyl]-2,4-dihydro-1,3-benzoxazin-8-yl]-2-morpholin-4-ylbenzoate.

LCMS: m/z 637[M+H]+

HPLC retention time: 1.01 min and 1.04 min (analysis condition A)

Compound 4-2

4-[3-[2,6-Dichloro-4-(3-ethoxy-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 211]

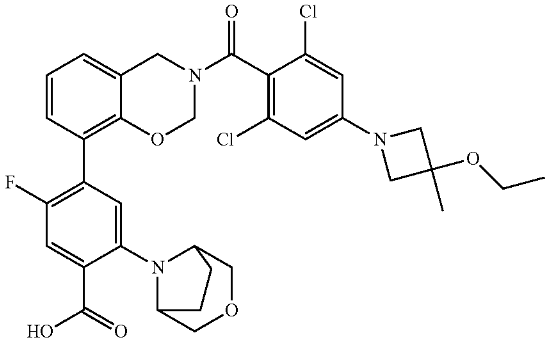

To 3-ethoxy-3-methylazetidine hydrochloride (27.0 mg, 0.178 mmol) and potassium carbonate (23.0 mg, 0.166 mmol), 1-methylpyrrolidin-2-one (0.600 mL) was added, and the mixture was stirred at room temperature for 10 minutes. Compound O (35.0 mg, 0.0590 mmol) was added into the reaction solution, and the mixture was stirred at 100° C. for 14 hours. After cooling of the reaction solution, an 8 M aqueous potassium hydroxide solution (0.0742 mL, 0.594 mmol) was added thereto, and the mixture was stirred at 60° C. for 1 hour. The reaction solution was neutralized with an aqueous formic acid solution, and the reaction mixture was then purified by HPLC (acetonitrile/water, 0.1% formic acid) to obtain the title compound (82%, 32.7 mg).

LCMS: m/z 670[M+H]+

HPLC retention time: 1.62 min and 1.66 min (analysis condition B)

Compounds shown in Table 4-1 were synthesized by the same operation as in the process of compound 4-2 using documented or commercially available amine shown in Table 4-2. However, potassium tert-butoxide was used instead of potassium carbonate in the synthesis of compounds 4-18, 4-7, and 4-17, and triethylamine was used in the synthesis of compounds 4-20, 4-22, 4-23, 4-24, 4-25, 4-27, 4-28, and 4-29.

TABLE 4-1

| Compound No. | Intermediate No. | Structure | Compound Name | Analysis conditions | HPLC retention time (min) | m/z [M + H]+ |
|---|---|---|---|---|---|---|
| 4-1 | Compound O | 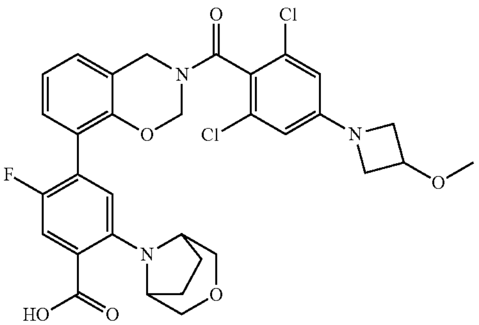 [SMILES: COC1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.50, 1.52 | 642 |
| 4-3 | Compound O | 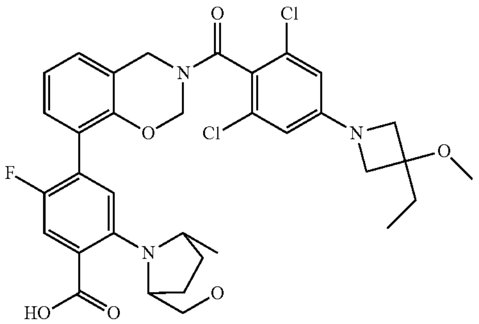 [SMILES: CCC1(OC)CN(c2cc(Cl)c(C(=O)N3COc4c(cccc4-c4cc(N5C(C)CCC5CO)c(C(=O)O)cc4F)C3)c(Cl)c2)C1] | 4-[3-[2,6-Dichloro-4-(3-ethyl-3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.62, 1.66 | 670 |

TABLE 4-1-continued

| Compound No. | Intermediate No. | Structure | Compound Name | Analysis conditions | HPLC retention time (min) | m/z [M + H]+ |
| --- | --- | --- | --- | --- | --- | --- |
| 4-4 | Compound O | 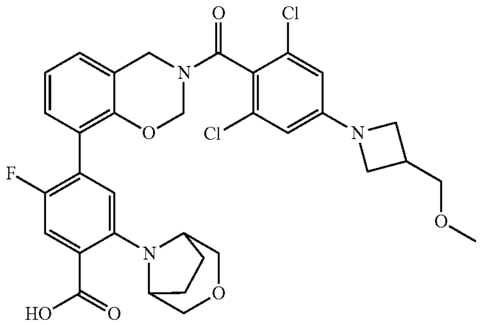 [SMILES: COCC1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-(methoxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.53, 1.56 | 656 |
| 4-5 | Compound O | 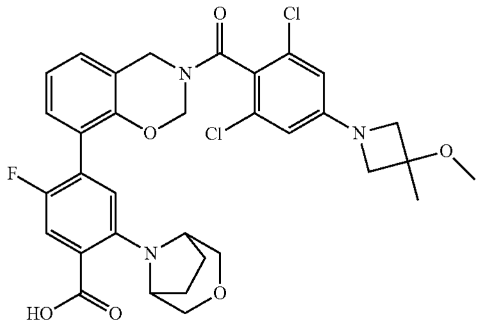 [SMILES: COC1(C)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-methoxy-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoic acid | 8 | 1.55, 1.58 | 656 |
| 4-6 | Compound O | 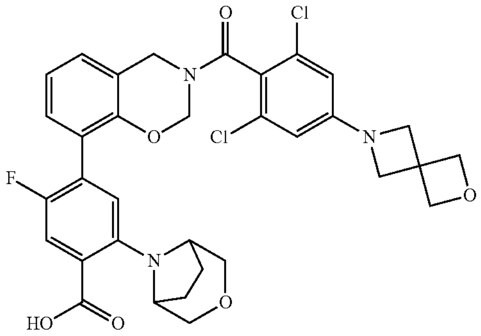 [SMILES: O=C(O)c1cc(F)c(-c2cccc3c2OCN(C(=O)c2c(Cl)cc(N4CC5(COC5)C4)cc2Cl)C3)cc1N1C2CCC1COC2] | 4-[3-[2,6-Dichloro-4-(2-oxa-6-azaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.42 | 654 |
| 4-7 | Compound O | 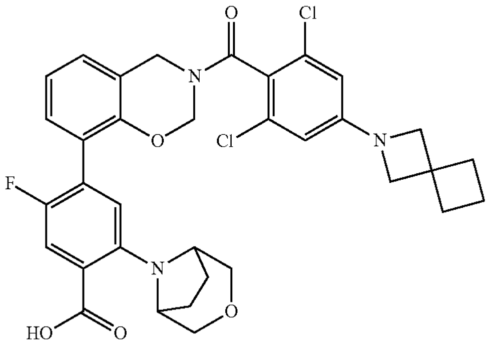 [SMILES: O=C(O)c1cc(F)c(-c2cccc3c2OCN(C(=O)c2c(Cl)cc(N4CC5(CCC5)C4)cc2Cl)C3)cc1N1C2CCC1COC2] | 4-[3-[4-(2-Azaspiro[3.3]heptan-2-yl)-2,6-dichlorobenzoyl]-2,4-dihydro-1,3-benzoxazin-8-yl]-5-fluoro-2-(3-oxa-8-azabicyclo[3.2.1]octan-8-yl)benzoic acid | B | 1.74, 1.81 | 652 |

TABLE 4-1-continued

| Compound No. | Intermediate No. | Structure | Compound Name | Analysis conditions | HPLC retention time (min) | m/z [M + H]+ |
|---|---|---|---|---|---|---|
| 4-11 | Compound O | 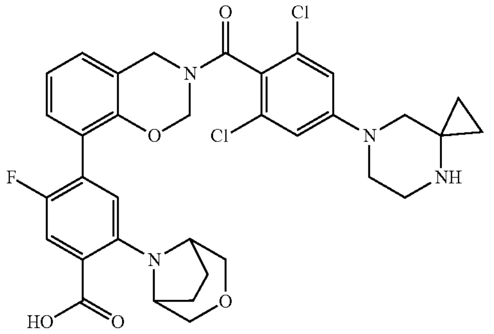 [SMILES: O=C(O)c1cc(F)c(-c2cccc3c2OCN(C(=O)c2c(Cl)cc(N4CCNC5(CC5)C4)cc2Cl)C3)cc1N1C2CCC1COC2] | 4-[3-[2,6-Dichloro-4-(4,7-diazaspiro[2.5]octan-7-yl)benzoyl]-2,4-dihydro-1,3-benzoxazin-8-yl]-5-fluoro-2-(3-oxa-8-azabicyclo[3.2.1]octan-8-yl)benzoic acid | B | 1.00, 1.05 | 667 |
| 4-17 | Compound O | 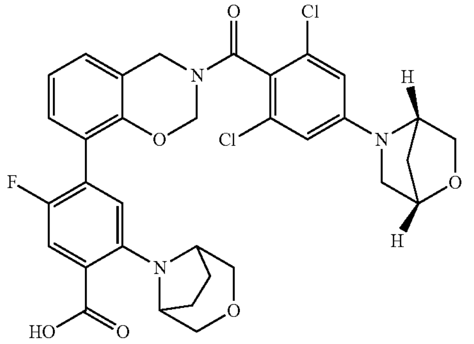 [SMILES: O=C(O)c1cc(F)c(-c2cccc3c2OCN(C(=O)c2c(Cl)cc(N4C[C@@H]5C[C@H]4CO5)cc2Cl)C3)cc1N1C2CCC1COC2] | 4-[3-[2,6-Dichloro-4-[(1S,4S)-2-oxa-5-azabicyclo[2.2.1]heptan-5-yl]benzoyl]-2,4-dihydro-1,3-benzoxazin-8-yl]-5-fluoro-2-(3-oxa-8-azabicyclo[3.2.1]octan-8-yl)benzoic acid | B | 1.43 | 654 |
| 4-18 | Compound O | 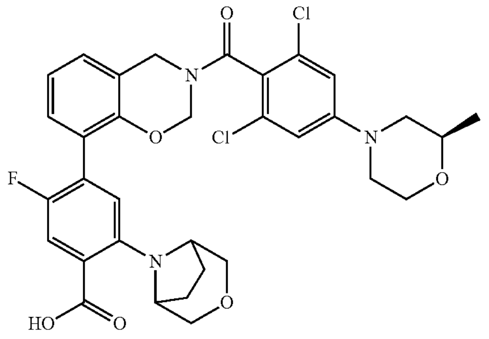 [SMILES: C[C@@H]1CN(c2cc(Cl)c(C(=O)N3COc4c(cccc4-c4cc(N5C6CCC5COC6)c(C(=O)O)cc4F)C3)c(Cl)c2)CCO1] | 4-[3-[2,6-Dichloro-4-[(2R)-2-methylmorpholin-4-yl]benzoyl]-2,4-dihydro-1,3-benzoxazin-8-yl]-5-fluoro-2-(3-oxa-8-azabicyclo[3.2.1]octan-8-yl)benzoic acid | B | 1.51, 1.53 | 656 |
| 4-20 | Compound Q | 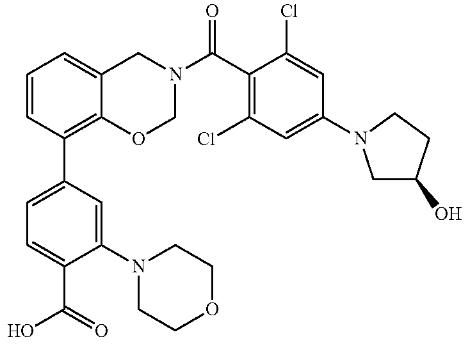 [SMILES: O=C(O)c1ccc(-c2cccc3c2OCN(C(=O)c2c(Cl)cc(N4CC[C@@H](O)C4)cc2Cl)C3)cc1N1CCOCC1] | 4-[3-[2,6-Dichloro-4-[(3R)-3-hydroxypyrrolidin-1-yl]benzoyl]-2,4-dihydro-1,3-benzoxazin-8-yl]-2-morpholin-4-ylbenzoic acid | A | 0.93, 0.95 | 598 |

TABLE 4-1-continued

| Compound No. | Intermediate No. | Structure | Compound Name | Analysis conditions | HPLC retention time (min) | m/z [M + H]+ |
|---|---|---|---|---|---|---|
| 4-21 | Compound R | 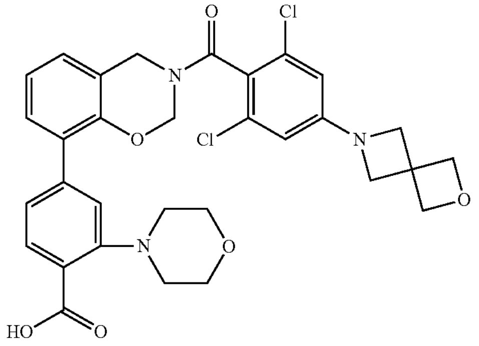 [SMILES: O=C(O)c1ccc(-c2cccc3c2OCN(C(=O)c2c(Cl)cc(N4CC5(COC5)C4)cc2Cl)C3)cc1N1CCOCC1] | 4-[3-[2,6-Dichloro-4-(2-oxa-6-azaspiro[3.3]heptan-6-yl)benzoyl]-2,4-dihydro-1,3-benzoxazin-8-yl]-2-morpholin-4-ylbenzoic acid | A | 1.00, 1.01 | 610 |
| 4-56 | Compound W | 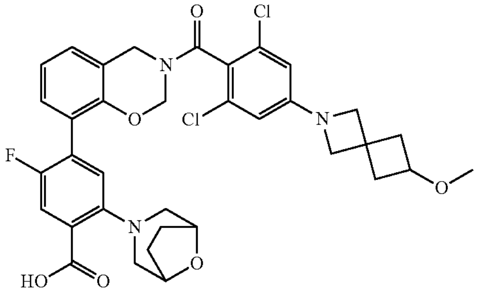 [SMILES: COC1CC2(C1)CN(c1cc(Cl)c(C(=O)N3COc4c(cccc4-c4cc(N5CC6CCC(C5)O6)c(C(=O)O)cc4F)C3)c(Cl)c1)C2] | 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(8-oxa-3-azabicyclo[3.2.1]octan-3-yl)benzoic acid | B | 1.69 | 682 |
| 4-22 | Compound S | 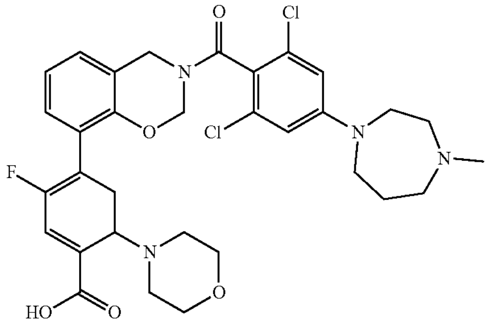 [SMILES: CN1CCCN(c2cc(Cl)c(C(=O)N3COc4c(cccc4C4=C(F)C=C(C(=O)O)C(N5CCOCC5)C4)C3)c(Cl)c2)CC1] | 4-[3-[2,6-Dichloro-4-(4-methyl-1,4-diazepan-1-yl)benzoyl]-2,4-dihydro-1,3-benzoxazin-8-yl]-5-fluoro-2-morpholin-4-ylbenzoic acid | A | 0.77, 0.81 | 643 |
| 4-23 | Compound S | 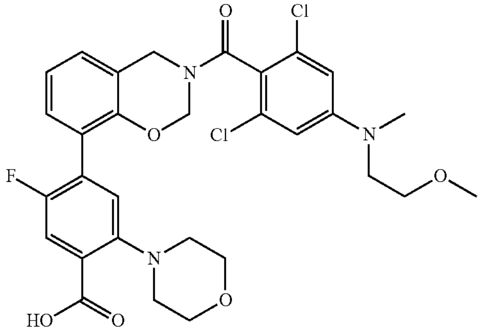 [SMILES: COCCN(C)c1cc(Cl)c(C(=O)N2COc3c(cccc3-c3cc(N4CCOCC4)c(C(=O)O)cc3F)C2)c(Cl)c1] | 4-[3-[2,6-Dichloro-4-[2-methoxyethyl(methyl)amino]benzoyl]-2,4-dihydro-1,3-benzoxazin-8-yl]-5-fluoro-2-morpholin-4-ylbenzoic acid | A | 1.10 | 618 |

TABLE 4-1-continued

| Compound No. | Intermediate No. | Structure | Compound Name | Analysis conditions | HPLC retention time (min) | m/z [M + H]+ |
|---|---|---|---|---|---|---|
| 4-24 | Compound S | 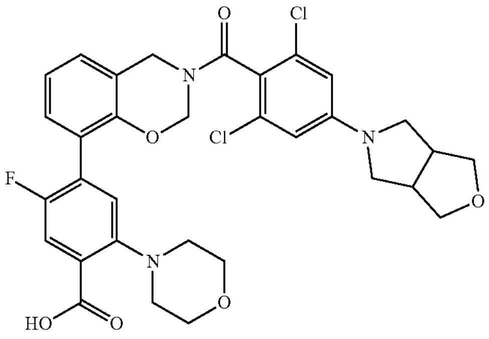 [SMILES: O=C(O)c1cc(F)c(-c2cccc3c2OCN(C(=O)c2c(Cl)cc(N4CC5COCC5C4)cc2Cl)C3)cc1N1CCOCC1] | 4-[3-[4-(1,3,3a,4,6,6a-Hexahydrofuro[3,4-c]pyrrol-5-yl)-2,6-dichlorobenzoyl]-2,4-dihydro-1,3-benzoxazin-8-yl]-5-fluoro-2-morpholin-4-ylbenzoic acid | B | 1.45 | 642 |
| 4-25 | Compound S | 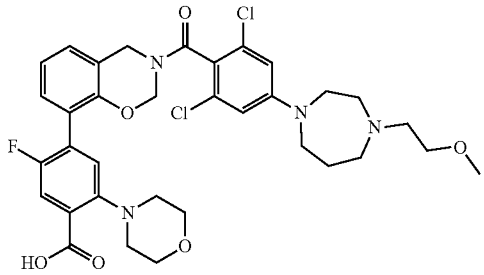 [SMILES: COCCN1CCCN(c2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-[4-(2-methoxyethyl)-1,4-diazepan-1-yl]benzoyl]-2,4-dihydro-1,3-benzoxazin-8-yl]-5-fluoro-2-morpholin-4-ylbenzoic acid | B | 1.00, 1.04 | 687 |
| 4-27 | Compound S | 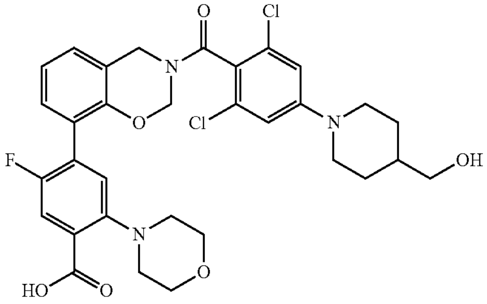 [SMILES: O=C(O)c1cc(F)c(-c2cccc3c2OCN(C(=O)c2c(Cl)cc(N4CCC(CO)CC4)cc2Cl)C3)cc1N1CCOCC1] | 4-[3-[2,6-Dichloro-4-[4-(hydroxymethyl)piperidin-1-yl]benzoyl]-2,4-dihydro-1,3-benzoxazin-8-yl]-5-fluoro-2-morpholin-4-ylbenzoic acid | B | 1.37, 1.39 | 644 |
| 4-28 | Compound S | 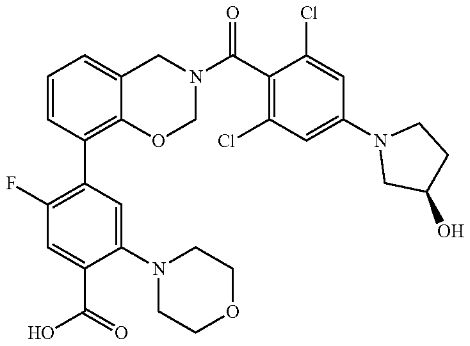 [SMILES: O=C(O)c1cc(F)c(-c2cccc3c2OCN(C(=O)c2c(Cl)cc(N4CC[C@@H](O)C4)cc2Cl)C3)cc1N1CCOCC1] | 4-[3-[2,6-Dichloro-4-[(3R)-3-hydroxypyrrolidin-1-yl]benzoyl]-2,4-dihydro-1,3-benzoxazin-8-yl]-5-fluoro-2-morpholin-4-ylbenzoic acid | A | 0.96, 0.98 | 616 |

TABLE 4-1-continued

| Compound No. | Intermediate No. | Structure | Compound Name | Analysis conditions | HPLC retention time (min) | m/z [M + H]+ |
|---|---|---|---|---|---|---|
| 4-29 | Compound S | 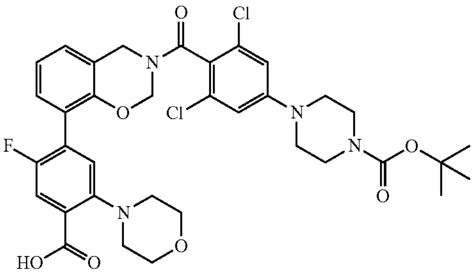 [SMILES: CC(C)(C)OC(=O)N1CCN(c2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-[4-[(2-methylpropan-2-yl)oxycarbonyl]piperazin-1-yl]benzoyl]-2,4-dihydro-1,3-benzoxazin-8-yl]-5-fluoro-2-morpholin-4-ylbenzoic acid | A | 1.25 | 715 |
| 4-33 | Compound U | 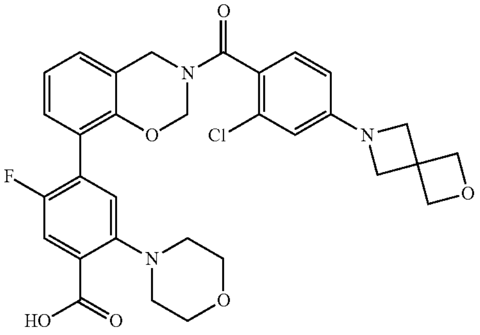 [SMILES: O=C(O)c1cc(F)c(-c2cccc3c2OCN(C(=O)c2ccc(N4CC5(COC5)C4)cc2Cl)C3)cc1N1CCOCC1] | 4-[3-[2-Chloro-4-(2-oxa-6-azaspiro[3.3]heptan-6-yl)benzoyl]-2,4-dihydro-1,3-benzoxazin-8-yl]-5-fluoro-2-morpholin-4-ylbenzoic acid | A | 0.96 | 594 |

TABLE 4-2

| Final compound No. | Amine |
|---|---|
| 4-1 | 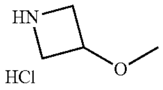 |
| 4-3 | 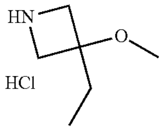 |
| 4-4 | 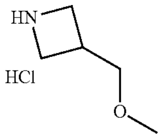 |
| 4-5 | 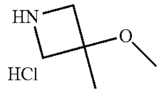 |
| 4-6 | 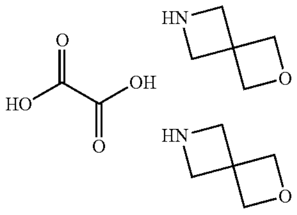 |

TABLE 4-2-continued

| Final compound No. | Amine |
|---|---|
| 4-7 | 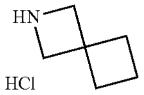 |
| 4-11 | 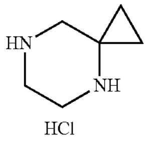 |
| 4-17 | 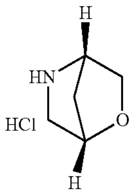 |
| 4-18 | 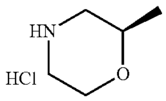 |
| 4-20 | 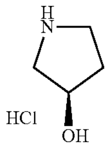 |

TABLE 4-2-continued

| Final compound No. | Amine |
|---|---|
| 4-21 | 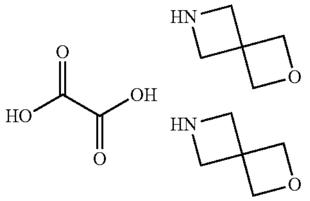 |
| 4-56 | 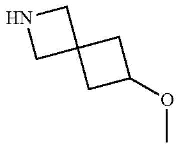 |
| 4-22 | 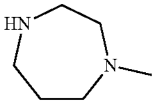 |
| 4-23 | 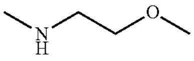 |
| 4-24 | 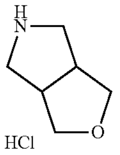 |
| 4-25 | 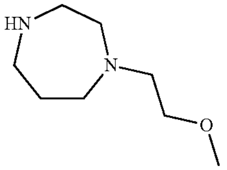 |
| 4-27 | 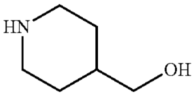 |
| 4-28 | 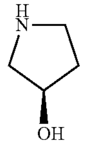 |
| 4-29 | 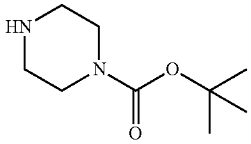 |
| 4-33 | 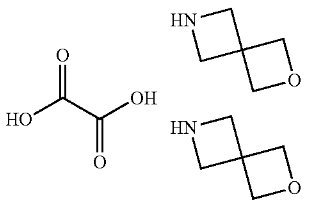 |

Compound 4-12

4-[3-[2,6-Dichloro-4-(4-cyclopropylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 212]

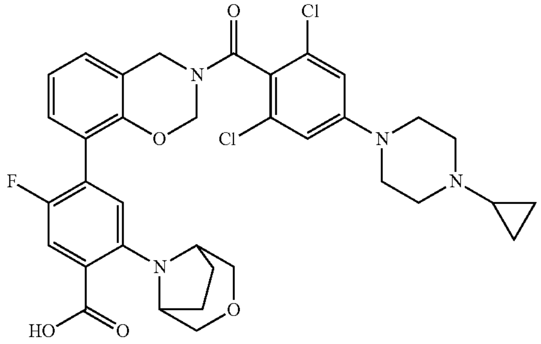

Compound O (25.0 mg, 0.0420 mmol) and 1-cyclopropylpiperazine (16.1 mg, 0.127 mmol) were stirred at 130° C. for 6 hours in 1-methylpyrrolidin-2-one (0.106 mL). After cooling of the reaction solution, an 8 M aqueous potassium hydroxide solution (0.0265 mL, 0.212 mmol) was added thereto, and the mixture was stirred at 60° C. for 30 minutes. The reaction solution was neutralized with an aqueous formic acid solution, and the reaction mixture was then purified by HPLC (acetonitrile/water, 0.1% formic acid) to obtain the title compound (73%, 21.1 mg).

LCMS: m/z 681 $[M+H]^+$

HPLC retention time: 1.03 min and 1.06 min (analysis condition B)

Compounds shown in Table 4-3 were synthesized by the same operation as in the process of compound 4-12 using documented or commercially available amine shown in Table 4-4.

TABLE 4-3

| Compound No. | Intermediate No. | Structure | Compound Name | Analysis conditions | HPLC retention time (min) | m/z [M + H] |
|---|---|---|---|---|---|---|
| 4-8 | Compound O | 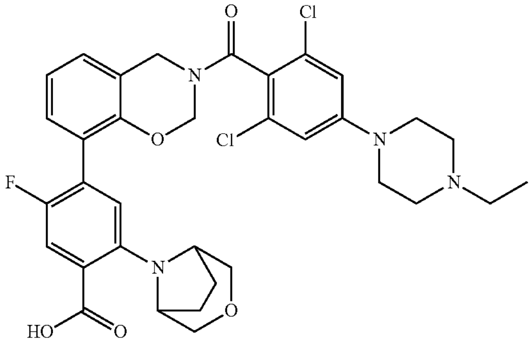 [SMILES: CCN1CCN(c2cc(Cl)c(C(=O)N3COc4c(cccc4-c4cc(N5C6CCC5COC6)c(C(=O)O)cc4F)C3)c(Cl)c2)CC1] | 4-[3-[2,6-Dichloro-4-(4-ethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid | B | 0.99, 1.04 | 669 |
| 4-9 | Compound O | 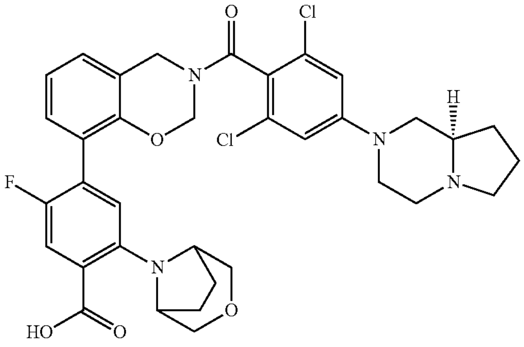 [SMILES: O=C(O)c1cc(F)c(-c2cccc3c2OCN(C(=O)c2c(Cl)cc(N4CCN5CCC[C@@H]5C4)cc2Cl)C3)cc1N1C2CCC1COC2] | 4-[3-[4-[(8aR)-3,4,6,7,8,8a-Hexahydro-1H-pyrrolo[1,2-a]pyrazin-2-yl]-2,6-dichlorobenzoyl]-2,4-dihydro-1,3-benzoxazin-8-yl]-5-fluoro-2-(3-oxa-8-azabicyclo[3.2.1]octan-8-yl)benzoic acid | B | 1.00, 1.05 | 681 |
| 4-10 | Compound O | 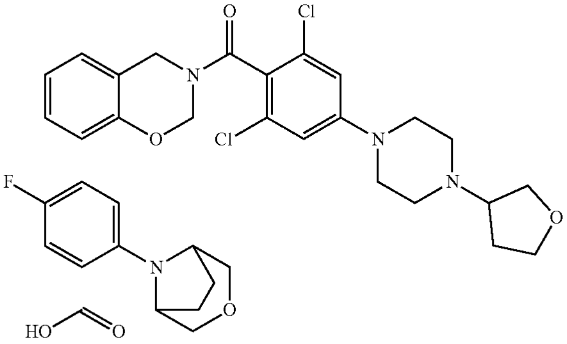 | 4-[3-[2,6-Dichloro-4-[4-(oxolan-3-yl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.00, 1.04 | 711 |
| 4-58 | Compound O | 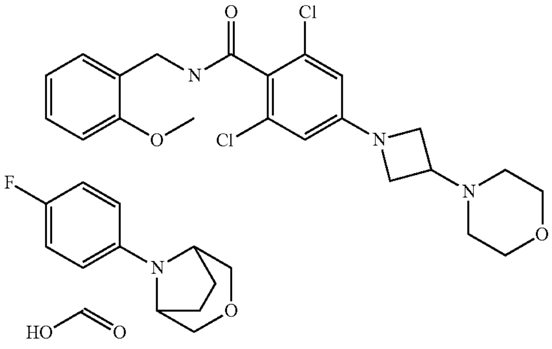 | 4-[3-[2,6-Dichloro-4-(3-morpholin-4-ylazetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.08, 1.09 | 697 |

TABLE 4-3-continued

| Compound No. | Intermediate No. | Structure | Compound Name | Analysis conditions | HPLC retention time (min) | m/z [M + H] |
|---|---|---|---|---|---|---|
| 4-26 | Compound S | 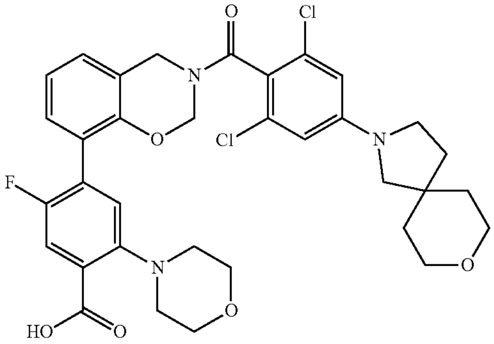 [SMILES: O=C(O)c1cc(F)c(-c2cccc3c2OCN(C(=O)c2c(Cl)cc(N4CCC5(CCOCC5)C4)cc2Cl)C3)cc1N1CCOCC1] | 4-[3-[2,6-Dichloro-4-(8-oxa-2-azaspiro[4.5]decan-2-yl)benzoyl]-2,4-dihydro-1,3-benzoxazin-8-yl]-5-fluoro-2-morpholin-4-ylbenzoic acid | B | 1.54, 1.56 | 670 |
| 4-30 | Compound S | 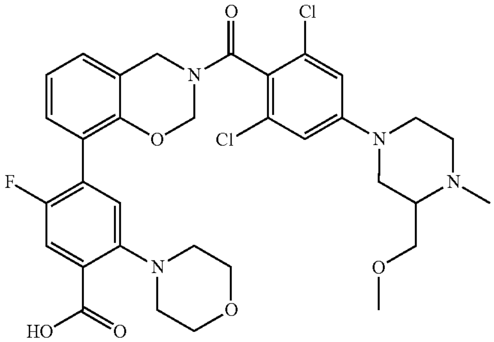 [SMILES: COCC1CN(c2cc(Cl)c(C(=O)N3COc4c(cccc4-c4cc(N5CCOCC5)c(C(=O)O)cc4F)C3)c(Cl)c2)CCN1C] | 4-[3-[2,6-Dichloro-4-[3-(methoxymethyl)-4-methylpiperazin-1-yl]benzoyl]-2,4-dihydro-1,3-benzoxazin-8-yl]-5-fluoro-2-morpholin-4-ylbenzoic acid | B | 0.98, 1.03 | 673 |
| 4-31 | Compound S | 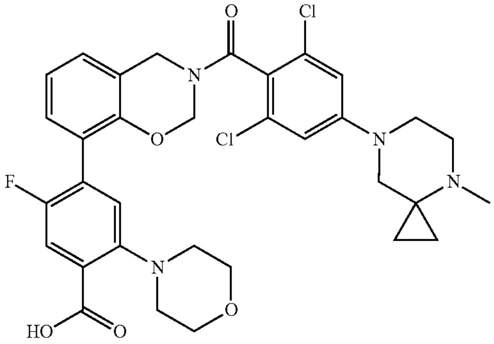 [SMILES: CN1CCN(c2cc(Cl)c(C(=O)N3COc4c(cccc4-c4cc(N5CCOCC5)c(C(=O)O)cc4F)C3)c(Cl)c2)CC12CC2] | 4-[3-[2,6-Dichloro-4-(4-methyl-4,7-diazaspiro[2.5]octan-7-yl)benzoyl]-2,4-dihydro-1,3-benzoxazin-8-yl]-5-fluoro-2-morpholin-4-ylbenzoic acid | B | 0.99, 1.03 | 655 |
| 4-32 | Compound T | 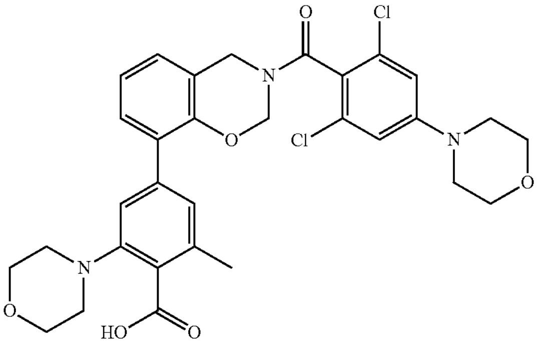 [SMILES: Cc1cc(-c2cccc3c2OCN(C(=O)c2c(Cl)cc(N4CCOCC4)cc2Cl)C3)cc(N2CCOCC2)c1C(=O)O] | 4-[3-(2,6-Dichloro-4-morpholin-4-ylbenzoyl)-2,4-dihydro-1,3-benzoxazin-8-yl]-2-methyl-6-morpholin-4-ylbenzoic acid | A | 1.09 | 612 |

TABLE 4-3-continued

| Compound No. | Intermediate No. | Structure | Compound Name | Analysis conditions | HPLC retention time (min) | m/z [M + H] |
|---|---|---|---|---|---|---|
| 4-57 | Compound S | 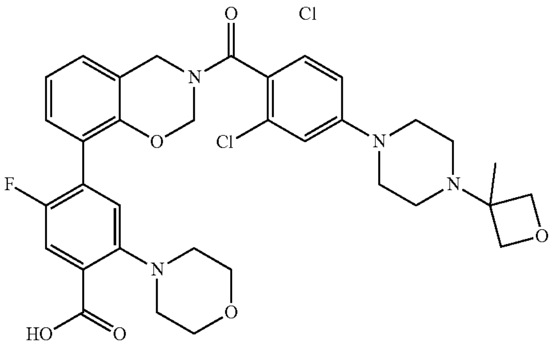 [SMILES: CC1(N2CCN(c3ccc(C(=O)N4COc5c(cccc5-c5cc(N6CCOCC6)c(C(=O)O)cc5F)C4)c(Cl)c3)CC2)COC1 ; Cl] | 4-[3-[2,6-Dichloro-4-[4-(3-methyloxetan-3-yl)piperazin-1-yl]benzoyl]-2,4-dihydro-1,3-benzoxazin-8-yl]-5-fluoro-2-morpholin-4-ylbenzoic acid | B | 1.03, 1.06 | 685 |

TABLE 4-4

| Final compound No. | Amine |
|---|---|
| 4-8 | 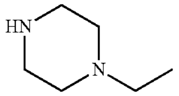 |
| 4-9 | 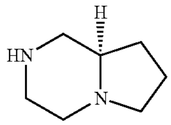 |
| 4-10 | 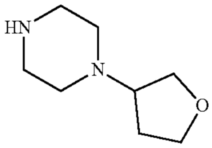 |
| 4-58 | 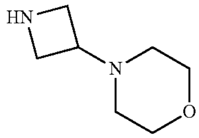 |
| 4-26 | 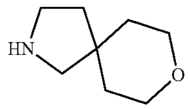 |
| 4-30 | 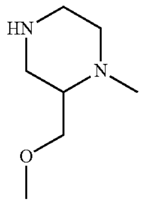 |
| 4-31 | 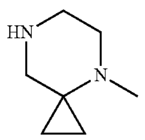 |

TABLE 4-4-continued

| Final compound No. | Amine |
|---|---|
| 4-32 | 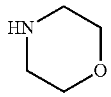 |
| 4-57 | 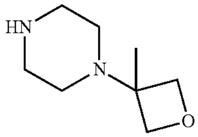 |

Compound 4-13

4-[3-[4-[(9aS)-3,4,6,7,9,9a-Hexahydro-1H-pyrazino[2,1-c][1,4]oxazin-8-yl]-2,6-dichlorobenzoyl]-2,4-dihydro-1,3-benzoxazin-8-yl]-5-fluoro-2-(3-oxa-8-azabicyclo[3.2.1]octan-8-yl)benzoic acid

[Formula 213]

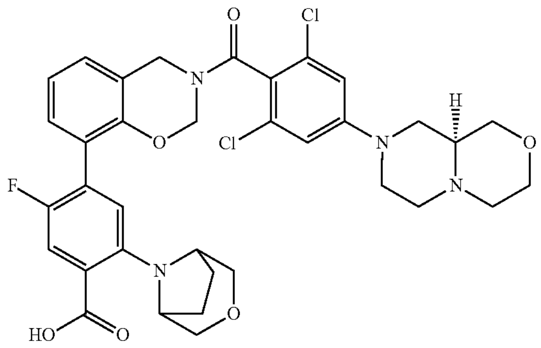

To (9aS)-1,3,4,6,7,8,9,9a-octahydropyrazino[2,1-c][1,4]oxazine dihydrochloride (37.4 mg, 0.174 mmol), potassium tert-butoxide (42 mg, 0.375 mmol) was added in 1-methylpyrrolidin-2-one (0.0870 mL), and the mixture was stirred at room temperature for 5 minutes. Compound P (20.0 mg, 0.0350 mmol) was added into the reaction solution, and the mixture was stirred at 130° C. for 4 hours. The reaction solution was cooled, diluted with methanol, and then neutralized with an aqueous formic acid solution. The reaction mixture was purified by HPLC (acetonitrile/water, 0.1% formic acid) to obtain the title compound (40%, 9.70 mg).

LCMS: m/z 697[M+H]$^+$

HPLC retention time: 1.03 min and 1.06 min (analysis condition B)

Compound 4-14

4-[3-[4-[(9aR)-3,4,6,7,9,9a-Hexahydro-1H-pyrazino[2,1-c][1,4]oxazin-8-yl]-2,6-dichlorobenzoyl]-2,4-dihydro-1,3-benzoxazin-8-yl]-5-fluoro-2-(3-oxa-8-azabicyclo[3.2.1]octan-8-yl)benzoic acid

[Formula 214]

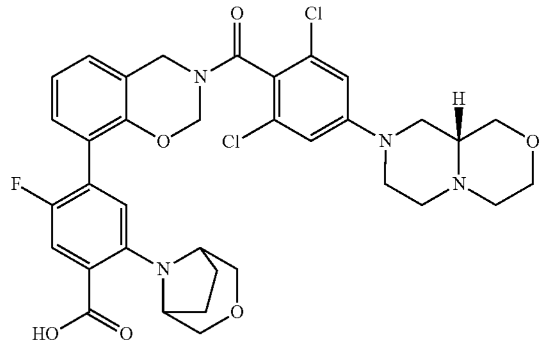

The title compound was synthesized by the same operation as in the process of compound 4-13 using compound P and (9aR)-1,3,4,6,7,8,9,9a-octahydropyrazino[2,1-c][1,4]oxazine dihydrochloride.

LCMS: m/z 697[M+H]$^+$

HPLC retention time: 1.03 min and 1.06 min (analysis condition B)

Compound 4-15

4-[3-[2,6-Dichloro-4-[4-(2-hydroxy-2-methylpropyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 215]

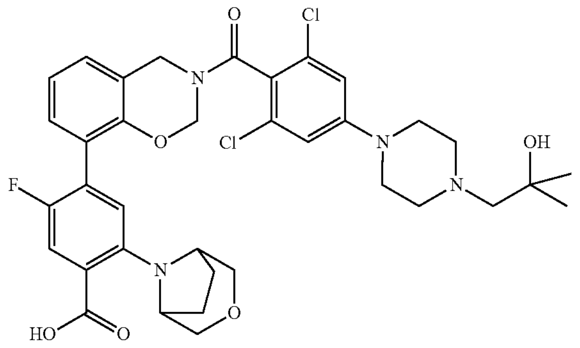

N,N-diisopropylethylamine (35.9 mg, 0.278 mmol), compound P (20.0 mg, 0.0350 mmol) and 2-methyl-1-piperazin-1-ylpropan-2-ol dihydrochloride (24.1 mg, 0.104 mmol) were stirred at 130° C. for 2 hours in 1-methylpyrrolidin-2-one (0.174 mL). The reaction solution was cooled and then neutralized with an aqueous formic acid solution. The reaction mixture was purified by HPLC (acetonitrile/water, 0.1% formic acid) to obtain the title compound (34%, 8.30 mg).

LCMS: m/z 713[M+H]$^+$

HPLC retention time: 1.00. min and 1.04 min (analysis condition B)

Compound 4-19

4-[3-(2,6-Dichloro-4-morpholin-4-ylbenzoyl)-2,4-dihydro-1,3-benzoxazin-8-yl]-5-fluoro-2-(3-oxa-8-azabicyclo[3.2.1]octan-8-yl)benzoic acid

[Formula 216]

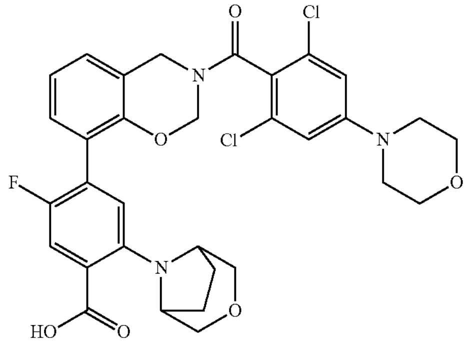

Compound P (20.0 mg, 0.0340 mmol) and morpholine (15.2 mg, 0.174 mmol) were stirred at 130° C. for 4 hours in 1-methylpyrrolidin-2-one (0.0870 mL). The reaction solution was cooled, then diluted with methanol, and then neutralized with an aqueous formic acid solution. The reaction mixture was purified by HPLC (acetonitrile/water, 0.1% formic acid) to obtain the title compound (65%, 14.5 mg).

LCMS: m/z 642[M+H]$^+$

HPLC retention time: 1.45 min (analysis condition B)

Compounds shown in Table 4-5 were synthesized by the same operation as in the process of compound 4-19 using documented or commercially available amine shown in Table 4-6.

TABLE 4-5

| Compound No. | Intermediate No. | Structure | Compound Name | Analysis conditions | HPLC retention time (min) | m/z [M + H] |
|---|---|---|---|---|---|---|
| 4-16 | Compound P | 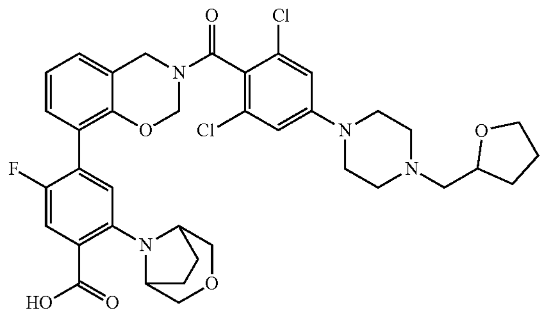 [SMILES: O=C(O)c1cc(F)c(-c2cccc3c2OCN(C(=O)c2c(Cl)cc(N4CCN(CC5CCCO5)CC4)cc2Cl)C3)cc1N1C2CCC1COC2] | 4-[3-[2,6-Dichloro-4-[4-(oxolan-2-ylmethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.02, 1.06 | 725 |
| 4-60 | Compound P | 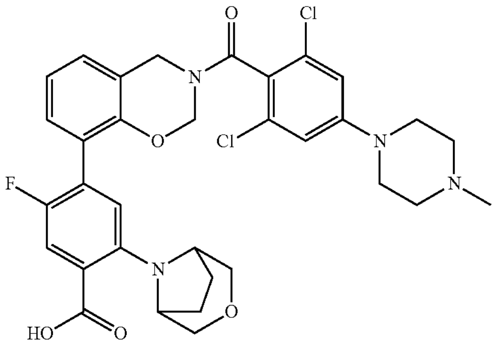 [SMILES: CN1CCN(c2cc(Cl)c(C(=O)N3COc4c(cccc4-c4cc(N5C6CCC5COC6)c(C(=O)O)cc4F)C3)c(Cl)c2)CC1] | 4-[3-[2,6-Dichloro-4-(4-methylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid | B | 0.97, 1.02 | 655 |
| 4-59 | Compound P | 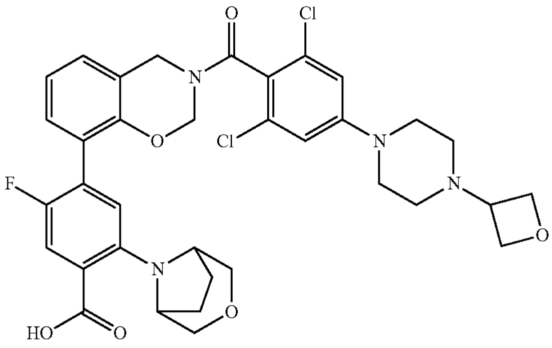 [SMILES: O=C(O)c1cc(F)c(-c2cccc3c2OCN(C(=O)c2c(Cl)cc(N4CCN(C5COC5)CC4)cc2Cl)C3)cc1N1C2CCC1COC2] | 4-[3-[2,6-Dichloro-4-[4-(oxetan-3-yl)piperazin-1-yl]benzoyl]-2,4-dihydro-1,3-benzoxazin-8-yl]-5-fluoro-2-(3-oxa-8-azabicyclo[3.2.1] octan-8-yl)benzoic acid | B | 1.05. 1.08 | 697 |

TABLE 4-6

| Final compound No. | Amine |
|---|---|
| 4-16 | 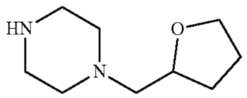 [SMILES: C1COC(CN2CCNCC2)C1] |
| 4-60 | 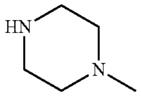 |
| 4-59 | 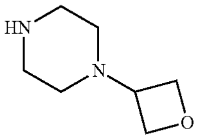 |

Compound 4-42

4-[3-[2,6-Dichloro-4-[[(2S)-1,4-dioxan-2-yl]methoxy]benzoyl]-2,4-dihydro-1,3-benzoxazin-8-yl]-5-fluoro-2-(3-oxa-8-azabicyclo[3.2.1]octan-8-yl)benzoic acid

[Formula 217]

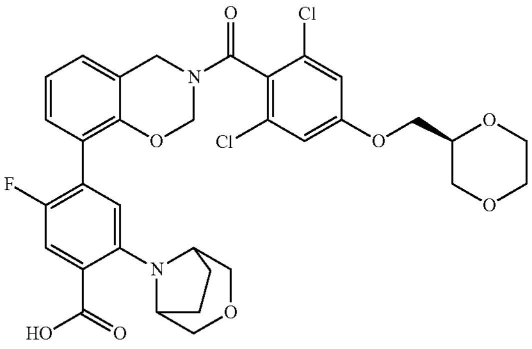

To [(2R)-1,4-dioxan-2-yl]methanol (0.0273 ml, 0.254 mmol) and potassium tert-butoxide (27.4 mg, 0.244 mmol), 1-methylpyrrolidin-2-one (0.254 mL) was added, and the mixture was stirred at room temperature for 10 minutes. Compound 0 (30.0 mg, 0.0510 mmol) was added into the reaction solution, and the mixture was stirred at room temperature for 1 hour. The reaction solution was neutralized with an aqueous formic acid solution, and the reaction mixture was then purified by HPLC (acetonitrile/water, 0.1% formic acid) to obtain the title compound (69%, 23.8 mg).

LCMS: m/z 673[M+H]$^+$

HPLC retention time: 1.43 min (analysis condition B)

Compounds shown in Table 4-7 were synthesized by the same operation as in the process of compound 4-42 using documented or commercially available alcohol shown in Table 4-8. However, sodium tert-butoxide was used instead of potassium tert-butoxide in the synthesis of compounds 4-43, 4-44, and 4-45, and sodium hydride was used in the synthesis of compound 4-46. While an ethyl ester intermediate for compound 4-43 and a methyl ester intermediate for compounds 4-44, 4-45, 4-46, and 4-47 were used, ester hydrolysis reaction also proceeded at the same time. As for compounds 4-48, 4-49, 4-50, 4-51, 4-52, and 4-53, hydrolysis reaction was performed by adding an 8 M aqueous potassium hydroxide solution after aromatic nucleophilic substitution reaction, and stirring the mixture at 60° C. for 30 minutes.

TABLE 4-7

| Compound No. | Intermediate No. | Structure | Compound Name | Analysis conditions | HPLC retention time (min) | m/z [M + H] |
|---|---|---|---|---|---|---|
| 4-34 | Compound P | 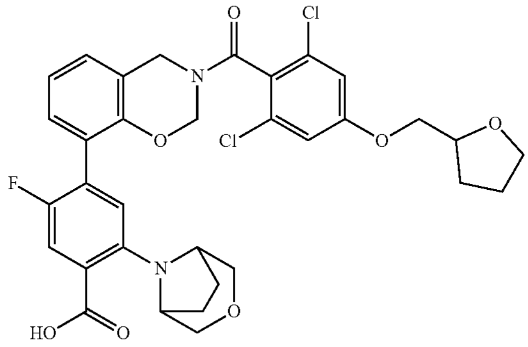 [SMILES: O=C(O)c1cc(F)c(-c2cccc3c2OCN(C(=O)c2c(Cl)cc(OCC4CCCO4)cc2Cl)C3)cc1N1C2CCC1COC2] | 4-[3-[2,6-Dichloro-4-[[(2R)-oxolan-2-yl]methoxy]benzoyl]-2,4-dihydro-1,3-benzoxazin-8-yl]-5-fluoro-2-(3-oxa-8-azabicyclo[3.2.1]octan-8-yl)benzoic acid | B | 1.51, 1.52 | 657 |

TABLE 4-7-continued

| Compound No. | Intermediate No. | Structure | Compound Name | Analysis conditions | HPLC retention time (min) | m/z [M + H] |
|---|---|---|---|---|---|---|
| 4-35 | Compound P | 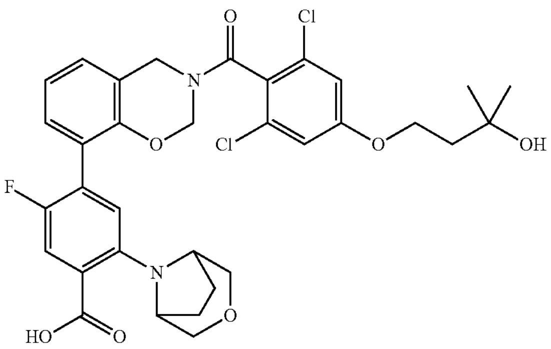 [SMILES: CC(C)(O)CCOc1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-(3-hydroxy-3-methylbutoxy)benzoyl]-2,4-dihydro-1,3-benzoxazin-8-yl]-5-fluoro-2-(3-oxa-8-azabicyclo[3.2.1]octan-8-yl)benzoic acid | B | 1.46 | 659 |
| 4-36 | Compound P | 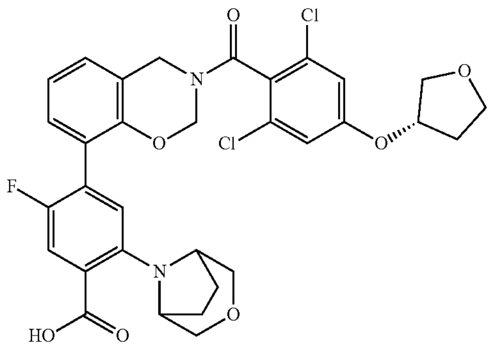 [SMILES: O=C(O)c1cc(F)c(-c2cccc3c2OCN(C(=O)c2c(Cl)cc(O[C@H]4CCOC4)cc2Cl)C3)cc1N1C2CCC1COC2] | 4-[3-[2,6-Dichloro-4-[(3R)-oxolan-3-yl]oxybenzoyl]-2,4-dihydro-1,3-benzoxazin-8-yl]-5-fluoro-2-(3-oxa-8-azabicyclo[3.2.1]octan-8-yl)benzoic acid | B | 1.45 | 643 |
| 4-37 | Compound P | 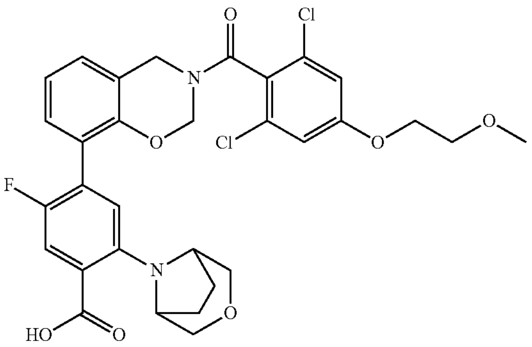 [SMILES: COCCOc1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-(2-methoxyethoxy)benzoyl]-2,4-dihydro-1,3-benzoxazin-8-yl]-5-fluoro-2-(3-oxa-8-azabicyclo[3.2.1]octan-8-yl)benzoic acid | B | 1.57 | 631 |
| 4-38 | Compound P | 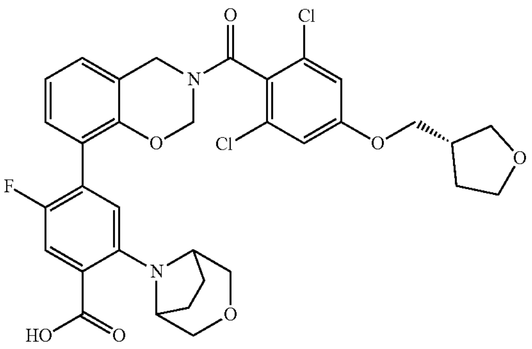 [SMILES: O=C(O)c1cc(F)c(-c2cccc3c2OCN(C(=O)c2c(Cl)cc(OC[C@H]4CCOC4)cc2Cl)C3)cc1N1C2CCC1COC2] | 4-[3-[2,6-Dichloro-4-[[(3S)-oxolan-3-yl]methoxy]benzoyl]-2,4-dihydro-1,3-benzoxazin-8-yl]-5-fluoro-2-(3-oxa-8-azabicyclo[3.2.1]octan-8-yl)benzoic acid | B | 1.50 | 657 |

TABLE 4-7-continued

| Compound No. | Intermediate No. | Structure | Compound Name | Analysis conditions | HPLC retention time (min) | m/z [M + H] |
|---|---|---|---|---|---|---|
| 4-39 | Compound P | 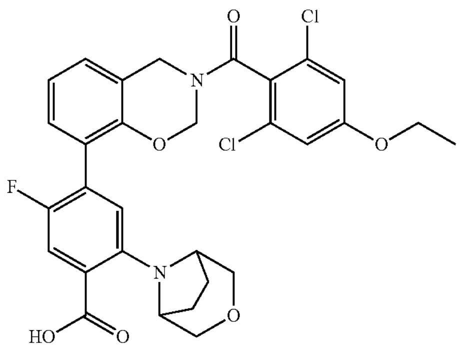 [SMILES: CCOc1cc(Cl)c(C(=O)N2COc3c(cccc3-c3cc(N4C5CCC4COC5)c(C(=O)O)cc3F)C2)c(Cl)c1] | 4-[3-(2,6-Dichloro-4-ethoxybenzoyl)-2,4-dihydro-1,3-benzoxazin-8-yl]-5-fluoro-2-(3-oxa-8-azabicyclo[3.2.1]octan-8-yl) benzoic acid | B | 1.67, 1.70 | 601 |
| 4-43 | Compound Q | 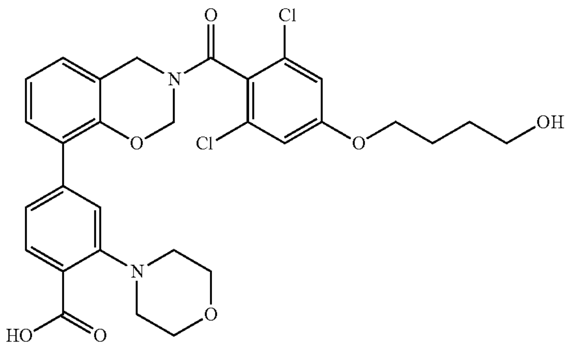 [SMILES: O=C(O)c1ccc(-c2cccc3c2OCN(C(=O)c2c(Cl)cc(OCCCCO)cc2Cl)C3)cc1N1CCOCC1] | 4-[3-[2,6-Dichloro-4-(4-hydroxybutoxy)benzoyl]-2,4-dihydro-1,3-benoxazin-8-yl]-2-morpholin-4-yl-benzoic acid | A | 0.95, 0.98 | 601 |
| 4-44 | Compound R | 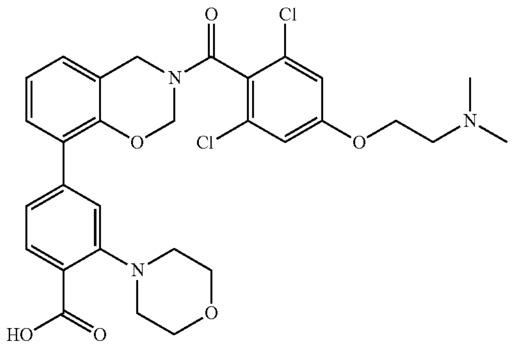 [SMILES: CN(C)CCOc1cc(Cl)c(C(=O)N2COc3c(cccc3-c3ccc(C(=O)O)c(N4CCOCC4)c3)C2)c(Cl)c1] | 4-[3-[2,6-Dichloro-4-[2-(dimethylamino)ethoxy] benzoyl]-2,4-dihydro-1,3-benzoxazin-8-yl]-2-morpholin-4-ylbenzoic acid | A | 0.73, 0.78 | 600 |
| 4-45 | Compound R | 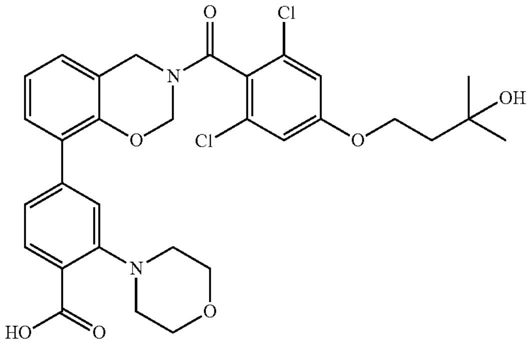 [SMILES: CC(C)(O)CCOc1cc(Cl)c(C(=O)N2COc3c(cccc3-c3ccc(C(=O)O)c(N4CCOCC4)c3)C2)c(Cl)c1] | 4-[3-[2,6-Dichloro-4-(3-hydroxy-3-methylbutoxy) benzoyl]-2,4-dihydro-1,3-benzoxazin-8-yl]-2-morpholin-4-ylbenzoic acid | A | 1.02, 1.03 | 615 |

TABLE 4-7-continued

| Compound No. | Intermediate No. | Structure | Compound Name | Analysis conditions | HPLC retention time (min) | m/z [M + H] |
|---|---|---|---|---|---|---|
| 4-46 | Compound S | 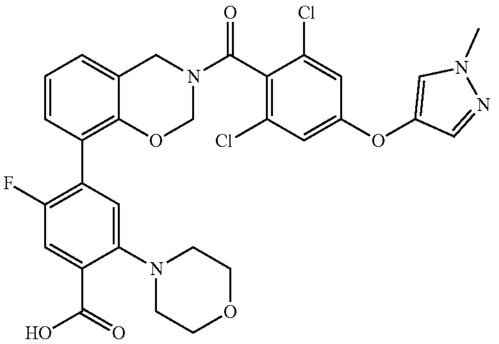 [SMILES: Cn1cc(Oc2cc(Cl)c(C(=O)N3COc4c(cccc4-c4cc(N5CCOCC5)c(C(=O)O)cc4F)C3)c(Cl)c2)cn1] | 4-[3-[2,6-Dichloro-4-(1-methyl-pyrazol-4-yl)oxybenzoyl]-2,4-dihydro-1,3-benzoxazin-8-yl]-5-fluoro-2-morpholin-4-ylbenzoic acid | B | 1.39, 1.40 | 627 |
| 4-47 | Compound S | 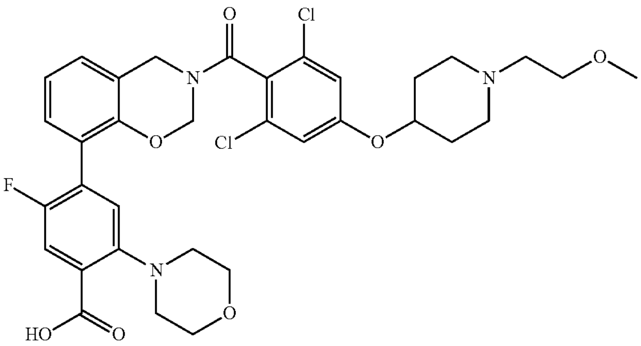 [SMILES: COCCN1CCC(Oc2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-[1-(2-methoxyethyl)piperidin-4-yl]oxybenzoyl]-2,4-dihydro-1,3-benzoxazin-8-yl]-5-fluoro-2-morpholin-4-ylbenzoic acid | B | 1.01, 1.06 | 688 |
| 4-48 | Compound S | 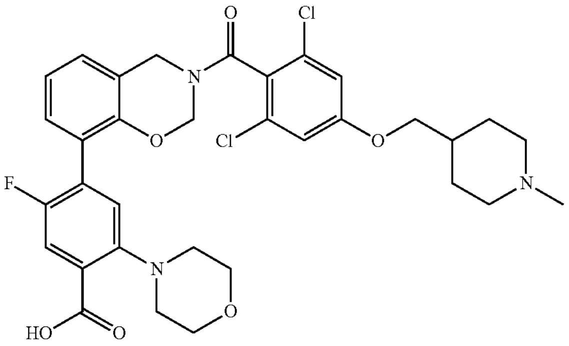 [SMILES: CN1CCC(COc2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-[(1-methyl-piperidin-4-yl)methoxy]benzoyl]-2,4-dihydro-1,3-benzoxazin-8-yl]-5-fluoro-2-morpholin-4-ylbenzoic acid | A | 0.80, 0.84 | 658 |
| 4-49 | Compound S | 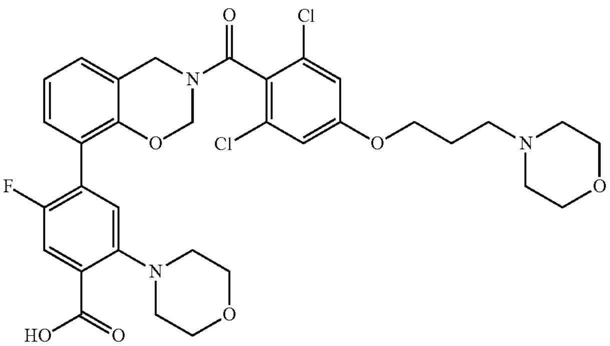 [SMILES: O=C(O)c1cc(F)c(-c2cccc3c2OCN(C(=O)c2c(Cl)cc(OCCCN4CCOCC4)cc2Cl)C3)cc1N1CCOCC1] | 4-[3-[2,6-Dichloro-4-(3-morpholin-4-ylpropoxy)benzoyl]-2,4-dihydro-1,3-benzoxazin-8-yl]-5-fluoro-2-morpholin-4-ylbenzoic acid | B | 0.98, 1.03 | 674 |

TABLE 4-7-continued

| Compound No. | Intermediate No. | Structure | Compound Name | Analysis conditions | HPLC retention time (min) | m/z [M + H] |
| --- | --- | --- | --- | --- | --- | --- |
| 4-50 | Compound S | 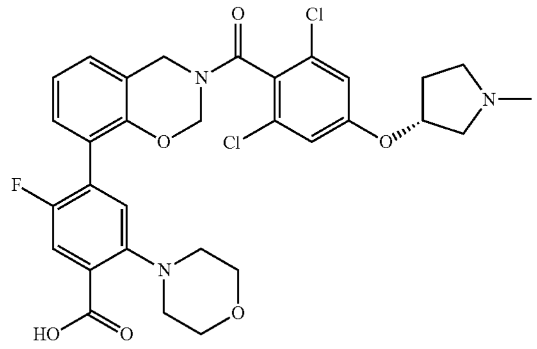 [SMILES: CN1CC[C@@H](Oc2cc(Cl)c(C(=O)N3COc4c(cccc4-c4cc(N5CCOCC5)c(C(=O)O)cc4F)C3)c(Cl)c2)C1] | 4-[3-[2,6-Dichloro-4-[(3R)-1-methylpyrrolidin-3-yl]oxybenzoyl]-2,4-dihydro-1,3-benzoxazin-8-yl]-5-fluoro-2-morpholin-4-ylbenzoic acid | A | 0.76, 0.80 | 630 |
| 4-51 | Compound S | 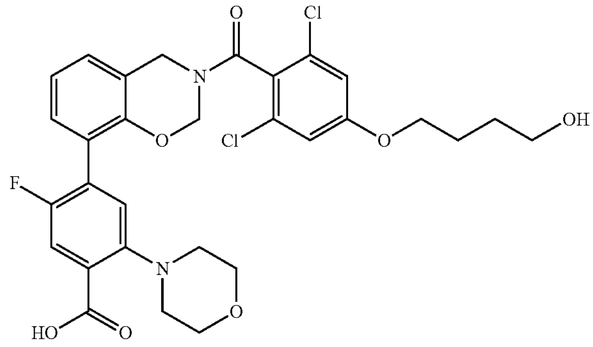 [SMILES: O=C(O)c1cc(F)c(-c2cccc3c2OCN(C(=O)c2c(Cl)cc(OCCCCO)cc2Cl)C3)cc1N1CCOCC1] | 4-[3-[2,6-Dichloro-4-(4-hydroxybutoxy)benzoyl]-2,4-dihydro-1,3-benzoxazin-8-yl]-5-fluoro-2-morpholin-4-ylbenzoic acid | A | 0.98, 1.00 | 619 |
| 4-52 | Compound S | 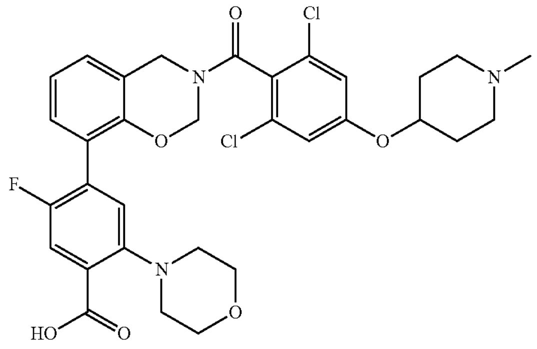 [SMILES: CN1CCC(Oc2cc(Cl)c(C(=O)N3COc4c(cccc4-c4cc(N5CCOCC5)c(C(=O)O)cc4F)C3)c(Cl)c2)CC1] | 4-[3-[2,6-Dichloro-4-(1-methylpiperidin-4-yl)oxybenzoyl]-2,4-dihydro-1,3-benzoxazin-8-yl]-5-fluoro-2-morpholin-4-ylbenzoic acid | A | 0.78, 0.82 | 644 |
| 4-53 | Compound S | 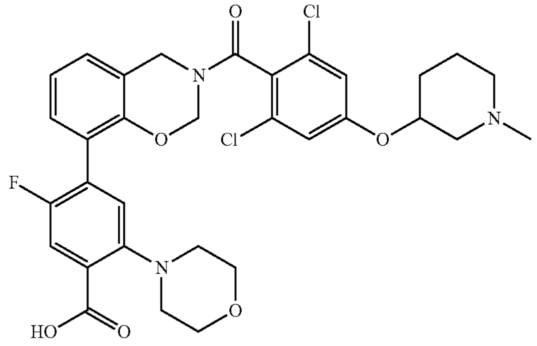 [SMILES: CN1CCCC(Oc2cc(Cl)c(C(=O)N3COc4c(cccc4-c4cc(N5CCOCC5)c(C(=O)O)cc4F)C3)c(Cl)c2)C1] | 4-[3-[2,6-Dichloro-4-(1-methylpiperidin-3-yl)oxybenzoyl]-2,4-dihydro-1,3-benzoxazin-8-yl]-5-fluoro-2-morpholin-4-ylbenzoic acid | A | 0.77, 0.81 | 644 |

TABLE 4-7-continued

| Compound No. | Intermediate No. | Structure | Compound Name | Analysis conditions | HPLC retention time (min) | m/z [M + H] |
|---|---|---|---|---|---|---|
| 4-54 | Compound V | 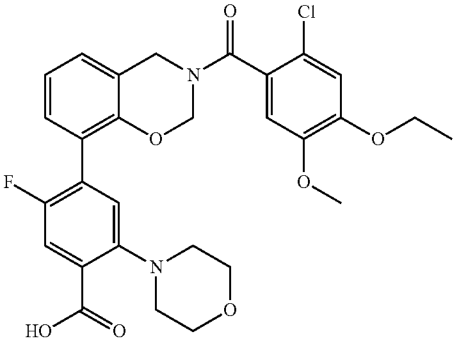 [SMILES: CCOc1cc(Cl)c(C(=O)N2COc3c(cccc3-c3cc(N4CCOCC4)c(C(=O)O)cc3F)C2)cc1OC] | 4-[3-(2-Chloro-4-ethoxy-5-methoxybenzoyl)-2,4-dihydro-1,3-benzoxazin-8-yl]-5-fluoro-2-morpholin-4-ylbenzoic acid | B | 1.40 | 571 |
| 4-55 | Compound V | 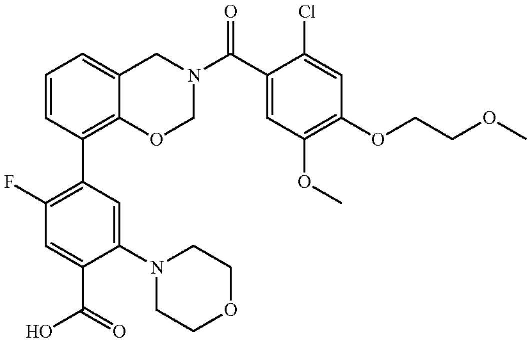 [SMILES: COCCOc1cc(Cl)c(C(=O)N2COc3c(cccc3-c3cc(N4CCOCC4)c(C(=O)O)cc3F)C2)cc1OC] | 4-[3-[2-Chloro-5-methoxy-4-(2-methoxyethoxy)benzoyl]-2,4-dihydro-1,3-benzoxazin-8-yl]-5-fluoro-2-morpholin-4-ylbenzoic acid | B | 1.34 | 601 |

TABLE 4-8

| Final compound No. | Alcohol |
|---|---|
| 4-34 | 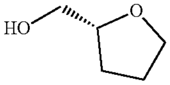 |
| 4-35 | 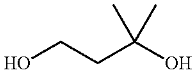 |
| 4-36 | 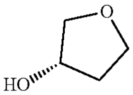 |
| 4-37 | 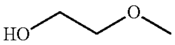 |
| 4-38 | 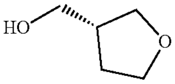 |
| 4-39 | 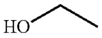 |
| 4-43 | 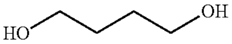 |
| 4-44 | 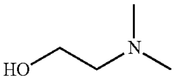 |

TABLE 4-8-continued

| Final compound No. | Alcohol |
|---|---|
| 4-45 | 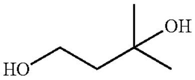 |
| 4-46 | 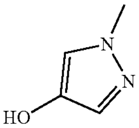 |
| 4-47 | 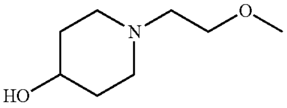 |
| 4-48 | 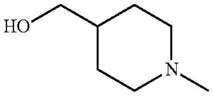 |
| 4-49 | 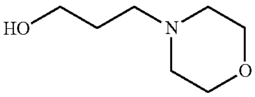 |
| 4-50 | 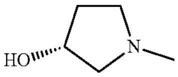 |

TABLE 4-8-continued

| Final compound No. | Alcohol |
|---|---|
| 4-51 | 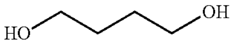 |
| 4-52 | 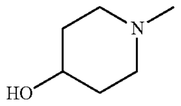 |
| 4-53 | 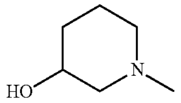 |
| 4-54 | 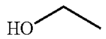 |
| 4-55 | 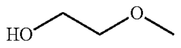 |

Compound 4-40

4-[3-(2,6-Dichloro-4-methoxybenzoyl)-2,4-dihydro-1,3-benzoxazin-8-yl]-5-fluoro-2-(3-oxa-8-azabicyclo[3.2.1]octan-8-yl)benzoic acid

[Formula 218]

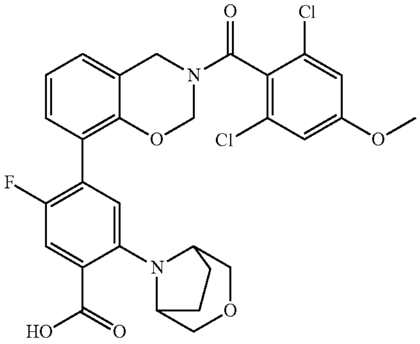

Compound 4-41

4-[3-[2,6-Dichloro-4-(oxan-4-ylmethoxy)benzoyl]-2,4-dihydro-1,3-benzoxazin-8-yl]-5-fluoro-2-(3-oxa-8-azabicyclo[3.2.1]octan-8-yl)benzoic acid

[Formula 219]

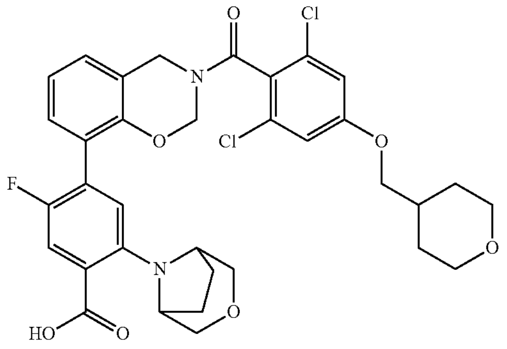

4-[3-(2,6-Dichloro-4-methoxybenzoyl)-2,4-dihydro-1,3-benzoxazin-8-yl]-5-fluoro-2-(3-oxa-8-azabicyclo[3.2.1]octan-8-yl)benzoic acid and 4-[3-[2,6-dichloro-4-(oxan-4-ylmethoxy)benzoyl]-2,4-dihydro-1,3-benzoxazin-8-yl]-5-fluoro-2-(3-oxa-8-azabicyclo[3.2.1]octan-8-yl)benzoic acid were obtained by the same operation as in the process of compound 42 using compound O and oxan-4-ylmethanol.

Compound 4-40

LCMS: m/z 587[M+H]$^+$

HPLC retention time: 1.47 min and 1.49 min (analysis condition B)

Compound 4-41

LCMS: m/z 671[M+H]$^+$

HPLC retention time: 1.54 min and 1.55 min (analysis condition B)

Compound 5-7

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid Synthesis Method A First Step Compound AZ1

Methyl 4-[3-[2,6-dichloro-4-(3-hydroxyazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 220]

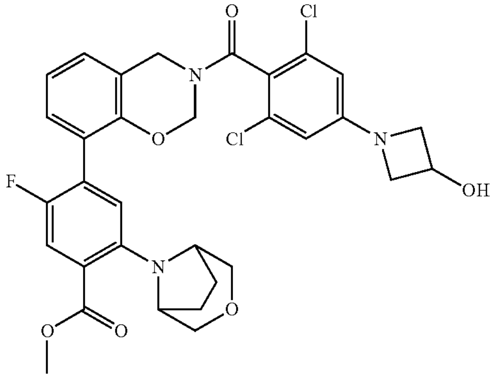

A suspension of compound A (2.00 g, 3.08 mmol), azetidin-3-ol hydrochloride (674 mg, 6.15 mmol), rac-BINAP Pd G4 (217 mg, 0.215 mmol) and cesium carbonate (4.01 g, 12.3 mmol) in 1-methylpyrrolidin-2-one (28.0 mL) and water (2.80 mL) was stirred at 100° C. for 4 hours. An aqueous formic acid solution was added to the reaction mixture, and the mixture was purified by reverse phase column chromatography (acetonitrile/water, 0.1% formic acid) to obtain the title compound (83%, 1.64 g).

LCMS: m/z 642[M+H]$^+$

HPLC retention time: 0.85 min (analysis condition D)

Second Step
Compound AZ2

Methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 221]

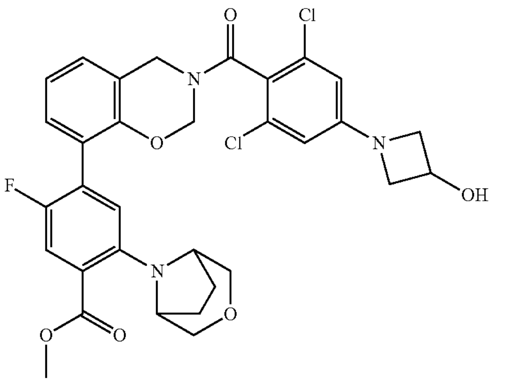

Methyl 4-[3-[2,6-dichloro-4-(3-hydroxyazetidin-1-yl)benzoyl]-2,4-dihydro-1,3-benzoxazin-8-yl]-5-fluoro-2-(3-oxa-8-azabicyclo[3.2.1]octan-8-yl)benzoate (1.64 g, 2.55 mmol) and Dess-Martin periodinane (1.08 g, 2.55 mmol) in dichloromethane (25.5 mL) were stirred at room temperature for 1 hour. Dess-Martin periodinane (0.866 g, 2.04 mmol) was added thereto, and the mixture was further stirred at room temperature for 2 hours. Dichloromethane and an aqueous sodium thiosulfate solution were added to the reaction solution, followed by extraction with ethyl acetate. The organic layer was washed with a saturated aqueous solution of sodium bicarbonate and a saturated aqueous solution of sodium chloride, followed by passing through a phase separator. Then, the organic layer was concentrated, and the obtained residue was purified by reverse phase column chromatography (acetonitrile/water, 0.1% formic acid) to obtain the title compound (81%, 1.33 g).

LCMS: m/z 640[M+H]$^+$

HPLC retention time: 0.91 min (analysis condition D)

Third Step
Compound 5-7

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 222]

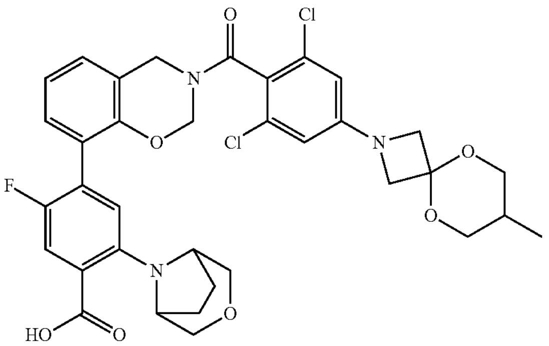

To a solution of methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate (25.0 mg, 0.0390 mmol) and 2-methyl-1,3-propanediol (0.00693 ml, 0.0780 mmol) in acetonitrile (0.195 ml), trimethylsilyl trifluoromethanesulfonate (0.00377 ml, 0.0200 mmol) was added, and the mixture was stirred at room temperature for 1 hour and then stirred at 70° C. for 4 hours. Tetrahydrofuran (0.0980 ml) and methanol (0.0980 ml) were added to the reaction solution, then an 8 M aqueous potassium hydroxide solution (0.0980 ml, 0.780 mmol) was added, and the mixture was stirred at 60° C. for 30 minutes. An aqueous formic acid solution was added to the reaction solution, and the mixture was purified by HPLC (acetonitrile/water, 0.1% formic acid) to obtain the title compound (75%, 20.3 mg).

LCMS: m/z 698[M+H]$^+$

HPLC retention time: 1.60 min and 1.63 min (analysis condition B)

Compound 5-7

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid Synthesis Method B First Step Compound ACP2

Benzyl 7-methyl-5,9-dioxa-2-azaspiro[3.5]nonane-2-carboxylate

[Formula 223]

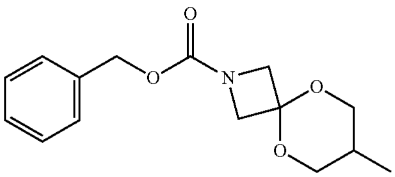

To a solution of benzyl 3-oxoazetidine-1-carboxylate (15.0 g, 73.1 mmol) in acetonitrile (300 mL), 2-methyl-1,3-propanediol (13.0 mL, 146 mmol) and trimethylsilyl trifluoromethanesulfonate (6.60 mL, 36.5 mmol) were added, and the mixture was stirred at 70° C. for 4.5 hours. The reaction solution was cooled to room temperature and concentrated. The obtained residue was dissolved in ethyl acetate and washed with a 5% aqueous sodium bicarbonate solution and a 15% aqueous sodium chloride solution, and the organic layer was then dried over magnesium sulfate and concentrated. The obtained residue was purified by silica gel column chromatography (hexane/ethyl acetate) to obtain the title compound (84%, 17.0 g).

LCMS: m/z 278[M+H]$^+$

HPLC retention time: 1.06 min (analysis condition G)

Second Step

Compound ACP3

7-Methyl-5,9-dioxa-2-azaspiro[3.5]nonane

[Formula 224]

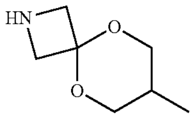

To a solution of benzyl 7-methyl-5,9-dioxa-2-azaspiro[3.5]nonane-2-carboxylate (13.5 g, 48.7 mmol) in 1,4-dioxane (135 mL), 20% palladium hydroxide-active carbon (containing water) (1.20 g, 1.70 mmol) was added, and the mixture was stirred for 16 hours in a hydrogen atmosphere. The reaction solution was filtered through celite and washed with 1,4-dioxane to obtain the title compound as a crude product in a 1,4-dioxane solution.

Third Step

Compound AC7

Methyl 4-[3-[2,6-dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate

[Formula 225]

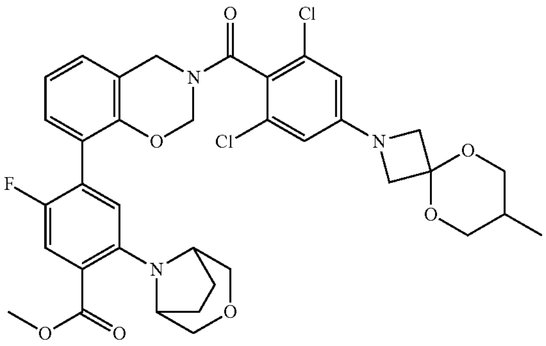

A solution of compound A (15.6 g, 24.0 mmol), 3.05 wt % 7-methyl-5,9-dioxa-2-azaspiro[3.5]nonane in a 1,4-dioxane solution (146 g, 31.2 mmol), cesium carbonate (23.5 g, 72.0 mmol) and rac-BINAP Pd G4 (724 mg, 0.720 mmol) in 1,4-dioxane (109 mL) was stirred at 60° C. for 16 hours. The reaction solution was filtered through celite and washed with ethyl acetate. A 5% aqueous N-acetylcysteine solution was added to the filtrate, and the mixture was stirred at room temperature for 30 minutes for extraction. The organic layer was washed with a 15% aqueous sodium chloride solution, dried over sodium sulfate, and concentrated. The obtained residue was purified by silica gel column chromatography (hexane/ethyl acetate) to obtain the title compound (20.3 g) as a mixture with ethyl acetate.

LCMS: m/z 712[M+H]$^+$

HPLC retention time: 3.22 min (analysis condition AF)

Fourth Step

Compound 5-7

4-[3-[2,6-Dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 226]

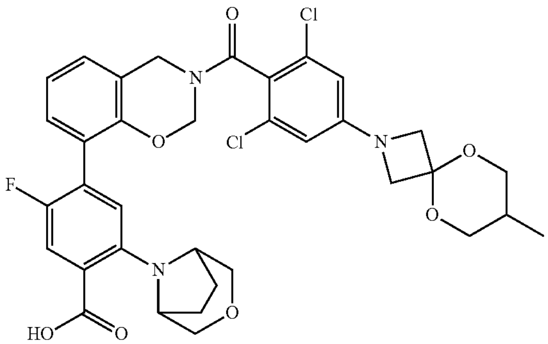

To a solution of methyl 4-[3-[2,6-dichloro-4-(7-methyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate (17.1 g, 24.0 mmol) in tetrahydrofuran (42.7 mL) and methanol (42.7 mL), an 8 M aqueous potassium hydroxide solution (9.00 mL, 72.0 mmol) was added, and the mixture was stirred at 50° C. for 3 hours. The reaction solution was cooled to room temperature. An 8 M aqueous potassium hydroxide solution (0.900 mL, 7.20 mmol) was added thereto, and the mixture was stirred at 50° C. for 1.5 hours. The reaction solution was cooled to room temperature. 1 M hydrochloric acid was added thereto, and the mixture was stirred at room temperature for 1 hour. The resulting solid was collected by filtration, washed with ethanol/water, then washed with ethanol and hexane/ethyl acetate, and further washed with ethanol to obtain the title compound (90%, 15.0 g).

LCMS: m/z 698[M+H]$^+$

HPLC retention time: 1.60 min and 1.63 min (analysis condition B)

Compound 5-9

4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound ACP4

Benzyl 7,7-dimethyl-5,9-dioxa-2-azaspiro[3.5]nonane-2-carboxylate

[Formula 227]

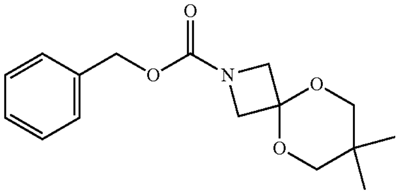

To a solution of benzyl 3-oxoazetidine-1-carboxylate (15.0 g, 73.1 mmol) in acetonitrile (300 mL), 2,2-dimethyl-1,3-propanediol (14.5 ml, 146 mmol) and trimethylsilyl trifluoromethanesulfonate (6.60 ml, 36.5 mmol) were added, and the mixture was stirred at 70° C. for 7 hours. The reaction solution was cooled to room temperature and concentrated. The obtained residue was dissolved in ethyl acetate and washed with a 5% aqueous sodium bicarbonate solution and a 15% aqueous sodium chloride solution, and the organic layer was then dried over magnesium sulfate and concentrated. The obtained residue was purified by silica gel column chromatography (hexane/ethyl acetate) to obtain the title compound (84%, 17.9 g).

LCMS: m/z 292[M+H]$^+$

HPLC retention time: 1.15 min (analysis condition G)

Second Step

Compound ACP5

7,7-Dimethyl-5,9-dioxa-2-azaspiro[3.5]nonane

[Formula 228]

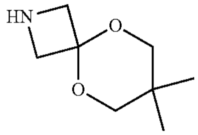

To a solution of benzyl 7,7-dimethyl-5,9-dioxa-2-azaspiro[3.5]nonane-2-carboxylate (3.63 g, 12.5 mmol) in 1,4-dioxane (36.3 mL), 20% palladium hydroxide-active carbon (containing water) (306 mg, 0.436 mmol) was added, and the mixture was stirred for 14 hours in a hydrogen atmosphere. The reaction solution was filtered through celite, washed with 1,4-dioxane, and concentrated to obtain the title compound as a crude product in a 1,4-dioxane solution.

Third Step

Compound AC9

Methyl 4-[3-[2,6-dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate

[Formula 229]

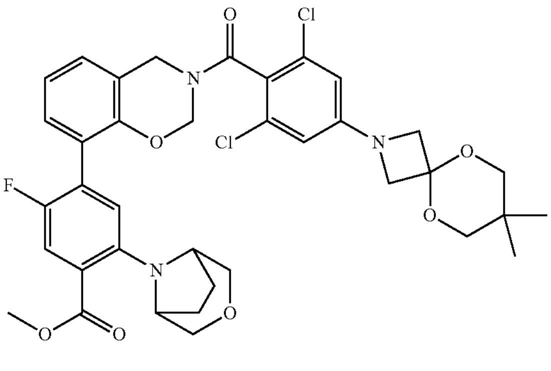

A solution of compound A (4.40 g, 6.77 mmol), 6.58 wt % 7,7-dimethyl-5,9-dioxa-2-azaspiro[3.5]nonane in a 1,4-dioxane solution (21.0 g, 8.80 mmol), cesium carbonate (6.61 g, 20.3 mmol) and rac-BINAP Pd G4 (204 mg, 0.203 mmol) in 1,4-dioxane (30.8 mL) was stirred at 60° C. for 4.5 hours. The reaction solution was filtered through celite and washed with ethyl acetate. The filtrate was washed with a 15% aqueous sodium chloride solution, followed by extraction. The organic layer was dried over sodium sulfate and concentrated. Ethyl acetate and hexane were added to the obtained residue, and the mixture was triturated to quantitatively obtain the title compound (4.96 g).

LCMS: m/z 726[M+H]$^+$

HPLC retention time: 1.48 min (analysis condition G)

Fourth Step

Compound 5-9

4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 230]

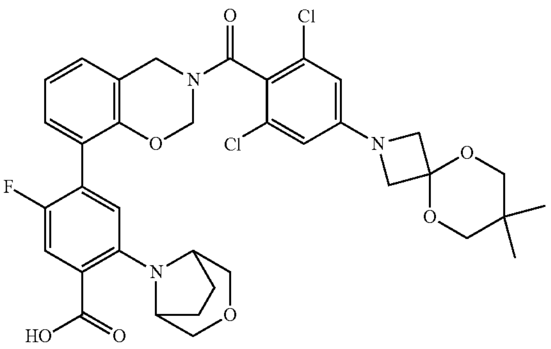

To a solution of methyl 4-[3-[2,6-dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate (12.8 g, 17.6 mmol) in tetrahydrofuran (32.0 mL) and methanol (32.0 mL), an 8 M aqueous potassium hydroxide solution (6.61 mL, 52.8 mmol) was added, and the mixture was stirred at 50° C. for 3 hours. The reaction solution was cooled to room temperature. 1 M hydrochloric acid was added thereto, and water was added, followed by extraction with ethyl acetate. The organic layer was washed with a 3% aqueous N-acetylcysteine solution and a 15% aqueous sodium chloride solution, dried over sodium sulfate, and concentrated. Ethanol was added to the residue, and the mixture was heated at 60° C. Then, water was added thereto, and the mixture was cooled to room temperature. Water was further added thereto, and the obtained solid was collected by filtration and washed with ethanol/water (1/6) to obtain the title compound (88%, 11.0 g).

LCMS: m/z 712[M+H]$^+$

HPLC retention time: 1.68 min and 1.72 min (analysis condition B)

Compound 5-16

4-[3-[2,6-Dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoic acid First Step Compound ACP6

Benzyl 3,3-dimethoxyazetidine-1-carboxylate

[Formula 231]

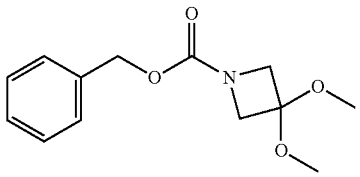

To benzyl 3-oxoazetidine-1-carboxylate (15.0 g, 73.1 mmol), methanol (89 ml, 2.19 mol) and trimethylsilyl trifluoromethanesulfonate (6.60 ml, 36.5 mmol) were added, and the mixture was stirred at 70° C. for 12 hours. The reaction solution was cooled to room temperature and concentrated. The obtained residue was dissolved in ethyl acetate and washed with a 5% aqueous sodium bicarbonate solution and a 15% aqueous sodium chloride solution, and the organic layer was then dried over magnesium sulfate and concentrated. The obtained residue was purified by silica gel column chromatography (hexane/ethyl acetate) to obtain the title compound (90%, 16.5 g).

LCMS: m/z 252[M+H]$^+$

HPLC retention time: 1.00 min (analysis condition G)

Second Step

Compound ACP7

3,3-Dimethoxyazetidine

[Formula 232]

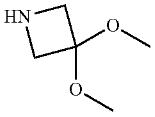

To a solution of benzyl 3,3-dimethoxyazetidine-1-carboxylate (14.5 g, 57.7 mmol) in 1,4-dioxane (145 mL), 20% palladium hydroxide-active carbon (containing water) (1.42 g, 2.02 mmol) was added, and the mixture was stirred for 7 hours in a hydrogen atmosphere. The reaction solution was filtered through celite and washed with 1,4-dioxane to obtain the title compound as a crude product in a 1,4-dioxane solution.

Third Step

Compound AC16

Methyl 4-[3-[2,6-dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoate

[Formula 233]

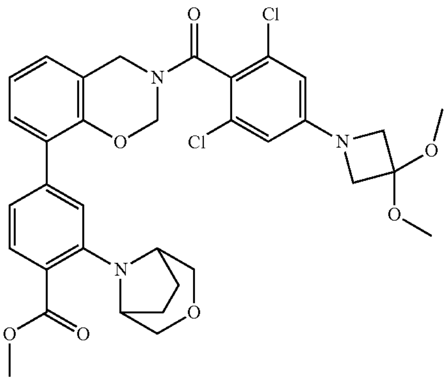

A solution of compound D (15.6 g, 24.7 mmol), 3.15 wt % 3,3-dimethoxyazetidine in a 1,4-dioxane solution (119 g, 32.1 mmol), cesium carbonate (24.1 g, 74.0 mmol) and rac-BINAP Pd G4 (745 mg, 0.740 mmol) in 1,4-dioxane (46.8 mL) was stirred at 60° C. for 16.5 hours. The reaction solution was filtered through celite and washed with ethyl acetate. 2-Methyltetrahydrofuran and a 5% aqueous N-acetylcysteine solution were added to the filtrate, and the mixture was stirred at room temperature for 30 minutes. After filtration, the organic layer was washed with a 15% aqueous sodium chloride solution, dried over sodium sulfate, and concentrated. The obtained residue was purified by silica gel column chromatography (hexane/ethyl acetate) to obtain the title compound (95%, 15.6 g).

LCMS: m/z 668[M+H]$^+$

HPLC retention time: 1.37 min (analysis condition G)

Fourth Step

Compound 5-16

4-[3-[2,6-Dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoic acid

[Formula 234]

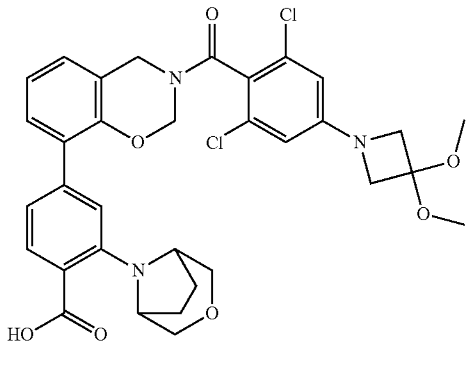

To a solution of methyl 4-[3-[2,6-dichloro-4-(3,3-dimethoxyazetidin-1-yl)benzoyl]-2,4-dihydro-1,3-benzoxazin-8-yl]-2-(3-oxa-8-azabicyclo[3.2.1]octan-8-yl)benzoate (15.6 g, 23.3 mmol) in tetrahydrofuran (39.0 mL) and methanol (39.0 mL), an 8 M aqueous potassium hydroxide solution (8.75 mL, 70.0 mmol) was added, and the mixture was stirred at 50° C. for 3 hours. The reaction solution was cooled to room temperature, and 1 M hydrochloric acid was added thereto. The obtained solid was collected by filtration and washed with ethanol/water (1/4) to obtain the title compound (90%, 13.7 g).

LCMS: m/z 654[M+H]$^+$

HPLC retention time: 1.63 min and 1.65 min (analysis condition B)

Compounds shown in Table 5-1 were synthesized by the same operation as in the third step of compound 5-7 synthesis method A using documented or commercially available diol shown in Table 5-2.

TABLE 5-1

| Compound No. | Structure | Compound Name | Analysis conditions | HPLC retention time (min) | m/z [M + H] |
|---|---|---|---|---|---|
| 5-2 | 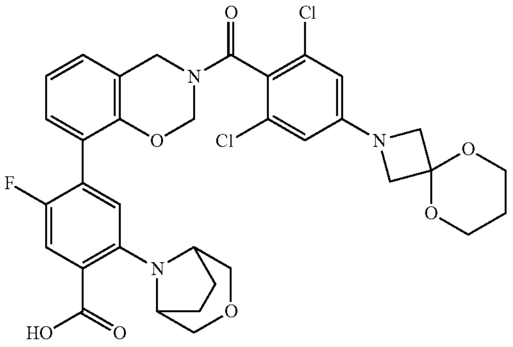 [SMILES: O=C(O)c1cc(F)c(-c2cccc3c2OCN(C(=O)c2c(Cl)cc(N4CC5(C4)OCCCO5)cc2Cl)C3)cc1N1C2CCC1COC2] | 4-[3-[2,6-Dichloro-4-(5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.51, 1.52 | 684 |
| 5-3 | 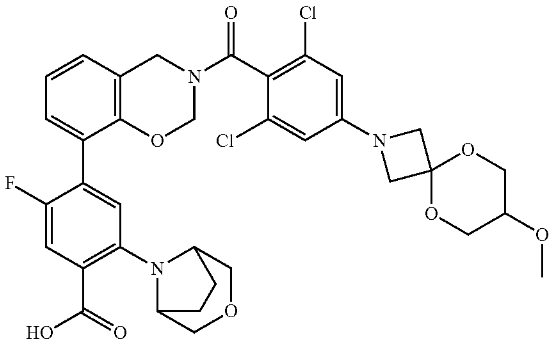 [SMILES: COC1COC2(CN(c3cc(Cl)c(C(=O)N4COc5c(cccc5-c5cc(N6C7CCC6COC7)c(C(=O)O)cc5F)C4)c(Cl)c3)C2)OC1] | 4-[3-[2,6-Dichloro-4-(7-methoxy-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.46 | 714 |
| 5-5 | 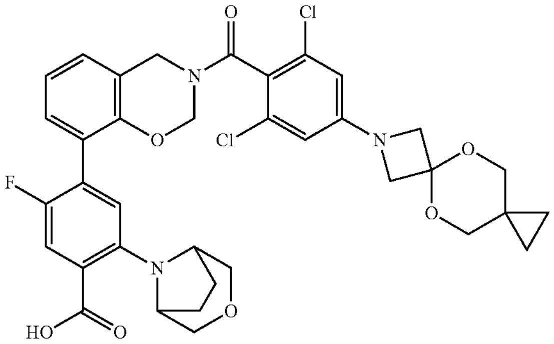 [SMILES: O=C(O)c1cc(F)c(-c2cccc3c2OCN(C(=O)c2c(Cl)cc(N4CC5(C4)OCC4(CC4)CO5)cc2Cl)C3)cc1N1C2CCC1COC2] | 4-[3-[2,6-Dichloro-4-(5,10-dioxa-8-azaspiro[2.2.36.23]undecan-8-yl)benzoyl]-2,4-dihydro-1,3-benzoxazin-8-yl]-5-fluoro-2-(3-oxa-8-azabicyclo[3.2.1]octan-8-yl)benzoic acid | B | 1.59, 1.61 | 710 |

TABLE 5-1-continued

| Compound No. | Structure | Compound Name | Analysis conditions | HPLC retention time (min) | m/z [M + H] |
|---|---|---|---|---|---|
| 5-8 | 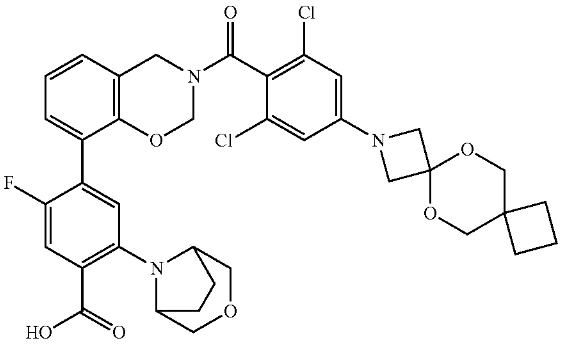 [SMILES: O=C(O)c1cc(F)c(-c2cccc3c2OCN(C(=O)c2c(Cl)cc(N4CC5(C4)OCC4(CCC4)CO5)cc2Cl)C3)cc1N1C2CCC1COC2] | 4-[3-[2,6-Dichloro-4-(6,11-dioxa-9-azadispiro[3.2.37.24]dodecan-9-yl)benzoyl]-2,4-dihydro-1,3-benzoxazin-8-yl]-5-fluoro-2-(3-oxa-8-azabicyclo[3.2.1]octan-8-yl)benzoic acid | B | 1.70, 1.74 | 724 |
| 5-6 | 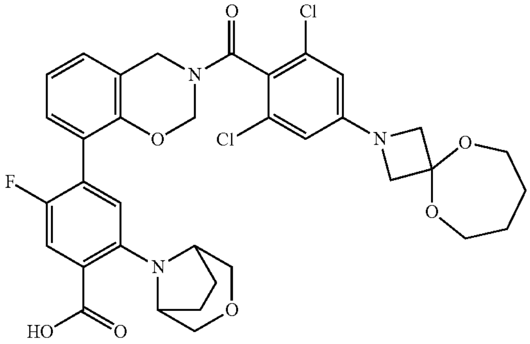 [SMILES: O=C(O)c1cc(F)c(-c2cccc3c2OCN(C(=O)c2c(Cl)cc(N4CC5(C4)OCCCCO5)cc2Cl)C3)cc1N1C2CCC1COC2] | 4-[3-[2,6-Dichloro-4-(5,10-dioxa-2-azaspiro[3.6]decan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.63, 1.67 | 698 |

TABLE 5-2

| Final compound No. | Diol |
|---|---|
| 5-2 | 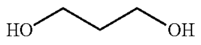 |
| 5-3 | 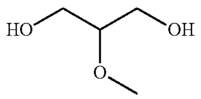 |
| 5-5 | 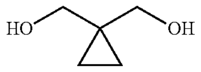 |
| 5-8 | 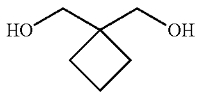 |
| 5-6 | 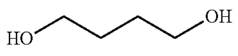 |

Compound 5-1

4-[3-[2,6-Dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid

First Step
Compound AC1

Methyl 4-[3-[2,6-dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 235]

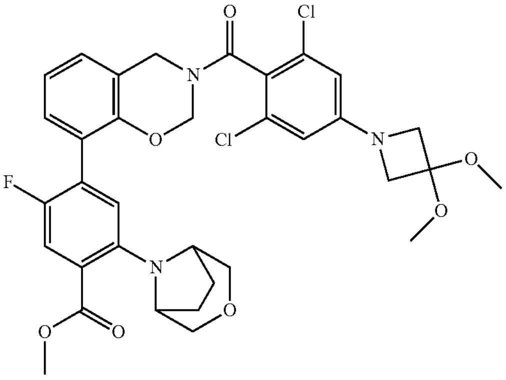

A solution of methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate (1.65 g, 2.58 mmol), p-toluenesulfonic acid monohydrate (147 mg, 0.774 mmol) and methanol (5.22 ml, 129 mmol) in trimethyl o-formate (7.00 ml) was heated at 100° C. for 5 hours. The reaction mixture was purified by reverse phase column chromatography (acetonitrile/water, 0.1% formic acid) to obtain the title compound (67%, 1.18 g).

LCMS: m/z 686[M+H]$^+$

HPLC retention time: 0.98 min (analysis condition D)

Second Step

Compound 5-1

4-[3-[2,6-Dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 236]

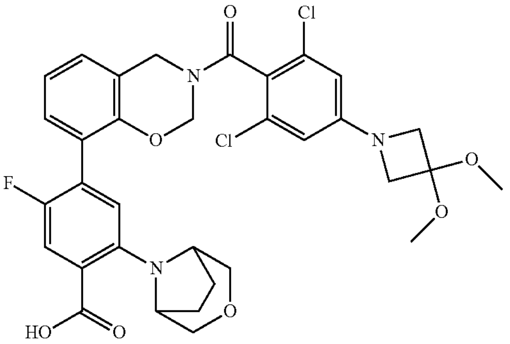

To a solution of methyl 4-[3-[2,6-dichloro-4-(3,3-dimethoxyazetidin-1-yl)benzoyl]-2,4-dihydro-1,3-benzoxazin-8-yl]-5-fluoro-2-(3-oxa-8-azabicyclo[3.2.1]octan-8-yl)benzoate (1.18 g, 1.72 mmol) in tetrahydrofuran (5.60 ml) and methanol (2.80 ml), an 8 M aqueous sodium hydroxide solution (2.15 ml, 17.2 mmol) was added, and the mixture was stirred at 60° C. for 1 hour. An aqueous formic acid solution was added to the reaction solution, and the mixture was then purified by reverse phase column chromatography (acetonitrile/water, 0.1% formic acid) and mixed with another compound obtained by the same method as described above. An organic layer was extracted by the addition of ethyl acetate and water and filtered. The title compound (1.36 g) was obtained by concentration.

LCMS: m/z 672[M+H]$^+$

HPLC retention time: 1.55 min and 1.58 min (analysis condition B)

Compound 5-4

4-[3-[2,6-Dichloro-4-(5,8-dioxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AC4

Methyl 4-[3-[2,6-dichloro-4-(5,8-dioxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate

[Formula 237]

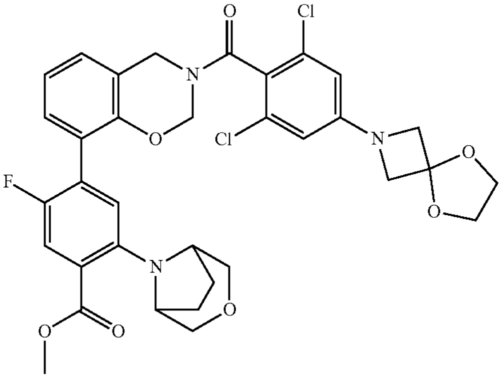

A solution of methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate (35.0 mg, 0.0550 mmol), ethylene glycol (0.00606 ml, 0.109 mmol) and p-toluenesulfonic acid monohydrate (1.04 mg, 0.00546 mmol) in toluene (0.273 ml) was stirred at 110° C. for 4 hours. The reaction solution was purified by HPLC (acetonitrile/water, 0.1% formic acid) to obtain the title compound (5%, 1.9 mg).

LCMS: m/z 684[M+H]$^+$

HPLC retention time: 0.97 min (analysis condition D)

Second Step

Compound 5-4

4-[3-[2,6-Dichloro-4-(5,8-dioxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 238]

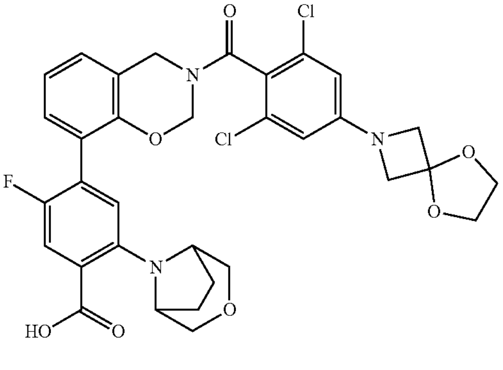

To a solution of methyl 4-[3-[2,6-dichloro-4-(5,8-dioxa-2-azaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate (1.90 mg, 0.00278 mmol) in tetrahydrofuran (0.00925 ml) and methanol (0.0185 ml), an 8 M aqueous sodium hydroxide solution (0.00867 ml, 0.00690 mmol) was added, and the mixture was heated at 60° C. for 1 hour. The reaction solution was purified by HPLC (acetonitrile/water, 0.1% formic acid) to obtain the title compound (32%, 0.60 mg).

LCMS: m/z 670[M+H]+

HPLC retention time: 1.50 min and 1.51 min (analysis condition B)

Compound 5-14

4-[3-[2,6-Dichloro-4-[3-[(3S)-3-methylmorpholin-4-yl]azetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 239]

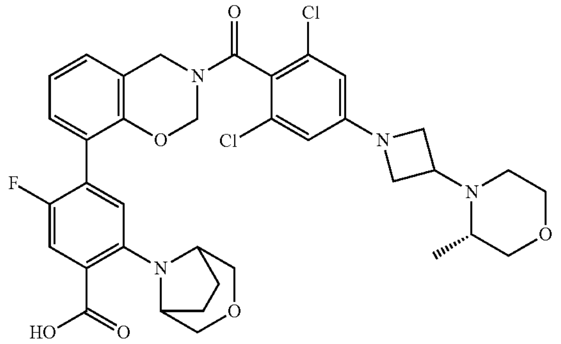

To a solution of methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate (19.2 mg, 0.0300 mmol), S-3-methylmorpholine (0.00606 ml, 0.0600 mmol) and acetic acid (0.00172 ml, 0.0300 mmol) in dichloromethane (0.300 ml), sodium triacetoxyborohydride (12.7 mg, 0.0600 mmol) was added, and the mixture was stirred at room temperature for 5 hours. The reaction solution was concentrated. Methanol (0.150 ml) and tetrahydrofuran (0.150 ml) were added to the residue, then a 5 M aqueous sodium hydroxide solution (0.120 mL, 0.600 mmol) was added, and the mixture was stirred at 60° C. for 1 hour. The reaction mixture was mixed with another compound obtained by the same method as described above, and purified by HPLC (acetonitrile/water, 0.1% formic acid) to obtain the title compound (10.4 mg).

LCMS: m/z 711[M+H]+

HPLC retention time: 1.09 min (analysis condition B)

Compounds shown in Table 5-3 were synthesized by the same operation as in the process of compound 5-14 using documented or commercially available amine shown in Table 5-4 and methyl 4-[3-[2,6-dichloro-4-(3-oxoazetidin-1-yl)benzoyl]-2,4-dihydro-1,3-benzoxazin-8-yl]-5-fluoro-2-(3-oxa-8-azabicyclo[3.2.1]octan-8-yl)benzoate.

TABLE 5-3

| Compound No. | Structure | Compound Name | Analysis conditions | HPLC retention time (min) | m/z [M + H] |
|---|---|---|---|---|---|
| 5-13 | 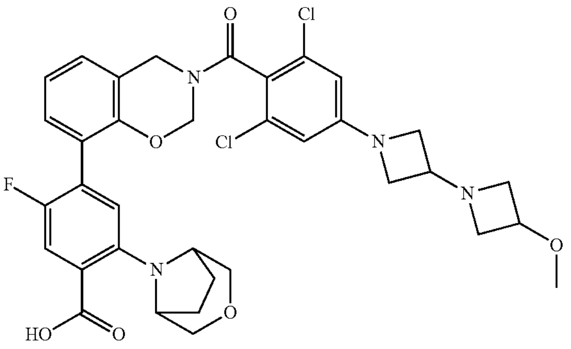 [SMILES: COC1CN(C2CN(c3cc(Cl)c(C(=O)N4COc5c(cccc5-c5cc(N6C7CCC6COC7)c(C(=O)O)cc5F)C4)c(Cl)c3)C2)C1] | 4-[3-[2,6-Dichloro-4-[3-(3-methoxyazetidin-1-yl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.01, 1.05 | 697 |

TABLE 5-3-continued

| Compound No. | Structure | Compound Name | Analysis con-ditions | HPLC retention time (min) | m/z [M + H] |
|---|---|---|---|---|---|
| 5-15 | 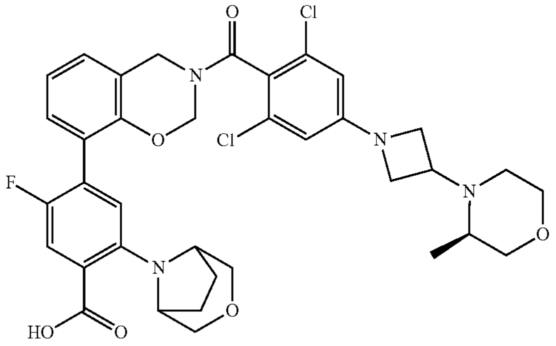 [SMILES: C[C@@H]1COCCN1C1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-[(3R)-3-methylmorpholin-4-yl]azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.08 | 711 |

TABLE 5-4

| Final compound No. | Amine |
|---|---|
| 5-13 | 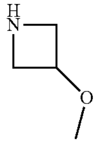 |
| 5-15 | 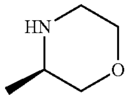 |

Compound 5-10

4-[3-[2,6-Dichloro-4-(7,11-dioxa-2-azadispiro[3.1.56.14]dodecan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AZ3

Methyl 4-[3-[2,6-dichloro-4-(6-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 240]

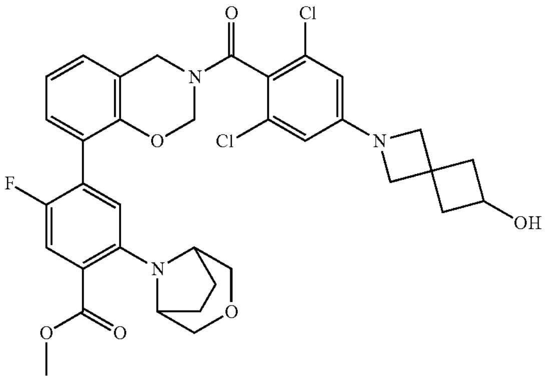

The title compound was obtained by the same operation as in the first step of compound 5-7 synthesis method A using compound A and 2-azaspiro[3.3]heptan-6-ol.

LCMS: m/z 682[M+H]$^+$

HPLC retention time: 0.88 min and 0.89 min (analysis condition D)

Second Step

Compound AZ4

Methyl 4-[3-[2,6-dichloro-4-(6-oxo-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 241]

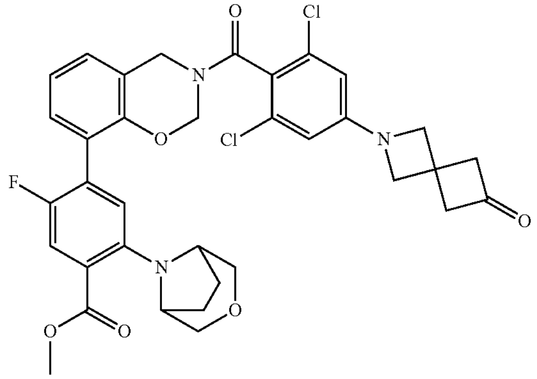

The title compound was obtained by the same operation as in the second step of compound 5-7 synthesis method A using methyl 4-[3-[2,6-dichloro-4-(6-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 680[M+H]$^+$

HPLC retention time: 0.92 min (analysis condition D)

Third Step

Compound 5-10

4-[3-[2,6-Dichloro-4-(7,11-dioxa-2-azadispiro[3.1.56.14]dodecan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 242]

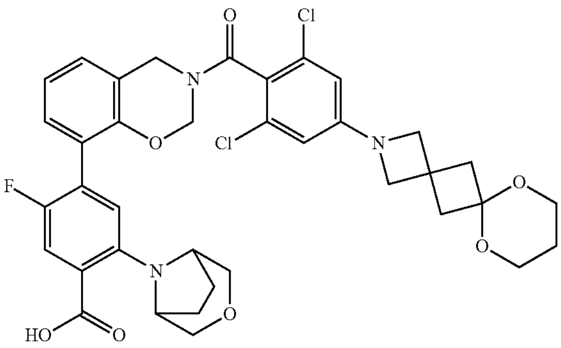

The title compound was obtained by the same operation as in the third step of compound 5-7 synthesis method A using methyl 4-[3-[2,6-dichloro-4-(6-oxo-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate and 1,3-propanediol.

LCMS: m/z 724[M+H]$^+$

HPLC retention time: 1.56 min and 1.57 min (analysis condition B)

Compound 5-11

4-[3-[2,6-Dichloro-4-(6,6-dimethoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AC14

Methyl 4-[3-[2,6-dichloro-4-(6,6-dimethoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 243]

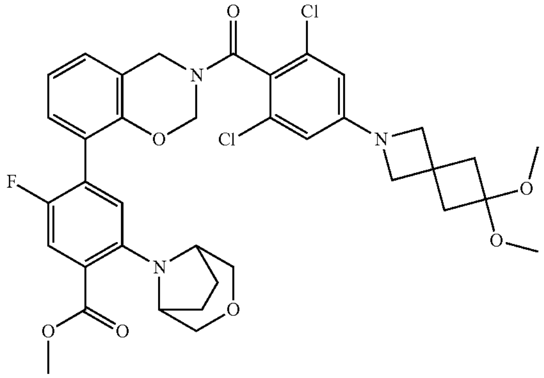

The title compound was obtained by the same operation as in the first step of compound 5-1 using methyl 4-[3-[2,6-dichloro-4-(6-oxo-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 726[M+H]$^+$

HPLC retention time: 1.03 min (analysis condition D)

Second Step

Compound 5-11

4-[3-[2,6-Dichloro-4-(6,6-dimethoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 244]

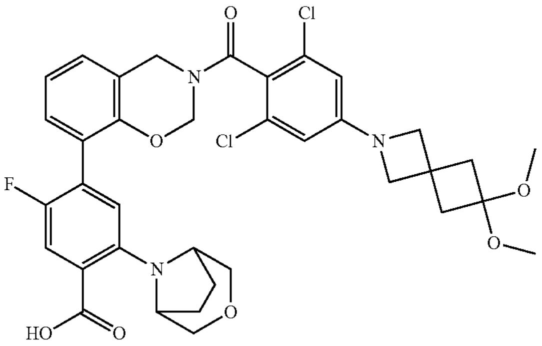

The title compound was obtained by the same operation as in the second step of compound 5-1 using methyl 4-[3-[2,6-dichloro-4-(6,6-dimethoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 712[M+H]$^+$

HPLC retention time: 1.61 min and 1.64 min (analysis condition B)

Compound 5-12

4-[3-[2,6-Dichloro-4-[(2R)-3,3-dimethoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound AZ5

Methyl 4-[3-[2,6-dichloro-4-[(2R)-3-hydroxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 245]

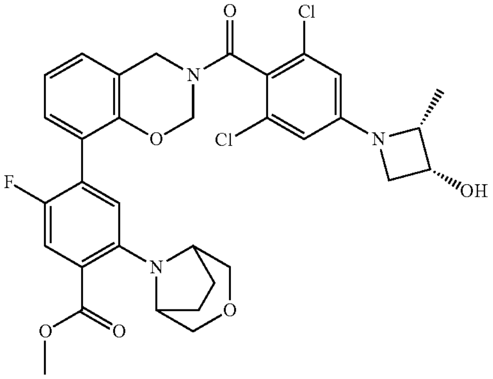

The title compound was obtained by the same operation as in the first step of compound 5-7 synthesis method A using compound A and (2R,3R)-2-methylazetidin-3-ol hydrochloride.

LCMS: m/z 656[M+H]$^+$

HPLC retention time: 0.87 min (analysis condition D)

Second Step

Compound AZ6

Methyl 4-[3-[2,6-dichloro-4-[(2R)-2-methyl-3-oxoazetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 246]

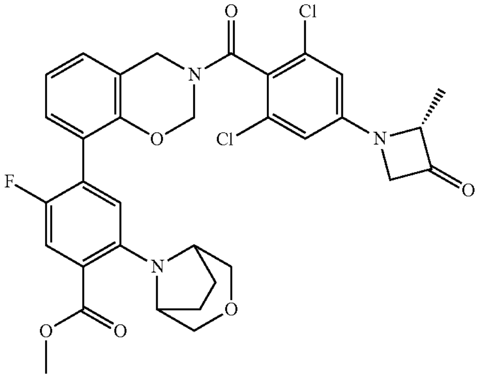

The title compound was obtained by the same operation as in the second step of compound 5-7 synthesis method A using methyl 4-[3-[2,6-dichloro-4-[(2R)-3-hydroxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoate.

LCMS: m/z 654[M+H]$^+$

HPLC retention time: 0.94 min (analysis condition D)

Third Step

Compound AC15

Methyl 4-[3-[2,6-dichloro-4-[(2R)-3,3-dimethoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 247]

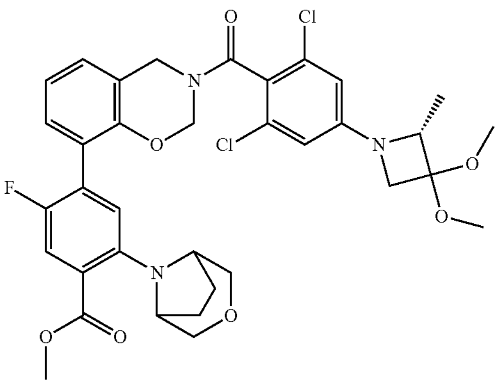

The title compound was obtained by the same operation as in the first step of compound 5-1 using methyl 4-[3-[2,6-dichloro-4-[(2R)-2-methyl-3-oxoazetidin-1-yl]benzoyl]-2,4-dihydro-1,3-benzoxazin-8-yl]-5-fluoro-2-(3-oxa-8-azabicyclo[3.2.1]octan-8-yl)benzoate.

LCMS: m/z 700[M+H]$^+$

HPLC retention time: 1.03 min (analysis condition D)

Fourth Step

Compound 5-12

4-[3-[2,6-Dichloro-4-[(2R)-3,3-dimethoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 248]

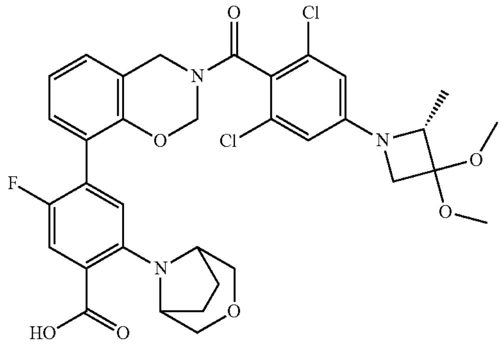

The title compound was obtained by the same operation as in the second step of compound 5-1 using methyl 4-[3-[2,6-dichloro-4-[(2R)-3,3-dimethoxy-2-methylazetidin-1-yl]benzoyl]-2,4-dihydro-1,3-benzoxazin-8-yl]-5-fluoro-2-(3-oxa-8-azabicyclo[3.2.1]octan-8-yl)benzoate.

LCMS: m/z 686[M+H]$^+$

HPLC retention time: 1.61 min and 1.64 min (Analysis condition B)

Compound 6-1

4-[3-[2,6-Dichloro-4-[3-methoxy-3-(methoxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound AL1

Methyl 4-[3-[2,6-dichloro-4-[3-hydroxy-3-(hydroxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 249]

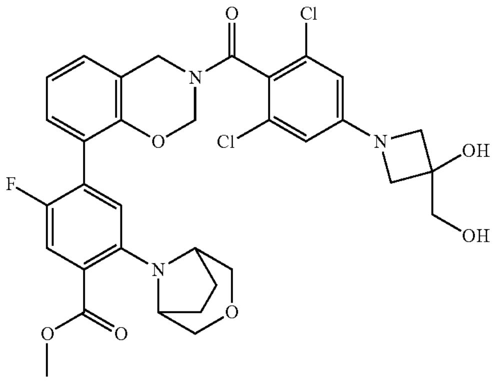

A suspension of compound A (30.0 mg, 0.460 mmol), 3-(hydroxymethyl)azetidin-3-ol oxalate (27.3 mg, 0.0920 mmol), rac-BINAP Pd G4 (2.32 mg, 0.00231 mmol) and cesium carbonate (75.0 mg, 0.231 mmol) in 1,4-dioxane (0.231 mL) was stirred at 110° C. for 1 hour. The reaction mixture was purified by HPLC (acetonitrile/water, 0.1% formic acid) to obtain the title compound (31%, 9.60 mg).

LCMS: m/z 672[M+H]+

HPLC retention time: 0.78 min and 0.80 min (analysis condition D)

Second Step

Compound 6-1

4-[3-[2,6-Dichloro-4-[3-methoxy-3-(methoxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 250]

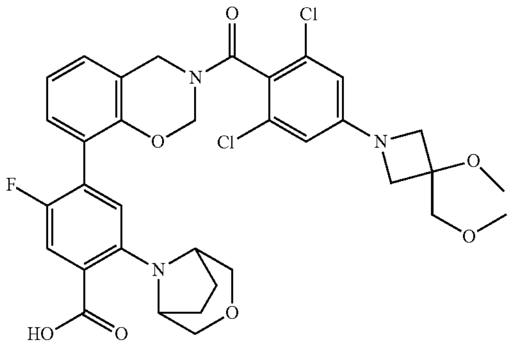

To a solution of methyl 4-[3-[2,6-dichloro-4-[3-hydroxy-3-(hydroxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoate (9.60 mg, 0.0140 mmol) and iodomethane (0.00268 mL, 0.0430 mmol) in tetrahydrofuran, sodium hydride (2.28 mg, 0.0570 mmol) was added at 0° C., and the mixture was stirred at room temperature for 5 hours. Then, an 8 M aqueous potassium hydroxide solution (0.0178 mL, 0.143 mmol) and methanol (0.143 mL) were added thereto at room temperature, and the reaction solution was stirred at 60° C. for 1 hour. The reaction mixture was purified by HPLC (acetonitrile/water, 0.1% formic acid) to obtain the title compound (58.2%, 5.70 mg).

LCMS: m/z 686[M+H]+

HPLC retention time: 1.51 min (analysis condition B)

Compound AL2

Methyl 4-[3-[2,6-dichloro-4-[3-hydroxy-3-(trifluoromethyl)azetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 251]

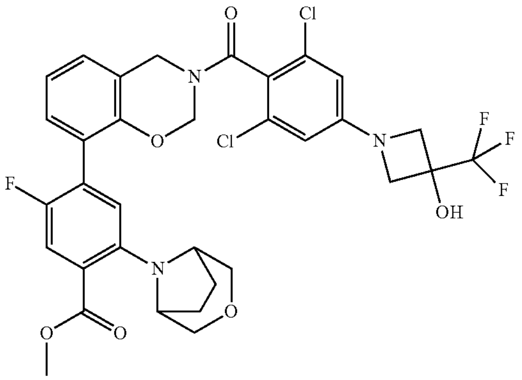

The title compound was synthesized by the same operation as in the first step of compound 6-1 using compound A and 3-(trifluoromethyl)azetidin-3-ol hydrochloride.

LCMS: m/z 710[M+H]+

HPLC retention time: 0.95 min (analysis condition D)

Compound AL3

Methyl 4-[3-[2,6-dichloro-4-[3-fluoro-3-(hydroxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoate

[Formula 252]

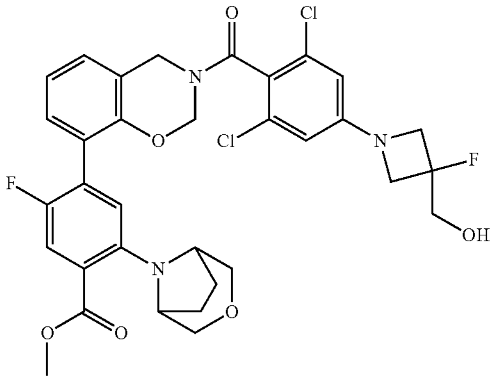

The title compound was synthesized by the same operation as in the first step of compound 6-1 using compound A and (3-fluoroazetidin-3-yl)methanol hydrochloride.

LCMS: m/z 674[M+H]+

HPLC retention time: 0.87 min and 0.88 min (analysis condition D)

Compound AL4

Methyl 4-[3-[2,6-dichloro-4-[rac-(1R,3r,5S)-3-hydroxy-8-azabicyclo[3.2.1]octan-8-yl]benzoyl]-2,4-dihydro-1,3-benzoxazin-8-yl]-5-fluoro-2-(3-oxa-8-azabicyclo[3.2.1]octan-8-yl)benzoate

[Formula 253]

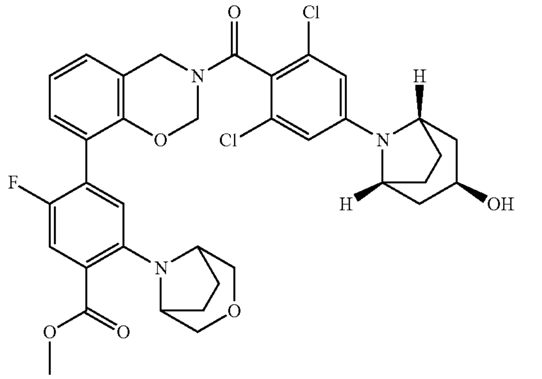

To a solution of compound A (25.0 mg, 0.0420 mmol) in 1-methylpyrrolidin-2-one (0.210 mL), rac-(1R,3r,5S)-8-azabicyclo[3.2.1]octan-3-ol (10.8 mg, 0.0850 mmol) and N,N-diisopropylethylamine (0.0222 mL, 0.127 mmol) were added, and the mixture was stirred at 130° C. for 5 hours under microwave. An aqueous formic acid solution was added to the reaction solution, and the mixture was purified by HPLC (acetonitrile/water, 0.1% formic acid) to obtain the title compound (49%, 14.5 mg).

LCMS: m/z 696[M+H]$^+$

HPLC retention time: 0.92 min (analysis condition D)

Compound AL5

Methyl 4-[3-[2,6-dichloro-4-[rac-(1R,5S,6S)-6-hydroxy-3-azabicyclo[3.2.0]heptan-3-yl]benzoyl]-2,4-dihydro-1,3-benzoxazin-8-yl]-5-fluoro-2-(3-oxa-8-azabicyclo[3.2.1]octan-8-yl)benzoate

[Formula 254]

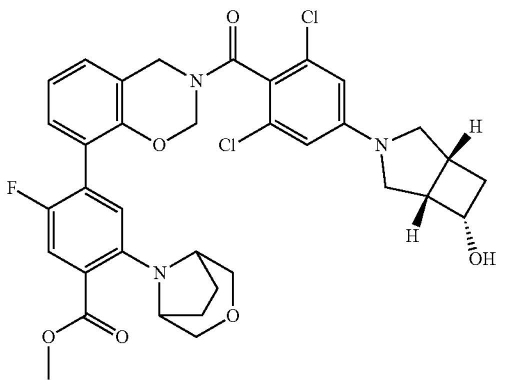

To a solution of tert-butyl rac-(1R,5S,6S)-6-hydroxy-3-azabicyclo[3.2.0]heptane-3-carboxylate (26.2 mg, 0.123 mmol) in dichloromethane (0.262 mL), trifluoroacetic acid (0.262 ml, 3.41 mmol) was added, and the mixture was stirred at room temperature for 1 hour. The reaction mixture was concentrated under reduced pressure to obtain rac-(1R,5S,6S)-3-azabicyclo[3.2.0]heptan-6-ol 2,2,2-trifluoroacetate as a crude product. A solution of the obtained crude product, compound A (40.0 mg, 0.062 mmol), rac-BINAP Pd G4 (6.19 mg, 0.00615 mmol), and cesium carbonate (100 mg, 0.308 mmol) in 1,4-dioxane (0.300 mL) was stirred at 100° C. for 1 hour and then stirred at 120° C. for 2 hours. The reaction solution was purified by HPLC (acetonitrile/water, 0.1% formic acid) to recover a fraction containing the title compound, which was then concentrated. To the obtained mixture of an alcohol form and a ketone form, dichloromethane (0.300 mL), methanol (0.300 mL) and sodium borohydride (4.65 mg, 0.123 mmol) were added, and the mixture was stirred at room temperature for 45 minutes. A saturated aqueous solution of sodium bicarbonate was added to the reaction solution, followed by extraction with dichloromethane. The organic layer was allowed to pass through a phase separator. Then, the organic layer was concentrated, and the obtained residue was purified by silica gel column chromatography (hexane/ethyl acetate) to obtain the title compound (34%, 14.1 mg).

LCMS: m/z 682[M+H]$^+$

HPLC retention time: 1.02 min (analysis condition D)

Compound AL6

Methyl 4-[3-[2,6-dichloro-4-(rac-7-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 255]

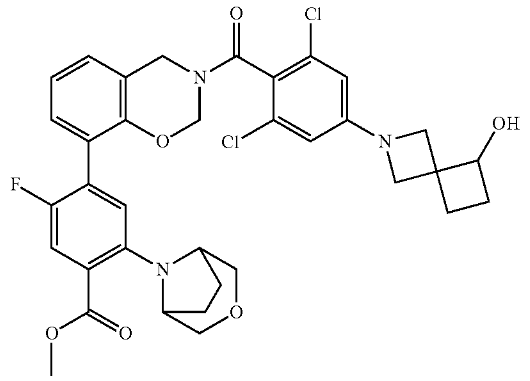

The title compound was synthesized by the same operation as in the process of compound AL5 using tert-butyl rac-7-hydroxy-2-azaspiro[3.3]heptane-2-carboxylate and compound A.

LCMS: m/z 682[M+H]$^+$

HPLC retention time: 1.02 min (analysis condition D)

Compounds shown in Table 6-1 were synthesized by the same operation as in the second step of compound 6-1 using alkylating agents and intermediates shown in Table 6-2. However, a N,N-dimethylformamide solution was used instead of the tetrahydrofuran solution in the synthesis of compounds 6-2, 6-4, 6-5, 6-6, 6-7, and 6-8, and a 1-methylpyrrolidin-2-one solution was used instead of the tetrahydrofuran solution in the synthesis of compounds 6-9, 6-10, 6-11, 6-12, and 6-13. Alkylation reaction was carried out at 80° C. in the synthesis of compound 6-7.

TABLE 6-1

| Compound No. | Structure | Compound Name | Analysis conditions | HPLC retention time (min) | m/z [M + H] |
|---|---|---|---|---|---|
| 6-2 | 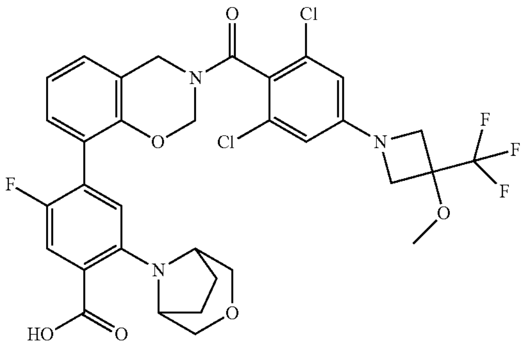 [SMILES: COC1(C(F)(F)F)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-methoxy-3-(trifluoromethyl) azetidin-1-yl] benzoyl]-2,4-dihydro-1,3-benzoxazin-8-yl]-5-fluoro-2-(3-oxa-8-azabicyclo[3.2.1] octan-8-yl)benzoic acid | B | 1.63, 1.65 | 710 |
| 6-3 | 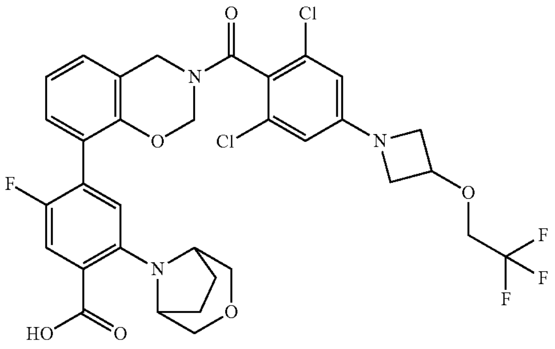 [SMILES: O=C(O)c1cc(F)c(-c2cccc3c2OCN(C(=O)c2c(Cl)cc(N4CC(OCC(F)(F)F)C4)cc2Cl)C3)cc1N1C2CCC1COC2] | 4-[3-[2,6-Dichloro-4-[3-(2,2,2-trifluoroethoxy) azetidin-1-yl] benzoyl]-2,4-dihydro-1,3-benzoxazin-8-yl]-5-fluoro-2-(3-oxa-8-azabicyclo[3.2.1] octan-8-yl)benzoic acid | B | 1.62, 1.63 | 710 |
| 6-4 | 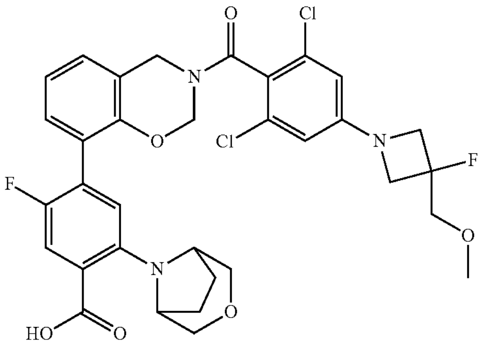 [SMILES: COCC1(F)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-fluoro-3-(methoxymethyl) azetidin-1-yl] benzoyl]-2,4-dihydro-1,3-benzoxazin-8-yl]-5-fluoro-2-(3-oxa-8-azabicyclo[3.2.1] octan-8-yl)benzoic acid | B | 1.53, 1.54 | 674 |
| 6-5 | 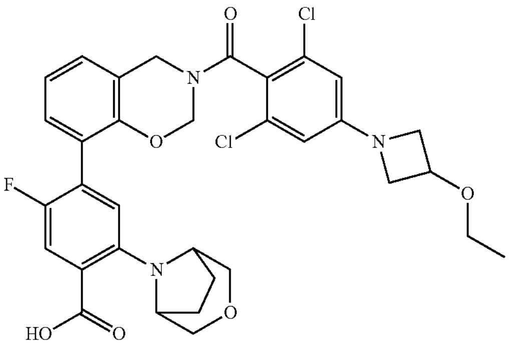 [SMILES: CCOC1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-ethoxyazetidin-1-yl)benzoyl]-2,4-dihydro-1,3-benzoxazin-8-yl]-5-fluoro-2-(3-oxa-8-azabicyclo[3.2.1] octan-8-yl) benzoic acid | B | 1.57, 1.60 | 656 |

TABLE 6-1-continued

| Compound No. | Structure | Compound Name | Analysis conditions | HPLC retention time (min) | m/z [M + H] |
|---|---|---|---|---|---|
| 6-6 | 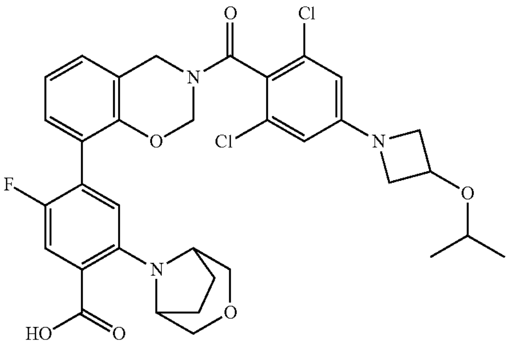 [SMILES: CC(C)OC1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-propan-2-yloxy-azetidin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.64, 1.69 | 670 |
| 6-7 | 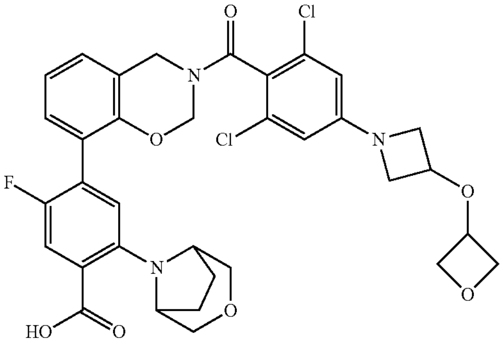 [SMILES: O=C(O)c1cc(F)c(-c2cccc3c2OCN(C(=O)c2c(Cl)cc(N4CC(OC5COC5)C4)cc2Cl)C3)cc1N1C2CCC1COC2] | 4-[3-[2,6-Dichloro-4-[3-(oxetan-3-yloxy)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.44 | 684 |
| 6-8 | 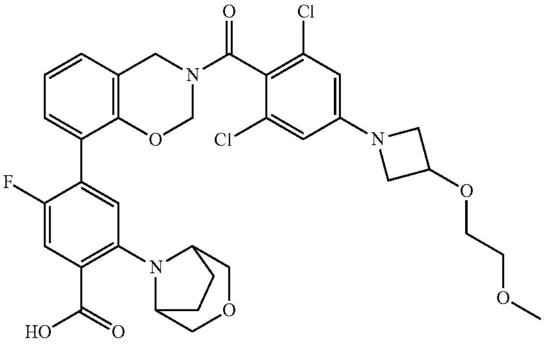 [SMILES: COCCOC1CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-[3-(2-methoxyethoxy)azetidin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.49 | 686 |
| 6-9 | 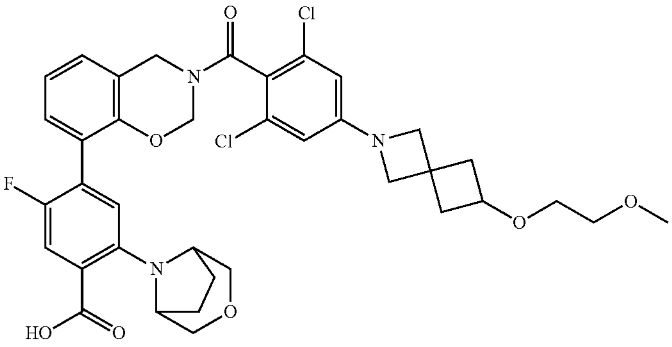 [SMILES: COCCOC1CC2(C1)CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-[6-(2-methoxyethoxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.56, 1.57 | 726 |

TABLE 6-1-continued

| Compound No. | Structure | Compound Name | Analysis conditions | HPLC retention time (min) | m/z [M + H] |
|---|---|---|---|---|---|
| 6-10 | 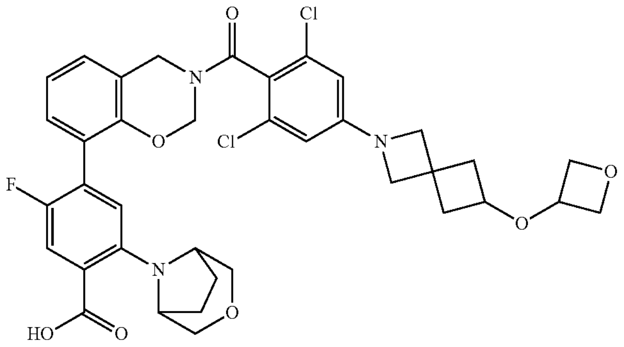 [SMILES: O=C(O)c1cc(F)c(-c2cccc3c2OCN(C(=O)c2c(Cl)cc(N4CC5(CC(OC6COC6)C5)C4)cc2Cl)C3)cc1N1C2CCC1COC2] | 4-[3-[2,6-Dichloro-4-[6-(oxetan-3-yloxy)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.52 | 724 |
| 6-11 | 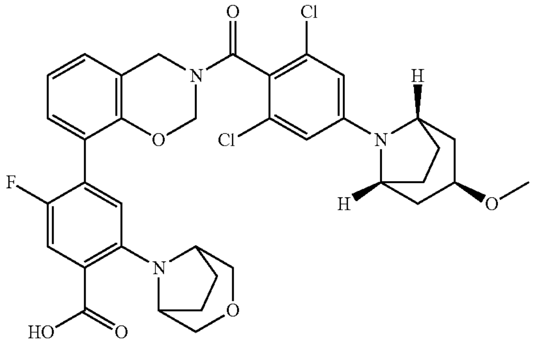 [SMILES: CO[C@H]1C[C@H]2CC[C@@H](C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[rac-(1R,3r,5S)-3-methoxy-8-azabicyclo[3.2.1]octan-8-yl]benzoyl]-2,4-dihydro-1,3-benzoxazin-8-yl]-5-fluoro-2-(3-oxa-8-azabicyclo[3.2.1]octan-8-yl)benzoic acid | B | 1.68, 1.73 | 696 |
| 6-12 | 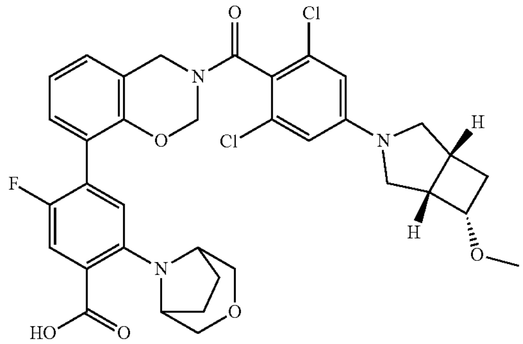 [SMILES: CO[C@H]1C[C@H]2CN(c3cc(Cl)c(C(=O)N4COc5c(cccc5-c5cc(N6C7CCC6COC7)c(C(=O)O)cc5F)C4)c(Cl)c3)C[C@H]21] | 4-[3-[2,6-Dichloro-4-[rac-(1R,5S,6S)-6-methoxy-3-azabicyclo[3.2.0]heptan-3-yl]benzoyl]-2,4-dihydro-1,3-benzoxazin-8-yl]-5-fluoro-2-(3-oxa-8-azabicyclo[3.2.1]octan-8-yl)benzoic acid | B | 1.73, 1.77 | 682 |
| 6-13 | 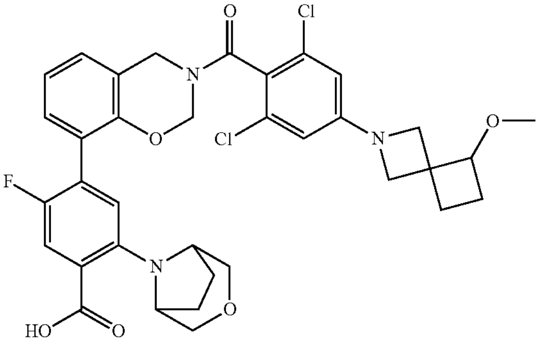 [SMILES: COC1CCC12CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-(rac-7-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.75, 1.80 | 682 |

TABLE 6-2

| Final compound No. | Intermediate | Alkylating agent |
|---|---|---|
| 6-2 | AL2 |  |
| 6-3 | AZ1 | 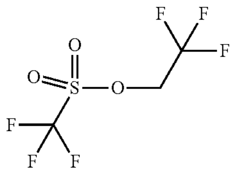 [SMILES: O=S(=O)(OCC(F)(F)F)C(F)(F)F] |
| 6-4 | AL3 |  |
| 6-5 | AZ1 | 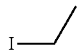 |
| 6-6 | AZ1 | 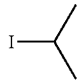 |
| 6-7 | AZ1 | 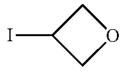 |
| 6-8 | AZ1 | 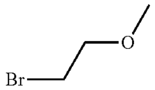 |
| 6-9 | AZ3 | 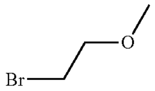 |
| 6-10 | AZ3 | 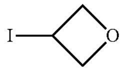 |
| 6-11 | AL4 |  |
| 6-12 | AL5 |  |
| 6-13 | AL6 | 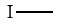 |

Compound 7-2

4-[3-[2,6-Dichloro-4-[6-(2,2-difluoroethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step
Compound BCA1 tert-Butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,6-diazaspiro[3.3]heptane-2-carboxylate

[Formula 256]

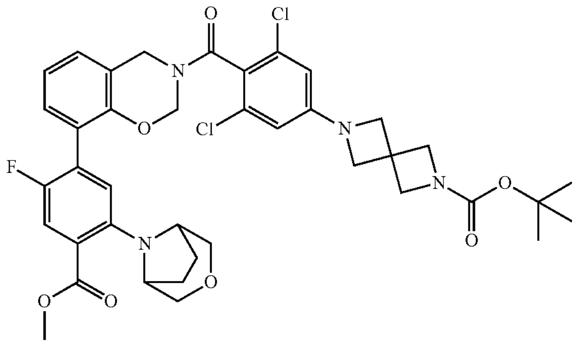

A suspension of compound A (300 mg, 0.461 mmol), tert-butyl 2,6-diazaspiro[3.3]heptane-2-carboxylate oxalate (224 mg, 0.461 mmol), rac-BINAP Pd G4 (46.4 mg, 0.0460 mmol) and cesium carbonate (752 mg, 2.31 mmol) in 1,4-dioxane (2.31 mL) was stirred at 100° C. for 2 hours. The reaction mixture was purified by reverse phase silica gel chromatography (acetonitrile/water, 0.1% formic acid) to obtain the title compound (68%, 240 mg).

LCMS: m/z 767[M+H]$^+$

HPLC retention time: 1.08 min (analysis condition D)

Second Step
Compound AM1

Methyl 4-[3-[2,6-dichloro-4-(2,6-diazaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 257]

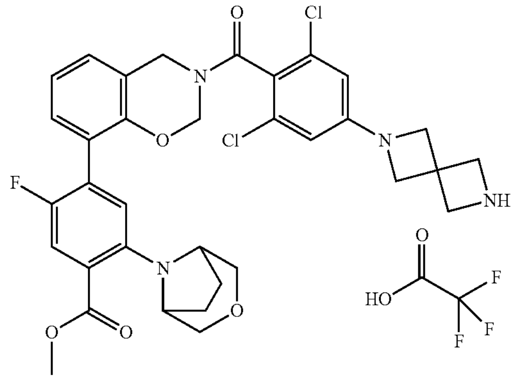

To a solution of tert-butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,6-diazaspiro[3.3]heptane-2-carboxylate (230 mg, 0.300 mmol) in dichloromethane (0.999 mL), trifluoroacetic acid (0.459 ml, 5.99 mmol) was added, and the mixture was stirred at room temperature for 3 hours. The reaction mixture was concentrated under reduced pressure to obtain the title compound as a crude product.

LCMS: m/z 667[M+H]$^+$

HPLC retention time: 0.64 min and 0.66 min (analysis condition D)

Third Step

Compound 7-2

4-[3-[2,6-Dichloro-4-[6-(2,2-difluoroethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 258]

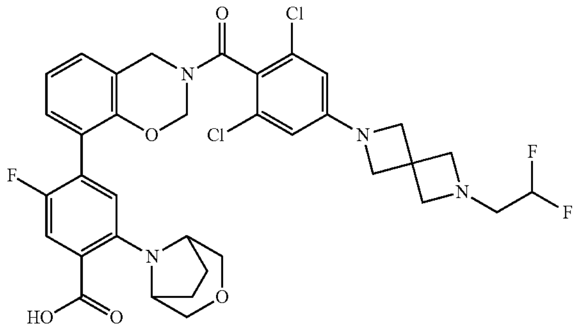

To a solution of methyl 4-[3-[2,6-dichloro-4-(2,6-diazaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (20.0 mg, 0.0260 mmol) in acetonitrile (0.128 mL), 2,2-difluoroethyl trifluoromethanesulfonate (0.00678 ml, 0.0510 mmol) and N,N-diisopropylethylamine (0.0134 ml, 0.0770 mmol) were added at 0° C., and the mixture was stirred at room temperature for 3 hours. Then, a 5 M aqueous sodium hydroxide solution (0.0512 ml, 0.256 mmol) and 1-methylpyrrolidin-2-one (0.256 mL) were added thereto at room temperature, and the reaction solution was stirred at 60° C. for 1 hour. The reaction mixture was purified by HPLC (acetonitrile/water, 0.1% formic acid) to obtain the title compound (43%, 7.90 mg).

LCMS: m/z 717[M+H]$^+$

HPLC retention time: 1.16 min and 1.18 min (analysis condition B)

Compound 7-7

4-[3-[2,6-Dichloro-4-[6-(2-cyano-2-methylpropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound AM77

Methyl 4-[3-[2,6-dichloro-4-[6-(2-cyano-2-methylpropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoate

[Formula 259]

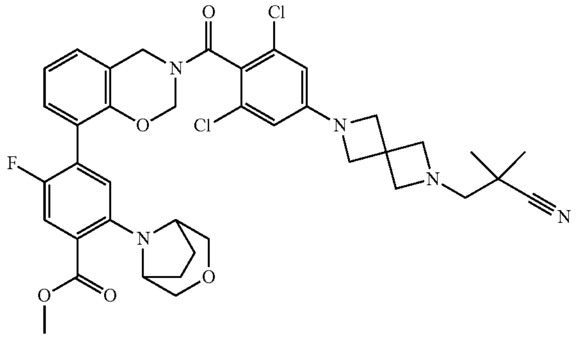

To a solution of methyl 4-[3-[2,6-dichloro-4-(2,6-diazaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (46.0 mg, 0.0690 mmol) in acetonitrile (2.00 mL), (2-cyano-2-methylpropyl)trifluoromethanesulfonate (47.8 mg, 0.207 mmol) and N,N-diisopropylethylamine (0.0840 mL, 0.482 mmol) were added, and the mixture was stirred at room temperature for 15 hours. The reaction mixture was purified by HPLC (acetonitrile/water, 0.1% formic acid) to obtain the title compound (58%, 29.8 mg).

LCMS: m/z 748[M+H]$^+$

HPLC retention time: 0.72 min (analysis condition D)

Second Step

Compound 7-7

4-[3-[2,6-Dichloro-4-[6-(2-cyano-2-methylpropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 260]

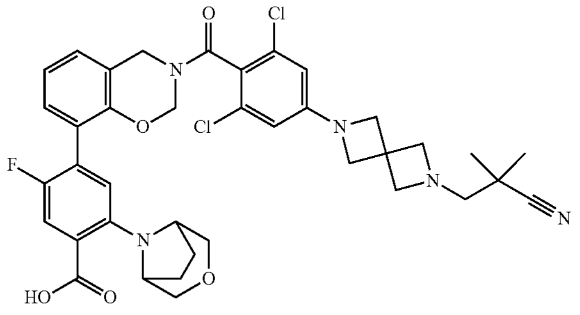

To a solution of methyl 4-[3-[2,6-dichloro-4-[6-(2-cyano-2-methylpropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoate (29.8 mg, 0.0400 mmol) in 1,4-dioxane (0.400 mL), hydroxy(trimethyl)stannane (72.0 mg, 0.398 mmol) was added, and the mixture was stirred at 110° C. for 24 hours. The reaction mixture was purified by HPLC (acetonitrile/water, 0.1% formic acid) to obtain the title compound (39%, 11.4 mg).

LCMS: m/z 734[M+H]$^+$

HPLC retention time: 1.23 min and 1.25 min (analysis condition B)

Compound BCA2 tert-Butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-1,6-diazaspiro[3.3]heptane-1-carboxylate

[Formula 261]

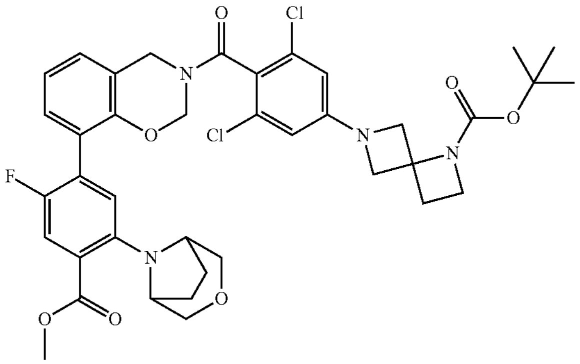

The title compound was synthesized by the same operation as in the first step of compound 7-2. However, tert-butyl 1,6-diazaspiro[3.3]heptane-1-carboxylate oxalate was used instead of tert-butyl 2,6-diazaspiro[3.3]heptane-2-carboxylate oxalate as amine.

LCMS: m/z 767[M+H]$^+$

HPLC retention time: 1.08 min (analysis condition D)

Compound BCA3 tert-Butyl (3S)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3-methylpiperazine-1-carboxylate

[Formula 262]

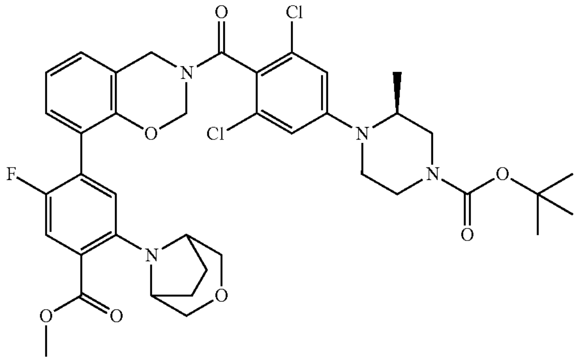

The title compound was synthesized by the same operation as in the first step of compound 7-2. However, tert-butyl (3S)-3-methylpiperazine-1-carboxylate was used instead of tert-butyl 2,6-diazaspiro[3.3]heptane-2-carboxylate oxalate as amine.

LCMS: m/z 769[M+H]$^+$

HPLC retention time: 1.08 min (analysis condition D)

Compound BCA4 tert-Butyl (3R)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3-methylpiperazine-1-carboxylate

[Formula 263]

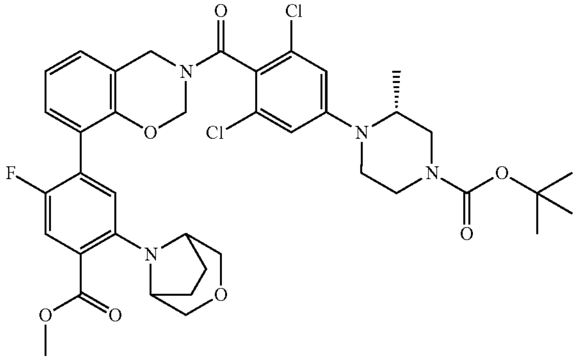

The title compound was synthesized by the same operation as in the first step of compound 7-2. However, tert-butyl (3R)-3-methylpiperazine-1-carboxylate was used instead of tert-butyl 2,6-diazaspiro[3.3]heptane-2-carboxylate oxalate as amine.

LCMS: m/z 769[M+H]$^+$

HPLC retention time: 1.08 min (analysis condition D)

Compound BCA5 tert-Butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,6-diazabicyclo[3.1.1]heptane-3-carboxylate

[Formula 264]

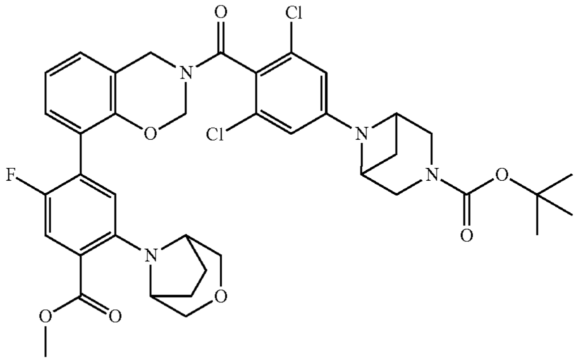

The title compound was synthesized by the same operation as in the first step of compound 7-2. However, tert-butyl 3,6-diazabicyclo[3.1.1]heptane-3-carboxylate was used instead of tert-butyl 2,6-diazaspiro[3.3]heptane-2-carboxylate oxalate as amine.

LCMS: m/z 767[M+H]+

HPLC retention time: 1.03 min (analysis condition D)

Compound BCA6 tert-Butyl 3-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,8-diazabicyclo[3.2.1]octane-8-carboxylate

[Formula 265]

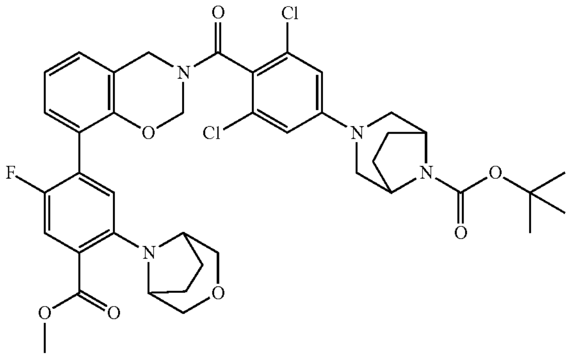

The title compound was synthesized by the same operation as in the first step of compound 7-2. However, tert-butyl 3,8-diazabicyclo[3.2.1]octane-8-carboxylate was used instead of tert-butyl 2,6-diazaspiro[3.3]heptane-2-carboxylate oxalate as amine.

LCMS: m/z 781[M+H]+

HPLC retention time: 1.10 min (analysis condition D)

Compound BCA7 tert-Butyl 8-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,8-diazabicyclo[3.2.1]octane-3-carboxylate

[Formula 266]

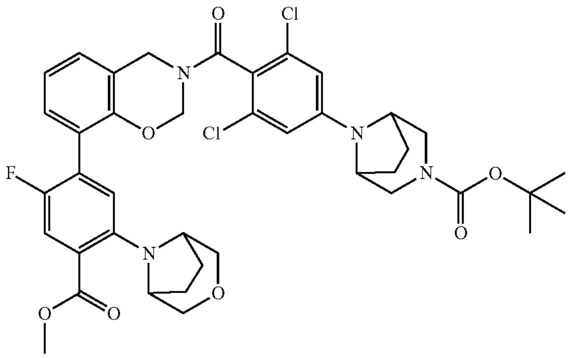

The title compound was synthesized by the same operation as in the first step of compound 7-2. However, tert-butyl 3,8-diazabicyclo[3.2.1]octane-3-carboxylate was used instead of tert-butyl 2,6-diazaspiro[3.3]heptane-2-carboxylate oxalate as amine.

LCMS: m/z 781 [M+H]+

HPLC retention time: 1.08 min (analysis condition D)

Compound BCA8 tert-Butyl 3-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,6-diazabicyclo[3.1.1]heptane-6-carboxylate

[Formula 267]

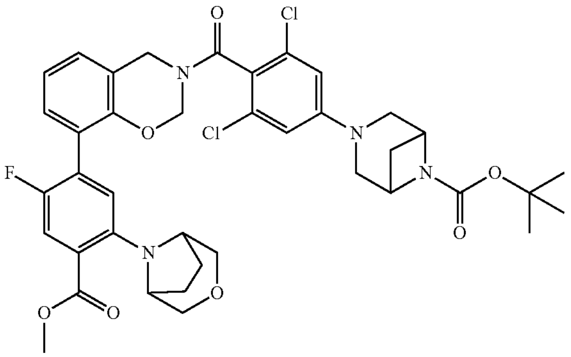

The title compound was synthesized by the same operation as in the first step of compound 7-2. However, tert-butyl 3,6-diazabicyclo[3.1.1]heptane-6-carboxylate was used instead of tert-butyl 2,6-diazaspiro[3.3]heptane-2-carboxylate oxalate as amine.

LCMS: m/z 767[M+H]+

HPLC retention time: 1.06 min (analysis condition D)

Compound BCA9 tert-Butyl (1R,4R)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate

[Formula 268]

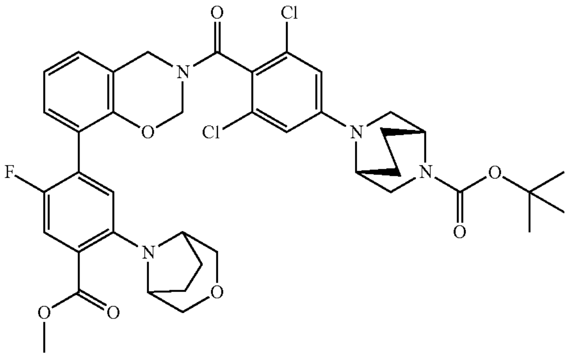

The title compound was synthesized by the same operation as in the first step of compound 7-2. However, tert-butyl (1R,4R)-2,5-diazabicyclo[2.2.2]octane-2-carboxylate was used instead of tert-butyl 2,6-diazaspiro[3.3]heptane-2-carboxylate oxalate as amine.

LCMS: m/z 781 [M+H]+

HPLC retention time: 1.11 min (analysis condition D)

Compound BCA10 tert-Butyl (1S,4S)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate

[Formula 269]

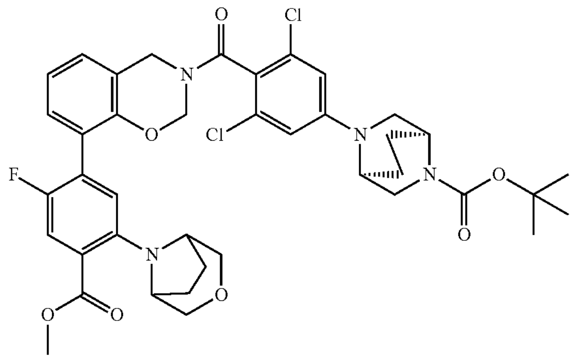

The title compound was synthesized by the same operation as in the first step of compound 7-2. However, tert-butyl (1S,4S)-2,5-diazabicyclo[2.2.2]octane-2-carboxylate was used instead of tert-butyl 2,6-diazaspiro[3.3]heptane-2-carboxylate oxalate as amine.

LCMS: m/z 781[M+H]$^+$

HPLC retention time: 1.11 min (analysis condition D)

Compound AM2

Methyl 4-[3-[2,6-dichloro-4-(1,6-diazaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoate

[Formula 270]

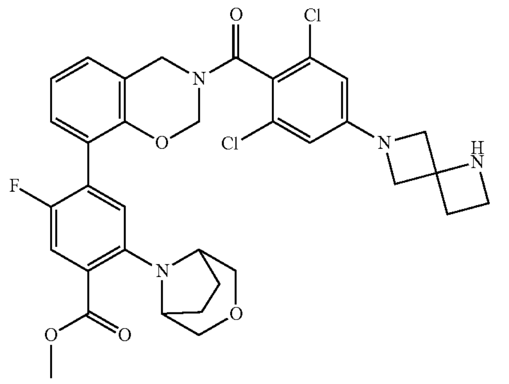

To a solution of tert-butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-1,6-diazaspiro[3.3]heptane-1-carboxylate (111 mg, 0.145 mmol) in dichloromethane (0.289 mL), trifluoroacetic acid (0.221 mL, 2.89 mmol) was added, and the mixture was stirred at room temperature for 2 hours. Ethyl acetate was added to the reaction solution, and the mixture was neutralized by the addition of an aqueous sodium hydroxide solution, followed by extraction with ethyl acetate. The organic layer was concentrated to obtain the title compound as a crude product.

LCMS: m/z 667[M+H]$^+$

HPLC retention time: 0.66 min and 0.67 min (analysis condition D)

Compound AM3

Methyl 4-[3-[2,6-dichloro-4-1[(2S)-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 271]

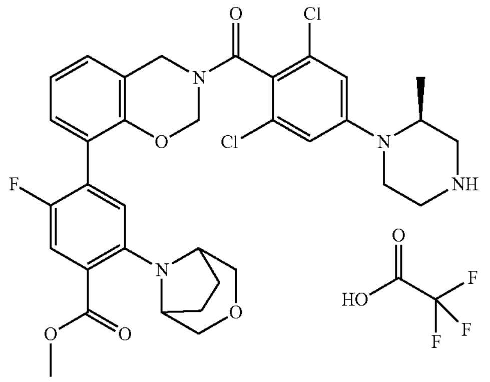

The title compound was synthesized by the same operation as in the second step of compound 7-2 using tert-butyl (3S)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3-methylpiperazine-1-carboxylate.

LCMS: m/z 669[M+H]$^+$

HPLC retention time: 0.62 min and 0.64 min (analysis condition D)

Compound AM4

Methyl 4-[3-[2,6-dichloro-4-1[(2R)-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 272]

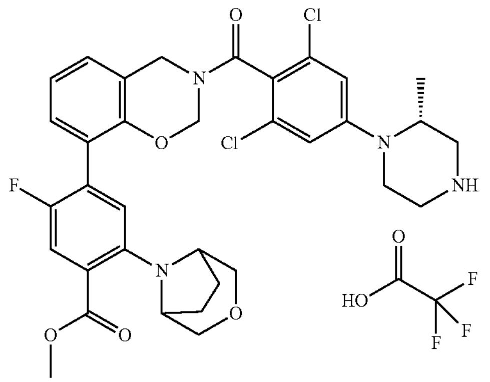

The title compound was synthesized by the same operation as in the second step of compound 7-2 using tert-butyl (3R)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3-methylpiperazine-1-carboxylate.

LCMS: m/z 669[M+H]$^+$

HPLC retention time: 0.63 min and 0.65 min (analysis condition D)

Compound AM5

Methyl 4-[3-[2,6-dichloro-4-(3,6-diazabicyclo[3.1.1]heptan-6-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 273]

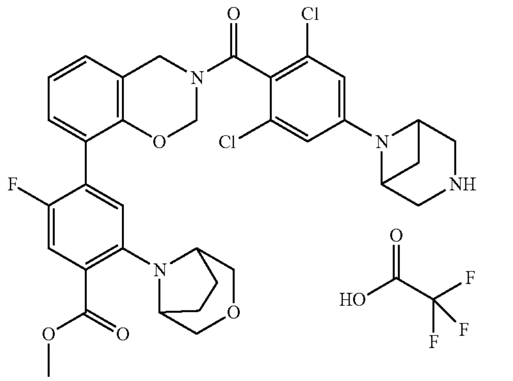

The title compound was synthesized by the same operation as in the second step of compound 7-2 using tert-butyl 6-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,6-diazabicyclo[3.1.1]heptan-3-carboxylate.

LCMS: m/z 667[M+H]$^+$

HPLC retention time: 0.66 min (analysis condition D)

Compound AM6

Methyl 4-[3-[2,6-dichloro-4-(3,8-diazabicyclo[3.2.1]octan-3-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 274]

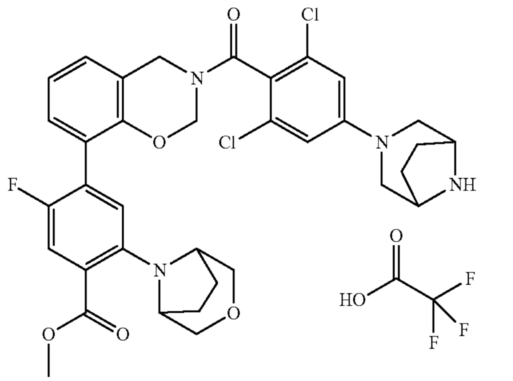

The title compound was synthesized by the same operation as in the second step of compound 7-2 using tert-butyl 3-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,8-diazabicyclo[3.2.1]octane-8-carboxylate.

LCMS: m/z 681 [M+H]$^+$

HPLC retention time: 0.64 min and 0.65 min (analysis condition D)

Compound AM7

Methyl 4-[3-[2,6-dichloro-4-(3,8-diazabicyclo[3.2.1]octan-8-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 275]

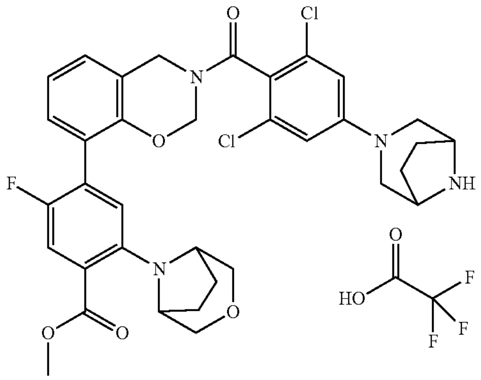

The title compound was synthesized by the same operation as in the second step of compound 7-2 using tert-butyl 8-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,8-diazabicyclo[3.2.1]octane-3-carboxylate.

LCMS: m/z 681 [M+H]$^+$

HPLC retention time: 0.64 min (analysis condition D)

Compound AM8

Methyl 4-[3-[2,6-dichloro-4-(3,5-dimethylpiperazin-1-yl)benzoyl]-2,4-dihydro-1,3-benzoxazin-8-yl]-5-fluoro-2-(3-oxa-8-azabicyclo[3.2.1]octan-8-yl)benzoate

[Formula 276]

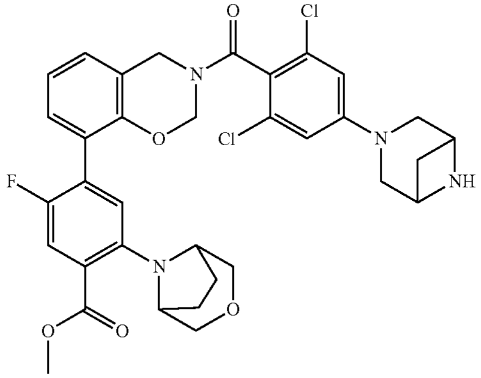

The title compound was synthesized by the same operation as in the process of compound AM2 using tert-butyl 3-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,6-diazabicyclo[3.1.1]heptane-6-carboxylate.

LCMS: m/z 667[M+H]$^+$

HPLC retention time: 0.64 min and 0.65 min (analysis condition D)

Compound AM9

Methyl 4-[3-[2,6-dichloro-4-[(1R,4R)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 277]

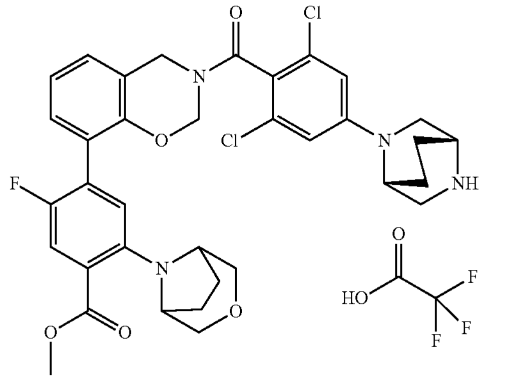

The title compound was synthesized by the same operation as in the second step of compound 7-2 using tert-butyl (1R,4R)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate.

LCMS: m/z 681[M+H]$^+$

HPLC retention time: 0.66 min and 0.67 min (analysis condition D)

Compound AM10

Methyl 4-[3-[2,6-dichloro-4-[(1S,4S)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 278]

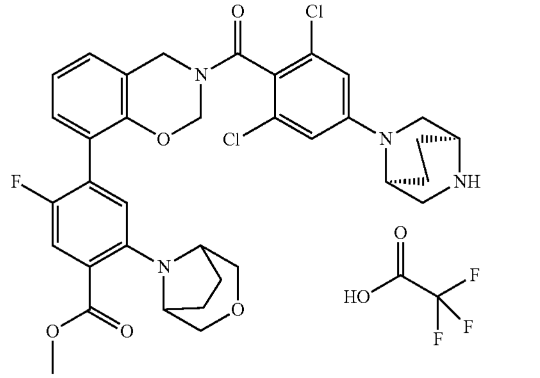

The title compound was synthesized by the same operation as in the second step of compound 7-2 using tert-butyl (1S,4S)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate.

LCMS: m/z 681 [M+H]$^+$

HPLC retention time: 0.66 min and 0.67 min (analysis condition D)

Compounds shown in Table 7-1 were synthesized by the same operation as in the third step of compound 7-2 using alkylating agents and intermediates shown in Table 7-2. However, a N,N-dimethylformamide solution was used instead of the acetonitrile solution in the synthesis of compounds 7-6, 7-10, 7-11, 7-12, 7-14, 7-16, and 7-17, and a 1-methylpyrrolidin-2-one solution was used instead of the acetonitrile solution in the synthesis of compounds 7-8 and 7-9. Tetramethylammonium iodide was added at 0.1 equivalents for compound 7-3. Potassium iodide was added at 0.2 equivalents for compounds 7-6, 7-8, 7-9, 7-10, 7-11, 7-12, 7-14, 7-16 and 7-17.

TABLE 7-1

| Compound No. | Structure | Compound Name | Analysis conditions | HPLC retention time (min) | m/z [M + H] |
|---|---|---|---|---|---|
| 7-1 | 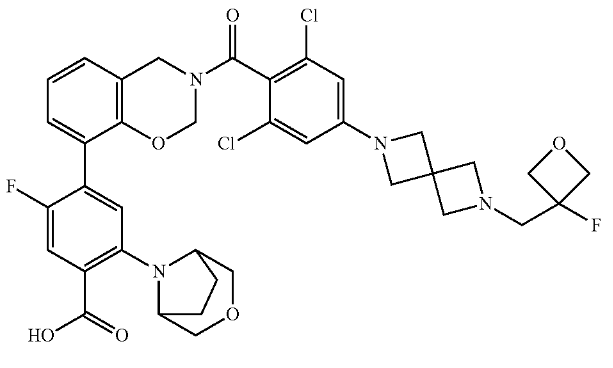 [SMILES: O=C(O)c1cc(F)c(-c2cccc3c2OCN(C(=O)c2c(Cl)cc(N4CC5(CN(CC6(F)COC6)C5)C4)cc2Cl)C3)cc1N1C2CCC1COC2] | 4-[3-[2,6-Dichloro-4-[6-[(3-fluorooxetan-3-yl)methyl]-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.14, 1.17 | 741 |

TABLE 7-1-continued

| Compound No. | Structure | Compound Name | Analysis conditions | HPLC retention time (min) | m/z [M + H] |
|---|---|---|---|---|---|
| 7-3 | 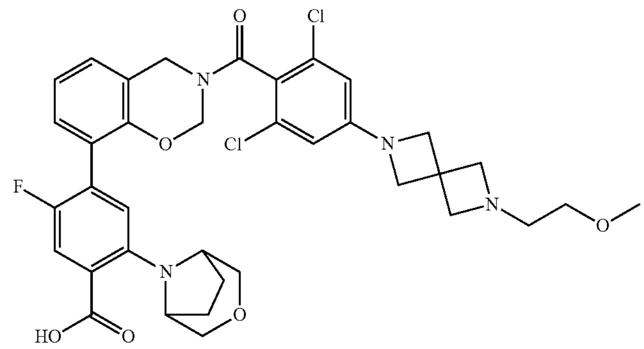 [SMILES: COCCN1CC2(C1)CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-[6-(2-methoxyethyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.03, 1.06 | 711 |
| 7-4 | 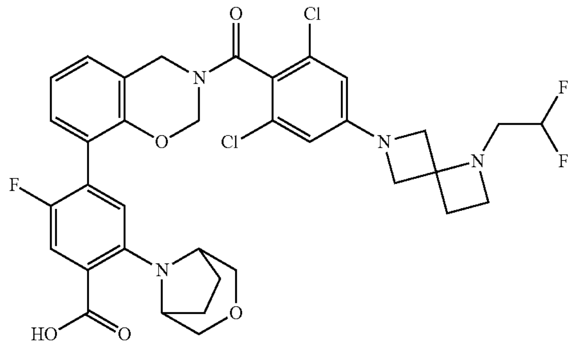 [SMILES: O=C(O)c1cc(F)c(-c2cccc3c2OCN(C(=O)c2c(Cl)cc(N4CC5(CCN5CC(F)F)C4)cc2Cl)C3)cc1N1C2CCC1COC2] | 4-[3-[2,6-Dichloro-4-[1-(2,2-difluoroethyl)-1,6-diazaspiro[3.3]heptan-6-yl] benzoyl]-2,4-dihydro-1,3-benzoxazin-8-yl]-5-fluoro-2-(3-oxa-8-azabicyclo [3.2.1]octan-8-yl)benzoic acid | B | 1.52, 1.55 | 717 |
| 7-5 | 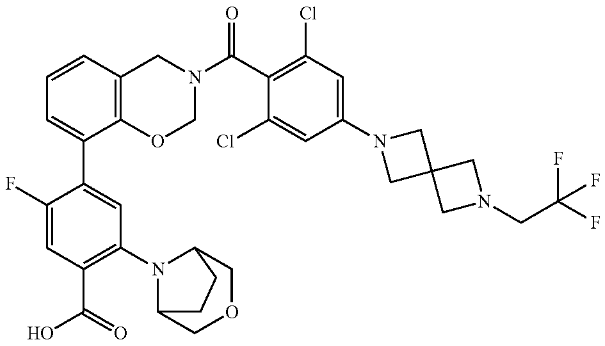 [SMILES: O=C(O)c1cc(F)c(-c2cccc3c2OCN(C(=O)c2c(Cl)cc(N4CC5(CN(CC(F)(F)F)C5)C4)cc2Cl)C3)cc1N1C2CCC1COC2] | 4-[3-[2,6-Dichloro-4-[6-(2,2,2-trifluoroethyl)-2,6-diazaspiro[3.3]heptan-2-yl]benzoyl]-2,4-dihydro-1,3-benzoxazin-8-yl]-5-fluoro-2-(3-oxa-8-azabicyclo [3.2.1]octan-8-yl) benzoic acid | B | 1.50, 1.54 | 735 |
| 7-6 | 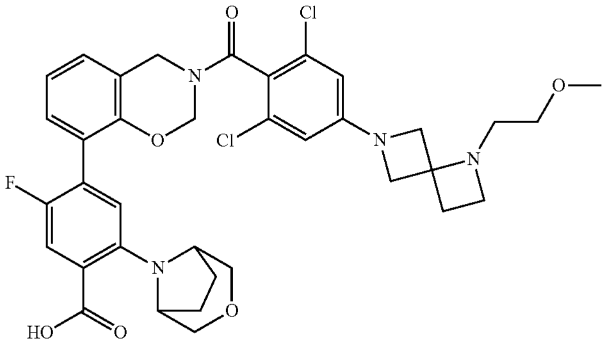 [SMILES: COCCN1CCC12CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-[1-(2-methoxyethyl)-1,6-diazaspiro[3.3]heptan-6-yl]benzoyl]-2,4-dihydro-1,3-benzoxazin-8-yl]-5-fluoro-2-(3-oxa-8-azabicyclo [3.2.1]octan-8-yl)benzoic acid | B | 1.13, 1.17 | 711 |

TABLE 7-1-continued

| Compound No. | Structure | Compound Name | Analysis conditions | HPLC retention time (min) | m/z [M + H] |
|---|---|---|---|---|---|
| 7-8 | 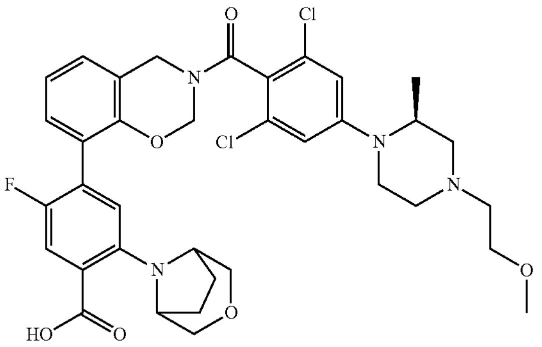 [SMILES: COCCN1CCN(c2cc(Cl)c(C(=O)N3COc4c(cccc4-c4cc(N5C6CCC5COC6)c(C(=O)O)cc4F)C3)c(Cl)c2)[C@@H](C)C1] | 4-[3-[2,6-Dichloro-4-[(2S)-4-(2-methoxyethyl)-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.03, 1.07 | 713 |
| 7-9 | 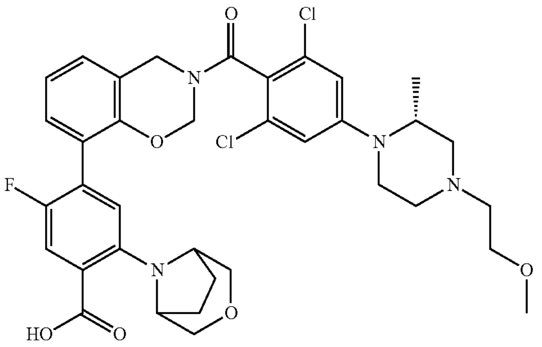 [SMILES: COCCN1CCN(c2cc(Cl)c(C(=O)N3COc4c(cccc4-c4cc(N5C6CCC5COC6)c(C(=O)O)cc4F)C3)c(Cl)c2)[C@H](C)C1] | 4-[3-[2,6-Dichloro-4-[(2R)-4-(2-methoxyethyl)-2-methylpiperazin-1-yl]benzoyl]-2,4-dihydro-1,3-benzoxazin-8-yl]-5-fluoro-2-(3-oxa-8-azabicyclo[3.2.1]octan-8-yl) benzoic acid | B | 1.02, 1.06 | 713 |
| 7-10 | 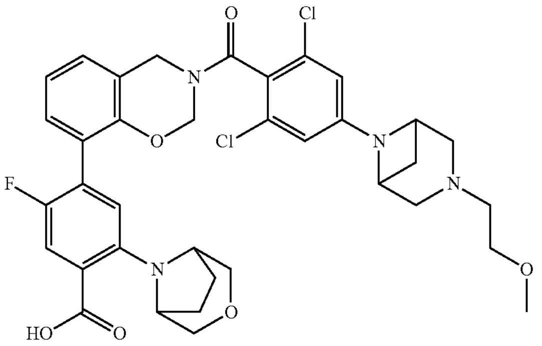 [SMILES: COCCN1CC2CC(C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[3-(2-methoxyethyl)-3,6-diazabicyclo[3.1.1]heptan-6-yl]benzoyl]-2,4-dihydro-1,3-benzoxazin-8-yl]-5-fluoro-2-(3-oxa-8-azabicyclo[3.2.1]octan-8-yl) benzoic acid | B | 1.13, 1.16 | 711 |
| 7-11 | 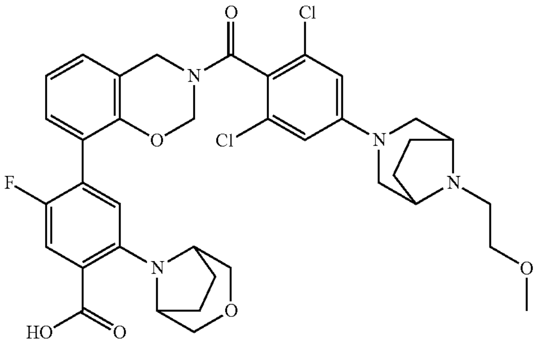 [SMILES: COCCN1C2CCC1CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-[8-(2-methoxyethyl)-3,8-diazabicyclo[3.2.1]octan-3-yl]benzoyl]-2,4-dihydro-1,3-benzoxazin-8-yl]-5-fluoro-2-(3-oxa-8-azabicyclo[3.2.1]octan-8-yl) benzoic acid | B | 1.04, 1.07 | 725 |

TABLE 7-1-continued

| Compound No. | Structure | Compound Name | Analysis conditions | HPLC retention time (min) | m/z [M + H] |
|---|---|---|---|---|---|
| 7-12 | 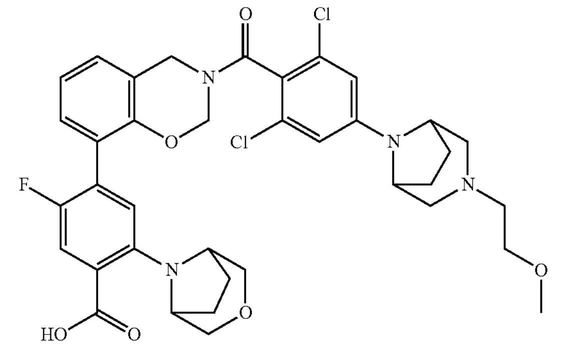 [SMILES: COCCN1CC2CCC(C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[3-(2-methoxyethyl)-3,8-diazabicyclo[3.2.1]octan-8-yl]benzoyl]-2,4-dihydro-1,3-benzoxazin-8-yl]-5-fluoro-2-(3-oxa-8-azabicyclo[3.2.1]octan-8-yl) benzoic acid | B | 1.06, 1.08 | 725 |
| 7-13 | 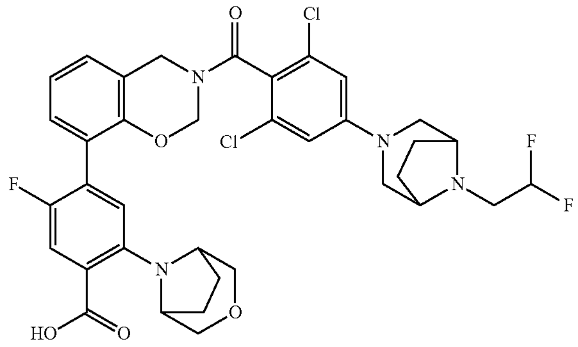 [SMILES: O=C(O)c1cc(F)c(-c2cccc3c2OCN(C(=O)c2c(Cl)cc(N4CC5CCC(C4)N5CC(F)F)cc2Cl)C3)cc1N1C2CCC1COC2] | 4-[3-[2,6-Dichloro-4-[8-(2,2-difluoroethyl)-3,8-diazabicyclo[3.2.1]octan-3-yl]benzoyl]-2,4-dihydro-1,3-benzoxazin-8-yl]-5-fluoro-2-(3-oxa-8-azabicyclo [3.2.1]octan-8-yl) benzoic acid | B | 1.38, 1.42 | 731 |
| 7-14 | 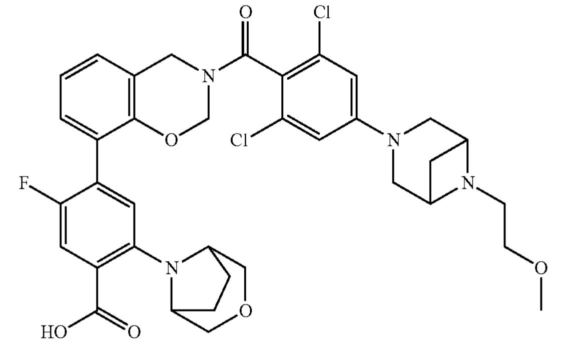 [SMILES: COCCN1C2CC1CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-[6-(2-methoxyethyl)-3,6-diazabicyclo[3.1.1]heptan-3-yl]benzoyl]-2,4-dihydro-1,3-benzoxazin-8-yl]-5-fluoro-2-(3-oxa-8-azabicyclo[3.2.1]octan-8-yl)benzoic acid | B | 1.11, 1.15 | 711 |
| 7-15 | 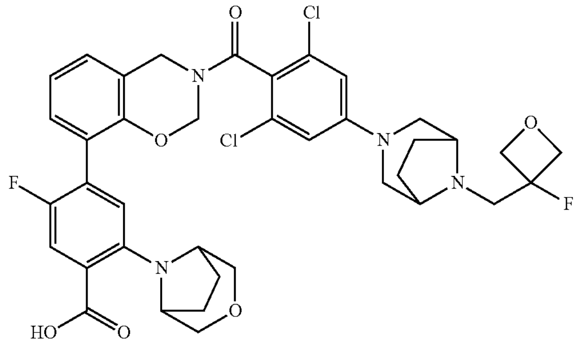 [SMILES: O=C(O)c1cc(F)c(-c2cccc3c2OCN(C(=O)c2c(Cl)cc(N4CC5CCC(C4)N5CC4(F)COC4)cc2Cl)C3)cc1N1C2CCC1COC2] | 4-[3-[2,6-Dichloro-4-[8-[(3-fluorooxetan-3-yl)methyl]-3,8-diazabicyclo[3.2.1] octan-3-yl]benzoyl]-2,4-dihydro-1,3-benzoxazin-8-yl]-5-fluoro-2-(3-oxa-8-azabicyclo[3.2.1]octan-8-yl) benzoic acid | B | 1.22 | 755 |

TABLE 7-1-continued

| Compound No. | Structure | Compound Name | Analysis conditions | HPLC retention time (min) | m/z [M + H] |
|---|---|---|---|---|---|
| 7-16 | 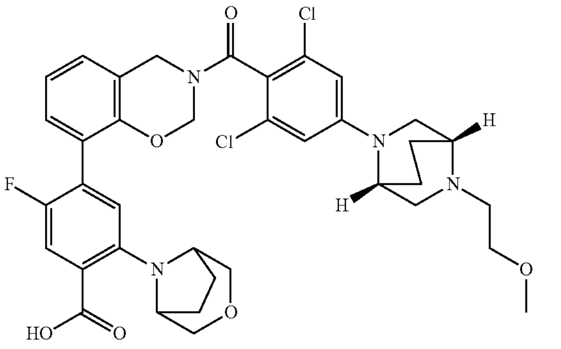 [SMILES: COCCN1C[C@H]2CC[C@@H]1CN2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(1R,4R)-5-(2-methoxyethyl)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.13, 1.16 | 725 |
| 7-17 | 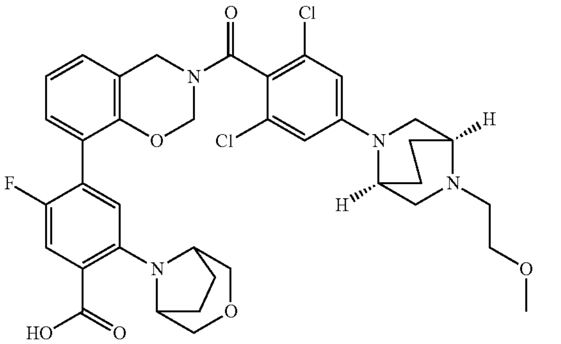 [SMILES: COCCN1C[C@@H]2CC[C@H]1CN2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(1S,4S)-5-(2-methoxyethyl)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.13, 1.16 | 725 |

TABLE 7-2

| Final compound No. | Intermediate | Alkylating agent |
|---|---|---|
| 7-1 | AM1 | 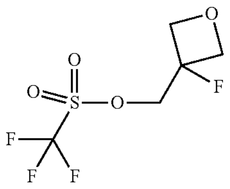 [SMILES: O=S(=O)(OCC1(F)COC1)C(F)(F)F] |
| 7-3 | AM1 | 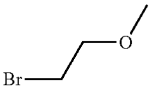 |
| 7-4 | AM2 | 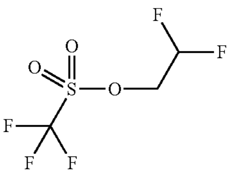 [SMILES: O=S(=O)(OCC(F)F)C(F)(F)F] |
| 7-5 | AM1 | 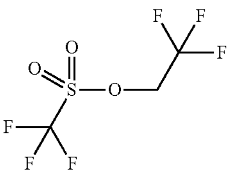 [SMILES: O=S(=O)(OCC(F)(F)F)C(F)(F)F] |

TABLE 7-2-continued

| Final compound No. | Intermediate | Alkylating agent |
|---|---|---|
| 7-6 | AM2 | 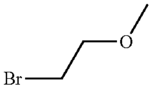 |
| 7-8 | AM3 | 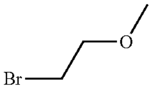 |
| 7-9 | AM4 | 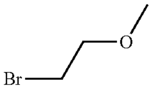 |
| 7-10 | AM5 | 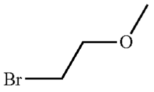 |
| 7-11 | AM6 | 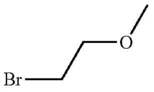 |
| 7-12 | AM7 | 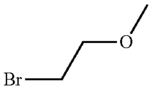 |

TABLE 7-2-continued

| Final compound No. | Intermediate | Alkylating agent |
|---|---|---|
| 7-13 | AM6 | 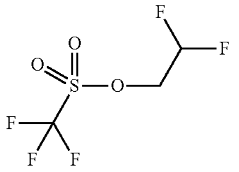 [SMILES: O=S(=O)(OCC(F)F)C(F)(F)F] |
| 7-14 | AM8 | 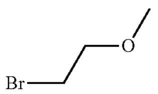 |
| 7-15 | AM6 | 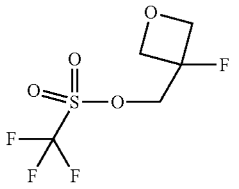 [SMILES: O=S(=O)(OCC1(F)COC1)C(F)(F)F] |
| 7-16 | AM9 | 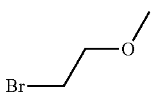 |
| 7-17 | AM10 | 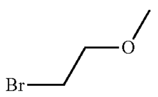 |

Compound 7-18

4-[3-[2,6-Dichloro-4-[8-(1,3-dimethoxypropan-2-yl)-3,8-diazabicyclo[3.2.1]octan-3-yl]benzoyl]-2,4-dihydro-1,3-benzoxazin-8-yl]-5-fluoro-2-(3-oxa-8-azabicyclo[3.2.1]octan-8-yl)benzoic acid

[Formula 279]

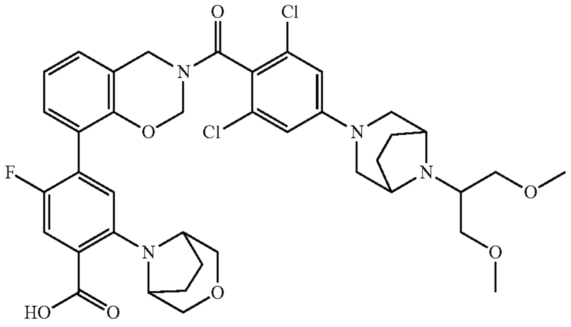

A solution of 1,3-dimethoxypropan-2-ol (25.0 mg, 0.208 mmol), triethylamine (0.0440 mL, 0.312 mmol), and 4-dimethylaminopyridine (0.763 mg, 0.00624 mmol) in dichloromethane (3.00 mL) was cooled to 0° C. Trifluoromethanesulfonic anhydride (0.0420 mL, 0.250 mmol) was added thereto, and the mixture was stirred at 0° C. for 3 hours. 1 M hydrochloric acid was added to the reaction solution, followed by extraction with dichloromethane. The organic layer was concentrated. The title compound was obtained by the same operation as in the third step of compound 7-2 using the obtained crude product, methyl 4-[3-[2,6-dichloro-4-(3,8-diazabicyclo[3.2.1]octan-3-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate and 1,3-dimethoxypropan-2-yl trifluoromethanesulfonate.

LCMS: m/z 769[M+H]$^+$

HPLC retention time: 1.21 min and 1.24 min (analysis condition B)

Compound 8-1

4-[3-[2,6-Dichloro-4-[7-(2-methoxyethyl)-2,7-diazaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound BCA11 tert-Butyl 2-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,7-diazaspiro[3.4]octane-7-carboxylate

[Formula 280]

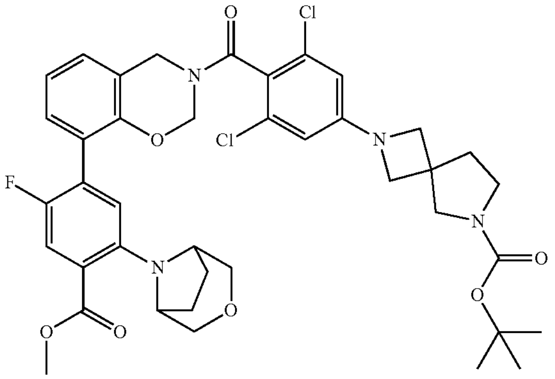

A suspension of compound O (60.0 mg, 0.102 mmol) and tert-butyl 2,6-diazaspiro[3.4]octane-6-carboxylate (64.8 mg, 0.305 mmol) in 1-methylpyrrolidin-2-one (0.509 mL) was stirred at 130° C. for 1 hour. The reaction mixture was purified by reverse phase silica gel chromatography (acetonitrile/water, 0.1% formic acid) to obtain the title compound (87%, 69.0 mg).

LCMS: m/z 781[M+H]$^+$

HPLC retention time: 1.07 min (analysis condition D)

Second Step

Compound AM 11

Methyl 4-[3-[2,6-dichloro-4-(2,7-diazaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 281]

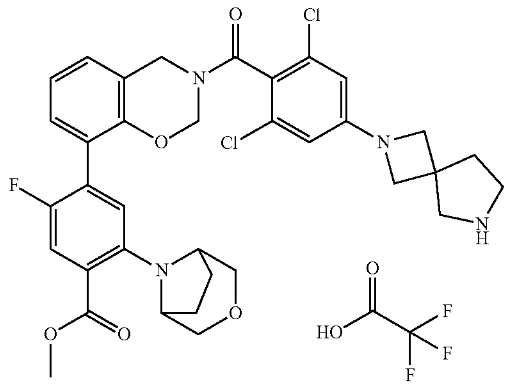

The title compound was synthesized by the same operation as in the second step of compound 7-2 using tert-butyl 2-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,7-diazaspiro[3.4]octane-7-carboxylate.

LCMS: m/z 681 $[M+H]^+$

HPLC retention time: 0.62 min (analysis condition D)

Third Step

Compound 8-1

4-[3-[2,6-Dichloro-4-[7-(2-methoxyethyl)-2,7-diazaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 282]

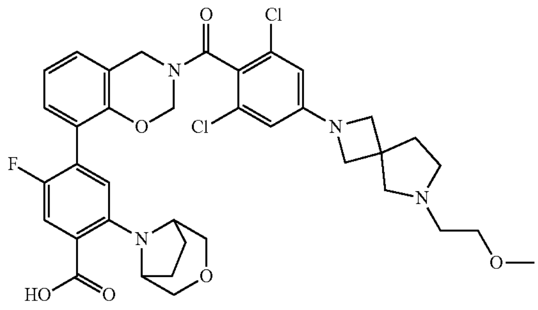

To a solution of methyl 4-[3-[2,6-dichloro-4-(2,7-diazaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (23.4 mg, 0.0290 mmol), 1-bromo-2-methoxyethane (0.0142 ml, 0.147 mmol), and N,N-diisopropylethylamine (0.0256 ml, 0.147 mmol) in N,N-dimethylformamide (0.147 mL), tetramethylammonium iodide (0.591 mg, 0.00294 mmol) was added, and the mixture was stirred overnight at room temperature. Then, a 5 M aqueous sodium hydroxide solution (0.0588 ml, 0.294 mmol) and methanol (0.100 mL) were added thereto at room temperature, and the reaction solution was stirred at 60° C. for 3 hours. The reaction mixture was purified by reverse phase silica gel chromatography (acetonitrile/water, 0.1% formic acid) to obtain the title compound (42%, 8.90 mg).

LCMS: m/z 725$[M+H]^+$

HPLC retention time: 1.03 min and 1.07 min (analysis condition B)

Compound 8-4

4-[3-[2,6-Dichloro-4-[meso-4-(2-methoxyethyl)-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound AM13

4-[3-[2,6-Dichloro-4-[meso-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 283]

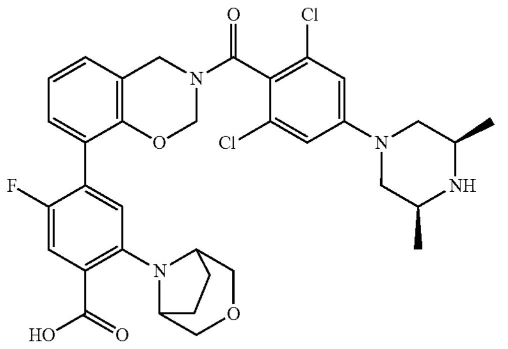

A suspension of compound O (70.0 mg, 0.119 mmol) and (2S,6R)-2,6-dimethylpiperazine (67.8 mg, 0.594 mmol) in 1-methylpyrrolidin-2-one (0.509 mL) was stirred at 110° C. for 3 hours. Then, an 8 M aqueous potassium hydroxide solution (0.148 ml, 1.19 mmol) was added thereto at room temperature, and the reaction solution was stirred at 60° C. for 30 minutes. The reaction mixture was purified by HPLC (acetonitrile/water, 0.1% formic acid) to obtain the title compound (95%, 75.3 mg).

LCMS: m/z 669$[M+H]^+$

HPLC retention time: 0.52 min and 0.55 min (analysis condition D)

Second Step
Compound 8-4

4-[3-[2,6-Dichloro-4-[meso-4-(2-methoxyethyl)-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 284]

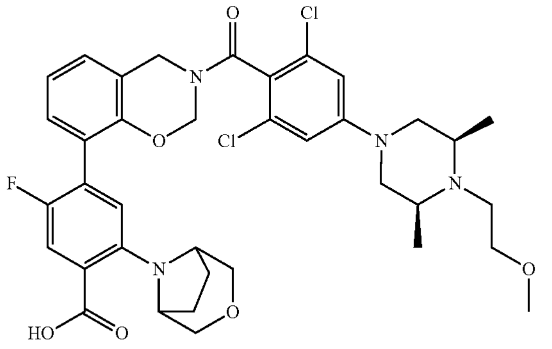

The title compound was synthesized by the same operation as in the third step of compound 8-1 using 4-[3-[2,6-dichloro-4-[meso-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

LCMS: m/z 727[M+H]$^+$

HPLC retention time: 1.04 min and 1.08 min (analysis condition B)

Compound 8-8

4-[3-[2,6-Dichloro-4-[1-(2,2,2-trifluoroethyl)azetidin-3-yl]oxybenzoyl]-2,4-dihydro-1,3-benzoxazin-8-yl]-5-fluoro-2-(3-oxa-8-azabicyclo[3.2.1]octan-8-yl)benzoic acid First Step
Compound BCA15

4-[3-[2,6-Dichloro-4-[1-[(2-methylpropan-2-yl)oxycarbonyl]azetidin-3-yl]oxybenzoyl]-2,4-dihydro-1,3-benzoxazin-8-yl]-5-fluoro-2-(3-oxa-8-azabicyclo[3.2.1]octan-8-yl)benzoic acid

[Formula 285]

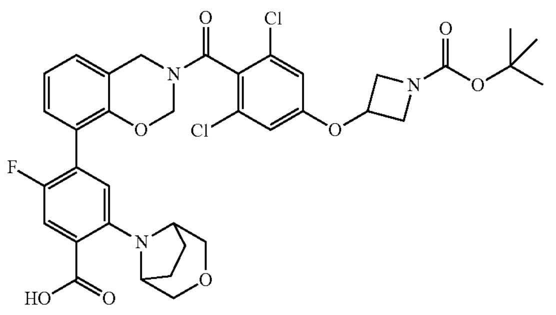

To a solution of compound O (150 mg, 0.254 mmol) in 1-methylpyrrolidin-2-one (0.509 mL), tert-butyl 3-hydroxyazetidine-1-carboxylate (220 mg, 1.27 mmol) and potassium tert-butoxide (137 mg, 1.22 mmol) were added, and the mixture was stirred at room temperature for 2.5 hours. The reaction mixture was purified by HPLC (acetonitrile/water, 0.1% formic acid) to obtain the title compound (85%, 188 mg).

LCMS: m/z 728[M+H]$^+$

HPLC retention time: 0.88 min (analysis condition D)

Second Step
Compound AM15

4-[3-[4-(Azetidin-3-yloxy)-2,6-dichlorobenzoyl]-2,4-dihydro-1,3-benzoxazin-8-yl]-5-fluoro-2-(3-oxa-8-azabicyclo[3.2.1]octan-8-yl)benzoic acid 2,2,2-trifluoroacetate

[Formula 286]

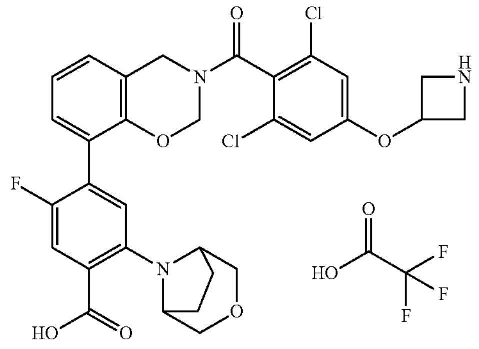

The title compound was synthesized by the same operation as in the second step of compound 7-2 using 4-[3-[2,6-dichloro-4-[1-[(2-methylpropan-2-yl)oxycarbonyl]azetidin-3-yl]oxybenzoyl]-2,4-dihydro-1,3-benzoxazin-8-yl]-5-fluoro-2-(3-oxa-8-azabicyclo[3.2.1]octan-8-yl)benzoic acid.

LCMS: m/z 628[M+H]$^+$

HPLC retention time: 0.50 min and 0.51 min (analysis condition D)

Third Step
Compound 8-8

4-[3-[2,6-Dichloro-4-[1-(2,2,2-trifluoroethyl)azetidin-3-yl]oxybenzoyl]-2,4-dihydro-1,3-benzoxazin-8-yl]-5-fluoro-2-(3-oxa-8-azabicyclo[3.2.1]octan-8-yl)benzoic acid

[Formula 287]

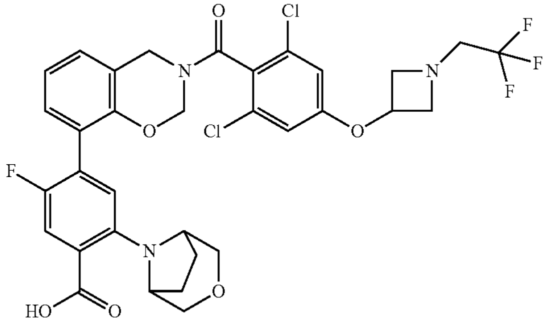

The title compound was synthesized by the same operation as in the third step of compound 7-2 using 4-[3-[4-(azetidin-3-yloxy)-2,6-dichlorobenzoyl]-2,4-dihydro-1,3-benzoxazin-8-yl]-5-fluoro-2-(3-oxa-8-azabicyclo[3.2.1]octan-8-yl)benzoic acid 2,2,2-trifluoroacetate. However, 2,2,2-trifluoroethyl trifluoromethanesulfonate was used instead of 2,2-difluoroethyl trifluoromethanesulfonate.

LCMS: m/z 710[M+H]$^+$

HPLC retention time: 1.55 min (analysis condition B)

Compound BCA12 tert-Butyl 7-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,7-diazaspiro[3.4]octane-2-carboxylate

[Formula 288]

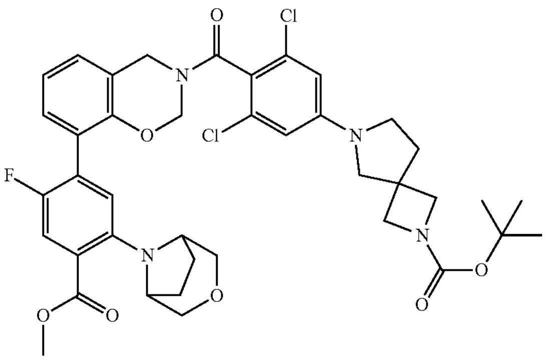

The title compound was synthesized by the same operation as in the first step of compound 8-1. However, tert-butyl 2,7-diazaspiro[3.4]octane-2-carboxylate was used instead of tert-butyl 2,6-diazaspiro[3.4]octane-6-carboxylate as amine.

LCMS: m/z 781[M+H]$^+$

HPLC retention time: 1.06 min (analysis condition D)

Compound BCA17

4-[3-[2,6-Dichloro-4-[(3R)-1-[(2-methylpropan-2-yl)oxycarbonyl]piperidin-3-yl]oxybenzoyl]-2,4-dihydro-1,3-benzoxazin-8-yl]-5-fluoro-2-morpholin-4-ylbenzoic acid

[Formula 289]

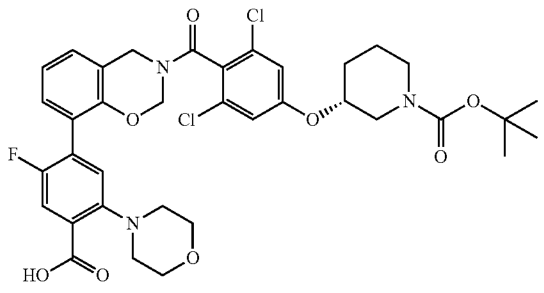

The title compound was synthesized by the same operation as in the first step of compound 8-8. However, compound S was used instead of compound 0, and tert-butyl (3R)-3-hydroxypiperidine-1-carboxylate was used instead of tert-butyl 3-hydroxyazetidine-1-carboxylate.

LCMS: m/z 730[M+H]$^+$

HPLC retention time: 0.91 min (analysis condition D)

Compound AM12

Methyl 4-[3-[2,6-dichloro-4-(2,6-diazaspiro[3.4]octan-6-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 290]

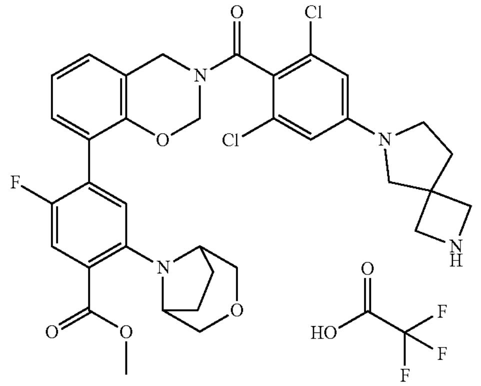

The title compound was synthesized by the same operation as in the second step of compound 8-1 using BCA12.

LCMS: m/z 681[M+H]$^+$

HPLC retention time: 0.64 min (analysis condition D)

Compound AM14

4-[3-[2,6-Dichloro-4-[(3S)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 291]

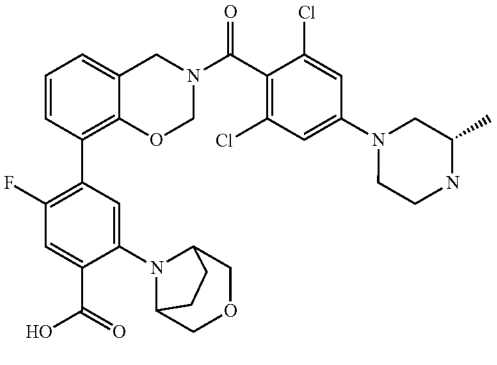

The title compound was synthesized by the same operation as in the first step of compound 8-4. However, (2S)-2-methylpiperazine was used instead of (2S,6R)-2,6-dimethylpiperazine as amine.

LCMS: m/z 655[M+H]$^+$

HPLC retention time: 0.51 min and 0.54 min (Analysis condition D)

Compound AM17

4-[3-[2,6-Dichloro-4-[(3R)-piperidin-3-yl]oxybenzoyl]-2,4-dihydro-1,3-benzoxazin-8-yl]-5-fluoro-2-morpholin-4-ylbenzoic acid 2,2,2-trifluoroacetate

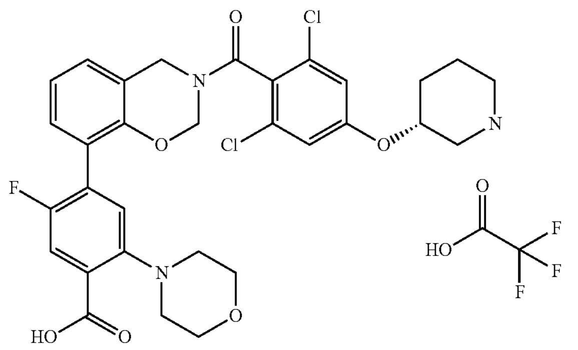

The title compound was synthesized by the same operation as in the second step of compound 8-8 using BCA17.

LCMS: m/z 630[M+H]$^+$

HPLC retention time: 0.50 min and 0.52 min (Analysis condition D)

Compound AM30

4-[3-(2,6-Dichloro-4-piperazin-1-ylbenzoyl)-2,4-dihydro-1,3-benzoxazin-8-yl]-5-fluoro-2-(3-oxa-8-azabicyclo[3.2.1]octan-8-yl)benzoic acid

[Formula 293]

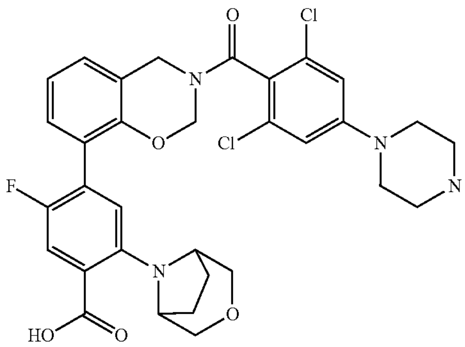

The title compound was synthesized by the same operation as in the first step of compound 8-4. However, piperazine was used instead of (2S,6R)-2,6-dimethylpiperazine as amine.

LCMS: m/z 641[M+H]$^+$

HPLC retention time: 0.49 min and 0.51 min (Analysis condition D)

Compound AM16

4-[3-[2,6-Dichloro-4-[(3S)-pyrrolidin-3-yl]oxybenzoyl]-2,4-dihydro-1,3-benzoxazin-8-yl]-5-fluoro-2-morpholin-4-ylbenzoic acid formate

[Formula 294]

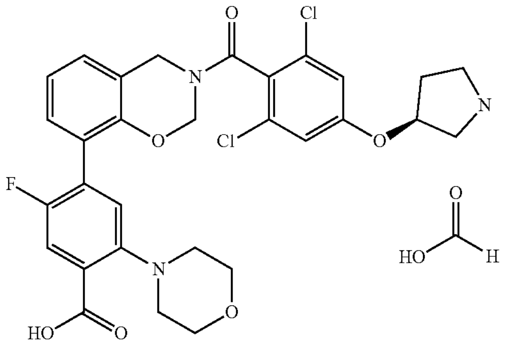

The title compound was synthesized by the same operation as in the first step and the second step of compound 8-8. However, compound S was used instead of compound 0, and tert-butyl (3S)-3-hydroxypyrrolidine-1-carboxylate was used instead of (tert-butyl 3-hydroxyazetidine-1-carboxylate.

LCMS: m/z 616[M+H]$^+$

HPLC retention time: 0.48 min and 0.51 min (Analysis condition D)

Compound AMOH4

4-[3-[2,6-Dichloro-4-(3,3-dimethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 295]

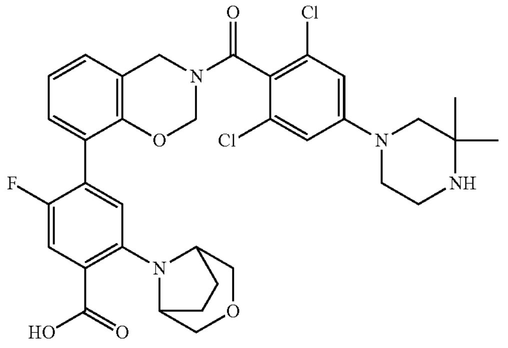

The title compound was synthesized by the same operation as in the first step of compound 8-4. However, 2,2-dimethylpiperazine was used instead of (2S,6R)-2,6-dimethylpiperazine as amine.

LCMS: m/z 669[M+H]$^+$

HPLC retention time: 0.53 min and 0.56 min (analysis condition D)

Compounds shown in Table 8-1 were synthesized by the same operation as in the third step of compound 8-1 using alkylating agents and intermediates shown in Table 8-2. However, a 1-methylpyrrolidin-2-one solution was used instead of the N,N-dimethylformamide solution in the synthesis of compounds 8-3 and 8-5, and an acetonitrile solution was used instead of the N,N-dimethylformamide solution in the synthesis of compound 8-2.

TABLE 8-1

| Compound No. | Structure | Compound Name | Analysis conditions | HPLC retention time (min) | m/z [M + H] |
|---|---|---|---|---|---|
| 8-2 | 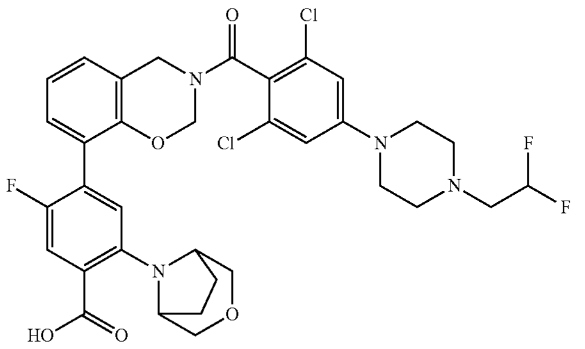 [SMILES: O=C(O)c1cc(F)c(-c2cccc3c2OCN(C(=O)c2c(Cl)cc(N4CCN(CC(F)F)CC4)cc2Cl)C3)cc1N1C2CCC1COC2] | 4-[3-[2,6-Dichloro-4-[4-(2,2-difluoroethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.35, 1.38 | 705 |
| 8-3 | 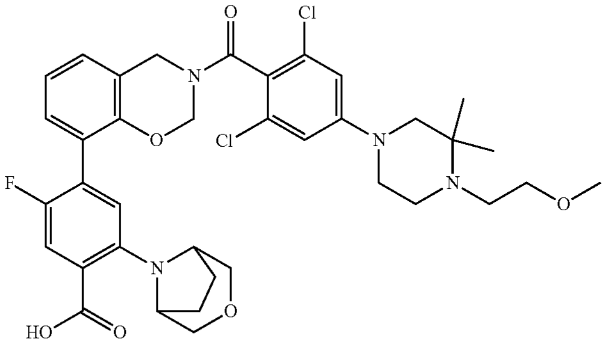 [SMILES: COCCN1CCN(c2cc(Cl)c(C(=O)N3COc4c(cccc4-c4cc(N5C6CCC5COC6)c(C(=O)O)cc4F)C3)c(Cl)c2)CC1(C)C] | 4-[3-[2,6-Dichloro-4-[4-(2-methoxyethyl)-3,3-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.04, 1.07 | 727 |
| 8-5 | 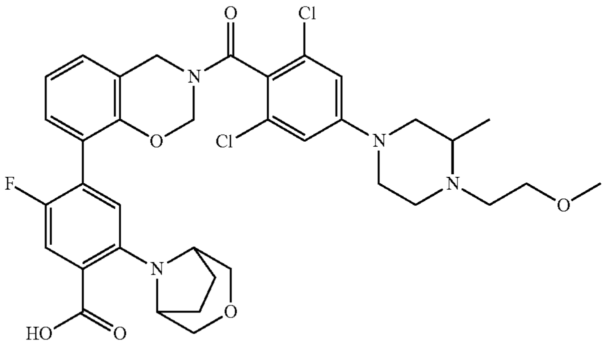 [SMILES: COCCN1CCN(c2cc(Cl)c(C(=O)N3COc4c(cccc4-c4cc(N5C6CCC5COC6)c(C(=O)O)cc4F)C3)c(Cl)c2)CC1C] | 4-[3-[2,6-Dichloro-4-[(3S)-4-(2-methoxyethyl)-3-methylpiperazan-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.02, 1.06 | 713 |
| 8-6 | 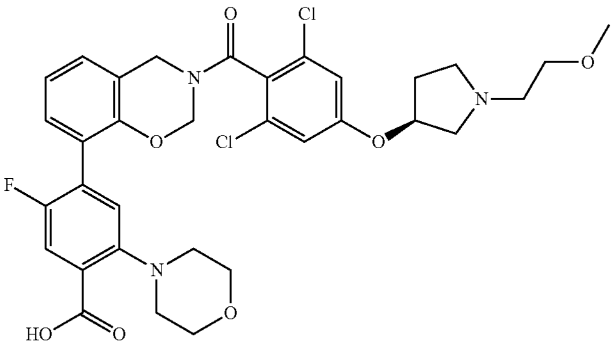 [SMILES: COCCN1CC[C@H](Oc2cc(Cl)c(C(=O)N3COc4c(cccc4-c4cc(N5CCOCC5)c(C(=O)O)cc4F)C3)c(Cl)c2)C1] | 4-[3-[2,6-Dichloro-4-[(3S)-1-(2-methoxyethyl)pyrrolidin-3-yl]oxybenzoyl]-2,4-dihydro-1,3-benzoxazin-8-yl]-5-fluoro-2-morpholin-4-ylbenzoic acid | B | 0.98, 1.03 | 674 |

TABLE 8-1-continued

| Compound No. | Structure | Compound Name | Analysis conditions | HPLC retention time (min) | m/z [M + H] |
|---|---|---|---|---|---|
| 8-7 | 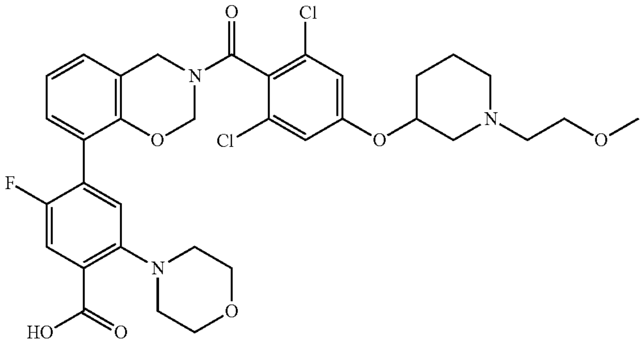 [SMILES: COCCN1CCCC(Oc2cc(Cl)c(C(=O)N3COc4c(cccc4-c4cc(N5CCOCC5)c(C(=O)O)cc4F)C3)c(Cl)c2)C1] | 4-[3-[2,6-Dichloro-4-[(3R)-1-(2-methoxyethyl)piperidin-3-yl]oxybenzoyl]-2,4-dihydro-1,3-benzoxazin-8-yl]-5-fluoro-2-morpholin-4-ylbenzoic acid | B | 1.00, 1.04 | 688 |
| 8-9 | 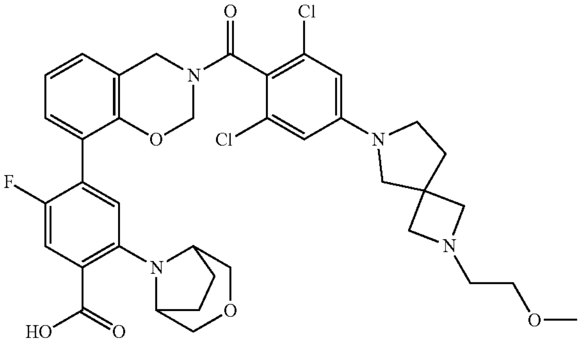 [SMILES: COCCN1CC2(CCN(c3cc(Cl)c(C(=O)N4COc5c(cccc5-c5cc(N6C7CCC6COC7)c(C(=O)O)cc5F)C4)c(Cl)c3)C2)C1] | 4-[3-[2,6-Dichloro-4-[2-(2-methoxyethyl)-2,7-diazaspiro[3.4]octan-7-yl]benzoyl]-2,4-dihydro-1,3-benzoxazin-8-yl]-5-fluoro-2-(3-oxa-8-azabicyclo[3.2.1]octan-8-yl)benzoic acid | B | 1.04, 1.07 | 725 |

TABLE 8-2

| Final compound No. | Intermediate | Alkylating agent |
|---|---|---|
| 8-2 | AM30 | 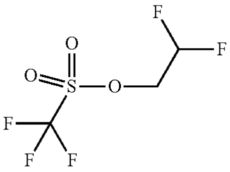 [SMILES: O=S(=O)(OCC(F)F)C(F)(F)F] |
| 8-3 | AMOH4 | 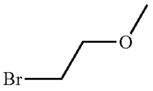 |
| 8-5 | AM14 | 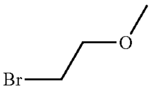 |

TABLE 8-2-continued

| Final compound No. | Intermediate | Alkylating agent |
|---|---|---|
| 8-6 | AM16 | 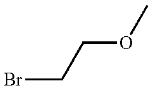 |
| 8-7 | AM17 | 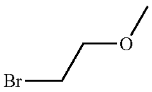 |
| 8-9 | AM12 | 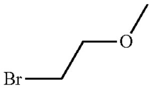 |

Compound 9-4

4-[3-[2,6-Dichloro-4-(2-cyclopropyl-2,6-diazaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoic acid First Step Compound AM27

Methyl 4-[3-[2,6-dichloro-4-(2-cyclopropyl-2,6-diazaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoate

[Formula 296]

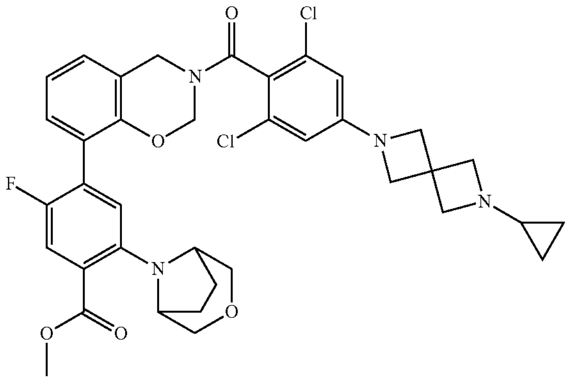

A suspension of methyl 4-[3-[2,6-dichloro-4-(2,6-diazaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (25.0 mg, 0.0320 mmol), (1-ethoxycyclopropyl)oxy-trimethylsilane (27.9 mg, 0.160 mmol), sodium triacetoxyborohydride (33.9 mg, 0.160 mmol) and acetic acid (0.0183 mL, 0.320 mmol) in dichloroethane (0.320 mL) was stirred at 80° C. for 1 hour. The reaction mixture was purified by reverse phase silica gel chromatography (methanol/water, 0.01 M ammonium acetate) to obtain the title compound (56%, 12.7 mg).

LCMS: m/z 707[M+H]$^+$

HPLC retention time: 0.72 min (analysis condition D)

Second Step

Compound 9-4

4-[3-[2,6-Dichloro-4-(2-cyclopropyl-2,6-diazaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoic acid

[Formula 297]

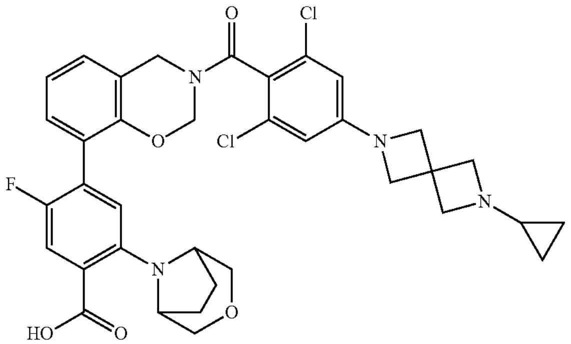

A solution of methyl 4-[3-[2,6-dichloro-4-(2-cyclopropyl-2,6-diazaspiro[3.3]heptan-6-yl)benzoyl]-2,4-dihydro-1,3-benzoxazin-8-yl]-5-fluoro-2-(3-oxa-8-azabicyclo[3.2.1]octan-8-yl)benzoate (19.6 mg, 0.0280 mmol) and a 5 M aqueous sodium hydroxide solution (0.0554 mL, 0.277 mmol) in acetonitrile (0.276 mL) was stirred at 60° C. for 1 hour. The reaction mixture was purified by reverse phase silica gel chromatography (acetonitrile/water, 0.1% formic acid) to obtain the title compound (15%, 2.90 mg).

LCMS: m/z 693[M+H]$^+$

HPLC retention time: 1.13 min and 1.17 min (analysis condition B)

Compound 9-12

4-[3-[2,6-Dichloro-4-[(2S)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 298]

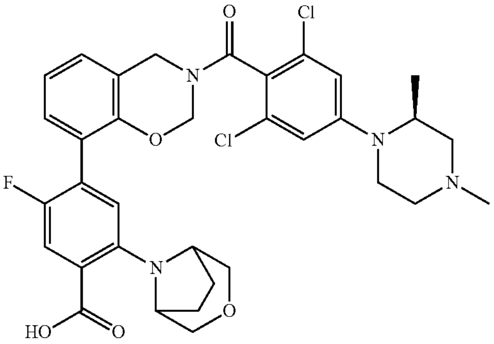

A suspension of methyl 4-[3-[2,6-dichloro-4-[(2S)-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (13.0 mg, 0.0170 mmol), paraformaldehyde (5.10 mg, 0.170 mmol), and sodium triacetoxyborohydride (18.0 mg, 0.0850 mmol) in dichloromethane (0.170 mL) was stirred at room temperature for 6 hours. The reaction solution was diluted with methanol and then filtered, and the filtrate was concentrated. An 8 M aqueous potassium hydroxide solution (0.0213 ml, 0.170 mmol), 1,4-dioxane (0.128 mL), and methanol (0.0425 mL) were added to the concentration residue, and the resulting solution was stirred at 60° C. for 1 hour. The reaction mixture was purified by HPLC (acetonitrile/water, 0.1% formic acid) to obtain the title compound (72%, 8.20 mg).

LCMS: m/z 669[M+H]$^+$

HPLC retention time: 0.99 min and 1.04 min (analysis condition B)

Compound 9-25

4-[3-[2,6-Dichloro-4-[(2R)-2-methylpiperazin-1-yl] benzoyl]-2,4-dihydro-1,3-benzoxazin-8-yl]-5-fluoro-2-(3-oxa-8-azabicyclo[3.2.1]octan-8-yl)benzoic acid

[Formula 299]

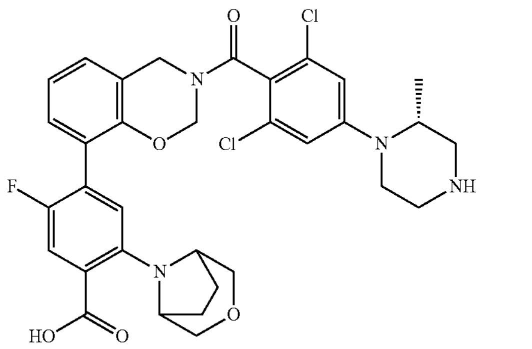

To a solution of methyl 4-[3-[2,6-dichloro-4-[(2R)-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (2.85 mg, 0.00364 mmol) in a mixed solution of 1,4-dioxane (0.0273 ml) and methanol (0.00900 ml), an 8 M aqueous potassium hydroxide solution (0.00455 ml, 0.0364 mmol) was added at room temperature, and the reaction solution was stirred at room temperature for 1 hour. The reaction mixture was purified by HPLC (acetonitrile/water, 0.1% formic acid) to obtain the title compound (55%, 1.30 mg).

LCMS: m/z 655[M+H]$^+$

HPLC retention time: 0.98 min and 1.04 min (analysis condition B)

Compound BCA18 tert-Butyl 2-[3,5-dichloro-4-[8-[2-fluoro-4-methoxycarbonyl-5-(3-oxa-8-azabicyclo[3.2.1]octan-8-yl) phenyl]-2,4-dihydro-1,3-benzoxazine-3-carbonyl] phenyl]-5-oxa-2,8-diazaspiro[3.5]nonane-8-carboxylate

[Formula 300]

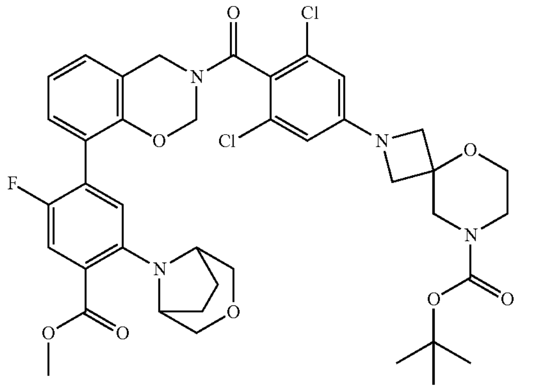

The title compound was synthesized by the same operation as in the first step of compound 7-2. However, tert-butyl 5-oxa-2,8-diazaspiro[3.5]nonane-8-carboxylate was used instead of tert-butyl 2,6-diazaspiro[3.3]heptane-2-carboxylate oxalate as amine.

LCMS: m/z 797[M+H]$^+$

HPLC retention time: 1.04 min (analysis condition D)

Compound BCA19 tert-Butyl 5-[3,5-dichloro-4-[8-[2-fluoro-4-methoxycarbonyl-5-(3-oxa-8-azabicyclo[3.2.1]octan-8-yl) phenyl]-2,4-dihydro-1,3-benzoxazine-3-carbonyl] phenyl]-2,5-diazabicyclo[4.1.0]heptane-2-carboxylate

[Formula 301]

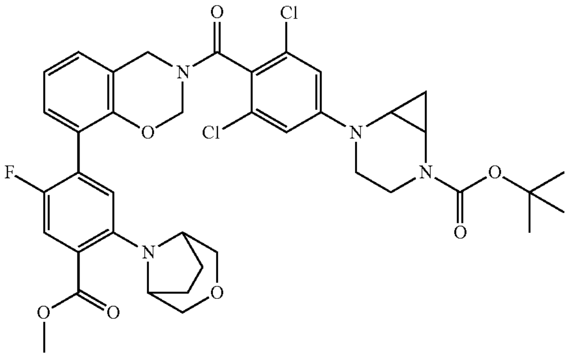

The title compound was synthesized by the same operation as in the first step of compound 7-2. However, tert-butyl 2,5-diazabicyclo[4.1.0]heptane-2-carboxylate was used instead of tert-butyl 2,6-diazaspiro[3.3]heptane-2-carboxylate oxalate as amine.

LCMS: m/z 767[M+H]$^+$

HPLC retention time: 1.05 min (analysis condition D)

Compound BCA20 tert-Butyl (2R,5S)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-dimethylpiperazine-1-carboxylate

[Formula 302]

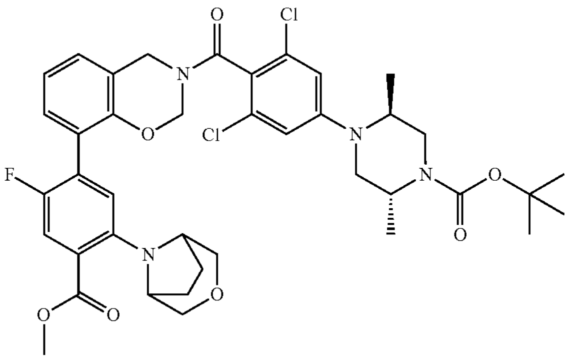

The title compound was synthesized by the same operation as in the first step of compound 7-2. However, tert-butyl (2R,5S)-2,5-dimethylpiperazine-1-carboxylate was used instead of tert-butyl 2,6-diazaspiro[3.3]heptane-2-carboxylate oxalate as amine.

LCMS: m/z 783[M+H]$^+$

HPLC retention time: 1.11 min (analysis condition D)

Compound BCA21 tert-Butyl (2R,5R)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-dimethylpiperazine-1-carboxylate

[Formula 303]

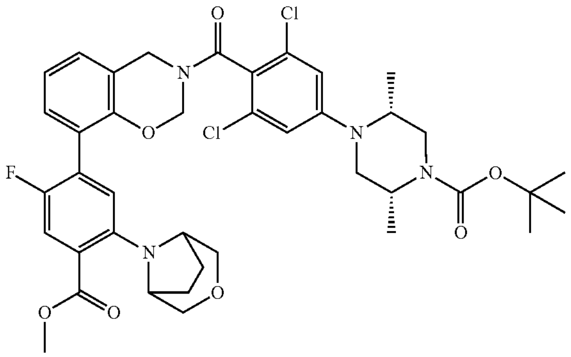

The title compound was synthesized by the same operation as in the first step of compound 7-2. However, tert-butyl (2R,5R)-2,5-dimethylpiperazine-1-carboxylate was used instead of tert-butyl 2,6-diazaspiro[3.3]heptane-2-carboxylate oxalate as amine.

LCMS: m/z 783[M+H]$^+$

HPLC retention time: 1.09 min (analysis condition D)

Compound BCA22 tert-Butyl (2S,5R)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-dimethylpiperazine-1-carboxylate

[Formula 304]

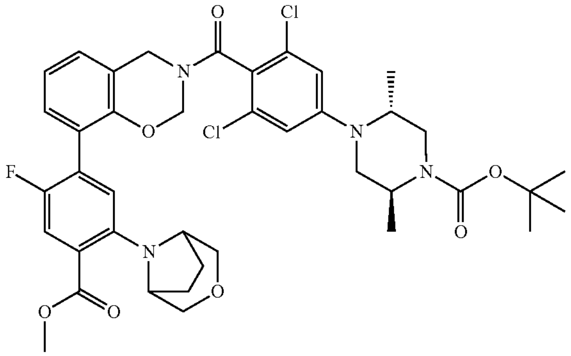

The title compound was synthesized by the same operation as in the first step of compound 7-2. However, tert-butyl (2S,5R)-2,5-dimethylpiperazine-1-carboxylate was used instead of tert-butyl 2,6-diazaspiro[3.3]heptane-2-carboxylate oxalate as amine.

LCMS: m/z 783[M+H]$^+$

HPLC retention time: 1.11 min (analysis condition D)

Compound BCA23 tert-Butyl (2S,5S)-4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-dimethylpiperazine-1-carboxylate

[Formula 305]

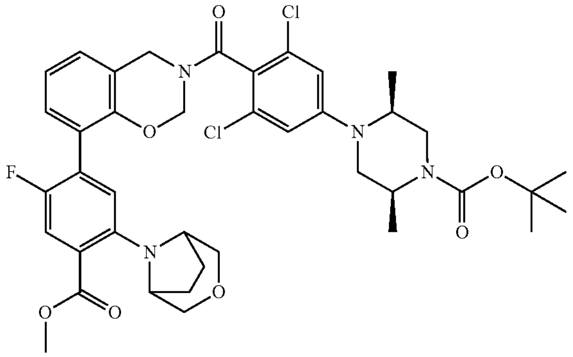

The title compound was synthesized by the same operation as in the first step of compound 7-2. However, tert-butyl (2S,5S)-2,5-dimethylpiperazine-1-carboxylate was used instead of tert-butyl 2,6-diazaspiro[3.3]heptane-2-carboxylate oxalate as amine.

LCMS: m/z 783[M+H]$^+$

HPLC retention time: 1.09 min (analysis condition D)

Compound BCA24 tert-Butyl 4-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-3,3-dimethylpiperazine-1-carboxylate

[Formula 306]

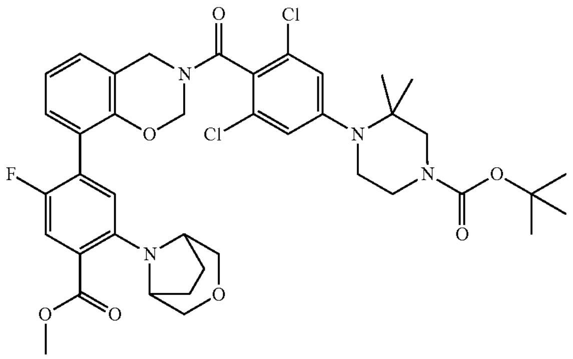

The title compound was synthesized by the same operation as in the first step of compound 7-2. However, tert-butyl 3,3-dimethylpiperazine-1-carboxylate was used instead of tert-butyl 2,6-diazaspiro[3.3]heptane-2-carboxylate oxalate as amine.

LCMS: m/z 783[M+H]$^+$

HPLC retention time: 1.12 min (analysis condition D)

Compound AM18

Methyl 4-[3-[2,6-dichloro-4-(5-oxa-2,8-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate

[Formula 307]

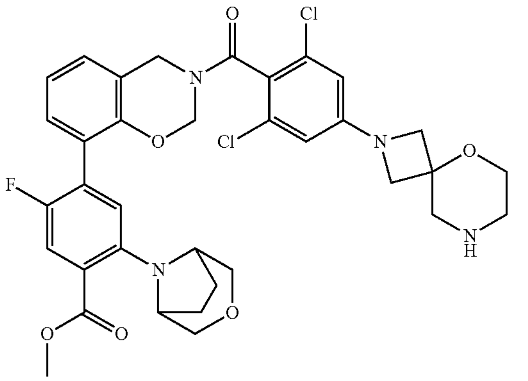

To a solution of tert-butyl 2-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-5-oxa-2,8-diazaspiro[3.5]nonane-8-carboxylate (67.5 mg, 0.300 mmol) in dichloromethane, trifluoroacetic acid (1.00 ml, 13.0 mmol) was added, and the mixture was stirred at room temperature for 3 hours. The reaction mixture was subjected to extraction with ethyl acetate. Then, the organic layer was concentrated under reduced pressure to obtain the title compound as a crude product.

LCMS: m/z 697[M+H]$^+$

HPLC retention time: 0.67 min (analysis condition D)

Compound AM19

Methyl 4-[3-[2,6-dichloro-4-(2,5-diazabicyclo[4.1.0]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 308]

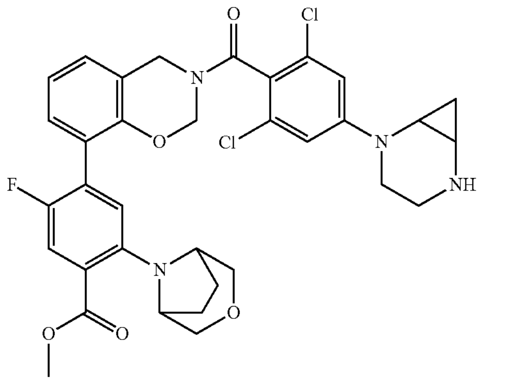

To a solution of tert-butyl 5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[4.1.0]heptane-2-carboxylate (37.3 mg, 0.0490 mmol) in dichloromethane, trifluoroacetic acid (0.50 ml, 6.5 mmol) was added, and the mixture was stirred at room temperature for 4 hours. The reaction mixture was purified by HPLC (acetonitrile/water, 0.1% formic acid) to obtain the title compound (66%, 21.4 mg).

LCMS: m/z 667[M+H]$^+$

HPLC retention time: 0.66 min (analysis condition D)

Compound AM20

Methyl 4-[3-[2,6-dichloro-4-1[(2S,5R)-2,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 309]

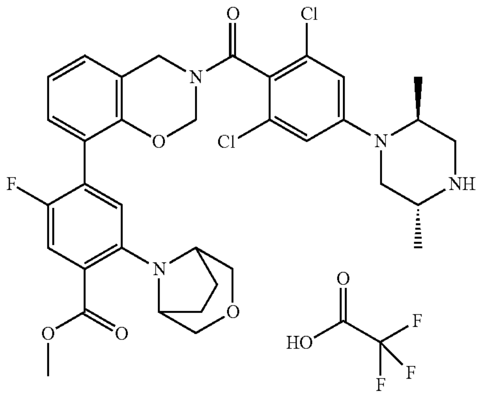

The title compound was synthesized by the same operation as in the second step of compound 7-2 using BCA20.

LCMS: m/z 683[M+H]$^+$

HPLC retention time: 0.63 min and 0.65 min (analysis condition D)

Compound AM21

Methyl 4-[3-[2,6-dichloro-4-[(2R,5R)-2,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 310]

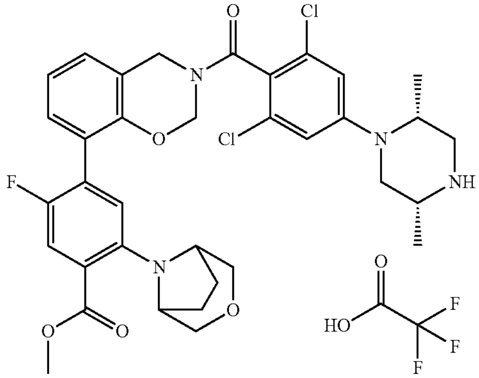

The title compound was synthesized by the same operation as in the second step of compound 7-2 using BCA21.

LCMS: m/z 683[M+H]$^+$

HPLC retention time: 0.63 min and 0.65 min (analysis condition D)

Compound AM22

Methyl 4-[3-[2,6-dichloro-4-[(2R,5S)-2,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 311]

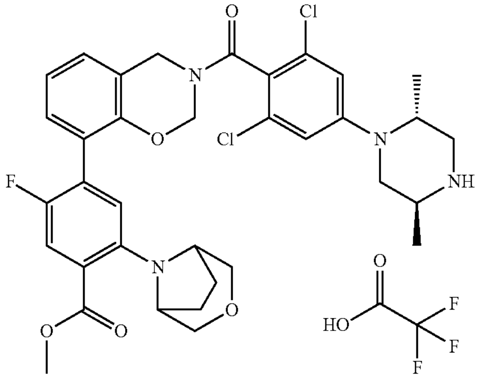

The title compound was synthesized by the same operation as in the second step of compound 7-2 using BCA22.

LCMS: m/z 683[M+H]$^+$

HPLC retention time: 0.63 min and 0.65 min (analysis condition D)

Compound AM23

Methyl 4-[3-[2,6-dichloro-4-[(2S,5S)-2,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 312]

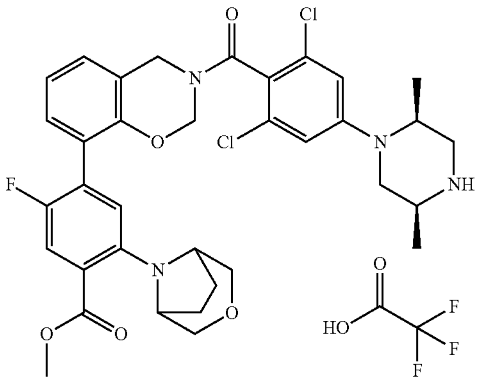

The title compound was synthesized by the same operation as in the second step of compound 7-2 using BCA23.

LCMS: m/z 683[M+H]$^+$

HPLC retention time: 0.63 min and 0.65 min (analysis condition D)

Compound AM24

Methyl 4-[3-[2,6-dichloro-4-(2,2-dimethylpiperazin-1-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 313]

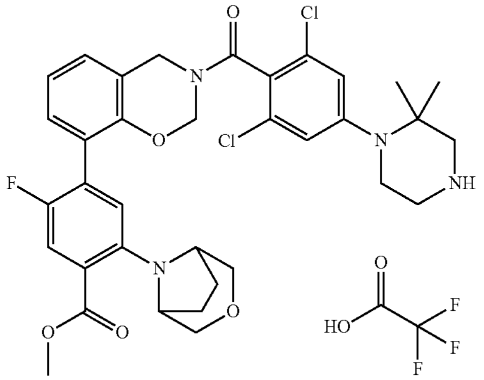

The title compound was synthesized by the same operation as in the second step of compound 7-2 using BCA24.

LCMS: m/z 683[M+H]$^+$

HPLC retention time: 0.62 min and 0.64 min (analysis condition D)

Compound AM25

Methyl 4-[3-[2,6-dichloro-4-[3-(trifluoromethyl)piperazin-1-yl]benzoyl]-2,4-dihydro-1,3-benzoxazin-8-yl]-5-fluoro-2-(3-oxa-8-azabicyclo[3.2.1]octan-8-yl)benzoate

[Formula 314]

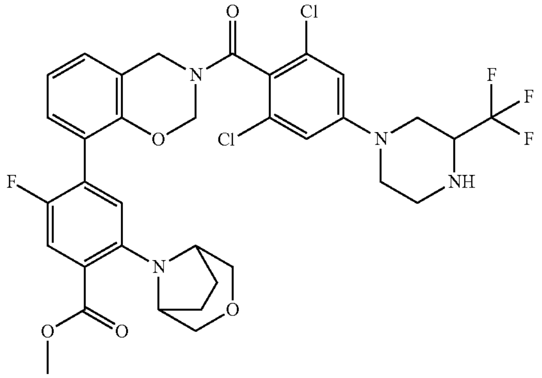

The title compound was synthesized by the same operation as in the first step of compound 7-2. However, 2-(trifluoromethyl)piperazine was used instead of tert-butyl 2,6-diazaspiro[3.3]heptane-2-carboxylate oxalate as amine.

LCMS: m/z 723[M+H]$^+$

HPLC retention time: 0.88 min (analysis condition D)

Compound AM26

Methyl 4-[3-[2,6-dichloro-4-(2,3-dimethylpiperazin-1-yl)benzoyl]-2,4-dihydro-1,3-benzoxazin-8-yl]-5-fluoro-2-(3-oxa-8-azabicyclo[3.2.1]octan-8-yl)benzoate

[Formula 315]

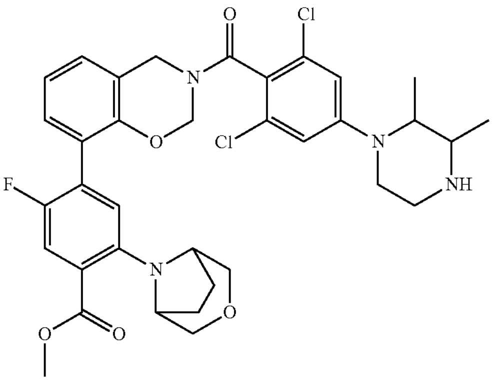

The title compound was synthesized by the same operation as in the first step of compound 7-2. However, 2,3-dimethylpiperazine was used instead of tert-butyl 2,6-diazaspiro[3.3]heptane-2-carboxylate oxalate as amine.

LCMS: m/z 683[M+H]$^+$

HPLC retention time: 0.63 min and 0.65 min (analysis condition D)

Compounds shown in Table 9-1 were synthesized using reagents and intermediates shown in Table 9-2. Compound 9-20 was synthesized by the same operation as in the first step and the second step of compound 9-4. The other compounds were synthesized by the same operation as in the conditions of the process of compound 9-12. However, a methanol solution was used instead of the dichloromethane solution in the synthesis of compounds 9-5, 9-7, 9-8, and 9-10.

TABLE 9-1

| Compound No. | Structure | Compound Name | Analysis conditions | HPLC retention time (min) | m/z [M + H] |
|---|---|---|---|---|---|
| 9-1 | 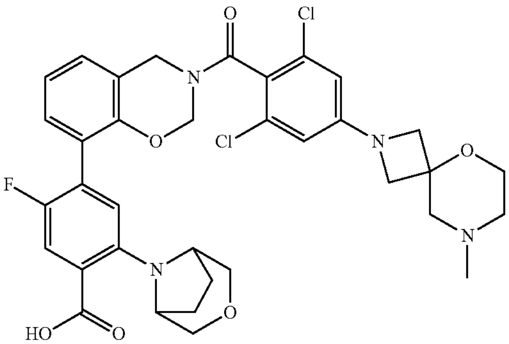 [SMILES: CN1CCOC2(C1)CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-(8-methyl-5-oxa-2,8-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.03. 1.06 | 697 |
| 9-2 | 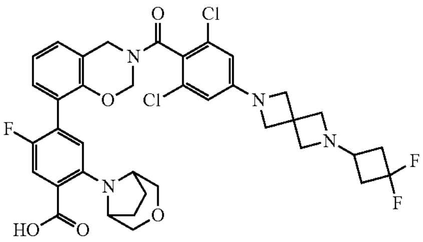 [SMILES: O=C(O)c1cc(F)c(-c2cccc3c2OCN(C(=O)c2c(Cl)cc(N4CC5(C4)CN(C4CC(F)(F)C4)C5)cc2Cl)C3)cc1N1C2CCC1COC2] | 4-[3-[2,6-Dichloro-4-[2-(3,3-difluorocyclobutyl)-2,6-diazaspiro[3.3]heptan-6-yl]benzoyl]-2,4-dihydro-1,3-benzoxazin-8-yl]-5-fluoro-2-(3-oxa-8-azabicyclo[3.2.1]octan-8-yl)benzoic acid | B | 1.18. 1.20 | 743 |
| 9-3 | 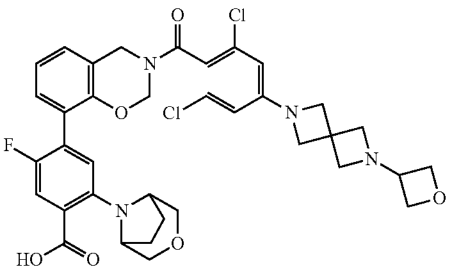 [SMILES: O=C(O)c1cc(F)c(-c2cccc3c2OCN(C(=O)/C=C(Cl)/C=C(\C=C\Cl)N2CC4(C2)CN(C2COC2)C4)C3)cc1N1C2CCC1COC2] | 4-[3-[2,6-Dichloro-4-[2-(oxetan-3-yl)-2,6-diazaspiro[3.3]heptan-6-yl]benzoyl]-2,4-dihydro-1,3-benzoxazin-8-yl]-5-fluoro-2-(3-oxa-8-azabicyclo[3.2.1]octan-8-yl)benzoic acid | B | 1.00. 1.05 | 709 |

TABLE 9-1-continued

| Compound No. | Structure | Compound Name | Analysis conditions | HPLC retention time (min) | m/z [M + H] |
|---|---|---|---|---|---|
| 9-5 | 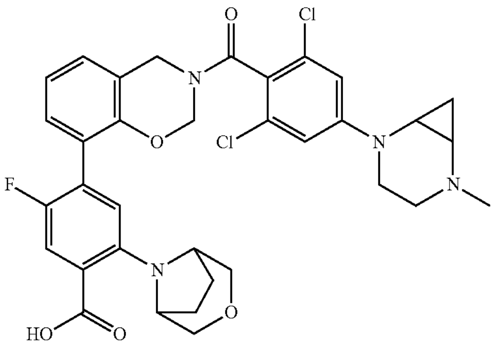 [SMILES: CN1CCN(c2cc(Cl)c(C(=O)N3COc4c(cccc4-c4cc(N5C6CCC5COC6)c(C(=O)O)cc4F)C3)c(Cl)c2)C2CC21] | 4-[3-[2,6-Dichloro-4-(5-methyl-2,5-diazabicyclo[4.1.0]heptan-2-yl)benzoyl]-2,4-dihydro-1,3-benzoxazin-8-yl]-5-fluoro-2-(3-oxa-8-azabicyclo[3.2.1]octan-8-yl)benzoic acid | B | 1.00. 1.04 | 667 |
| 9-6 | 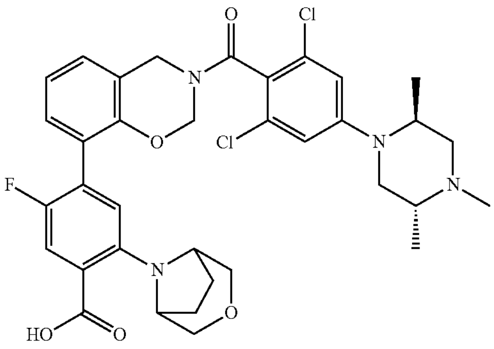 [SMILES: C[C@@H]1CN(c2cc(Cl)c(C(=O)N3COc4c(cccc4-c4cc(N5C6CCC5COC6)c(C(=O)O)cc4F)C3)c(Cl)c2)[C@@H](C)CN1C] | 4-[3-[2,6-Dichloro-4-[(2S,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.00. 1.05 | 683 |
| 9-7 | 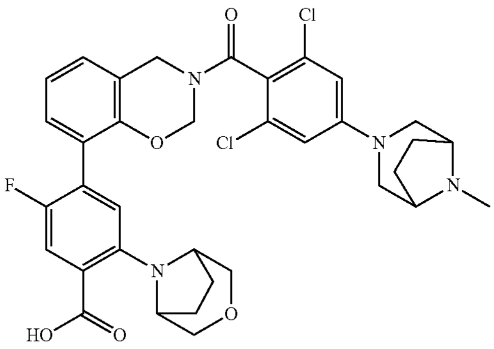 [SMILES: CN1C2CCC1CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-(8-methyl-3,8-diazabicyclo[3.2.1]octan-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.01. 1.05 | 681 |
| 9-8 | 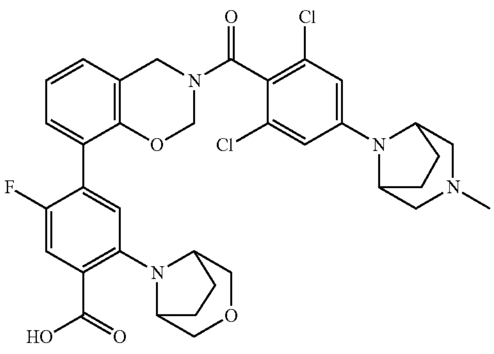 [SMILES: CN1CC2CCC(C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-(3-methyl-3,8-diazabicyclo[3.2.1]octan-8-yl)benzoyl]-2,4-dihydro-1,3-benzoxazin-8-yl]-5-fluoro-2-(3-oxa-8-azabicyclo[3.2.1]octan-8-yl)benzoic acid | B | 1.02. 1.05 | 681 |

TABLE 9-1-continued

| Compound No. | Structure | Compound Name | Analysis conditions | HPLC retention time (min) | m/z [M + H] |
|---|---|---|---|---|---|
| 9-9 | 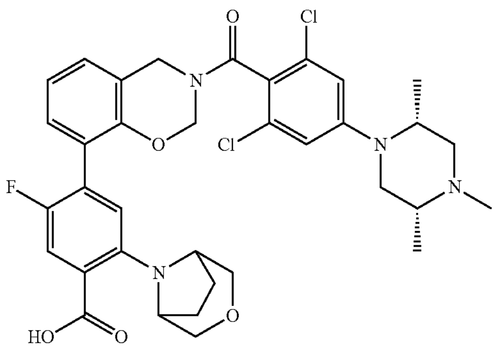 [SMILES: C[C@@H]1CN(c2cc(Cl)c(C(=O)N3COc4c(cccc4-c4cc(N5C6CCC5COC6)c(C(=O)O)cc4F)C3)c(Cl)c2)[C@H](C)CN1C] | 4-[3-[2,6-Dichloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.01. 1.08 | 683 |
| 9-10 | 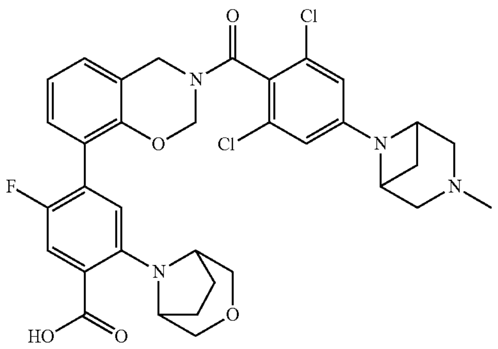 [SMILES: CN1CC2CC(C1)N2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-(3-methyl-3,6-diazabicyclo[3.1.1]heptan-6-yl)benzoyl]-2,4-dihydro-1,3-benzoxazin-8-yl]-5-fluoro-2-(3-oxa-8-azabicyclo[3.2.1]octan-8-yl)benzoic acid | B | 1.10. 1.13 | 687 |
| 9-11 | 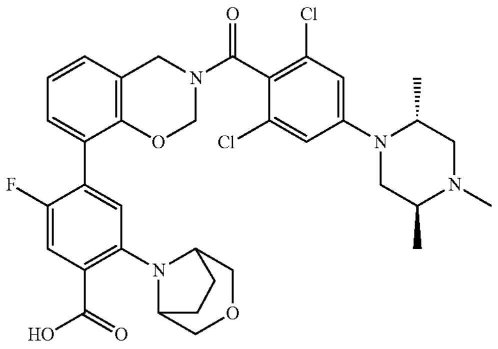 [SMILES: C[C@@H]1CN(C)[C@@H](C)CN1c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(2R,5S)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.01. 1.08 | 683 |
| 9-13 | 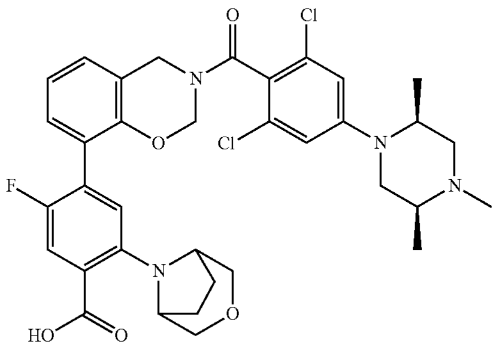 [SMILES: C[C@H]1CN(c2cc(Cl)c(C(=O)N3COc4c(cccc4-c4cc(N5C6CCC5COC6)c(C(=O)O)cc4F)C3)c(Cl)c2)[C@@H](C)CN1C] | 4-[3-[2,6-Dichloro-4-[(2S,5S)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.01. 1 06 | 683 |

TABLE 9-1-continued

| Compound No. | Structure | Compound Name | Analysis conditions | HPLC retention time (min) | m/z [M + H] |
|---|---|---|---|---|---|
| 9-14 | 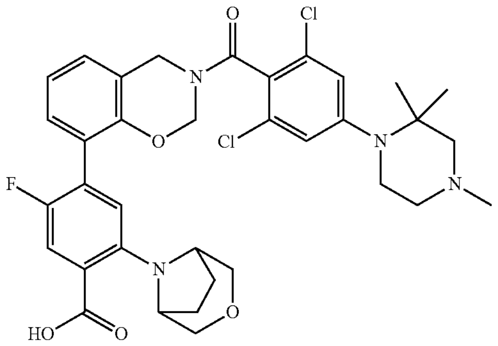 [SMILES: CN1CCN(c2cc(Cl)c(C(=O)N3COc4c(cccc4-c4cc(N5C6CCC5COC6)c(C(=O)O)cc4F)C3)c(Cl)c2)C(C)(C)C1] | 4-[3-[2,6-Dichloro-4-(2,2,4-trimethylpiperazin-1-yl)benzoyl]-2,4-dihydro-1,3-benzoxazin-8-yl]-5-fluoro-2-(3-oxa-8-azabicyclo[3.2.1] octan-8-yl)benzoic acid | B | 3.01. 1.06 | 683 |
| 9-15 | 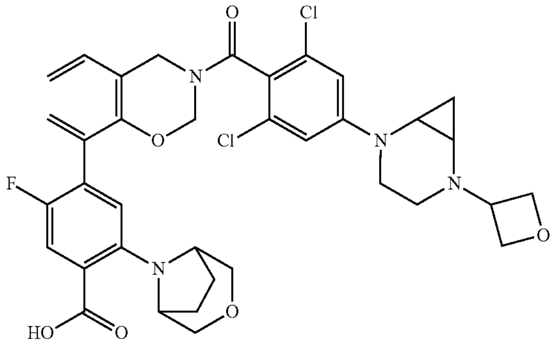 [SMILES: C=CC1=C(C(=C)c2cc(N3C4CCC3COC4)c(C(=O)O)cc2F)OCN(C(=O)c2c(Cl)cc(N3CCN(C4COC4)C4CC43)cc2Cl)C1] | 4-[3-[2,6-Dichloro-4-[5-(oxetan-3-yl)-2,5-diazabicyclo[4.1.0] heptan-2-yl]benzoyl]-2,4-dihydro-1,3-benzoxazin-8-yl]-5-fluoro-2-(3-oxa-8-azabicyclo [3.2.1]octan-8-yl)benzoic acid | B | 1.34 | 709 |
| 9-16 | 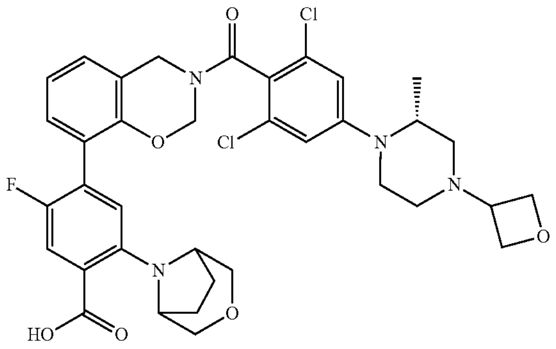 [SMILES: C[C@@H]1CN(C2COC2)CCN1c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(2R)-2-methyl-4-(oxetan-3-yl)piperazin-1-yl]benzoyl]-2,4-dihydro-1,3-benzoxazin-8-yl]-5-fluoro-2-(3-oxa-8-azabicyclo [3.2.1]octan-8-yl)benzoic acid | B | 1.15 | 711 |
| 9-17 | 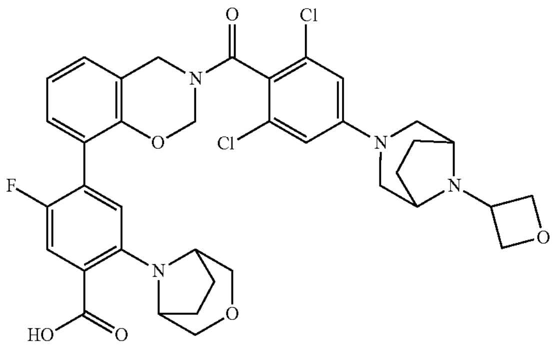 [SMILES: O=C(O)c1cc(F)c(-c2cccc3c2OCN(C(=O)c2c(Cl)cc(N4CC5CCC(C4)N5C4COC4)cc2Cl)C3)cc1N1C2CCC1COC2] | 4-[3-[2,6-Dichloro-4-[8-(oxetan-3-yl)-3,8-diazabicyclo [3.2.1]octan-3-yl]benzoyl]-2,4-dihydro-1,3-benzoxazin-8-yl]-5-fluoro-2-(3-oxa-8-azabicyclo [3.2.1]octan-8-yl)benzoic acid | B | 1.02. 1.06 | 723 |

TABLE 9-1-continued

| Compound No. | Structure | Compound Name | Analysis conditions | HPLC retention time (min) | m/z [M + H] |
|---|---|---|---|---|---|
| 9-18 | 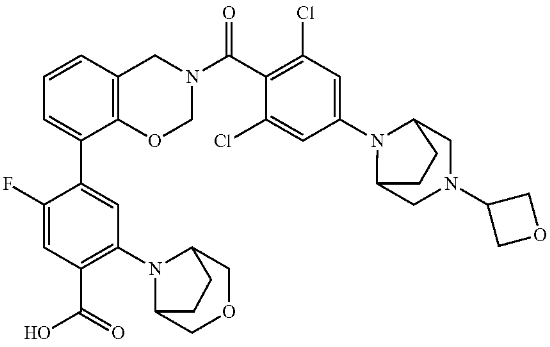 [SMILES: O=C(O)c1cc(F)c(-c2cccc3c2OCN(C(=O)c2c(Cl)cc(N4C5CCC4CN(C4COC4)C5)cc2Cl)C3)cc1N1C2CCC1COC2] | 4-[3-[2,6-Dichloro-4-[3-(oxetan-3-yl)-3,8-diazabicyclo[3.2.1] octan-8-yl]benzoyl]-2,4-dihydro-1,3-benzoxazin-8-yl]-5-fluoro-2-(3-oxa-8-azabicyclo[3.2.1]octan-8-yl)benzoic acid | B | 1.17 | 723 |
| 9-19 | 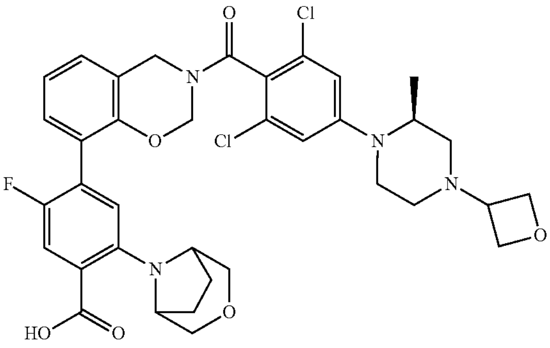 [SMILES: C[C@H]1CN(C2COC2)CCN1c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(2S)-2-methyl-4-(oxetan-3-yl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.15 | 711 |
| 9-20 | 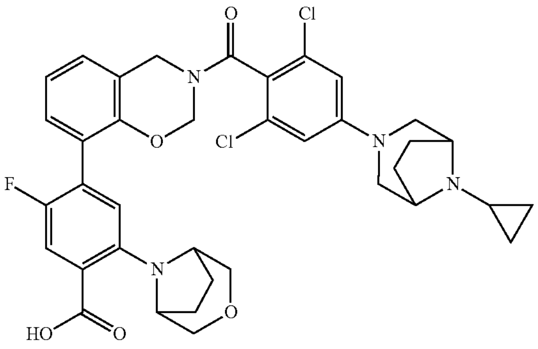 [SMILES: O=C(O)c1cc(F)c(-c2cccc3c2OCN(C(=O)c2c(Cl)cc(N4CC5CCC(C4)N5C4CC4)cc2Cl)C3)cc1N1C2CCC1COC2] | 4-[3-[2,6-Dichloro-4-(8-cyclopropyl-3,8-diazabicyclo[3.2.1]octan-3-yl)benzoyl]-2,4-dihydro-1,3-benzoxazin-8-yl]-5-fluoro-2-(3-oxa-8-azabicyclo[3.2.1] octan-8-yl)benzoic acid | B | 1.15. 1.18 | 707 |
| 9-21 | 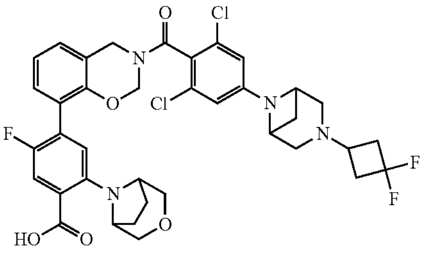 [SMILES: O=C(O)c1cc(F)c(-c2cccc3c2OCN(C(=O)c2c(Cl)cc(N4C5CC4CN(C4CC(F)(F)C4)C5)cc2Cl)C3)cc1N1C2CCC1COC2] | 4-[3-[2,6-Dichloro-4-[3-(3,3-difluorocyclobutyl)-3,6-diazabicyclo[3.1.1]heptan-6-yl]benzoyl]-2,4-dihydro-1,3-benzoxazin-8-yl]-5-fluoro-2-(3-oxa-8-azabicyclo[3.2.1] octan-8-yl)benzoic acid | B | 1.30. 1.32 | 143 |

TABLE 9-1-continued

| Compound No. | Structure | Compound Name | Analysis conditions | HPLC retention time (min) | m/z [M + H] |
|---|---|---|---|---|---|
| 9-22 | 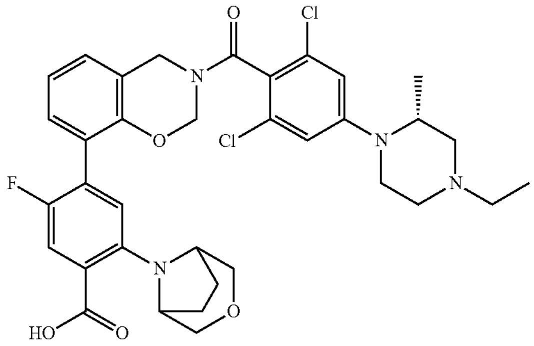 [SMILES: CCN1CCN(c2cc(Cl)c(C(=O)N3COc4c(cccc4-c4cc(N5C6CCC5COC6)c(C(=O)O)cc4F)C3)c(Cl)c2)[C@H](C)C1] | 4-[3-[2,6-Dichloro-4-[(2R)-4-ethyl-2-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.02. 1.06 | 683 |
| 9-23 | 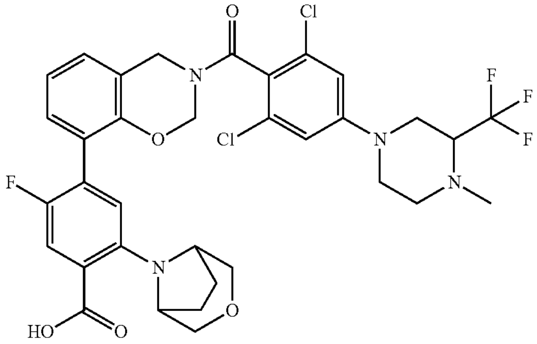 [SMILES: CN1CCN(c2cc(Cl)c(C(=O)N3COc4c(cccc4-c4cc(N5C6CCC5COC6)c(C(=O)O)cc4F)C3)c(Cl)c2)CC1C(F)(F)F] | 4-[3-[2,6-Dichloro-4-[4-methyl-3-(trifluoromethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.69. 1.71 | 723 |
| 9-24 | 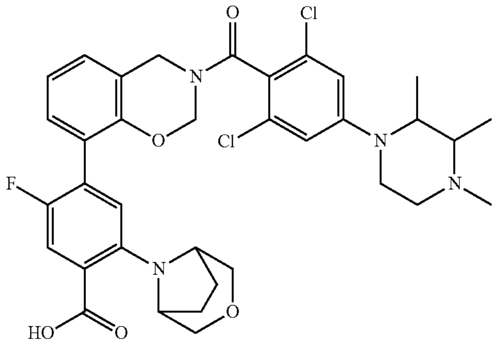 [SMILES: CC1C(C)N(c2cc(Cl)c(C(=O)N3COc4c(cccc4-c4cc(N5C6CCC5COC6)c(C(=O)O)cc4F)C3)c(Cl)c2)CCN1C] | 4-[3-[2,6-Dichloro-4-(2,3,4-trimethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid | B | 1.01. 1.05 | 683 |

TABLE 9-2

| Final compound No. | Intermediate | Alkylating agent |
|---|---|---|
| 9-1 | A M 1 8 | Paraformaldehyde |
| 9-2 | A M 1 | 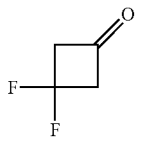 |
| 9-3 | A M 1 | 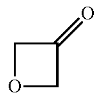 |
| 9-5 | A M 1 9 | Paraformaldehyde |
| 9-6 | A M 2 0 | Paraformaldehyde |
| 9-7 | A M 6 | Paraformaldehyde |

TABLE 9-2-continued

| Final compound No. | Intermediate | Alkylating agent |
|---|---|---|
| 9-8 | A M 7 | Paraformaldehyde |
| 9-9 | A M 2 1 | Paraformaldehyde |
| 9-10 | A M 5 | Paraformaldehyde |
| 9-11 | A M 2 2 | Paraformaldehyde |
| 9-13 | A M 2 3 | Paraformaldehyde |
| 9-14 | A M 2 4 | Paraformaldehyde |
| 9-15 | A M 1 9 | 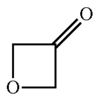 |
| 9-16 | A M 4 | 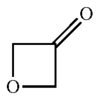 |

TABLE 9-2-continued

| Final compound No. | Intermediate | Alkylating agent |
|---|---|---|
| 9-17 | AM 6 | 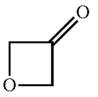 |
| 9-18 | AM 7 | 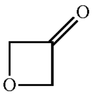 |
| 9-19 | AM 3 | 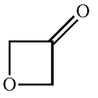 |
| 9-20 | AM 6 | 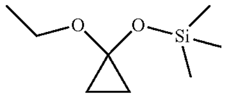 |
| 9-21 | AM 5 | 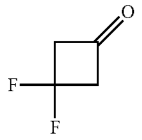 |
| 9-22 | AM 4 | 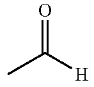 |
| 9-23 | AM 25 | Paraformaldehyde |
| 9-24 | AM 26 | Paraformaldehyde |

Compound 10-11

4-[3-[2,6-Dichloro-4-[2-(oxetan-3-yl)-2,6-diazaspiro[3.3]heptan-6-yl]benzoyl]-2,4-dihydro-1,3-benzoxazin-8-yl]-5-fluoro-2-morpholin-4-ylbenzoic acid First Step
Compound BCA28 tert-Butyl 6-[3,5-dichloro-4-[8-(2-fluoro-4-methoxycarbonyl-5-morpholin-4-ylphenyl)-2,4-dihydro-1,3-benzoxazine-3-carbonyl]phenyl]-2,6-diazaspiro[3.3]heptane-2-carboxylate

[Formula 316]

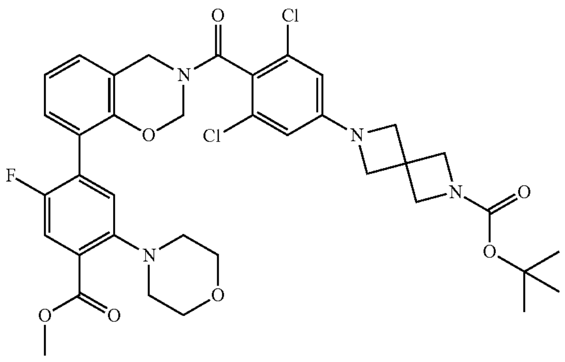

A suspension of compound B (50.0 mg, 0.0890 mmol), tert-butyl 2,6-diazaspiro[3.3]heptane-2-carboxylate oxalate (108 mg, 0.222 mmol), and triethylamine (0.0617 ml, 0.444 mmol) in 1-methylpyrrolidin-2-one (0.222 mL) was stirred at 130° C. for 3 hours. The reaction mixture was purified by reverse phase silica gel chromatography (acetonitrile/water, 0.1% formic acid) to obtain the title compound (96%, 63.0 mg).

LCMS: m/z 741 $[M+H]^+$

HPLC retention time: 1.02 min (analysis condition D)

Second Step
Compound AM28

Methyl 4-[3-[2,6-dichloro-4-(2,6-diazaspiro[3.3]heptan-2-yl)benzoyl]-2,4-dihydro-1,3-benzoxazin-8-yl]-5-fluoro-2-morpholin-4-ylbenzoate 2,2,2-trifluoroacetate

[Formula 317]

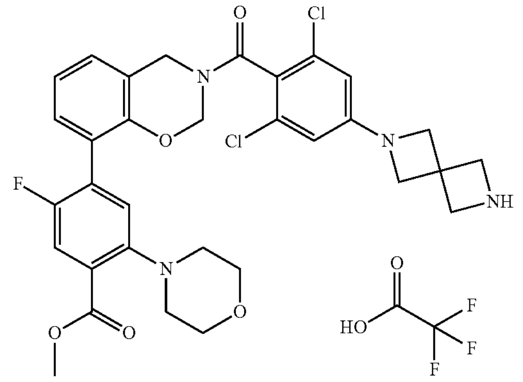

The title compound was synthesized by the same operation as in the second step of compound 7-2 using tert-butyl 6-[3,5-dichloro-4-[8-(2-fluoro-4-methoxycarbonyl-5-morpholin-4-ylphenyl)-2,4-dihydro-1,3-benzoxazine-3-carbonyl]phenyl]-2,6-diazaspiro[3.3]heptane-2-carboxylate.

LCMS: m/z 641$[M+H]^+$

HPLC retention time: 0.59 min and 0.61 min (analysis condition D)

Third Step
Compound 10-11

4-[3-[2,6-Dichloro-4-[2-(oxetan-3-yl)-2,6-diazaspiro[3.3]heptan-6-yl]benzoyl]-2,4-dihydro-1,3-benzoxazin-8-yl]-5-fluoro-2-morpholin-4-ylbenzoic acid

[Formula 318]

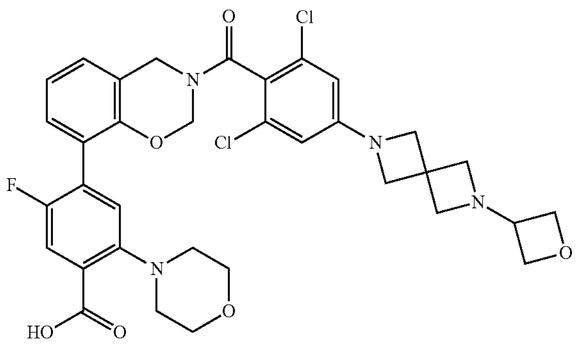

The title compound was synthesized by the same operation as in the process of compound 9-12 using methyl 4-[3-[2,6-dichloro-4-(2,6-diazaspiro[3.3]heptan-2-yl)benzoyl]-2,4-dihydro-1,3-benzoxazin-8-yl]-5-fluoro-2-morpholin-4-ylbenzoate 2,2,2-trifluoroacetate. However, oxetan-3-one was used instead of paraformaldehyde.

LCMS: m/z 683[M+H]+

HPLC retention time: 0.98 min and 1.03 min (analysis condition B)

Compound 10-3

4-[3-[2,6-Dichloro-4-[(3R)-3,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step Compound AMOH1

4-[3-[2,6-Dichloro-4-[(3R)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 319]

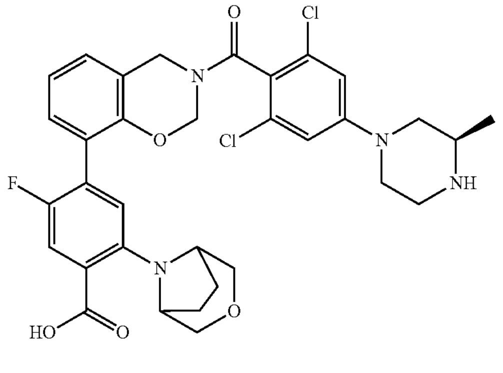

A solution of compound O (20.0 mg, 0.0340 mmol) and (2R)-2-methylpiperazine (0.0554 mL, 0.277 mmol) in 1-methylpyrrolidin-2-one (0.0850 mL) was stirred at 120° C. for 4 hours. Then, an 8 M aqueous potassium hydroxide solution (0.0424 mL, 0.339 mmol) was added to the reaction mixture, and the mixture was stirred at 60° C. for 30 minutes. The reaction mixture was purified by HPLC (acetonitrile/water, 0.1% formic acid) to obtain the title compound (79%, 17.5 mg).

LCMS: m/z 655[M+H]+

HPLC retention time: 0.51 min and 0.59 min (analysis condition D)

Second Step

Compound 10-3

4-[3-[2,6-Dichloro-4-[(3R)-3,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 320]

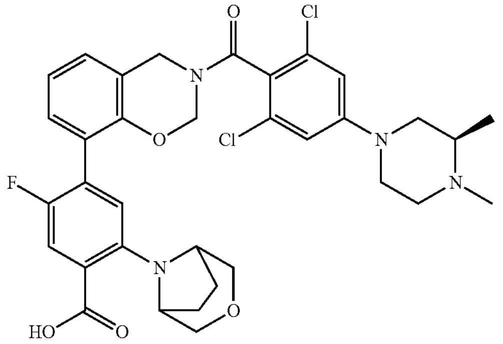

A suspension of 4-[3-[2,6-dichloro-4-[(3R)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid (8.00 mg, 0.0120 mmol), paraformaldehyde (3.66 mg, 0.122 mmol), and sodium triacetoxyborohydride (12.9 mg, 0.0610 mmol) in dichloromethane (0.0610 mL) was stirred at room temperature for 6 hours. The reaction mixture was diluted with methanol and then concentrated, and the obtained residue was purified by HPLC (acetonitrile/water, 0.1% formic acid) to obtain the title compound (88%, 7.20 mg).

LCMS: m/z 669[M+H]+

HPLC retention time: 0.99 min and 1.04 min (analysis condition B)

Compound BCA29

4-[3-[2,6-Dichloro-4-[1-[(2-methylpropan-2-yl)oxycarbonyl]piperidin-4-yl]oxybenzoyl]-2,4-dihydro-1,3-benzoxazin-8-yl]-2-morpholin-4-ylbenzoic acid

[Formula 321]

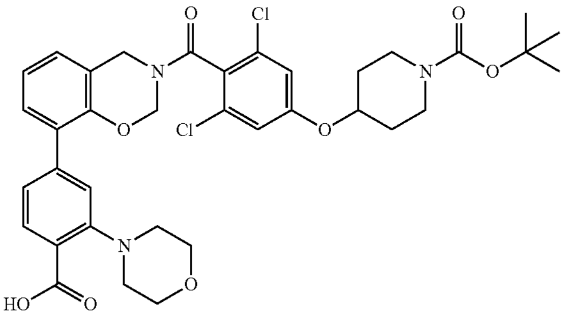

The title compound was synthesized by the same operation as in the first step of compound 8-8 using compound R. However, tert-butyl 4-hydroxypiperidine-1-carboxylate was used instead of tert-butyl 3-hydroxyazetidine-1-carboxylate as amine.

LCMS: m/z 712[M+H]+

HPLC retention time: 1.29 min (analysis condition G)

Compound AM29

4-[3-(2,6-Dichloro-4-piperidin-4-yloxybenzoyl)-2,4-dihydro-1,3-benzoxazin-8-yl]-2-morpholin-4-ylbenzoic acid hydrochloride

[Formula 322]

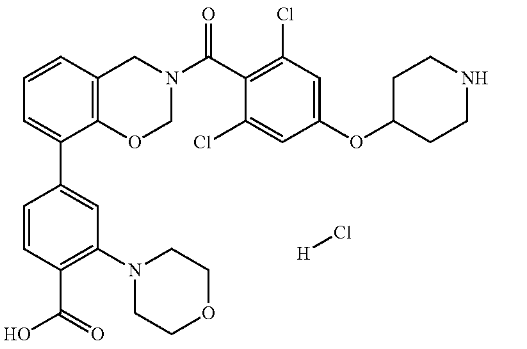

The title compound was synthesized by the same operation as in the second step of compound 7-2 using 4-[3-[2,6-dichloro-4-[1-[(2-methylpropan-2-yl)oxycarbonyl]piperidin-4-yl]oxybenzoyl]-2,4-dihydro-1,3-benzoxazin-8-yl]-2-morpholin-4-ylbenzoic acid. However, a 4 N solution of hydrochloric acid in dioxane was used instead of trifluoroacetic acid.

LCMS: m/z 612[M+H]$^+$

HPLC retention time: 0.72 min (analysis condition G)

Compound AMOH2

4-[3-[2,6-Dichloro-4-[(3S,5R)-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 323]

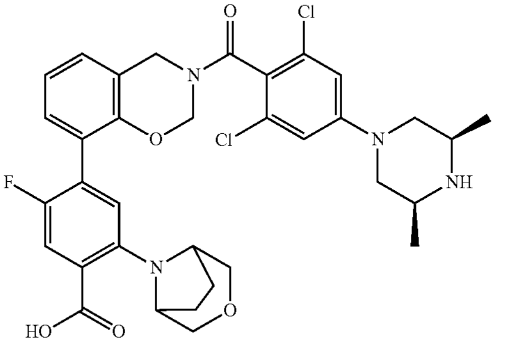

The title compound was synthesized by the same operation as in the first step of compound 10-3. However, (2S,6R)-2,6-dimethylpiperazine was used instead of (2R)-2-methylpiperazine as amine.

LCMS: m/z 669[M+H]$^+$

HPLC retention time: 0.52 min and 0.55 min (analysis condition D)

Compound AMOH3

4-[3-[2,6-Dichloro-4-[(3S)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 324]

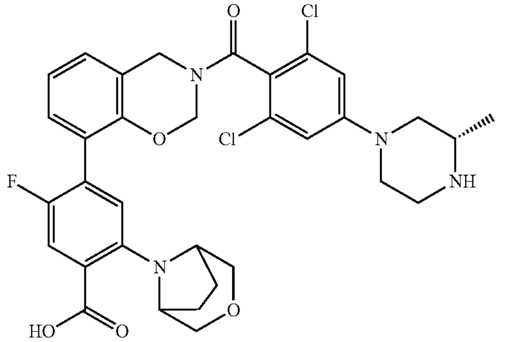

The title compound was synthesized by the same operation as in the first step of compound 10-3. However, (2S)-2-methylpiperazine was used instead of (2R)-2-methylpiperazine as amine.

LCMS: m/z 655[M+H]$^+$

HPLC retention time: 0.51 min and 0.54 min (analysis condition D)

Compound AMOH5

4-[3-[2,6-Dichloro-4-[(1S,4S)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 325]

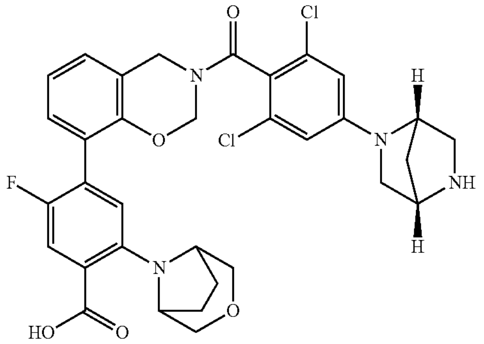

The title compound was synthesized by the same operation as in the first step of compound 10-3. However, (1S,4S)-2,5-diazabicyclo[2.2.1]heptane hydrobromide was used instead of (2R)-2-methylpiperazine as amine.

LCMS: m/z 653[M+H]$^+$

HPLC retention time: 0.50 min and 0.52 min (analysis condition D)

Compound AMOH6

4-[3-[2,6-Dichloro-4-(1,4-diazepan-1-yl)benzoyl]-2,4-dihydro-1,3-benzoxazin-8-yl]-5-fluoro-2-morpholin-4-ylbenzoic acid

[Formula 326]

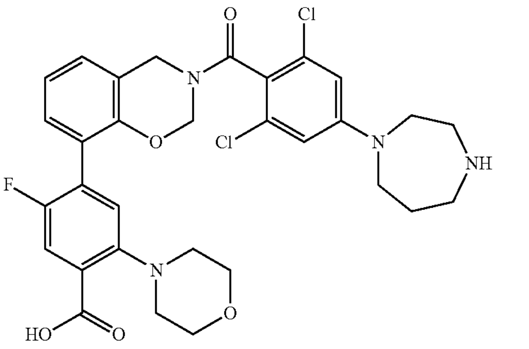

The title compound was synthesized by the same operation as in the first step of compound 10-3. However, 1,4-diazepane was used instead of (2R)-2-methylpiperazine as amine.

LCMS: m/z 629[M+H]$^+$

HPLC retention time: 0.49 min and 0.52 min (analysis condition D)

Compound 10-1

4-[3-[2,6-Dichloro-4-(7-methyl-2,7-diazaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 327]

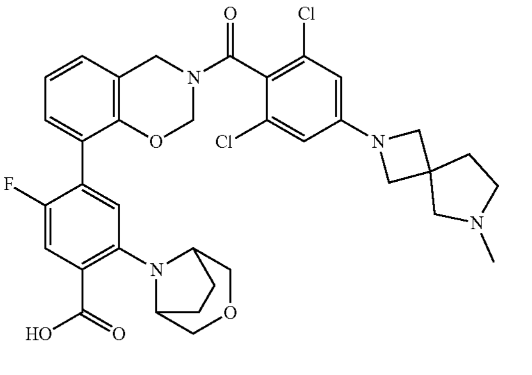

The title compound was synthesized by the same operation as in the process of compound 9-12 using methyl 4-[3-[2,6-dichloro-4-(2,7-diazaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate.

LCMS: m/z 681[M+H]$^+$

HPLC retention time: 1.01 min and 1.05 min (analysis condition B)

Compound 10-2

4-[3-[2,6-Dichloro-4-[7-(oxetan-3-yl)-2,7-diazaspiro[3.4]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 328]

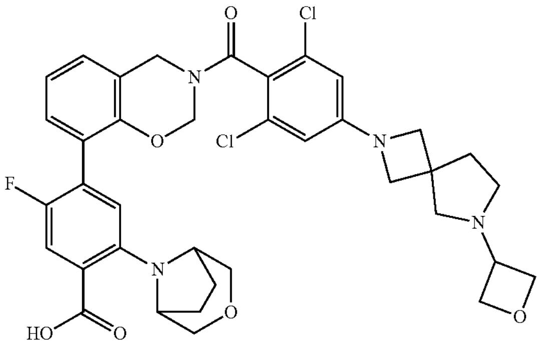

The title compound was synthesized by the same operation as in the process of compound 9-12 using methyl 4-[3-[2,6-dichloro-4-(2,7-diazaspiro[3.4]octan-2-yl)benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate. However, oxetan-3-one was used instead of paraformaldehyde.

LCMS: m/z 723[M+H]$^+$

HPLC retention time: 1.01 min and 1.05 min (analysis condition B)

Compound 10-12

4-[3-[2,6-Dichloro-4-(6-methyl-2,6-diazaspiro[3.3]heptan-2-yl)benzoyl]-2,4-dihydro-1,3-benzoxazin-8-yl]-5-fluoro-2-morpholin-4-ylbenzoic acid

[Formula 329]

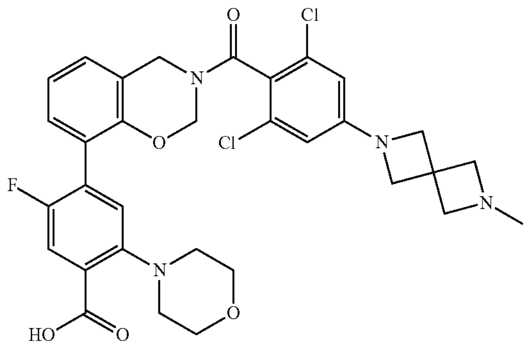

The title compound was synthesized by the same operation as in the process of compound 9-12 using methyl 4-[3-[2,6-dichloro-4-(2,6-diazaspiro[3.3]heptan-2-yl)benzoyl]-2,4-dihydro-1,3-benzoxazin-8-yl]-5-fluoro-2-morpholin-4-ylbenzoate 2,2,2-trifluoroacetate.

LCMS: m/z 641[M+H]$^+$

HPLC retention time: 0.78 min and 0.82 min (analysis condition A)

Compound 10-4

4-[3-[2,6-Dichloro-4-[meso-4-(2-methoxyethyl)-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 330]

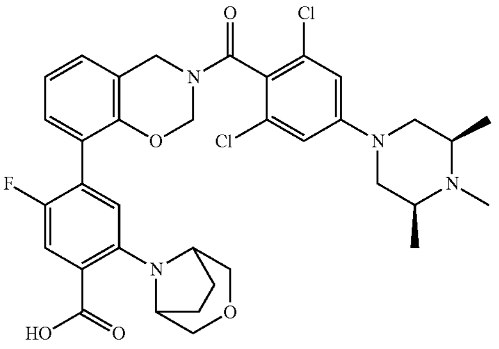

The title compound was synthesized by the same operation as in the second step of compound 10-3 using 4-[3-[2,6-dichloro-4-[(3S,5R)-3,5-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

LCMS: m/z 683[M+H]$^+$

HPLC retention time: 1.00 min and 1.05 min (analysis condition B)

Compound 10-5

4-[3-[2,6-Dichloro-4-[(3S)-3,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 331]

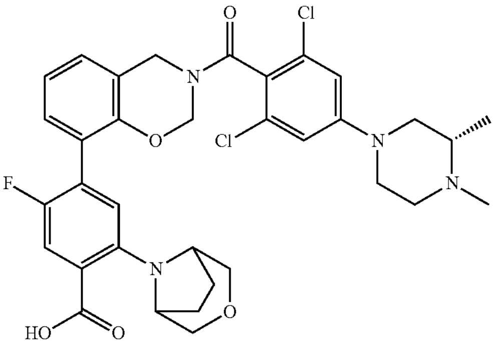

The title compound was synthesized by the same operation as in the second step of compound 10-3 using 4-[3-[2,6-dichloro-4-[(3S)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

LCMS: m/z 669[M+H]$^+$

HPLC retention time: 0.99 min and 1.04 min (analysis condition B)

Compound 10-6

4-[3-[2,6-Dichloro-4-(3,3,4-trimethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid

[Formula 332]

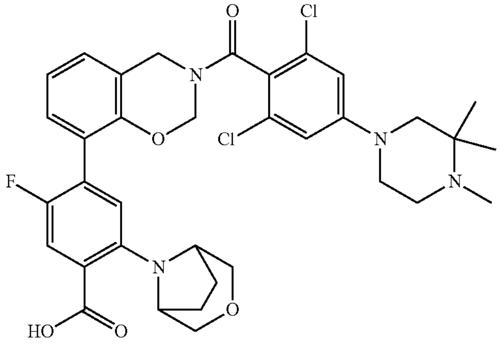

The title compound was synthesized by the same operation as in the second step of compound 10-3 using 4-[3-[2,6-dichloro-4-(3,3-dimethylpiperazin-1-yl)benzoyl]-2,4-dihydro-1,3-benzoxazin-8-yl]-5-fluoro-2-(3-oxa-8-azabicyclo[3.2.1]octan-8-yl)benzoic acid.

LCMS: m/z 683[M+H]$^+$

HPLC retention time: 1.01 min and 1.05 min (analysis condition B)

Compound 10-10

4-[3-[2,6-Dichloro-4-[(1S,4S)-5-methyl-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 333]

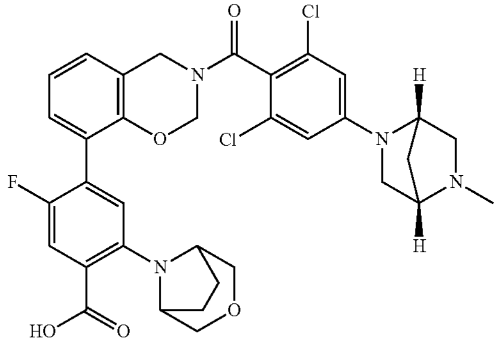

The title compound was synthesized by the same operation as in the second step of compound 10-3 using 4-[3-[2,6-dichloro-4-[(1S,4S)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid.

LCMS: m/z 667[M+H]$^+$

HPLC retention time: 0.99 min and 1.02 min (analysis condition B)

Compound 10-7

4-[3-[2,6-Dichloro-4-[(1S,4S)-5-(oxetan-3-yl)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 334]

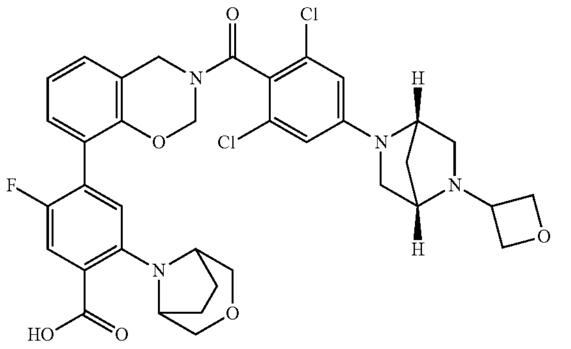

The title compound was synthesized by the same operation as in the second step of compound 10-3 using 4-[3-[2,6-dichloro-4-[(1S,4S)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid. However, oxetan-3-one was used instead of paraformaldehyde.

LCMS: m/z 709[M+H]$^+$

HPLC retention time: 1.00 min and 1.03 min (analysis condition B)

Compound 10-8

4-[3-[2,6-Dichloro-4-[(3R)-3-methyl-4-(oxetan-3-yl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 335]

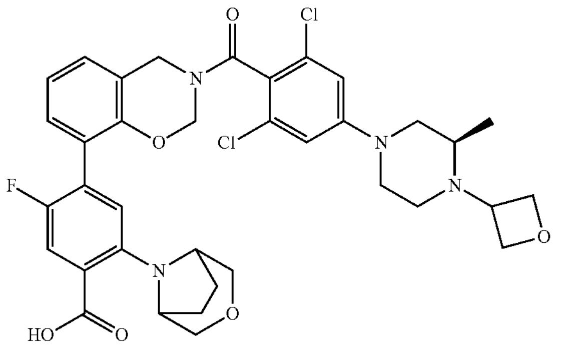

The title compound was synthesized by the same operation as in the second step of compound 10-3 using 4-[3-[2,6-dichloro-4-[(3R)-3-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid. However, oxetan-3-one was used instead of paraformaldehyde.

LCMS: m/z 711[M+H]$^+$

HPLC retention time: 1.05 min and 1.07 min (analysis condition B)

Compound 10-9

4-[3-[2,6-Dichloro-4-[4-(oxetan-3-yl)-1,4-diazepan-1-yl]benzoyl]-2,4-dihydro-1,3-benzoxazin-8-yl]-5-fluoro-2-morpholin-4-ylbenzoic acid

[Formula 336]

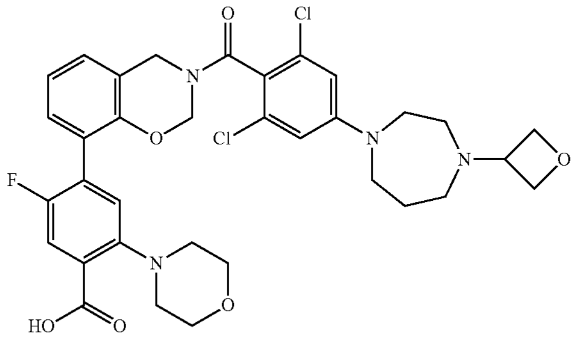

The title compound was synthesized by the same operation as in the second step of compound 10-3 using 4-[3-[2,6-dichloro-4-(1,4-diazepan-1-yl)benzoyl]-2,4-dihydro-1,3-benzoxazin-8-yl]-5-fluoro-2-morpholin-4-ylbenzoic acid. However, oxetan-3-one was used instead of paraformaldehyde.

LCMS: m/z 685[M+H]$^+$

HPLC retention time: 0.98 min and 1.02 min (analysis condition B)

Compound 10-13

4-[3-[2,6-Dichloro-4-(1-propan-2-ylpiperidin-4-yl)oxybenzoyl]-2,4-dihydro-1,3-benzoxazin-8-yl]-2-morpholin-4-ylbenzoic acid

[Formula 337]

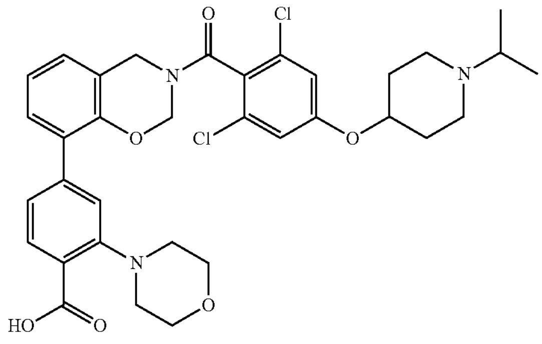

The title compound was synthesized by the same operation as in the second step of compound 10-3 using 4-[3-(2,6-dichloro-4-piperidin-4-yloxybenzoyl)-2,4-dihydro-1,3-benzoxazin-8-yl]-2-morpholin-4-ylbenzoic acid hydrochloride. However, acetone was used instead of paraformaldehyde.

LCMS: m/z 654[M+H]$^+$

HPLC retention time: 0.80 min and 0.84 min (analysis condition A)

Compound 11-4

4-[3-[2,6-Dichloro-4-[3-[3-(difluoromethoxy)azetidin-1-yl]azetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 338]

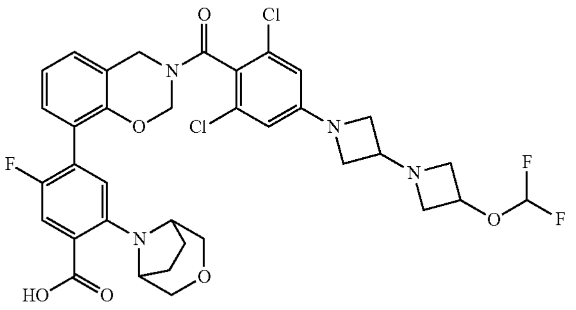

A solution of methyl 4-[3-[2,6-dichloro-4-(3-hydroxyazetidin-1-yl)benzoyl]-2,4-dihydro-1,3-benzoxazin-8-yl]-5-fluoro-2-(3-oxa-8-azabicyclo[3.2.1]octan-8-yl)benzoate (46.5 mg, 0.0620 mmol) and N,N-diisopropylethylamine (0.0199 mL, 0.0930 mmol) in dichloromethane (0.623 mL) was cooled to −78° C. Trifluoromethanesulfonic anhydride (0.0163 mL, 0.0930 mmol) was added thereto, and the mixture was stirred at −78° C. for 30 minutes. 3-(Difluoromethoxy)azetidine hydrochloride (19.9 mg, 0.125 mmol) and N,N-diisopropylethylamine (0.0434 mL, 0.249 mmol) were added thereto, and the mixture was stirred overnight at room temperature. Methanol was added to the reaction solution, and the mixture was concentrated. Tetrahydrofuran (0.311 mL), methanol (0.311 mL) and a 5 M aqueous sodium hydroxide solution (0.124 mL, 0.622 mmol) were added to the residue, and the mixture was stirred at 60° C. for 30 minutes. The reaction mixture was purified by HPLC (acetonitrile/water, 0.1% formic acid) to obtain the title compound (27%, 12.3 mg).

LCMS: m/z 733[M+H]$^+$

HPLC retention time: 1.10 min and 1.11 min (analysis condition B)

Compound 11-5

4-[3-[2,6-Dichloro-4-[3-(3-methoxyazetidin-1-yl)-3-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound AZA7

Methyl 4-[3-[2,6-dichloro-4-(3-hydroxy-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 339]

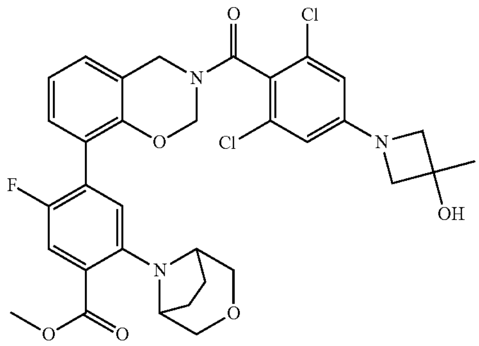

The title compound was obtained by the same operation as in the first step of compound 1-47 using compound A and 3-methylazetidin-3-ol hydrochloride.

LCMS: m/z 656[M+H]$^+$

HPLC retention time: 0.89 min (analysis condition D)

Second Step
Compound 11-5

4-[3-[2,6-Dichloro-4-[3-(3-methoxyazetidin-1-yl)-3-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 340]

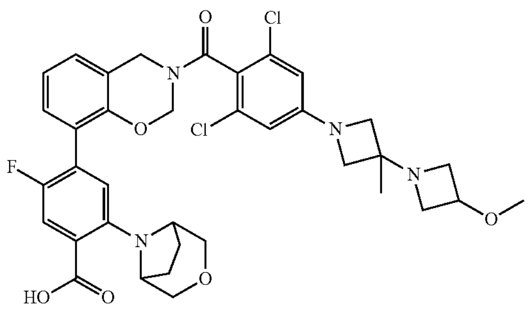

The title compound was obtained by the same operation as in the process of compound 11-4 using methyl 4-[3-[2,6-dichloro-4-(3-hydroxy-3-methylazetidin-1-yl)benzoyl]-2,4-dihydro-1,3-benzoxazin-8-yl]-5-fluoro-2-(3-oxa-8-azabicyclo[3.2.1]octan-8-yl)benzoate. However, 3-methoxyazetidine was used instead of 3-(difluoromethoxy)azetidine hydrochloride.

LCMS: m/z 711 [M+H]$^+$

HPLC retention time: 1.05 min and 1.09 min (analysis condition B)

Compounds shown in Table 11-1 were synthesized by the same operation as in the process of compound 11-4 using the corresponding intermediates and each amine shown in Table 11-2.

TABLE 11-1

| Compound No. | Intermediate | Structure | Compound Name |
|---|---|---|---|
| 11-2 | A Z 1 | 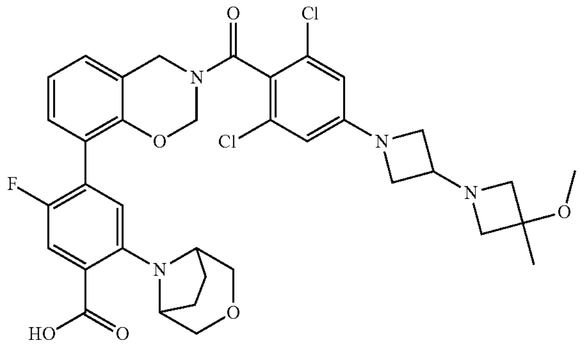 [SMILES: COC1(C)CN(C2CN(c3cc(Cl)c(C(=O)N4COc5c(cccc5-c5cc(N6C7CCC6COC7)c(C(=O)O)cc5F)C4)c(Cl)c3)C2)C1] | 4-[3-[2,6-Dichloro-4-[3-(3-methoxy-3-methylazetidin-1-yl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid |
| 11-3 | A Z 1 | 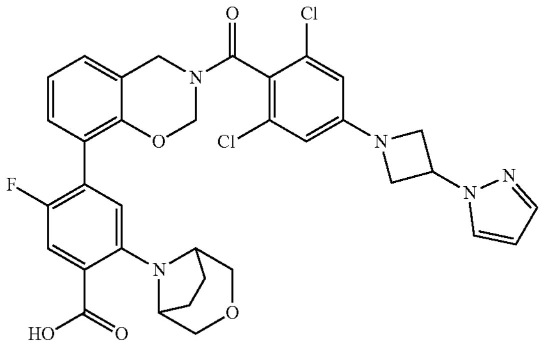 [SMILES: O=C(O)c1cc(F)c(-c2cccc3c2OCN(C(=O)c2c(Cl)cc(N4CC(n5cccn5)C4)cc2Cl)C3)cc1N1C2CCC1COC2] | 4-[3-[2,6-Dichloro-4-(3-pyrazol-1-ylazetidin-1-yl)benzoyl]-2,4-dihydro-1,3-benzoxazin-8-yl]-5-fluoro-2-(3-oxa-8-azabicyclo[3.2.1]octan-8-yl)benzoic acid |
| 11-7 | A Z 1 | 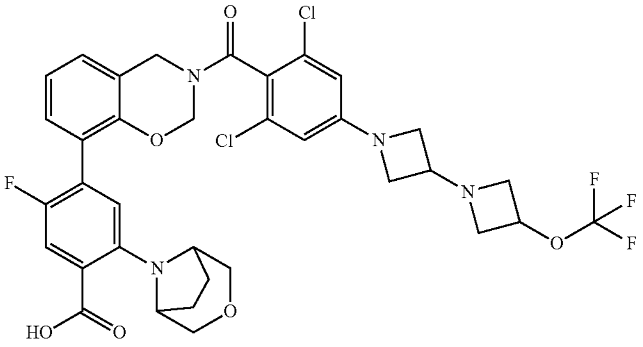 [SMILES: O=C(O)c1cc(F)c(-c2cccc3c2OCN(C(=O)c2c(Cl)cc(N4CC(N5CC(OC(F)(F)F)C5)C4)cc2Cl)C3)cc1N1C2CCC1COC2] | 4-[3-[2,6-Dichloro-4-[3-[3-(trifluoromethoxy)azetidin-1-yl]azetidin-1-yl]benzoyl]-2,4-dihydro-1,3-benzoxazin-8-yl]-5-fluoro-2-(3-oxa-8-azabicyclo[3.2.1]octan-8-yl)benzoic acid |
| 11-8 | A Z 1 | 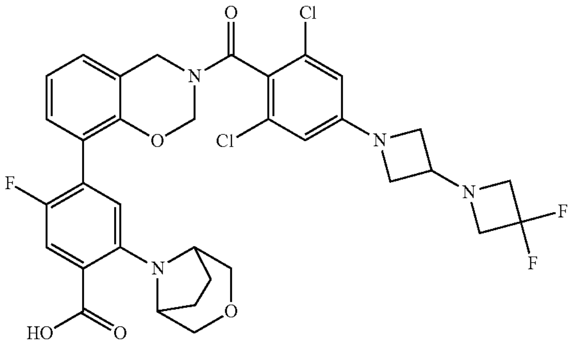 [SMILES: O=C(O)c1cc(F)c(-c2cccc3c2OCN(C(=O)c2c(Cl)cc(N4CC(N5CC(F)(F)C5)C4)cc2Cl)C3)cc1N1C2CCC1COC2] | 4-[3-[2,6-Dichloro-4-[3-(3,3-difluoroazetidin-1-yl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid |

TABLE 11-1-continued

| | | | |
|---|---|---|---|
| 11-9 | A Z 1 | 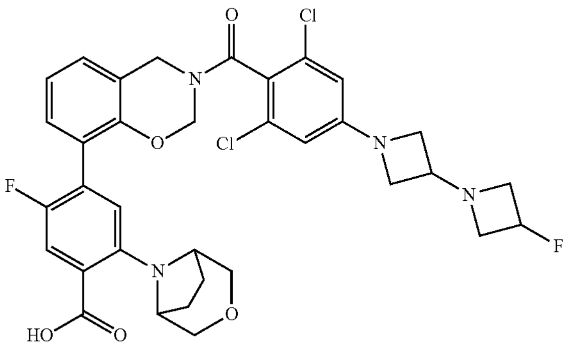 [SMILES: O=C(O)c1cc(F)c(-c2cccc3c2OCN(C(=O)c2c(Cl)cc(N4CC(N5CC(F)C5)C4)cc2Cl)C3)cc1N1C2CCC1COC2] | 4-[3-[2,6-Dichloro-4-[3-(3-fluoroazetidin-1-yl)azetidin-1-yl]benzoyl]-2,4-dihydro-1,3-benzoxazin-8-yl]-5-fluoro-2-(3-oxa-8-azabicyclo[3.2.1]octan-8-yl)benzoic acid |
| 11-1 | A Z 3 | 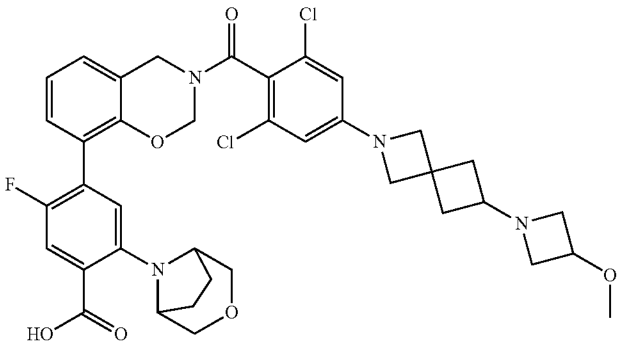 [SMILES: COC1CN(C2CC3(C2)CN(c2cc(Cl)c(C(=O)N4COc5c(cccc5-c5cc(N6C7CCC6COC7)c(C(=O)O)cc5F)C4)c(Cl)c2)C3)C1] | 4-[3-[2,6-Dichloro-4-[6-(3-methoxyazetidin-1-yl)-2-azaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid |
| 11-5 | A Z A 7 | 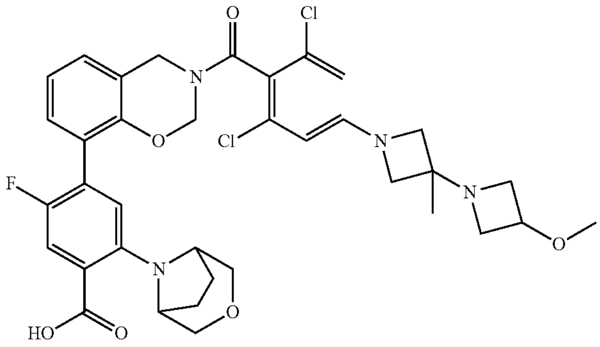 [SMILES: C=C(Cl)/C(C(=O)N1COc2c(cccc2-c2cc(N3C4CCC3COC4)c(C(=O)O)cc2F)C1)=C(Cl)\C=C\N1CC(C)(N2CC(OC)C2)C1] | 4-[3-[2,6-Dichloro-4-[3-(3-methoxyazetidin-1-yl)-3-methylazetidin-1-yl]benzoyl]-2,4-dihydro-1,3-benzoxazin-8-yl]-5-fluoro-2-(3-oxa-8-azabicyclo[3.2.1]octan-8-yl)benzoic acid |
| 11-6 | A Z A 7 | 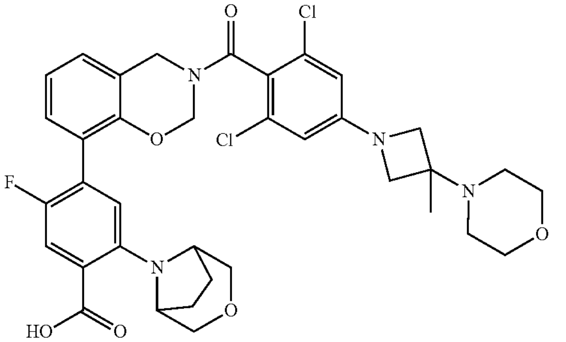 [SMILES: CC1(N2CCOCC2)CN(c2cc(Cl)c(C(=O)N3COc4c(cccc4-c4cc(N5C6CCC5COC6)c(C(=O)O)cc4F)C3)c(Cl)c2)C1] | 4-[3-[2,6-Dichloro-4-(3-methyl-3-morpholin-4-ylazetidin-1-yl)benzoyl]-2,4-dihydro-1,3-benzoxazin-8-yl]-5-fluoro-2-(3-oxa-8-azabicyclo[3.2.1]octan-8-yl)benzoic acid |

TABLE 11-1-continued

| Final compound No. | Analysis conditions | HPLC retention time (min) | m/z [M + H]+ |
|---|---|---|---|
| 11-2 | B | 1.04. 1.07 | 713 |
| 11-3 | B | 1.49 | 678 |
| 11-7 | B | 1.25. 1.27 | 761 |
| 11-8 | B | 1.47. 1.48 | 703 |
| 11-9 | B | 1.04. 1.07 | 685 |
| 11-1 | B | 1 07. 1.10 | 737 |
| 11-5 | B | 3.05. 1.09 | 711 |
| 11-6 | D | 0.57 | 709.6 [M − H] − |

TABLE 11-2

| Final compound No. | Amine |
|---|---|
| 11-1 | 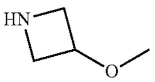 |
| 11-2 | 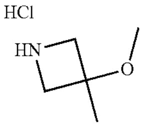 |
| 11-3 | 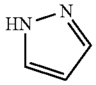 |
| 11-5 | 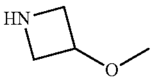 |
| 11-6 | 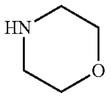 |
| 11-7 | 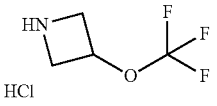 |
| 11-8 | 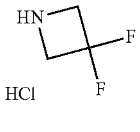 |
| 11-9 | 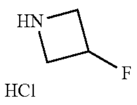 |

Compound 11-10

4-[3-[2,6-Dichloro-4-(6-cyclopropyloxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AZA8

Methyl 4-[3-[2,6-dichloro-4-(6-cyclopropyloxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 341]

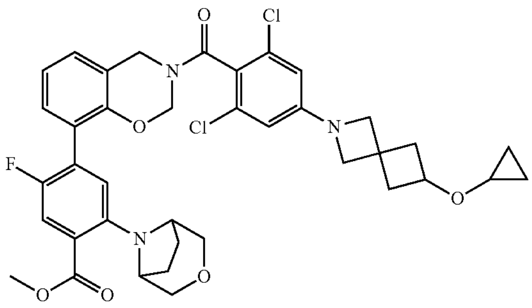

A solution of methyl 4-[3-[2,6-dichloro-4-(6-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (36.5 mg, 0.0530 mmol) and N,N-diisopropylethylamine (0.0121 mL, 0.0700 mmol) in dichloromethane (0.530 mL) was cooled to −78° C. Trifluoromethanesulfonic anhydride (0.0137 mL, 0.0640 mmol) was added thereto, and the mixture was stirred at −78° C. for 1.5 hours. Cyclopropanol (0.0102 mL, 0.160 mmol) and a 1 M potassium tert-butoxide solution (0.160 mL, 0.160 mmol) were added to the reaction solution, and the mixture was stirred at room temperature for 1.5 hours. The reaction mixture was purified by HPLC (acetonitrile/water, 0.1% formic acid) to obtain the title compound (38%, 22.7 mg).

LCMS: m/z 722[M+H]+

HPLC retention time: 1.08 min (analysis condition D)

Second Step
Compound 11-10

4-[3-[2,6-Dichloro-4-(6-cyclopropyloxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 342]

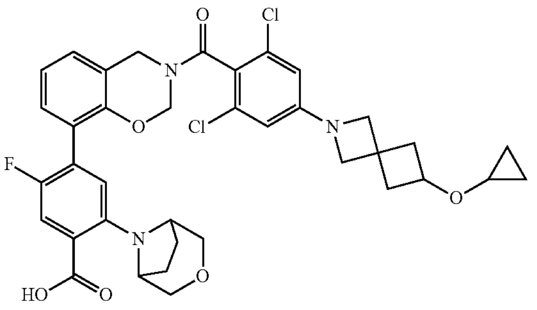

To a solution of methyl 4-[3-[2,6-dichloro-4-(6-cyclopropyloxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (22.7 mg, 0.0310 mmol) in methanol (0.157 mL) and 1,4-dioxane (0.472 mL), an 8 M aqueous potassium hydroxide solution (0.0393 mL, 0.314 mmol) was added, and the mixture was stirred at 60° C. for 1 hour. The reaction mixture was purified by HPLC (acetonitrile/water, 0.1% formic acid) to obtain the title compound (78%, 17.4 mg).

LCMS: m/z 708[M+H]$^+$

HPLC retention time: 1.79 min and 1.82 min (analysis condition B)

Compound 12-2

4-[3-[2,6-Dichloro-4-(1-methylpyrazol-4-yl)benzoyl]-2,4-dihydro-1,3-benzoxazin-8-yl]-5-fluoro-2-(8-oxa-3-azabicyclo[3.2.1]octan-3-yl)benzoic acid First Step
Compound LN2

Methyl 4-[3-[2,6-dichloro-4-(1-methylpyrazol-4-yl)benzoyl]-2,4-dihydro-1,3-benzoxazin-8-yl]-5-fluoro-2-(8-oxa-3-azabicyclo[3.2.1]octan-3-yl)benzoate

[Formula 343]

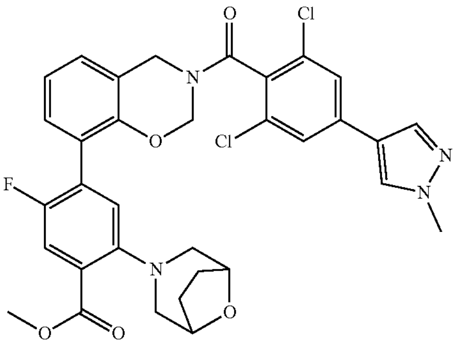

To a solution of compound X (40.0 mg, 0.0620 mmol), 3-oxa-8-azabicyclo[3.2.1]octane hydrochloride (17.4 mg, 0.116 mmol), and cesium carbonate (95.0 mg, 0.291 mmol) in toluene (0.581 mL), Xantphos Pd G4 (5.59 mg, 0.00581 mmol) was added, and the mixture was stirred at 100° C. for 2 hours. The reaction mixture was purified by HPLC (acetonitrile/water, 0.1% formic acid) to obtain the title compound (38%, 14.2 mg).

LCMS: m/z 651[M+H]$^+$

HPLC retention time: 0.93 min (analysis condition D)

Second Step

Compound 12-2

4-[3-[2,6-Dichloro-4-(1-methylpyrazol-4-yl)benzoyl]-2,4-dihydro-1,3-benzoxazin-8-yl]-5-fluoro-2-(8-oxa-3-azabicyclo[3.2.1]octan-3-yl)benzoic acid

[Formula 344]

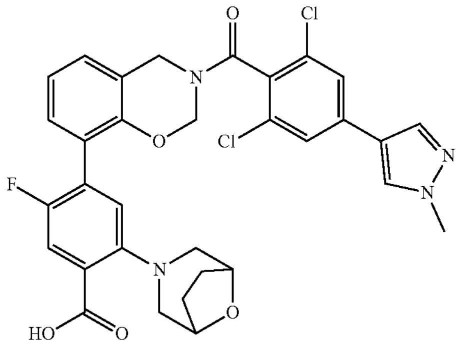

To a solution of methyl 4-[3-[2,6-dichloro-4-(1-methylpyrazol-4-yl)benzoyl]-2,4-dihydro-1,3-benzoxazin-8-yl]-5-fluoro-2-(8-oxa-3-azabicyclo[3.2.1]octan-3-yl)benzoate (14.2 mg, 0.0220 mmol) in tetrahydrofuran (0.109 mL)-methanol (0.109 mL), a 5 M aqueous sodium hydroxide solution (0.0436 mL, 0.218 mmol) was added, and the mixture was stirred at 60° C. for 30 minutes. The reaction mixture was purified by HPLC (acetonitrile/water, 0.1% formic acid) to obtain the title compound (30%, 4.2 mg).

LCMS: m/z 637[M+H]$^+$

HPLC retention time: 1.38 min and 1.41 min (analysis condition B)

Intermediates shown in Table 12-1 were synthesized by the same operation as in the first step of compound 12-2 using compound X and each amine shown in Table 12-2.

TABLE 12-1

| Compound No. | Intermediate | Structure | Compound Name | Analysis conditions | HPLC retention time (min) | m/z [M + H]+ |
|---|---|---|---|---|---|---|
| L N 1 | X | 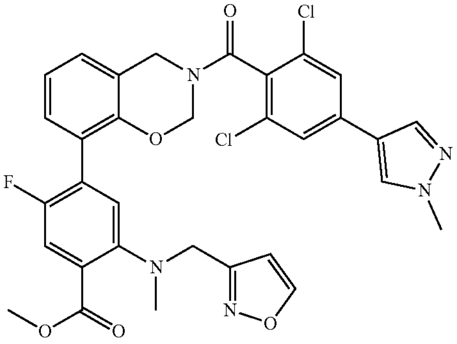 [SMILES: COC(=O)c1cc(F)c(-c2cccc3c2OCN(C(=O)c2c(Cl)cc(-c4cnn(C)c4)cc2Cl)C3)cc1N(C)Cc1ccon1] | Methyl 4-[3-[2,6-dichloro-4-(1-methylpyrazol-4-yl)benzoyl]-2,4-dihydro-1,3-benzoxazin-8-yl]-5-fluoro-2-[methyl(1,2-oxazol-3-ylmethyl)amino]benzoate | D | 0.89. 0.90 | 650 |
| L N 3 | X | 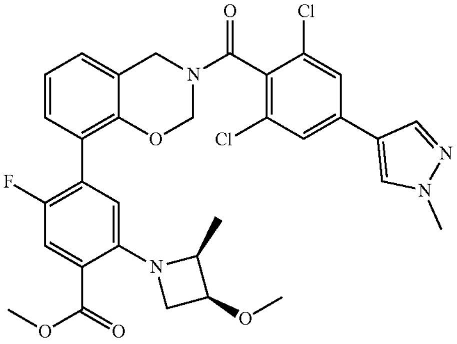 [SMILES: COC(=O)c1cc(F)c(-c2cccc3c2OCN(C(=O)c2c(Cl)cc(-c4cnn(C)c4)cc2Cl)C3)cc1N1C[C@H](OC)[C@@H]1C] | Methyl 4-[3-[2,6-dichloro-4-(1-methylpyrazol-4-yl)benzoyl]-2,4-dihydro-1,3-benzoxazin-8-yl]-5-fluoro-2-[(2S,3S)-3-methoxy-2-methylazetidin-1-yl]benzoate | D | 0.94 | 639 |
| L N 4 | X | 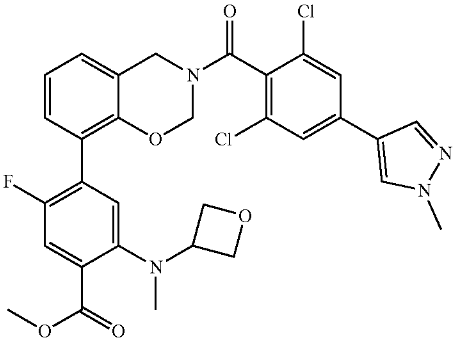 [SMILES: COC(=O)c1cc(F)c(-c2cccc3c2OCN(C(=O)c2c(Cl)cc(-c4cnn(C)c4)cc2Cl)C3)cc1N(C)C1COC1] | Methyl 4-[3-[2,6-dichloro-4-(1-methylpyrazol-4-yl)benzoyl]-2,4-dihydro-1,3-benzoxazin-8-yl]-5-fluoro-2-[methyl(oxetan-3-yl)amino]benzoate | D | 0.86. 0.87 | 625 |

TABLE 12-2

| Final compound No. | Amine |
|---|---|
| 12-1 | 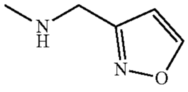 |
| 12-3 | 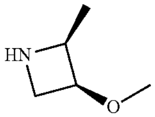 |
| 12-4 | 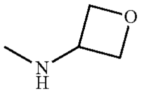 |

Synthesis of Amine Compound z1

Benzyl (2S,3S)-3-hydroxy-2-methylazetidine-1-carboxylate

[Formula 345]

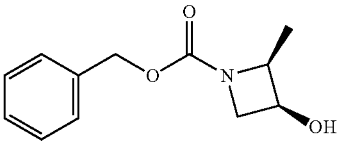

A solution of benzyl (2S)-2-methyl-3-oxoazetidine-1-carboxylate (100 mg, 0.456 mmol) in tetrahydrofuran (2.28 mL) was cooled to −78° C. A 1 M solution of lithium tri(sec-butyl)borohydride in tetrahydrofuran (0.547 mL, 0.547 mmol) was added dropwise thereto, and the mixture was stirred at −78° C. for 1 hour. An aqueous formic acid solution was added to the reaction mixture, and the mixture was purified by HPLC (acetonitrile/water, 0.1% formic acid) to obtain the title compound (87%, 88.0 mg).

LCMS: m/z 222[M+H]$^+$

HPLC retention time: 0.55 min (analysis condition D)

Compound z2

Benzyl (2S,3S)-3-methoxy-2-methylazetidine-1-carboxylate

[Formula 346]

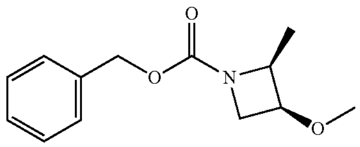

The title compound was obtained by the same method as in compound a1 using benzyl (2S,3S)-3-hydroxy-2-methylazetidine-1-carboxylate.

LCMS: m/z 236[M+H]$^+$

HPLC retention time: 0.71 min (analysis condition D)

Compound z3

(2S,3S)-3-Methoxy-2-methylazetidine hydrochloride

[Formula 347]

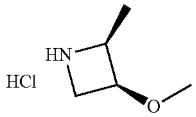

To a solution of benzyl (2S,3S)-3-methoxy-2-methylazetidine-1-carboxylate (0.0568 g, 0.241 mmol) in methanol, 10% palladium/carbon (0.077 mg, 0.0720 mmol) was added, and the mixture was stirred at room temperature for 2 hours in a hydrogen atmosphere. The reaction solution was filtered through celite, and a hydrochloric acid-methanol solution was added to the filtrate. The reaction solution was concentrated to obtain the title compound as a crude product.

LCMS: m/z 102[M+H]$^+$ $^1$H-NMR (400 MHz, $CDCl_3$) δ: 4.71-4.64 (1H, m), 4.28 (1H, q, J=6.4 Hz), 4.17 (1H, m), 3.98-3.90 (1H, m), 3.31 (3H, s), 1.61 (3H, d, J=7.0 Hz).

Compounds shown in Table 12-3 were synthesized by the same operation as in the second step of compound 12-2 using intermediates shown in Table 12-1.

TABLE 12-3

| Compound No. | Intermediate | Structure | Compound Name | Analysis conditions | HPLC retention time (min) | [M + H]$^+$ |
|---|---|---|---|---|---|---|
| 12-1 | L N 1 | 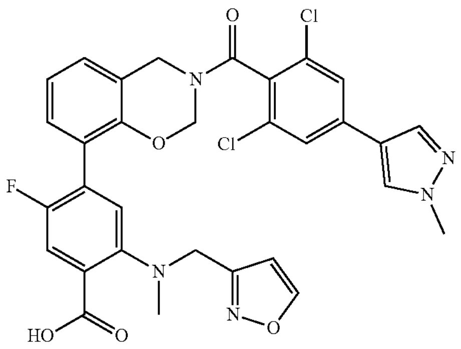 [SMILES: CN(Cc1ccon1)c1cc(-c2cccc3c2OCN(C(=O)c2c(Cl)cc(-c4cnn(C)c4)cc2Cl)C3)c(F)cc1C(=O)O] | 4-[3-[2,6-Dichloro-4-(1-methylpyrazol-4-yl)benzoyl]-2,4-dihydro-1,3-benzoxazin-8-yl]-5-fluoro-2-[methyl(1,2-oxazol-3-ylmethyl)amino] benzoic acid | B | 1.42, 1.44 | 636 |
| 12-3 | L N 3 | 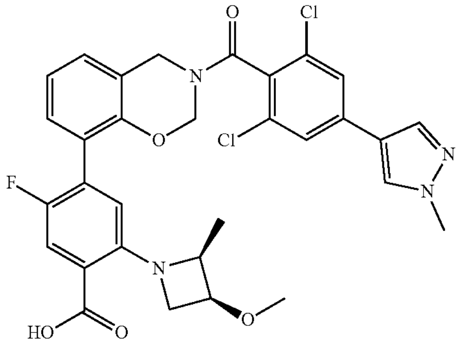 [SMILES: CO[C@H]1CN(c2cc(-c3cccc4c3OCN(C(=O)c3c(Cl)cc(-c5cnn(C)c5)cc3Cl)C4)c(F)cc2C(=O)O)[C@H]1C] | 4-[3-[2,6-Dichloro-4-(1-methylpyrazol-4-yl)benzoyl]-2,4-dihydro-1,3-benzoxazin-8-yl]-5-fluoro-2-[(2S,3S)-3-methoxy-2-methylazetidin-1-yl]benzoic acid | B | 1.48, 1.49 | 625 |

TABLE 12-3-continued

| Compound No. | Intermediate | Structure | Compound Name | Analysis conditions | HPLC retention time (min) | [M + H]+ |
|---|---|---|---|---|---|---|
| 12-4 | L N 4 | 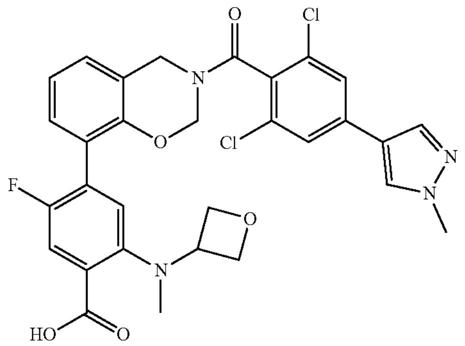 [SMILES: CN(c1cc(-c2cccc3c2OCN(C(=O)c2c(Cl)cc(-c4cnn(C)c4)cc2Cl)C3)c(F)cc1C(=O)O)C1COC1] | 4-[3-[2,6-Dichloro-4-(1-methylpyrazol-4-yl)benzoyl]-2,4-dihydro-1,3-benzoxazin-8-yl]-5-fluoro-2-[methyl(oxetan-3-yl) amino]benzoic acid | B | 1.35, 1.38 | 611 |

Compound 13-1

4-[3-[2,6-Dichloro-4-(1-methylpyrazol-4-yl)benzoyl]-2,4-dihydro-1,3-benzoxazin-8-yl]-5-fluoro-2-(3-oxa-8-azabicyclo[3.2.1]octan-8-yl)benzoic acid First Step Compound CL2

2,6-Dichloro-4-(1-methylpyrazol-4-yl)benzoyl Chloride

[Formula 348]

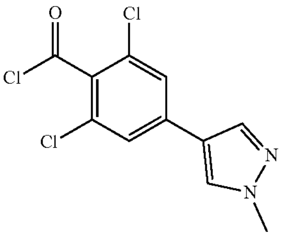

A solution of 2,6-dichloro-4-(1-methylpyrazol-4-yl)benzoic acid (2.00 g, 7.38 mmol) in dichloromethane (36.9 mL) was cooled to 0° C., and oxalyl chloride (0.129 mL, 1.48 mmol) and N,N-dimethylformamide (0.0170 mL, 0.221 mmol) were added thereto. The mixture was stirred at room temperature for 2.5 hours, and the reaction mixture was concentrated to obtain the title compound as a crude product.

LCMS: m/z 340[M+H]+

HPLC retention time: 0.80 min (analysis condition O)

Second Step

Compound ME19

Methyl 4-[3-[2,6-dichloro-4-(1-methylpyrazol-4-yl) benzoyl]-2,4-dihydro-1,3-benzoxazin-8-yl]-5-fluoro-2-(3-oxa-8-azabicyclo[3.2.1]octan-8-yl)benzoate

[Formula 349]

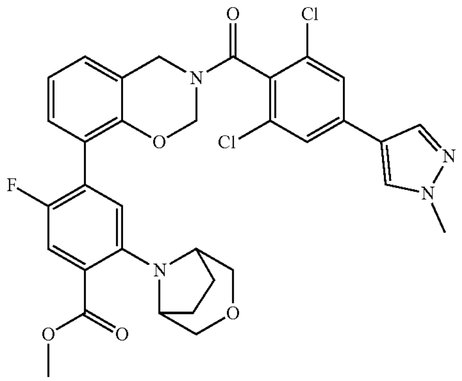

A solution of tert-butyl 8-[2-fluoro-4-methoxycarbonyl-5-(3-oxa-8-azabicyclo[3.2.1]octan-8-yl)phenyl]-2,4-dihydro-1,3-benzoxazine-3-carboxylate (14.0 mg, 0.0280 mmol) in dichloromethane (0.281 mL) was cooled to 0° C., and trifluoromethanesulfonic acid (0.00274 mL, 0.0310 mmol) was added thereto. The reaction solution was stirred at room temperature for 1 hour, and trifluoromethanesulfonic acid (0.00274 mL, 0.0310 mmol) was then further added thereto. The reaction solution was stirred at room temperature for 1 hour. Then, the solution was cooled to 0° C., and 2,6-dichloro-4-(1-methylpyrazol-4-yl)benzoyl chloride (8.94 mg, 0.0310 mmol) and N,N-diisopropylethylamine (0.0245 mL, 0.140 mmol) were added thereto. The reaction solution was stirred at room temperature for 2 hours, and the reaction mixture was then concentrated to obtain a crude product of the title compound.

LCMS: m/z 651 [M+H]+

HPLC retention time: 1.25 min (analysis condition G)

Third Step

Compound 13-1

4-[3-[2,6-Dichloro-4-(1-methylpyrazol-4-yl)benzoyl]-2,4-dihydro-1,3-benzoxazin-8-yl]-5-fluoro-2-(3-oxa-8-azabicyclo[3.2.1]octan-8-yl)benzoic acid

[Formula 350]

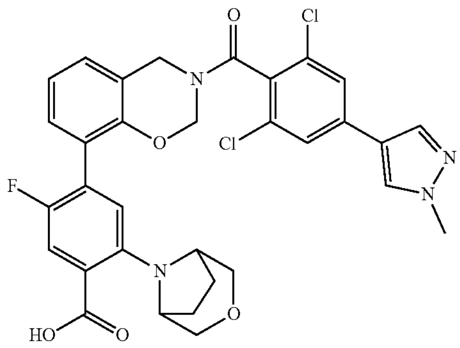

A solution of the crude product of methyl 4-[3-[2,6-dichloro-4-(1-methylpyrazol-4-yl)benzoyl]-2,4-dihydro-1,3-benzoxazin-8-yl]-5-fluoro-2-(3-oxa-8-azabicyclo[3.2.1]octan-8-yl)benzoate and a 5 M aqueous sodium hydroxide solution (0.0560 mL, 0.280 mmol) in tetrahydrofuran (0.0700 mL) and methanol (0.070 mL) was stirred at 60° C. for 1 hour. The reaction mixture was diluted with an aqueous formic acid solution and dimethyl sulfoxide and then purified by HPLC (acetonitrile/water, 0.1% formic acid) to obtain the title compound (63%, 11.2 mg).

LCMS: m/z 637[M+H]$^+$

HPLC retention time: 1.02 min and 1.03 min (analysis condition A)

Compound 13-2

4-[2-[2,6-Dichloro-4-(1-methylpyrazol-4-yl)benzoyl]-3,4-dihydro-1H-phthalazin-5-yl]-2-morpholin-4-ylbenzoic acid First Step Compound INT1 di-tert-Butyl 5-iodo-1,4-dihydrophthalazine-2,3-dicarboxylate

[Formula 351]

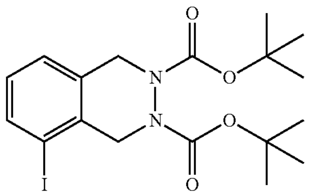

To a solution of di-tert-butyl hydrazodicarboxylate (236 mg, 1.01 mmol) in tetrahydrofuran (4.98 mL), potassium tert-butoxide (223 mg, 1.99 mmol) was added. After stirring at room temperature for 1 hour, the solution was cooled to 0° C., and a solution of 1,2-bis(bromomethyl)-3-iodobenzene (388 mg, 0.995 mmol) in tetrahydrofuran (2.00 mL) was added thereto. The reaction solution was stirred at room temperature for 1 hour, and a saturated aqueous solution of ammonium chloride and methanol were then added thereto. The reaction mixture was purified by reverse phase column chromatography (acetonitrile/water) to obtain the title compound (49%, 222 mg).

LCMS: m/z 305[M−Boc-tBu+H]$^+$

HPLC retention time: 1.56 min (analysis condition Q)

Second Step

Compound INT2 di-tert-Butyl 5-(4,4,5,5-tetramethyl-1,3,2-dioxaborolan-2-yl)-1,4-dihydrophthalazine-2,3-dicarboxylate

[Formula 352]

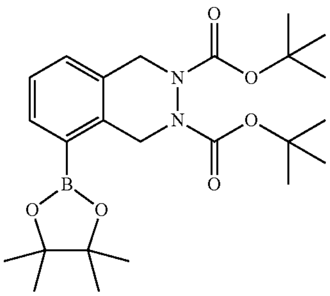

A solution of di-tert-butyl 5-iodo-1,4-dihydrophthalazine-2,3-dicarboxylate (222 mg, 0.482 mmol), bis(pinacolato) diboron (223 mg, 1.99 mmol), potassium acetate (142 mg, 1.45 mmol), and [1,1'-bis(diphenylphosphino)ferrocene]palladium(II) dichloride dichloromethane adduct (19.8 mg, 0.0240 mmol) in 1,4-dioxane (2.41 mL) was stirred at 80° C. for 3 hours. The reaction solution was further stirred at 120° C. for 12 hours, and the reaction mixture was then filtered and concentrated. The residue was purified by reverse phase column chromatography (acetonitrile/water) to obtain the title compound (66%, 147 mg).

LCMS: m/z 305[M−Boc-tBu+H]$^+$

HPLC retention time: 1.64 min (analysis condition Q)

Third Step

Compound LP12b di-tert-Butyl 5-(4-ethoxycarbonyl-3-morpholin-4-ylphenyl)-1,4-dihydrophthalazine-2,3-dicarboxylate

[Formula 353]

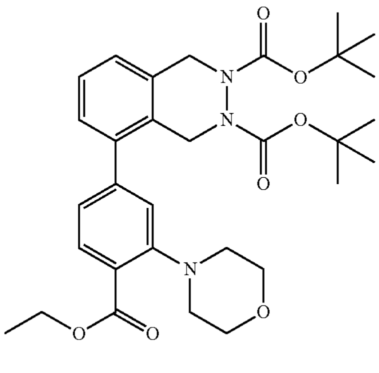

A solution of di-tert-butyl 5-(4,4,5,5-tetramethyl-1,3,2-dioxaborolan-2-yl)-1,4-dihydrophthalazine-2,3-dicarboxylate (29.0 mg, 0.0630 mmol), ethyl 4-bromo-2-morpholin-4-ylbenzoate (21.7 mg, 0.0690 mmol), sodium carbonate (20.0 mg, 0.189 mmol), and [1,1'-bis(diphenylphosphino) ferrocene]palladium(II) dichloride (4.61 mg, 0.00630 mmol) in 1,4-dioxane (0.300 mL) was stirred at 90° C. for 2 hours. An aqueous formic acid solution was added to the reaction mixture, and the mixture was then purified by reverse phase column chromatography (acetonitrile/water, 0.1% formic acid) to obtain the title compound (64%, 23.0 mg).

LCMS: m/z 568[M+H]$^+$

HPLC retention time: 1.51 min (analysis condition A)

Fourth Step

Compound ME12

Ethyl 4-[2-[2,6-dichloro-4-(1-methylpyrazol-4-yl) benzoyl]-3,4-dihydro-1H-phthalazin-5-yl]-2-morpholin-4-ylbenzoate

[Formula 354]

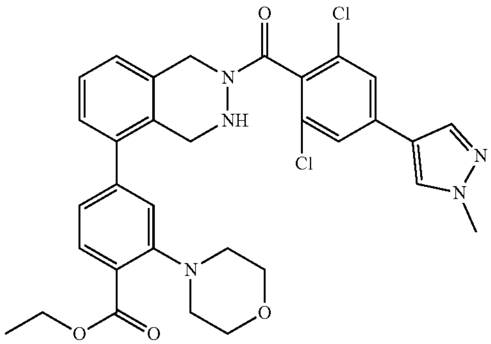

To di-tert-butyl 5-(4-ethoxycarbonyl-3-morpholin-4-ylphenyl)-1,4-dihydrophthalazine-2,3-dicarboxylate (19.0 mg, 0.0330 mmol), a 4 M solution of hydrochloric acid in 1,4-dioxane (0.167 mL, 0.669 mmol) was added, and the mixture was stirred at room temperature for 1 hour. The reaction mixture was concentrated, and the residue was then diluted with dichloromethane (5.00 mL). The resulting solution was cooled to 0° C., and 2,6-dichloro-4-(1-methylpyrazol-4-yl)benzoyl chloride (12.6 mg, 0.0440 mmol) and N,N-diisopropylethylamine (0.0300 mL, 0.167 mmol) were added thereto. The mixture was stirred at room temperature for 2 hours to obtain a crude product of the title compound.

LCMS: m/z 620[M+H]$^+$

HPLC retention time: 1.19 min and 1.22 min (analysis condition A)

Fifth Step

Compound 13-2

4-[2-[2,6-Dichloro-4-(1-methylpyrazol-4-yl)benzoyl]-3,4-dihydro-1H-phthalazin-5-yl]-2-morpholin-4-ylbenzoic acid

[Formula 355]

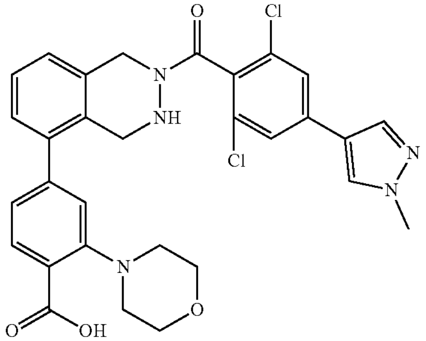

A solution of the crude product of ethyl 4-[2-[2,6-dichloro-4-(1-methylpyrazol-4-yl)benzoyl]-3,4-dihydro-1H-phthalazin-5-yl]-2-morpholin-4-ylbenzoate and a 5 M aqueous sodium hydroxide solution (0.0330 mL, 0.165 mmol) in methanol (5.00 mL) was stirred at room temperature for 1 hour. An aqueous formic acid solution was added to the reaction solution, and the mixture was purified by HPLC (acetonitrile/water, 0.1% formic acid) to obtain the title compound (31%, 6.00 mg).

LCMS: m/z 592[M+H]$^+$

HPLC retention time: 0.93 min (analysis condition N)

Compound 13-3

4-[3-[2,6-Dichloro-4-(1-methylpyrazol-4-yl)benzoyl]-2,4-dihydro-1,3-benzoxazin-8-yl]-3-fluoro-2-methyl-6-morpholin-4-ylbenzoic acid First Step Compound DP12

3-Fluoro-2-methyl-6-morpholin-4-ylbenzoic acid

[Formula 356]

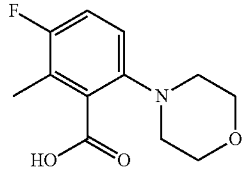

To a solution of morpholine (74.6 mg, 0.856 mmol) in 1,4-dioxane (1.30 mL), tert-butyl hypochlorite (0.0970 mL, 0.856 mmol) was added. While the reaction mixture was added dropwise to a solution of 3-fluoro-2-methylbenzoic acid (100 mg, 0.649 mmol), (pentamethylcyclopentadienyl) rhodium(II) dichloride (dimer) (12.0 mg, 0.0190 mmol), and silver acetate (162 mg, 0.973 mmol) in methanol (1.30 mL), and the mixture was stirred at 60° C. for 12 hours. 0.1 M hydrochloric acid was added to the reaction mixture, followed by extraction with ethyl acetate. The organic layer was washed with saturated saline, followed by passing through a phase separator. Then, the organic layer was concentrated to obtain a crude product of the title compound.

LCMS: m/z 240[M+H]$^+$

HPLC retention time: 0.69 min (analysis condition G)

Second Step

Compound DP13

Methyl 3-fluoro-2-methyl-6-morpholin-4-ylbenzoate

[Formula 357]

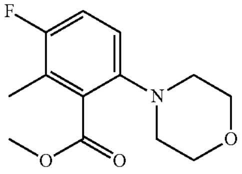

To a solution of the crude product of 3-fluoro-2-methyl-6-morpholin-4-ylbenzoic acid in dichloromethane (5.19 mL) and methanol (1.30 mL), a 2 M solution of trimethylsilyldiazomethane in hexane (0.422 mL, 0.844 mmol) was added. After stirring at room temperature for 1 hour, the solution was cooled to 0° C., and a solution of di-tert-butyl hydrazodicarboxylate (236 mg, 1.01 mmol) in tetrahydrofuran (2.00 mL) was added thereto. The reaction solution was stirred at room temperature for 1 hour. Then, acetic acid was added to the reaction mixture, and the mixture was concentrated. The obtained residue was purified by silica gel column chromatography (ethyl acetate/hexane) to obtain the title compound (37%, 60.0 mg).

LCMS: m/z 254[M+H]$^+$

HPLC retention time: 1.04 min (analysis condition G)

Third Step

Compound DP14

Methyl 3-fluoro-2-methyl-6-morpholin-4-yl-4-(4,4,5,5-tetramethyl-1,3,2-dioxaborolan-2-yl)benzoate

[Formula 358]

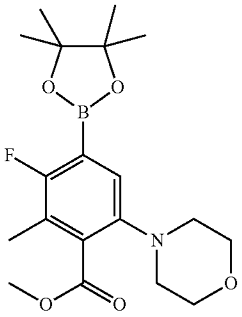

A solution of methyl 3-fluoro-2-methyl-6-morpholin-4-ylbenzoate (25.0 mg, 0.0990 mmol), bis(pinacolato)diboron (37.6 mg, 0.148 mmol), 4,4'-di-tert-butyl-2,2'-bipyridyl (1.59 mg, 0.00592 mmol), and (1,5-cyclooctadiene)(methoxy)iridium(I) (dimer) (1.96 mg, 0.00296 mmol) in hexane (0.395 mL) was stirred at 60° C. for 1.5 hours. The reaction mixture was concentrated to obtain a crude product of the title compound.

LCMS: m/z 380[M+H]$^+$

HPLC retention time: 1.27 min (analysis condition G)

Fourth Step

Compound DP17b tert-Butyl 8-(2-fluoro-4-methoxycarbonyl-3-methyl-5-morpholin-4-ylphenyl)-2,4-dihydro-1,3-benzoxazine-3-carboxylate

[Formula 359]

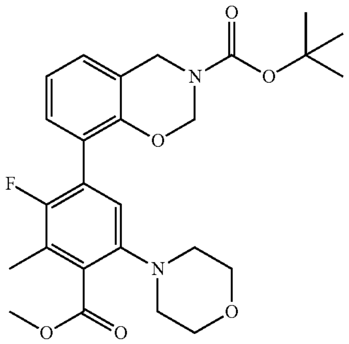

A solution of the crude product of methyl 3-fluoro-2-methyl-6-morpholin-4-yl-4-(4,4,5,5-tetramethyl-1,3,2-dioxaborolan-2-yl)benzoate, tert-butyl 8-bromo-2,4-dihydro-1,3-benzoxazine-3-carboxylate (25.9 mg, 0.0830 mmol), potassium carbonate (34.2 mg, 0.248 mmol), and [1,1'-bis(diphenylphosphino)ferrocene]palladium(II) dichloride dichloromethane adduct (6.74 mg, 0.00825 mmol) in 1,4-dioxane (0.250 mL) and water (0.0250 mL) was stirred at 90° C. for 1 hour. An aqueous formic acid solution and methanol were added to the reaction mixture, and the mixture was then purified by reverse phase column chromatography (acetonitrile/water, 0.1% formic acid) to obtain the title compound (100%, 40.0 mg).

LCMS: m/z 487[M+H]$^+$

HPLC retention time: 1.38 min (analysis condition G)

Fifth Step

Compound 13-3

4-[3-[2,6-Dichloro-4-(1-methylpyrazol-4-yl)benzoyl]-2,4-dihydro-1,3-benzoxazin-8-yl]-3-fluoro-2-methyl-6-morpholin-4-ylbenzoic acid

[Formula 360]

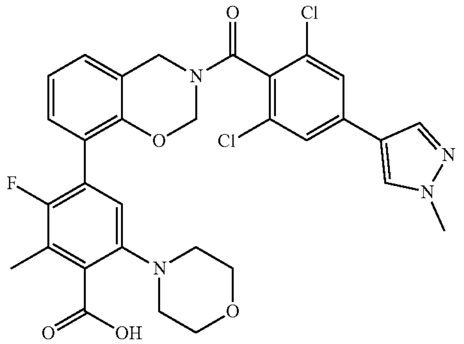

The title compound was synthesized by the same operation as in the fourth step and the fifth step of compound 13-2 using the crude product of tert-butyl 8-(2-fluoro-4-methoxycarbonyl-3-methyl-5-morpholin-4-ylphenyl)-2,4-dihydro-1,3-benzoxazine-3-carboxylate.

LCMS: m/z 625[M+H]$^+$

HPLC retention time: 1.06 min and 1.08 min (analysis condition A)

Compound 13-4

4-[3-[2,6-Dichloro-4-(1-methylpyrazol-4-yl)benzoyl]-2,4-dihydro-1,3-benzoxazin-8-yl]-3,5-difluoro-2-morpholin-4-ylbenzoic acid First Step Compound DP7

Ethyl 3,5-difluoro-2-morpholin-4-ylbenzoate

[Formula 361]

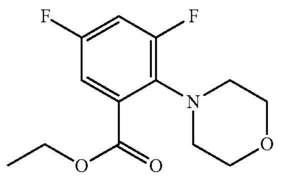

A solution of ethyl 2,3,5-trifluorobenzoate (1.40 g, 6.86 mmol) and morpholine (1.49 g, 17.1 mmol) in toluene (20.0 mL) was stirred overnight at 110° C. The reaction mixture was concentrated and then purified by silica gel column chromatography (ethyl acetate/hexane) to obtain the title compound (30%, 558 mg).

LCMS: m/z 272[M+H]$^+$

HPLC retention time: 1.13 min (analysis condition G)

Second Step

Compound DP8

Ethyl 3,5-difluoro-2-morpholin-4-yl-4-(4,4,5,5-tetramethyl-1,3,2-dioxaborolan-2-yl)benzoate

[Formula 362]

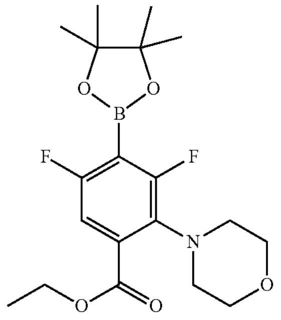

A crude product of the title compound was synthesized by the same operation as in the third step of compound 13-3 using ethyl 3,5-difluoro-2-morpholin-4-ylbenzoate.

LCMS: m/z 398[M+H]$^+$

HPLC retention time: 1.32 min (analysis condition G)

Third Step

Compound DP9

4-Bromo-3,5-difluoro-2-morpholin-4-ylbenzoic acid

[Formula 363]

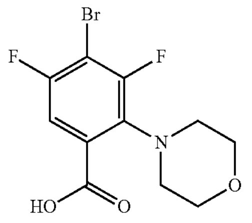

A solution of ethyl 3,5-difluoro-2-morpholin-4-yl-4-(4,4,5,5-tetramethyl-1,3,2-dioxaborolan-2-yl)benzoate (806 mg, 2.03 mmol) and copper(II) bromide (679 mg, 3.04 mmol) in methanol (2.00 mL) and water (2.00 mL) was stirred at 60° C. for 2 hours. The reaction mixture was purified by reverse phase column chromatography (acetonitrile/water, 0.1% formic acid) to obtain the title compound (22%, 142 mg).

LCMS: m/z 322[M+H]$^+$

HPLC retention time: 0.89 min (analysis condition G)

Fourth Step

Compound DP10

Methyl 4-bromo-3,5-difluoro-2-morpholin-4-ylbenzoate

[Formula 364]

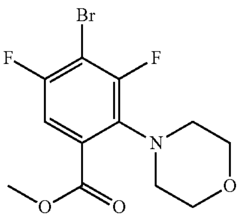

The title compound was synthesized by the same operation as in the second step of compound 13-3 using 4-bromo-3,5-difluoro-2-morpholin-4-ylbenzoic acid.

LCMS: m/z 336[M+H]$^+$

HPLC retention time: 1.18 min (analysis condition G)

Fifth Step

Compound LP16b tert-Butyl 8-(2,6-difluoro-4-methoxycarbonyl-3-morpholin-4-ylphenyl)-2,4-dihydro-1,3-benzoxazine-3-carboxylate

[Formula 365]

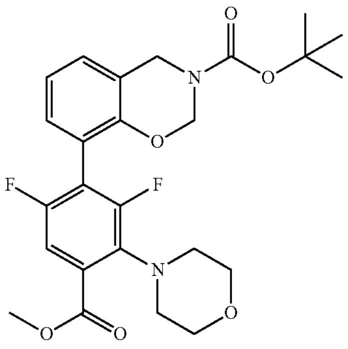

A solution of methyl 4-bromo-3,5-difluoro-2-morpholin-4-ylbenzoate (135 mg, 0.402 mmol), tert-butyl 8-(4,4,5,5-tetramethyl-1,3,2-dioxaborolan-2-yl)-2,4-dihydro-1,3-benzoxazine-3-carboxylate (508 mg, 1.41 mmol), tripotassium phosphate (171 mg, 0.803 mmol), palladium(II) acetate (9.02 mg, 0.040 mmol), and 2-dicyclohexylphosphino-2',6'-dimethoxybiphenyl (33.0 mg, 0.080 mmol) in toluene (4.00 mL) was stirred at 90° C. for 5 hours. The reaction mixture was purified by reverse phase column chromatography (acetonitrile/water, 0.1% formic acid) to obtain the title compound (53%, 104 mg).

LCMS: m/z 491[M+H]$^+$

HPLC retention time: 1.36 min (analysis condition G)

Sixth Step

Compound 13-4

4-[3-[2,6-Dichloro-4-(1-methylpyrazol-4-yl)benzoyl]-2,4-dihydro-1,3-benzoxazin-8-yl]-3,5-difluoro-2-morpholin-4-ylbenzoic acid

[Formula 366]

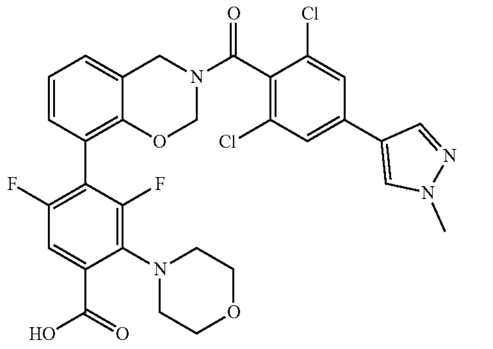

The title compound was synthesized by the same operation as in the fourth step and the fifth step of compound 13-2 using tert-butyl 8-(2,6-difluoro-4-methoxycarbonyl-3-morpholin-4-ylphenyl)-2,4-dihydro-1,3-benzoxazine-3-carboxylate.

LCMS: m/z 629[M+H]$^+$

HPLC retention time: 1.07 min (analysis condition A)

Compound 13-5

4-[3-[2,6-Dichloro-4-(1-methylpyrazol-4-yl)benzoyl]-2,4-dihydro-1,3-benzoxazin-8-yl]-3-fluoro-2-morpholin-4-ylbenzoic acid First Step Compound INT3

4-Bromo-3-fluoro-2-morpholin-4-ylbenzoic acid

[Formula 367]

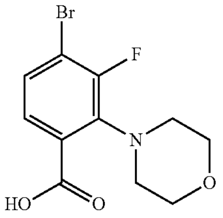

A mixture of 4-bromo-2,3-difluorobenzoic acid (50.0 mg, 0.211 mmol) and morpholine (368 mL, 4.22 mmol) was stirred at 100° C. for 2 hours. 1 M hydrochloric acid was added to the reaction mixture, followed by extraction with ethyl acetate. The organic layer was washed with saturated saline, followed by passing through a phase separator. Then, the organic layer was concentrated to obtain a crude product of the title compound.

LCMS: m/z 304[M+H]$^+$

HPLC retention time: 0.84 min (analysis condition G)

Second Step

Compound LP13b

3-Fluoro-4-[3-[(2-methylpropan-2-yl)oxycarbonyl]-2,4-dihydro-1,3-benzoxazin-8-yl]-2-morpholin-4-ylbenzoic acid

[Formula 368]

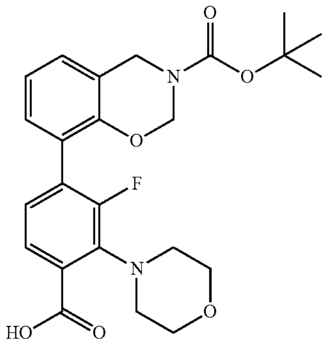

The title compound was synthesized by the same operation as in the fourth step of compound 13-3 using tert-butyl 8-(4,4,5,5-tetramethyl-1,3,2-dioxaborolan-2-yl)-2,4-dihydro-1,3-benzoxazine-3-carboxylate and 4-bromo-3-fluoro-2-morpholin-4-ylbenzoic acid.

LCMS: m/z 459[M+H]$^+$

HPLC retention time: 1.15 min (analysis condition G)

Third Step
Compound 13-5

4-[3-[2,6-Dichloro-4-(1-methylpyrazol-4-yl)benzoyl]-2,4-dihydro-1,3-benzoxazin-8-yl]-3-fluoro-2-morpholin-4-ylbenzoic acid

[Formula 369]

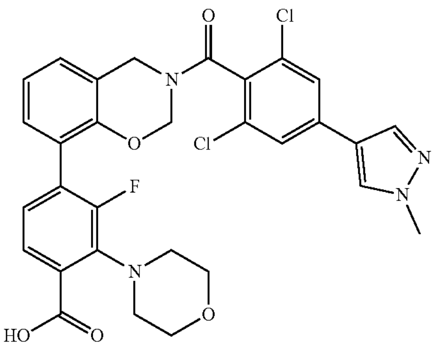

The title compound was synthesized by the same operation as in the fourth step of compound 13-2 using 3-fluoro-4-[3-[(2-methylpropan-2-yl)oxycarbonyl]-2,4-dihydro-1,3-benzoxazin-8-yl]-2-morpholin-4-ylbenzoic acid.

LCMS: m/z 611[M+H]$^+$

HPLC retention time: 1.05 min (analysis condition A)

Compound 13-6

4-[3-(4-Chloro-1-methylindazole-5-carbonyl)-2,4-dihydro-1,3-benzoxazin-8-yl]-2-morpholin-4-ylbenzoic acid First Step
Compound RP9 tert-Butyl 2-chloro-4-fluoro-3-formylbenzoate

[Formula 370]

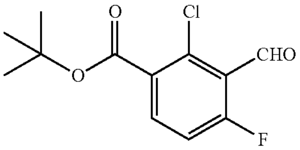

To a solution of tert-butyl 2-chloro-4-fluorobenzoate (50.0 mg, 0.217 mmol) in tetrahydrofuran (0.602 mL), 1.13 M lithium diisopropylamide (0.192 mL, 0.217 mmol) was added at −78° C. The reaction mixture was stirred at −78° C. for 30 minutes, and morpholine-4-carbaldehyde (0.0651 mL, 0.650 mmol) was then added thereto. A saturated aqueous solution of ammonium chloride was added to the reaction mixture, followed by extraction with ethyl acetate. The organic layer was concentrated, and the obtained residue was purified by reverse phase column chromatography (acetonitrile/water, 0.1% formic acid) to obtain the title compound (95%, 53.4 mg).

HPLC retention time: 1.18 min (analysis condition G)

$^1$H-NMR (400 MHz, $CDCl_3$) δ: 10.49 (1H, s), 7.88 (1H, dd, J=8.8, 5.6 Hz), 7.13 (1H, t, J=9.0 Hz), 1.59 (9H, s).

Second Step
Compound RP10 tert-Butyl 4-chloro-1H-indazole-5-carboxylate

[Formula 371]

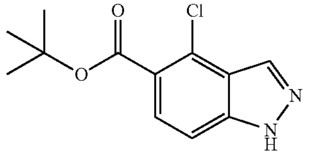

A solution of tert-butyl 2-chloro-4-fluoro-3-formylbenzoate (20.2 mg, 0.0780 mmol) and hydrazine monohydrate (0.090 mL, 1.85 mmol) in dimethoxyethane (0.156 mL) was stirred at 90° C. for 1 hour. 1 M hydrochloric acid was added to the reaction mixture, followed by extraction with ethyl acetate. The reaction mixture was purified by reverse phase column chromatography (acetonitrile/water, 0.1% formic acid) to obtain the title compound (65%, 12.9 mg).

LCMS: m/z 253[M+H]$^+$

HPLC retention time: 1.08 min (analysis condition G)

Third Step
Compound RP11 tert-Butyl 4-chloro-1-methylindazole-5-carboxylate

[Formula 372]

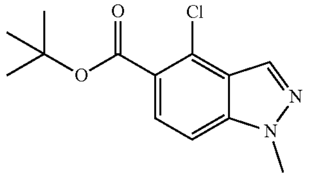

A solution of tert-butyl 4-chloro-1H-indazole-5-carboxylate (260 mg, 1.03 mmol), iodomethane (0.160 mL, 2.57 mmol), and cesium carbonate (1.17 g, 3.60 mmol) in N,N-dimethylformamide (2.57 mL) was stirred at room temperature for 1 hour. The reaction mixture was purified by reverse phase column chromatography (acetonitrile/water, 0.1% formic acid) to obtain the title compound (56%, 154 mg).

LCMS: m/z 267[M+H]$^+$

HPLC retention time: 1.11 min (analysis condition G)

Fourth Step
Compound CMA15

4-Chloro-1-methylindazole-5-carboxylic acid

[Formula 373]

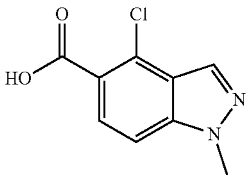

To tert-butyl 4-chloro-1-methylindazole-5-carboxylate (137 mg, 0.513 mmol), TFA (0.786 mL, 10.3 mmol) was added, and the mixture was stirred at room temperature for 1 hour. The reaction mixture was concentrated to obtain a crude product of the title compound.

LCMS: m/z 211[M+H]$^+$

HPLC retention time: 0.71 min (analysis condition G)

Fifth Step

Compound ME17

Methyl 4-[3-(4-chloro-1-methylindazole-5-carbonyl)-2,4-dihydro-1,3-benzoxazin-8-yl]-2-morpholin-4-ylbenzoate

[Formula 374]

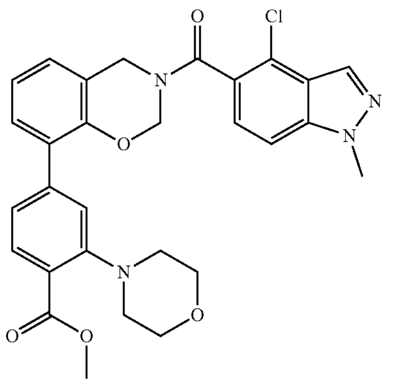

A solution of the crude product of 4-chloro-1-methylindazole-5-carboxylic acid, oxalyl chloride (0.0539 mL, 0.615 mmol), and N,N-dimethylformamide (0.00397 mL, 0.00513 mmol) in dichloromethane (1.03 mL) was stirred at room temperature for 1 hour. The reaction mixture was concentrated to obtain a crude product of 4-chloro-1-methylindazole-5-carbonyl chloride. A solution of the crude product of 4-chloro-1-methylindazole-5-carbonyl chloride, methyl 4-(3,4-dihydro-2H-1,3-benzoxazin-8-yl)-2-morpholin-4-ylbenzoate dihydrochloride (18.1 mg, 0.0790 mmol), and N,N-diisopropylethylamine (0.0300 mL, 0.167 mmol) in dichloromethane (0.330 mL) was stirred at room temperature for 1 hour. Morpholine (0.0115 mL, 0.132 mmol) was added to the reaction mixture, and the mixture was then concentrated. The obtained residue was purified by reverse phase column chromatography (acetonitrile/water, 0.1% formic acid) to obtain the title compound (54%, 19.3 mg).

LCMS: m/z 547[M+H]$^+$

HPLC retention time: 1.14 min (analysis condition G)

Sixth Step

Compound 13-6

4-[3-(4-Chloro-1-methylindazole-5-carbonyl)-2,4-dihydro-1,3-benzoxazin-8-yl]-2-morpholin-4-ylbenzoic acid

[Formula 375]

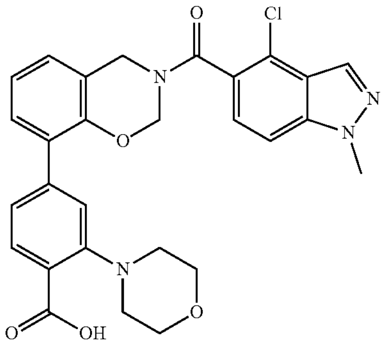

The title compound was synthesized by the same operation as in the fifth step of compound 13-2 using methyl 4-[3-(4-chloro-1-methylindazole-5-carbonyl)-2,4-dihydro-1,3-benzoxazin-8-yl]-2-morpholin-4-ylbenzoate.

LCMS: m/z 533[M+H]$^+$

HPLC retention time: 0.92 min (analysis condition A)

Compounds shown in Table 13-1 were synthesized by the same operation as in the fifth step and the sixth step of compound 13-6 using each documented or commercially available carboxylic acid or carboxylic acid chloride, or carboxylic acid or carboxylic acid chloride shown in Table 13-2 and methyl 4-(3,4-dihydro-2H-1,3-benzoxazin-8-yl)-5-fluoro-2-morpholin-4-ylbenzoate dihydrochloride. However, reaction was performed by the addition of a catalytic amount of 4-dimethylaminopyridine in the synthesis of compound 13-10.

TABLE 13-1

| Compound No. | Structure | Compound Name | Analysis conditions | HPLC retention time (min) | [M + H]$^+$ |
|---|---|---|---|---|---|
| 13-7 | 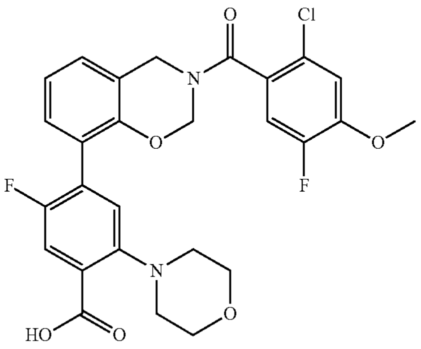 [SMILES: COc1cc(Cl)c(C(=O)N2COc3c(cccc3-c3cc(N4CCOCC4)c(C(=O)O)cc3F)C2)cc1F] | 4-[3-(2-Chloro-5-fluoro-4-methoxybenzoyl)-2,4-dihydro-1,3-benzoxazin-8-yl]-5-fluoro-2-morpholin-4-ylbenzoic acid | B | 1.39 | 545 |

TABLE 13-1-continued

| Compound No. | Structure | Compound Name | Analysis conditions | HPLC retention time (min) | [M + H]$^+$ |
|---|---|---|---|---|---|
| 13-10 | 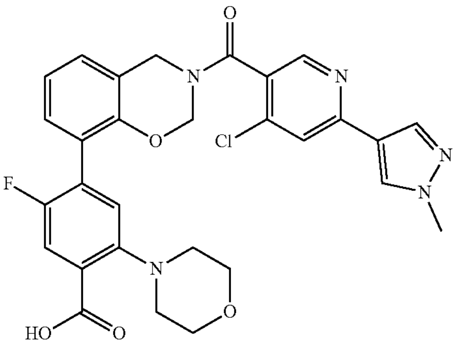 [SMILES: Cn1cc(-c2cc(Cl)c(C(=O)N3COc4c(cccc4-c4cc(N5CCOCC5)c(C(=O)O)cc4F)C3)cn2)cn1] | 4-[3-[4-Chloro-6-(1-methylpyrazol-4-yl)pyridine-3-carbonyl]-2,4-dihydro-1,3-benzoxazin-8-yl]-5-fluoro-2-morpholin-4-ylbenzoic acid | A | 0.89 | 578 |
| 13-13 | 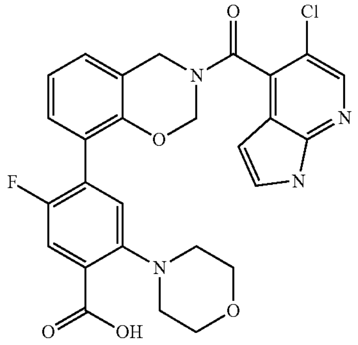 [SMILES: O=C(O)c1cc(F)c(-c2cccc3c2OCN(C(=O)c2c(Cl)cnc4[nH]ccc24)C3)cc1N1CCOCC1] | 4-[3-(5-Chloro-1-methylpyrrolo[2,3-b]pyridine-4-carbonyl)-2,4-dihydro-1,3-benzoxazin-8-yl]-5-fluoro-2-morpholin-4-ylbenzoic acid | B | 1.33 | 551 |
| 13-14 | 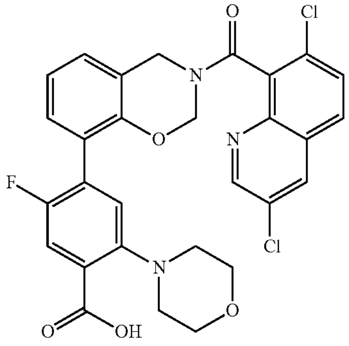 [SMILES: O=C(O)c1cc(F)c(-c2cccc3c2OCN(C(=O)c2c(Cl)ccc4cc(Cl)cnc24)C3)cc1N1CCOCC1] | 4-[3-(3,7-Dichloroquinoline-8-carbonyl)-2,4-dihydro-1,3-benzoxazin-8-yl]-5-fluoro-2-morpholin-4-ylbenzoic acid | B | 1.41 | 582 |
| 13-15 | 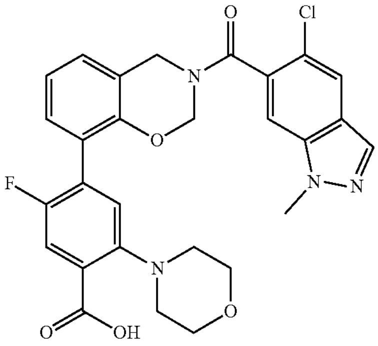 [SMILES: Cn1ncc2cc(Cl)c(C(=O)N3COc4c(cccc4-c4cc(N5CCOCC5)c(C(=O)O)cc4F)C3)cc21] | 4-[3-(5-Chloro-1-methylindazole-6-carbonyl)-2,4-dihydro-1,3-benzoxazin-8-yl]-5-fluoro-2-morpholin-4-ylbenzoic acid | B | 1.43 | 551 |

TABLE 13-1-continued

| Compound No. | Structure | Compound Name | Analysis conditions | HPLC retention time (min) | [M + H]+ |
|---|---|---|---|---|---|
| 13-19 | 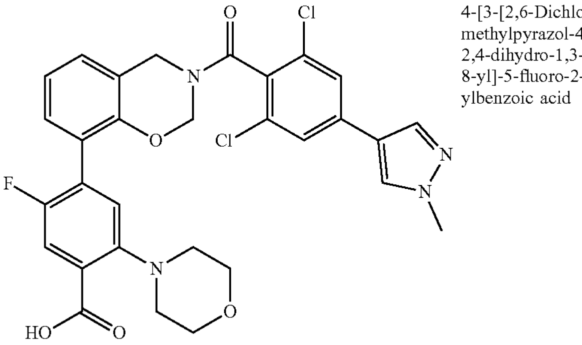 | 4-[3-[2,6-Dichloro-4-(1-methylpyrazol-4-yl)benzoyl]-2,4-dihydro-1,3-benzoxazin-8-yl]-5-fluoro-2-morpholin-4-ylbenzoic acid | A | 1.01. 1.03 | 611 |
| 13-17 | 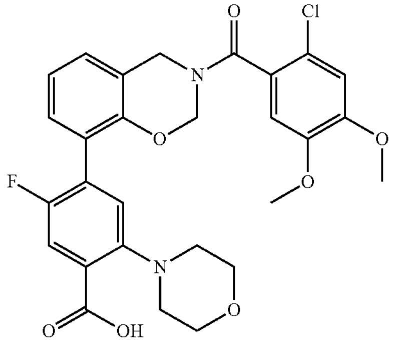 [SMILES: COc1cc(Cl)c(C(=O)N2COc3c(cccc3-c3cc(N4CCOCC4)c(C(=O)O)cc3F)C2)cc1OC] | 4-[3-(2-Chloro-4,5-dimethoxybenzoyl)-2,4-dihydro-1,3-benzoxazin-8-yl]-5-fluoro-2-morpholin-4-ylbenzoic acid | A | 0.97 | 557 |

TABLE 13-2

| Final compound No. | Carboxylic acid |
|---|---|
| 13-10 | 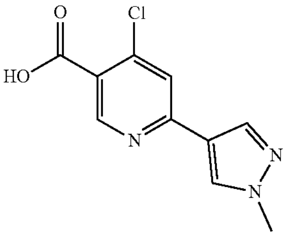 [SMILES: Cn1cc(-c2cc(Cl)c(C(=O)O)cn2)cn1] |
| 13-7 | 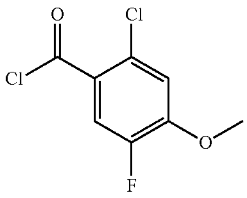 |
| 13-13 | 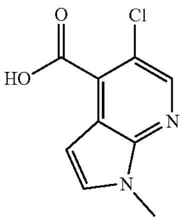 |

TABLE 13-2-continued

| Final compound No. | Carboxylic acid |
|---|---|
| 13-14 | 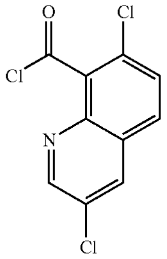 [SMILES: O=C(Cl)c1c(Cl)ccc2cc(Cl)cnc12] |
| 13-15 | 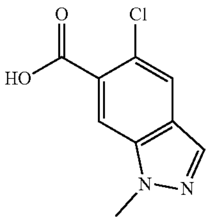 |
| 13-17 | 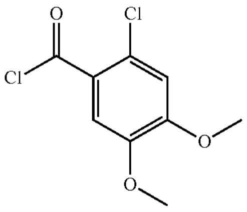 |

TABLE 13-2-continued

| Final compound No. | Carboxylic acid |
|---|---|
| 13-19 | 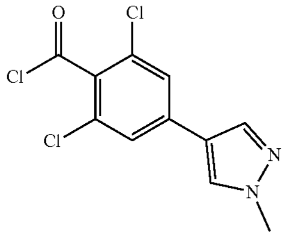 [SMILES: Cn1cc(-c2cc(Cl)c(C(=O)Cl)c(Cl)c2)cn1] |

The carboxylic acid or the carboxylic acid chloride used in the synthesis of compound 13-10 or 13-13 was synthesized as follows.

Compound CMA4

4-Chloro-6-(1-methylpyrazol-4-yl)pyridine-3-carboxylic acid

First Step

Compound RP2

Methyl 4-chloro-6-(1-methylpyrazol-4-yl)pyridine-3-carboxylate

[Formula 376]

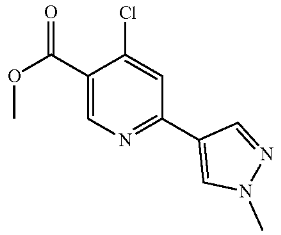

A solution of methyl 4,6-dichloropyridine-3-carboxylate (315 mg, 1.53 mmol), 1-methyl-4-(4,4,5,5-tetramethyl-1,3,2-dioxaborolan-2-yl)-1H-pyrazole (349 mg, 1.68 mmol), cesium carbonate (1.49 g, 4.58 mmol) and [1,1'-bis(diphenylphosphino)ferrocene]palladium(II) dichloride (112 mg, 0.513 mmol) in 1,4-dioxane (7.00 mL) and water (0.778 mL) was stirred at 70° C. for 1 hour. The reaction mixture was purified by reverse phase column chromatography (acetonitrile/water, 0.1% formic acid) to obtain the title compound (100%, 384 mg) as an isomeric mixture.

LCMS: m/z 252$[M+H]^+$

HPLC retention time: 0.82 min (analysis condition G)

Second Step

Compound CMA4

4-Chloro-6-(1-methylpyrazol-4-yl)pyridine-3-carboxylic acid

[Formula 377]

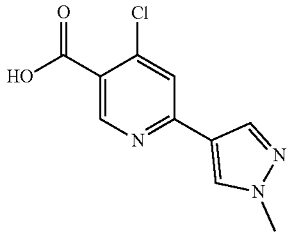

A solution of methyl 4-chloro-6-(1-methylpyrazol-4-yl)pyridine-3-carboxylate (384 mg, 1.53 mmol) and a 5 M aqueous sodium hydroxide solution (3.05 mL, 15.3 mmol) in methanol (7.00 mL) and tetrahydrofuran (7.00 mL) was stirred at room temperature for 1 hour. Formic acid was added to the reaction mixture, and the mixture was then purified by reverse phase column chromatography (acetonitrile/water, 0.1% formic acid) to obtain the title compound (35%, 127 mg).

LCMS: m/z 238$[M+H]^+$

HPLC retention time: 0.58 min (analysis condition G)

Compound CMA7

5-Chloro-1-methylpyrrolo[2,3-b]pyridine-4-carboxylic acid

First Step

Compound RP6

Methyl 5-chloro-1-methylpyrrolo[2,3-b]pyridine-4-carboxylate

[Formula 378]

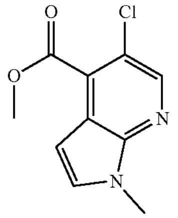

A solution of 5-chloro-1H-pyrrolo[2,3-b]pyridine-4-carboxylic acid (700 mg, 3.56 mmol) and sodium hydride (350 mg, 14.6 mmol) in N,N-dimethylformamide (11.0 mL) was stirred at 0° C. for 20 minutes. Iodomethane (0.500 mL, 7.12 mmol) was added to the reaction mixture at 0° C. The reaction solution was stirred at room temperature for 1 hour, and water was then added to the reaction mixture, followed by extraction with ethyl acetate. The organic layer was washed with a saturated aqueous solution of sodium bicarbonate and saturated saline, dried over sodium sulfate, and concentrated. The residue was purified by silica gel column chromatography (ethyl acetate/hexane) to obtain the title compound (78%, 620 mg).

LCMS: m/z 225$[M+H]^+$

HPLC retention time: 0.77 min (analysis condition U)

Second Step
Compound CMA7

5-Chloro-1-methylpyrrolo[2,3-b]pyridine-4-carboxylic acid

[Formula 379]

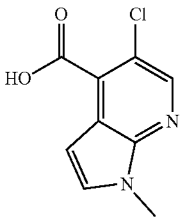

To a solution of methyl 5-chloro-1-methylpyrrolo[2,3-b]pyridine-4-carboxylate (620 mg, 2.76 mmol) in methanol (30.0 mL) and tetrahydrofuran (30.0 mL), a solution of lithium hydroxide monohydrate (2.32 g, 55.0 mmol) in water (12.0 mL) was added. The reaction solution was stirred at room temperature for 4 hours, and the reaction mixture was then concentrated. The residue was purified by reverse phase column chromatography (acetonitrile/water) to obtain the title compound (23%, 145 mg).

LCMS: m/z 211 $[M+H]^+$

HPLC retention time: 1.03 min (analysis condition V)

Compound 13-8

4-[3-[2,6-Dichloro-4-(1-methylpyrazol-4-yl)benzoyl]-7-fluoro-2,4-dihydro-1,3-benzoxazin-8-yl]-5-fluoro-2-morpholin-4-ylbenzoic acid First Step
Compound LP14b tert-Butyl 7-fluoro-8-(2-fluoro-4-methoxycarbonyl-5-morpholin-4-ylphenyl)-2,4-dihydro-1,3-benzoxazine-3-carboxylate

[Formula 380]

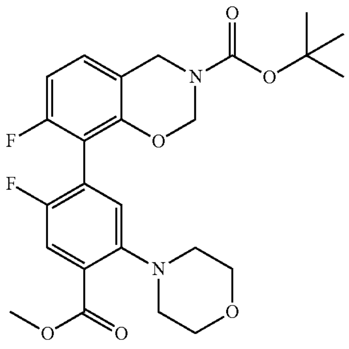

A solution of tert-butyl 8-bromo-7-fluoro-2,4-dihydro-1,3-benzoxazine-3-carboxylate (61.0 mg, 0.184 mmol), (2-fluoro-4-methoxycarbonyl-5-morpholin-4-ylphenyl)boronic acid (62.4 mg, 0.220 mmol), tripotassium phosphate (117 mg, 0.551 mmol), and XPhos Pd G3 (16.7 mg, 0.0180 mmol) in 1,4-dioxane (1.00 mL) and water (0.250 mL) was stirred at room temperature for 1.5 hours. An aqueous formic acid solution was added to the reaction mixture, and the mixture was then purified by reverse phase column chromatography (acetonitrile/water, 0.1% formic acid) to obtain the title compound (73%, 77.0 mg).

LCMS: m/z 491$[M+H]^+$

HPLC retention time: 1.31 min (analysis condition G)

Second Step
Compound 13-8

4-[3-[2,6-Dichloro-4-(1-methylpyrazol-4-yl)benzoyl]-7-fluoro-2,4-dihydro-1,3-benzoxazin-8-yl]-5-fluoro-2-morpholin-4-ylbenzoic acid

[Formula 381]

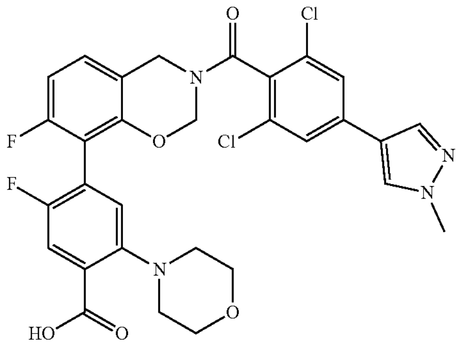

The title compound was synthesized by the same operation as in the fourth step and the fifth step of compound 13-2 using tert-butyl 7-fluoro-8-(2-fluoro-4-methoxycarbonyl-5-morpholin-4-ylphenyl)-2,4-dihydro-1,3-benzoxazine-3-carboxylate.

LCMS: m/z 629$[M+H]^+$

HPLC retention time: 1.01 min and 1.04 min (analysis condition A)

Compound 13-9

4-[3-[2,6-Dichloro-4-(1-methylpyrazol-4-yl)benzoyl]-7-fluoro-2,4-dihydro-1,3-benzoxazin-8-yl]-2-morpholin-4-ylbenzoic acid

[Formula 382]

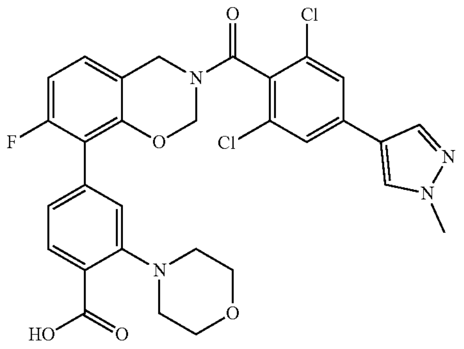

The title compound was synthesized by the same operation as in the fourth step and the fifth step of compound 13-2 using tert-butyl 7-fluoro-8-(4-methoxycarbonyl-3-morpholin-4-ylphenyl)-2,4-dihydro-1,3-benzoxazine-3-carboxylate.

LCMS: m/z 611$[M+H]^+$

HPLC retention time: 0.99 min and 1.01 min (analysis condition A)

Compound 13-11

4-[3-(6-Chloro-1-methylindole-5-carbonyl)-2,4-dihydro-1,3-benzoxazin-8-yl]-5-fluoro-2-morpholin-4-ylbenzoic acid First Step
Compound ME5

Methyl 4-[3-(6-chloro-1-methylindole-5-carbonyl)-2,4-dihydro-1,3-benzoxazin-8-yl]-5-fluoro-2-morpholin-4-ylbenzoate

[Formula 383]

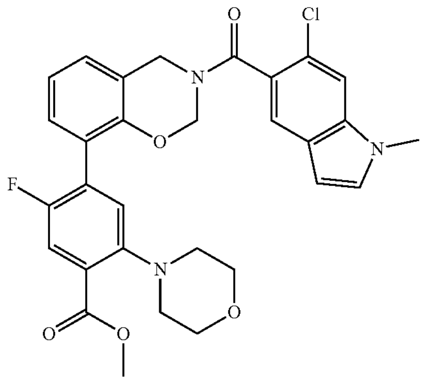

A solution of 6-chloro-1-methylindole-5-carboxylic acid (100 mg, 0.480 mmol), HATU (140 mg, 0.370 mmol), and N,N-diisopropylethylamine (0.200 mL, 1.11 mmol) in N,N-dimethylformamide (5.00 mL) was stirred at room temperature for 30 minutes. The reaction mixture was added dropwise to a solution of methyl 4-(3,4-dihydro-2H-1,3-benzoxazin-8-yl)-5-fluoro-2-morpholin-4-ylbenzoate dihydrochloride (137 mg, 0.370 mmol) and N,N-diisopropylethylamine (0.130 mL, 0.740 mmol) in N,N-dimethylformamide (5.00 mL) at 0° C. The reaction mixture was stirred at room temperature for 2 hours and then purified by reverse phase column chromatography (acetonitrile/water, 0.1% formic acid) to obtain the title compound (14%, 30.0 mg).

LCMS: m/z 564[M+H]$^+$

HPLC retention time: 0.95 min (analysis condition U)

Second Step
Compound 13-11

4-[3-(6-Chloro-1-methylindole-5-carbonyl)-2,4-dihydro-1,3-benzoxazin-8-yl]-5-fluoro-2-morpholin-4-ylbenzoic acid

[Formula 384]

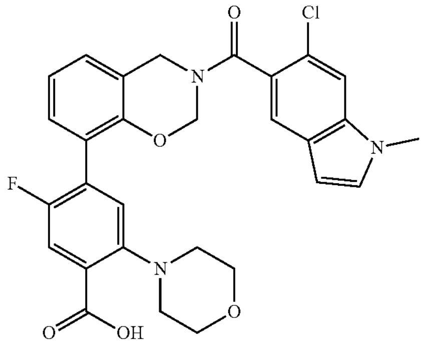

To a solution of methyl 4-[3-(6-chloro-1-methylindole-5-carbonyl)-2,4-dihydro-1,3-benzoxazin-8-yl]-5-fluoro-2-morpholin-4-ylbenzoate (30.0 mg, 0.0530 mmol) in methanol (3.00 mL) and tetrahydrofuran (3.00 mL), a solution of lithium hydroxide monohydrate (50.0 mg, 1.19 mmol) in water (1.20 mL) was added. The reaction solution was stirred at room temperature for 4 hours, and the reaction mixture was then concentrated. The residue was purified by reverse phase column chromatography (acetonitrile/water) to obtain the title compound (32%, 9.40 mg).

LCMS: m/z 550[M+H]$^+$

HPLC retention time: 1.52 min (analysis condition B)

Compound 13-12

4-[3-(5-Chloro-1-methylindole-5-carbonyl)-2,4-dihydro-1,3-benzoxazin-8-yl]-5-fluoro-2-morpholin-4-ylbenzoic acid First Step Compound ME6

Methyl 4-[3-(5-chloro-1-methylindole-6-carbonyl)-2,4-dihydro-1,3-benzoxazin-8-yl]-5-fluoro-2-morpholin-4-ylbenzoate

[Formula 385]

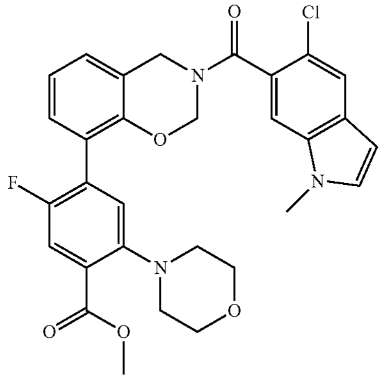

The title compound was synthesized by the same operation as in the first step of compound 13-11 using (3,4-dihydro-2H-1,3-benzoxazin-8-yl)-5-fluoro-2-morpholin-4-ylbenzoate dihydrochloride.

LCMS: m/z 564[M+H]$^+$

HPLC retention time: 1.38 min (analysis condition V)

Second Step

Compound 13-12

4-[3-(5-Chloro-1-methylindole-6-carbonyl)-2,4-dihydro-1,3-benzoxazin-8-yl]-5-fluoro-2-morpholin-4-ylbenzoic acid

[Formula 386]

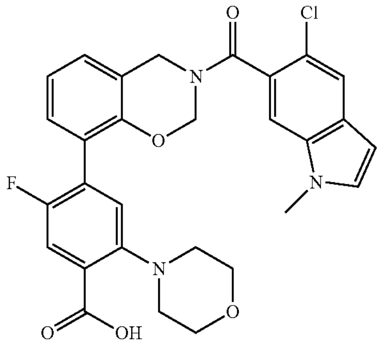

The title compound was synthesized by the same operation as in the second step of compound 13-11 using methyl 4-[3-(5-chloro-1-methylindole-6-carbonyl)-2,4-dihydro-1,3-benzoxazin-8-yl]-5-fluoro-2-morpholin-4-ylbenzoate.

LCMS: m/z 550[M+H]$^+$

HPLC retention time: 1.42 min (analysis condition B)

Compound 13-16

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid Synthesis Method A First Step Compound CMA1

2,6-Dichloro-4-(6-methoxy-2-azaspiro[3.3]heptan-2-yl)benzoic acid

[Formula 387]

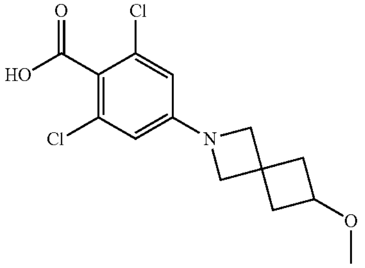

To a solution of 4-bromo-2,6-dichlorobenzoic acid (1.28 g, 4.74 mmol), 6-methoxy-2-azaspiro[3.3]heptane hydrochloride (1.55 g, 9.48 mmol), Xantphos (137 mg, 0.237 mmol), allylpalladium(II) chloride (dimer) (87.0 mg, 0.237 mmol), and trans,trans-1,5-diphenyl-1,4-pentadien-3-one (56.0 mg, 0.237 mmol) in 1,3-dimethyl-2-imidazolidinone (23.7 mL), a 1 M solution of sodium bis(trimethylsilyl) amide in tetrahydrofuran (19.0 mL, 19.0 mmol) was added dropwise. The reaction mixture was stirred at room temperature for 17 hours. Then, an aqueous formic acid solution and dimethyl sulfoxide were added thereto, and the mixture was purified by reverse phase column chromatography (acetonitrile/water, 0.1% formic acid) to obtain the title compound (84%, 1.26 g).

LCMS: m/z 316[M+H]$^+$

HPLC retention time: 1.01 min (analysis condition G)

Second Step

Compound ASO

Methyl 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 388]

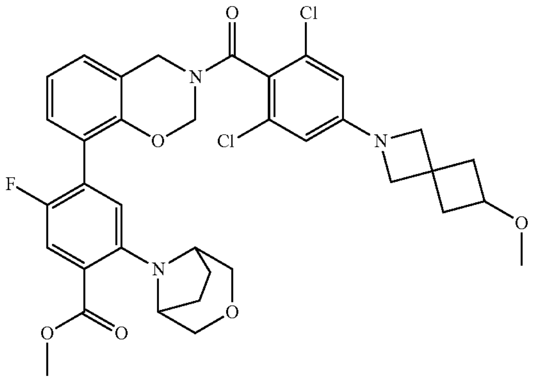

To a solution of 2,6-dichloro-4-(6-methoxy-2-azaspiro[3.3]heptan-2-yl)benzoic acid (698 mg, 2.21 mmol) in ethyl acetate (14.0 mL), a Ghosez reagent (0.350 mL, 2.65 mmol) was added. The mixture was stirred at room temperature for 30 minutes. 4-Methylmorpholine (1.54 mL, 14.1 mmol) and methyl 4-(3,4-dihydro-2H-1,3-benzoxazin-8-yl)-5-fluoro-2-(3-oxa-8-azabicyclo[3.2.1]octan-8-yl)benzoate dihydrochloride (944 mg, 2.01 mmol) were added to the reaction mixture. The reaction mixture was stirred overnight at 50° C. Then, the solution was cooled to room temperature, and 0.5 M sulfuric acid was added thereto, followed by extraction with ethyl acetate. The organic layer was washed with a saturated aqueous solution of sodium bicarbonate and concentrated to obtain a crude product of the title compound.

LCMS: m/z 696[M+H]$^+$

HPLC retention time: 3.22 min (analysis condition AF)

Third Step

Compound 13-16

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 389]

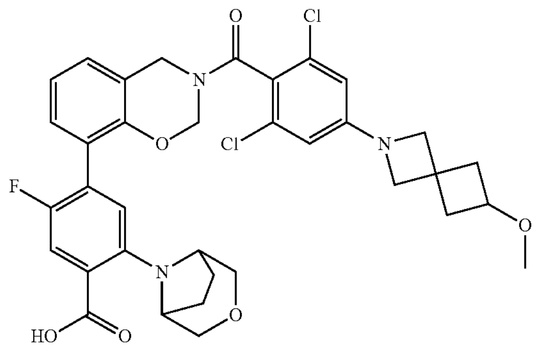

A solution of methyl 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (196 mg, 0.281 mmol) and an 8 M aqueous potassium hydroxide solution (0.352 mL, 2.81 mmol) in tetrahydrofuran (0.471 mL) and ethanol (1.57 mL) was stirred at 60° C. for 1 hour. The reaction mixture was cooled to room temperature. Then, an aqueous formic acid solution and dimethyl sulfoxide were added thereto, and the mixture was purified by reverse phase column chromatography (acetonitrile/water, 0.1% formic acid) to obtain the title compound (95%, 183 mg).

LCMS: m/z 682[M+H]$^+$

HPLC retention time: 1.58 min and 1.61 min (analysis condition B)

Compound 13-16

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid Synthesis Method B First Step Compound ASO Methyl 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 390]

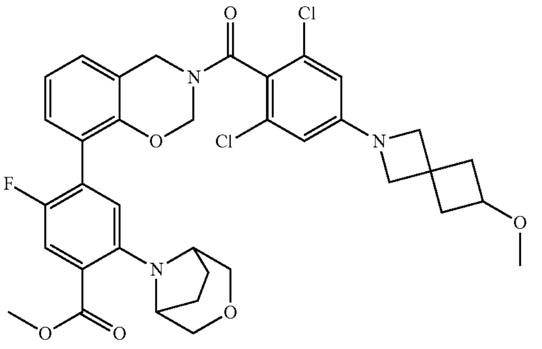

A solution of compound A (12.0 g, 18.5 mmol), 6-methoxy-2-azaspiro[3.3]heptane hydrochloride (4.53 g, 27.7 mmol), rac-BINAP (1.15 g, 1.85 mmol), tris(dibenzylideneacetone)dipalladium(0) (846 mg, 0.923 mmol) and cesium carbonate (30.1 g, 92.0 mmol) in 1-methylpyrrolidin-2-one (84.0 mL) and water (8.39 mL) was stirred at 100° C. for 3 hours. The reaction solution was cooled to room temperature, followed by extraction by the addition of ethyl acetate and water. The organic layer was washed with an aqueous N-acetylcysteine solution and an aqueous sodium chloride solution, dried over magnesium sulfate, and then concentrated, and the obtained residue was purified by silica gel column chromatography (hexane/ethyl acetate) to obtain the title compound (12.6 g) as a mixture with ethyl acetate.

LCMS: m/z 696[M+H]$^+$

HPLC retention time: 3.22 min (analysis condition AF)

Second Step
Compound 13-16

4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 391]

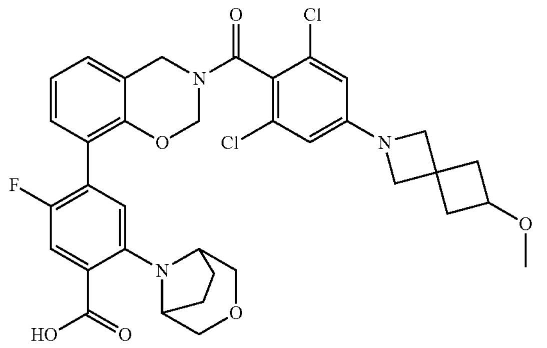

To a solution of methyl 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (12.3 g, 17.6 mmol) in tetrahydrofuran (22.0 mL)/ethanol (22.0 mL), an 8 M aqueous potassium hydroxide solution (11.0 mL, 88.0 mmol) was added, and the mixture was stirred at 60° C. for 2.5 hours. The reaction solution was cooled to room temperature. 0.5 M hydrochloric acid and water were added thereto, and the mixture was stirred. The obtained solid was collected by filtration, washed with water, and then dried under reduced pressure. An ethanol/water (1/9) solution was added to the obtained solid, and the solution was frozen in a freezer of −80° C. and then freeze-dried to obtain the title compound (91%, 10.9 g).

LCMS: m/z 682$[M+H]^+$

HPLC retention time: 1.58 min and 1.61 min (analysis condition B)

Compound 13-18

4-[3-[2,6-Dichloro-4-(1-methylpyrazol-4-yl)benzoyl]-2,4-dihydro-1,3-benzothiazin-8-yl]-5-fluoro-2-morpholin-4-ylbenzoic acid

[Formula 392]

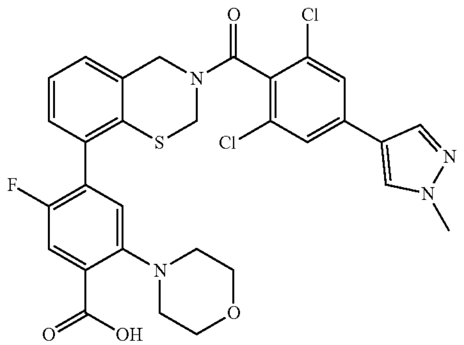

The title compound was synthesized by the same operation as in the fourth step and the fifth step of compound 13-2 using methyl 4-(3,4-dihydro-2H-1,3-benzothiazin-8-yl)-5-fluoro-2-morpholin-4-ylbenzoate dihydrochloride.

LCMS: m/z 627$[M+H]^+$

HPLC retention time: 0.99, 1.01 min (analysis condition A)

Compound 13-20

4-[3-[2,6-Dichloro-4-(1-methylpyrazol-4-yl)benzoyl]-2,4-dihydro-1,3-benzoxazin-8-yl]-2-methyl-6-morpholin-4-ylbenzoic acid

[Formula 393]

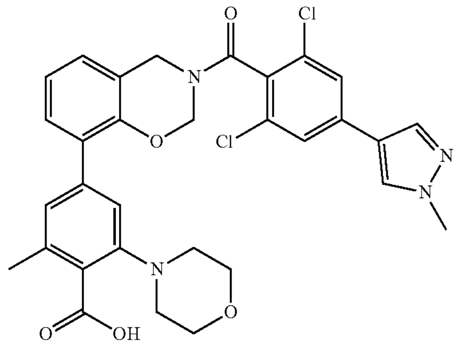

The title compound was synthesized by the same operation as in the fourth step and the fifth step of compound 13-2 using methyl 4-(3,4-dihydro-2H-1,3-benzoxazin-8-yl)-2-methyl-6-morpholin-4-ylbenzoate dihydrochloride.

LCMS: m/z 607$[M+H]^+$

HPLC retention time: 1.05 min and 1.08 min (analysis condition A)

Compound 13-21

4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound PIP1

(2R,5R)-1,2,5-Trimethylpiperazine

[Formula 394]

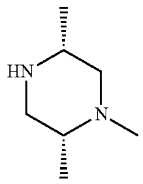

To a solution of (2R,5R)-1,2,5-trimethylpiperazine dihydrochloride (10.3 g, 51.0 mmol) in tetrahydrofuran (49.6 mL), a 50% aqueous potassium hydroxide solution (11.4 g, 102 mmol) was added, and the mixture was stirred at room temperature, then filtered, and washed with tetrahydrofuran. The filtrate was concentrated to obtain the title compound in a tetrahydrofuran solution.

$^{1}$H-NMR (400 MHz, DMSO-$D_6$) δ: 5.75 (1H, s), 2.78-2.68 (2H, m), 2.56 (1H, dd, J=12.0, 4.6 Hz), 2.39-2.36 (1H, m), 2.19 (1H, dd, J=11.0, 3.4 Hz), 2.13-2.09 (4H, m), 0.99 (3H, d, J=6.4 Hz), 0.91 (3H, d, J=6.6 Hz).

Second Step

Compound MCL2

2-Chloro-4-[(2R,5R)-2,4,5-trimethylpiperazin-1-yl] benzoic acid

[Formula 395]

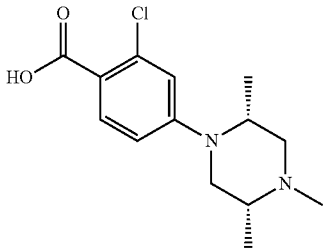

To a solution of (2R,5R)-1,2,5-trimethylpiperazine (1.63 g, 12.7 mmol) in tetrahydrofuran (18.4 mL), sodium tert-butoxide (2.78 g, 28.9 mmol) was added. A solution of 4-bromo-2-chlorobenzoic acid (2.00 g, 8.49 mmol) and rac-BINAP (0.264 g, 0.425 mmol) in 4-methyltetrahydropyran (6.00 mL) was added to the reaction solution. In another container, 4-methyltetrahydropyran (4.00 mL) was added to allylpalladium(II) chloride (dimer) (0.0780 g, 0.212 mmol) and rac-BINAP (0.264 g, 0.425 mmol), and the mixture was stirred for 30 minutes. The solution thus prepared in another container was added to the reaction solution, and the mixture was stirred at 90° C. for 2 hours. The reaction solution was cooled to room temperature. Then, an aqueous N-acetylcysteine solution was added thereto, and the mixture was stirred at 45° C. for 3 hours. 6 M hydrochloric acid and 4-methyltetrahydropyran were added to the reaction solution for back-extraction. Ethyl acetate was added to the aqueous layer, and back-extraction was performed by the addition of an 8 M aqueous sodium hydroxide solution. Ammonium sulfate was added to the obtained aqueous layer, followed by extraction with tetrahydrofuran. The organic layer was concentrated. Trifluoroethanol was added to the residue, and the mixture was heated to 75° C. Acetonitrile was added to the reaction mixture, and the mixture was stirred at 75° C. The reaction mixture was cooled to 25° C., and the obtained solid was collected by filtration, washed with acetonitrile, and then dried under reduced pressure to obtain the title compound (60%, 1.22 g).

LCMS: m/z 283[M+H]$^+$

HPLC retention time: 0.33 min (analysis condition F)

Third Step

Compound MCL4

Methyl 4-(3,4-dihydro-2H-1,3-benzoxazin-8-yl)-5-fluoro-2-(3-oxa-8-azabicyclo[3.2.1]octan-8-yl)benzoate methanesulfonate

[Formula 396]

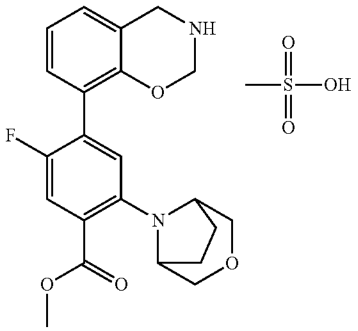

To a solution of tert-butyl 8-[2-fluoro-4-methoxycarbonyl-5-(3-oxa-8-azabicyclo[3.2.1]octan-8-yl)phenyl]-2,4-dihydro-1,3-benzoxazine-3-carboxylate (7.04 g, 14.1 mmol) in acetonitrile (28.1 mL), methanesulfonic acid (4.58 mL, 70.6 mmol) was added, and the mixture was stirred at room temperature for 2 hours to obtain the title compound in an acetonitrile solution.

LCMS: m/z 399[M+H]$^+$

HPLC retention time: 0.52 min (analysis condition D)

Fourth Step

Compound MCL3

2-Chloro-4-[(2R,5R)-2,4,5-trimethylpiperazin-1-yl] benzoyl Chloride

[Formula 397]

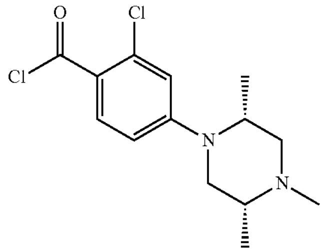

To a mixture of 2-chloro-4-[(2R,5R)-2,4,5-trimethylpiperazin-1-yl]benzoic acid (4.99 g, 16.9 mmol) and acetonitrile (42.2 mL), a Ghosez reagent (3.97 mL, 28.8 mmol) was added, and the mixture was stirred at room temperature for 1 hour. Methanesulfonic acid (1.19 mL, 18.3 mmol) was added to the reaction mixture. The title compound in an acetonitrile solvent was obtained.

Fifth Step

Compound MCL5

Methyl 4-[3-[2-chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate

[Formula 398]

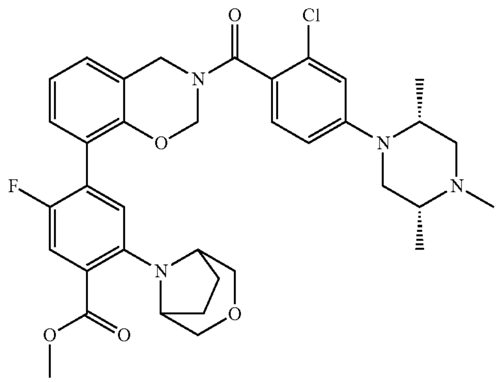

To the solution of 2-chloro-4-[(2R,5R)-2,4,5-trimethylpiperazin-1-yl]benzoyl chloride in acetonitrile obtained in the fourth step, the solution of methyl 4-(3,4-dihydro-2H-1,3-benzoxazin-8-yl)-5-fluoro-2-(3-oxa-8-azabicyclo[3.2.1]octan-8-yl)benzoate methanesulfonate in acetonitrile obtained in the third step was added. N,N-Diisopropylethylamine (16.0 mL, 92.0 mmol) was added to the reaction solution, and the mixture was stirred at 25° C. for 1 hour. Ethyl acetate and water were added to the reaction solution, and water, a 15% aqueous sodium chloride solution, an 8 M aqueous sodium hydroxide solution, and 1 M hydrochloric acid were then added for extraction. The obtained organic layer was concentrated. 1 M hydrochloric acid and ethyl acetate were added to the obtained residue for back-extraction. An 8 M aqueous sodium hydroxide solution and 2 M hydrochloric acid were added to the obtained aqueous layer, followed by extraction with 4-methyltetrahydropyran. The organic layer was washed with a 15% aqueous sodium chloride solution, concentrated, and dried under reduced pressure to obtain the title compound (69%, 8.99 g).

LCMS: m/z 663[M+H]$^+$

HPLC retention time: 0.86 min (analysis condition G)

Sixth Step

Compound 13-21

4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 399]

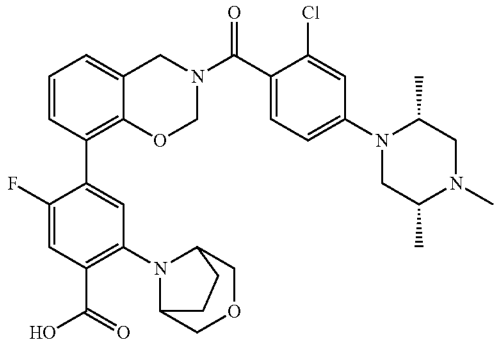

To methyl 4-[3-[2-chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate (5.74 g, 8.66 mmol), tetrahydrofuran (29.3 mL), 4-methyltetrahydropyran (1.38 mL) and methanol (8.61 mL) were added, then a 50% aqueous potassium hydroxide solution (1.93 mL, 26.0 mmol) was added, and the mixture was stirred at 25° C. for 3 hours. Water and cyclopentyl methyl ether were added to the reaction solution for back-extraction. 6 M hydrochloric acid was added to the obtained aqueous layer, and the mixture was washed with ethyl acetate. 2-Butanone and 8 M sodium hydroxide were added to the aqueous layer, and sodium chloride was added. The reaction mixture was subjected to extraction with 2-butanone. The obtained organic layer was concentrated, filtered, and washed with 2-butanone. The obtained filtrate and wash were concentrated, and acetone was added to the residue. Water was added to the obtained solution, and the mixture was stirred at 25° C. The obtained solid was collected by filtration and washed with water. The solid was dried to obtain the title compound (83%, 4.67 g).

LCMS: m/z 649[M+H]$^+$

HPLC retention time: 1.13 min (analysis condition B)

Compound 14-1

4-[3-[2,6-Dichloro-4-(1-methylpyrazol-4-yl)benzoyl]-2,4-dihydro-1,3-benzoxazin-8-yl]-2-morpholin-4-ylbenzoic acid First Step Compound BA1

2-Morpholin-4-yl-4-(4,4,5,5-tetramethyl-1,3,2-dioxaborolan-2-yl)benzoic acid

[Formula 400]

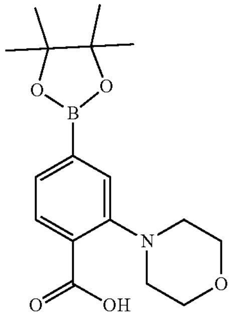

A solution of 4-bromo-2-morpholin-4-ylbenzoic acid (337 mg, 1.18 mmol), bis(pinacolato)diboron (359 mg, 1.41 mmol), potassium acetate (323 mg, 3.30 mmol), and [1,1'-bis(diphenylphosphino)ferrocene]palladium(II) dichloride (43.0 mg, 0.0590 mmol) in 1,4-dioxane (4.00 mL) was stirred at 90° C. for 2 hours to obtain the title compound as a crude product.

LCMS: m/z 334[M+H]$^+$

HPLC retention time: 0.89 min (analysis condition G)

Second Step

Compound 14-1

4-[3-[2,6-Dichloro-4-(1-methylpyrazol-4-yl)benzoyl]-2,4-dihydro-1,3-benzoxazin-8-yl]-2-morpholin-4-ylbenzoic acid

[Formula 401]

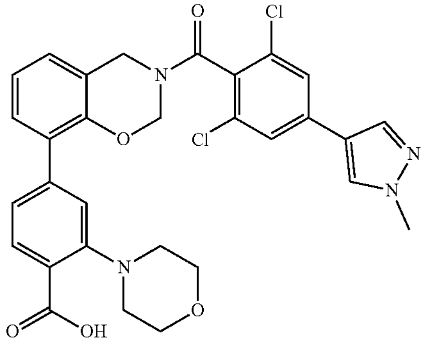

A solution of the crude product of 2-morpholin-4-yl-4-(4,4,5,5-tetramethyl-1,3,2-dioxaborolan-2-yl)benzoic acid (4.09 g, 12.3 mmol), (8-bromo-2,4-dihydro-1,3-benzoxazin-3-yl)-[2,6-dichloro-4-(1-methylpyrazol-4-yl)phenyl]methanone (5.74 g, 12.3 mmol), potassium carbonate (5.10 g, 36.9 mmol), and [1,1'-bis(diphenylphosphino)ferrocene]palladium(II) dichloride (225 mg, 0.307 mmol) in 1,4-dioxane (40.0 mL) and water (12.5 mL) was stirred at 90° C. for 2.5 hours. An aqueous trifluoroacetic acid solution was added to the reaction mixture, and the mixture was then purified by reverse phase column chromatography (acetonitrile/water, 0.1% trifluoroacetic acid) to obtain the title compound (54%, 3.95 g).

LCMS: m/z 593[M+H]$^+$

HPLC retention time: 0.99 min and 1.02 min (analysis condition A)

Compound 14-2

2-(1,3,3a,4,6,6a-Hexahydrofuro[3,4-c]pyrrol-5-yl)-4-[3-[2,6-dichloro-4-(1-methylpyrazol-4-yl)benzoyl]-2,4-dihydro-1,3-benzoxazin-8-yl]-5-fluorobenzoic acid First Step Compound EE1

Ethyl 4-bromo-2,5-difluorobenzoate

[Formula 402]

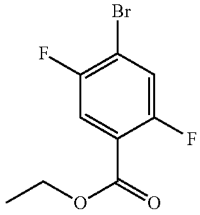

A solution of 4-bromo-2,5-difluorobenzoic acid (300 mg, 1.27 mmol), iodoethane (0.153 mL, 1.90 mmol) and cesium carbonate (619 mg, 1.90 mmol) in N,N-dimethylformamide (10.0 mL) was stirred overnight at room temperature. Water was added to the reaction mixture, followed by extraction with diethyl ether. The organic layer was dried over anhydrous sodium sulfate and concentrated. The residue was purified by silica gel column chromatography (ethyl acetate/hexane) to obtain the title compound (94%, 317 mg).

LCMS: m/z 265[M+H]$^+$

HPLC retention time: 1.23 min (analysis condition G)

Second Step

Compound EE2

Ethyl 2-(1,3,3a,4,6,6a-hexahydrofuro[3,4-c]pyrrol-5-yl)-4-bromo-5-fluorobenzoate

[Formula 403]

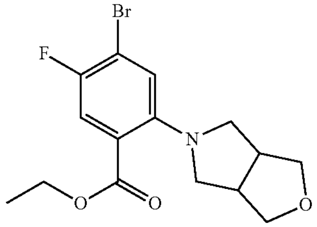

A solution of ethyl 4-bromo-2,5-difluorobenzoate (30.0 mg, 0.113 mmol) and 3,3a,4,5,6,6a-hexahydro-1H-furo[3,4-c]pyrrole hydrochloride (38.9 mg, 0.260 mmol) in toluene (0.300 mL) was stirred overnight at 110° C. The reaction mixture was concentrated, and the residue was purified by silica gel column chromatography (ethyl acetate/hexane) to obtain the title compound (35%, 14.0 mg).

LCMS: m/z 358[M+H]$^+$

HPLC retention time: 1.21 min (analysis condition G)

Third Step

Compound EE3

Ethyl 2-(1,3,3a,4,6,6a-hexahydrofuro[3,4-c]pyrrol-5-yl)-4-[3-[2,6-dichloro-4-(1-methylpyrazol-4-yl)benzoyl]-2,4-dihydro-1,3-benzoxazin-8-yl]-5-fluorobenzoate

[Formula 404]

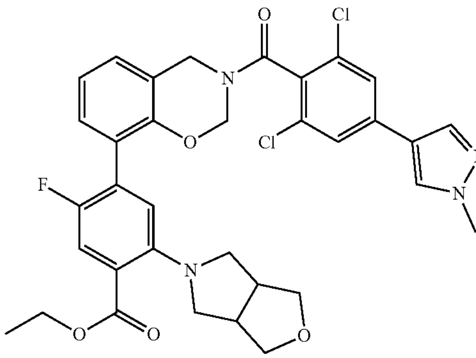

The title compound was synthesized by the same operation as in the third step and the fourth step of compound 13-3 using (8-bromo-2,4-dihydro-1,3-benzoxazin-3-yl)-[2,6-dichloro-4-(1-methylpyrazol-4-yl)phenyl]methanone and ethyl 2-(1,3,3a,4,6,6a-hexahydrofuro[3,4-c]pyrrol-5-yl)-4-bromo-5-fluorobenzoate.

LCMS: m/z 665[M+H]$^+$

HPLC retention time: 1.24 min and 1.26 min (analysis condition G)

Fourth Step

Compound 14-2

2-(1,3,3a,4,6,6a-Hexahydrofuro[3,4-c]pyrrol-5-yl)-4-[3-[2,6-dichloro-4-(1-methylpyrazol-4-yl)benzoyl]-2,4-dihydro-1,3-benzoxazin-8-yl]-5-fluorobenzoic acid

[Formula 405]

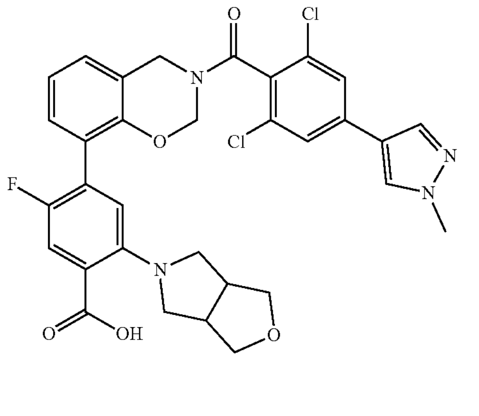

The title compound was synthesized by the same operation as in the fifth step of compound 13-2 using ethyl 2-(1,3,3a,4,6,6a-hexahydrofuro[3,4-c]pyrrol-5-yl)-4-[3-[2,6-dichloro-4-(1-methylpyrazol-4-yl)benzoyl]-2,4-dihydro-1,3-benzoxazin-8-yl]-5-fluorobenzoate.

LCMS: m/z 637[M+H]$^+$

HPLC retention time: 0.94 min and 0.96 min (analysis condition G)

Compound 14-3

4-[3-[2,6-Dichloro-4-(1-methylpyrazol-4-yl)benzoyl]-2,4-dihydro-1,3-benzoxazin-8-yl]-2-(4,4-difluoropiperidin-1-yl)benzoic acid First Step Compound DP1

4-Bromo-2-(4,4-difluoropiperidin-1-yl)benzoic acid

[Formula 406]

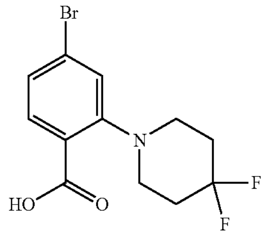

A solution of 4-bromo-2-fluorobenzoic acid (100 mg, 0.457 mmol), 4,4-difluoropiperidine hydrochloride (108 mg, 0.685 mmol) and triethylamine (139 mg, 1.37 mmol) in dimethyl sulfoxide (1.50 mL) was stirred overnight at 150° C. The reaction mixture was purified by reverse phase column chromatography (acetonitrile/water, 0.1% formic acid) to obtain the title compound (39%, 56.8 mg).

LCMS: m/z 320[M+H]$^+$

HPLC retention time: 0.98 min (analysis condition G)

Second Step

Compound BA2

[3-[2,6-Dichloro-4-(1-methylpyrazol-4-yl)benzoyl]-2,4-dihydro-1,3-benzoxazin-8-yl]boronic acid

[Formula 407]

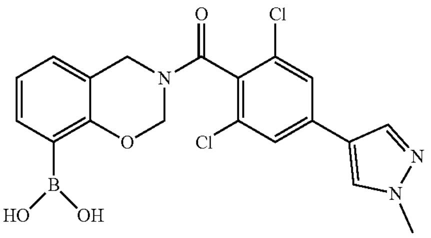

A crude product of the title compound was synthesized by the same operation as in the second step of compound 13-2 using (8-bromo-2,4-dihydro-1,3-benzoxazin-3-yl)-[2,6-dichloro-4-(1-methylpyrazol-4-yl)phenyl]methanone.

LCMS: m/z 432[M+H]$^+$

HPLC retention time: 0.89 min and 0.91 min (analysis condition G)

Third Step

Compound 14-3

4-[3-[2,6-Dichloro-4-(1-methylpyrazol-4-yl)benzoyl]-2,4-dihydro-1,3-benzoxazin-8-yl]-2-(4,4-difluoropiperidin-1-yl)benzoic acid

[Formula 408]

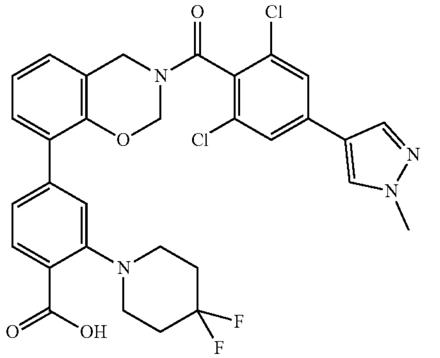

The title compound was synthesized by the same operation as in the fourth step of compound 13-3 using [3-[2,6-dichloro-4-(1-methylpyrazol-4-yl)benzoyl]-2,4-dihydro-1,3-benzoxazin-8-yl]boronic acid.

LCMS: m/z 627[M+H]$^+$

HPLC retention time: 1.12 min and 1.14 min (analysis condition A)

Compound 14-4

4-[2-[2,6-Dichloro-4-(1-methylpyrazol-4-yl)benzoyl]-4-oxo-1,3-dihydrophthalazin-5-yl]-2-morpholin-4-ylbenzoic acid First Step Compound UP4

8-Bromo-3-[2,6-dichloro-4-(1-methylpyrazol-4-yl)benzoyl]-2,4-dihydrophthalazin-1-one

[Formula 409]

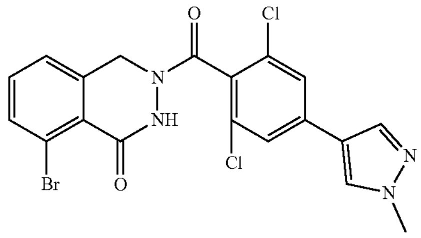

The title compound was synthesized by the same operation as in the second step of compound 13-1 using tert-butyl 5-bromo-4-oxo-1,3-dihydrophthalazine-2-carboxylate.

LCMS: m/z 479[M+H]$^+$

HPLC retention time: 0.95 min (analysis condition G)

Second Step

Compound ME18

Methyl 4-[2-[2,6-dichloro-4-(1-methylpyrazol-4-yl)benzoyl]-4-oxo-1,3-dihydrophthalazin-5-yl]-2-morpholin-4-ylbenzoate

[Formula 410]

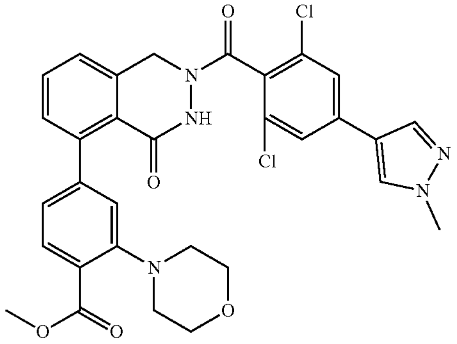

The title compound was synthesized by the same operation as in the fourth step of compound 13-3 using 8-bromo-3-[2,6-dichloro-4-(1-methylpyrazol-4-yl)benzoyl]-2,4-dihydrophthalazin-1-one.

LCMS: m/z 620[M+H]$^+$

HPLC retention time: 1.04 min (analysis condition G)

Third Step

Compound 14-4

4-[2-[2,6-Dichloro-4-(1-methylpyrazol-4-yl)benzoyl]-4-oxo-1,3-dihydrophthalazin-5-yl]-2-morpholin-4-ylbenzoic acid

[Formula 411]

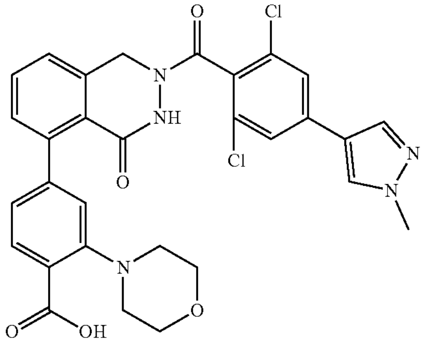

The title compound was synthesized by the same operation as in the fifth step of compound 13-2 using methyl 4-[2-[2,6-dichloro-4-(1-methylpyrazol-4-yl)benzoyl]-4-oxo-1,3-dihydrophthalazin-5-yl]-2-morpholin-4-ylbenzoate.

LCMS: m/z 606[M+H]$^+$

HPLC retention time: 0.82 min and 0.89 min (analysis condition A)

Compound 14-5

4-[3-[2,6-Dichloro-4-(1-methylpyrazol-4-yl)benzoyl]-2,4-dihydro-1H-quinazolin-8-yl]-2-morpholin-4-ylbenzoic acid First Step
Compound UP5

N-[(2-Amino-3-bromophenyl)methyl]-2,6-dichloro-4-(1-methylpyrazol-4-yl)benzamide

[Formula 412]

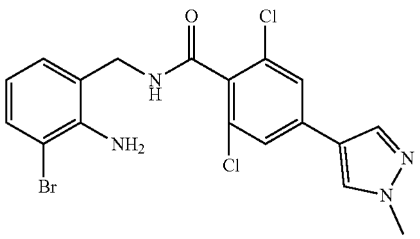

To a solution of 2,6-dichloro-4-(1-methylpyrazol-4-yl) benzoyl chloride (453 mg, 1.09 mmol) in dichloromethane (5.00 mL), 2-(aminomethyl)-6-bromoaniline (200 mg, 1.00 mmol) and N,N-diisopropylethylamine (0.534 mL, 2.98 mmol) were added at 0° C. After stirring at room temperature for 1 hour, an aqueous sodium hydroxide solution was added to the reaction mixture, followed by extraction with dichloromethane. The organic layer was allowed to pass through a phase separator, and the organic layer was then concentrated. The residue was purified by silica gel column chromatography (ethyl acetate/hexane) to obtain the title compound (77%, 346 mg).

LCMS: m/z 453[M+H]$^+$

HPLC retention time: 1.08 min (analysis condition G)

Second Step
Compound UP6

(8-Bromo-2,4-dihydro-1H-quinazolin-3-yl)-[2,6-dichloro-4-(1-methylpyrazol-4-yl)phenyl]methanone

[Formula 413]

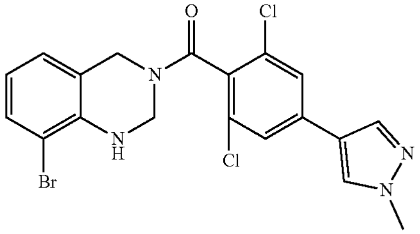

A solution of N-[(2-amino-3-bromophenyl)methyl]-2,6-dichloro-4-(1-methylpyrazol-4-yl)benzamide (59.0 mg, 0.130 mmol) and paraformaldehyde (39.0 mg, 1.30 mmol) in toluene (0.300 mL) was stirred at 90° C. for 1 hour. p-Toluenesulfonic acid monohydrate (24.7 mg, 0.130 mmol) was added to the reaction mixture, and the mixture was stirred at 90° C. for 1 hour. The reaction mixture was purified by silica gel column chromatography (ethyl acetate/hexane) to obtain the title compound (46%, 28.0 mg).

LCMS: m/z 465[M+H]$^+$

HPLC retention time: 1.13 min (analysis condition G)

Third Step
Compound 14-5

4-[3-[2,6-Dichloro-4-(1-methylpyrazol-4-yl)benzoyl]-2,4-dihydro-1H-quinazolin-8-yl]-2-morpholin-4-ylbenzoic acid

[Formula 414]

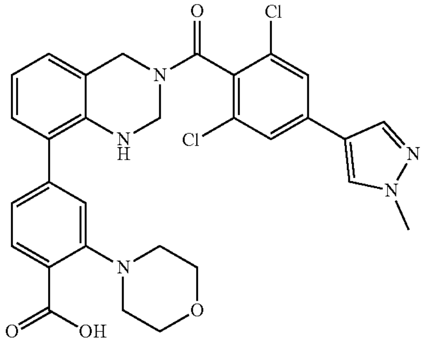

The title compound was synthesized by the same operation as in the fourth step of compound 13-3 using (8-bromo-2,4-dihydro-1H-quinazolin-3-yl)-[2,6-dichloro-4-(1-methylpyrazol-4-yl)phenyl]methanone and 2-morpholin-4-yl-4-(4,4,5,5-tetramethyl-1,3,2-dioxaborolan-2-yl)benzoic acid.

LCMS: m/z 592[M+H]$^+$

HPLC retention time: 0.96 min (analysis condition A)

Compound 14-6

4-[3-[2,6-Dichloro-4-(1-methylpyrazol-4-yl)benzoyl]-2-oxo-1,4-dihydroquinazolin-8-yl]-2-morpholin-4-ylbenzoic acid First Step
Compound UP7

8-Bromo-3-[2,6-dichloro-4-(1-methylpyrazol-4-yl) benzoyl]-1,4-dihydroquinazolin-2-one

[Formula 415]

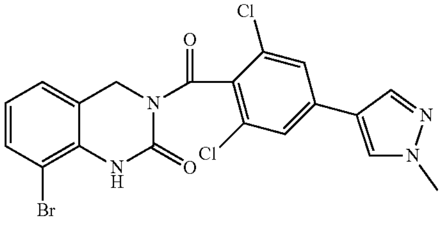

To a solution of N-[(2-amino-3-bromophenyl)methyl]-2,6-dichloro-4-(1-methylpyrazol-4-yl)benzamide (200 mg, 0.440 mmol) in 1,2-dichloroethane (4.40 mL), triphosgene (65.3 mg, 0.220 mmol) and triethylamine (0.184 mL, 1.32 mmol) were added at 0° C. The mixture was stirred at room temperature for 2 hours, and triphosgene (26.1 mg, 0.0880 mmol) and triethylamine (0.246 mL, 1.76 mmol) were then further added thereto at 0° C. The mixture was stirred at room temperature for 2 hours, and triphosgene (39.2 mg, 0.132 mmol) and triethylamine (0.123 mL, 0.881 mmol)

were then further added thereto at 0° C. The reaction mixture was stirred at room temperature for 30 minutes, and a saturated aqueous solution of sodium bicarbonate was then added thereto, followed by extraction with ethyl acetate. The organic layer was washed with water and a saturated aqueous solution of sodium chloride, followed by passing through a phase separator. Then, the organic layer was concentrated. The residue was purified by reverse phase column chromatography (acetonitrile/water, 0.1% formic acid) to obtain the title compound (66%, 140.0 mg).

LCMS: m/z 453[M+H]$^+$

HPLC retention time: 1.01 min (analysis condition G)

Second Step

Compound 14-6

4-[3-[2,6-Dichloro-4-(1-methylpyrazol-4-yl)benzoyl]-2-oxo-1,4-dihydroquinazolin-8-yl]-2-morpholin-4-ylbenzoic acid

[Formula 416]

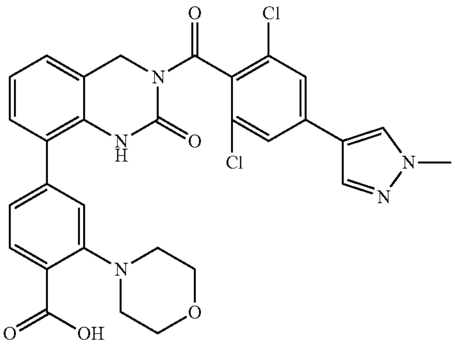

The title compound was synthesized by the same operation as in the fourth step of compound 13-3 using 8-bromo-3-[2,6-dichloro-4-(1-methylpyrazol-4-yl)benzoyl]-1,4-dihydroquinazolin-2-one and 2-morpholin-4-yl-4-(4,4,5,5-tetramethyl-1,3,2-dioxaborolan-2-yl)benzoic acid.

LCMS: m/z 606[M+H]$^+$

HPLC retention time: 1.03 min (analysis condition A)

Compound 14-7

4-[4,4-Dideuterio-3-[2,6-dichloro-4-(1-methylpyrazol-4-yl)benzoyl]-2H-1,3-benzoxazin-8-yl]-2-morpholin-4-ylbenzoic acid First Step Compound UD1 tert-Butyl 8-bromo-4,4-dideuterio-2H-1,3-benzoxazine-3-carboxylate

[Formula 417]

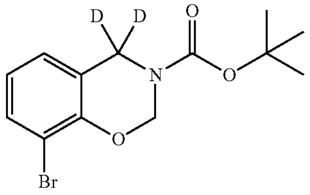

A mixture of tert-butyl 8-bromo-2,4-dihydro-1,3-benzoxazine-3-carboxylate (2.00 g, 6.37 mmol), dimethyl sulfoxide-d6 (20.0 mL, 283 mmol) and a 1 M solution of potassium tert-butoxide in tetrahydrofuran (1.27 mL, 1.27 mmol) was stirred at 80° C. for 1 hour. Water was added to the reaction mixture, followed by extraction with ethyl acetate. The organic layer was dried over sodium sulfate and concentrated. The residue was purified by reverse phase column chromatography (acetonitrile/water, 0.1% formic acid) to obtain the title compound (79%, 1.60 g).

LCMS: m/z 316[M+H]$^+$

HPLC retention time: 0.94 min (analysis condition D)

Second Step

Compound UD2

(8-Bromo-4,4-dideuterio-2H-1,3-benzoxazin-3-yl)-[2,6-dichloro-4-(1-methylpyrazol-4-yl)phenyl]methanone

[Formula 418]

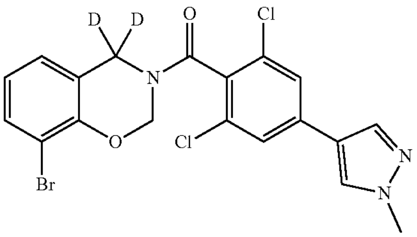

The title compound was synthesized by the same operation as in the fourth step of compound 13-2 using tert-butyl 8-bromo-4,4-dideuterio-2H-1,3-benzoxazine-3-carboxylate.

LCMS: m/z 468[M+H]$^+$

HPLC retention time: 1.17 min (analysis condition G)

Third Step

Compound 14-7

4-[4,4-Dideuterio-3-[2,6-dichloro-4-(1-methylpyrazol-4-yl)benzoyl]-2H-1,3-benzoxazin-8-yl]-2-morpholin-4-ylbenzoic acid

[Formula 419]

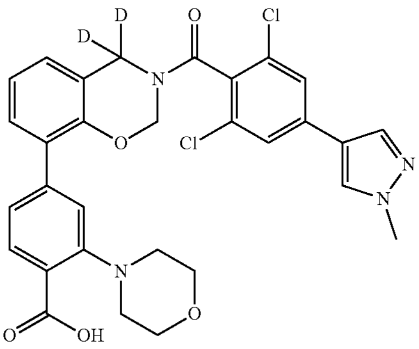

A solution of 4-bromo-2-morpholin-4-ylbenzoic acid (30.5 mg, 0.107 mmol), bis(pinacolato)diboron (27.1 mg, 0.107 mmol), potassium acetate (15.7 mg, 0.160 mmol), and [1,1'-bis(diphenylphosphino)ferrocene]palladium(II)

dichloride (3.90 mg, 0.00533 mmol) in 1,4-dioxane (0.300 mL) was stirred at 80° C. for 3 hours. (8-Bromo-4,4-dideuterio-2H-1,3-benzoxazin-3-yl)-[2,6-dichloro-4-(1-methylpyrazol-4-yl)phenyl]methanone (25.0 mg, 0.053 mmol), [1,1'-bis(diphenylphosphino)ferrocene]palladium (II) dichloride (3.90 mg, 0.00533 mmol), and a 2 M aqueous sodium carbonate solution (0.133 mL, 0.266 mmol) were added to the reaction mixture, and the mixture was stirred at 80° C. for 3 hours. An aqueous formic acid solution was added to the reaction mixture, and the mixture was filtered and then purified by HPLC (acetonitrile/water, 0.1% formic acid) to obtain the title compound (60%, 19.0 mg).

LCMS: m/z 595[M+H]$^+$

HPLC retention time: 0.97 min and 1.00 min (analysis condition A)

Compound 14-8

4-[3-[2,6-Dichloro-4-(1-methylpyrazol-4-yl)benzoyl]-1,4-dihydro-2,3-benzoxazin-8-yl]-2-morpholin-4-ylbenzoic acid First Step Compound UP8 tert-Butyl 8-bromo-1,4-dihydro-2,3-benzoxazine-3-carboxylate

[Formula 420]

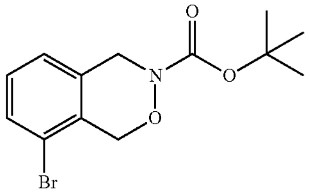

A solution of 1-bromo-2,3-bis(bromomethyl)benzene (700 mg, 2.04 mmol), tert-butyl N-hydroxycarbamate (326 mg, 2.45 mmol) and potassium hydroxide (286 mg, 5.10 mmol) in ethanol (4.08 mL) was stirred at 70° C. for 2 hours. The reaction mixture was cooled to room temperature. Then, di-tert-butyl dicarbonate (446 mg, 2.04 mmol) was added thereto, and the mixture was stirred at room temperature for 2 hours. 1 M hydrochloric acid was added to the reaction mixture, followed by extraction with ethyl acetate. The organic layer was washed with a saturated aqueous solution of sodium bicarbonate and a saturated aqueous solution of sodium chloride, followed by passing through a phase separator. Then, the organic layer was concentrated. The residue was purified by silica gel column chromatography (ethyl acetate/hexane) to obtain the title compound (21%, 137 mg).

LCMS: m/z 258[M-tBu+H]$^+$

HPLC retention time: 1.33 min (analysis condition G)

Second Step

Compound UP10

(8-Bromo-1,4-dihydro-2,3-benzoxazin-3-yl)-[2,6-dichloro-4-(1-methylpyrazol-4-yl)phenyl]methanone

[Formula 421]

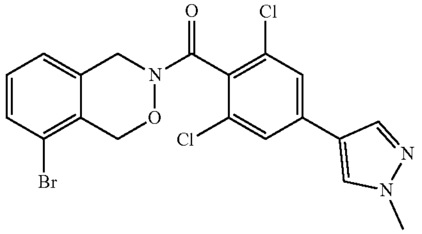

The title compound was synthesized by the same operation as in the fourth step of compound 13-2 using tert-butyl 8-bromo-1,4-dihydro-2,3-benzoxazine-3-carboxylate.

LCMS: m/z 466[M+H]$^+$

HPLC retention time: 0.89 min (analysis condition O)

Third Step

Compound 14-8

4-[3-[2,6-Dichloro-4-(1-methylpyrazol-4-yl)benzoyl]-1,4-dihydro-2,3-benzoxazin-8-yl]-2-morpholin-4-ylbenzoic acid

[Formula 422]

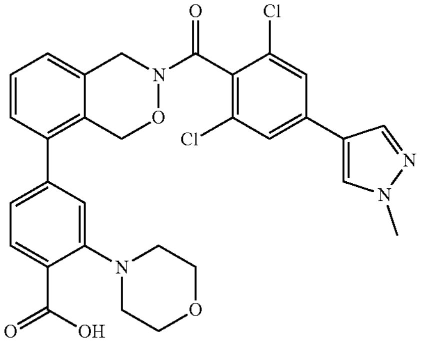

The title compound was synthesized by the same operation as in the fourth step of compound 13-3 using (8-bromo-1,4-dihydro-2,3-benzoxazin-3-yl)-[2,6-dichloro-4-(1-methylpyrazol-4-yl)phenyl]methanone and 4-bromo-2-morpholin-4-ylbenzoic acid.

LCMS: m/z 593[M+H]$^+$

HPLC retention time: 1.00 min (analysis condition A)

Compound 14-9

4-[3-[2,6-Dichloro-4-[4-(2-methoxyethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound UP11

(8-Bromo-2,4-dihydro-1,3-benzoxazin-3-yl)-[2,6-dichloro-4-[4-(2-methoxyethyl)piperazin-1-yl]phenyl]methanone

[Formula 423]

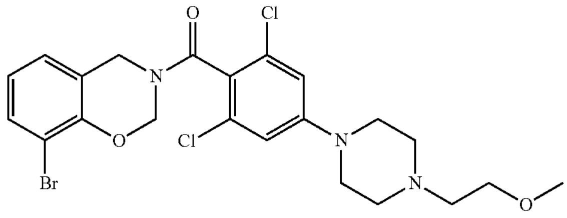

A solution of (8-bromo-2,4-dihydro-1,3-benzoxazin-3-yl)-(2,6-dichloro-4-fluorophenyl)methanone (200 mg, 0.494 mmol) and 1-(2-methoxyethyl)piperazine (367 mL, 2.47 mmol) in 1-methylpyrrolidin-2-one (0.988 mL) was stirred at 130° C. for 2 hours. The reaction mixture was purified by reverse phase column chromatography (acetonitrile/water, 0.1% formic acid) to obtain the title compound (100%, 277 mg).

LCMS: m/z 528[M+H]$^+$

HPLC retention time: 0.58 min (analysis condition D)

Second Step
Compound 14-9

4-[3-[2,6-Dichloro-4-[4-(2-methoxyethyl)piperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 424]

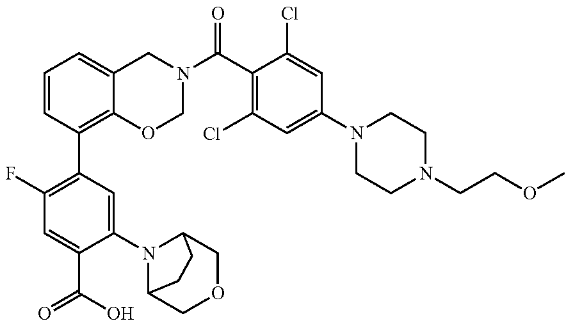

The title compound was synthesized by the same operation as in the third step of compound 14-7 using (8-bromo-2,4-dihydro-1,3-benzoxazin-3-yl)-[2,6-dichloro-4-[4-(2-methoxyethyl)piperazin-1-yl]phenyl]methanone and 4-bromo-5-fluoro-2-(3-oxa-8-azabicyclo[3.2.1]octan-8-yl)benzoic acid.

LCMS: m/z 699[M+H]$^+$

HPLC retention time: 1.00 min and 1.04 min (analysis condition B)

Compound 15-1

4-[3-[2,6-Dichloro-4-[1-(2-hydroxy-2-methylpropyl)pyrazol-4-yl]benzoyl]-2,4-dihydro-1,3-benzoxazin-8-yl]-2-morpholin-4-ylbenzoic acid First Step
Compound PT1

Methyl 4-[3-[2,6-dichloro-4-[1-(oxan-2-yl)pyrazol-4-yl]benzoyl]-2,4-dihydro-1,3-benzoxazin-8-yl]-2-morpholin-4-ylbenzoate

[Formula 425]

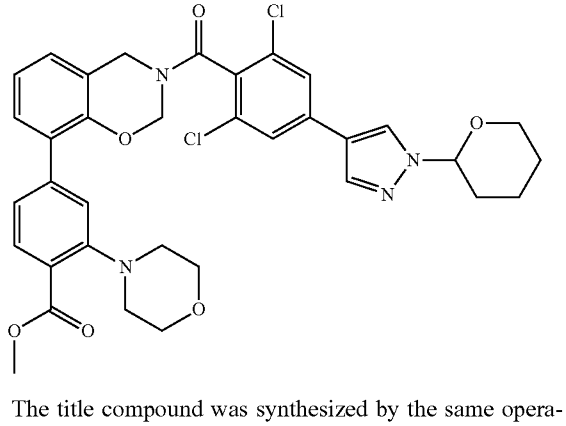

The title compound was synthesized by the same operation as in the fourth step of compound 13-3 using [3,5-dichloro-4-[8-(4-methoxycarbonyl-3-morpholin-4-ylphenyl)-2,4-dihydro-1,3-benzoxazine-3-carbonyl]phenyl]boronic acid and 4-bromo-1-(oxan-2-yl)pyrazole.

LCMS: m/z 677[M+H]$^+$

HPLC retention time: 1.31 min (analysis condition G)

Second Step
Compound PN1

Methyl 4-[3-[2,6-dichloro-4-(1H-pyrazol-4-yl)benzoyl]-2,4-dihydro-1,3-benzoxazin-8-yl]-2-morpholin-4-ylbenzoate

[Formula 426]

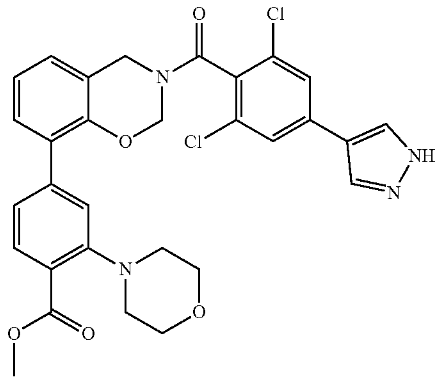

A solution of methyl 4-[3-[2,6-dichloro-4-[1-(oxan-2-yl)pyrazol-4-yl]benzoyl]-2,4-dihydro-1,3-benzoxazin-8-yl]-2-morpholin-4-ylbenzoate (34.1 mg, 0.0500 mmol) and a 4 M solution of hydrochloric acid in ethyl acetate (0.315 mL, 1.26 mmol) in ethanol (0.336 mL) was stirred at room temperature for 1 hour. The reaction mixture was concentrated, and the residue was then purified by reverse phase column chromatography (acetonitrile/water, 0.1% formic acid) to obtain the title compound (64%. 19.2 mg).

LCMS: m/z 593$[M+H]^+$

HPLC retention time: 1.10 min and 1.13 min (analysis condition G)

Third Step

Compound 15-1

4-[3-[2,6-Dichloro-4-[1-(2-hydroxy-2-methylpropyl) pyrazol-4-yl]benzoyl]-2,4-dihydro-1,3-benzoxazin-8-yl]-2-morpholin-4-ylbenzoic acid

[Formula 427]

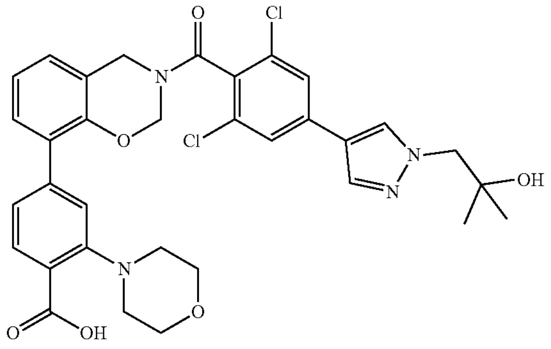

A solution of methyl 4-[3-[2,6-dichloro-4-(1H-pyrazol-4-yl)benzoyl]-2,4-dihydro-1,3-benzoxazin-8-yl]-2-morpholin-4-ylbenzoate (14.5 mg, 0.0240 mmol), isobutylene oxide (0.00328 mL, 0.0370 mmol) and cesium carbonate (15.9 mg, 0.0490 mmol) in N,N-dimethylformamide (0.200 mL) was stirred at 60° C. for 4 hours. Isobutylene oxide (0.00328 mL, 0.0370 mmol) was further added thereto, and the mixture was stirred at 60° C. for 2 hours. Isobutylene oxide (0.00328 mL, 0.0370 mmol) was further added thereto, and the mixture was stirred at 60° C. for 3 hours. A 5 M aqueous sodium hydroxide solution (0.0460 mL, 0.230 mmol) was added to the reaction mixture, and the mixture was stirred at 50° C. for 30 minutes. Formic acid was added to the reaction mixture, and the mixture was then purified by reverse phase column chromatography (acetonitrile/water, 0.1% formic acid) to obtain the title compound (81%, 12.1 mg).

LCMS: m/z 651$[M+H]^+$

HPLC retention time: 0.96 min and 0.99 min (analysis condition A)

Compound 15-2

4-[3-[2,6-Dichloro-4-[1-[(2S)-2-hydroxypropyl] pyrazol-4-yl]benzoyl]-2,4-dihydro-1,3-benzoxazin-8-yl]-2-morpholin-4-ylbenzoic acid

[Formula 428]

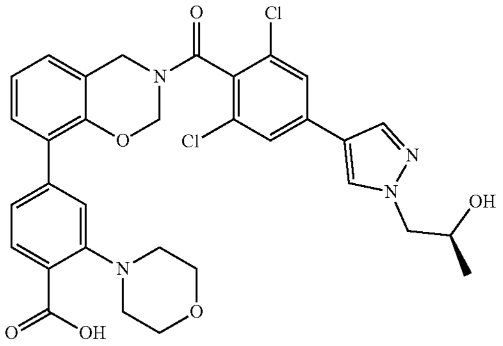

The title compound was synthesized by the same operation as in the third step of compound 15-1 using methyl 4-[3-[2,6-dichloro-4-(1H-pyrazol-4-yl)benzoyl]-2,4-dihydro-1,3-benzoxazin-8-yl]-2-morpholin-4-ylbenzoate and (S)-propylene oxide.

LCMS: m/z 637$[M+H]^+$

HPLC retention time: 0.92 min and 0.96 min (analysis condition A)

Compound 15-4

4-[3-[2,6-Dichloro-4-[1-[(2R)-2-hydroxy-3-methoxypropyl]pyrazol-4-yl]benzoyl]-2,4-dihydro-1,3-benzoxazin-8-yl]-2-morpholin-4-ylbenzoic acid

[Formula 429]

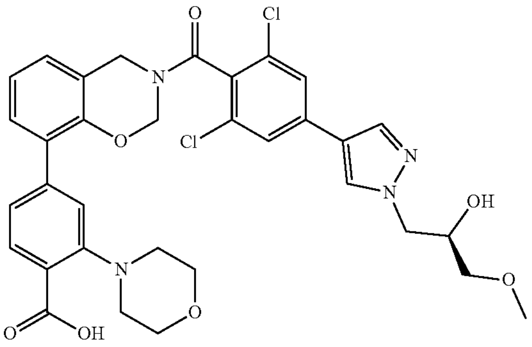

The title compound was synthesized by the same operation as in the third step of compound 15-1 using methyl 4-[3-[2,6-dichloro-4-(1H-pyrazol-4-yl)benzoyl]-2,4-dihydro-1,3-benzoxazin-8-yl]-2-morpholin-4-ylbenzoate and (R)-glycidyl methyl ether.

LCMS: m/z 667$[M+H]^+$

HPLC retention time: 0.91 min and 0.96 min (analysis condition A)

Compound 15-3

4-[3-[2,6-Dichloro-4-[1-[(2R)-2-hydroxy-3-methoxypropyl]pyrazol-4-yl]benzoyl]-2,4-dihydro-1,3-benzoxazin-8-yl]-5-fluoro-2-morpholin-4-ylbenzoic acid First Step Compound PT2

Methyl 4-[3-[2,6-dichloro-4-[1-(oxan-2-yl)pyrazol-4-yl]benzoyl]-2,4-dihydro-1,3-benzoxazin-8-yl]-5-fluoro-2-morpholin-4-ylbenzoate

[Formula 430]

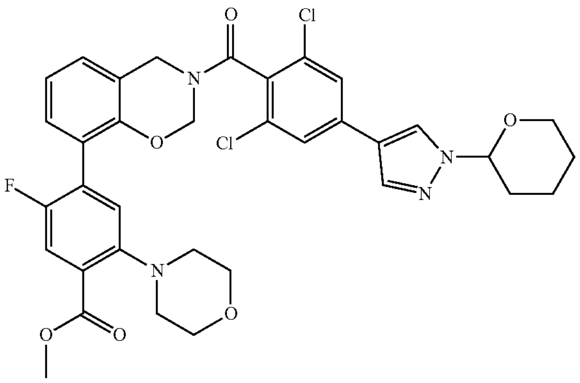

The title compound was synthesized by the same operation as in the fourth step of compound 13-3 using compound B and 1-(oxan-2-yl)-4-(4,4,5,5-tetramethyl-1,3,2-dioxaborolan-2-yl)pyrazole.

LCMS: m/z 695[M+H]$^+$

HPLC retention time: 0.94 min (analysis condition D)

Second Step

Compound PN2

Methyl 4-[3-[2,6-dichloro-4-(1H-pyrazol-4-yl)benzoyl]-2,4-dihydro-1,3-benzoxazin-8-yl]-5-fluoro-2-morpholin-4-ylbenzoate

[Formula 431]

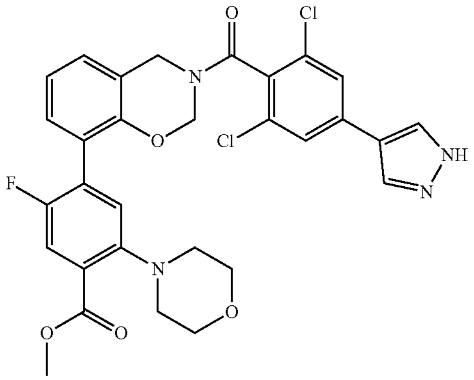

The title compound was synthesized by the same operation as in the second step of compound 15-1 using methyl 4-[3-[2,6-dichloro-4-[1-(oxan-2-yl)pyrazol-4-yl]benzoyl]-2,4-dihydro-1,3-benzoxazin-8-yl]-5-fluoro-2-morpholin-4-ylbenzoate.

LCMS: m/z 611[M+H]$^+$

HPLC retention time: 0.78 min and 0.81 min (analysis condition G)

Third Step

Compound 15-3

4-[3-[2,6-Dichloro-4-[1-[(2R)-2-hydroxy-3-methoxypropyl]pyrazol-4-yl]benzoyl]-2,4-dihydro-1,3-benzoxazin-8-yl]-5-fluoro-2-morpholin-4-ylbenzoic acid

[Formula 432]

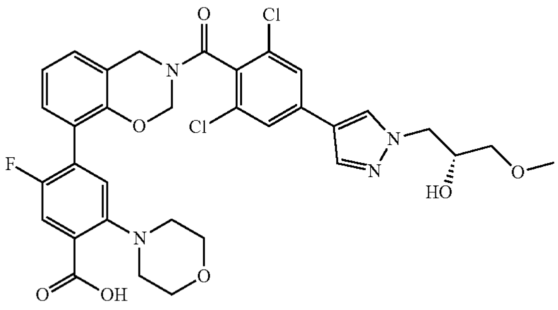

The title compound was synthesized by the same operation as in the third step of compound 15-1 using methyl 4-[3-[2,6-dichloro-4-(1H-pyrazol-4-yl)benzoyl]-2,4-dihydro-1,3-benzoxazin-8-yl]-5-fluoro-2-morpholin-4-ylbenzoate and (R)-glycidyl methyl ether.

LCMS: m/z 685[M+H]$^+$

HPLC retention time: 0.94 min and 0.98 min (analysis condition A)

Compound 16-1

4-[3-[2,6-Dichloro-4-(6-hydroxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AME1

Methyl 4-[3-[2,6-dichloro-4-(6-hydroxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 433]

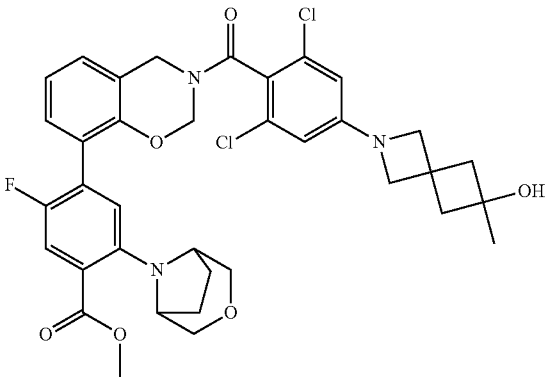

A solution of methyl 4-[3-[2,6-dichloro-4-(6-oxo-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (59.2 mg, 0.0870 mmol) in tetrahydrofuran (1.70 mL) was cooled to −78° C., and a 3 M solution of methyl magnesium chloride in tetrahydrofuran (0.0350 mL, 0.104 mmol) was slowly added thereto. The reaction mixture was stirred at −78° C. for 1 hour, and additionally, a 3 M solution of methyl magnesium chloride in tetrahydrofuran (0.0350 mL, 0.104 mmol) was then slowly added thereto. The reaction mixture was stirred at −78° C. for 1 hour, and a saturated aqueous solution of ammonium chloride was then added thereto, followed by extraction with ethyl acetate. The organic layer was dried over sodium sulfate and concentrated. The residue was purified by silica gel column chromatography ($NH_2$ silica gel, ethyl acetate/dichloromethane) to obtain the title compound (87%, 52.9 mg).

LCMS: m/z 696[M+H]$^+$

HPLC retention time: 0.91 min (analysis condition D)

Second Step

Compound 16-1

4-[3-[2,6-Dichloro-4-(6-hydroxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 434]

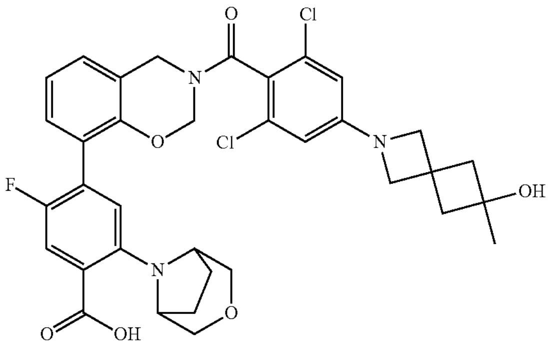

A solution of methyl 4-[3-[2,6-dichloro-4-(6-hydroxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (52.9 mg, 0.0760 mmol) and an 8 M aqueous potassium hydroxide solution (0.0950 mL, 0.759 mmol) in 1-methylpyrrolidin-2-one (0.760 mL) was stirred at 60° C. for 1 hour. An aqueous formic acid solution was added to the reaction mixture, and the mixture was then purified by HPLC (acetonitrile/water, 0.1% formic acid) to obtain the title compound (82%, 42.6 mg).

LCMS: m/z 682[M+H]$^+$

HPLC retention time: 1.45 min (analysis condition B)

Compound 16-2

4-[3-[2,6-Dichloro-4-(6-methoxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AME2

Methyl 4-[3-[2,6-dichloro-4-(6-methoxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 435]

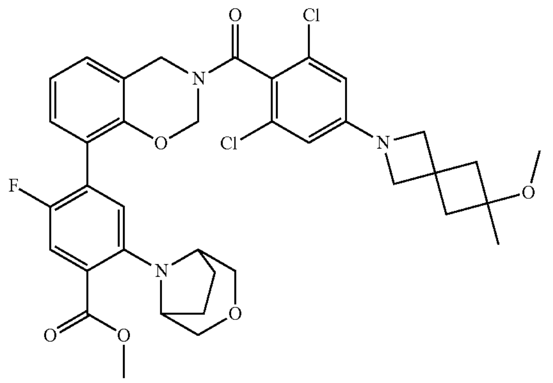

A solution of 4-[3-[2,6-dichloro-4-(6-hydroxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid (20.0 mg, 0.0290 mmol) and sodium hydride (4.22 mg, 0.0880 mmol) in 1-methylpyrrolidin-2-one (0.293 mL) was stirred at 0° C. for 10 minutes. Iodomethane (0.0110 mL, 0.176 mmol) was added to the reaction mixture at 0° C. The reaction mixture was stirred at 0° C. for 6 hours. Then, an aqueous formic acid solution was added thereto, and the mixture was purified by reverse phase column chromatography (acetonitrile/water, 0.1% formic acid) to obtain the title compound (67%, 14.0 mg).

LCMS: m/z 710[M+H]$^+$

HPLC retention time: 1.05 min (analysis condition D)

Second Step

Compound 16-2

4-[3-[2,6-Dichloro-4-(6-methoxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 436]

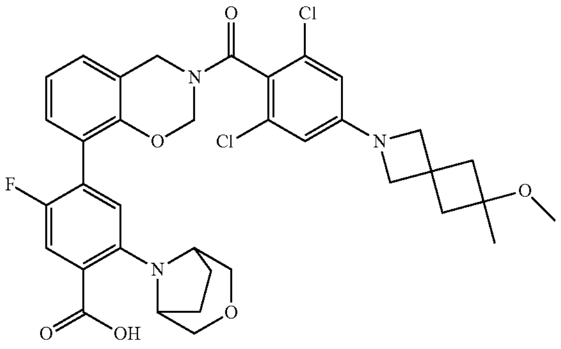

The title compound was synthesized by the same operation as in the second step of compound 16-1 using methyl 4-[3-[2,6-dichloro-4-(6-methoxy-6-methyl-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 696$[M+H]^+$

HPLC retention time: 1.74 min and 1.78 min (analysis condition B)

Compound 16-3

5-[4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)phenyl]-3H-1,3,4-oxadiazol-one First Step Compound BI1

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzohydrazide

[Formula 437]

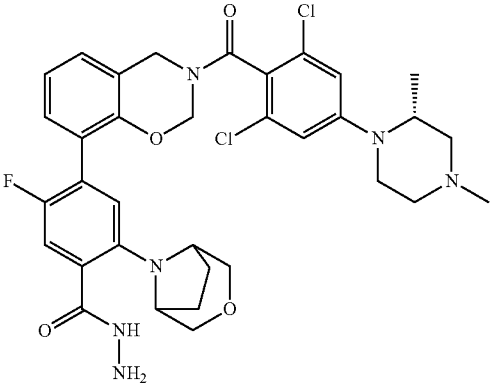

A solution of methyl 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoate (40.0 mg, 0.0590 mmol) and hydrazine monohydrate (0.600 mL, 12.4 mmol) in 2-propanol (0.300 mL) was stirred at 140° C. for 30 minutes under microwave. A saturated aqueous solution of sodium bicarbonate was added to the reaction solution, followed by extraction with ethyl acetate. The organic layer was washed with a saturated aqueous solution of sodium chloride, dried over sodium sulfate, and concentrated to obtain a crude product of the title compound.

LCMS: m/z 683$[M+H]^+$

HPLC retention time: 0.51 min and 0.56 min (analysis condition K)

Second Step

Compound 16-3

5-[4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)phenyl]-3H-1,3,4-oxadiazol-2-one

[Formula 438]

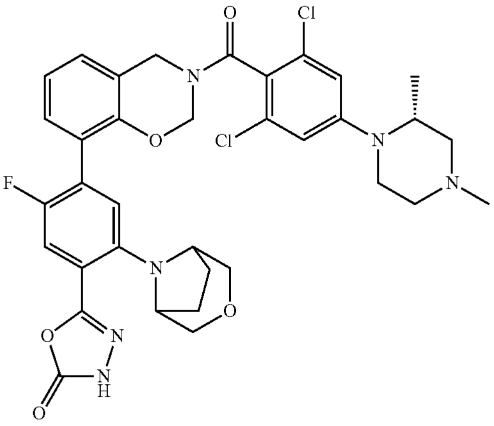

To a solution of 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzohydrazide (54.4 mg, 0.0800 mmol) and triethylamine (0.0222 mL, 0.159 mmol) in dichloromethane (0.796 mL), triphosgene (23.6 mg, 0.0800 mmol) was added. The reaction mixture was stirred at room temperature for 1 hour. Then, an aqueous formic acid solution was added thereto, and the mixture was purified by HPLC (acetonitrile/water, 0.1% formic acid) to obtain the title compound (40%, 22.4 mg).

LCMS: m/z 709$[M+H]^+$

HPLC retention time: 1.10 min and 1.17 min (analysis condition B)

Compound 16-4

[2,6-Dichloro-4-[(2R)-2,4-dimethylpiperazin-1-yl]phenyl]-[8-[2-fluoro-5-(3-oxa-8-azabicyclo[3.2.1]octan-8-yl)-4-(1H-tetrazol-5-yl)phenyl]-2,4-dihydro-1,3-benzoxazin-3-yl]methanone First Step
Compound DP2

4-Bromo-5-fluoro-2-(3-oxa-8-azabicyclo[3.2.1]octan-8-yl)benzonitrile

[Formula 439]

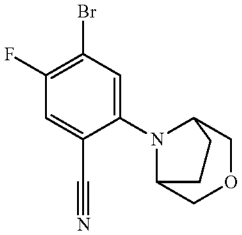

A solution of 4-bromo-2,5-difluorobenzonitrile (250 mg, 1.15 mmol), 3-oxa-8-azabicyclo[3.2.1]octane (260 mg, 2.29 mmol) and N,N-diisopropylethylamine (0.401 mL, 2.29 mmol) in dimethyl sulfoxide (3.80 mL) was stirred at 80° C. for 38 hours. An aqueous formic acid solution was added to the reaction mixture, and the mixture was purified by reverse phase column chromatography (acetonitrile/water, 0.1% formic acid) to obtain the title compound (42%, 151 mg).

LCMS: m/z 311 $[M+H]^+$

HPLC retention time: 0.83 min (analysis condition D)

Second Step
Compound DP3

5-Fluoro-2-(3-oxa-8-azabicyclo[3.2.1]octan-8-yl)-4-(4,4,5,5-tetramethyl-1,3,2-dioxaborolan-2-yl)benzonitrile

[Formula 440]

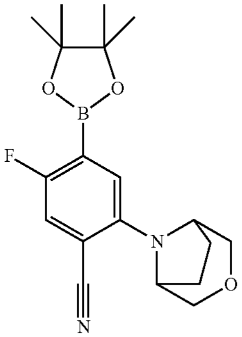

A crude product of the title compound was synthesized by the same operation as in the first step of compound 14-1 using 4-bromo-5-fluoro-2-(3-oxa-8-azabicyclo[3.2.1]octan-8-yl)benzonitrile.

LCMS: m/z 359$[M+H]^+$

HPLC retention time: 0.92 min (analysis condition D)

Third Step
Compound DP4

[4-Cyano-2-fluoro-5-(3-oxa-8-azabicyclo[3.2.1]octan-8-yl)phenyl]boronic acid

[Formula 441]

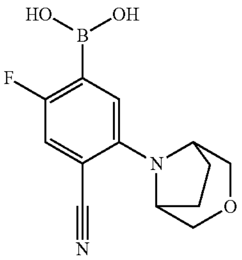

A solution of the crude product of 5-fluoro-2-(3-oxa-8-azabicyclo[3.2.1]octan-8-yl)-4-(4,4,5,5-tetramethyl-1,3,2-dioxaborolan-2-yl)benzonitrile, sodium periodate (428 mg, 2.00 mmol) and ammonium acetate (193 mg, 2.50 mmol) in acetone (2.50 mL) and water (2.50 mL) was stirred at room temperature for 3.5 hours. An aqueous formic acid solution was added to the reaction mixture, and the mixture was purified by reverse phase column chromatography (acetonitrile/water, 0.1% formic acid) to obtain the title compound (79%, 110 mg).

LCMS: m/z 277$[M+H]^+$

HPLC retention time: 0.51 min (analysis condition D)

Fourth Step
Compound BI2

4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzonitrile

[Formula 442]

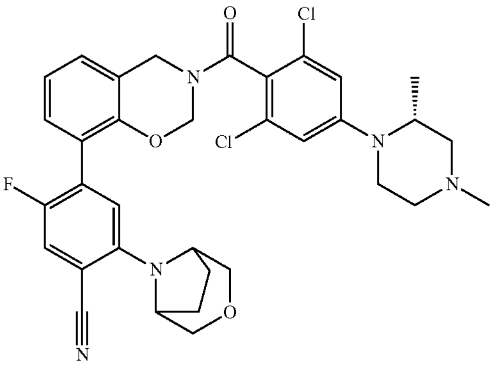

The title compound was synthesized by the same operation as in the third step of compound 13-2 using (8-bromo-2,4-dihydro-1,3-benzoxazin-3-yl)-[2,6-dichloro-4-[(2R)-2,4-dimethylpiperazin-1-yl]phenyl]methanone.

LCMS: m/z 650$[M+H]^+$

HPLC retention time: 0.64 min (analysis condition D)

Fifth Step

Compound 16-4

[2,6-Dichloro-4-[(2R)-2,4-dimethylpiperazin-1-yl]phenyl]-[8-[2-fluoro-5-(3-oxa-8-azabicyclo[3.2.1]octan-8-yl)-4-(1H-tetrazol-5-yl)phenyl]-2,4-dihydro-1,3-benzoxazin-3-yl]methanone

[Formula 443]

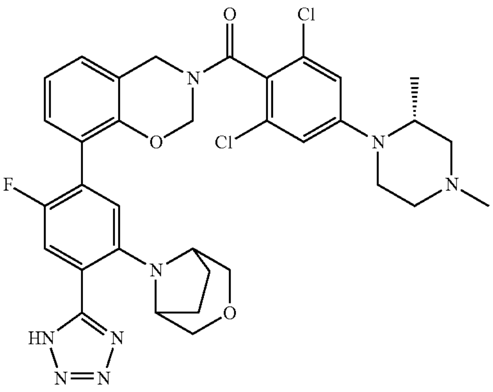

A solution of 4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzonitrile (40.0 mg, 0.061 mmol) and tributyltin azide (0.0840 mL, 0.307 mmol) in chlorobenzene (0.308 mL) was stirred at 130° C. for 14 hours. An aqueous formic acid solution was added to the reaction mixture, and the mixture was purified by HPLC (acetonitrile/water, 0.1% formic acid) to obtain the title compound (71%, 30.1 mg).

LCMS: m/z 693[M+H]$^+$

HPLC retention time: 1.06 min and 1.11 min (analysis condition B)

Compound 16-5

[2,6-Dichloro-4-(1-methylpyrazol-4-yl)phenyl]-[8-[3-morpholin-4-yl-4-(1H-tetrazol-5-yl)phenyl]-2,4-dihydro-1,3-benzoxazin-3-yl]methanone First Step Compound BI4 tert-Butyl 8-(4-cyano-3-morpholin-4-ylphenyl)-2,4-dihydro-1,3-benzoxazine-3-carboxylate

[Formula 444]

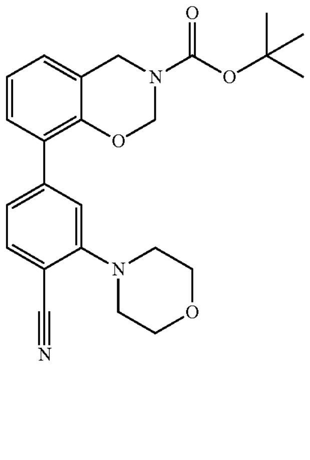

The title compound was synthesized by the same operation as in the third step of compound 13-2 using tert-butyl 8-(4,4,5,5-tetramethyl-1,3,2-dioxaborolan-2-yl)-2,4-dihydro-1,3-benzoxazine-3-carboxylate and 4-bromo-2-morpholin-4-ylbenzonitrile.

LCMS: m/z 422[M+H]$^+$

HPLC retention time: 1.36 min (analysis condition G)

Second Step

Compound BI6

4-[3-[2,6-Dichloro-4-(1-methylpyrazol-4-yl)benzoyl]-2,4-dihydro-1,3-benzoxazin-8-yl]-2-morpholin-4-ylbenzonitrile

[Formula 445]

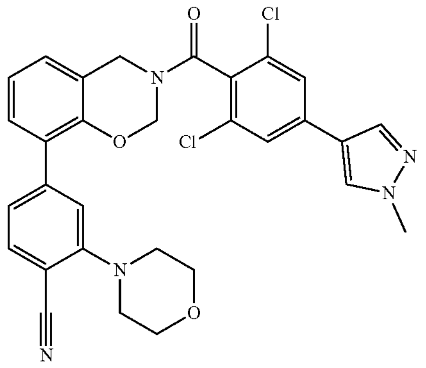

The title compound was synthesized by the same operation as in the fourth step of compound 13-2 using tert-butyl 8-(4-cyano-3-morpholin-4-ylphenyl)-2,4-dihydro-1,3-benzoxazine-3-carboxylate.

LCMS: m/z 574[M+H]$^+$

HPLC retention time: 1.24 min (analysis condition G)

Third Step

Compound 16-5

[2,6-Dichloro-4-(1-methylpyrazol-4-yl)phenyl]-[8-[3-morpholin-4-yl-4-(1H-tetrazol-5-yl)phenyl]-2,4-dihydro-1,3-benzoxazin-3-yl]methanone

[Formula 446]

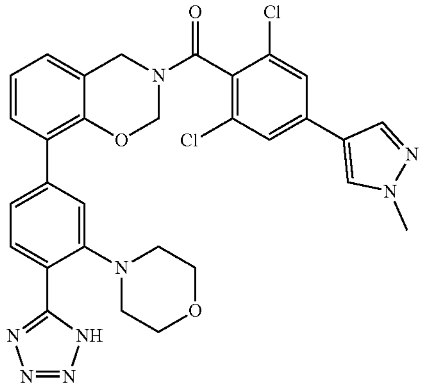

The title compound was synthesized by the same operation as in the fifth step of compound 16-4 using 4-[3-[2,6-dichloro-4-(1-methylpyrazol-4-yl)benzoyl]-2,4-dihydro-1,3-benzoxazin-8-yl]-2-morpholin-4-ylbenzonitrile.

LCMS: m/z 617[M+H]$^+$

HPLC retention time: 1.04 min and 1.06 min (analysis condition A)

Compound 16-6

4-[3-[2,6-Dichloro-4-(3-methoxyazetidin-1-yl)benzoyl]-2,4-dihydro-1,3-benzoxazin-8-yl]-5-fluoro-N-methylsulfonyl-2-(3-oxa-8-azabicyclo[3.2.1]octan-8-yl)benzamide

[Formula 447]

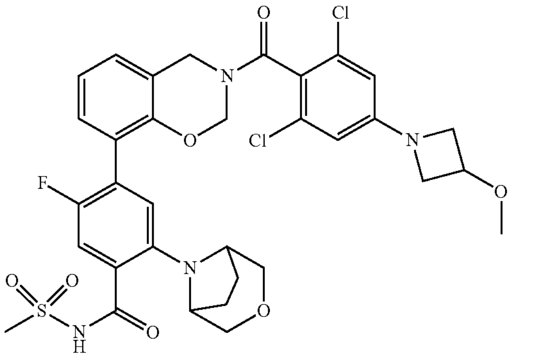

A solution of 4-[3-[2,6-dichloro-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoic acid (35.0 mg, 0.0540 mmol) and carbonyldiimidazole (26.5 mg, 0.163 mmol) in N,N-dimethylformamide (0.272 mL) was stirred at room temperature for 2 hours. Then, methanesulfonamide (31.1 mg, 0.327 mmol) and 1,8-diazabicyclo[5.4.0]-7-undecene (0.0246 mL, 0.163 mmol) were added to the reaction mixture, and the mixture was stirred at 60° C. for 1 hour. An aqueous formic acid solution was added to the reaction mixture, and the mixture was purified by HPLC (acetonitrile/water, 0.1% formic acid) to obtain the title compound (71%, 32.1 mg).

LCMS: m/z 719[M+H]$^+$

HPLC retention time: 1.61 min and 1.63 min (analysis condition B)

Compound 16-7

4-[3-[2,6-Dichloro-4-(6,6-difluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound AF1

Methyl 4-[3-[2,6-dichloro-4-(6,6-difluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 448]

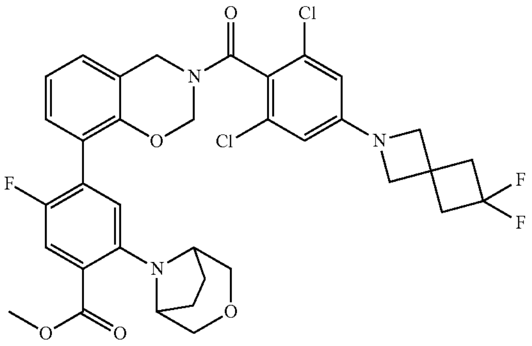

To a solution of methyl 4-[3-[2,6-dichloro-4-(6-oxo-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (40.0 mg, 0.0590 mmol) in dichloromethane (1.70 mL), Deoxo-Fluor (0.0433 mL, 0.235 mmol) was added at 0° C. The reaction mixture was stirred overnight at room temperature and then concentrated. An aqueous formic acid solution was added to the residue, and the mixture was purified by HPLC (acetonitrile/water, 0.1% formic acid) to obtain the title compound (69%, 28.5 mg).

LCMS: m/z 702[M+H]$^+$

HPLC retention time: 1.04 min (analysis condition D)

Second Step
Compound 16-7

4-[3-[2,6-Dichloro-4-(6,6-difluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 449]

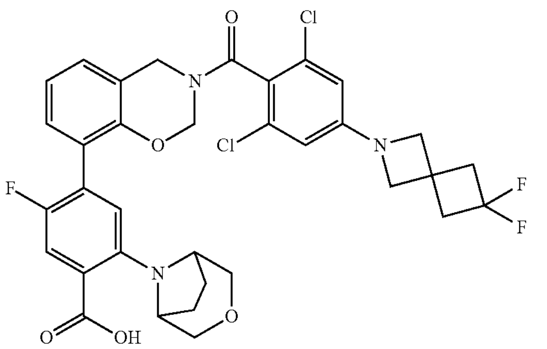

A solution of methyl 4-[3-[2,6-dichloro-4-(6,6-difluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (28.5 mg, 0.0410 mmol) and an 8 M aqueous potassium hydroxide solution (0.0254 mL, 0.203 mmol) in 1,4-dioxane (0.304 mL) and methanol (0.101 mL) was stirred at 60° C. for 1 hour. An aqueous formic acid solution was added to the reaction mixture, and the mixture was purified by HPLC (acetonitrile/water, 0.1% formic acid) to obtain the title compound (61%, 17.0 mg).

LCMS: m/z 688[M+H]$^+$

HPLC retention time: 1.73 min and 1.75 min (analysis condition B)

Compound 16-8

4-[3-[2,6-Dichloro-4-(6-fluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid First Step
Compound AF2

Methyl 4-[3-[2,6-dichloro-4-(6-fluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate

[Formula 450]

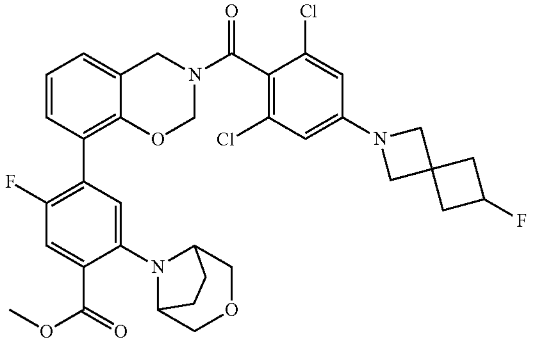

To a solution of methyl 4-[3-[2,6-dichloro-4-(6-hydroxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (50.0 mg, 0.0730 mmol) in dichloromethane (1.47 mL), Deoxo-Fluor (0.0270 mL, 0.147 mmol) was added at 0° C. The reaction mixture was stirred overnight at room temperature and then concentrated. An aqueous formic acid solution was added to the residue, and the mixture was purified by HPLC (acetonitrile/water, 0.1% formic acid) to obtain the title compound (25%, 12.3 mg).

LCMS: m/z 684[M+H]$^+$

HPLC retention time: 1.04 min (analysis condition G)

Second Step

Compound 16-8

4-[3-[2,6-Dichloro-4-(6-fluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 451]

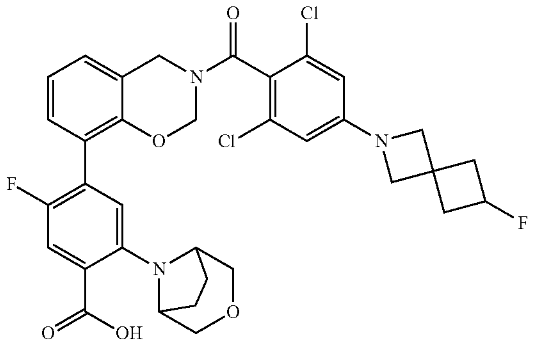

The title compound was synthesized by the same operation as in the second step of compound 16-7 using methyl 4-[3-[2,6-dichloro-4-(6-fluoro-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 670[M+H]$^+$

HPLC retention time: 1.72 min and 1.74 min (analysis condition B)

Compound 16-9

4-[3-[2,6-Dichloro-4-(2-methyltetrazol-5-yl)benzoyl]-2,4-dihydro-1,3-benzoxazin-8-yl]-5-fluoro-2-(3-oxa-8-azabicyclo[3.2.1]octan-8-yl)benzoic acid First Step
Compound CN1

Methyl 4-[3-(2,6-dichloro-4-cyanobenzoyl)-2,4-dihydro-1,3-benzoxazin-8-yl]-5-fluoro-2-(3-oxa-8-azabicyclo[3.2.1]octan-8-yl)benzoate

[Formula 452]

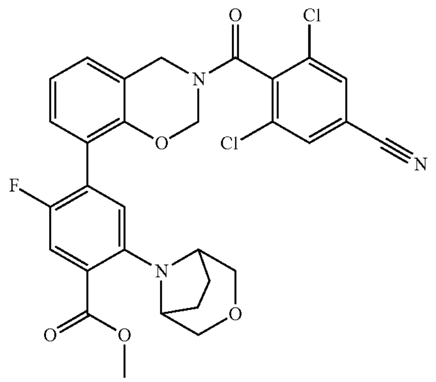

A solution of compound A (50.0 mg, 0.0770 mmol), zinc cyanide (27.1 mg, 0.231 mmol) and [1,1'-bis(diphenylphosphino)ferrocene]palladium(II) dichloride dichloromethane adduct (12.6 mg, 0.0150 mmol) in N,N-dimethylformamide (0.769 mL) was stirred overnight at 100° C. A saturated aqueous solution of sodium bicarbonate was added to the reaction mixture, followed by extraction with ethyl acetate. The organic layer was dried over sodium sulfate and concentrated. The residue was purified by HPLC (acetonitrile/water, 0.1% formic acid) to obtain the title compound (72%, 33.0 mg).

LCMS: m/z 596[M+H]$^+$

HPLC retention time: 0.92 min and 0.94 min (analysis condition D)

Second Step
Compound CN2

Methyl 4-[3-[2,6-dichloro-4-(2H-tetrazol-5-yl)benzoyl]-2,4-dihydro-1,3-benzoxazin-8-yl]-5-fluoro-2-(3-oxa-8-azabicyclo[3.2.1]octan-8-yl)benzoate

[Formula 453]

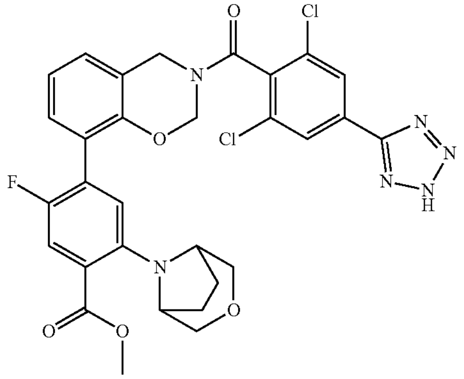

A solution of methyl 4-[3-(2,6-dichloro-4-cyanobenzoyl)-2,4-dihydro-1,3-benzoxazin-8-yl]-5-fluoro-2-(3-oxa-8-azabicyclo[3.2.1]octan-8-yl)benzoate (33.0 mg, 0.0550 mmol), sodium azide (5.40 mg, 0.0830 mmol) and copper(I) iodide (1.05 mg, 0.00553 mmol) in N,N-dimethylformamide (0.769 mL) was stirred at 100° C. for 2 hours. An aqueous formic acid solution and methanol were added to the reaction mixture, and the mixture was filtered and purified by HPLC (acetonitrile/water, 0.1% formic acid) to obtain the title compound (23%, 8.00 mg).

LCMS: m/z 639[M+H]$^+$

HPLC retention time: 0.83 min and 0.86 min (analysis condition D)

Third Step
Compound 16-9

4-[3-[2,6-Dichloro-4-(2-methyltetrazol-5-yl)benzoyl]-2,4-dihydro-1,3-benzoxazin-8-yl]-5-fluoro-2-(3-oxa-8-azabicyclo[3.2.1]octan-8-yl)benzoic acid

[Formula 454]

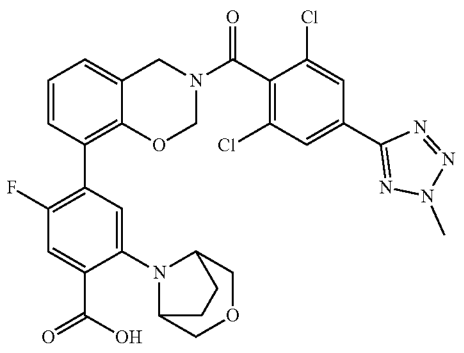

A solution of methyl 4-[3-[2,6-dichloro-4-(2H-tetrazol-5-yl)benzoyl]-2,4-dihydro-1,3-benzoxazin-8-yl]-5-fluoro-2-(3-oxa-8-azabicyclo[3.2.1]octan-8-yl)benzoate (8.00 mg, 0.0130 mmol), iodomethane (0.00117 mL, 0.0190 mmol) and cesium carbonate (6.11 mg, 0.0190 mmol) in N,N-dimethylformamide (0.125 mL) was stirred at room temperature for 2 hours. An 8 M aqueous sodium hydroxide solution (0.00782 mL, 0.0630 mmol) and methanol were added to the reaction mixture, and the mixture was stirred at 60° C. for 30 minutes. The reaction mixture was purified by HPLC (acetonitrile/water, 0.1% formic acid) to obtain the title compound (60%, 4.80 mg).

LCMS: m/z 639[M+H]$^+$

HPLC retention time: 1.47 min and 1.48 min (analysis condition B)

Compound 16-10

4-[3-(2,6-Dichloro-4-propan-2-ylsulfanylbenzoyl)-2,4-dihydro-1,3-benzoxazin-8-yl]-2-morpholin-4-ylbenzoic acid First Step
Compound SE1

Methyl 4-[3-[2,6-dichloro-4-[3-(2-ethylhexaoxy)-3-oxopropyl]sulfanylbenzoyl]-2,4-dihydro-1,3-benzoxazin-8-yl]-2-morpholin-4-ylbenzoate

[Formula 455]

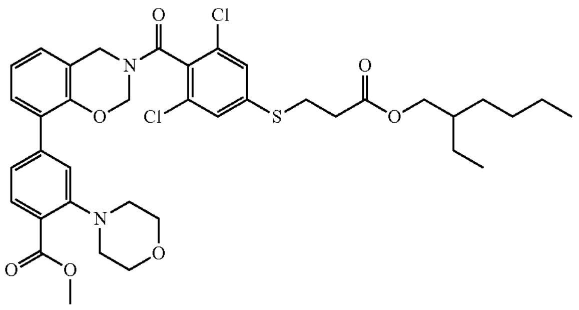

A solution of compound E (30.0 mg, 0.0490 mmol), 2-ethylhexyl 3-mercaptopropionate (0.0230 mL, 0.0990 mmol), XantPhos Pd G3 (4.69 mg, 0.00495 mmol) and N,N-diisopropylethylamine (0.0250 mL, 0.148 mmol) in toluene (1.00 mL) was stirred overnight at 90° C. The reaction mixture was purified by silica gel column chromatography (ethyl acetate/hexane) to obtain the title compound (94%, 34.7 mg).

LCMS: m/z 743[M+H]$^+$

HPLC retention time: 1.66 min (analysis condition G)

Second Step
Compound 16-10

4-[3-(2,6-Dichloro-4-propan-2-ylsulfanylbenzoyl)-2,4-dihydro-1,3-benzoxazin-8-yl]-2-morpholin-4-ylbenzoic acid

[Formula 456]

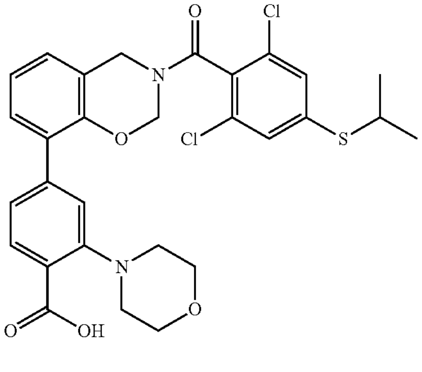

A solution of methyl 4-[3-[2,6-dichloro-4-[3-(2-ethylhexaoxy)-3-oxopropyl]sulfanylbenzoyl]-2,4-dihydro-1,3-benzoxazin-8-yl]-2-morpholin-4-ylbenzoate (10.0 mg, 0.0130 mmol) and 2-bromopropane (0.00379 mL, 0.040 mmol) in tetrahydrofuran (0.500 mL) was cooled to −78° C. Then, a 1.7 M solution of potassium 2-methylbutan-2-olate in tetrahydrofuran (0.0400 mL, 0.0670 mmol) was added thereto, and the mixture was stirred at −78° C. for 30 minutes. 2-Bromopropane (0.00379 mL, 0.040 mmol) was further added to the reaction mixture, and the mixture was stirred overnight at room temperature. Tetrahydrofuran (0.500 mL), methanol (0.500 mL) and a 5 M aqueous potassium hydroxide solution (0.106 mL, 0.532 mmol) were added to the reaction mixture, and the mixture was stirred at room temperature for 2 hours. An aqueous formic acid solution was added to the reaction mixture, and the mixture was then purified by reverse phase column chromatography (acetonitrile/water, 0.1% formic acid) to obtain the title compound (46%, 3.60 mg).

LCMS: m/z 587[M+H]$^+$

HPLC retention time: 1.23 min and 1.26 min (analysis condition A)

Compound 16-11

4-[3-[2,6-Dichloro-4-[1-(2-methoxyethyl)piperidin-4-yl]benzoyl]-2,4-dihydro-1,3-benzoxazin-8-yl]-5-fluoro-2-morpholin-4-ylbenzoic acid First Step
Compound NA1 tert-Butyl 4-[3,5-dichloro-4-[8-(2-fluoro-4-methoxycarbonyl-5-morpholin-4-ylphenyl)-2,4-dihydro-1,3-benzoxazine-3-carbonyl]phenyl]piperidine-1-carboxylate

[Formula 457]

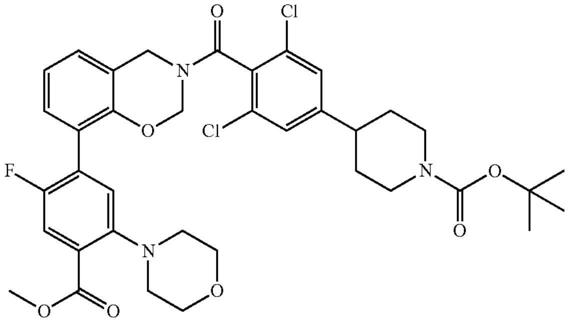

To a suspension of zinc (289 mg, 4.42 mmol) in N,N-dimethylacetamide (0.589 mL), chlorotrimethylsilane (0.0492 mL, 0.389 mmol) and 1,2-dibromoethane (0.0336 mL, 0.389 mmol) were slowly added at room temperature. The reaction mixture was stirred at room temperature for 15 minutes. Then, a solution of tert-butyl 4-iodopiperidine-1-carboxylate (1.10 g, 3.54 mmol) in N,N-dimethylacetamide (1.77 mL) was added thereto, and the mixture was stirred at room temperature for 1 hour to obtain a solution of a crude product of iodo-[1-[(2-methylpropan-2-yl)oxycarbonyl]piperidin-4-yl]zinc in N,N-dimethylacetamide. The solution of iodo-[1-[(2-methylpropan-2-yl)oxycarbonyl]piperidin-4-yl]zinc in N,N-dimethylacetamide (0.615 mL) was added to a solution of compound B (192 mg, 0.308 mmol), copper(I) iodide (29.3 mg, 0.154 mmol), and [1,1'-bis(diphenylphosphino)ferrocene]palladium(II) dichloride dichloromethane adduct (25.1 mg, 0.0310 mmol) in N,N-dimethylacetamide (3.08 mL), and the mixture was stirred at 90° C. for 1 hour. The reaction mixture was purified by reverse phase column chromatography (acetonitrile/water, 0.1% formic acid) to obtain the title compound (72%, 203 mg).

LCMS: m/z 728[M+H]$^+$

HPLC retention time: 1.45 min (analysis condition G)

Second Step

Compound 16-11

4-[3-[2,6-Dichloro-4-[1-(2-methoxyethyl)piperidin-4-yl]benzoyl]-2,4-dihydro-1,3-benzoxazin-8-yl]-5-fluoro-2-morpholin-4-ylbenzoic acid

[Formula 458]

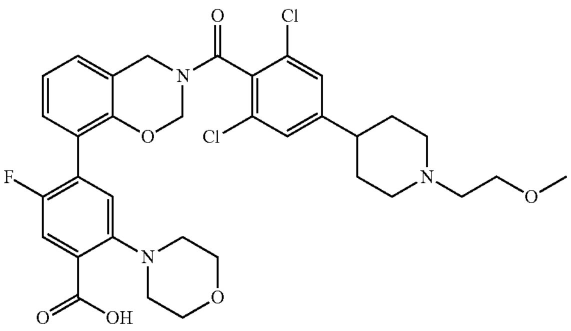

To tert-butyl 4-[3,5-dichloro-4-[8-(2-fluoro-4-methoxycarbonyl-5-morpholin-4-ylphenyl)-2,4-dihydro-1,3-benzoxazine-3-carbonyl]phenyl]piperidine-1-carboxylate (30.0 mg, 0.041 mmol), a 4 M solution of hydrochloric acid in 1,4-dioxane (0.103 mL, 0.412 mmol) was added. The reaction mixture was stirred at room temperature for 1 hour and then concentrated, and the obtained residue was diluted with N,N-dimethylformamide (0.412 mL). 2-Bromoethyl methyl ether (0.103 mL, 0.412 mmol) and N,N-diisopropylethylamine (31.9 mg, 0.247 mmol) were added thereto. The reaction mixture was stirred at 100° C. for 1 hour, and 1,4-dioxane (0.205 mL), dimethyl sulfoxide (0.205 mL), and an aqueous sodium hydroxide solution were then added thereto. An aqueous formic acid solution was added to the reaction mixture, and the mixture was then purified by HPLC (acetonitrile/water, 0.1% formic acid) to obtain the title compound (22%, 6.00 mg).

LCMS: m/z 672[M+H]$^+$

HPLC retention time: 0.79 min and 0.83 min (analysis condition A)

Compound 16-12

4-[3-[2,6-Dichloro-4-(oxetan-3-yl)benzoyl]-2,4-dihydro-1,3-benzoxazin-8-yl]-5-fluoro-2-morpholin-4-ylbenzoic acid First Step Compound OX1

Methyl 4-[3-[2,6-dichloro-4-(oxetan-3-yl)benzoyl]-2,4-dihydro-1,3-benzoxazin-8-yl]-5-fluoro-2-morpholin-4-ylbenzoate

[Formula 459]

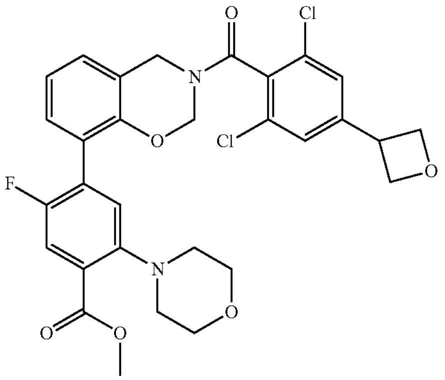

A solution of compound B (200 mg, 0.320 mmol), 3-bromooxetane (0.0489 mL, 0.641 mmol), nickel iodide (20.2 mg, 0.0640 mmol), 4,4'-di-tert-butyl-2,2'-bipyridine (17.2 mg, 0.0640 mmol), 4-ethylpyridine (0.0364 mL, 0.320 mmol), magnesium chloride (30.5 mg, 0.320 mmol) and manganese (35.2 mg, 0.641 mmol) in N,N-dimethylacetamide (2.00 mL) was stirred at 65° C. for 2 hours. The reaction mixture was cooled to room temperature. Then, an aqueous formic acid solution and dimethyl sulfoxide were added thereto, and the mixture was purified by HPLC (acetonitrile/water, 0.1% formic acid) to obtain the title compound (8%, 15.0 mg).

LCMS: m/z 601 [M+H]$^+$

HPLC retention time: 0.86 min (analysis condition D)

Second Step

Compound 16-12

4-[3-[2,6-Dichloro-4-(oxetan-3-yl)benzoyl]-2,4-dihydro-1,3-benzoxazin-8-yl]-5-fluoro-2-morpholin-4-ylbenzoic acid

[Formula 460]

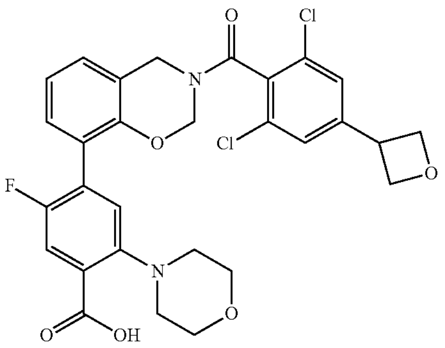

The title compound was synthesized by the same operation as in the second step of compound 16-1 using methyl 4-[3-[2,6-dichloro-4-(oxetan-3-yl)benzoyl]-2,4-dihydro-1,3-benzoxazin-8-yl]-5-fluoro-2-morpholin-4-ylbenzoate.

LCMS: m/z 587[M+H]+

HPLC retention time: 1.34 min and 1.36 min (analysis condition B)

Compound 16-13

4-[3-[2,6-Dichloro-4-[(2R)-2,4-dimethylpiperazin-1-yl]benzoyl]-2,4-dihydro-1,3-benzoxazin-8-yl]-5-fluoro-2-[methyl-[(3R)-oxolan-3-yl]amino]benzoic acid First Step Compound LN5

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-[[(3R)-oxolan-3-yl]amino]benzoate

[Formula 461]

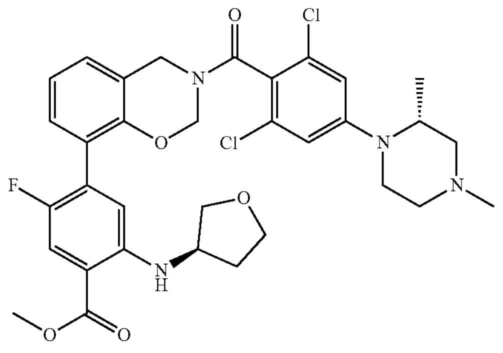

A solution of compound Y (200 mg, 0.320 mmol), (R)-tetrahydrofuran-3-amine (0.00970 mL, 0.111 mmol), potassium carbonate (30.7 mg, 0.222 mmol) and Xantphos Pd G4 (17.2 mg, 0.0640 mmol) in 1,4-dioxane (0.555 mL) was stirred at 110° C. for 3 hours. The reaction mixture was purified by reverse phase column chromatography (acetonitrile/water, 0.05% trifluoroacetic acid) to obtain the title compound (91%, 39.0 mg).

LCMS: m/z 657[M+H]+

HPLC retention time: 0.67 min (analysis condition D)

Second Step

Compound LN6

Methyl 4-[3-[2,6-dichloro-4-[(2R)-2,4-dimethylpiperazin-1-yl]benzoyl]-2,4-dihydro-1,3-benzoxazin-8-yl]-5-fluoro-2-[methyl-[(3R)-oxolan-3-yl]amino]benzoate 2,2,2-trifluoroacetate

[Formula 462]

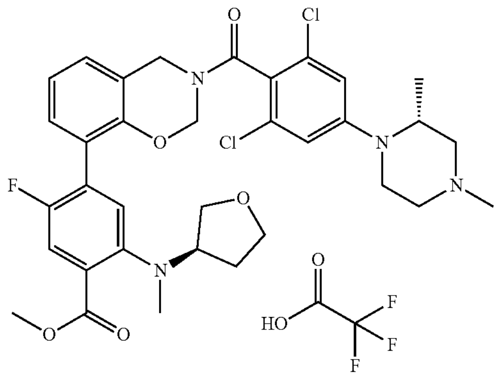

A solution of methyl 4-[3-[2,6-dichloro-4-[(2R)-2,4-dimethylpiperazin-1-yl]benzoyl]-2,4-dihydro-1,3-benzoxazin-8-yl]-5-fluoro-2-[[(3R)-oxolan-3-yl]amino]benzoate (12.0 mg, 0.0180 mmol) in 1,3-dimethyl-2-imidazolidinone (0.0910 mL) and tetrahydrofuran (0.0910 mL) was cooled to 0° C., and a 20% solution of lithium diisopropylamide in tetrahydrofuran/ethylbenzene/heptane (0.0183 mL, 0.027 mmol) was then added thereto. The reaction mixture was stirred at 0° C. for 20 minutes, and a 1 M solution of potassium bis(trimethylsilyl)amide in toluene (0.0274 mL, 0.0270 mmol) and iodomethane (0.00227 mL, 0.036 mmol) were then added thereto. The reaction mixture was stirred at 0° C. for 20 minutes and then further stirred at room temperature for 1 hour. The reaction mixture was purified by reverse phase column chromatography (acetonitrile/water, 0.05% trifluoroacetic acid) to obtain the title compound (66%, 9.40 mg).

LCMS: m/z 671[M+H]+

HPLC retention time: 0.66 min (analysis condition D)

Compound 16-13

4-[3-[2,6-Dichloro-4-[(2R)-2,4-dimethylpiperazin-1-yl]benzoyl]-2,4-dihydro-1,3-benzoxazin-8-yl]-5-fluoro-2-[methyl-[(3R)-oxolan-3-yl]amino]benzoic acid

[Formula 463]

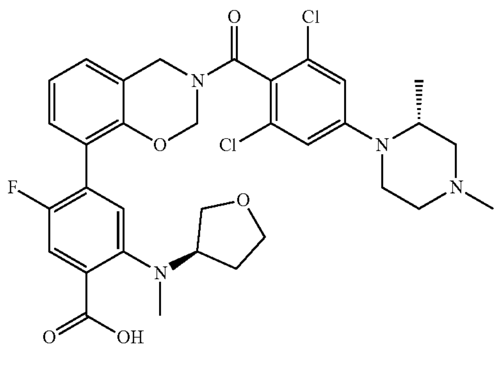

The title compound was synthesized by the same operation as in the second step of compound 16-1 using methyl 4-[3-[2,6-dichloro-4-[(2R)-2,4-dimethylpiperazin-1-yl]benzoyl]-2,4-dihydro-1,3-benzoxazin-8-yl]-5-fluoro-2-[methyl-[(3R)-oxolan-3-yl]amino]benzoate 2,2,2-trifluoroacetate.

LCMS: m/z 657[M+H]$^+$

HPLC retention time: 0.94 min and 1.00 min (analysis condition B)

Compound 16-14

4-[3-[2,6-Dichloro-4-(1-methylpyrazol-4-yl)benzoyl]-2,4-dihydro-1,3-benzoxazin-8-yl]-5-fluoro-2-[methyl-(3-methyloxetan-3-yl)amino]benzoic acid First Step Compound LN7

Methyl 4-[3-[2,6-dichloro-4-(1-methylpyrazol-4-yl)benzoyl]-2,4-dihydro-1,3-benzoxazin-8-yl]-5-fluoro-2-[(3-methyloxetan-3-yl)amino]benzoate

[Formula 464]

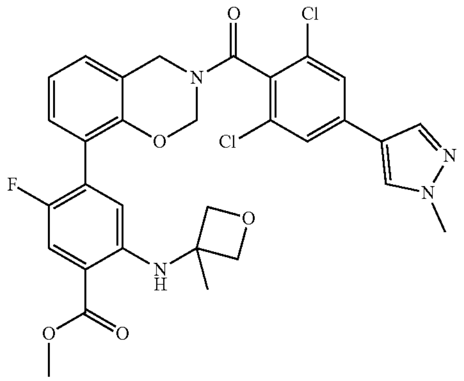

The title compound was synthesized by the same operation as in the first step of compound 16-13 using compound Y and 3-methyloxetan-3-amine.

LCMS: m/z 625[M+H]$^+$

HPLC retention time: 0.93 min (analysis condition B)

Second Step

Compound LN8

Methyl 4-[3-[2,6-dichloro-4-(1-methylpyrazol-4-yl)benzoyl]-2,4-dihydro-1,3-benzoxazin-8-yl]-5-fluoro-2-[methyl-(3-methyloxetan-3-yl)amino]benzoate

[Formula 465]

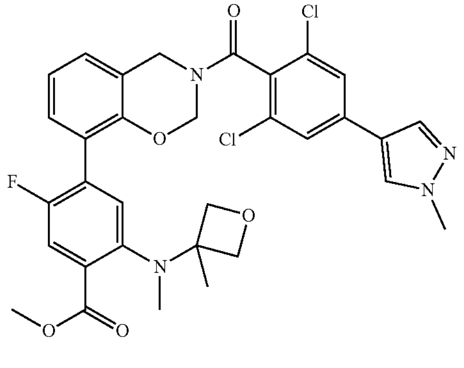

To a solution of methyl 4-[3-[2,6-dichloro-4-(1-methylpyrazol-4-yl)benzoyl]-2,4-dihydro-1,3-benzoxazin-8-yl]-5-fluoro-2-[(3-methyloxetan-3-yl)amino]benzoate (31.4 mg, 0.050 mmol) in 1,3-dimethyl-2-imidazolidinone (0.0910 mL), sodium hydride (21.9 mg, 0.502 mmol) was added, and the mixture was stirred at room temperature for 15 minutes. Then, iodomethane (0.0469 mL, 0.753 mmol) was added thereto. The reaction mixture was stirred at room temperature for 20 minutes. Sodium hydride (21.9 mg, 0.502 mmol) and iodomethane (0.0469 mL, 0.753 mmol) were further added to the reaction mixture, and the mixture was then stirred at 60° C. for 1 hour to obtain a crude product of the title compound.

LCMS: m/z 639[M+H]$^+$

HPLC retention time: 0.90 min and 0.93 min (analysis condition D)

Third Step

Compound 16-14

4-[3-[2,6-Dichloro-4-(1-methylpyrazol-4-yl)benzoyl]-2,4-dihydro-1,3-benzoxazin-8-yl]-5-fluoro-2-[methyl-(3-methyloxetan-3-yl)amino]benzoic acid

[Formula 466]

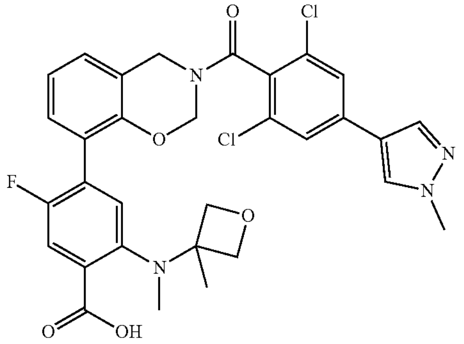

The title compound was synthesized by the same operation as in the second step of compound 16-13 using the crude product of methyl 4-[3-[2,6-dichloro-4-(1-methylpyrazol-4-yl)benzoyl]-2,4-dihydro-1,3-benzoxazin-8-yl]-5-fluoro-2-[methyl-(3-methyloxetan-3-yl)amino]benzoate.

LCMS: m/z 625[M+H]$^+$

HPLC retention time: 1.38 min and 1.40 min (analysis condition B)

Compound 16-15

4-[3-[2,6-Dichloro-4-(5,8-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid First Step

[Formula 467]

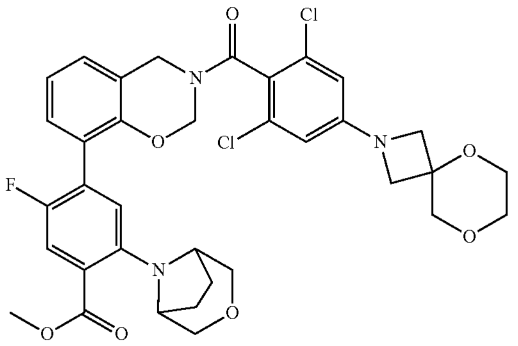

To a solution of methyl 4-[3-[2,6-dichloro-4-[3-hydroxy-3-(hydroxymethyl)azetidin-1-yl]benzoyl]-2,4-dihydro-1,3-benzoxazin-8-yl]-5-fluoro-2-(3-oxa-8-azabicyclo[3.2.1]octan-8-yl)benzoate (23.0 mg, 0.0340 mmol) in 1,2-dichloroethane (0.271 mL, 3.420 mmol), an aqueous sodium hydroxide solution (0.342 mL, 1.710 mmol) and tetrabutylammonium bromide (3.31 mg, 0.0103 mmol) were added. The reaction mixture was stirred at room temperature for 2 hours, at 60° C. for 24 hours, and at 70° C. for 24 hours. A saturated aqueous solution of ammonium chloride was added to the reaction mixture, followed by extraction with ethyl acetate. The organic layer was washed with a saturated aqueous solution of sodium bicarbonate and a saturated aqueous solution of sodium chloride, followed by passing through a phase separator. The organic layer was concentrated to obtain a crude product of the title compound.

LCMS: m/z 698[M+H]$^+$

HPLC retention time: 0.93 min (analysis condition D)

Second Step

Compound 16-15

4-[3-[2,6-Dichloro-4-(5,8-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 482]

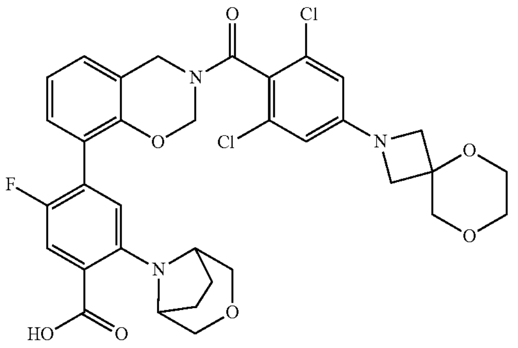

The title compound was synthesized by the same operation as in the second step of compound 16-13 using the crude product of methyl 4-[3-[2,6-dichloro-4-(5,8-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate.

LCMS: m/z 684[M+H]$^+$

HPLC retention time: 1.49 min (analysis condition B)

Compound 16-16

4-[3-[2,6-Dichloro-4-(3-cyano-3-fluoroazetidin-1-yl)benzoyl]-2,4-dihydro-1,3-benzoxazin-8-yl]-5-fluoro-2-(3-oxa-8-azabicyclo[3.2.1]octan-8-yl)benzoic acid First Step Compound INT4

4-[3-(4-Bromo-2,6-dichlorobenzoyl)-2,4-dihydro-1,3-benzoxazin-8-yl]-5-fluoro-2-(3-oxa-8-azabicyclo[3.2.1]octan-8-yl)benzoic acid

[Formula 469]

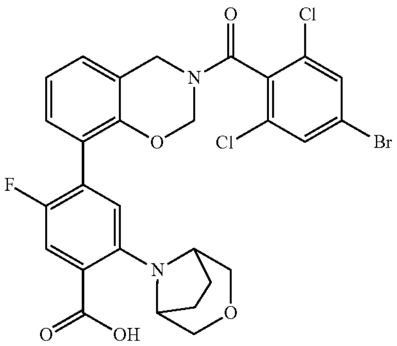

A solution of compound A (80.0 mg, 0.123 mmol) and an 8 M aqueous potassium hydroxide solution (0.0770 mL, 0.615 mmol) in 1,4-dioxane (0.308 mL) and methanol (0.923 mL) was stirred at room temperature for 1 hour. The reaction mixture was concentrated and then diluted with acetonitrile and water. 1 M hydrochloric acid was added thereto, and the mixture was filtered to obtain the title compound (67%, 52.2 mg).

LCMS: m/z 635[M+H]$^+$

HPLC retention time: 0.85 min and 0.87 min (analysis condition D)

Second Step

Compound AMD1

4-[3-[4-(3-Carbamoyl-3-fluoroazetidin-1-yl)-2,6-dichlorobenzoyl]-2,4-dihydro-1,3-benzoxazin-8-yl]-5-fluoro-2-(3-oxa-8-azabicyclo[3.2.1]octan-8-yl) benzoic acid

[Formula 470]

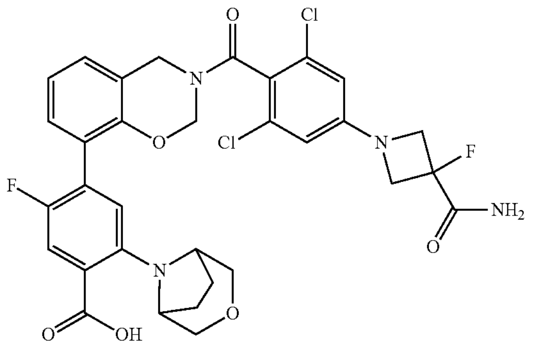

To a solution of tert-butyl 3-cyano-3-fluoroazetidine-1-carboxylate (32.0 mg, 0.160 mmol) in dichloromethane (0.800 mL), trifluoroacetic acid (0.247 mL, 3.20 mmol) was added. The reaction mixture was stirred at room temperature for 1 hour and then concentrated. To a solution of the obtained residue in 1-methylpyrrolidin-2-one (0.629 mL), 4-[3-(4-bromo-2,6-dichlorobenzoyl)-2,4-dihydro-1,3-benzoxazin-8-yl]-5-fluoro-2-(3-oxa-8-azabicyclo[3.2.1]octan-8-yl)benzoic acid (40.0 mg, 0.0630 mmol), rac-BINAP Pd G4 (6.33 mg, 0.00629 mmol) and cesium carbonate (102 mg, 0.314 mmol) were added. The reaction mixture was stirred at 100° C. for 1 hour. Then, an aqueous formic acid solution was added thereto, and the mixture was purified by reverse phase column chromatography (acetonitrile/water, 0.1% formic acid) to obtain the title compound (59%, 24.8 mg).

LCMS: m/z 673[M+H]$^+$

HPLC retention time: 0.67 min and 0.69 min (analysis condition D)

Third Step

Compound 16-16

4-[3-[2,6-Dichloro-4-(3-cyano-3-fluoroazetidin-1-yl) benzoyl]-2,4-dihydro-1,3-benzoxazin-8-yl]-5-fluoro-2-(3-oxa-8-azabicyclo[3.2.1]octan-8-yl)benzoic acid

[Formula 471]

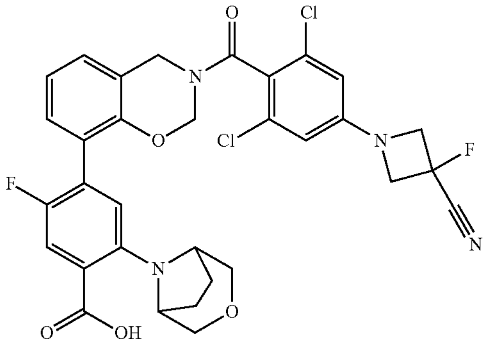

A solution of 4-[3-[4-(3-carbamoyl-3-fluoroazetidin-1-yl)-2,6-dichlorobenzoyl]-2,4-dihydro-1,3-benzoxazin-8-yl]-5-fluoro-2-(3-oxa-8-azabicyclo[3.2.1]octan-8-yl)benzoic acid (20.0 mg, 0.0300 mmol) and a Burgess reagent (35.4 mg, 0.148 mmol) in dichloromethane (0.297 mL) was stirred at room temperature for 5 hours. After concentration of the reaction mixture, an aqueous formic acid solution and 1,4-dioxane were added to the residue, and the mixture was purified by HPLC (acetonitrile/water, 0.1% formic acid) to obtain the title compound (28%, 5.40 mg).

LCMS: m/z 655[M+H]$^+$

HPLC retention time: 1.51 min (analysis condition B)

Compound 16-17

4-[3-[2,6-Dichloro-4-[6-(2,2-difluoro-3-methoxypropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound FM1

Methyl 4-[3-[4-[6-[3-[tert-butyl(diphenyl)silyl]oxy-2,2-difluoropropyl]-2,6-diazaspiro[3.3]heptan-2-yl]-2,6-dichlorobenzoyl]-2,4-dihydro-1,3-benzoxazin-8-yl]-5-fluoro-2-(3-oxa-8-azabicyclo[3.2.1]octan-8-yl) benzoate

[Formula 472]

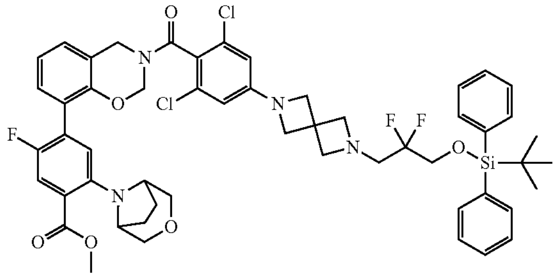

A solution of methyl 4-[3-[2,6-dichloro-4-(2,6-diazaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoate (42.5 mg, 0.064 mmol), [3-[tert-butyl(diphenyl)silyl]oxy-2,2-difluoropropyl]trifluoromethanesulfonate (61.4 mg, 0.127 mmol) and N,N-diisopropylethylamine (0.0780 mL, 0.446 mmol) in acetonitrile (1.27 mL) was stirred at room temperature for 4 hours. An aqueous formic acid solution was added to the reaction mixture, and the mixture was then purified by HPLC (acetonitrile/water, 0.1% formic acid) to obtain the title compound (60%, 38.4 mg).

LCMS: m/z 999[M+H]$^+$

HPLC retention time: 1.12 min (analysis condition D)

Second Step
Compound FM2

Methyl 4-[3-[2,6-dichloro-4-[6-(2,2-difluoro-3-hydroxypropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoate

[Formula 473]

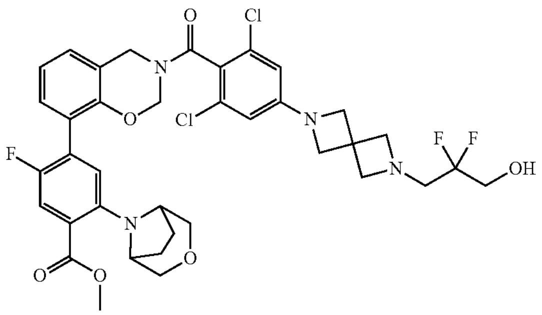

A solution of methyl 4-[3-[4-[6-[3-[tert-butyl(diphenyl)silyl]oxy-2,2-difluoropropyl]-2,6-diazaspiro[3.3]heptan-2-yl]-2,6-dichlorobenzoyl]-2,4-dihydro-1,3-benzoxazin-8-yl]-5-fluoro-2-(3-oxa-8-azabicyclo[3.2.1]octan-8-yl)benzoate (38.4 mg, 0.038 mmol) and a 1 M solution of tetrabutylammonium fluoride in tetrahydrofuran (0.058 mL, 0.058 mmol) in tetrahydrofuran (1.20 mL) was stirred at room temperature for 2 hours. The reaction mixture was concentrated. An aqueous formic acid solution was added to the residue, and the mixture was then purified by HPLC (acetonitrile/water, 0.1% formic acid) to obtain the title compound (77%, 22.5 mg).

LCMS: m/z 761[M+H]$^+$

HPLC retention time: 0.70 min (analysis condition D)

Third Step
Compound 16-17

4-[3-[2,6-Dichloro-4-[6-(2,2-difluoro-3-methoxypropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 474]

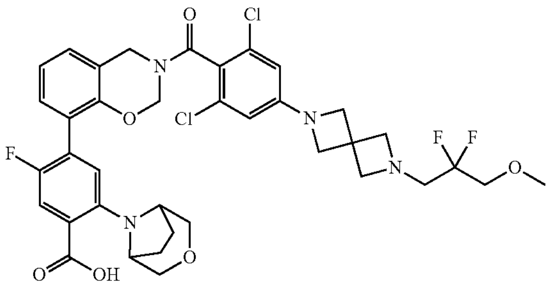

To a solution of methyl 4-[3-[2,6-dichloro-4-[6-(2,2-difluoro-3-hydroxypropyl)-2,6-diazaspiro[3.3]heptan-2-yl]benzoyl]-2,4-dihydro-1,3-benzoxazin-8-yl]-5-fluoro-2-(3-oxa-8-azabicyclo[3.2.1]octan-8-yl)benzoate (22.5 mg, 0.0300 mmol) and sodium hydride (1.93 mg, 0.0440 mmol) in tetrahydrofuran (0.298 mL), iodomethane (0.00368 mg, 0.0590 mmol) was added, and the mixture was stirred at room temperature for 16 hours. A 5 M aqueous sodium hydroxide solution (0.0591 mL, 0.295 mmol) was added to the reaction mixture, and the mixture was stirred at 60° C. for 1 hour. An aqueous formic acid solution was added to the reaction mixture, and the mixture was then purified by HPLC (acetonitrile/water, 0.1% formic acid) to obtain the title compound (60%, 13.5 mg).

LCMS: m/z 761[M+H]$^+$

HPLC retention time: 1.24 min and 1.26 min (analysis condition B)

Compound 17-1

(2S,3R)-3-[2-[2,6-Dichloro-4-(1-methylpyrazol-4-yl)benzoyl]-4-oxo-1,3-dihydrophthalazin-5-yl]-2-methylpentanoic acid First Step
Compound Rh1

[2,6-Bis[(4S)-4-propan-2-yl-4,5-dihydro-1,3-oxazol-2-yl]phenyl]-dichlororhodium hydrate

[Formula 475]

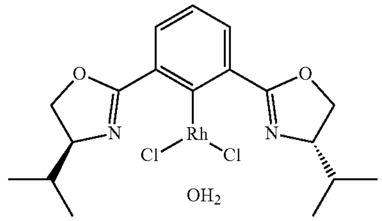

To a solution of (4S)-4-propan-2-yl-2-[3-[(4S)-4-propan-2-yl-4,5-dihydro-1,3-oxazol-2-yl]phenyl]-4,5-dihydro-1,3-oxazole (6.67 g, 22.2 mmol) in methanol (42.3 ml) and water (2.12 ml), rhodium(III) chloride hydrate (5.55 g, 24.2 mmol) was added, and the mixture was stirred at 60° C. for 4.5 hours. The solvent was removed, and the obtained residue was purified by silica gel column chromatography (hexane/ethyl acetate) to obtain the title compound (50%, 5.46 g).

HPLC retention time: 1.03 min (analysis condition G)

$^1$H-NMR (400 MHz, $CDCl_3$) δ 7.55 (2H, d, J=7.6 Hz), 7.25 (1H, dd, J=12.7, 5.1 Hz), 4.73-4.67 (4H, m), 4.27-4.22 (2H, m), 2.40-2.37 (2H, m), 0.94 (6H, d, J=7.1 Hz), 0.90 (6H, d, J=6.6 Hz).

Second Step
Compound Rh2

Diacetyloxy-[2,6-bis[(4S)-4-propan-2-yl-4,5-dihydro-1,3-oxazol-2-yl]phenyl]rhodium hydrate

[Formula 476]

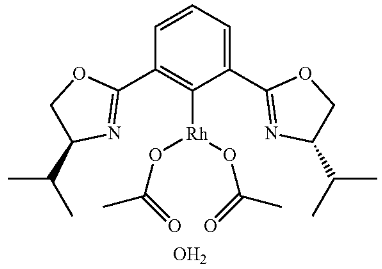

To a solution of [2,6-bis[(4S)-4-propan-2-yl-4,5-dihydro-1,3-oxazol-2-yl]phenyl]-dichlororhodium hydrate (5.46 g, 11.1 mmol) in dichloromethane (111 ml), silver(I) acetate (7.42 g, 44.5 mmol) was added, and the mixture was stirred at room temperature for 2 days. The reaction solution was filtered and concentrated, and the obtained residue was purified by silica gel column chromatography (hexane/ethyl acetate) to obtain the title compound (81%, 4.83 g).

LCMS: m/z 521[M+H]$^+$

HPLC retention time: 0.99 min (analysis condition G)

Third Step

Compound ALN1 tert-Butyl 5-[(E)-1-ethoxy-1-oxopent-2-en-3-yl]-4-oxo-1,3-dihydrophthalazine-2-carboxylate

[Formula 477]

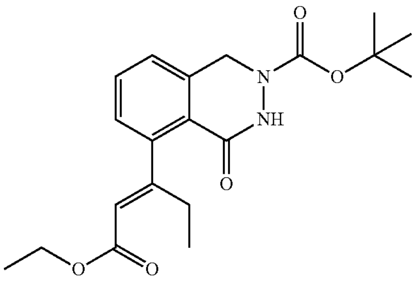

To a mixture of tert-butyl 5-bromo-4-oxo-1,3-dihydrophthalazine-2-carboxylate (1.00 g, 3.06 mmol) and a 1,1'-bis(diphenylphosphino)ferrocene-palladium(II) dichloride dichloromethane complex (125 mg, 0.153 mmol), a 0.6 M solution of ethyl (Z)-3-(4,4,5,5-tetramethyl-1,3,2-dioxaborolan-2-yl)pent-2-enoate in 1,4-dioxane (7.64 ml, 3.58 mmol) and a 2 M aqueous sodium carbonate solution (4.58 ml, 9.17 mmol) were added, and the mixture was heated at 95° C. for 3.5 hours. The reaction solution was subjected to extraction with ethyl acetate. The organic layer was washed with water and a saturated aqueous solution of sodium chloride and filtered. The obtained residue was purified by reverse phase column chromatography (acetonitrile/water, 0.1% formic acid) to obtain the title compound (79%, 907 mg).

LCMS: m/z 375[M+H]$^+$

HPLC retention time: 1.19 min (analysis condition G)

Fourth Step

Compound ALN2 tert-Butyl 5-[(3R)-1-ethoxy-1-oxopentan-3-yl]-4-oxo-1,3-dihydrophthalazine-2-carboxylate

[Formula 478]

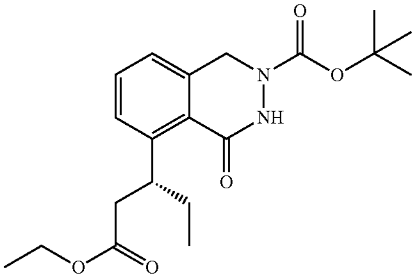

To a solution of tert-butyl 5-[(E)-1-ethoxy-1-oxopent-2-en-3-yl]-4-oxo-1,3-dihydrophthalazine-2-carboxylate (305 mg, 0.815 mmol) in toluene (0.815 ml), diacetyloxy-[2,6-bis[(4S)-4-propan-2-yl-4,5-dihydro-1,3-oxazol-2-yl]phenyl]rhodium hydrate (88 mg, 0.163 mmol) was added, then diethoxy-methylsilane (0.660 ml, 4.08 mmol) was added, and the mixture was stirred at room temperature for 9 hours. The reaction solution was subjected to extraction with ethyl acetate. The organic layer was washed with water and a saturated aqueous solution of sodium chloride and filtered. The obtained residue was purified by silica gel column chromatography (hexane/ethyl acetate) to obtain the title compound (79%, 242 mg).

LCMS: m/z 377[M+H]$^+$

HPLC retention time: 1.17 min (analysis condition G)

Fifth Step

Compound ALN3 tert-Butyl 5-[(2S,3R)-1-ethoxy-2-methyl-1-oxopentan-3-yl]-4-oxo-1,3-dihydrophthalazine-2-carboxylate

[Formula 479]

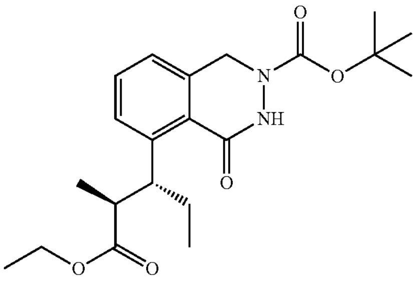

Compound ALN6 tert-Butyl 5-[(2R,3R)-1-ethoxy-2-methyl-1-oxopentan-3-yl]-4-oxo-1,3-dihydrophthalazine-2-carboxylate

[Formula 480]

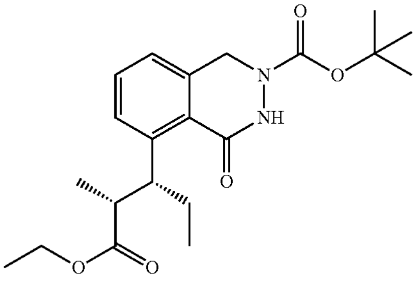

A solution of tert-butyl 5-[(3R)-1-ethoxy-1-oxopentan-3-yl]-4-oxo-1,3-dihydrophthalazine-2-carboxylate (616 mg, 1.64 mmol) in tetrahydrofuran (8.18 ml) was cooled to −78° C. 1 M sodium bis(trimethylsilyl)amide (3.60 ml, 3.60 mmol) was added thereto, and the mixture was stirred for 1 hour. Iodomethane (0.112 ml, 1.80 mmol) was added thereto, and the mixture was further stirred for 2 hours. The reaction solution was subjected to extraction. The organic layer was washed with water and a saturated aqueous solution of sodium chloride and filtered. The obtained residue was purified by silica gel column chromatography (hexane/ethyl acetate) to obtain tert-butyl 5-[(2S,3R)-1-ethoxy-2-methyl-1-oxopentan-3-yl]-4-oxo-1,3-dihydrophthalazine-2-carboxylate (35%, 222 mg) and tert-butyl 5-[(2R,3R)-1-ethoxy-2-methyl-1-oxopentan-3-yl]-4-oxo-1,3-dihydrophthalazine-2-carboxylate (25%, 160 mg).

Compound ALN3

LCMS: m/z 391[M+H]$^+$

HPLC retention time: 1.22 min (analysis condition G)

Compound ALN6

LCMS: m/z 391[M+H]$^+$

HPLC retention time: 1.24 min (analysis condition G)

Sixth Step

Compound ALN4

Ethyl (2S,3R)-2-methyl-3-(4-oxo-2,3-dihydro-1H-phthalazin-5-yl)pentanoate hydrochloride

[Formula 481]

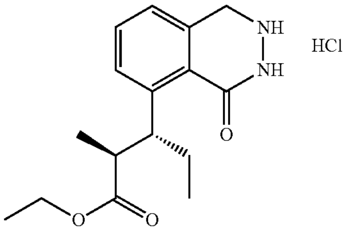

To tert-butyl 5-[(2S,3R)-1-ethoxy-2-methyl-1-oxopentan-3-yl]-4-oxo-1,3-dihydrophthalazine-2-carboxylate (160 mg, 0.411 mmol), a 4 M solution of hydrochloric acid in 1,4-dioxane (2.05 ml, 8.22 mmol) was added, and the mixture was stirred at room temperature for 1.5 hours. The reaction solution was concentrated to obtain the title compound as a crude product.

LCMS: m/z 291[M+H]$^+$

HPLC retention time: 0.93 min (analysis condition G)

Seventh Step

Compound ALN5

Ethyl (2S,3R)-3-[2-[2,6-dichloro-4-(1-methylpyrazol-4-yl)benzoyl]-4-oxo-1,3-dihydrophthalazin-5-yl]-2-methylpentanoate

[Formula 482]

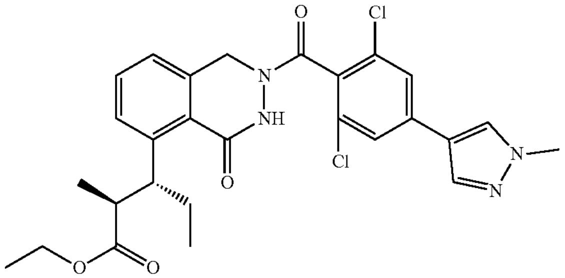

A solution of ethyl (2S,3R)-2-methyl-3-(4-oxo-2,3-dihydro-1H-phthalazin-5-yl)pentanoate hydrochloride (134 mg, 0.410 mmol) in dichloromethane (2.05 ml) was cooled to 0° C. N,N-Diisopropylethylamine (0.354 ml, 2.05 mmol) was added thereto, then 2,6-dichloro-4-(1-methylpyrazol-4-yl)benzoyl chloride (154 mg, 0.533 mmol) was added, and the mixture was stirred at room temperature for 1.5 hours. 2,6-Dichloro-4-(1-methylpyrazol-4-yl)benzoyl chloride (23.7 mg, 0.083 mmol) was added thereto, and the mixture was stirred overnight at room temperature. The reaction solution was purified by reverse phase column chromatography (acetonitrile/water, 0.1% formic acid) to obtain the title compound (85%, 190 mg).

LCMS: m/z 543[M+H]$^+$

HPLC retention time: 1.15 min and 1.18 min (analysis condition G)

Eighth Step

Compound 17-1

(2S,3R)-3-[2-[2,6-Dichloro-4-(1-methylpyrazol-4-yl)benzoyl]-4-oxo-1,3-dihydrophthalazin-5-yl]-2-methylpentanoic acid

[Formula 483]

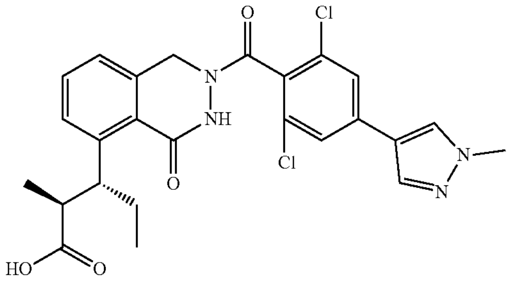

To ethyl (2S,3R)-3-[2-[2,6-dichloro-4-(1-methylpyrazol-4-yl)benzoyl]-4-oxo-1,3-dihydrophthalazin-5-yl]-2-methylpentanoate (190 mg, 0.349 mmol), tetrahydrofuran (1.75 ml) and methanol (1.75 ml) were added, then a 5 M aqueous sodium hydroxide solution (0.698 ml, 6.98 mmol) was added, and the mixture was stirred overnight at room temperature. Then, a 5 M aqueous sodium hydroxide solution (0.698 ml, 6.98 mmol) was further added thereto, and the mixture was stirred at 60° C. for 3.5 hours. The reaction solution was purified by reverse phase column chromatography (acetonitrile/water, 0.1% formic acid) to obtain the title compound (69%, 125 mg).

LCMS: m/z 515[M+H]$^+$

HPLC retention time: 0.95 min and 0.98 min (analysis condition A)

Compound 17-5

(2R,3R)-3-[2-[2,6-Dichloro-4-(1-methylpyrazol-4-yl)benzoyl]-4-oxo-1,3-dihydrophthalazin-5-yl]-2-methylpentanoic acid

[Formula 484]

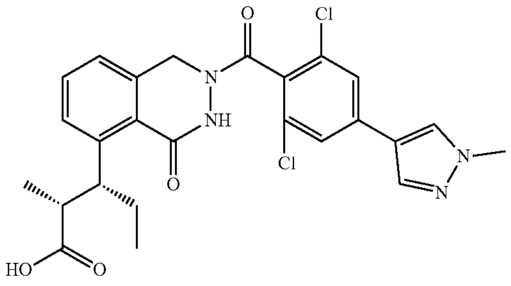

The title compound was obtained by the same operation as in the sixth step to the eighth step of compound 17-1 using tert-butyl 5-[(2R,3R)-1-ethoxy-2-methyl-1-oxopentan-3-yl]-4-oxo-1,3-dihydrophthalazine-2-carboxylate obtained in the fifth step of compound 17-1.

LCMS: m/z 515[M+H]$^+$

HPLC retention time: 0.97 min and 1.01 min (analysis condition A)

Compound 17-4

(3R)-3-[2-[2,6-Dichloro-4-(1-methylpyrazol-4-yl)benzoyl]-4-oxo-1,3-dihydrophthalazin-5-yl]pentanoic acid

[Formula 485]

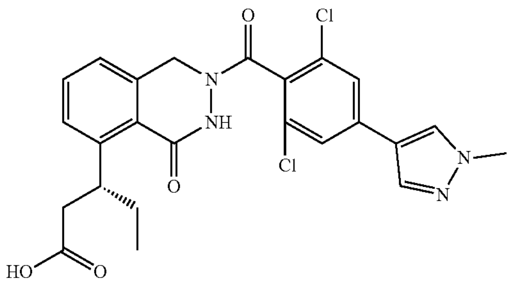

The title compound was obtained by the same operation as in the sixth step to the eighth step of compound 17-1 using tert-butyl 5-[(3R)-1-ethoxy-1-oxopentan-3-yl]-4-oxo-1,3-dihydrophthalazine-2-carboxylate obtained in the fourth step of compound 17-1.

LCMS: m/z 501[M+H]$^+$

HPLC retention time: 0.92 min and 0.94 min (analysis condition A)

Compound 17-9

3-[2-[2,6-Dichloro-4-(1-methylpyrazol-4-yl)benzoyl]-4-oxo-1,3-dihydrophthalazin-5-yl]pentanoic acid

[Formula 486]

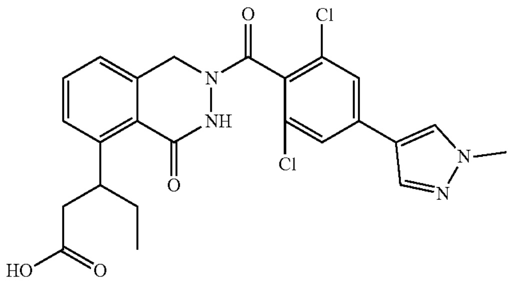

To a solution of tert-butyl 5-[(E)-1-ethoxy-1-oxopent-2-en-3-yl]-4-oxo-1,3-dihydrophthalazine-2-carboxylate (125 mg, 0.334 mmol) in ethyl acetate (5.00 ml), Pearlman's catalyst (141 mg, 0.100 mmol) was added, and the mixture was stirred at room temperature for 24 hours in a hydrogen atmosphere. The reaction solution was filtered, and the filtrate was concentrated. The title compound was obtained by the same operation as in the sixth step to the eighth step of compound 17-1 using the obtained residue.

LCMS: m/z 501[M+H]$^+$

HPLC retention time: 0.91 min and 0.94 min (analysis condition A)

Compound 17-2

(2S,3R)-3-[3-[2,6-Dichloro-4-(1-methylpyrazol-4-yl)benzoyl]-1,4-dihydro-2,3-benzoxazin-8-yl]-2-methylpentanoic acid First Step Compound ALN14 tert-Butyl 8-[(E)-1-ethoxy-1-oxopent-2-en-3-yl]-1,4-dihydro-2,3-benzoxazine-3-carboxylate

[Formula 487]

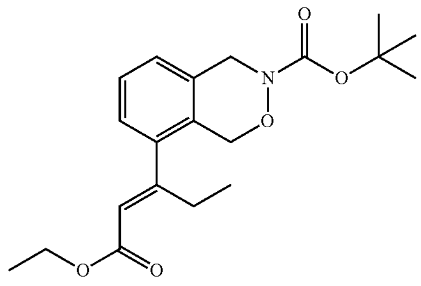

The title compound was obtained by the same operation as in the third step of compound 17-1 using tert-butyl 8-bromo-1,4-dihydro-2,3-benzoxazine-3-carboxylate.

LCMS: m/z 306[M-tBu+H]$^+$

HPLC retention time: 1.50 min (analysis condition G)

Second Step

Compound ALN15 tert-Butyl 8-(1-ethoxy-1-oxopentan-3-yl)-1,4-dihydro-2,3-benzoxazine-3-carboxylate

[Formula 488]

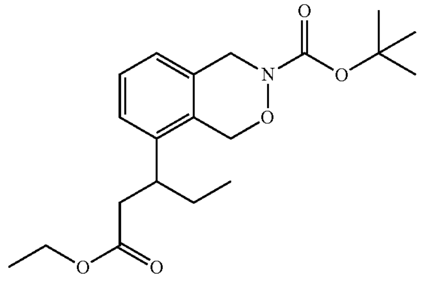

To a solution of tert-butyl 8-[(E)-1-ethoxy-1-oxopent-2-en-3-yl]-1,4-dihydro-2,3-benzoxazine-3-carboxylate (147 mg, 0.407 mmol) in ethyl acetate (2.03 ml), Pearlman's catalyst (29.4 mg, 0.209 mmol) was added, and the mixture was stirred at room temperature for 3 hours in a hydrogen atmosphere. The reaction solution was filtered and concentrated, and the obtained residue was purified by reverse phase column chromatography (acetonitrile/water, 0.1% formic acid) to obtain the title compound (94%, 139 mg).

LCMS: m/z 386[M+Na]$^+$

HPLC retention time: 1.46 min (analysis condition G)

Third Step
Compound ALN16

3-[3-[(2-Methylpropan-2-yl)oxycarbonyl]-1,4-dihydro-2,3-benzoxazin-8-yl]pentanoic acid

[Formula 489]

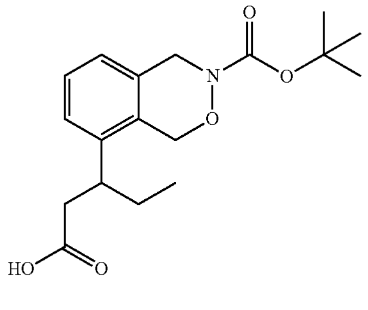

To a solution of tert-butyl 8-(1-ethoxy-1-oxopentan-3-yl)-1,4-dihydro-2,3-benzoxazine-3-carboxylate (137 mg, 0.377 mmol) in tetrahydrofuran (0.942 ml) and methanol (0.942 ml), a 5 M aqueous sodium hydroxide solution (0.226 ml, 1.13 mmol) was added, and the mixture was stirred at room temperature for 1 hour. An aqueous hydrochloric acid solution was added to the reaction solution, followed by extraction with ethyl acetate. The organic layer was washed with a saturated aqueous solution of sodium hydroxide, followed by passing through a phase separator. Then, the organic layer was concentrated to obtain the title compound as a crude product.

LCMS: m/z 358[M+Na]$^+$

HPLC retention time: 1.20 min (analysis condition G)

Fourth Step
Compound ALN17 tert-Butyl 8-[1-oxo-1-[(4S)-2-oxo-4-propan-2-yl-1,3-oxazolidin-3-yl]pentan-3-yl]-1,4-dihydro-2,3-benzoxazine-3-carboxylate

[Formula 490]

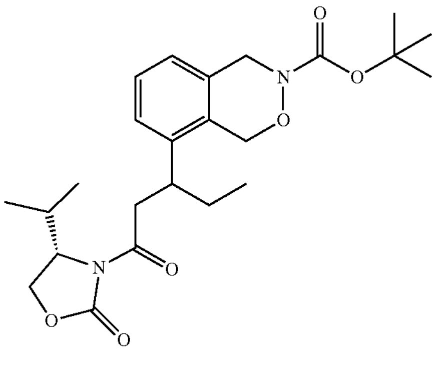

A solution of 3-[3-[(2-methylpropan-2-yl)oxycarbonyl]-1,4-dihydro-2,3-benzoxazin-8-yl]pentanoic acid (126 mg, 0.377 mmol) and triethylamine (0.157 ml, 1.13 mmol) in tetrahydrofuran (0.157 ml) was cooled to 0° C., then pivaloyl chloride (0.0511 ml, 0.415 mmol) was added, and the mixture was stirred at 0° C. for 1 hour. (S)-4-Isopropyl-2-oxazolidinone (53.6 mg, 0.415 mmol) and lithium chloride (20.7 mg, 0.490 mmol) were added thereto at 0° C., and the mixture was stirred at room temperature for 1 hour. The reaction solution was purified by reverse phase column chromatography (acetonitrile/water) to obtain the title compound (75%, 126 mg).

LCMS: m/z 469[M+Na]$^+$

HPLC retention time: 1.46 min and 1.49 min (analysis condition G)

Fifth Step
Compound 17-2

(2S,3R)-3-[3-[2,6-Dichloro-4-(1-methylpyrazol-4-yl)benzoyl]-1,4-dihydro-2,3-benzoxazin-8-yl]-2-methylpentanoic acid

[Formula 491]

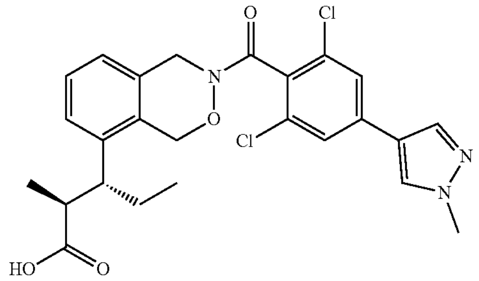

The title compound was obtained by the same operation as in the fifth step to the eighth step of compound 17-1 using tert-butyl 8-[1-oxo-1-[(4S)-2-oxo-4-propan-2-yl-1,3-oxazolidin-3-yl]pentan-3-yl]-1,4-dihydro-2,3-benzoxazine-3-carboxylate.

LCMS: m/z 502[M+Na]$^+$

HPLC retention time: 1.09 min (analysis condition A)

Compound 17-3

(2S,3R)-3-[3-[2,6-Dichloro-4-(1-methylpyrazol-4-yl)benzoyl]-2,4-dihydro-1,3-benzoxazin-8-yl]-2-methylpentanoic acid First Step
Compound ALN21 tert-Butyl 8-[(E)-1-ethoxy-1-oxopent-2-en-3-yl]-2,4-dihydro-1,3-benzoxazine-3-carboxylate

[Formula 492]

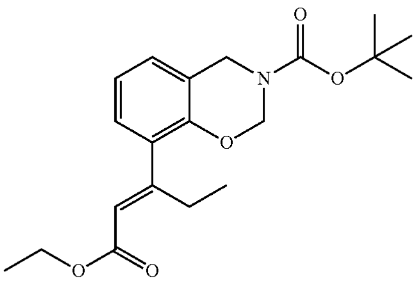

The title compound was obtained by the same operation as in the third step of compound 17-1 using tert-butyl 8-bromo-2,4-dihydro-1,3-benzoxazine-3-carboxylate.

LCMS: m/z 262[M+H-Boc]$^+$

HPLC retention time: 1.45 min (analysis condition N)

Second Step

Compound ALN22 tert-Butyl 8-[(3R)-1-ethoxy-1-oxopentan-3-yl]-2,4-dihydro-1,3-benzoxazine-3-carboxylate

[Formula 493]

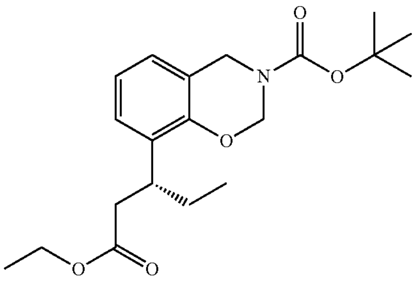

The title compound was obtained by the same operation as in the fourth step of compound 17-1 using tert-butyl 8-[(E)-1-ethoxy-1-oxopent-2-en-3-yl]-2,4-dihydro-1,3-benzoxazine-3-carboxylate.

LCMS: m/z 264[M+H-Boc]+

HPLC retention time: 1.42 min (analysis condition N)

Third Step

Compound 17-3

(2S,3R)-3-[3-[2,6-Dichloro-4-(1-methylpyrazol-4-yl)benzoyl]-2,4-dihydro-1,3-benzoxazin-8-yl]-2-methylpentanoic acid

[Formula 494]

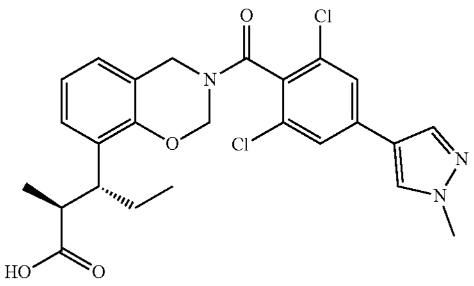

The title compound was obtained by the same operation as in the third step to the fifth step of compound 17-2 using tert-butyl 8-[(E)-1-ethoxy-1-oxopent-2-en-3-yl]-2,4-dihydro-1,3-benzoxazine-3-carboxylate.

LCMS: m/z 524[M+Na]+

HPLC retention time: 1.09 min and 1.10 min (analysis condition A)

Compound 17-8

(2S,3R)-3-[2-[2,6-Dichloro-4-(1-methylpyrazol-4-yl)benzoyl]-3,4-dihydro-1H-isoquinolin-5-yl]-2-methylpentanoic acid First Step Compound ALN28 tert-Butyl 5-[(3R)-1-ethoxy-1-oxopentan-3-yl]-3,4-dihydro-1H-isoquinoline-2-carboxylate

[Formula 495]

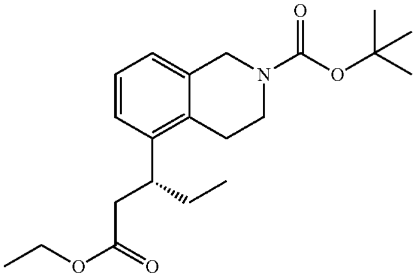

The title compound was obtained by the same operation as in the first step and the second step of compound 17-3 using tert-butyl 5-bromo-3,4-dihydro-1H-isoquinoline-2-carboxylate.

LCMS: m/z 262[M+H-Boc]+

HPLC retention time: 0.80 min (analysis condition N)

Second Step

Compound ALN29

(3R)-3-[2-[(2-Methylpropan-2-yl)oxycarbonyl]-3,4-dihydro-1H-isoquinolin-5-yl]pentanoic acid

[Formula 496]

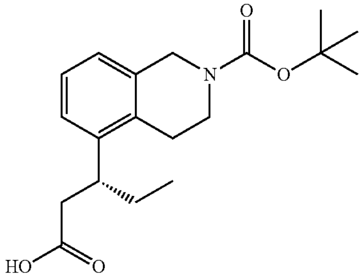

The title compound was obtained by the same operation as in the third step of compound 17-2 using tert-butyl 5-[(3R)-1-ethoxy-1-oxopentan-3-yl]-3,4-dihydro-1H-isoquinoline-2-carboxylate.

LCMS: m/z 234[M+H-Boc]+

HPLC retention time: 0.47 min (analysis condition N)

Third Step

Compound ALN30 tert-Butyl 5-[(3R)-1-[(4S)-4-benzyl-2-oxo-1,3-oxazolidin-3-yl]-1-oxopentan-3-yl]-3,4-dihydro-1H-isoquinoline-2-carboxylate

[Formula 497]

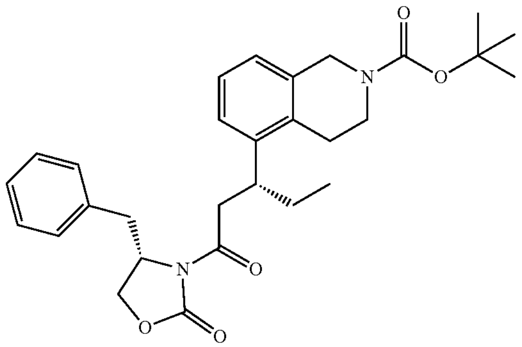

The title compound was obtained by the same operation as in the fourth step of compound 17-2 using (3R)-3-[2-[(2-methylpropan-2-yl)oxycarbonyl]-3,4-dihydro-1H-isoquinolin-5-yl]pentanoic acid. However, (S)-4-benzyl-2-oxazolidinone was used instead of (S)-4-isopropyl-2-oxazolidinone.

LCMS: m/z 393[M+H-Boc]$^+$

HPLC retention time: 1.46 min (analysis condition N)

Fourth Step

Compound 17-8

(2S,3R)-3-[2-[2,6-Dichloro-4-(1-methylpyrazol-4-yl)benzoyl]-3,4-dihydro-1H-isoquinolin-5-yl]-2-methylpentanoic acid

[Formula 498]

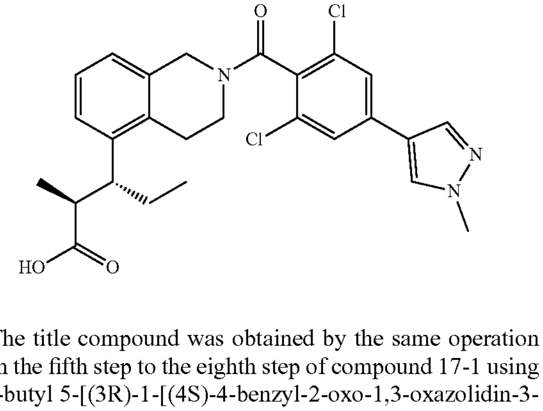

The title compound was obtained by the same operation as in the fifth step to the eighth step of compound 17-1 using tert-butyl 5-[(3R)-1-[(4S)-4-benzyl-2-oxo-1,3-oxazolidin-3-yl]-1-oxopentan-3-yl]-3,4-dihydro-1H-isoquinoline-2-carboxylate.

LCMS: m/z 500[M+H]$^+$

HPLC retention time: 1.16 min (analysis condition C)

Compound 17-10

(2S,3R)-3-[2-[2,6-Dibromo-4-(1-methylpyrazol-4-yl)benzoyl]-3,4-dihydro-1H-isoquinolin-5-yl]-2-methylpentanoic acid First Step Compound ALN53

2,6-Dibromo-4-(1-methylpyrazol-4-yl)benzoic acid

[Formula 499]

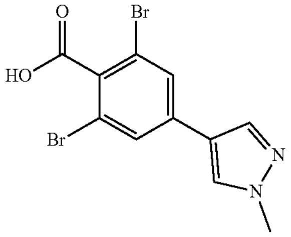

To a solution of 2,4,6-tribromobenzoic acid (200 mg, 0.557 mmol) and (1-methyl-4-(4,4,5,5-tetramethyl-1,3,2-dioxaborolan-2-yl)pyrazole (348 mg, 1.67 mmol) in NMP (1.39 ml) and water (1.39 ml), palladium acetate (1.88 mg, 0.00836 mmol), (oxydi-2,1-phenylene)bis(diphenylphosphine) (9.01 mg, 0.0170 mmol) and lithium hydroxide monohydrate (51.5 mg, 1.23 mmol) were added, and the mixture was stirred at 65° C. for 5 hours. Palladium acetate (1.88 mg, 0.00836 mmol), (oxydi-2,1-phenylene)bis(diphenylphosphine) (9.01 mg, 0.0170 mmol) and lithium hydroxide monohydrate (51.5 mg, 1.23 mmol) were added to the reaction solution, and the mixture was further stirred at 65° C. for 1 hour. The reaction solution was purified by reverse phase column chromatography (acetonitrile/water) to obtain the title compound (100%, 218 mg).

LCMS: m/z 359[M+H]$^+$

HPLC retention time: 0.74 min (analysis condition G)

Second Step

Compound 17-10

(2S,3R)-3-[2-[2,6-Dibromo-4-(1-methylpyrazol-4-yl)benzoyl]-3,4-dihydro-1H-isoquinolin-5-yl]-2-methylpentanoic acid

[Formula 500]

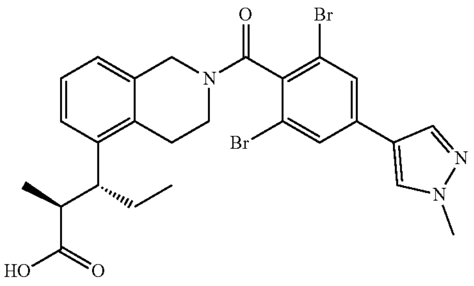

The title compound was obtained by the same operation as in the fourth step of compound 17-2 using (3R)-3-[2-[(2-methylpropan-2-yl)oxycarbonyl]-3,4-dihydro-1H-isoquinolin-5-yl]pentanoic acid, followed by the same operation as in the fifth step to the eighth step of compound 17-1. However, 2,6-dibromo-4-(1-methylpyrazol-4-yl)benzoyl chloride was used instead of 2,6-dichloro-4-(1-methylpyrazol-4-yl)benzoyl chloride.

LCMS: m/z 588[M+H]$^+$

HPLC retention time: 1.08 min (analysis condition A)

Compound 17-15

3-[2-[2,6-Dichloro-4-(1-methylpyrazol-4-yl)benzoyl]-3,4-dihydro-1H-isoquinolin-5-yl]-3-(1,4-dimethylbenzotriazol-5-yl)propanoic acid First Step Compound ALN44

Ethyl (E)-3-(1,4-dimethylbenzotriazol-5-yl)prop-2-enoate

[Formula 501]

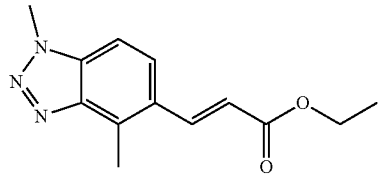

To a solution of 5-bromo-1,4-dimethylbenzotriazole (32.0 mg, 0.142 mmol), tris(2-methylphenyl)phosphine (8.62 mg, 0.0280 mmol) and palladium(II) acetate (3.18 mg, 0.0140 mmol) in N,N-dimethylformamide (0.472 ml), N,N-diisopropylethylamine (0.0742 ml, 0.425 mmol) and ethyl acrylate (0.0307 ml, 0.283 mmol) were added, and the mixture was stirred at 100° C. for 24 hours. The reaction solution was purified by reverse phase column chromatography (acetonitrile/water) to obtain the title compound (96%, 33.5 mg).

LCMS: m/z 246[M+H]$^+$

HPLC retention time: 0.95 min (analysis condition G)

Second Step

Compound ALN40 tert-Butyl 5-(4,4,5,5-tetramethyl-1,3,2-dioxaborolan-2-yl)-3,4-dihydro-1H-isoquinoline-2-carboxylate

[Formula 502]

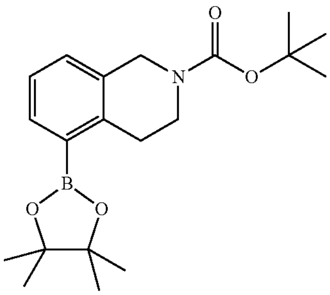

A solution of tert-butyl 5-bromo-3,4-dihydro-1H-isoquinoline-2-carboxylate (650 mg, 2.08 mmol), potassium acetate (613 mg, 6.25 mmol), a 1,1'-bis(diphenylphosphino) ferrocene-palladium(II) dichloride dichloromethane complex (86.0 mg, 0.104 mmol) and bis(pinacol)diboron (793 mg, 3.12 mmol) in 1,4-dioxane (10.0 ml) was stirred at 80° C. for 3 hours. The reaction solution was purified by reverse phase column chromatography (acetonitrile/water) to obtain the title compound (71%, 533 mg).

LCMS: m/z 304[M-tBu+H]$^+$

HPLC retention time: 1.55 min (analysis condition Q)

Third Step

Compound ALN41 tert-Butyl 5-[1-(1,4-dimethylbenzotriazol-5-yl)-3-ethoxy-3-oxopropyl]-3,4-dihydro-1H-isoquinoline-2-carboxylate

[Formula 503]

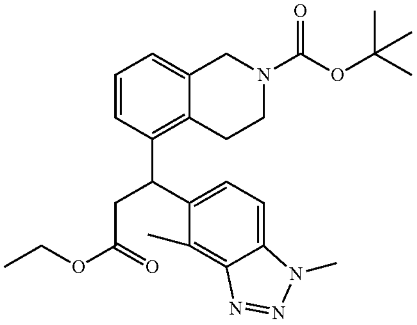

To a solution of ethyl (E)-3-(1,4-dimethylbenzotriazol-5-yl)prop-2-enoate (20.0 mg, 0.0820 mmol), tert-butyl 5-(4,4,5,5-tetramethyl-1,3,2-dioxaborolan-2-yl)-3,4-dihydro-1H-isoquinoline-2-carboxylate (88.0 mg, 0.245 mmol) and a cyclooctadiene rhodium dimer (12.4 mg, 0.122 mmol) in 1,4-dioxane (0.204 ml) and water (0.0678 ml), triethylamine (0.0171 ml) was added, and the mixture was stirred at 80° C. for 9 hours. The reaction solution was purified by reverse phase column chromatography (acetonitrile/water) to obtain the title compound.

LCMS: m/z 479[M+H]$^+$

HPLC retention time: 1.21 min (analysis condition Q)

Fourth Step

Compound 17-15

3-[2-[2,6-Dichloro-4-(1-methylpyrazol-4-yl)benzoyl]-3,4-dihydro-1H-isoquinolin-5-yl]-3-(1,4-dimethylbenzotriazol-5-yl)propanoic acid

[Formula 504]

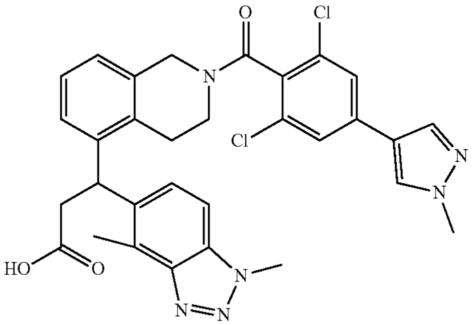

The title compound was obtained by the same operation as in the sixth step to the eighth step of compound 17-1 using tert-butyl 5-[1-(1,4-dimethylbenzotriazol-5-yl)-3-ethoxy-3-oxopropyl]-3,4-dihydro-1H-isoquinoline-2-carboxylate.

LCMS: m/z 603[M+H]$^+$

HPLC retention time: 0.93 min (analysis condition A)

Compound 17-16

3-[3-[2,6-Dichloro-4-(1-methylpyrazol-4-yl)benzoyl]-1,4-dihydro-2,3-benzoxazin-8-yl]-3-(1,4-dimethylbenzotriazol-5-yl)propanoic acid

[Formula 505]

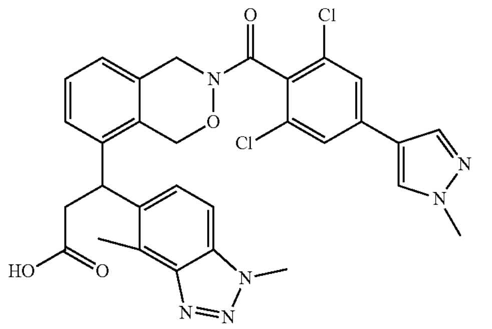

The title compound was obtained by the same operation as in the first step to the fourth step of compound 17-15 using tert-butyl 8-bromo-1,4-dihydro-2,3-benzoxazine-3-carboxylate.

LCMS: m/z 605[M+H]$^+$

HPLC retention time: 0.95 min (analysis condition A)

Compound 17-18

4-[2-[2,6-Dichloro-4-(1-methylpyrazol-4-yl)benzoyl]-3,4-dihydro-1H-isoquinolin-5-yl]-2-morpholin-4-ylbenzoic acid First Step Compound ALN49 tert-Butyl 5-(4-methoxycarbonyl-3-morpholin-4-ylphenyl)-3,4-dihydro-1H-isoquinoline-2-carboxylate

[Formula 506]

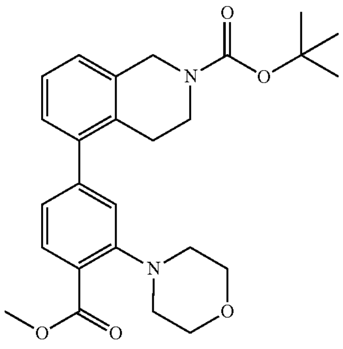

A solution of tert-butyl 5-(4,4,5,5-tetramethyl-1,3,2-dioxaborolan-2-yl)-3,4-dihydro-1H-isoquinoline-2-carboxylate (134 mg, 0.373 mmol), methyl 4-bromo-2-morpholin-4-ylbenzoate (112 mg, 0.372 mmol), a 1,1'-bis(diphenylphosphino)ferrocene-palladium(II) dichloride dichloromethane complex (13.6 mg, 0.0190 mmol) and cesium carbonate (182 mg, 0.558 mmol) in 1,4-dioxane (1.59 ml) and water (0.266 ml) was stirred at 80° C. for 2.5 hours. The reaction solution was purified by reverse phase column chromatography (acetonitrile/water, 0.1% formic acid) to obtain the title compound (88%, 149 mg).

LCMS: m/z 453[M+H]$^+$

HPLC retention time: 1.47 min (analysis condition H)

Second Step

Compound 17-18

4-[2-[2,6-Dichloro-4-(1-methylpyrazol-4-yl)benzoyl]-3,4-dihydro-1H-isoquinolin-5-yl]-2-morpholin-4-ylbenzoic acid

[Formula 507]

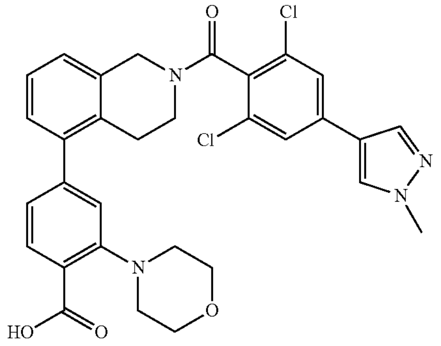

The title compound was obtained by the same operation as in the sixth step to the eighth step of compound 17 using tert-butyl 5-(4-methoxycarbonyl-3-morpholin-4-ylphenyl)-3,4-dihydro-1H-isoquinoline-2-carboxylate.

LCMS: m/z 591[M+H]$^+$

HPLC retention time: 0.98 min (analysis condition C)

Compound 17-21

4-[3-[2,6-Dichloro-4-(1-methylpyrazol-4-yl)benzoyl]-2,4-dihydro-1,3-benzothiazin-8-yl]-2-morpholin-4-ylbenzoic acid First Step Compound NCS1 tert-Butyl 8-(4-methoxycarbonyl-3-morpholin-4-ylphenyl)-2,4-dihydro-1,3-benzothiazine-3-carboxylate

[Formula 508]

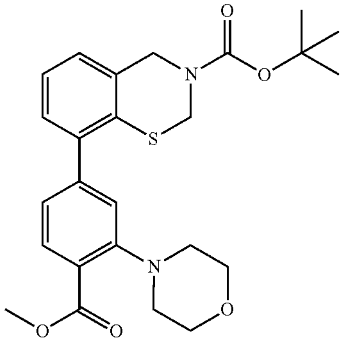

The title compound was obtained by the same operation as in the first step of compound 17-18 using tert-butyl 8-bromo-2,4-dihydro-1,3-benzothiazine-3-carboxylate and methyl 2-morpholin-4-yl-4-(4,4,5,5-tetramethyl-1,3,2-dioxaborolan-2-yl)benzoate. However, potassium carbonate was used instead of cesium carbonate.

LCMS: m/z 471[M+H]$^+$

HPLC retention time: 1.38 min (analysis condition G)

Second Step

Compound 17-21

4-[3-[2,6-Dichloro-4-(1-methylpyrazol-4-yl)benzoyl]-2,4-dihydro-1,3-benzothiazin-8-yl]-2-morpholin-4-ylbenzoic acid

[Formula 509]

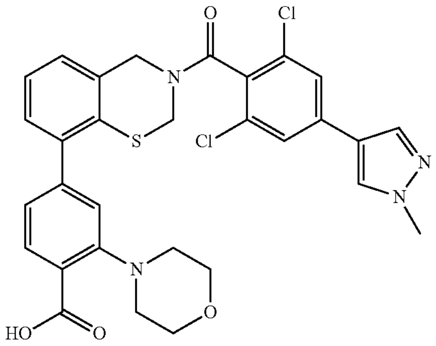

The title compound was obtained by the same operation as in the sixth step to the eighth step of compound 17-1 using tert-butyl 8-(4-methoxycarbonyl-3-morpholin-4-ylphenyl)-2,4-dihydro-1,3-benzothiazine-3-carboxylate.

LCMS: m/z 609[M+H]$^+$

HPLC retention time: 0.99 min and 1.01 min (analysis condition A)

Compound 17-23

(2S,3R)-3-[2-[2,6-Dichloro-4-(2-methoxyethoxy)benzoyl]-3,4-dihydro-1H-isoquinolin-5-yl]-2-methylbutanoic acid First Step Compound ALNP51

Ethyl (E)-3-(3,4-dihydroisoquinolin-5-yl)but-2-enoate

[Formula 510]

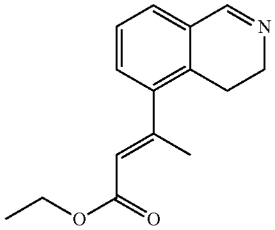

A solution of 5-bromo-3,4-dihydroisoquinoline (500 mg, 2.38 mmol), ethyl (E)-but-2-enoate (678 mg, 5.94 mmol), dichlorobis(triphenylphosphine)palladium(II) (175 mg, 0.250 mmol) and potassium carbonate (1.15 g, 8.32 mmol) in N,N-dimethylformamide (5.00 ml) was stirred at 120° C. for 16 hours. The reaction solution was diluted with water, followed by extraction with ethyl acetate. The organic layer was dried over sodium sulfate and concentrated, and the obtained residue was purified by reverse phase column chromatography (acetonitrile/water, 0.1% formic acid) to obtain the title compound (35%, 200 mg).

LCMS: m/z 244[M+H]$^+$

HPLC retention time: 1.22 min (analysis condition AI)

Second Step

Compound ALNP52

Ethyl 3-(1,2,3,4-tetrahydroisoquinolin-5-yl)butanoate

[Formula 511]

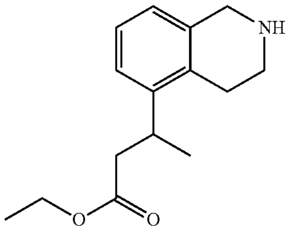

A solution of ethyl (E)-3-(3,4-dihydroisoquinolin-5-yl)but-2-enoate (100 mg, 0.410 mmol) and 10% palladium carbon (20.0 mg) in ethanol (10.0 ml) was stirred for 10 days in a hydrogen atmosphere. The reaction solution was filtered, and the filtrate was concentrated to obtain the title compound as a crude product.

LCMS: m/z 248[M+H]$^+$

HPLC retention time: 1.35 min (analysis condition AH)

Third Step

Compound ALNP53

Ethyl 3-(1,2,3,4-tetrahydroisoquinolin-5-yl)butanoate hydrochloride

[Formula 512]

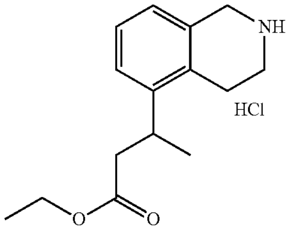

To a solution of ethyl 3-(1,2,3,4-tetrahydroisoquinolin-5-yl)butanoate (500 mg, 2.02 mmol) in ethyl acetate (20.0 ml), hydrochloric acid gas was bubbled at room temperature for 30 minutes. The obtained solid was collected by filtration to obtain the title compound as a crude product.

LCMS: m/z 248[M+H]$^+$

HPLC retention time: 1.34 min (analysis condition AH)

Fourth Step
Compound ALNP53-1

Ethyl (3R)-3-(1,2,3,4-tetrahydroisoquinolin-5-yl) butanoate

[Formula 513]

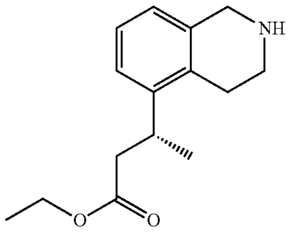

Ethyl 3-(1,2,3,4-tetrahydroisoquinolin-5-yl)butanoate hydrochloride (300 mg) was resolved into both stereoisomers by SFC (Chiralpak IBZ×25 cm, 0.005 mm chiral-PCIB, hexane (0.2% isopropanol)/ethanol (0.2% isopropanol)) to obtain the title compound (47.9 mg) and its isomer (121.2 mg).

LCMS: 248[M+H]$^+$

HPLC retention time: 1.36 min (analysis condition AH)

SFC retention time: 3.19 min (isomer retention time: 4.90 min) (analysis condition: CHIRALPAK IB-3, 0.46×15 cm, 3 μm, hexane (0.2%2-propanol):ethanol=70:30, 9.0 min), 25° C., 220 nm)

Fifth Step
Compound ALN54 tert-Butyl 5-[(2R)-4-ethoxy-4-oxobutan-2-yl]-3,4-dihydro-1H-isoquinoline-2-carboxylate

[Formula 514]

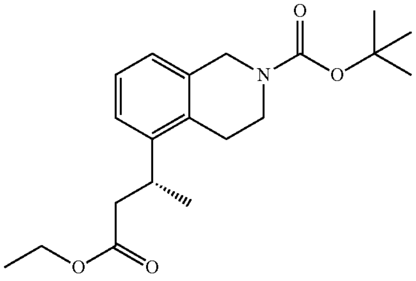

Ethyl (3R)-3-(1,2,3,4-tetrahydroisoquinolin-5-yl)butanoate (29.0 mg, 0.117 mmol), di-tert-butyl dicarbonate (30.7 mg, 0.141 mmol) and triethylamine (0.0245 ml, 0.176 mmol) in dichloromethane (0.391 ml) were stirred at room temperature for 3 hours. The reaction solution was poured to 1 N hydrochloric acid, followed by extraction with ethyl acetate. The organic layer was washed with a saturated aqueous solution of sodium bicarbonate, followed by passing through a phase separator. Then, the organic layer was concentrated, and the obtained residue was purified by silica gel column chromatography (hexane/ethyl acetate) to obtain the title compound (74%, 30.2 mg).

LCMS: m/z 248[M+H−tBu]$^+$

HPLC retention time: 1.40 min (analysis condition Q)

Sixth Step
Compound ALN58

(4S)-3-[(2S,3R)-2-Methyl-3-(1,2,3,4-tetrahydroisoquinolin-5-yl)butanoyl]-4-propan-2-yl-1,3-oxazolidin-2-one hydrochloride

[Formula 515]

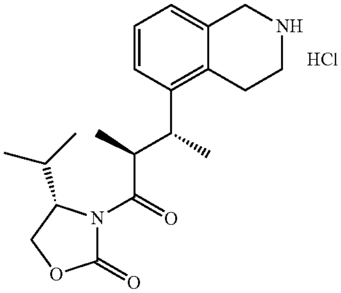

The title compound was obtained by the same operation as in the third step and the fourth step of compound 17-2 using tert-butyl 5-[(2R)-4-ethoxy-4-oxobutan-2-yl]-3,4-dihydro-1H-isoquinoline-2-carboxylate, followed by the same operation as in the fifth step and the sixth step of compound 17-1.

LCMS: m/z 345[M+H]$^+$

HPLC retention time: 0.73 min (analysis condition H)

Seventh Step
Compound ALN59

(4S)-3-[(2S,3R)-3-[2-[2,6-Dichloro-4-(2-methoxyethoxy)benzoyl]-3,4-dihydro-1H-isoquinolin-5-yl]-2-methylbutanoyl]-4-propan-2-yl-1,3-oxazolidin-2-one

[Formula 516]

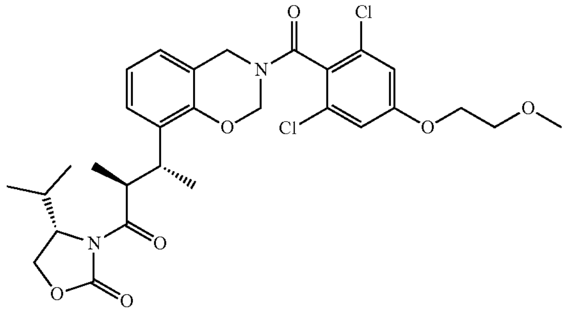

To a solution of 2,6-dichloro-4-(2-methoxyethoxy)benzoic acid (119 mg, 0.448 mmol) in dichloromethane (2.00 ml), oxalyl chloride (0.0710 ml, 0.814 mmol) and N,N-dimethylformamide (0.00315 ml, 0.0410 mmol) were added, and the mixture was stirred at room temperature for 1 hour. The reaction solution was concentrated and azeotroped with toluene to obtain 2,6-dichloro-4-(2-methoxyethoxy)benzoyl chloride as a crude product. A solution of (4S)-3-[(2S,3R)-2-methyl-3-(1,2,3,4-tetrahydroisoquinolin-5-yl)butanoyl]-4-propan-2-yl-1,3-oxazolidin-2-one hydrochloride (155 mg, 0.407 mmol) in dichloromethane (2.00 ml) was cooled to 0° C. 2,6-Dichloro-4-(2-methoxyethoxy) benzoyl chloride and triethylamine (0.170 ml, 1.22 mmol)

were added thereto, and the mixture was stirred at room temperature for 30 minutes. The reaction solution was poured to 1 N hydrochloric acid, followed by extraction with ethyl acetate. The organic layer was washed with a saturated aqueous solution of sodium bicarbonate, followed by passing through a phase separator. Then, the organic layer was concentrated to obtain the title compound as a crude product.

LCMS: m/z 591[M+H]$^+$

HPLC retention time: 1.39 min (analysis condition H)

Eighth Step

Compound 17-23

(2S,3R)-3-[2-[2,6-Dichloro-4-(2-methoxyethoxy)benzoyl]-3,4-dihydro-1H-isoquinolin-5-yl]-2-methylbutanoic acid

[Formula 517]

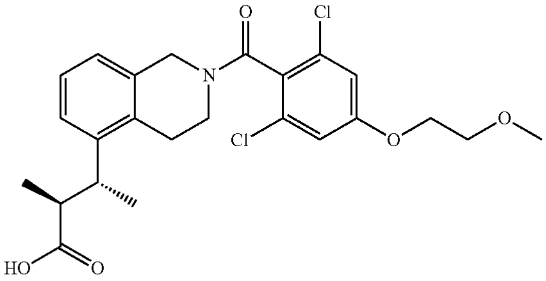

A solution of (4S)-3-[(2S,3R)-3-[2-[2,6-dichloro-4-(2-methoxyethoxy)benzoyl]-3,4-dihydro-1H-isoquinolin-5-yl]-2-methylbutanoyl]-4-propan-2-yl-1,3-oxazolidin-2-one (241 mg, 0.407 mmol) in tetrahydrofuran (2.17 ml) and water (0.543 ml) was cooled to 0° C. 34.5% hydrogen peroxide water (0.281 ml, 2.85 mmol) and lithium hydroxide monohydrate (51.2 mg, 1.22 mmol) were added thereto, and the mixture was stirred at room temperature for 3 hours. Methanol and formic acid were added to the reaction solution, and the mixture was purified by reverse phase column chromatography (acetonitrile/water, 0.1% formic acid) to obtain the title compound (96%, 187 mg).

LCMS: m/z 480[M+H]$^+$

HPLC retention time: 1.07 min and 1.09 min (analysis condition C)

Compound 18-4

4-[3-(2-Chloro-5-ethyl-4-methoxybenzoyl)-2,4-dihydro-1,3-benzoxazin-8-yl]-5-fluoro-2-morpholin-4-ylbenzoic acid First Step Compound RPM1

2-Chloro-5-iodo-4-methoxybenzoic acid

[Formula 518]

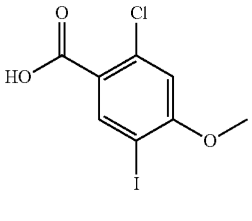

A solution of 2-chloro-4-fluoro-5-iodobenzoic acid (3.06 g, 10.2 mmol) and sodium methoxide (2.20 g, 40.7 mmol) in N,N-dimethylformamide (67.9 ml) was stirred at 50° C. for 8 hours. An aqueous formic acid solution was added to the reaction solution, followed by extraction with ethyl acetate. The organic layer was washed with water and an aqueous sodium chloride solution. The solvent was concentrated. Hexane was added to the residue, and the obtained solid was collected by filtration to obtain the title compound (60%, 1.90 g).

LCMS: m/z 313[M+H]$^+$

HPLC retention time: 0.95 min (analysis condition G)

Second Step

Compound RPM2

2-Chloro-5-ethenyl-4-methoxybenzoic acid

[Formula 519]

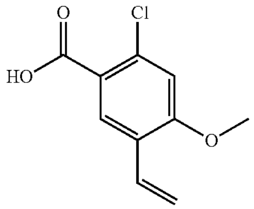

A solution of 2-chloro-5-iodo-4-methoxybenzoic acid (500 mg, 1.50 mmol), potassium vinyl trifluoroborate (302 mg, 2.26 mmol), a 1,1'-bis(diphenylphosphino)ferrocene-palladium(II) dichloride dichloromethane complex (123 mg, 0.150 mmol) and triethylamine (0.629 ml, 4.51 mmol) in ethanol (5.01 ml) was stirred at 80° C. for 1 hour. The reaction solution was purified by reverse phase column chromatography (acetonitrile/water, 0.1% formic acid) to obtain the title compound (83%, 267 mg).

LCMS: m/z 213[M+H]$^+$

HPLC retention time: 0.95 min (analysis condition G)

Third Step

Compound RPM 11

2-Chloro-5-ethyl-4-methoxybenzoic acid

[Formula 520]

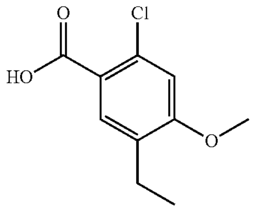

To a solution of 2-chloro-5-ethenyl-4-methoxybenzoic acid (100 mg, 0.447 mmol) in ethyl acetate (7.15 ml) and methanol (1.79 ml), 10% palladium carbon (14.3 mg, 0.0130 mmol) was added, and the mixture was stirred at room temperature for 1 hour in a hydrogen atmosphere. The reaction solution was filtered, and the obtained residue was then purified by reverse phase column chromatography (acetonitrile/water, 0.1% formic acid) to obtain the title compound (100%, 101 mg).

LCMS: m/z 215[M+H]$^+$

HPLC retention time: 0.99 min (analysis condition G)

Fourth Step

Compound RPM13

Methyl 4-[3-(2-chloro-5-ethyl-4-methoxybenzoyl)-2,4-dihydro-1,3-benzoxazin-8-yl]-5-fluoro-2-morpholin-4-ylbenzoate

[Formula 521]

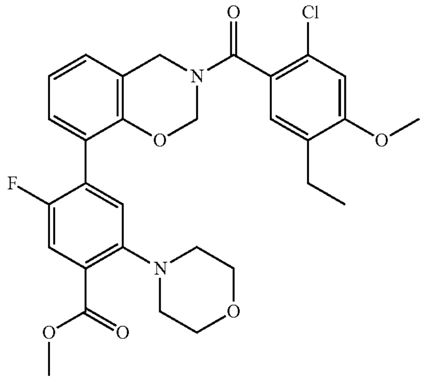

To a solution of 2-chloro-5-ethyl-4-methoxybenzoic acid (79.6 mg, 0.371 mmol) in dichloromethane (0.927 ml), N,N-dimethylformamide (0.00172 ml) and oxalyl chloride (0.0390 ml, 0.445 mmol) were added, and the mixture was stirred at room temperature for 1 hour. The reaction solution was concentrated. Methyl 4-(3,4-dihydro-2H-1,3-benzoxazin-8-yl)-5-fluoro-2-morpholin-4-ylbenzoate hydrochloride (151 mg, 0.369 mmol) and dichloromethane (3.69 ml) were added to the obtained residue, and the mixture was stirred for 15 minutes. Then, N,N-diisopropylethylamine (0.258 ml, 1.48 mmol) was added thereto, and the mixture was stirred at room temperature for 2 hours. The reaction solution was purified by reverse phase column chromatography (acetonitrile/water, 0.1% formic acid) to obtain the title compound (88%, 185 mg).

LCMS: m/z 569[M+H]$^+$

HPLC retention time: 1.37 min (analysis condition G)

Fifth Step

Compound 18-4

4-[3-(2-Chloro-5-ethyl-4-methoxybenzoyl)-2,4-dihydro-1,3-benzoxazin-8-yl]-5-fluoro-2-morpholin-4-ylbenzoic acid

[Formula 522]

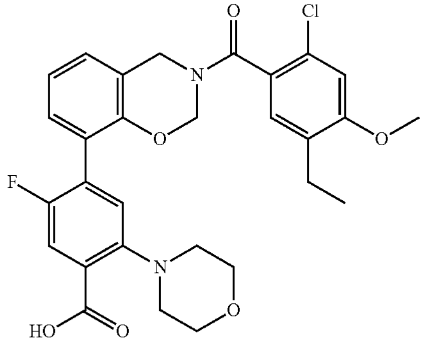

To a solution of methyl 4-[3-(2-chloro-5-ethyl-4-methoxybenzoyl)-2,4-dihydro-1,3-benzoxazin-8-yl]-5-fluoro-2-morpholin-4-ylbenzoate (185 mg, 0.325 mmol) in methanol (1.63 ml) and tetrahydrofuran (1.63 ml), a 2 M aqueous sodium hydroxide solution (0.813 ml, 1.63 mmol) was added, and the mixture was stirred at room temperature for 1.5 hours. The reaction solution was purified by reverse phase column chromatography (acetonitrile/water, 0.1% formic acid) to obtain the title compound (95%, 171 mg).

LCMS: m/z 555[M+H]$^+$

HPLC retention time: 1.52 min (analysis condition B)

Compound RPM5

2-Chloro-5-cyclopropyl-4-methoxybenzoic acid

[Formula 523]

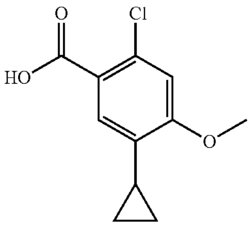

A solution of 2-chloro-5-iodo-4-methoxybenzoic acid (300 mg, 0.902 mmol), cyclopropylboronic acid (233 mg, 2.71 mmol), cesium carbonate (1.18 g, 3.61 mmol) and a 1,1'-bis(diphenylphosphino)ferrocene-palladium(II) dichloride dichloromethane complex (73.7 mg, 0.0900 mmol) in 1,4-dioxane (4.51 ml) was stirred at 90° C. for 2 hours. The reaction solution was purified by reverse phase column chromatography (acetonitrile/water, 0.1% formic acid) to obtain the title compound (55%, 114 mg).

LCMS: m/z 227[M+H]$^+$

HPLC retention time: 0.98 min (analysis condition G)

Compounds shown in Table 18-1 were synthesized by the same operation as in the fourth step and the fifth step of compound 18-4 using carboxylic acid shown in Table 18-2 and methyl 4-(3,4-dihydro-2H-1,3-benzoxazin-8-yl)-5-fluoro-2-morpholin-4-ylbenzoate hydrochloride.

TABLE 18-1

| Compound No | Structure | Compound Name | Analysis conditions | HPLC retention time (min) | m/z [M + H]+ |
|---|---|---|---|---|---|
| 18-1 | 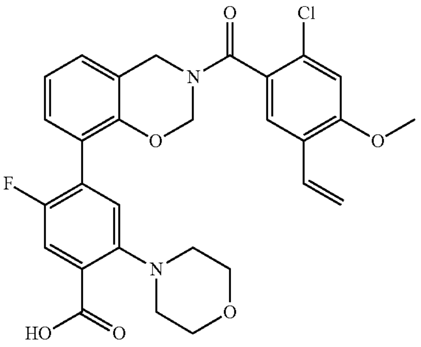 [SMILES: C=Cc1cc(C(=O)N2COc3c(cccc3-c3cc(N4CCOCC4)c(C(=O)O)cc3F)C2)c(Cl)cc1OC] | 4-[3-(2-Chloro-5-ethenyl-4-methoxybenzoyl)-2,4-dihydro-1,3-benzoxazin-8-yl]-5-fluoro-2-morpholin-4-ylbenzoic acid | B | 1.48 | 553 |
| 18-2 | 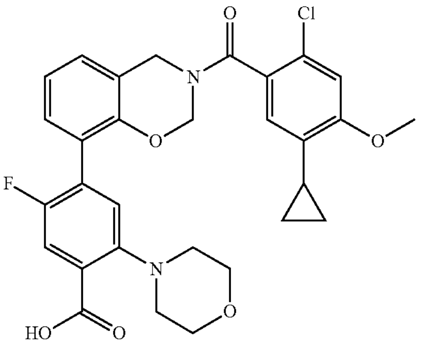 [SMILES: COc1cc(Cl)c(C(=O)N2COc3c(cccc3-c3cc(N4CCOCC4)c(C(=O)O)cc3F)C2)cc1C1CC1] | 4-[3-(2-Chloro-5-cyclopropyl-4-methoxybenzoyl)-2,4-dihydro-1,3-benzoxazin-8-yl]-5-fluoro-2-morpholin-4-ylbenzoic acid | B | 1.5 | 567 |
| 18-3 | 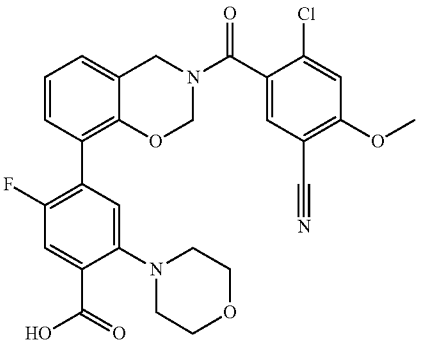 [SMILES: COc1cc(Cl)c(C(=O)N2COc3c(cccc3-c3cc(N4CCOCC4)c(C(=O)O)cc3F)C2)cc1C#N] | 4-[3-(2-Chloro-5-cyano-4-methoxybenzoyl)-2,4-dihydro-1,3-benzoxazin-8-yl]-5-fluoro-2-morpholin-4-ylbenzoic acid | B | 1.35 | 552 |

TABLE 18-2

| Final compound No. | Carboxylic acid |
|---|---|
| 18-1 | 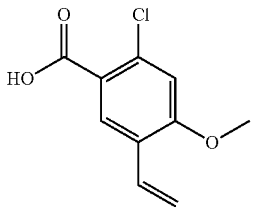 |

TABLE 18-2-continued

| Final compound No. | Carboxylic acid |
|---|---|
| 18-2 | 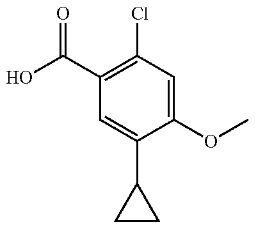 |

TABLE 18-2-continued

| Final compound No. | Carboxylic acid |
| --- | --- |
| 18-3 | 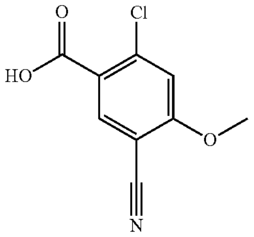 |

Compound 18-5

4-[3-[2,6-Dichloro-4-(1-methylpyrazol-4-yl)benzoyl]-2,4-dihydro-1,3-benzoxazin-8-yl]-2-thiomorpholin-4-ylbenzoic acid First Step Compound LAC2

Methyl 4-(3,4-dihydro-2H-1,3-benzoxazin-8-yl)-2-fluorobenzoate hydrochloride

[Formula 524]

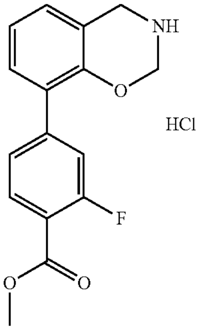

The title compound was obtained by the same operation as in the fifth step and the sixth step of compound 1-7 using tert-butyl 8-bromo-2,4-dihydro-1,3-benzoxazine-3-carboxylate and methyl 4-bromo-2-fluorobenzoate.

LCMS: m/z 288[M+H]+

HPLC retention time: 0.74 min (analysis condition G)

Second Step

Compound LAC3

Methyl 4-[3-[2,6-dichloro-4-(1-methylpyrazol-4-yl)benzoyl]-2,4-dihydro-1,3-benzoxazin-8-yl]-2-fluorobenzoate

[Formula 525]

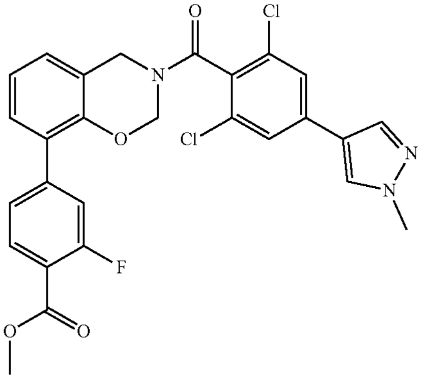

The title compound was obtained by the same operation as in the fifth step of compound B using methyl 4-(3,4-dihydro-2H-1,3-benzoxazin-8-yl)-2-fluorobenzoate hydrochloride and 2,6-dichloro-4-(1-methylpyrazol-4-yl)benzoyl chloride.

LCMS: m/z 540[M+H]+

HPLC retention time: 1.27 min (analysis condition G)

Third Step

Compound 18-5

4-[3-[2,6-Dichloro-4-(1-methylpyrazol-4-yl)benzoyl]-2,4-dihydro-1,3-benzoxazin-8-yl]-2-thiomorpholin-4-ylbenzoic acid

[Formula 526]

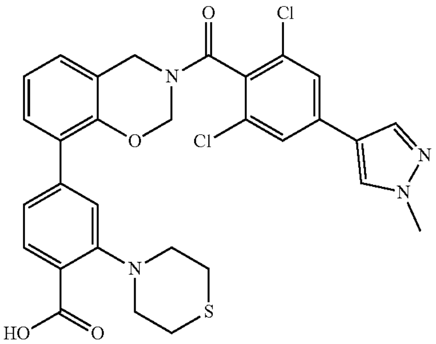

A solution of methyl 4-[3-[2,6-dichloro-4-(1-methylpyrazol-4-yl)benzoyl]-2,4-dihydro-1,3-benzoxazin-8-yl]-2-fluorobenzoate (20.0 mg, 0.037 mmol) and thiomorpholine (11.5 mg, 0.111 mmol) in dimethyl sulfoxide (0.200 ml) was stirred at 150° C. for 3 hours. A 2 M aqueous sodium hydroxide solution (0.0370 ml, 0.074 mmol) was added to the reaction solution, and the mixture was stirred at room temperature for 3 hours. The reaction solution was purified by reverse phase column chromatography (acetonitrile/water, 0.1% formic acid) to obtain the title compound (82%, 18.6 mg).

LCMS: m/z 609[M+H]$^+$

HPLC retention time: 1.07 min and 1.08 min (analysis condition A)

Compound 18-6

4-[3-[2,6-Dichloro-4-(4-methylpiperazin-1-yl)benzoyl]-2,4-dihydro-1,3-benzoxazin-8-yl]-5-fluoro-2-pyrrolidin-1-ylbenzoic acid First Step Compound LAC5 tert-Butyl 8-(2,5-difluoro-4-methoxycarbonylphenyl)-2,4-dihydro-1,3-benzoxazine-3-carboxylate

[Formula 527]

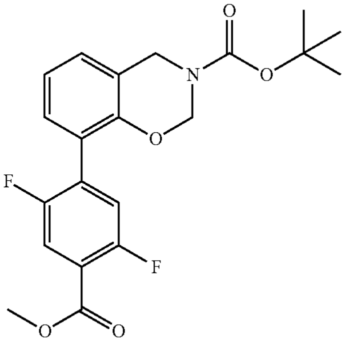

A solution of tert-butyl 8-(4,4,5,5-tetramethyl-1,3,2-dioxaborolan-2-yl)-2,4-dihydro-1,3-benzoxazine-3-carboxylate (50.0 mg, 0.138 mmol), methyl 4-bromo-2,5-difluorobenzoate (34.7 mg, 0.138 mmol), potassium carbonate (57.4 mg, 0.415 mmol) and a 1,1'-bis(diphenylphosphino) ferrocene-palladium(II) dichloride dichloromethane complex (5.06 mg, 0.00692 mmol) in 1,4-dioxane (0.419 ml) and water (0.0419 ml) was stirred at 100° C. for 2 hours. The reaction solution was purified by reverse phase column chromatography (acetonitrile/water, 0.1% formic acid) to obtain the title compound (70%, 39.5 mg).

LCMS: m/z 306[M-tBu+H]$^+$

HPLC retention time: 0.98 min (analysis condition D)

Second Step

Compound LAC7

Methyl 4-[3-(4-bromo-2,6-dichlorobenzoyl)-2,4-dihydro-1,3-benzoxazin-8-yl]-2,5-difluorobenzoate

[Formula 528]

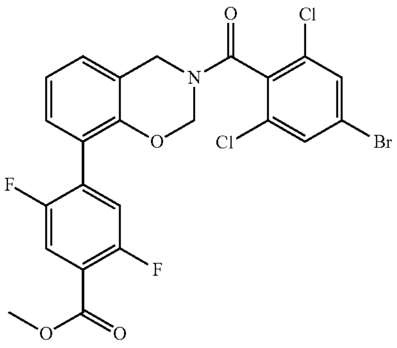

The title compound was obtained by the same operation as in the fourth step and the fifth step of compound B using tert-butyl 8-(2,5-difluoro-4-methoxycarbonylphenyl)-2,4-dihydro-1,3-benzoxazine-3-carboxylate.

LCMS: m/z 556[M+H]$^+$

HPLC retention time: 1.01 min (analysis condition D)

Third Step

Compound LAC8

Methyl 4-[3-[2,6-dichloro-4-(4-methylpiperazin-1-yl)benzoyl]-2,4-dihydro-1,3-benzoxazin-8-yl]-2,5-difluorobenzoate

[Formula 529]

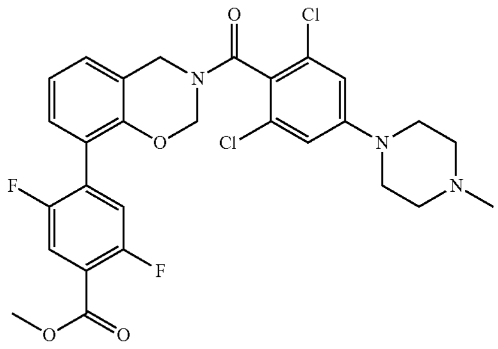

A solution of methyl 4-[3-(4-bromo-2,6-dichlorobenzoyl)-2,4-dihydro-1,3-benzoxazin-8-yl]-2,5-difluorobenzoate (300 mg, 0.538 mmol), 1-methylpiperazine (0.119 ml, 1.08 mmol), cesium carbonate (526 mg, 1.62 mmol), tris (dibenzylideneacetone)dipalladium(II) (49.3 mg, 0.0540 mmol) and 2,2'-bis(diphenylphosphino)-1,1'-binaphthyl (67.1 mg, 0.108 mmol) in toluene (5.38 ml) was stirred at 100° C. for 2.5 hours. The reaction solution was purified by reverse phase column chromatography (acetonitrile/water, 0.1% formic acid) to obtain the title compound (84%, 262 mg).

LCMS: m/z 576[M+H]$^+$

HPLC retention time: 0.60 min (analysis condition D)

Fourth Step
Compound 18-6

4-[3-[2,6-Dichloro-4-(4-methylpiperazin-1-yl)benzoyl]-2,4-dihydro-1,3-benzoxazin-8-yl]-5-fluoro-2-pyrrolidin-1-ylbenzoic acid

[Formula 530]

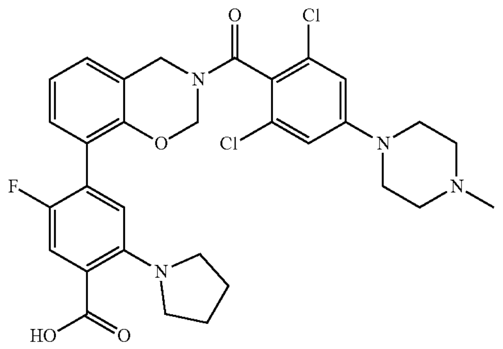

A solution of methyl 4-[3-[2,6-dichloro-4-(4-methylpiperazin-1-yl)benzoyl]-2,4-dihydro-1,3-benzoxazin-8-yl]-2,5-difluorobenzoate (30.0 mg, 0.052 mmol) and pyrrolidine (0.0430 ml, 0.520 mmol) in 1-methylpyrrolidin-2-one (0.347 ml) was stirred at 130° C. for 1 hour. After cooling to room temperature, a 2 M aqueous potassium hydroxide solution (0.260 ml, 0.520 mmol) was added thereto, and the mixture was stirred at 60° C. for 1 hour. The reaction solution was purified by reverse phase column chromatography (acetonitrile/water, 0.1% formic acid) to obtain the title compound (26%, 8.2 mg).

LCMS: m/z 613[M+H]$^+$

HPLC retention time: 0.90 min and 0.96 min (analysis condition B)

Compound 18-7

4-[3-[2,6-Dichloro-4-(3-methoxyazetidin-1-yl)benzoyl]-6-methoxy-2,4-dihydro-1,3-benzoxazin-8-yl]-5-fluoro-2-(3-oxa-8-azabicyclo[3.2.1]octan-8-yl) benzoic acid First Step
Compound MO1

Methyl 4-[3-[2,6-dichloro-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoate

[Formula 531]

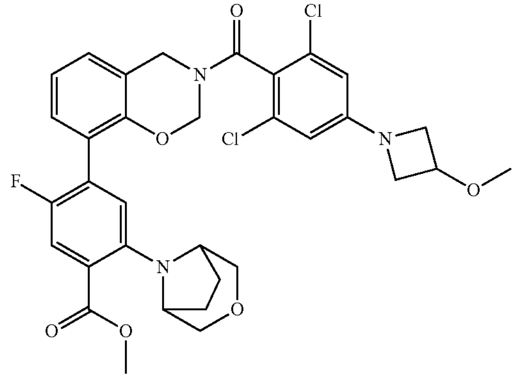

A suspension of compound A (300 mg, 0.461 mmol), 3-methoxyazetidine hydrochloride (114 mg, 0.923 mmol), rac-BINAP Pd G4 (46.4 mg, 0.0460 mmol) and cesium carbonate (601 mg, 1.84 mmol) in 1,4-dioxane (4.62 mL) was stirred at 100° C. for 1 hour. A 50% aqueous formic acid solution was added to the reaction mixture, and the mixture was then purified by HPLC (acetonitrile/water, 0.1% formic acid) to obtain the title compound (79%, 240 mg).

LCMS: m/z 657[M+H]$^+$

HPLC retention time: 0.95 min (analysis condition D)

Second Step

Compound MO2

Methyl 4-[3-[2,6-dichloro-4-(3-methoxyazetidin-1-yl)benzoyl]-6-(4,4,5,5-tetramethyl-1,3,2-dioxaborolan-2-yl)-2,4-dihydro-1,3-benzoxazin-8-yl]-5-fluoro-2-(3-oxa-8-azabicyclo[3.2.1]octan-8-yl)benzoate

[Formula 532]

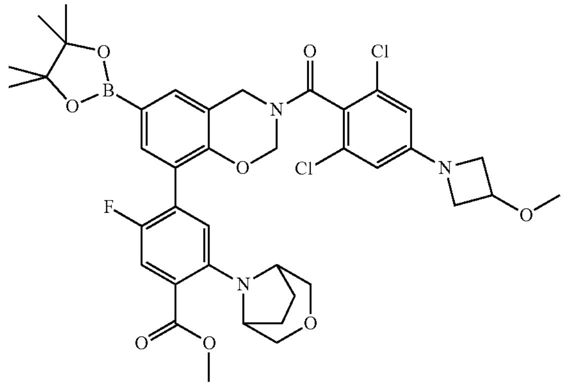

A solution of methyl 4-[3-[2,6-dichloro-4-(3-methoxyazetidin-1-yl)benzoyl]-2,4-dihydro-1,3-benzoxazin-8-yl]-5-fluoro-2-(3-oxa-8-azabicyclo[3.2.1]octan-8-yl)benzoate (240 mg, 0.366 mmol), 4,4,4',4',5,5,5',5'-octamethyl-2,2'-bi-1,3,2-dioxaborolane (371 mg, 1.46 mmol), 4,4'-di-tert-butyl-2,2'-bipyridine (39.2 mg, 0.146 mmol) and bis(1,5-cyclooctadiene)di-μ-methoxy diiridium (J) (48.5 mg, 0.073 mmol) in tetrahydrofuran (3.60 mL) was stirred at room temperature for 15 hours. Methanol was added to the reaction mixture, and the mixture was concentrated. Then, the residue was purified by column chromatography (hexane/ethyl acetate) to obtain the title compound (98%, 281 mg, purity: 89%) as a mixture with an isomer.

LCMS: m/z 782[M+H]$^+$

HPLC retention time: 1.09 min (analysis condition D)

Third Step

Compound MO3

Methyl 4-[3-[2,6-dichloro-4-(3-methoxyazetidin-1-yl)benzoyl]-6-hydroxy-2,4-dihydro-1,3-benzoxazin-8-yl]-5-fluoro-2-(3-oxa-8-azabicyclo[3.2.1]octan-8-yl)benzoate

[Formula 533]

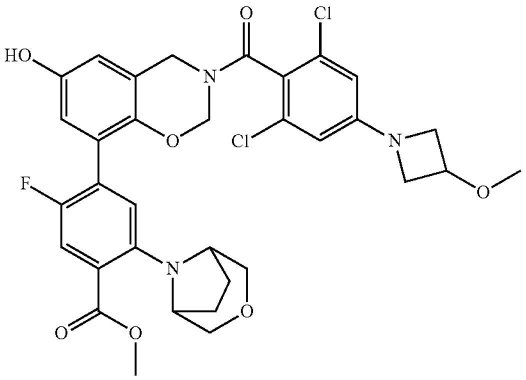

A solution of methyl 4-[3-[2,6-dichloro-4-(3-methoxyazetidin-1-yl)benzoyl]-6-(4,4,5,5-tetramethyl-1,3,2-dioxaborolan-2-yl)-2,4-dihydro-1,3-benzoxazin-8-yl]-5-fluoro-2-(3-oxa-8-azabicyclo[3.2.1]octan-8-yl)benzoate (256 mg, 0.327 mmol) and 35% hydrogen peroxide water (0.0318 mL, 0.327 mmol) in methanol (1.63 mL) was stirred at room temperature for 3 hours. A solution of 35% hydrogen peroxide water (0.0318 mL, 0.327 mmol) in methanol (1.63 mL) was further added thereto, and the mixture was stirred at room temperature for 3 hours. A solution of 35% hydrogen peroxide water (0.0318 mL, 0.327 mmol) in methanol (1.63 mL) was further added thereto, and the mixture was stirred at room temperature for 1.5 hours. A solution of 35% hydrogen peroxide water (0.0318 mL, 0.327 mmol) in methanol (1.63 mL) was further added thereto, and the mixture was stirred at room temperature for 13.5 hours. A saturated aqueous solution of sodium thiosulfate was added to the reaction mixture, and the mixture was diluted with ethyl acetate and washed with water. The organic layer was dried over sodium sulfate, filtered, and then concentrated, and the obtained residue was purified by HPLC (acetonitrile/water, 0.1% formic acid) to obtain the title compound (85%, 186 mg).

LCMS: m/z 672[M+H]$^+$

HPLC retention time: 0.81 min (analysis condition D)

Fourth Step

Compound MO4

Methyl 4-[3-[2,6-dichloro-4-(3-methoxyazetidin-1-yl)benzoyl]-6-methoxy-2,4-dihydro-1,3-benzoxazin-8-yl]-5-fluoro-2-(3-oxa-8-azabicyclo[3.2.1]octan-8-yl)benzoate

[Formula 534]

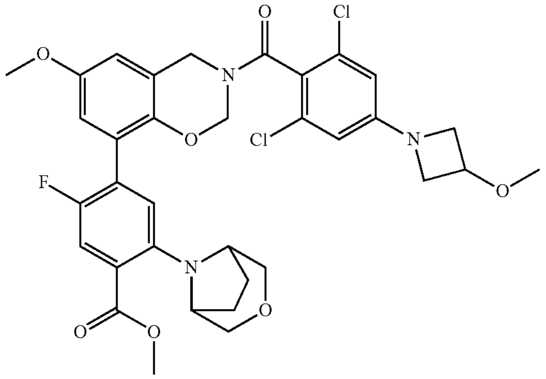

A suspension of methyl 4-[3-[2,6-dichloro-4-(3-methoxyazetidin-1-yl)benzoyl]-6-hydroxy-2,4-dihydro-1,3-benzoxazin-8-yl]-5-fluoro-2-(3-oxa-8-azabicyclo[3.2.1]octan-8-yl)benzoate (40.0 mg, 0.059 mmol), iodomethane (0.0186 mL, 0.297 mmol) and potassium carbonate (12.3 mg, 0.0890 mmol) in 1-methylpyrrolidin-2-one (0.600 mL) was stirred at room temperature for 1.5 hours. A 50% aqueous formic acid solution was added to the reaction mixture, and the mixture was then purified by HPLC (acetonitrile/water, 0.1% formic acid) to obtain the title compound (67%, 27.5 mg).

LCMS: m/z 686[M+H]$^+$

HPLC retention time: 0.95 min (analysis condition D)

Fifth Step

Compound 18-7

4-[3-[2,6-Dichloro-4-(3-methoxyazetidin-1-yl)benzoyl]-6-methoxy-2,4-dihydro-1,3-benzoxazin-8-yl]-5-fluoro-2-(3-oxa-8-azabicyclo[3.2.1]octan-8-yl) benzoic acid

[Formula 535]

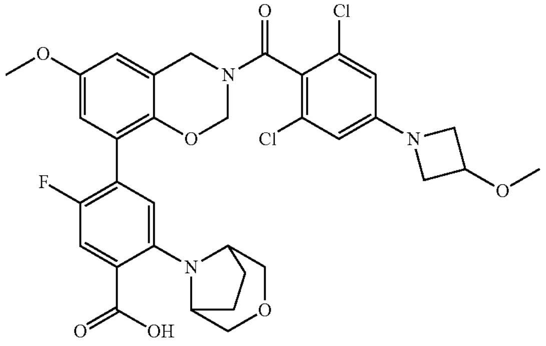

A solution of methyl 4-[3-[2,6-dichloro-4-(3-methoxyazetidin-1-yl)benzoyl]-6-methoxy-2,4-dihydro-1,3-benzoxazin-8-yl]-5-fluoro-2-(3-oxa-8-azabicyclo[3.2.1]octan-8-yl)benzoate (33.2 mg, 0.0480 mmol) and potassium hydroxide (27.1 mg, 0.484 mmol) in 1-methylpyrrolidin-2-one (0.480 mL) was stirred at 60° C. for 1 hour. A 50% aqueous formic acid solution was added to the reaction mixture, and the mixture was then purified by HPLC (acetonitrile/water, 0.1% formic acid) to obtain the title compound (80%, 26.1 mg).

LCMS: m/z 672[M+H]$^+$

HPLC retention time: 1.51 min and 1.52 min (analysis condition B)

Compound 18-8

4-[3-[2,6-Dichloro-4-(1-methylpyrazol-4-yl)benzoyl]-2,4-dihydro-1H-quinazolin-8-yl]-5-fluoro-2-morpholin-4-ylbenzoic acid First Step Compound COR1

4-Bromo-5-fluoro-2-morpholin-4-ylbenzoic acid

[Formula 536]

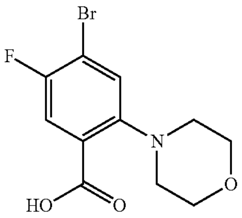

To 4-bromo-2,5-difluorobenzoic acid (950 mg, 4.01 mmol), morpholine (6.98 ml, 80.0 mmol) was added, and the mixture was stirred at 100° C. for 24 hours. Ethyl acetate and hydrochloric acid were added to the reaction solution for extraction. Then, the organic layer was washed with a saturated aqueous solution of sodium chloride, followed by passing through a phase separator. Then, the organic layer was concentrated. Ethyl acetate and hexane were added to the obtained residue, and the mixture was triturated to obtain the title compound (98%, 1.20 g).

LCMS: m/z 304[M+H]$^+$

HPLC retention time: 0.77 min (analysis condition N)

Second Step

Compound 18-8

4-[3-[2,6-Dichloro-4-(1-methylpyrazol-4-yl)benzoyl]-2,4-dihydro-1H-quinazolin-8-yl]-5-fluoro-2-morpholin-4-ylbenzoic acid

[Formula 537]

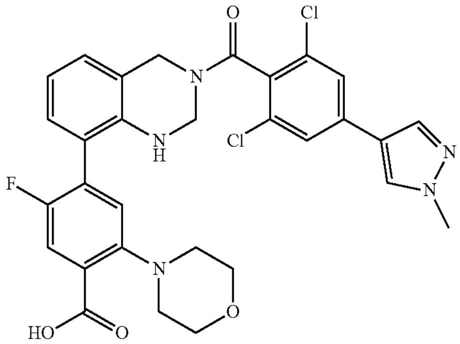

A solution of 4-bromo-5-fluoro-2-morpholin-4-ylbenzoic acid (36.5 mg, 0.120 mmol), a 1,1'-bis(diphenylphosphino)ferrocene-palladium(II) dichloride dichloromethane complex (4.40 mg, 0.00601 mmol) and potassium acetate (17.7 mg, 0.180 mmol) in 1,4-dioxane (0.300 ml) was stirred at 90° C. for 2 hours. (8-Bromo-2,4-dihydro-1H-quinazolin-3-yl)-[2,6-dichloro-4-(1-methylpyrazol-4-yl)phenyl]methanone (28.0 mg, 0.0600 mmol), a 1,1'-bis(diphenylphosphino)ferrocene-palladium(II) dichloride dichloromethane complex (4.40 mg, 0.00601 mmol) and a 2 M aqueous sodium carbonate solution (0.0900 ml, 0.180 mmol) were added to the reaction solution, and the mixture was stirred at 90° C. for 2 hours. The reaction solution was purified by HPLC (acetonitrile/water, 0.1% formic acid) to obtain the title compound (57%, 21.0 mg).

LCMS: m/z 610[M+H]$^+$

HPLC retention time: 0.98 min (analysis condition A)

Compound 18-9

4-[3-[2,6-Dichloro-4-(1-methylpyrazol-4-yl)benzoyl]-2-oxo-1,4-dihydroquinazolin-8-yl]-5-fluoro-2-morpholin-4-ylbenzoic acid

[Formula 538]

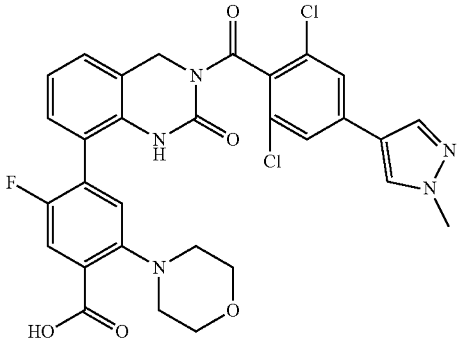

The title compound (52%, 13.4 mg) was obtained by the same operation as in the second step of compound 18-8 using 4-bromo-5-fluoro-2-morpholin-4-ylbenzoic acid and 8-bromo-3-[2,6-dichloro-4-(1-methylpyrazol-4-yl)benzoyl]-1,4-dihydroquinazolin-2-one.

LCMS: m/z 624[M+H]$^+$

HPLC retention time: 1.03 min (analysis condition A)

Compound 18-10

6-[3-[2,6-Dichloro-4-(4-morpholin-4-ylpiperidin-1-yl)benzoyl]-2,4-dihydro-1,3-benzoxazin-8-yl]-2-piperidin-1-ylpyridine-3-carboxylic acid First Step Compound CC1

Methyl 6-chloro-2-piperidin-1-ylpyridine-3-carboxylate

[Formula 539]

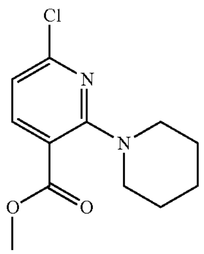

To a solution of 6-chloro-2-piperidin-1-ylpyridine-3-carboxylic acid (1.46 g, 6.07 mmol) and potassium carbonate (2.52 g, 18.2 mmol) in N,N-dimethylformamide (10.0 mL), iodomethane (1.29 g, 9.10 mmol) was added, and the mixture was stirred at room temperature for 1 hour. The reaction solution was subjected to extraction with ethyl acetate. The organic layer was washed with water. The organic layer was concentrated, and the obtained residue was purified by silica gel column chromatography (hexane/ethyl acetate) to obtain the title compound (100%, 1.54 g).

LCMS: m/z 255[M+H]$^+$

HPLC retention time: 0.98 min (analysis condition O)

Second Step

Compound CC2 tert-Butyl 8-(5-methoxycarbonyl-6-piperidin-1-ylpyridin-2-yl)-2,4-dihydro-1,3-benzoxazine-3-carboxylate

[Formula 540]

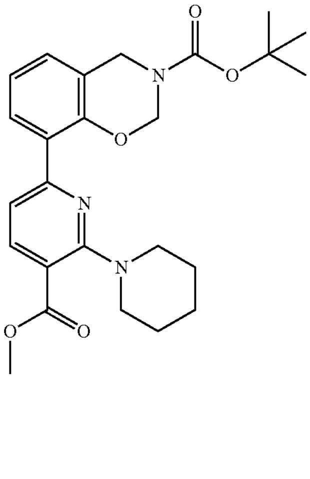

To a solution of tert-butyl 8-bromo-2,4-dihydro-1,3-benzoxazine-3-carboxylate (649 mg, 2.07 mmol), potassium acetate (608 mg, 6.20 mmol) and bis(pinacolato)diboron (682 mg, 2.69 mmol) in 1,4-dioxane (12.0 mL), a 1,1'-bis(diphenylphosphino)ferrocene-palladium(II) dichloride dichloromethane complex (151 mg, 0.207 mmol) was added, and the mixture was stirred at 90° C. for 16 hours. Potassium carbonate (856 mg, 6.20 mmol), water (4.00 mL) and methyl 6-chloro-2-piperidin-1-ylpyridine-3-carboxylate (526 mg, 2.07 mmol) were added to the reaction solution, and the mixture was stirred at 90° C. for 1 hour. 1,4-Dioxane was removed, followed by extraction with ethyl acetate. The extract was washed with a saturated aqueous solution of sodium chloride. The obtained residue was purified by silica gel column chromatography (hexane/ethyl acetate) to obtain the title compound (71%, 695 mg).

LCMS: m/z 454[M+H]$^+$

HPLC retention time: 1.14 min (analysis condition O)

Third Step

Compound CC3

Methyl 6-[3-(aminomethyl)-2-hydroxyphenyl]-2-piperidin-1-ylpyridine-3-carboxylate

[Formula 541]

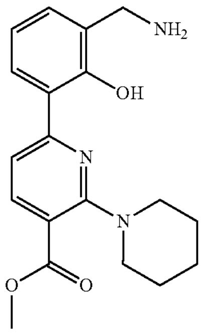

A solution of tert-butyl 8-(5-methoxycarbonyl-6-piperidin-1-ylpyridin-2-yl)-2,4-dihydro-1,3-benzoxazine-3-carboxylate (710 mg, 1.57 mmol) in ethyl acetate (5.00 mL) was cooled to 0° C. A 4 M solution of hydrochloric acid in 1,4-dioxane (10.0 mL, 40.0 mmol) was added thereto, and the mixture was stirred at 0° C. for 1 hour. Ethyl acetate was added to the reaction solution, and the mixture was filtered and washed with hexane. The reaction solution was mixed with another compound obtained by the same method as described above, purified by reverse phase column chromatography (acetonitrile/water, 0.1% formic acid), and then purified by silica gel column chromatography ($NH_2$ silica gel, dichloromethane/ethyl acetate) to obtain the title compound (362 mg).

LCMS: m/z 342[M+H]$^+$

HPLC retention time: 0.50 min (analysis condition O)

Fourth Step

Compound CC4

Methyl 6-[3-[[(4-bromo-2,6-dichlorobenzoyl)amino]methyl]-2-hydroxyphenyl]-2-piperidin-1-ylpyridine-3-carboxylate

[Formula 542]

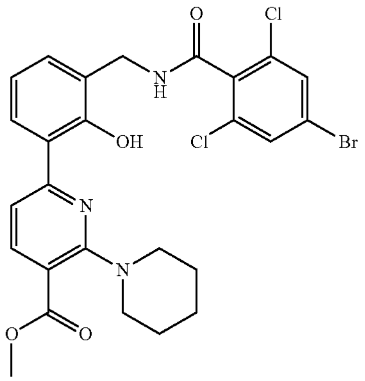

To a solution of methyl 6-[3-(aminomethyl)-2-hydroxyphenyl]-2-piperidin-1-ylpyridine-3-carboxylate (460 mg, 1.35 mmol) and 4-bromo-2,6-dichlorobenzoyl chloride (389 mg, 1.35 mmol) in dichloromethane (10.0 mL), N,N-diisopropylethylamine (0.742 mL, 4.04 mmol) was added, and the mixture was stirred at room temperature for 1 hour. The reaction solution was subjected to extraction with ethyl acetate. The extract was washed with water and then concentrated. The obtained residue was purified by reverse phase column chromatography (acetonitrile/water, 0.1% formic acid) to obtain the title compound (92%, 620 mg).

LCMS: m/z 592$[M+H]^+$

HPLC retention time: 1.08 min (analysis condition 0)

Fifth Step

Compound CC5

Methyl 6-[3-(4-bromo-2,6-dichlorobenzoyl)-2,4-dihydro-1,3-benzoxazin-8-yl]-2-piperidin-1-ylpyridine-3-carboxylate

[Formula 543]

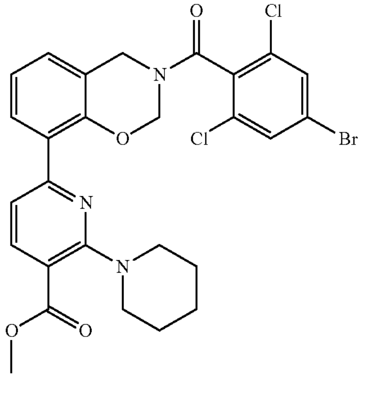

To a solution of methyl 6-[3-[[(4-bromo-2,6-dichlorobenzoyl)amino]methyl]-2-hydroxyphenyl]-2-piperidin-1-ylpyridine-3-carboxylate (620 mg, 1.05 mmol) and p-toluenesulfonic acid monohydrate (209 mg, 1.10 mmol) in toluene (25.0 mL), paraformaldehyde (314 mg, 10.5 mmol) was added, and the mixture was stirred at 90° C. for 3 hours. The reaction mixture was further stirred at 90° C. for 1 hour. The reaction solution was subjected to extraction with ethyl acetate. The organic layer was washed with a saturated aqueous solution of sodium bicarbonate, and the obtained residue was purified by NH silica gel column chromatography and then purified by reverse phase column chromatography (acetonitrile/water, 0.1% formic acid) to obtain the title compound (17%, 110 mg).

LCMS: m/z 604$[M+H]^+$

HPLC retention time: 1.16 min (analysis condition O)

Sixth Step

Compound CC6

Methyl 6-[3-[2,6-dichloro-4-(4-morpholin-4-ylpiperidin-1-yl)benzoyl]-2,4-dihydro-1,3-benzoxazin-8-yl]-2-piperidin-1-ylpyridine-3-carboxylate

[Formula 544]

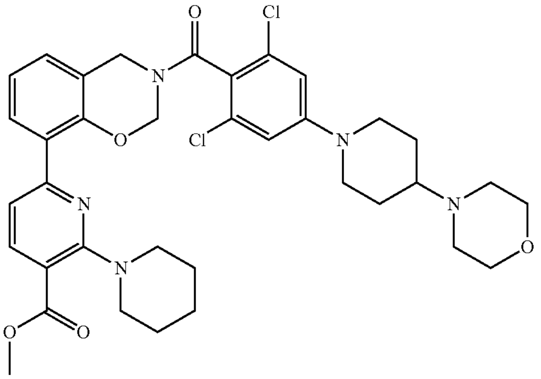

A solution of methyl 6-[3-(4-bromo-2,6-dichlorobenzoyl)-2,4-dihydro-1,3-benzoxazin-8-yl]-2-piperidin-1-ylpyridine-3-carboxylate (27.0 mg, 0.045 mmol), 4-(piperidin-4-yl)morpholine (9.11 mg, 0.054 mmol), tris(dibenzylideneacetone)dipalladium(0) (4.08 mg, 0.00446 mmol), cesium carbonate (43.6 mg, 0.134 mmol) and 2,2'-bis(diphenylphosphino)-1,1'-binaphthyl (4.17 mg, 0.00669 mmol) in toluene was stirred at 90° C. for 2 hours. Ethyl acetate was added to the reaction solution, and the mixture was filtered through celite. The filtrate was concentrated, and the obtained residue was purified by NH silica gel column chromatography (hexane/ethyl acetate) to obtain the title compound (77%, 24.0 mg).

LCMS: m/z 694$[M+H]^+$

HPLC retention time: 0.66 min and 0.68 min (analysis condition O)

Seventh Step
Compound 18-10

6-[3-[2,6-Dichloro-4-(4-morpholin-4-ylpiperidin-1-yl)benzoyl]-2,4-dihydro-1,3-benzoxazin-8-yl]-2-piperidin-1-ylpyridine-3-carboxylic acid

[Formula 545]

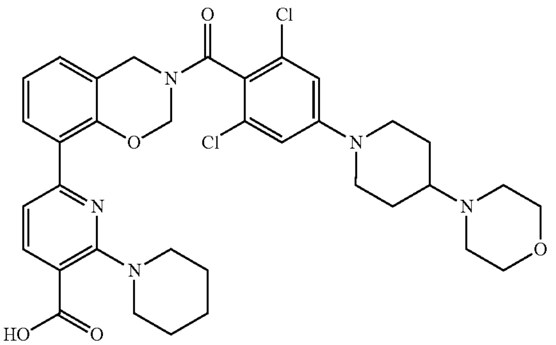

To a solution of methyl 6-[3-[2,6-dichloro-4-(4-morpholin-4-ylpiperidin-1-yl)benzoyl]-2,4-dihydro-1,3-benzoxazin-8-yl]-2-piperidin-1-ylpyridine-3-carboxylate (23.0 mg, 0.0330 mmol) in tetrahydrofuran (1.00 mL), sodium hydroxide (13.2 mg, 0.331 mmol) and water (0.500 mL) were added, and the mixture was stirred at 65° C. for 16 hours. The reaction solution was purified by reverse phase column chromatography (acetonitrile/water, 0.1% formic acid) to obtain the title compound (89%, 20.0 mg).

LCMS: m/z 680[M+H]$^+$

HPLC retention time: 0.81 min (analysis condition A)

Compound 18-11

6-[2-[2,6-Dichloro-4-(1-methylpyrazol-4-yl)benzoyl]-3,4-dihydro-1H-isoquinolin-5-yl]-2-piperidin-1-ylpyridine-3-carboxylic acid First Step
Compound COR4

5-(4,4,5,5-Tetramethyl-1,3,2-dioxaborolan-2-yl)-1,2,3,4-tetrahydroisoquinoline hydrochloride

[Formula 546]

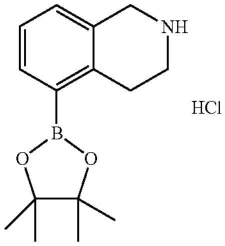

To tert-butyl 5-(4,4,5,5-tetramethyl-1,3,2-dioxaborolan-2-yl)-3,4-dihydro-1H-isoquinoline-2-carboxylate (1.00 g, 2.78 mmol), a 4 M solution of hydrochloric acid in 1,4-dioxane (17.4 ml, 69.6 mmol) was added, and the mixture was stirred at room temperature for 30 minutes. The reaction solution was concentrated to obtain the title compound as a crude product.

LCMS: m/z 260[M+H]$^+$

HPLC retention time: 0.70 min (analysis condition H)

Second Step
Compound COR2

[2,6-Dichloro-4-(1-methylpyrazol-4-yl)phenyl]-[5-(4,4,5,5-tetramethyl-1,3,2-dioxaborolan-2-yl)-3,4-dihydro-1H-isoquinolin-2-yl]methanone

[Formula 547]

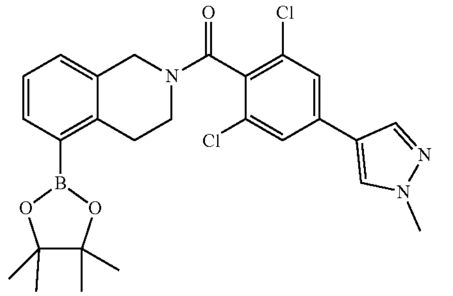

The title compound was obtained by the same operation as in the fifth step of compound B using 5-(4,4,5,5-tetramethyl-1,3,2-dioxaborolan-2-yl)-1,2,3,4-tetrahydroisoquinoline hydrochloride and 2,6-dichloro-4-(1-methylpyrazol-4-yl)benzoyl chloride.

LCMS: m/z 512[M+H]$^+$

HPLC retention time: 1.37 min and 1.39 min (analysis condition H)

Third Step
Compound COR3

2-Chloro-6-[2-[2,6-dichloro-4-(1-methylpyrazol-4-yl)benzoyl]-3,4-dihydro-1H-isoquinolin-5-yl]pyridine-3-carboxylic acid

[Formula 548]

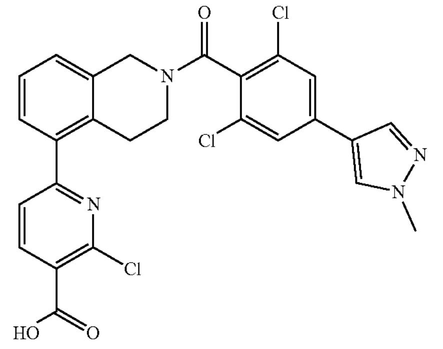

A solution of [2,6-dichloro-4-(1-methylpyrazol-4-yl)phenyl]-[5-(4,4,5,5-tetramethyl-1,3,2-dioxaborolan-2-yl)-3,4-dihydro-1H-isoquinolin-2-yl]methanone (50.0 mg, 0.0890 mmol), 2,6-dichloropyridine-3-carboxylic acid (20.5 mg, 0.107 mmol), sodium carbonate (18.8 mg, 0.178 mmol) and tetrakis(triphenylphosphine)palladium(0) in N,N-dimethylformamide (0.200 ml) and water (0.0500 ml) was stirred at 100° C. for 4 hours. The reaction solution was purified by reverse phase column chromatography (acetonitrile/water, 0.1% formic acid) to obtain the title compound (100%, 49.1 mg).

LCMS: m/z 541[M+H]$^+$

HPLC retention time: 1.03 min (analysis condition H)

Fourth Step

Compound 18-11

6-[2-[2,6-Dichloro-4-(1-methylpyrazol-4-yl)benzoyl]-3,4-dihydro-1H-isoquinolin-5-yl]-2-piperidin-1-ylpyridine-3-carboxylic acid

[Formula 549]

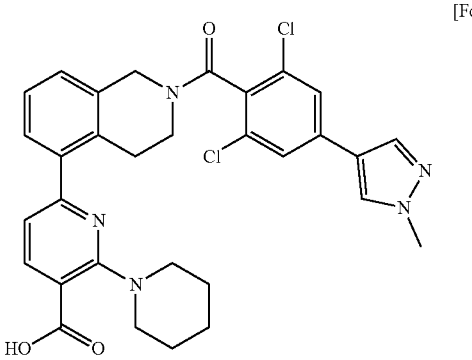

A solution of 2-chloro-6-[2-[2,6-dichloro-4-(1-methylpyrazol-4-yl)benzoyl]-3,4-dihydro-1H-isoquinolin-5-yl]pyridine-3-carboxylic acid (24.0 mg, 0.0440 mmol) and piperidine (18.9 mg, 0.221 mmol) in 1-methylpyrrolidin-2-one (0.200 ml) was stirred overnight at 120° C. The reaction solution was purified by reverse phase column chromatography (acetonitrile/water, 0.1% formic acid) to obtain the title compound (26.4%, 6.90 mg).

LCMS: m/z 590[M+H]$^+$

HPLC retention time: 1.00 min (analysis condition C)

Compound 18-12

4-[3-[2,6-Dichloro-4-(1-methylpyrazol-4-yl)benzoyl]-2,4-dihydropyrido[4,3-e][1,3]oxazin-8-yl]-2-morpholin-4-ylbenzoic acid First Step Compound RPD1 tert-Butyl N-[(2-bromo-3-hydroxypyridin-4-yl)methyl]carbamate

[Formula 550]

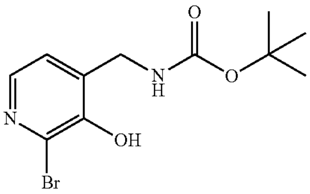

A solution of 2-bromo-3-hydroxypyridine-4-carbaldehyde (208 mg, 1.03 mmol), tert-butyl carbamate (362 mg, 3.09 mmol), rhenium(VII) oxide (15.0 mg, 0.0310 mmol) and triethylsilane (0.493 ml, 3.09 mmol) in dichloromethane (10.3 ml) was stirred overnight at room temperature. Triethylsilane (0.493 ml, 3.09 mmol) was further added thereto, and the mixture was stirred at room temperature for 3 days. The reaction solution was purified by reverse phase column chromatography (acetonitrile/water, 0.1% formic acid) to obtain the title compound (25%, 79.0 mg).

LCMS: m/z 303[M+H]$^+$

HPLC retention time: 0.90 min (analysis condition G)

Second Step

Compound PRD2 tert-Butyl 8-bromo-2,4-dihydropyrido[4,3-e][1,3]oxazine-3-carboxylate

[Formula 551]

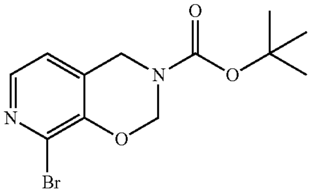

The title compound was obtained by the same operation as in the fourth step of compound G using tert-butyl N-[(2-bromo-3-hydroxypyridin-4-yl)methyl]carbamate.

LCMS: m/z 315[M+H]$^+$

HPLC retention time: 1.06 min (analysis condition G)

Third Step

Compound PRD3 tert-Butyl 8-(4-methoxycarbonyl-3-morpholin-4-ylphenyl)-2,4-dihydropyrido[4,3-e][1,3]oxazine-3-carboxylate

[Formula 552]

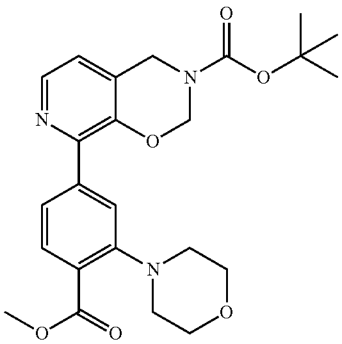

A solution of tert-butyl 8-bromo-2,4-dihydropyrido[4,3-e][1,3]oxazine-3-carboxylate (30.0 mg, 0.0950 mmol), methyl 2-morpholin-4-yl-4-(4,4,5,5-tetramethyl-1,3,2-dioxaborolan-2-yl)benzoate (31.5 mg, 0.0910 mmol), a 1,1'-bis(diphenylphosphino)ferrocene-palladium(II) dichloride dichloromethane complex (7.40 mg, 0.00907 mmol) and potassium carbonate (37.6 mg, 0.272 mmol) in 1,4-dioxane (0.363 ml) and water (0.091 ml) was stirred at 100° C. for 30 minutes. The reaction solution was purified by reverse phase column chromatography (acetonitrile/water, 0.1% formic acid) to obtain the title compound (75%, 30.8 mg).

LCMS: m/z 456[M+H]$^+$

HPLC retention time: 1.06 min (analysis condition G)

Fourth Step

Compound PRD4

Methyl 4-[3-[2,6-dichloro-4-(1-methylpyrazol-4-yl)benzoyl]-2,4-dihydropyrido[4,3-e][1,3]oxazin-8-yl]-2-morpholin-4-ylbenzoate

[Formula 553]

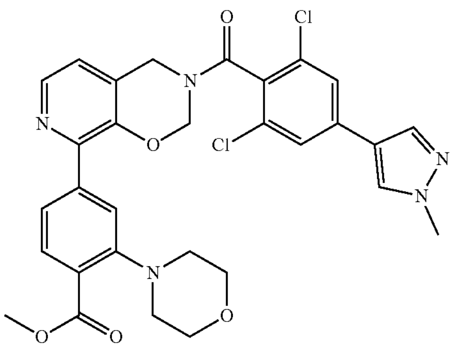

To a solution of tert-butyl 8-(4-methoxycarbonyl-3-morpholin-4-ylphenyl)-2,4-dihydropyrido[4,3-e][1,3]oxazine-3-carboxylate (30.8 mg, 0.068 mmol) in dichloromethane (0.338 ml), trifluoromethanesulfonic acid (0.0150 ml, 0.169 mmol) was added, and the mixture was stirred at room temperature for 1 hour. Trifluoromethanesulfonic acid (0.0150 ml, 0.169 mmol) was further added thereto, and the mixture was stirred at room temperature for 10 minutes. 2,6-Dichloro-4-(1-methylpyrazol-4-yl)benzoyl chloride (21.5 mg, 0.0740 mmol) and N,N-diisopropylethylamine (0.118 ml, 0.676 mmol) were added thereto, and the mixture was stirred at room temperature for 4 hours. The reaction solution was purified by HPLC (acetonitrile/water, 0.1% formic acid) to obtain the title compound (16%, 6.6 mg).

LCMS: m/z 608[M+H]$^+$

HPLC retention time: 1.00 min (analysis condition G)

Fifth Step

Compound 18-12

4-[3-[2,6-Dichloro-4-(1-methylpyrazol-4-yl)benzoyl]-2,4-dihydropyrido[4,3-e][1,3]oxazin-8-yl]-2-morpholin-4-ylbenzoic acid

[Formula 554]

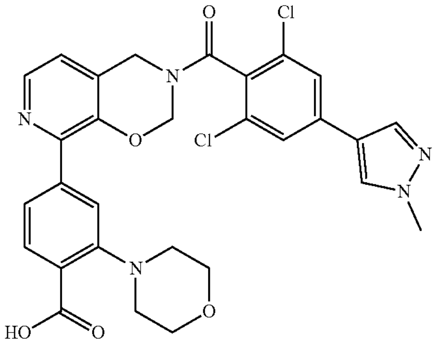

To a solution of methyl 4-[3-[2,6-dichloro-4-(1-methylpyrazol-4-yl)benzoyl]-2,4-dihydropyrido[4,3-e][1,3]oxazin-8-yl]-2-morpholin-4-ylbenzoate in tetrahydrofuran (0.0540 ml) and methanol (0.0540 ml), a 5 M aqueous sodium hydroxide solution (0.0217 ml, 0.108 mmol) was added, and the mixture was stirred at room temperature for 2 hours. The reaction solution was purified by HPLC (acetonitrile/water, 0.1% formic acid) to obtain the title compound (79%, 5.1 mg).

LCMS: m/z 594[M+H]$^+$

HPLC retention time: 0.85 min (analysis condition A)

Compound 19-5

4-[3-[2-Chloro-6-cyano-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 555]

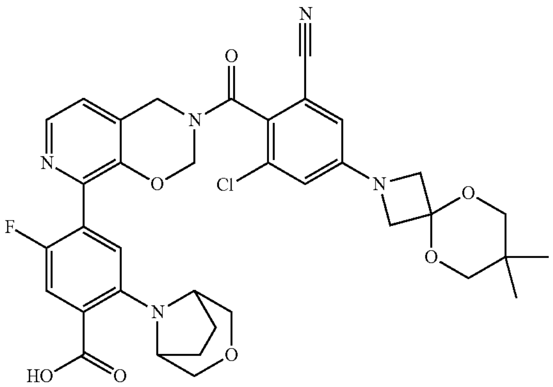

A solution of 4-[3-[2,6-dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid (200 mg, 0.281 mmol), zinc cyanide (19.8 mg, 0.168 mmol) and XPhos Pd G4 (24.2 mg, 0.0280 mmol) in N,N-dimethylacetamide (2.80 mL) was stirred at 120° C. for 20 minutes. The reaction mixture was purified by HPLC (acetonitrile/water, 0.1% formic acid) to obtain the title compound (20%, 40.0 mg).

LCMS: m/z 703[M+H]$^+$

HPLC retention time: 1.71 min (analysis condition B)

Compound 19-12

4-[3-[5-Chloro-7-(7,7-dimethyl-5,9-dioxa-2-azaspiro[3.5]nonan-2-yl)-3-methylbenzotriazole-4-carbonyl]-2,4-dihydro-1,3-benzoxazin-8-yl]-5-fluoro-2-(3-oxa-8-azabicyclo[3.2.1]octan-8-yl)benzoic acid First Step Compound BUa2

Methyl 5-acetamido-4-bromo-2-chlorobenzoate

[Formula 556]

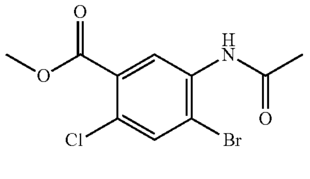

A solution of methyl 5-amino-4-bromo-2-chlorobenzoate (1.10 g, 4.16 mmol) and acetic anhydride (0.785 mL, 8.32 mmol) in toluene (11.0 mL) was stirred at 80° C. for 5 hours. The reaction solution was cooled to room temperature, and the obtained precipitate was washed with hexane to obtain the title compound (93%, 1.19 g).

LCMS: m/z 306[M+H]$^+$

HPLC retention time: 0.65 min (analysis condition D)

Second Step

Compound BUa3

Methyl 3-acetamido-4-bromo-6-chloro-2-nitrobenzoate

[Formula 557]

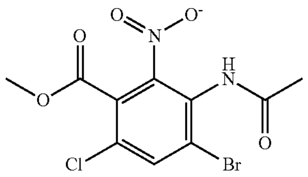

A mixture of fuming nitric acid (1.45) (5.00 mL, 90.0 mmol) and sulfuric acid (5.00 mL, 94.0 mmol) was cooled to 0° C. Methyl 5-acetamido-4-bromo-2-chlorobenzoate (1.10 g, 3.60 mmol) was added thereto, and the mixture was stirred at 0° C. for 65 minutes. Fuming nitric acid (1.45) (5.00 mL, 90.0 mmol) and sulfuric acid (5.00 mL, 94.0 mmol) were added thereto, and the mixture was stirred at 0° C. for 20 minutes. The reaction solution was added to ice water, followed by extraction with dichloromethane to obtain the title compound (103%, 1.30 g).

LCMS: m/z 351[M+H]$^+$

HPLC retention time: 0.64 min (analysis condition D)

Third Step

Compound BUa4

Methyl 3-acetamido-2-amino-4-bromo-6-chlorobenzoate

[Formula 558]

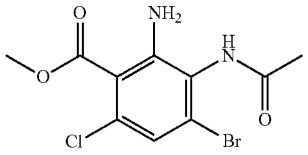

To a solution of methyl 3-acetamido-4-bromo-6-chloro-2-nitrobenzoate (1.22 g, 3.47 mmol) in tetrahydrofuran (15.0 mL), a solution of sodium dithionite (6.04 g, 34.7 mmol) in water (45.0 mL) was added, and the mixture was stirred at 50° C. for 1 hour. Sodium dithionite (3.02 g, 17.35 mmol) was added thereto, and the mixture was stirred at 50° C. for 4 hours. The reaction solution was subjected to extraction with ethyl acetate. The extract was concentrated to obtain the title compound (78%, 874 mg).

LCMS: m/z 321[M+H]$^+$

HPLC retention time: 0.59 min (analysis condition D)

Fourth Step

Compound BUa5

Methyl 7-bromo-5-chloro-3H-benzotriazole-4-carboxylate

[Formula 559]

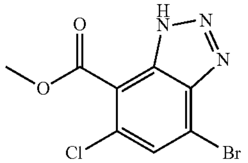

To a solution of methyl 3-acetamido-2-amino-4-bromo-6-chlorobenzoate (643 mg, 2.00 mmol) in acetic acid (10.0 mL), sodium nitrite (690 mg, 10.0 mmol) was added, and the mixture was stirred at room temperature for 45 minutes. Water was added to the reaction solution, and the mixture was filtered to obtain the title compound (68%, 397 mg).

LCMS: m/z 290[M+H]$^+$

HPLC retention time: 0.68 min (analysis condition D)

Fifth Step

Compound BUa6

7-Bromo-5-chloro-3-methylbenzotriazole-4-carboxylic acid

[Formula 560]

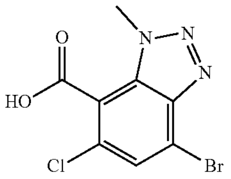

Compound BUa7

7-Bromo-5-chloro-2-methylbenzotriazole-4-carboxylic acid

[Formula 561]

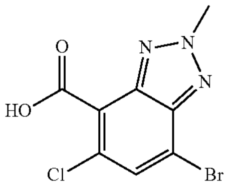

Compound BUa8

7-Bromo-5-chloro-1-methylbenzotriazole-4-carboxylic acid

[Formula 562]

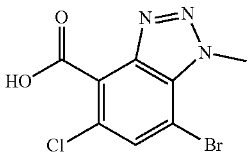

A solution of methyl 7-bromo-5-chloro-3H-benzotriazole-4-carboxylate (385 mg, 1.33 mmol), 55% sodium hydride (69.4 mg, 1.59 mmol) and iodomethane (0.249 mL, 3.98 mmol) in 1-methylpyrrolidin-2-one (5.00 mL) was stirred at room temperature for 1 hour. A 5 M aqueous sodium hydroxide solution (2.50 mL, 12.5 mmol) was added thereto, and the mixture was stirred at room temperature for 90 minutes. The reaction solution was purified by HPLC (acetonitrile/water, 0.1% formic acid) to obtain 7-bromo-5-chloro-3-methylbenzotriazole-4-carboxylic acid (33%, 129 mg), 7-bromo-5-chloro-2-methylbenzotriazole-4-carboxylic acid (34%, 132 mg) and 7-bromo-5-chloro-1-methylbenzotriazole-4-carboxylic acid (18%, 67.7 mg).

Compound BUa6

LCMS: m/z 290[M+H]$^+$

HPLC retention time: 0.41 min (analysis condition D)

Compound BUa7

LCMS: m/z 290[M+H]$^+$

HPLC retention time: 0.54 min (analysis condition D)

Compound BUa8

LCMS: m/z 290[M+H]$^+$

HPLC retention time: 0.49 min (analysis condition D)

Sixth Step

Compound BUa9

Methyl 4-[3-(7-bromo-5-chloro-3-methylbenzotriazole-4-carbonyl)-2,4-dihydro-1,3-benzoxazin-8-yl]-5-fluoro-2-(3-oxa-8-azabicyclo[3.2.1]octan-8-yl)benzoate

[Formula 563]

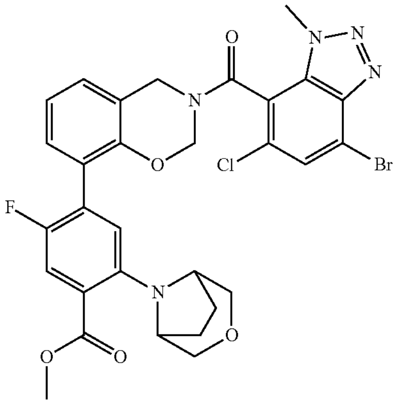

To a solution of 7-bromo-5-chloro-3-methylbenzotriazole-4-carboxylic acid (123 mg, 0.424 mmol) and N,N-dimethylformamide (0.000657 mL, 0.00848 mmol) in dichloromethane (4.00 mL), oxalyl chloride (0.0740 mL, 0.848 mmol) was added, and the mixture was stirred at room temperature for 90 minutes. The reaction solution was concentrated. Dichloromethane (4.00 mL), compound A7 (260 mg, 0.551 mmol) and N-methylmorpholine (0.326 mL, 2.97 mmol) were added to the residue, and the mixture was stirred overnight at room temperature. The reaction solution was purified by reverse phase column chromatography (acetonitrile/water, 0.1% formic acid) to obtain the title compound (82%, 232 mg).

LCMS: m/z 670[M+H]$^+$

HPLC retention time: 0.95 min (analysis condition D)

Seventh Step

Compound 19-12

4-[3-[5-Chloro-7-(7,7-dimethyl-5,9-dioxa-2-azaspiro[3.5]nonan-2-yl)-3-methylbenzotriazole-4-carbonyl]-2,4-dihydro-1,3-benzoxazin-8-yl]-5-fluoro-2-(3-oxa-8-azabicyclo[3.2.1]octan-8-yl)benzoic acid

[Formula 564]

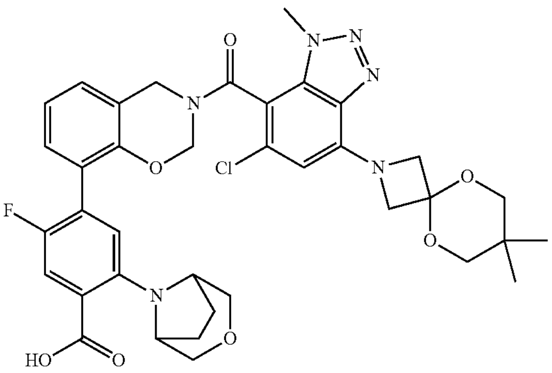

The title compound was obtained by the same operation as in the ninth step of compound 1-7 using methyl 4-[3-(7-bromo-5-chloro-3-methylbenzotriazole-4-carbonyl)-2,4-dihydro-1,3-benzoxazin-8-yl]-5-fluoro-2-(3-oxa-8-azabicyclo[3.2.1]octan-8-yl)benzoate (53.7 mg, 0.080 mmol) and (7,7-dimethyl-5,9-dioxa-2-azaspiro[3.5]nonane (13.8 mg, 0.0880 mmol).

LCMS: m/z 733[M+H]$^+$

HPLC retention time: 1.73 min and 1.76 min (analysis condition B)

Compounds shown in Table 19-1 were synthesized by the same operation as in the sixth step and the seventh step of compound 9-12 using 7-bromo-5-chloro-2-methylbenzotriazole-4-carboxylic acid and 7-bromo-5-chloro-1-methylbenzotriazole-4-carboxylic acid obtained in the fifth step of compound 19-12.

TABLE 19-1

| Compound No. | Structure | Compound Name | Analysis conditions | HPLC retention time (min) | m/z [M + H]+ |
|---|---|---|---|---|---|
| 19-13 | 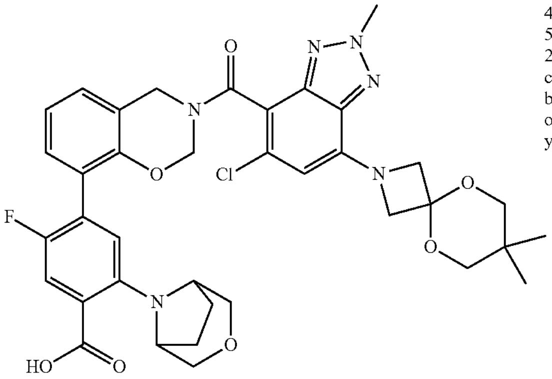 | 4-[3-[5-Chloro-7-(7,7-dimethyl-5,9-dioxa-2-azaspiro[3.5]nonan-2-yl)-2-methylbenzotriazole-4-carbonyl]-2,4-dihydro-1,3-benzoxazin-8-yl]-5-fluoro-2-(3-oxa-8-azabicyclo[3.2.1]octan-8-yl)benzoic acid | B | 1.71 | 733 |
| 19-14 | 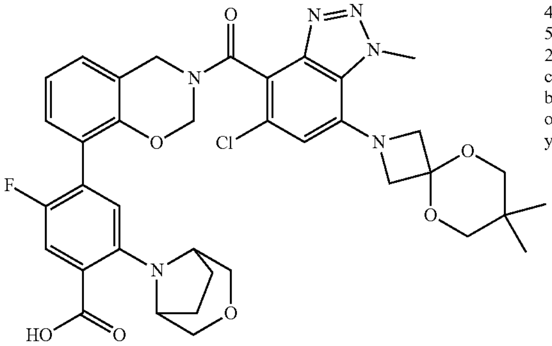 | 4-[3-[5-Chloro-7-(7,7-dimethyl-5,9-dioxa-2-azaspiro[3.5]nonan-2-yl)-1-methylbenzotriazole-4-carbonyl]-2,4-dihydro-1,3-benzoxazin-8-yl]-5-fluoro-2-(3-oxa-8-azabicyclo[3.2.1]octan-8-yl)benzoic acid | B | 1.62 | 733 |

Compound 19-15

4-[3-[5-Chloro-7-(6-methoxy-2-azaspiro[3.3]heptan-2-yl)-2,3-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid First Step Compound BUb1

Methyl 7-bromo-5-chloro-2-methyl-3H-benzimidazole-4-carboxylate

[Formula 565]

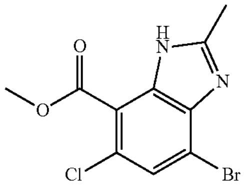

To methyl 3-acetamido-2-amino-4-bromo-6-chlorobenzoate (227 mg, 0.705 mmol), acetic acid (4.53 mL, 79 mmol) was added, and the mixture was stirred at 80° C. for 1 hour. The reaction solution was purified by reverse phase column chromatography (acetonitrile/water, 0.1% formic acid) to obtain the title compound (87%, 187 mg).

LCMS: m/z 303[M+H]+

HPLC retention time: 0.60 min (analysis condition D)

Second Step

Compound BUb2

7-Bromo-5-chloro-2,3-dimethylbenzimidazole-4-carboxylic acid

[Formula 566]

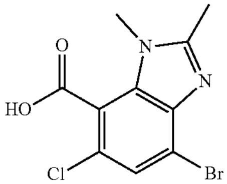

Compound BUb4

7-Bromo-5-chloro-1,2-dimethylbenzimidazole-4-carboxylic acid

[Formula 567]

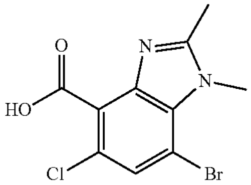

To a solution of methyl 7-bromo-5-chloro-2-methyl-3H-benzimidazole-4-carboxylate (187 mg, 0.614 mmol) and 55% sodium hydride (32.2 mg, 0.737 mmol) in N-methylpyrrolidin-2-one (2.40 mL), iodomethane (0.0580 mL, 0.922 mmol) was added, and the mixture was stirred at room temperature for 2 hours. A 5 M aqueous sodium hydroxide solution (0.614 mL, 3.07 mmol) was added to the reaction solution, and the mixture was stirred at room temperature for 2 hours. A 5 M aqueous sodium hydroxide solution (0.614 mL, 3.07 mmol) was added to the reaction solution, and the mixture was stirred overnight at room temperature and then stirred at 60° C. for 2 hours. The reaction solution was purified by reverse phase column chromatography (acetonitrile/water, 0.1% formic acid) to obtain 7-bromo-5-chloro-2,3-dimethylbenzimidazole-4-carboxylic acid (38%, 71.1 mg) and 7-bromo-5-chloro-1,2-dimethylbenzimidazole-4-carboxylic acid (39%, 72.3 mg).

Compound BUb2

LCMS: m/z 301[M−H]$^-$

HPLC retention time: 0.30 min (analysis condition D)

Compound BUb4

LCMS: m/z 301[M−H]$^-$

HPLC retention time: 0.42 min (analysis condition D)

Third Step

Compound BUb3

Methyl 4-[3-(7-bromo-5-chloro-2,3-dimethylbenzimidazole-4-carbonyl)-2,4-dihydro-1,3-benzoxazin-8-yl]-5-fluoro-2-(3-oxa-8-azabicyclo[3.2.1]octan-8-yl)benzoate

[Formula 568]

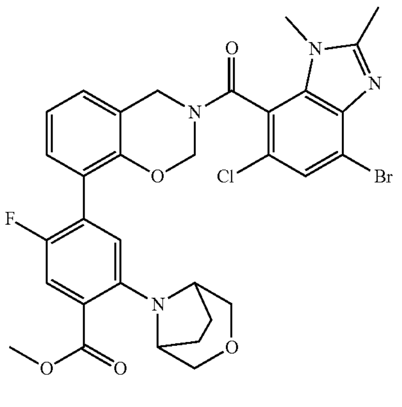

The title compound was obtained by the same operation as in the sixth step of compound 19-12 using compound A7 (71.1 mg, 0.234 mmol), and 7-bromo-5-chloro-2,3-dimethylbenzimidazole-4-carboxylic acid (144 mg, 0.305 mmol).

LCMS: m/z 683[M+H]$^+$

HPLC retention time: 0.89 min (analysis condition D)

Fourth Step

Compound 19-15

4-[3-[5-Chloro-7-(6-methoxy-2-azaspiro[3.3]heptan-2-yl)-2,3-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid

[Formula 569]

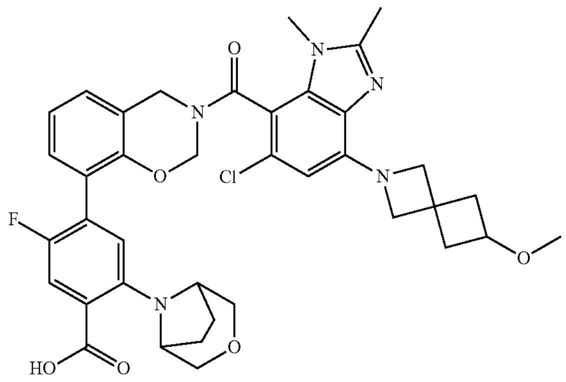

The title compound was obtained by the same operation as in the ninth step of compound 1-7 using methyl 4-[3-(7-bromo-5-chloro-2,3-dimethylbenzimidazole-4-carbonyl)-2,4-dihydro-1,3-benzoxazin-8-yl]-5-fluoro-2-(3-oxa-8-azabicyclo[3.2.1]octan-8-yl)benzoate (34.2 mg, 0.050 mmol) and 6-methoxy-2-azaspiro[3.3]heptane hydrochloride (12.3 mg, 0.0750 mmol).

LCMS: m/z 716[M+H]$^+$

HPLC retention time: 1.46 min and 1.48 min (analysis condition B)

Compound 19-16

4-[3-[5-Chloro-7-(6-methoxy-2-azaspiro[3.3]heptan-2-yl)-1,2-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid First Step Compound BUb5

Methyl 4-[3-(7-bromo-5-chloro-1,2-dimethylbenzimidazole-4-carbonyl)-2,4-dihydro-1,3-benzoxazin-8-yl]-5-fluoro-2-(3-oxa-8-azabicyclo[3.2.1]octan-8-yl)benzoate

[Formula 570]

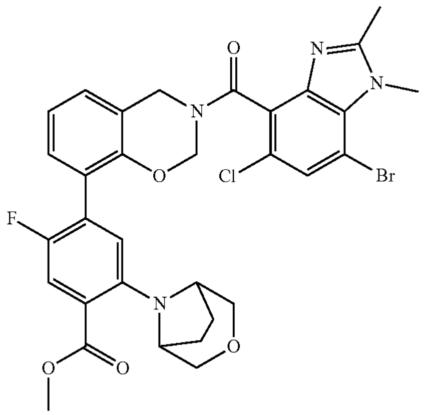

The title compound was obtained by the same operation as in the sixth step of compound 19-12 using compound A7 (71.1 mg, 0.234 mmol) and 7-bromo-5-chloro-1,2-dimethylbenzimidazole-4-carboxylic acid (144 mg, 0.305 mmol).

LCMS: m/z 683[M+H]$^+$

HPLC retention time: 0.91 min (analysis condition D)

Second Step

Compound 19-16

4-[3-[5-Chloro-7-(6-methoxy-2-azaspiro[3.3]heptan-2-yl)-1,2-dimethylbenzimidazole-4-carbonyl]-2,4-dihydro-1,3-benzoxazin-8-yl]-5-fluoro-2-(3-oxa-8-azabicyclo[3.2.1]octan-8-yl)benzoic acid

[Formula 571]

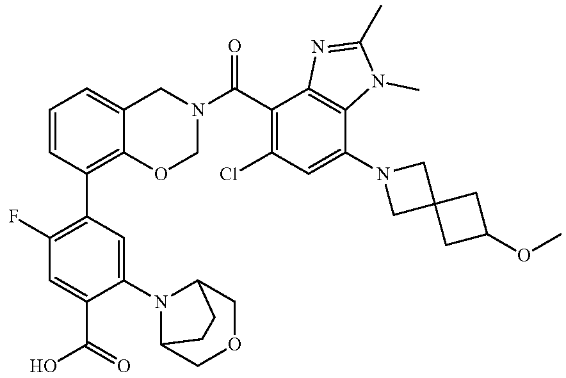

The title compound was obtained by the same operation as in the ninth step of compound 1-7 using methyl 4-[3-(7-bromo-5-chloro-1,2-dimethylbenzimidazole-4-carbonyl)-2,4-dihydro-1,3-benzoxazin-8-yl]-5-fluoro-2-(3-oxa-8-azabicyclo[3.2.1]octan-8-yl)benzoate (41.0 mg, 0.060 mmol) and 6-methoxy-2-azaspiro[3.3]heptane hydrochloride (14.7 mg, 0.0900 mmol).

LCMS: m/z 716[M+H]$^+$

HPLC retention time: 1.36 min (analysis condition B)

Compound 19-17

4-[3-[2,6-Dichloro-4-(7-methyl-2,7-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid First Step Compound BUc1 tert-Butyl 2-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,7-diazaspiro[3.5]nonane-7-carboxylate

[Formula 572]

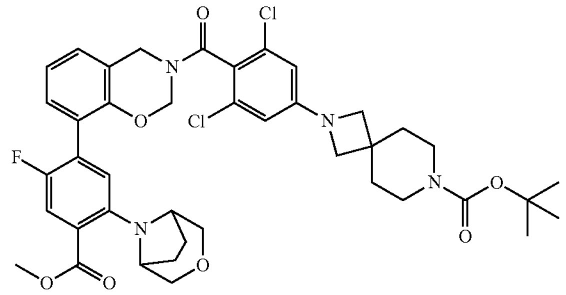

The title compound was obtained by the same operation as in the ninth step of compound 1-7 using compound A (130 mg, 0.200 mmol) and tert-butyl 2,7-diazaspiro[3.5]nonane-7-carboxylate (67.9 mg, 0.300 mmol). However, a dichloroethane solution was used instead of 1,4-dioxane as a solvent.

LCMS: m/z 795[M+H]$^+$

HPLC retention time: 1.13 min (analysis condition D)

Second Step

BUc2

Methyl 4-[3-[2,6-dichloro-4-(2,7-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate

[Formula 573]

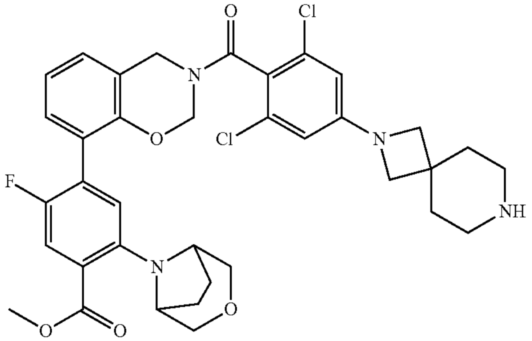

To a solution of tert-butyl 2-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,7-diazaspiro[3.5]nonane-7-carboxylate (148 mg, 0.186 mmol) in dichloromethane (1.86 ml), trifluoroacetic acid (0.287 ml, 3.72 mmol) was added, and the mixture was stirred at room temperature for 2 hours. The reaction solution was concentrated, and a saturated aqueous solution of sodium bicarbonate was added to the residue, followed by extraction with dichloromethane. The organic layer was concentrated to obtain the title compound (100%, 130 mg).

LCMS: m/z 695[M+H]$^+$

HPLC retention time: 0.66 min (analysis condition D)

Third Step

Compound 19-17

4-[3-[2,6-Dichloro-4-(7-methyl-2,7-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 574]

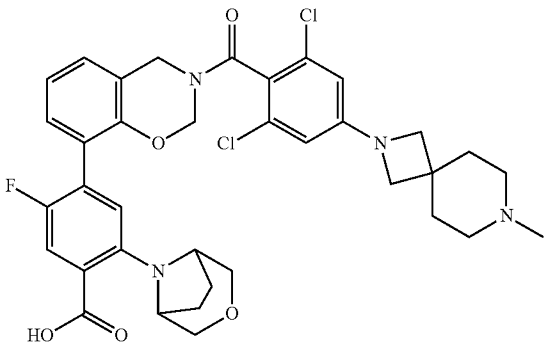

To a solution of methyl 4-[3-[2,6-dichloro-4-(2,7-diazaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoate (41.7 mg, 0.060 mmol) and an aqueous formaldehyde solution (0.00676 ml, 0.090 mmol) in dichloromethane (0.600 ml), sodium triacetoxyborohydride (25.4 mg, 0.120 mmol) was added, and the mixture was stirred at room temperature for 35 minutes. An 8 M aqueous potassium hydroxide solution (0.15 ml, 1.20 mmol) and methanol (15.0 ml) were added thereto, and the mixture was stirred at 70° C. for 1 hour. The reaction solution was purified by HPLC (acetonitrile/water, 0.1% formic acid) to obtain the title compound (83%, 34.8 mg).

LCMS: m/z 695[M+H]$^+$

HPLC retention time: 1.15 min and 1.19 min (analysis condition B)

Compound BUd1 tert-Butyl (3R)-4-[3,5-dichloro-4-[8-[2-fluoro-4-methoxycarbonyl-5-[(1S,5R)-3-oxa-8-azabicyclo[3.2.1]octan-8-yl]phenyl]-2,4-dihydro-1,3-benzoxazine-3-carbonyl]phenyl]-3-ethylpiperazine-1-carboxylate

[Formula 575]

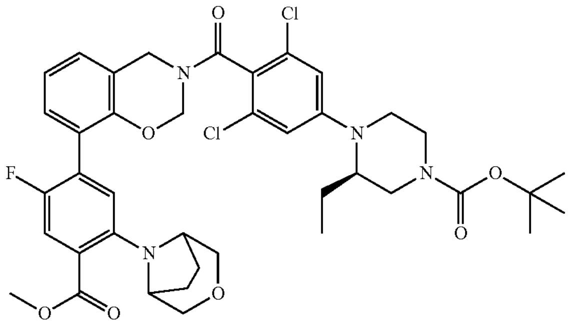

The title compound was obtained by the same operation as in the ninth step of compound 1-7 using compound A (39.0 mg, 0.060 mmol) and tert-butyl (3R)-3-ethylpiperazine-1-carboxylate (25.7 mg, 0.120 mmol). However, dichloroethane was used instead of 1,4-dioxane as a solvent.

LCMS: m/z 783[M+H]$^+$

HPLC retention time: 1.12 min (analysis condition D)

Compound BUe1 tert-Butyl (3S)-4-[3,5-dichloro-4-[8-[2-fluoro-4-methoxycarbonyl-5-[(1S,5R)-3-oxa-8-azabicyclo[3.2.1]octan-8-yl]phenyl]-2,4-dihydro-1,3-benzoxazine-3-carbonyl]phenyl]-3-(methoxymethyl)piperazine-1-carboxylate

[Formula 576]

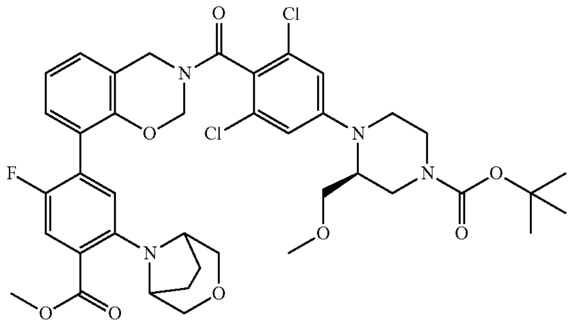

The title compound was obtained by the same operation as in the ninth step of compound 1-7 using compound A (39.0 mg, 0.060 mmol) and tert-butyl (3S)-3-(methoxymethyl)piperazine-1-carboxylate (27.6 mg, 0.120 mmol).

LCMS: m/z 799[M+H]$^+$

HPLC retention time: 1.07 min (analysis condition D)

Compounds shown in Table 19-2 were synthesized by the same operation as in the second step and the third step of compound 19-17 using reagents and intermediates shown in Table 19-3.

TABLE 19-2

| Compound No. | Structure | Compound Name | Analysis conditions | HPLC retention time (min) | m/z [M + H]$^+$ |
|---|---|---|---|---|---|
| 19-16 | 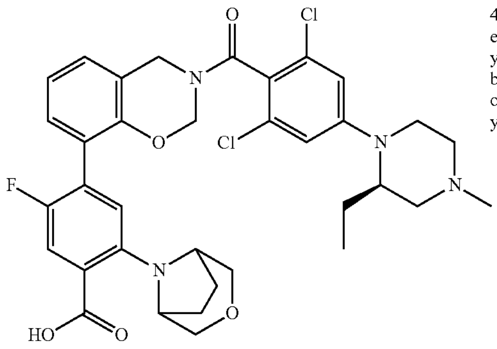 | 4-[3-[2,6-Dichloro-4-[(2R)-2-ethyl-4-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.15. 1.20 | 683 |

TABLE 19-2-continued

| Compound No. | Structure | Compound Name | Analysis conditions | HPLC retention time (min) | m/z [M + H]+ |
|---|---|---|---|---|---|
| 19-19 | 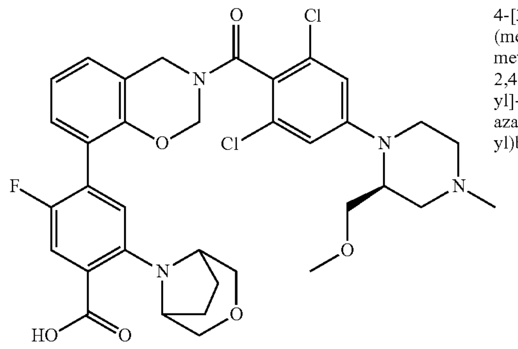 | 4-[3-[2,6-Dichloro-4-[(2S)-2-(methoxymethyl)-4-methylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid | B | 1.14. 1.19 | 699 |

TABLE 19-3

| Final compound No. | Intermediate | Reagent |
|---|---|---|
| 19-18 | Bud1 | Paraformaldehyde |
| 19-19 | Bue1 | Paraformaldehyde |

Compound 19-2

4-[3-[4-(7,7-Dimethyl-5,9-dioxa-2-azaspiro[3.5]nonan-2-yl)-2,6-dimethylbenzoyl]-2,4-dihydro-1,3-benzoxazin-8-yl]-5-fluoro-2-(3-oxa-8-azabicyclo[3.2.1]octan-8-yl)benzoic acid First Step Compound BUP02

Methyl 4-[3-(4-bromo-2,6-dimethylbenzoyl)-2,4-dihydro-1,3-benzoxazin-8-yl]-5-fluoro-2-(3-oxa-8-azabicyclo[3.2.1]octan-8-yl)benzoate

[Formula 577]

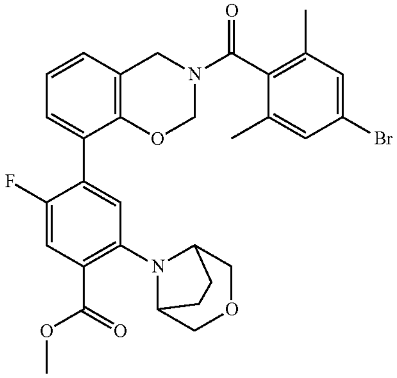

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2,6-dimethylbenzoyl chloride.

LCMS: m/z 609[M+H]+

HPLC retention time: 1.92 min (analysis condition AC)

Second Step

Compound 19-2

4-[3-[4-(7,7-Dimethyl-5,9-dioxa-2-azaspiro[3.5]nonan-2-yl)-2,6-dimethylbenzoyl]-2,4-dihydro-1,3-benzoxazin-8-yl]-5-fluoro-2-(3-oxa-8-azabicyclo[3.2.1]octan-8-yl)benzoic acid

[Formula 578]

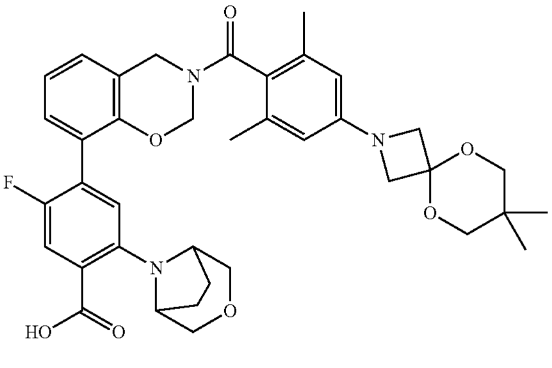

The title compound was obtained by the same operation as in the ninth step of compound 1-7 using methyl 4-[3-(4-bromo-2,6-dimethylbenzoyl)-2,4-dihydro-1,3-benzoxazin-8-yl]-5-fluoro-2-(3-oxa-8-azabicyclo[3.2.1]octan-8-yl)benzoate and 7,7-dimethyl-5,9-dioxa-2-azaspiro[3.5]nonane.

LCMS: m/z 672[M+H]+

HPLC retention time: 1.69 min and 1.74 min (analysis condition B)

Compound 19-3

4-[3-[2-Chloro-6-fluoro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound BUP06

Methyl 4-[3-(4-bromo-2-chloro-6-fluorobenzoyl)-2,4-dihydro-1,3-benzoxazin-8-yl]-5-fluoro-2-(3-oxa-8-azabicyclo[3.2.1]octan-8-yl)benzoate

[Formula 579]

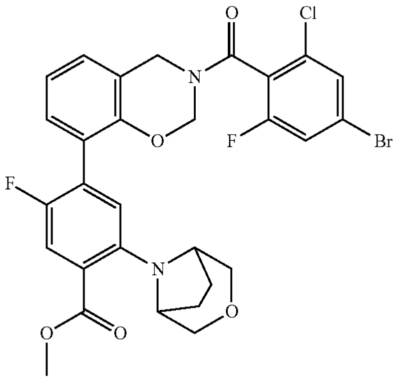

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2-chloro-6-fluorobenzoyl chloride.

LCMS: m/z 633$[M+H]^+$

HPLC retention time: 1.64 min (analysis condition AD)

Second Step
Compound 19-3

4-[3-[2-Chloro-6-fluoro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 580]

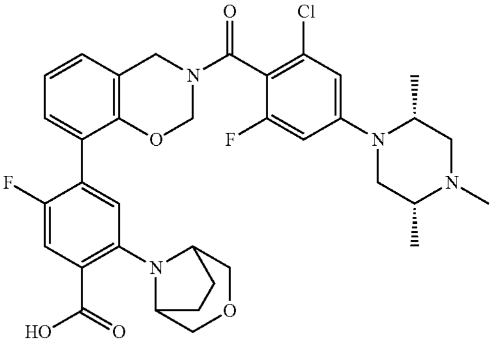

The title compound was obtained by the same operation as in the ninth step of compound 1-7 using methyl 4-[3-(4-bromo-2-chloro-6-fluorobenzoyl)-2,4-dihydro-1,3-benzoxazin-8-yl]-5-fluoro-2-(3-oxa-8-azabicyclo[3.2.1]octan-8-yl)benzoate and (2R,5R)-1,2,5-trimethylpiperazine hydrochloride.

LCMS: m/z 667$[M+H]^+$

HPLC retention time: 1.16 min (analysis condition B)

Compound 19-4

4-[3-[2-Chloro-6-methyl-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid First Step
Compound BUP09

Methyl 4-[3-(4-bromo-2-chloro-6-methylbenzoyl)-2,4-dihydro-1,3-benzoxazin-8-yl]-5-fluoro-2-(3-oxa-8-azabicyclo[3.2.1]octan-8-yl)benzoate

[Formula 581]

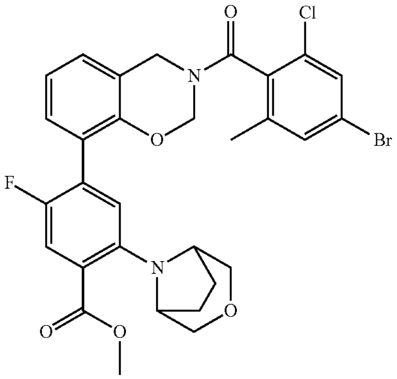

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4-bromo-2-chloro-6-methylbenzoyl chloride.

LCMS: m/z 629$[M+H]^+$

HPLC retention time: 2.17 min (analysis condition AB)

Second Step
Compound 19-4

4-[3-[2-Chloro-6-methyl-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 582]

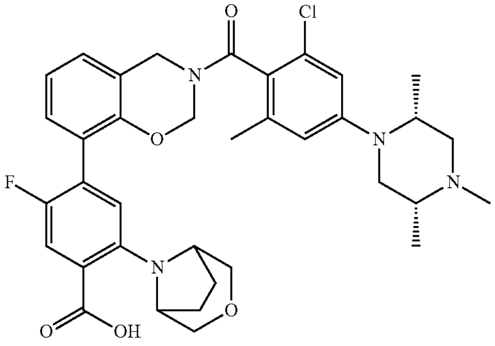

The title compound was obtained by the same operation as in the ninth step of compound 1-7 using methyl 4-[3-(4-bromo-2-chloro-6-methylbenzoyl)-2,4-dihydro-1,3-benzoxazin-8-yl]-5-fluoro-2-(3-oxa-8-azabicyclo[3.2.1]octan-8-yl)benzoate and (2R,5R)-1,2,5-trimethylpiperazine hydrochloride.

LCMS: m/z 663$[M+H]^+$

HPLC retention time: 1.11 min and 1.16 min (analysis condition B)

Compound 19-6

4-[3-[3-Chloro-5-[(2R,5R)-2,4,5-trimethylpiperazin-1-yl]pyridine-2-carbonyl]-2,4-dihydro-1,3-benzoxazin-8-yl]-5-fluoro-2-(3-oxa-8-azabicyclo[3.2.1]octan-8-yl)benzoic acid First Step Compound BUP12

Methyl 4-[3-(5-bromo-3-chloropyridine-2-carbonyl)-2,4-dihydro-1,3-benzoxazin-8-yl]-5-fluoro-2-(3-oxa-8-azabicyclo[3.2.1]octan-8-yl)benzoate

[Formula 583]

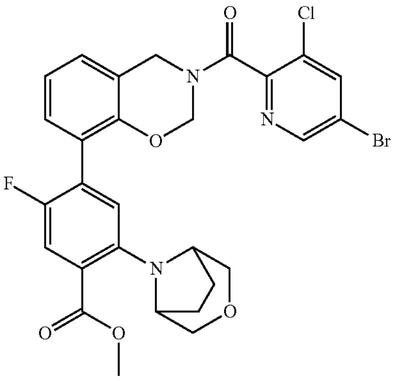

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 5-bromo-3-chloropyridine-2-carbonyl chloride.

LCMS: m/z 616[M+H]+

HPLC retention time: 1.47 min (analysis condition AE)

Second Step

Compound 19-6

4-[3-[3-Chloro-5-[(2R,5R)-2,4,5-trimethylpiperazin-1-yl]pyridine-2-carbonyl]-2,4-dihydro-1,3-benzoxazin-8-yl]-5-fluoro-2-(3-oxa-8-azabicyclo[3.2.1]octan-8-yl)benzoic acid

[Formula 584]

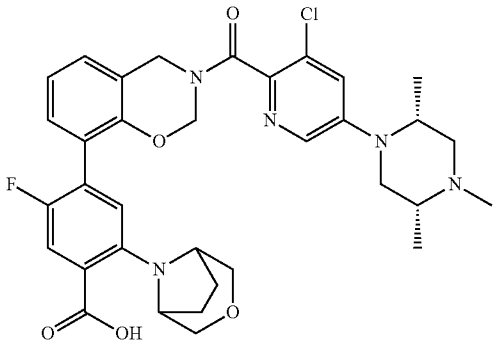

The title compound was obtained by the same operation as in the ninth step of compound 1-7 using methyl 4-[3-(5-bromo-3-chloropyridine-2-carbonyl)-2,4-dihydro-1,3-benzoxazin-8-yl]-5-fluoro-2-(3-oxa-8-azabicyclo[3.2.1]octan-8-yl)benzoate and (2R,5R)-1,2,5-trimethylpiperazine hydrochloride.

LCMS: m/z 650[M+H]+

HPLC retention time: 1.08 min (analysis condition B)

Compound 19-7

4-[3-[2-Chloro-4-[(2R)-2,4-dimethylpiperazin-1-yl]-6-fluorobenzoyl]-2,4-dihydro-1,3-benzoxazin-8-yl]-5-fluoro-2-(3-oxa-8-azabicyclo[3.2.1]octan-8-yl)benzoic acid

[Formula 585]

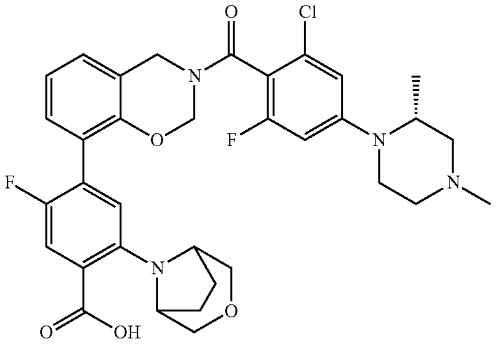

The title compound was obtained by the same operation as in the ninth step of compound 1-7 using methyl 4-[3-(4-bromo-2-chloro-6-fluorobenzoyl)-2,4-dihydro-1,3-benzoxazin-8-yl]-5-fluoro-2-(3-oxa-8-azabicyclo[3.2.1]octan-8-yl)benzoate and (3R)-1,3-dimethylpiperazine.

LCMS: m/z 653[M+H]+

HPLC retention time: 1.14 min (analysis condition B)

Compound 19-8

4-[3-[2-Chloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid

[Formula 586]

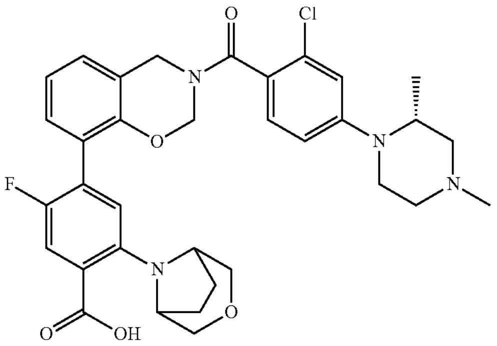

The title compound was obtained by the same operation as in the ninth step of compound 1-7 using compound H and (3R)-1,3-dimethylpiperazine.

LCMS: m/z 635[M+H]+

HPLC retention time: 1.11 min (analysis condition B)

Compound 19-9

4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid First Step Compound BUP16

4,6-Dichloro-2-methylpyridine-3-carbonyl Chloride

[Formula 587]

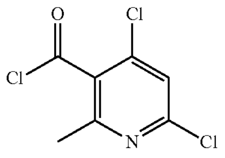

A crude product of the title compound was obtained by the same operation as in the third step of compound J using 4,6-dichloro-2-methylpyridine-3-carboxylic acid.

Second Step

Compound BUP17

Methyl 4-[3-(4,6-dichloro-2-methylpyridine-3-carbonyl)-2,4-dihydro-1,3-benzoxazin-8-yl]-5-fluoro-2-(3-oxa-8-azabicyclo[3.2.1]octan-8-yl)benzoate

[Formula 588]

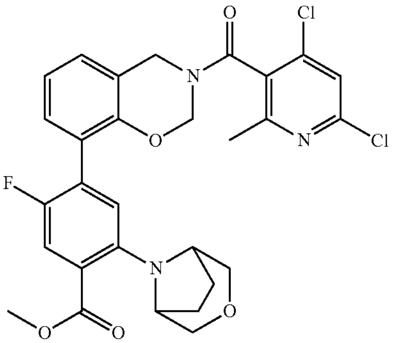

The title compound was obtained by the same operation as in the fifth step of compound B using methyl 4-(3,4-dihydro-2H-1,3-benzoxazin-8-yl)-5-fluoro-2-(3-oxa-8-azabicyclo[3.2.1]octan-8-yl)benzoate dihydrochloride and 4,6-dichloro-2-methylpyridine-3-carbonyl chloride. However, 4-methylmorpholine was used instead of N,N-diisopropylethylamine.

LCMS: m/z 586$[M+H]^+$

HPLC retention time: 1.30 min (analysis condition G)

Third Step

Compound BUP18

Methyl 4-[3-[4-chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoate

[Formula 589]

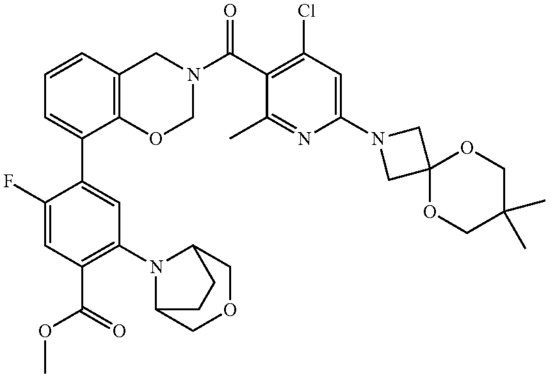

A suspension of methyl 4-[3-(4,6-dichloro-2-methylpyridine-3-carbonyl)-2,4-dihydro-1,3-benzoxazin-8-yl]-5-fluoro-2-(3-oxa-8-azabicyclo[3.2.1]octan-8-yl)benzoate (5.00 g, 7.93 mmol), 7,7-dimethyl-5,9-dioxa-2-azaspiro[3.5]nonane (1.31 g, 8.33 mmol), XantPhos Pd G3 (0.376 g, 0.396 mmol) and cesium carbonate (10.3 g, 31.7 mmol) in 1,4-dioxane (52.9 mL) was stirred overnight at 60° C. The reaction solution was cooled to room temperature. XantPhos Pd G3 (0.376 g, 0.396 mmol) was added thereto, and the mixture was stirred at 60° C. for 8 hours. Water was added to the reaction solution, followed by extraction using ethyl acetate. The organic layer was washed with a saturated aqueous solution of sodium chloride, dried over magnesium sulfate, and filtered. The obtained residue was purified by silica gel column chromatography (hexane/ethyl acetate) to obtain the title compound (36%, 2.01 g).

LCMS: m/z 707$[M+H]^+$

HPLC retention time: 1.39 min (analysis condition G)

Fourth Step

Compound 19-9

4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid

[Formula 590]

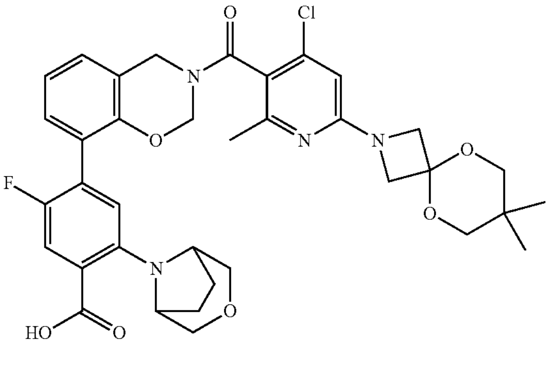

To a solution of methyl 4-[3-[4-chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoate (5.97 g, 8.44 mmol) in tetrahydrofuran (16.9 mL) and methanol (16.9 mL), an 8 M aqueous potassium hydroxide solution (3.17 mL, 25.3 mmol) was added thereto, and the mixture was stirred at 50° C. for 1.5 hours. An aqueous formic acid solution was added to the reaction solution, and the mixture was then purified by reverse phase column chromatography (acetonitrile/water, 0.1% formic acid) to obtain the title compound (91%, 5.33 g).

LCMS: m/z 693[M+H]$^+$

HPLC retention time: 1.62 min and 1.65 min (analysis condition B)

Compound 19-10

4-[3-[2-Chloro-4-(7,7-dimethyl-5,9-dioxa-2-azaspiro[3.5]nonan-2-yl)-6-fluorobenzoyl]-2,4-dihydro-1,3-benzoxazin-8-yl]-5-fluoro-2-(3-oxa-8-azabicyclo[3.2.1]octan-8-yl)benzoic acid

[Formula 591]

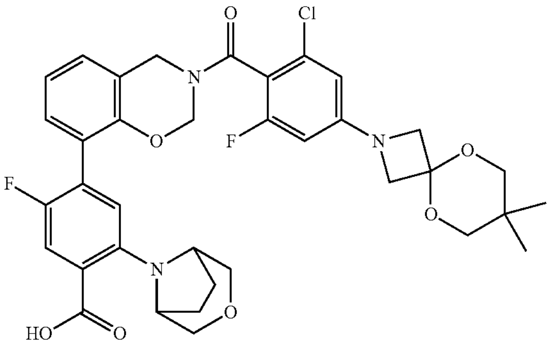

The title compound was obtained by the same operation as in the ninth step of compound 1-7 using methyl 4-[3-(4-bromo-2-chloro-6-fluorobenzoyl)-2,4-dihydro-1,3-benzoxazin-8-yl]-5-fluoro-2-(3-oxa-8-azabicyclo[3.2.1]octan-8-yl)benzoate and 7,7-dimethyl-5,9-dioxa-2-azaspiro[3.5]nonane.

LCMS: m/z 696[M+H]$^+$

HPLC retention time: 1.74 min (analysis condition B)

Compound 19-11

4-[3-[2-Chloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid

[Formula 592]

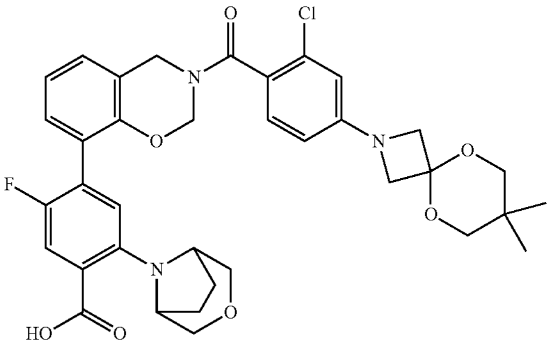

The title compound was obtained by the same operation as in the ninth step of compound 1-7 using compound H and 7,7-dimethyl-5,9-dioxa-2-azaspiro[3.5]nonane.

LCMS: m/z 678[M+H]$^+$

HPLC retention time: 1.72 min (analysis condition B)

Compound 20-1

4-[3-[2,6-Dichloro-4-(1-methylpyrazol-4-yl)benzoyl]-2,4-dihydro-1,3-benzoxazin-8-yl]-5-fluoro-2-(3-oxa-6-azabicyclo[3.1.1]heptan-6-yl)benzoic acid N,N-diethylethanamine salt First Step Compound tui5

4-Bromo-5-fluoro-2-(3-oxa-6-azabicyclo[3.1.1]heptan-6-yl)benzoic acid

[Formula 593]

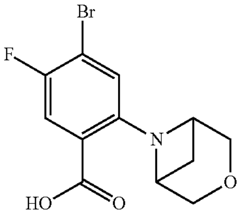

A solution of 3-oxa-6-azabicyclo[3.1.1]heptane (50.0 mg, 0.504 mmol) in tetrahydrofuran (403 mL) was cooled to −30° C. A 1.63 M solution of n-butyllithium in hexane (0.309 mL) was added thereto, and the mixture was stirred for 30 minutes. A solution of 4-bromo-2,5-difluorobenzoic acid (47.8 mg, 0.202 mmol) in tetrahydrofuran (0.403 mL) cooled to −30° C. was added thereto, and the mixture was stirred at 0° C. for 30 minutes. The reaction solution was purified by reverse phase column chromatography (acetonitrile/water, 0.1% triethylamine) to obtain the title compound (33%, 20.7 mg).

LCMS: m/z 316[M+H]$^+$

HPLC retention time: 0.81 min (analysis condition G)

Second Step

Compound 20-1

4-[3-[2,6-Dichloro-4-(1-methylpyrazol-4-yl)benzoyl]-2,4-dihydro-1,3-benzoxazin-8-yl]-5-fluoro-2-(3-oxa-6-azabicyclo[3.1.1]heptan-6-yl)benzoic acid N,N-diethylethanamine salt

[Formula 594]

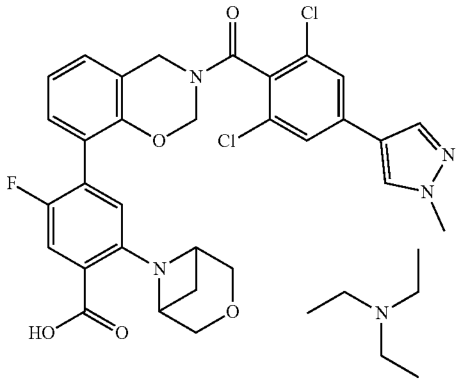

The title compound was obtained by the same operation as in the third step of compound B using (8-bromo-2,4-dihydro-1,3-benzoxazin-3-yl)-[2,6-dichloro-4-(1-methylpyrazol-4-yl)phenyl]methanone and 4-bromo-5-fluoro-2-(3-oxa-6-azabicyclo[3.1.1]heptan-6-yl)benzoic acid. However, reverse phase column chromatography (acetonitrile/water, 0.1% triethylamine) was used in purification.

LCMS: m/z 623[M+H]$^+$

HPLC retention time: 0.95 min and 0.97 min (analysis condition A)

Compound 20-2

4-[3-[2,6-Dichloro-4-[(1R,4R)-5-methyl-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoic acid First Step Compound tui1 tert-Butyl (1R,4R)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate

[Formula 595]

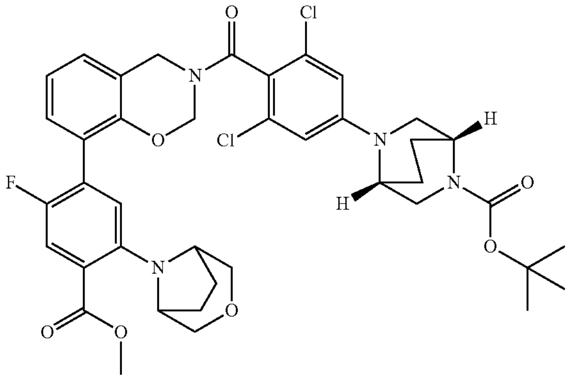

A solution of compound A (50.0 mg, 0.077 mmol), tert-butyl (1R,4R)-2,5-diazabicyclo[2.2.2]octane-2-carboxylate (21.2 mg, 0.100 mmol), cesium carbonate (75.0 mg, 0.231 mmol) and rac-BINAP Pd G4 (7.74 mg, 0.0769 mmol) in 1,4-dioxane (0.384 mL) was stirred at 110° C. for 2 hours. The reaction mixture was purified by reverse phase column chromatography (acetonitrile/water, 0.1% formic acid) to obtain the title compound (80%, 48.1 mg).

LCMS: m/z 781 [M+H]$^+$

HPLC retention time: 1.11 min (analysis condition D)

Second Step

Compound tui2

Methyl 4-[3-[2,6-dichloro-4-[(1R,4R)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate

[Formula 596]

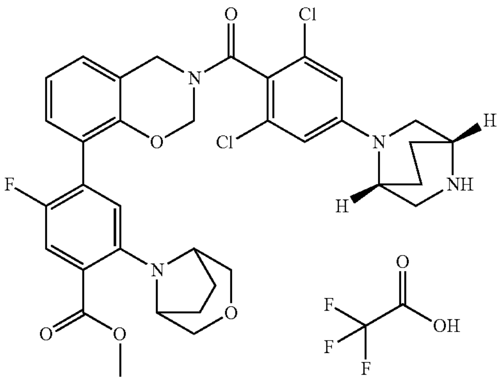

To a solution of tert-butyl (1R,4R)-5-[3,5-dichloro-4-[8-[2-fluoro-4-methoxycarbonyl-5-(3-oxa-8-azabicyclo[3.2.1]octan-8-yl)phenyl]-2,4-dihydro-1,3-benzoxazine-3-carbonyl]phenyl]-2,5-diazabicyclo[2.2.2]octane-2-carboxylate (48.1 mg, 0.0620 mmol) in dichloromethane (0.308 mL), trifluoroacetic acid (0.236 mL, 3.08 mmol) was added, and the mixture was stirred at room temperature for 1 hour. The reaction solution was concentrated to obtain the title compound as a crude product.

LCMS: m/z 681 [M+H]$^+$

HPLC retention time: 0.66 min and 0.67 min (analysis condition D)

Third Step

Compound tui3

Methyl 4-[3-[2,6-dichloro-4-[(1R,4R)-5-methyl-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate

[Formula 597]

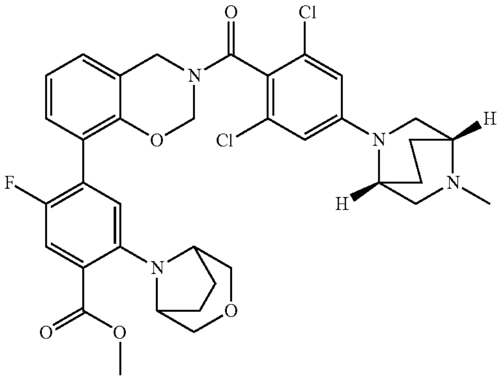

A suspension of methyl 4-[3-[2,6-dichloro-4-[(1R,4R)-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate 2,2,2-trifluoroacetate (24.5 mg, 0.0310 mmol), a 37% aqueous formaldehyde solution (0.0125 mL, 0.154 mmol), and sodium triacetoxyborohydride (32.6 mg, 0.154 mmol) in dichloromethane (0.154 mL) was stirred at room temperature for 2 hours. The reaction solution was diluted with methanol and then concentrated to obtain the title compound as a crude product.

LCMS: m/z 695[M+H]$^+$

HPLC retention time: 1.10 min (analysis condition D)

Fourth Step

Compound 20-2

4-[3-[2,6-Dichloro-4-[(1R,4R)-5-methyl-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 598]

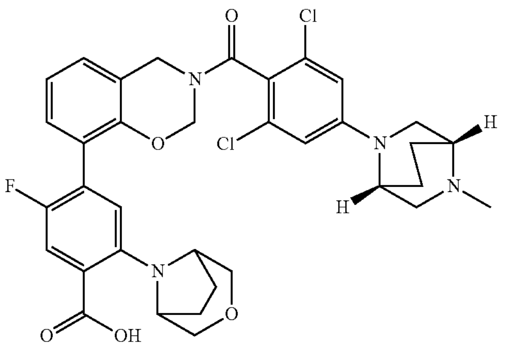

To a solution of methyl 4-[3-[2,6-dichloro-4-[(1R,4R)-5-methyl-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoate (21.4 mg, 0.0310 mmol) in tetrahydrofuran (0.308 mL) and methanol (0.308 mL), a 5 M aqueous sodium hydroxide solution (0.185 mL, 0.924 mmol) was added, and the reaction solution was stirred at 60° C. for 30 minutes. An aqueous formic acid solution was added to the reaction solution, and the mixture was purified by HPLC (acetonitrile/water, 0.1% formic acid) to obtain the title compound (60%, 12.6 mg).

LCMS: m/z 681 [M+H]$^+$

HPLC retention time: 1.11 min and 1.15 min (analysis condition B)

Compounds shown in Table 22-1 were synthesized by the same operation as in the first step to the fourth step of compound 20-2 using amine and aldehyde or ketone shown in Table 22-2 and compound A.

TABLE 22-1

| Compound No. | Structure | Compound Name | Analysis conditions | HPLC retention time (min) | m/z [M + H]$^+$ |
|---|---|---|---|---|---|
| 20-3 | 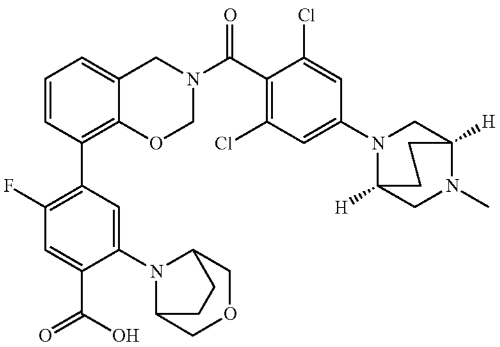 [SMILES: CN1C[C@@H]2CC[C@H]1CN2c1cc(Cl)c(C(=O)N2COc3c(cccc3-c3cc(N4C5CCC4COC5)c(C(=O)O)cc3F)C2)c(Cl)c1] | 4-[3-[2,6-Dichloro-4-[(1S,4S)-5-methyl-2,5-diazabicyclo[2.2.2]octan-2-yl]benzoyl]-2,4-dihydro-1,3-benzoxazin-8-yl]-5-fluoro-2-(3-oxa-8-azabicyclo[3.2.1]octan-8-yl)benzoic acid | B | 1.10, 1.14 | 681 |

TABLE 22-1-continued

| Compound No. | Structure | Compound Name | Analysis conditions | HPLC retention time (min) | m/z [M + H]+ |
|---|---|---|---|---|---|
| 20-4 | 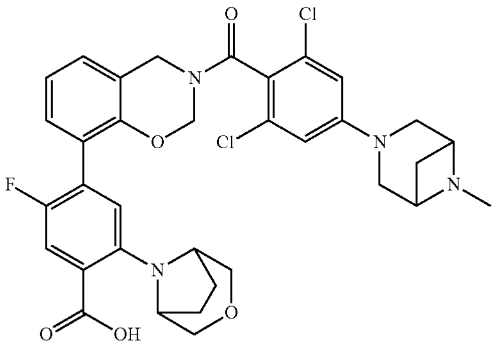 [SMILES: CN1C2CC1CN(c1cc(Cl)c(C(=O)N3COc4c(cccc4-c4cc(N5C6CCC5COC6)c(C(=O)O)cc4F)C3)c(Cl)c1)C2] | 4-[3-[2,6-Dichloro-4-(6-methyl-3,6-diazabicyclo[3.1.1]heptan-3-yl)benzoyl]-2,4-dihydro-1,3-benzoxazin-8-yl]-5-fluoro-2-(3-oxa-8-azabicyclo[3.2.1]octan-8-yl)benzoic acid | B | 1.08, 1.12 | 667 |
| 20-5 | 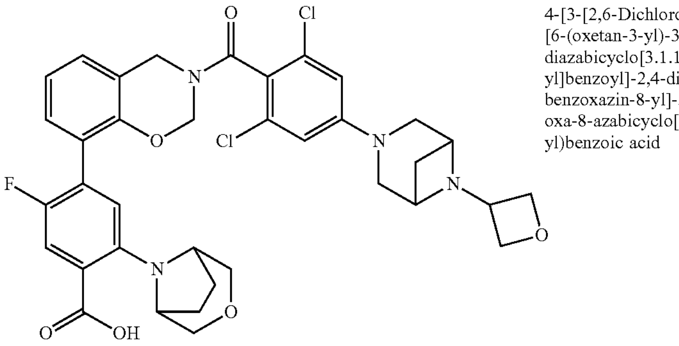 | 4-[3-[2,6-Dichloro-4-[6-(oxetan-3-yl)-3,6-diazabicyclo[3.1.1]heptan-3-yl]benzoyl]-2,4-dihydro-1,3-benzoxazin-8-yl]-5-fluoro-2-(3-oxa-8-azabicyclo[3.2.1]octan-8-yl)benzoic acid | B | 1.08. 1.13 | 709 |
| 20-6 | 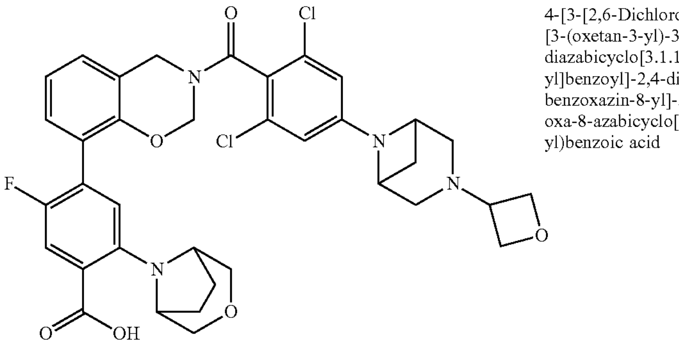 | 4-[3-[2,6-Dichloro-4-[3-(oxetan-3-yl)-3,6-diazabicyclo[3.1.1]heptan-6-yl]benzoyl]-2,4-dihydro-1,3-benzoxazin-8-yl]-5-fluoro-2-(3-oxa-8-azabicyclo[3.2.1]octan-8-yl)benzoic acid | B | 1.17 | 709 |

TABLE 22-2

| Final compound No. | Amine | Aldehyde or ketone |
|---|---|---|
| 20-3 | 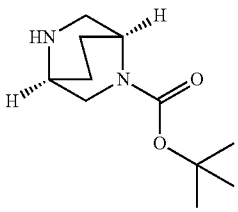 | 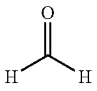 |

TABLE 22-2-continued

| Final compound No. | Amine | Aldehyde or ketone |
|---|---|---|
| 20-4 | 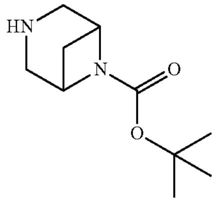 | 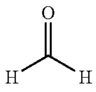 |

TABLE 22-2-continued

| Final compound No. | Amine | Aldehyde or ketone |
|---|---|---|
| 20-5 | 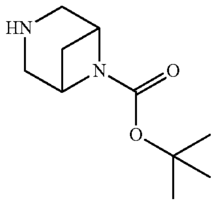 | 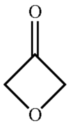 |
| 20-6 | 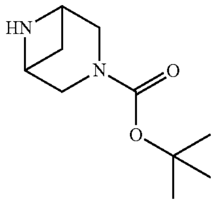 | 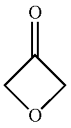 |

Compound 20-7

4-[3-[2,6-Dichloro-4-[(1S,4S)-5-(2-methoxyethyl)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid First Step
Compound tui4

4-[3-[2,6-Dichloro-4-[(1S,4S)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 599]

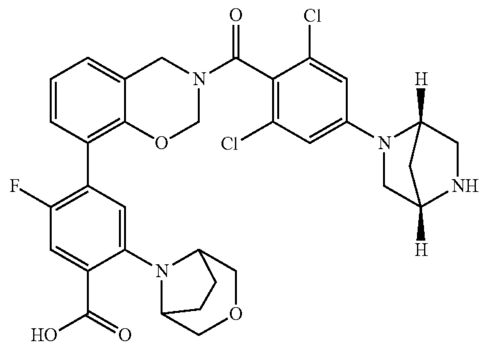

A solution of compound O (80.0 mg, 0.136 mmol), (1S,4S)-2,5-diazabicyclo[2.2.1]heptane dihydrobromide (176 mg, 0.679 mmol) and potassium tert-butoxide (149 mg, 1.33 mmol) in 1-methylpyrrolidin-2-one (0.339 mL) was stirred at 140° C. for 10 hours. An 8 M aqueous potassium hydroxide solution (0.170 mL, 1.36 mmol) was added to the reaction solution, and the mixture was then stirred at 60° C. for 1 hour. An aqueous formic acid solution and methanol were added to the reaction solution, and the mixture was filtered. Then, the filtrate was purified by HPLC (acetonitrile/water, 0.1% formic acid) to obtain the title compound (87%, 77.4 mg).

LCMS: m/z 653[M+H]$^+$

HPLC retention time: 0.51 min (analysis condition D)

Second Step

Compound 20-7

4-[3-[2,6-Dichloro-4-[(1S,4S)-5-(2-methoxyethyl)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid

[Formula 600]

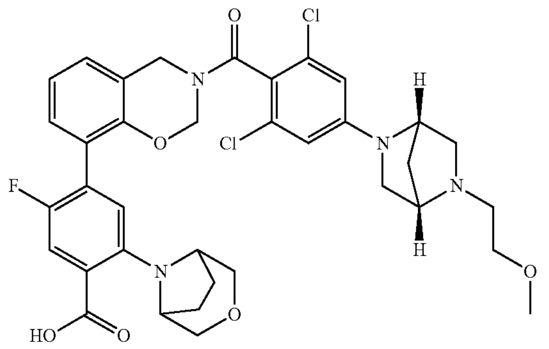

To a solution of 4-[3-[2,6-dichloro-4-[(1S,4S)-2,5-diazabicyclo[2.2.1]heptan-2-yl]benzoyl]-2,4-dihydro-1,3-benzoxazin-8-yl]-5-fluoro-2-(3-oxa-8-azabicyclo[3.2.1]octan-8-yl)benzoic acid (25.0 mg, 0.0380 mmol), N,N-diisopropylethylamine (0.0334 mL, 0.191 mmol) and potassium iodide (1.64 mg, 0.00765 mmol) in N,N-dimethylformamide (0.191 mL), 2-bromoethyl methyl ether (0.0180 mL, 0.191 mmol) was added, and the mixture was stirred at room temperature for 2 hours and then stirred at 50° C. for 6 hours. Methanol (0.100 mL) and a 5 M aqueous potassium hydroxide solution (0.0383 mL, 0.191 mmol) were added to the reaction solution, and the mixture was then stirred at 60° C. for 30 minutes. An aqueous formic acid solution and methanol were added to the reaction solution, and the mixture was then purified by reverse phase column chromatography (methanol/water, 10 mM ammonium acetate) and HPLC (methanol/water, 10 mM ammonium acetate) to obtain the title compound (64%, 17.5 mg).

LCMS: m/z 711 [M+H]$^+$

HPLC retention time: 1.01 min and 1.04 min (analysis condition B)

Compound 20-8

4-[3-(2,6-Dichloro-4-piperazin-1-ylbenzoyl)-2,4-dihydro-1,3-benzoxazin-8-yl]-5-fluoro-2-(3-oxa-8-azabicyclo[3.2.1]octan-8-yl)benzoic acid

[Formula 601]

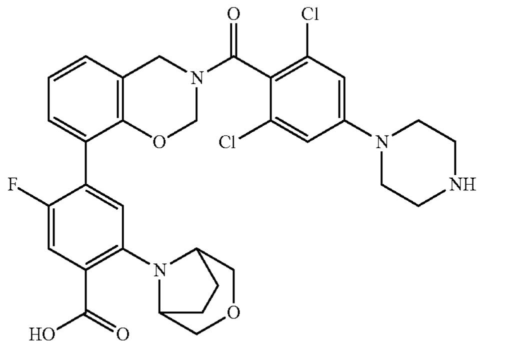

A solution of intermediate O (30.0 mg, 0.0510 mmol) and piperidine (13.2 mg, 0.153 mmol) in N-methyl-2-pyrrolidone (0.127 mL) was stirred at 130° C. for 17 hours. 8 M potassium hydroxide (0.0318 mL, 0.254 mmol) was added thereto, and the mixture was stirred at room temperature for 1 hour. The reaction solution was purified by HPLC (acetonitrile/water, 0.1% formic acid) to obtain the title compound (73%, 23.9 mg).

LCMS: m/z 641[M+H]$^+$

HPLC retention time: 0.97 min and 1.02 min (analysis condition B)

Compound 20-9

4-[3-[2,6-Dichloro-4-(4-methyl-4,7-diazaspiro[2.5]octan-7-yl)benzoyl]-2,4-dihydro-1,3-benzoxazin-8-yl]-5-fluoro-2-(3-oxa-8-azabicyclo[3.2.1]octan-8-yl)benzoic acid First Step Compound tui6

4-[3-[2,6-Dichloro-4-(4,7-diazaspiro[2.5]octan-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 602]

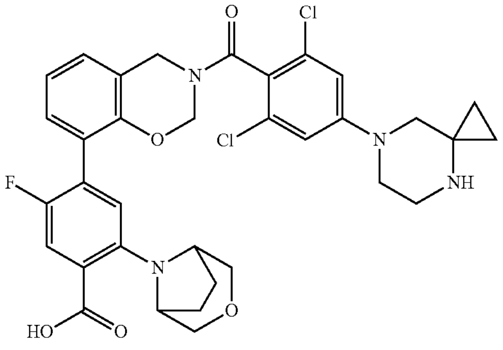

A solution of intermediate O (35.0 mg, 0.0590 mmol), 4,7-diazaspiro[2.5]octane dihydrochloride (33.0 mg, 0.178 mmol) and t-butoxy potassium (36.6 mg, 0.327 mmol) in N-methyl-2-pyrrolidone (0.148 mL) was stirred at 130° C. for 7 hours. An 8 M aqueous potassium hydroxide solution (0.0371 mL, 0.297 mmol) was added thereto, and the mixture was stirred at 60° C. for 1 hour. The reaction solution was purified by HPLC (acetonitrile/water, 0.1% formic acid) to obtain the title compound (37%, 14.5 mg).

LCMS: m/z 667[M+H]$^+$

HPLC retention time: 0.49 min and 0.53 min (analysis condition D)

Second Step

Compound 20-9

4-[3-[2,6-Dichloro-4-(4-methyl-4,7-diazaspiro[2.5]octan-7-yl)benzoyl]-2,4-dihydro-1,3-benzoxazin-8-yl]-5-fluoro-2-(3-oxa-8-azabicyclo[3.2.1]octan-8-yl)benzoic acid

[Formula 603]

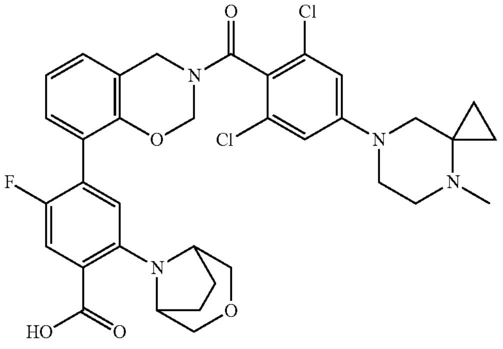

A solution of 4-[3-[2,6-dichloro-4-(4,7-diazaspiro[2.5]octan-7-yl)benzoyl]-2,4-dihydro-1,3-benzoxazin-8-yl]-5-fluoro-2-(3-oxa-8-azabicyclo[3.2.1]octan-8-yl)benzoic acid (12.3 mg, 0.0180 mmol), formaldehyde (5.53 mg, 0.184 mmol), and sodium triacetoxyborohydride (19.5 mg, 0.0920 mmol) in dichloromethane (0.0920 mL) was stirred at room temperature for 13 hours. The reaction solution was diluted with methanol and then concentrated, and the reaction solution was purified by HPLC (acetonitrile/water, 0.1% formic acid) to obtain the title compound (34%, 4.30 mg).

LCMS: m/z 681 [M+H]$^+$

HPLC retention time: 1.01 min and 1.05 min (analysis condition B)

Compound 20-10 rac-2-(3-Cyanomorpholin-4-yl)-4-[3-[2,6-dichloro-4-[4-(2-methoxyethyl)piperazin-1-yl]benzoyl]-2,4-dihydro-1,3-benzoxazin-8-yl]-5-fluorobenzoic acid First Step Compound tui7 rac-Methyl 4-bromo-2-(3-cyanomorpholin-4-yl)-5-fluorobenzoate

[Formula 604]

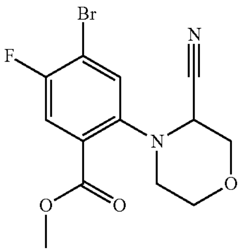

To a solution of methyl 4-bromo-5-fluoro-2-morpholin-4-ylbenzoate (200 mg, 0.629 mmol), iron(II) chloride (7.97 mg, 0.0630 mmol) and trimethylsilyl cyanide (0.157 mL, 1.26 mmol) in methanol (1.26 mL), 5.5 M tert-butyl hydroperoxide (0.286 mL, 1.57 mmol) was added, and the mixture was stirred overnight at room temperature. The reaction solution was purified by reverse phase column chromatography (acetonitrile/water, 0.1% formic acid) to obtain the title compound (50%, 109 mg).

LCMS: m/z 343[M+H]$^+$

HPLC retention time: 0.77 min (analysis condition D)

Second Step

Compound tui8 rac-Methyl 2-(3-cyanomorpholin-4-yl)-4-[3-[2,6-dichloro-4-[4-(2-methoxyethyl)piperazin-1-yl]benzoyl]-2,4-dihydro-1,3-benzoxazin-8-yl]-5-fluorobenzoate

[Formula 605]

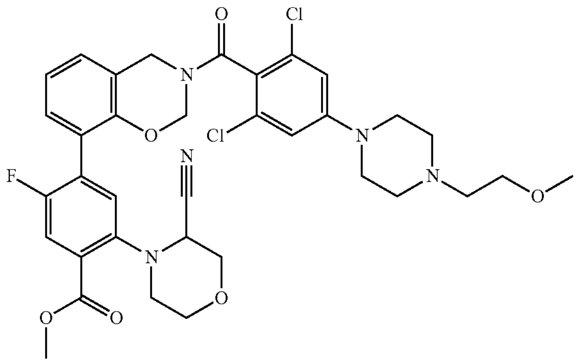

The title compound was obtained by the same operation as in the third step of compound B using rac-methyl 4-bromo-2-(3-cyanomorpholin-4-yl)-5-fluorobenzoate and (8-bromo-2,4-dihydro-1,3-benzoxazin-3-yl)-[2,6-dichloro-4-[4-(2-methoxyethyl)piperazin-1-yl]phenyl]methanone.

LCMS: m/z 712[M+H]$^+$

HPLC retention time: 0.63 min (analysis condition D)

Third Step

Compound 20-10 rac-2-(3-Cyanomorpholin-4-yl)-4-[3-[2,6-dichloro-4-[4-(2-methoxyethyl)piperazin-1-yl]benzoyl]-2,4-dihydro-1,3-benzoxazin-8-yl]-5-fluorobenzoic acid

[Formula 606]

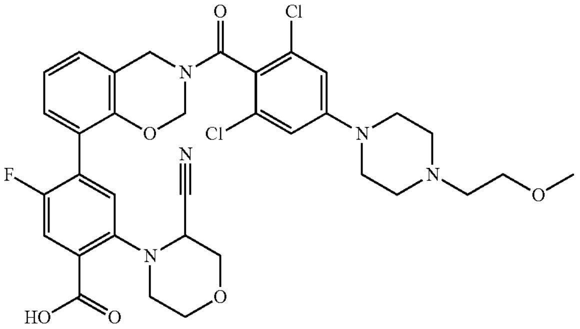

A solution of rac-methyl 2-(3-cyanomorpholin-4-yl)-4-[3-[2,6-dichloro-4-[4-(2-methoxyethyl)piperazin-1-yl]benzoyl]-2,4-dihydro-1,3-benzoxazin-8-yl]-5-fluorobenzoate (5.80 mg, 0.00814 mmol) and a 5 M aqueous lithium hydroxide solution (0.0163 mL, 0.0810 mmol) in tetrahydrofuran (0.0407 mL) and methanol (0.0407 mL) was stirred at 60° C. for 1 hour. The reaction solution was purified by HPLC (acetonitrile/water, 0.1% formic acid) to obtain the title compound (33%, 1.90 mg).

LCMS: m/z 698[M+H]$^+$

HPLC retention time: 1.08 min and 1.11 min (analysis condition B)

Compound 20-11 rac-4-[3-[2,6-Dichloro-4-[2-cyano-4-(2-methoxyethyl)piperazin-1-yl]benzoyl]-2,4-dihydro-1,3-benzoxazin-8-yl]-5-fluoro-2-morpholin-4-ylbenzoic acid First Step Compound tui9 rac-1-[3,5-Dichloro-4-[8-(2-fluoro-4-methoxycarbonyl-5-morpholin-4-ylphenyl)-2,4-dihydro-1,3-benzoxazine-3-carbonyl]phenyl]piperazine-2-carboxylic acid

[Formula 607]

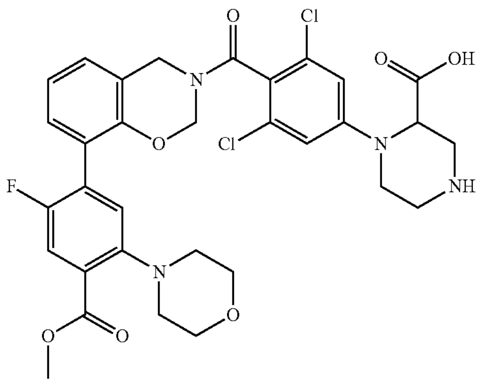

To a solution of compound B (50.0 mg, 0.0800 mmol), rac-piperazine-2-carboxylic acid dihydrochloride (32.5 mg, 0.160 mmol) and cesium carbonate (130 mg, 0.400 mmol) in dimethyl sulfoxide (0.400 mL), copper iodide (3.05 mg, 0.0160 mmol) was added, and the mixture was stirred at 100° C. for 3 hours. The reaction solution was purified by HPLC (acetonitrile/water, 0.1% formic acid) to obtain the title compound (37%, 20.0 mg).

LCMS: m/z 673[M+H]+

HPLC retention time: 0.59 min and 0.61 min (analysis condition D)

Second Step

Compound tui10 rac-1-[3,5-Dichloro-4-[8-(2-fluoro-4-methoxycarbonyl-5-morpholin-4-ylphenyl)-2,4-dihydro-1,3-benzoxazine-3-carbonyl]phenyl]-4-(2-methoxyethyl)piperazine-2-carboxylic acid

[Formula 608]

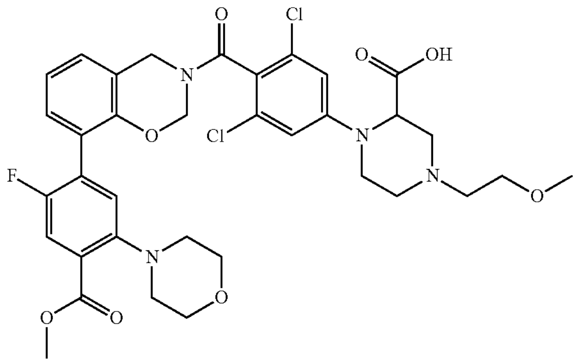

To a solution of rac-1-[3,5-dichloro-4-[8-(2-fluoro-4-methoxycarbonyl-5-morpholin-4-ylphenyl)-2,4-dihydro-1,3-benzoxazine-3-carbonyl]phenyl]piperazine-2-carboxylic acid (6.70 mg, 0.00995 mmol), 2-bromoethyl methyl ether (0.00288 mL, 0.0300 mmol) and N,N-diisopropyl ethyl ether (0.00520 mL, 0.0300 mmol) in N.N-dimethylformamide (0.0497 mL), tetramethylammonium iodide (0.200 mg, 0.000995 mmol) was added, and the mixture was stirred overnight at room temperature. The reaction solution was purified by HPLC (acetonitrile/water, 0.1% formic acid) to obtain the title compound (76%, 5.50 mg).

LCMS: m/z 731[M+H]+

HPLC retention time: 0.61 min and 0.63 min (analysis condition D)

Third Step

Compound tui11 rac-Methyl 4-[3-[4-[2-carbamoyl-4-(2-methoxyethyl)piperazin-1-yl]-2,6-dichlorobenzoyl]-2,4-dihydro-1,3-benzoxazin-8-yl]-5-fluoro-2-morpholin-4-ylbenzoate

[Formula 609]

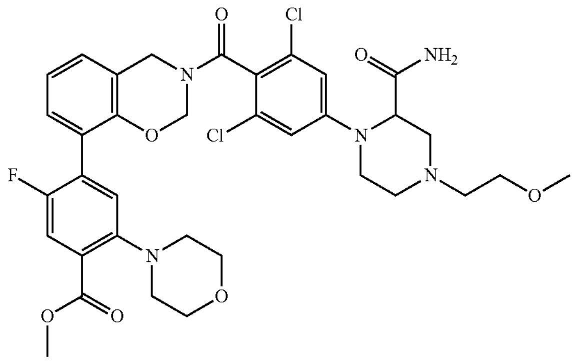

To a solution of rac-1-[3,5-dichloro-4-[8-(2-fluoro-4-methoxycarbonyl-5-morpholin-4-ylphenyl)-2,4-dihydro-1,3-benzoxazine-3-carbonyl]phenyl]-4-(2-methoxyethyl)piperazine-2-carboxylic acid (2.70 mg, 0.00369 mmol), N,N-diisopropylethylamine (0.00193 mL, 0.0110 mmol) and HATU (2.11 mg, 0.00554 mmol) in N-methylpyrrolidone (0.0369 mL), a 7 M solution of ammonia in methanol (0.00158 mL, 0.0110 mmol) was added, and the mixture was stirred at room temperature for 2 hours. The reaction solution was purified by HPLC (acetonitrile/water, 0.1% formic acid) to obtain the title compound (37%, 1.00 mg).

LCMS: m/z 730[M+H]+

HPLC retention time: 0.60 min and 0.61 min (analysis condition D)

Fourth Step

Compound 20-11 rac-4-[3-[2,6-Dichloro-4-[2-cyano-4-(2-methoxyethyl)piperazin-1-yl]benzoyl]-2,4-dihydro-1,3-benzoxazin-8-yl]-5-fluoro-2-morpholin-4-ylbenzoic acid

[Formula 610]

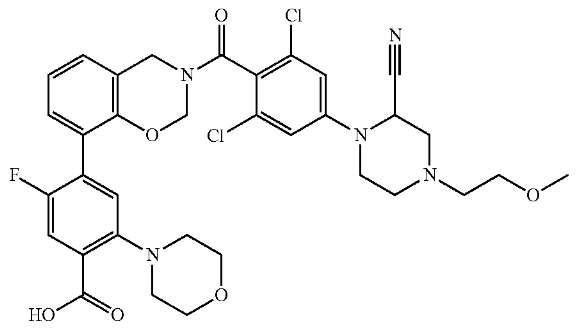

A solution of rac-methyl 4-[3-[4-[2-carbamoyl-4-(2-methoxyethyl)piperazin-1-yl]-2,6-dichlorobenzoyl]-2,4-dihydro-1,3-benzoxazin-8-yl]-5-fluoro-2-morpholin-4-ylbenzoate (1.00 mg, 0.00137 mmol) and a Burgess reagent (1.63 mg, 0.00684 mmol) in acetonitrile (0.0137 mL) was stirred overnight at room temperature. A 5 M aqueous lithium hydroxide solution (0.00137 mL, 0.00684 mmol) and methanol (0.0130 mL) were added to the reaction solution, and the mixture was stirred overnight at room temperature. The reaction solution was purified by HPLC (acetonitrile/water, 0.1% formic acid) to obtain the title compound (63%, 0.600 mg).

LCMS: m/z 698[M+H]$^+$

HPLC retention time: 1.29 min (analysis condition B)

Compound 20-12 rac-4-[3-[2,6-Dichloro-4-[3-cyano-4-(2-methoxyethyl)piperazin-1-yl]benzoyl]-2,4-dihydro-1,3-benzoxazin-8-yl]-5-fluoro-2-morpholin-4-ylbenzoic acid First Step Compound tui12 rac-4-[3,5-Dichloro-4-[8-(2-fluoro-4-methoxycarbonyl-5-morpholin-4-ylphenyl)-2,4-dihydro-1,3-benzoxazine-3-carbonyl]phenyl]-1-[(2-methylpropan-2-yl)oxycarbonyl]piperazine-2-carboxylic acid

[Formula 611]

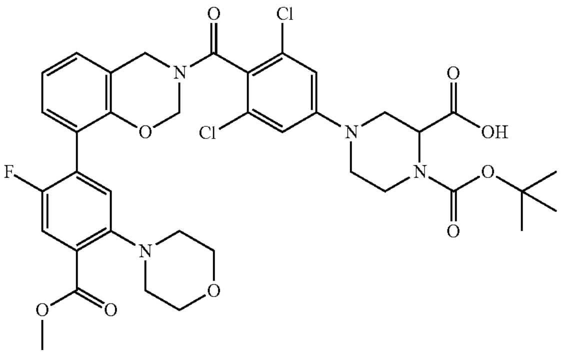

A solution of compound S (50.0 mg, 0.0890 mmol), rac-1-[(2-methylpropan-2-yl)oxycarbonyl]piperazine-2-carboxylic acid (61.3 mg, 0.266 mmol) and potassium carbonate (36.8 mg, 0.266 mmol) in N-methylpyrrolidone (0.296 mL) was stirred at 130° C. for 5 hours. The reaction solution was purified by reverse phase column chromatography (acetonitrile/water, 0.1% formic acid) to obtain the title compound (64%, 44.2 mg).

LCMS: m/z 773[M+H]$^+$

HPLC retention time: 0.94 min (analysis condition D)

Second Step

Compound tui13 rac-4-[3,5-Dichloro-4-[8-(2-fluoro-4-methoxycarbonyl-5-morpholin-4-ylphenyl)-2,4-dihydro-1,3-benzoxazine-3-carbonyl]phenyl]piperazine-2-carboxylic acid

[Formula 612]

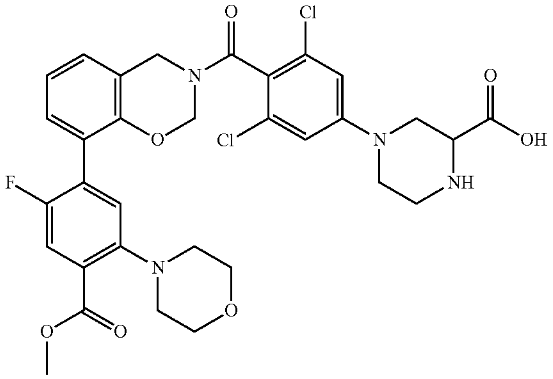

To a solution of rac-4-[3,5-dichloro-4-[8-(2-fluoro-4-methoxycarbonyl-5-morpholin-4-ylphenyl)-2,4-dihydro-1,3-benzoxazine-3-carbonyl]phenyl]-1-[(2-methylpropan-2-yl)oxycarbonyl]piperazine-2-carboxylic acid (22.0 mg, 0.0280 mmol) in dichloromethane (0.142 mL), a 4 M solution of hydrochloric acid in dioxane (0.0355 mL, 0.142 mmol) was added, and the mixture was stirred at room temperature for 1 hour. The reaction solution was concentrated and purified by reverse phase column chromatography (acetonitrile/water, 0.1% formic acid) to obtain the title compound (75%, 14.3 mg).

LCMS: m/z 673[M+H]$^+$

HPLC retention time: 0.61 min and 0.64 min (analysis condition D)

Third Step

Compound tui14 rac-4-[3,5-Dichloro-4-[8-(2-fluoro-4-methoxycarbonyl-5-morpholin-4-ylphenyl)-2,4-dihydro-1,3-benzoxazine-3-carbonyl]phenyl]-1-(2-methoxyethyl)piperazine-2-carboxylic acid

[Formula 613]

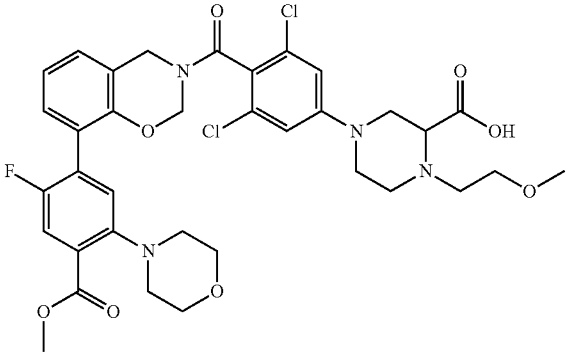

To a solution of rac-4-[3,5-dichloro-4-[8-(2-fluoro-4-methoxycarbonyl-5-morpholin-4-ylphenyl)-2,4-dihydro-1,3-benzoxazine-3-carbonyl]phenyl]piperazine-2-carboxylic acid (11.0 mg, 0.0160 mmol), 2-bromoethyl methyl ether (0.00178 mL, 0.0190 mmol) and N,N-diisopropylethylamine (0.0108 mL, 0.0620 mmol) in N,N-dimethylformamide (0.0770 mL), tetramethylammonium iodide (0.311 mg, 0.00155 mmol) was added, and the mixture was stirred overnight at room temperature. The reaction solution was purified by reverse phase column chromatography (acetonitrile/water, 0.1% formic acid) to obtain the title compound (19%, 2.30 mg).

LCMS: m/z 731[M+H]$^+$

HPLC retention time: 0.65 min and 0.68 min (analysis condition D)

Fourth Step

Compound tui15 rac-Methyl 4-[3-[4-[3-carbamoyl-4-(2-methoxyethyl)piperazin-1-yl]-2,6-dichlorobenzoyl]-2,4-dihydro-1,3-benzoxazin-8-yl]-5-fluoro-2-morpholin-4-ylbenzoate

[Formula 614]

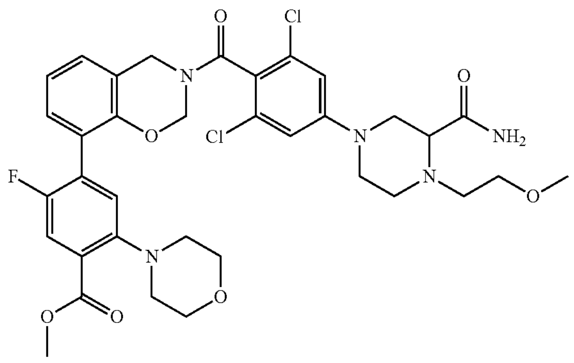

To a solution of rac-4-[3,5-dichloro-4-[8-(2-fluoro-4-methoxycarbonyl-5-morpholin-4-ylphenyl)-2,4-dihydro-1,3-benzoxazine-3-carbonyl]phenyl]-1-(2-methoxyethyl)piperazine-2-carboxylic acid (2.30 mg, 0.00314 mmol), N,N-diisopropylethylamine (0.00164 mL, 0.00943 mmol) and HATU (1.79 mg, 0.00472 mmol) in N-methylpyrrolidone (0.0314 mL), a 0.5 M solution of ammonia in 1,4-dioxane (0.0189 mL, 0.00943 mmol) was added, and the mixture was stirred at room temperature for 1 hour. The reaction solution was purified by reverse phase column chromatography (acetonitrile/water, 0.1% formic acid) to obtain the title compound (44%, 1.00 mg).

LCMS: m/z 730[M+H]$^+$

HPLC retention time: 0.64 min and 0.65 min (analysis condition D)

Fifth Step

Compound tui16 rac-Methyl 4-[3-[2,6-dichloro-4-[3-cyano-4-(2-methoxyethyl)piperazin-1-yl]benzoyl]-2,4-dihydro-1,3-benzoxazin-8-yl]-5-fluoro-2-morpholin-4-ylbenzoate

[Formula 615]

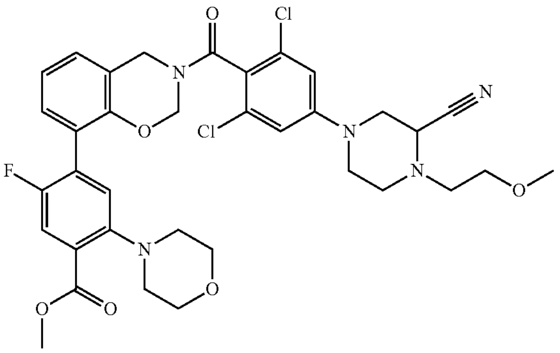

A solution of rac-methyl 4-[3-[4-[3-carbamoyl-4-(2-methoxyethyl)piperazin-1-yl]-2,6-dichlorobenzoyl]-2,4-dihydro-1,3-benzoxazin-8-yl]-5-fluoro-2-morpholin-4-ylbenzoate (1.00 mg, 0.00137 mmol) and a Burgess reagent (1.63 mg, 0.00684 mmol) in acetonitrile (0.0274 mL) was stirred at room temperature for 1 hour. The reaction solution was purified by HPLC (acetonitrile/water, 0.1% formic acid) to obtain the title compound (62%, 0.600 mg).

LCMS: m/z 712[M+H]$^+$

HPLC retention time: 0.91 min (analysis condition D)

Sixth Step

Compound 20-12 rac-4-[3-[2,6-Dichloro-4-[3-cyano-4-(2-methoxyethyl)piperazin-1-yl]benzoyl]-2,4-dihydro-1,3-benzoxazin-8-yl]-5-fluoro-2-morpholin-4-ylbenzoic acid

[Formula 616]

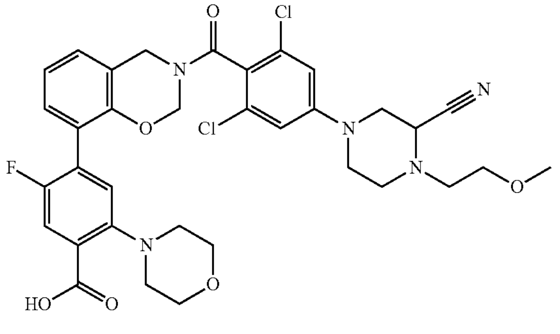

To a solution of rac-methyl 4-[3-[2,6-dichloro-4-[3-cyano-4-(2-methoxyethyl)piperazin-1-yl]benzoyl]-2,4-dihydro-1,3-benzoxazin-8-yl]-5-fluoro-2-morpholin-4-ylbenzoate (1.00 mg, 0.00140 mmol) in tetrahydrofuran (0.0140 mL) and methanol (0.0140 mL), a 5 M aqueous lithium hydroxide solution (0.00281 mL, 0.0140 mmol) was added, and the mixture was stirred overnight at room temperature.

The reaction solution was purified by HPLC (acetonitrile/water, 0.1% formic acid) to obtain the title compound (61%, 0.600 mg).

LCMS: m/z 698[M+H]$^+$

HPLC retention time: 1.42 min and 1.44 min (analysis condition B)

Compound 20-13

4-[3-[2,6-Dichloro-4-[3-(4-methylpyrazol-1-yl)azetidin-1-yl]benzoyl]-2,4-dihydro-1,3-benzoxazin-8-yl]-5-fluoro-2-(3-oxa-8-azabicyclo[3.2.1]octan-8-yl) benzoic acid

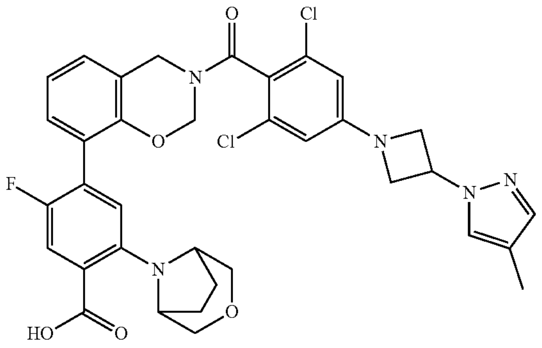 [SMILES: Cc1cnn(C2CN(c3cc(Cl)c(C(=O)N4COc5c(cccc5-c5cc(N6C7CCC6COC7)c(C(=O)O)cc5F)C4)c(Cl)c3)C2)c1]

A solution of methyl 4-[3-[2,6-dichloro-4-(3-hydroxyazetidin-1-yl)benzoyl]-2,4-dihydro-1,3-benzoxazin-8-yl]-5-fluoro-2-(3-oxa-8-azabicyclo[3.2.1]octan-8-yl)benzoate (25.0 mg, 0.0390 mmol) and N,N-diisopropylethylamine (0.00881 mL, 0.0510 mmol) in dichloromethane (0.389 mL) was cooled to −78° C. Trifluoromethanesulfonic anhydride (0.00997 mL, 0.0470 mmol) was added thereto, and the mixture was stirred at room temperature for 1 hour. 4-Methylpyrazole (0.0161 mL, 0.195 mmol) was added thereto, and the mixture was stirred overnight at room temperature. Methanol was added thereto, and the reaction solution was concentrated. Methanol (0.0970 mL), tetrahydrofuran (0.0970 mL) and a 5 M aqueous sodium hydroxide solution (0.0389 mL, 0.195 mmol) were added to the residue, and the mixture was stirred at 60° C. for 2 hours. The reaction solution was purified by HPLC (acetonitrile/water, 0.1% formic acid) to obtain the title compound (35%, 9.50 mg).

LCMS: m/z 692[M+H]$^+$

HPLC retention time: 1.54 min and 1.55 min (analysis condition B)

Test Example 1: In Vitro Nrf2 Transcriptional Activity Measurement by ARE-Dependent Reporter Assay in HepG2 Cell A human liver cancer-derived cell line HepG2 was transfected with pGL4.37 vector (pARE-Luc, Promega Corp.) and incubated overnight at 37° C. in a humidified atmosphere containing 5% $CO_2$. The cells were dissociated by trypsin treatment, inoculated to a 384-well plate supplemented with a test compound, and incubated at 37° C. for 4 hours. Then, Bright-Glo Reagent (Promega Corp.) was added to the plate, and luciferase activity was measured with Envision plate reader.

Luciferase activity obtained through the action of the compound of Example 1-54 or Example 17-23 at a concentration of 3.75 µM was defined as 100%. The luciferase activity of each well was converted to a response rate (%).

The dose-response curve of the compound of each Example was prepared to calculate a 50% effective concentration ($EC_{50}$). The results are shown in Table 20. These results demonstrated that the compound group of the present invention has a Nrf2-activating effect in vitro.

TABLE 20

| Compound No. | EC50 (nM) |
|---|---|
| 1-1 | 2.8 |
| 1-2 | 8.6 |
| 1-3 | 5.8 |
| 1-4 | 1.6 |
| 1-5 | 3.1 |
| 1-6 | 9.6 |
| 1-7 | 2.0 |
| 1-8 | 2.2 |
| 1-9 | 4.6 |
| 1-10 | 3.1 |
| 1-11 | 2.1 |
| 1-12 | 16 |
| 1-13 | 2.4 |
| 1-14 | 4.4 |
| 1-15 | 2.7 |
| 1-16 | 11 |
| 1-17 | 19 |
| 1-18 | 4.3 |
| 1-19 | 6.3 |
| 1-20 | 3.2 |
| 1-21 | 2.9 |
| 1-22 | 2.1 |
| 1-23 | 1.9 |
| 1-24 | 1.4 |
| 1-25 | 1.5 |
| 1-26 | 1.4 |
| 1-27 | 2.9 |
| 1-30 | 2.6 |
| 1-31 | 1.9 |
| 1-32 | 1.5 |
| 1-33 | 1.9 |
| 1-34 | 39 |
| 1-35 | 5.8 |
| 1-36 | 1.8 |
| 1-37 | 2.1 |
| 1-38 | 1.8 |
| 1-39 | 18 |
| 1-40 | 3.0 |
| 1-41 | 2.0 |
| 1-42 | 2.6 |
| 1-43 | 1.8 |
| 1-44 | 6.5 |
| 1-45 | 3.7 |
| 1-46 | 1.9 |
| 1-47 | 12 |
| 1-48 | 2.3 |
| 1-49 | 1.9 |
| 1-50 | 4.6 |
| 1-51 | 10 |
| 1-52 | 14 |
| 1-53 | 5.0 |
| 1-54 | 1.5 |
| 1-55 | 1.5 |
| 1-56 | 1.3 |
| 1-57 | 1.4 |
| 1-58 | 4.2 |
| 1-59 | 1.2 |
| 1-60 | 4.2 |
| 1-61 | 2.6 |
| 1-62 | 3.2 |
| 1-63 | 2.1 |
| 1-64 | 3.0 |
| 1-65 | 3.7 |
| 1-66 | 2.7 |
| 1-67 | 4.4 |
| 1-68 | 8.1 |
| 1-69 | 5.4 |
| 1-70 | 4.7 |
| 1-71 | 6.1 |
| 1-72 | 5.8 |

TABLE 20-continued

| Compound No. | EC50 (nM) |
|---|---|
| 1-73 | 5.1 |
| 1-74 | 2.7 |
| 1-75 | 8.0 |
| 1-76 | 5.3 |
| 1-77 | 5.6 |
| 1-78 | 15 |
| 1-79 | 3.6 |
| 1-80 | 1.9 |
| 1-81 | 5.1 |
| 1-82 | 3.5 |
| 1-83 | 2.4 |
| 1-84 | 2.4 |
| 1-85 | 0.90 |
| 1-86 | 1.1 |
| 1-87 | 1.0 |
| 1-88 | 2.1 |
| 2-1 | 6.2 |
| 2-2 | 6.5 |
| 2-3 | 1.4 |
| 2-4 | 5.7 |
| 2-5 | 2.4 |
| 2-6 | 6.0 |
| 3-1 | 1.3 |
| 3-2 | 6.8 |
| 3-3 | 9.4 |
| 3-4 | 6.2 |
| 3-5 | 6.9 |
| 3-6 | 9.0 |
| 3-7 | 9.6 |
| 3-8 | 17 |
| 3-9 | 10 |
| 3-10 | 4.7 |
| 3-11 | 5.7 |
| 3-12 | 8.7 |
| 3-13 | 9.7 |
| 3-14 | 8.8 |
| 3-15 | 8.4 |
| 3-16 | 11 |
| 3-17 | 12 |
| 3-18 | 20 |
| 3-19 | 8.0 |
| 3-20 | 9.0 |
| 3-21 | 6.4 |
| 3-22 | 21 |
| 3-23 | 21 |
| 3-24 | 31 |
| 3-25 | 7.7 |
| 3-26 | 9.8 |
| 3-27 | 8.8 |
| 3-28 | 2.1 |
| 4-1 | 3.1 |
| 4-2 | 1.2 |
| 4-3 | 1.7 |
| 4-4 | 3.2 |
| 4-5 | 1.3 |
| 4-6 | 8.0 |
| 4-7 | 3.3 |
| 4-8 | 5.8 |
| 4-9 | 2.2 |
| 4-10 | 4.2 |
| 4-11 | 25 |
| 4-12 | 2.1 |
| 4-13 | 5.8 |
| 4-14 | 9.0 |
| 4-15 | 3.1 |
| 4-16 | 2.9 |
| 4-17 | 4.0 |
| 4-18 | 3.6 |
| 4-19 | 2.9 |
| 4-20 | 3.0 |
| 4-21 | 7.4 |
| 4-22 | 1.8 |
| 4-23 | 1.5 |
| 4-24 | 2.7 |
| 4-25 | 1.9 |
| 4-26 | 8.2 |
| 4-27 | 1.1 |

TABLE 20-continued

| Compound No. | EC50 (nM) |
|---|---|
| 4-28 | 1.6 |
| 4-29 | 2.1 |
| 4-30 | 1.1 |
| 4-31 | 1.2 |
| 4-32 | 6.9 |
| 4-33 | 5.1 |
| 4-34 | 3.8 |
| 4-35 | 20 |
| 4-36 | 8.7 |
| 4-37 | 6.3 |
| 4-38 | 5.1 |
| 4-39 | 6.9 |
| 4-40 | 8.9 |
| 4-41 | 4.7 |
| 4-42 | 4.4 |
| 4-43 | 7.4 |
| 4-44 | 16 |
| 4-45 | 10 |
| 4-46 | 14 |
| 4-47 | 3.3 |
| 4-48 | 2.6 |
| 4-49 | 1.2 |
| 4-50 | 2.8 |
| 4-51 | 2.6 |
| 4-52 | 1.1 |
| 4-53 | 2.9 |
| 4-54 | 1.2 |
| 4-55 | 2.0 |
| 4-56 | 1.9 |
| 4-57 | 4.8 |
| 4-58 | 5.2 |
| 4-59 | 12 |
| 4-60 | 7.5 |
| 5-1 | 1.6 |
| 5-2 | 1.3 |
| 5-3 | 9.5 |
| 5-4 | 2.4 |
| 5-5 | 1.0 |
| 5-6 | 2.3 |
| 5-7 | 1.7 |
| 5-8 | 2.0 |
| 5-9 | 1.7 |
| 5-10 | 3.2 |
| 5-11 | 3.4 |
| 5-12 | 2.1 |
| 5-13 | 2.7 |
| 5-14 | 2.9 |
| 5-15 | 3.1 |
| 5-16 | 3.5 |
| 6-1 | 2.1 |
| 6-2 | 2.8 |
| 6-3 | 5.7 |
| 6-4 | 2.0 |
| 6-5 | 10 |
| 6-6 | 12 |
| 6-7 | 5.7 |
| 6-8 | 2.4 |
| 6-9 | 2.2 |
| 6-10 | 3.7 |
| 6-11 | 1.5 |
| 6-12 | 3.9 |
| 6-13 | 3.8 |
| 7-1 | 4.8 |
| 7-2 | 4.6 |
| 7-3 | 18 |
| 7-4 | 4.3 |
| 7-5 | 3.7 |
| 7-6 | 5.4 |
| 7-7 | 3.4 |
| 7-8 | 3.2 |
| 7-9 | 8.4 |
| 7-10 | 27 |
| 7-11 | 3.2 |
| 7-12 | 2.3 |
| 7-13 | 5.7 |
| 7-14 | 24 |
| 7-15 | 2.5 |

TABLE 20-continued

| Compound No. | EC50 (nM) |
|---|---|
| 7-16 | 7.4 |
| 7-17 | 9.0 |
| 7-18 | 1.7 |
| 8-1 | 1.6 |
| 8-2 | 4.0 |
| 8-3 | 2.6 |
| 8-4 | 3.6 |
| 8-5 | 2.4 |
| 8-6 | 2.7 |
| 8-7 | 2.1 |
| 8-8 | 4.8 |
| 8-9 | 9.5 |
| 9-1 | 3.5 |
| 9-2 | 7.4 |
| 9-3 | 19 |
| 9-4 | 7.5 |
| 9-5 | 4.6 |
| 9-6 | 5.7 |
| 9-7 | 14 |
| 9-8 | 3.5 |
| 9-9 | 1.5 |
| 9-10 | 8.8 |
| 9-11 | 19 |
| 9-12 | 3.1 |
| 9-13 | 6.7 |
| 9-14 | 11 |
| 9-15 | 14 |
| 9-16 | 4.8 |
| 9-17 | 7.5 |
| 9-18 | 6.4 |
| 9-19 | 5.9 |
| 9-20 | 4.6 |
| 9-21 | 6.0 |
| 9-22 | 0.90 |
| 9-23 | 3.1 |
| 9-24 | 2.5 |
| 9-25 | 8.8 |
| 10-1 | 6.5 |
| 10-2 | 5.2 |
| 10-3 | 1.5 |
| 10-4 | 4.8 |
| 10-5 | 4.3 |
| 10-6 | 9.1 |
| 10-7 | 23 |
| 10-8 | 1.5 |
| 10-9 | 1.2 |
| 10-10 | 25 |
| 10-11 | 2.4 |
| 10-12 | 1.2 |
| 10-13 | 4.2 |
| 11-1 | 3.6 |
| 11-2 | 4.2 |
| 11-3 | 9.5 |
| 11-4 | 2.0 |
| 11-5 | 2.0 |
| 11-6 | 2.4 |
| 11-7 | 5.2 |
| 11-8 | 3.1 |
| 11-9 | 2.7 |
| 11-10 | 3.8 |
| 12-1 | 11 |
| 12-2 | 2.6 |
| 12-3 | 6.0 |
| 12-4 | 15 |
| 13-1 | 7.1 |
| 13-2 | 18 |
| 13-3 | 5.3 |
| 13-4 | 24 |
| 13-5 | 16 |
| 13-6 | 7.5 |
| 13-7 | 6.7 |
| 13-8 | 5.4 |
| 13-9 | 5.2 |
| 13-10 | 17 |
| 13-11 | 7.5 |
| 13-12 | 17 |
| 13-13 | 7.1 |

TABLE 20-continued

| Compound No. | EC50 (nM) |
|---|---|
| 13-14 | 13 |
| 13-15 | 10 |
| 13-16 | 0.95 |
| 13-17 | 5.9 |
| 13-18 | 21 |
| 13-19 | 1.6 |
| 13-20 | 7.2 |
| 13-21 | 2.3 |
| 14-1 | 3.2 |
| 14-2 | 6.5 |
| 14-3 | 12 |
| 14-4 | 3.8 |
| 14-5 | 3.1 |
| 14-6 | 20 |
| 14-7 | 2.5 |
| 14-8 | 70 |
| 14-9 | 3.7 |
| 15-1 | 4.9 |
| 15-2 | 21 |
| 15-3 | 1.5 |
| 15-4 | 6.8 |
| 16-1 | 13 |
| 16-2 | 1.5 |
| 16-3 | 17 |
| 16-4 | 110 |
| 16-5 | 200 |
| 16-6 | 170 |
| 16-7 | 1.4 |
| 16-8 | 3.9 |
| 16-9 | 12 |
| 16-10 | 9.3 |
| 16-11 | 7.5 |
| 16-12 | 9.8 |
| 16-13 | 4.4 |
| 16-14 | 6.8 |
| 16-15 | 3.0 |
| 16-16 | 13 |
| 16-17 | 2.7 |
| 17-1 | 2.2 |
| 17-2 | 7.7 |
| 17-3 | 9.7 |
| 17-4 | 10 |
| 17-5 | 17 |
| 17-8 | 20 |
| 17-9 | 21 |
| 17-10 | 21 |
| 17-15 | 58 |
| 17-16 | 74 |
| 17-18 | 97 |
| 17-21 | 22 |
| 17-23 | 110 |
| 18-1 | 4.1 |
| 18-2 | 5.8 |
| 18-3 | 14 |
| 18-4 | 3.7 |
| 18-5 | 12 |
| 18-6 | 10 |
| 18-7 | 17 |
| 18-8 | 2.8 |
| 18-9 | 23 |
| 18-10 | 36 |
| 18-11 | 310 |
| 18-12 | 24 |
| 19-2 | 1.6 |
| 19-3 | 1.2 |
| 19-4 | 1.9 |
| 19-5 | 2.7 |
| 19-6 | 6.3 |
| 19-7 | 2.3 |
| 19-8 | 3.9 |
| 19-9 | 1.4 |
| 19-10 | 2.5 |
| 19-11 | 4.3 |
| 19-12 | 2.5 |
| 19-13 | 2.1 |
| 19-14 | 4.1 |
| 19-15 | 2.3 |

TABLE 20-continued

| Compound No. | EC50 (nM) |
|---|---|
| 19-16 | 17 |
| 19-17 | 6.1 |
| 19-18 | 1.3 |
| 19-19 | 2.6 |
| 20-1 | 850 |
| 20-2 | 24 |
| 20-3 | 40 |
| 20-4 | 150 |
| 20-5 | 75 |
| 20-6 | 48 |
| 20-7 | 14 |
| 20-8 | 18 |
| 20-9 | 14 |
| 20-10 | 25 |
| 20-13 | 5.5 |

Test Example 2: In Vivo Nrf2 Transcriptional Activity Measurement

A test compound (solvent: 10 vol % dimethyl sulfoxide/50 mM glycine/32 mM sodium hydroxide/physiological saline) was administered to C57BL/6J mice (7-8 weeks old), which were euthanized by whole blood collection under isoflurane anesthesia 7 to 8 hours later, followed by the collection of various organs. mRNA was purified from the collected organs, and the mRNA expression level of Mapk1 as an internal control and the mRNA expression level of Nqo1 (NAD(P)H quinone dehydrogenase 1) as a typical Nrf2 downstream molecule were each measured by qPCR. The Nqo1 mRNA expression level was quantified by comparative CT, and an expression level ratio to a non-administration group was calculated. The administration of the test compound elevated the Nqo1 mRNA expression level in the various organs, confirming that the test compound also has a Nrf2-activating effect in vivo. The results are shown in Table 21.

TABLE 21

| Compound | Administration | Dose | Nqo1 mRNA expression level ratio to non-administration group | | |
|---|---|---|---|---|---|
| No. | route | (mg/kg) | Kidney | Lung | Liver |
| 1-4 | Intraperitoneal | 10 | 4.4 | 13 | 6.5 |
| 1-4 | Oral | 30 | 5.0 | 20 | 8.1 |
| 1-18 | Intraperitoneal | 10 | 2.5 | 8.7 | 6.0 |
| 1-21 | Intraperitoneal | 10 | 3.7 | 10 | 4.7 |
| 1-33 | Intraperitoneal | 10 | 3.7 | 13 | 5.5 |
| 1-33 | Oral | 30 | 5.1 | 18 | 5.2 |
| 1-54 | Intraperitoneal | 10 | 4.6 | 18 | 6.7 |
| 1-54 | Oral | 30 | 4.9 | 20 | 7.4 |
| 1-83 | Intraperitoneal | 15 | 4.7 | 21 | 6.5 |
| 1-88 | Intraperitoneal | 15 | 3.0 | 6.1 | 4.3 |
| 1-88 | Oral | 15 | 3.4 | 8.9 | 5.4 |
| 2-2 | Intraperitoneal | 10 | 5.3 | 17 | 5.8 |
| 4-8 | Intraperitoneal | 10 | 3.4 | 6.2 | 6.7 |
| 4-37 | Intraperitoneal | 10 | 4.0 | 5.4 | 8.0 |
| 5-1 | Intraperitoneal | 10 | 4.4 | 19 | 6.8 |
| 5-1 | Oral | 30 | 5.1 | 17 | 3.9 |
| 5-2 | Intraperitoneal | 10 | 4.3 | 20 | 6.9 |
| 5-2 | Oral | 30 | 4.0 | 20 | 6.9 |
| 5-7 | Intraperitoneal | 10 | 4.0 | 18 | 5.4 |
| 5-9 | Intraperitoneal | 15 | 3.7 | 15 | 6.7 |
| 5-9 | Oral | 30 | 5.2 | 19 | 6.0 |
| 5-10 | Intraperitoneal | 15 | 5.1 | 17 | 5.4 |
| 5-16 | Oral | 15 | 3.6 | 14 | 4.8 |
| 7-2 | Intraperitoneal | 15 | 4.3 | 11 | 6.2 |
| 13-16 | Intraperitoneal | 15 | 4.8 | 20 | 6.6 |
| 13-16 | Oral | 30 | 4.5 | 22 | 6.0 |
| 13-21 | Oral | 30 | 2.9 | 3.6 | 4.9 |
| 14-1 | Oral | 30 | 5.7 | 17 | 4.2 |

INDUSTRIAL APPLICABILITY

The present invention provides a low-molecular compound having a Nrf2-activating effect. The present invention also provides a medicament for the prevention and/or treatment of various diseases, for example, neurodegenerative disease, lung disease, and kidney disease.

The invention claimed is:

1. A compound selected from the following compounds, or a salt thereof, or a solvate thereof:

4-[3-[2,6-dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, 4-[3-[2,6-dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid, 4-[3-[2,6-dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid, 4-[3-[2-chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, and 4-[3-[4-chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

2. The compound of claim 1, which is 4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, or a salt thereof, or a solvate thereof.

3. The compound of claim 1, which is 4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid, or a salt thereof, or a solvate thereof.

4. The compound of claim 1, which is 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid, or a salt thereof, or a solvate thereof.

5. The compound of claim 1, which is 4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, or a salt thereof, or a solvate thereof.

6. The compound of claim 1, which is 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid, or a salt thereof, or a solvate thereof.

7. The compound of claim 1, which is 4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

8. The compound of claim 1, which is 4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

9. The compound of claim 1, which is 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

10. The compound of claim 1, which is 4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

11. The compound of claim 1, which is 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

12. The salt of the compound of claim 1, which is a salt of 4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, or a solvate thereof.

13. The salt of the compound of claim 1, which is a salt of 4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid, or a solvate thereof.

14. The salt of the compound of claim 1, which is a salt of 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid, or a solvate thereof.

15. The salt of the compound of claim 1, which is a salt of 4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid, or a solvate thereof.

16. The salt of the compound of claim 1, which is a salt of 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid, or a solvate thereof.

17. The salt of the compound of claim 1, which is a salt of 4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

18. The salt of the compound of claim 1, which is a salt of 4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

19. The salt of the compound of claim 1, which is a salt of 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

20. The salt of the compound of claim 1, which is a salt of 4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

21. The salt of the compound of claim 1, which is a salt of 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

22. The solvate of the compound of claim 1, which is a solvate of 4-[3-[2,6-Dichloro-4-[(2R)-2,4-dimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

23. The solvate of the compound of claim 1, which is a solvate of 4-[3-[2,6-Dichloro-4-(7,7-dimethyl-5,9-dioxa-2-azaspiro[3.5]nonan-2-yl)benzoyl]-2,4-dihydro-1,3-benzoxazin-8-yl]-5-fluoro-2-(3-oxa-8-azabicyclo[3.2.1]octan-8-yl)benzoic acid.

24. The solvate of the compound of claim 1, which is a solvate of 4-[3-[2,6-Dichloro-4-(6-methoxy-2-azaspiro[3.3]heptan-2-yl)benzoyl]-2,4-dihydro-1,3-benzoxazin-8-yl]-5-fluoro-2-(3-oxa-8-azabicyclo[3.2.1]octan-8-yl)benzoic acid.

25. The solvate of the compound of claim 1, which is a solvate of 4-[3-[2-Chloro-4-[(2R,5R)-2,4,5-trimethylpiperazin-1-yl]benzoyl]-2,4-dihydro-1,3-benzoxazin-8-yl]-5-fluoro-2-(3-oxa-8-azabicyclo[3.2.1]octan-8-yl)benzoic acid.

26. The solvate of the compound of claim 1, which is a solvate of 4-[3-[4-Chloro-6-(7,7-dimethyl-5,9-dioxa-2-azaspiro[3.5]nonan-2-yl)-2-methylpyridine-3-carbonyl]-2,4-dihydro-1,3-benzoxazin-8-yl]-5-fluoro-2-(3-oxa-8-azabicyclo[3.2.1]octan-8-yl)benzoic acid.

27. A pharmaceutical composition comprising the compound according to claim 1, or the salt thereof, or the solvate thereof.

28. A method for treating neurodegenerative disease, lung disease, or kidney disease, comprising administering an effective amount of the compound according to claim 1, or the salt thereof, or the solvate thereof to a subject, wherein the neurodegenerative disease is selected from the group consisting of Alzheimer's disease, Parkinson's disease, Huntington's disease, Friedreich's ataxia, and amyotrophic lateral sclerosis, the lung disease is selected from the group consisting of idiopathic pulmonary fibrosis, acute respiratory distress syndrome, chronic obstructive pulmonary disease, pulmonary arterial hypertension, and asthma, and the kidney disease is selected from the group consisting of chronic kidney disease and acute kidney injury.

* * * * *